US011524998B2

(12) United States Patent
Bigelow et al.

(10) Patent No.: US 11,524,998 B2
(45) Date of Patent: Dec. 13, 2022

(54) ANTI-BETACELLULIN ANTIBODIES, FRAGMENTS THEREOF, AND MULTI-SPECIFIC BINDING MOLECULES

(71) Applicant: NOVARTIS AG, Basel (CH)

(72) Inventors: Chad Eric Bigelow, Somerville, MA (US); Ana Maria Carrion, Wellesley, MA (US); James Edgar Chastain, Acton, MA (US); Kirk Lee Clark, Stow, MA (US); Bijan Alexandre Etemad-Gilbertson, Jamaica Plain, MA (US); Joy Gispati Ghosh, Boston, MA (US); Shawn Michael Hanks, Sudbury, MA (US); Nicole Haubst, Munich (DE); Ganesh Rajan Iyer, South Grafton, MA (US); Nina Moker, Cologne (DE); Andrew Anh Nguyen, Brookline, MA (US); Stephen Hedrick Poor, Winthrop, MA (US); Yubin Qiu, Newton, MA (US); Nalini Velamur Rangaswamy, Wakefield, MA (US); Michael Stefanidakis, Brookline, MA (US); Engin Toksoz, Munich (DE); Michael Zbigniew Twarog, Cambridge, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 17/375,860

(22) Filed: Jul. 14, 2021

(65) Prior Publication Data
US 2022/0025032 A1 Jan. 27, 2022

Related U.S. Application Data

(60) Provisional application No. 63/156,709, filed on Mar. 4, 2021, provisional application No. 63/052,789, filed on Jul. 16, 2020.

(51) Int. Cl.
| *C07K 16/22* | (2006.01) |
| *A61P 27/02* | (2006.01) |
| *C07K 16/46* | (2006.01) |
| *A61K 39/00* | (2006.01) |

(52) U.S. Cl.
CPC .............. *C07K 16/22* (2013.01); *A61P 27/02* (2018.01); *C07K 16/468* (2013.01); *A61K 2039/507* (2013.01); *A61K 2039/545* (2013.01); *C07K 2317/31* (2013.01); *C07K 2317/55* (2013.01); *C07K 2317/565* (2013.01); *C07K 2317/92* (2013.01)

(58) Field of Classification Search
CPC .. C07K 16/22; C07K 16/468; C07K 2317/31; A61K 2039/507
USPC .......................................... 424/133.1, 136.1
See application file for complete search history.

(56) References Cited

U.S. PATENT DOCUMENTS

| 5,229,493 A | 7/1993 | Folkman et al. |
| 6,183,971 B1 | 2/2001 | Sasada et al. |
| 6,825,165 B1 | 11/2004 | Ito et al. |
| 8,168,588 B2 | 5/2012 | Williams et al. |
| 8,409,577 B2 | 4/2013 | Thompson et al. |
| 2009/0181008 A1 | 7/2009 | Ray et al. |
| 2009/0318346 A1 | 12/2009 | Bacus et al. |
| 2014/0186350 A1* | 7/2014 | Ghosh ................ A61K 31/713 424/134.1 |
| 2016/0297854 A1* | 10/2016 | Ghosh ................ C12N 15/115 |
| 2017/0290876 A1* | 10/2017 | Ghosh ................ A61K 38/005 |
| 2017/0327553 A1* | 11/2017 | Dawson King ...... C07K 16/241 |

FOREIGN PATENT DOCUMENTS

| EP | 1 890 721 B1 | 9/2010 |
| WO | 1996/030506 | 10/1996 |
| WO | 2001/49845 A1 | 7/2001 |
| WO | 2004/083241 A2 | 9/2004 |
| WO | 2007/146968 A2 | 12/2007 |
| WO | 2011/132182 A1 | 10/2011 |
| WO | 2014/099997 A1 | 6/2014 |
| WO | 2015/017529 A2 | 2/2015 |
| WO | 2017/053807 A2 | 3/2017 |
| WO | WO2022013787 | * 1/2022 |

OTHER PUBLICATIONS

Notification of Transmittal of The International Search Report And The Written Opinion of the International Searching Authority, or the Declaration, dated Dec. 6, 2021, issued in International Application No. PCT/IB2021/056363, dated Jul. 14, 2021.
Ahuja et al., "Serum vascular endothelial growth factor is a biomolecular biomarker of severity of diabetic retinopathy", International Journal of Retina and Vitreous, 5;29, pp. 1-6, (2019).
Apte et al., "Betacellulin Induces Increased Retinal Vascular Permeability in Mice", PLoS ONE, 5;10, pp. 1-7, (2010).
Araki et al., "Central serous chorioretinopathy with and without steroids: A multicenter survey", PLoS ONE, 14;2, pp. 1-9, (2019).
Bressler et al., "Persistent Macular Thickening Following Intravitreous Aflibercept, Bevacizumab, or Ranibizumab for Central-Involved Diabetic Macular Edema With Vision Impairment A Secondary Analysis of a Randomized Clinical Trial", JAMA Ophthalmol, 136;3, pp. 257-269, (2018).
Brown et al., "Intravitreal Aflibercept for Diabetic Macular Edema 100-Week Results From the VISTA and VIVID Studies", American Academy of Ophthalmology, 122;10, pp. 2044-2052, (2015).
Das et al., Expression of Betacellulin and Epiregulin Genes in the Mouse Uterus Temporally by the Blastocyst Solely at the Site of Its Apposition Is Coincident with the "Window" of Implantation, Developmental Biology, 190, pp. 178-190, (1997).

(Continued)

*Primary Examiner* — Lynn A Bristol
(74) *Attorney, Agent, or Firm* — Xinsong Xu

(57) ABSTRACT

The present disclosure provides anti-BTC antibodies, methods of producing said antibodies, pharmaceutical compositions comprising said antibodies, and methods of using said antibodies. The present disclosure also provides multi-specific binding molecules, e.g., bispecific antibodies, comprising a BTC binding moiety and an anti-VEGF binding moiety.

20 Claims, 37 Drawing Sheets

Specification includes a Sequence Listing.

(56) References Cited

OTHER PUBLICATIONS

Dunbar et al., "Structure-function and biological role of betacellulin", The International Journal of Biochemistry & Cell Biology, 32, pp. 805-815 (2000).
Ferrara et al., "The Biology of Vascular Endothelial Growth Factor", Endocrine Reviews, 18;1, pp. 4-25-, (1997).
Funatsu et al., "Association of Vitreous Inflammatory Factors with Diabetic Macular Edema", Ophthalmology, 116;1, pp. 73-79, (2009).
Houck et al., "The Vascular Endothelial Growth Factor Family: Identification of a Fourth Molecular Species and Characterization of Alternative Splicing of RNA", Molecular Endocrinology, pp. 1806-1814, (1991).
Jackson et al., "Defective valvulogenesis in HB-EGF and TACE-null mice is associated with aberrant BMP signaling", The EMBO Journal, 22;11, pp. 2704-2716, (2003).
Jemal et al., "Global Cancer Statistics", CA Cancer J Clin, 61, pp. 69-90 (2011).
Jin et al., "Serum Levels Of Vascular Endothelial Growth Factor Before And After Intravitreal Injection Of Ranibizumab Or Conbercept For Neovascular Agerelated Macular Degeneration", Retina The Journal Of Retinal And Vitreous Diseases, 37, pp. 971-977, (2017).
Leung et al., "Vascular Endothelial Growl Angiogenic Mitogen", Science, 246, pp. 1306-1309, (1989).
Paul Mitchell, "A systematic review of the efficacy and safety outcomes of anti-VEGF agents used for treating neovascular age-related macular degeneration: comparison of ranibizumab and bevacizumab", Current Medical Research and Opinion, 27:7, pp. 1465-1475, (2011).
Miyagawa et al., "Immunohisto chemical Localization of Betacellulin, a New Member of the EGF Family, in Normal Human Pancreas and Islet Tumor Cells", Endocrine Journal, 46;6, pp. 755-764, (1999).
Moon et al., "Expression of betacellulin and epidermal growth factor receptor in hepatocellular carcinoma: implications for angiogenesis", Human Pathology, 37, pp. 1324-1332, (2006).
Nguyen et al., "Ranibizumab for Diabetic Macular Edema—Results from 2 Phase III Randomized Trials: RISE and RIDE", Ophthalmology, 119;4, pp. 789-800, (2012).
Nielsen et al., "Expression of the EGF Family in Gastric Cancer:Downregulation of HER4 and Its Activating Ligand NRG4", PLoS ONE, 9;4, pp. 1-9, (2014).
O-Charoenrat et al., "Epidermal Growth Factor-like Ligands Differentially Up-Regulate Matrix Metalloproteinase 9 in Head and Neck Squamous Carcinoma Cells", Cancer Research, 60, pp. 1121-1128, (2000).
Orozco et al., "Integration of eQTL and a Single-Cell Atlas in the Human Eye Identifies Causal Genes for Age-Related Macular Degeneration", Cell Reports, 30, pp. 1246-1259, (2020).
Poulaki et al., Acute intensive insulin therapy exacerbates diabetic blood-retinal barrier breakdown via hypoxia-inducible factor-1a and VEGF, The Journal of Clinical Investigation, 109, pp. 805-815, (2002).
Rezende et al., "Omega-3 Supplementation Combined With Anti-Vascular Endothelial Growth Factor Lowers Vitreal Levels of Vascular Endothelial Growth Factor in Wet Age-Related Macular Degeneration", Am J Ophthalmol., 158;5, pp. 1071-1078, (2014).
Sahin et al., "Distinct roles for ADAM10 and ADAM17 in ectodomain shedding of six EGFR ligands", The Journal of Cell Biology, 164, pp. 769-779, (2004).
Sahin et al., "Ectodomain shedding of the EGF-receptor ligand epigen is mediated by ADAM17", FEBS, 581, pp. 41-44, (2007).
Samuels et al., "Early retinal pigment epithelium dysfunction is concomitant with hyperglycemia in mouse models of type 1 and type 2 diabetes", J Neurophysiol, 113, pp. 1085-1099, (2015).
Sanderson et al., "ADAM10 Mediates Ectodomain Shedding of the Betacellulin Precursor Activated by p-Aminophenylmercuric Acetate and Extracellular Calcium Influx", The Journal of Biological Chemistry, 280; 3, pp. 1826-1837, (2005).
Sasada et al., "Cloning and Expression of cDNA encoding Human betacellulin, A New Member of the EGF family", Biochemical and Biophysical Research Communications, 190;3, pp. 1173-1179, (1993).
Schwartz et al., "Intravitreal Corticosteroids in the Management of Diabetic Macular Edema", Curr Ophthalmol Rep., 1;3, pp. 1-10, (2013).
Seno et al., "Human Betacellulin, a Member of the EGF Family Dominantly Expressed in Pancreas and Small Intestine, is Fully Active in a Monomeric Form", Growth Factors, 13:3-4, pp. 181-191, (1996), published online 2009.
Shimada et al., Concentration Gradient of Vascular Endothelial Growth Factor in the Vitreous of Eyes with Diabetic Macular Edema, IOVS, 50;6, pp. 2953-2955, (2009).
Shing et al., Betacellulin: A Mitogen from Pancreatic P3 Cell Tumors, Science, 259, pp. 1604-1607, (1993).
Srinivasan et al., "Expression of the c-erbB-3/HER-3 and c-erbB-4/HER-4 Growth Factor Receptors and Their Ligands, Neuregulin-1 a, Neuregulin-1 b, and Betacellulin, in Normal Endometrium and Endometrial Cancer", Clinical Cancer Research, 5, pp. 2877-2883, (1999).
Sugimoto et al., "Inhibition of EGF Signaling Protects the Diabetic Retina from Insulin-Induced Vascular Leakage", The American Journal of Pathology, 183;3, pp. 987-995, (2013).
Wang et al., "Vitreous and Plasma VEGF Levels as Predictive Factors in the Progression of Proliferative Diabetic Retinopathy after Vitrectomy", PLoS ONE, 9;10, pp. 1-8, (2014).
Xia et al., "Effects of diabetic retinopathy on the barrier functions of the retinal pigment epithelium", Vision Research, 139, pp. 72-81, (2017).
Xu et al., "Significance of Outer Blood-Retina Barrier Breakdown in Diabetes and Ischemia", IOVS, 52;5, pp. 2160-2164, (2011).
Yokoyama et al., "Betacellulin, a member of the epidermal growth factor family, is overexpressed in human pancreatic cancer", International Journal of Oncology, 7, pp. 825-829, (1995).

\* cited by examiner

FIG. 2A-2D
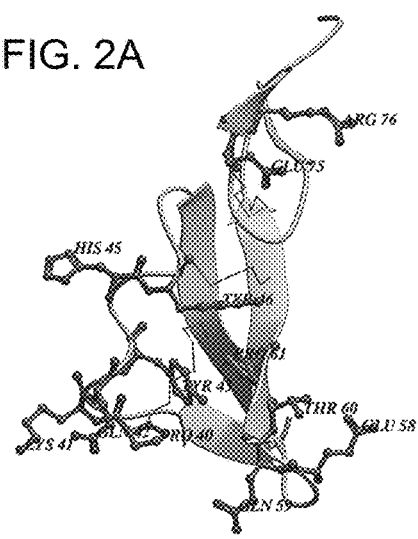
FIG. 2A
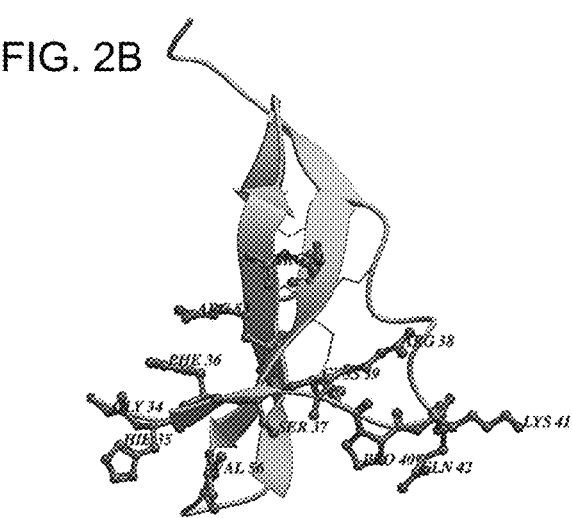
FIG. 2B
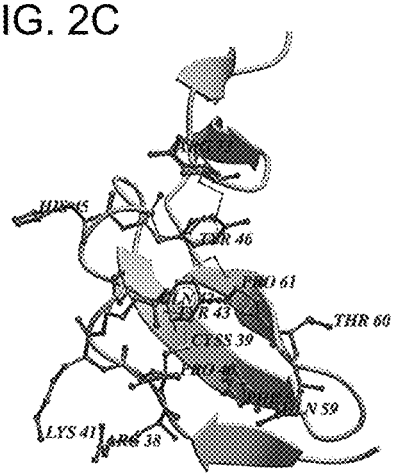
FIG. 2C
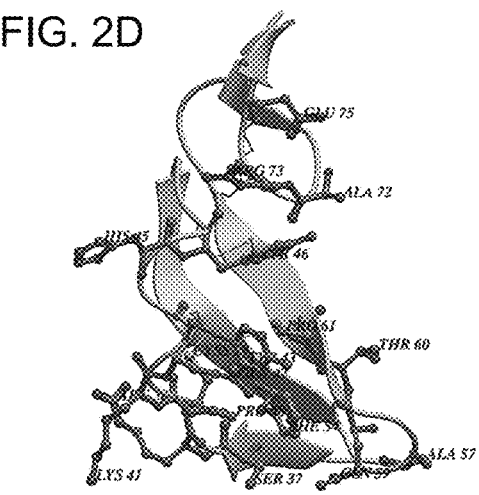
FIG. 2D

FIG. 6A-6B
FIG. 6A.
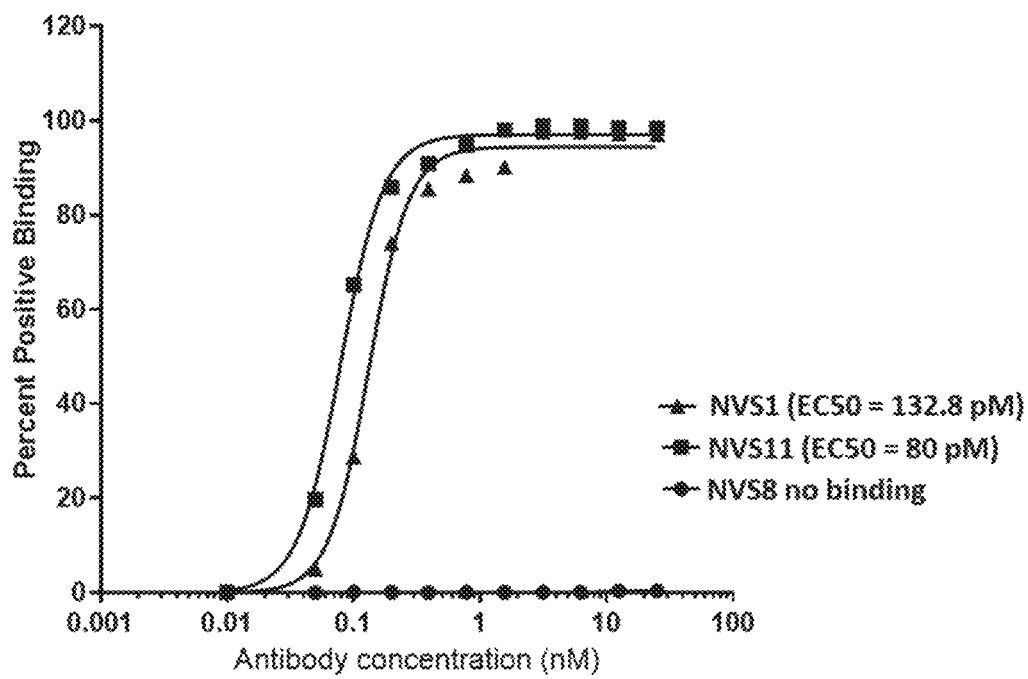
FIG. 6B.
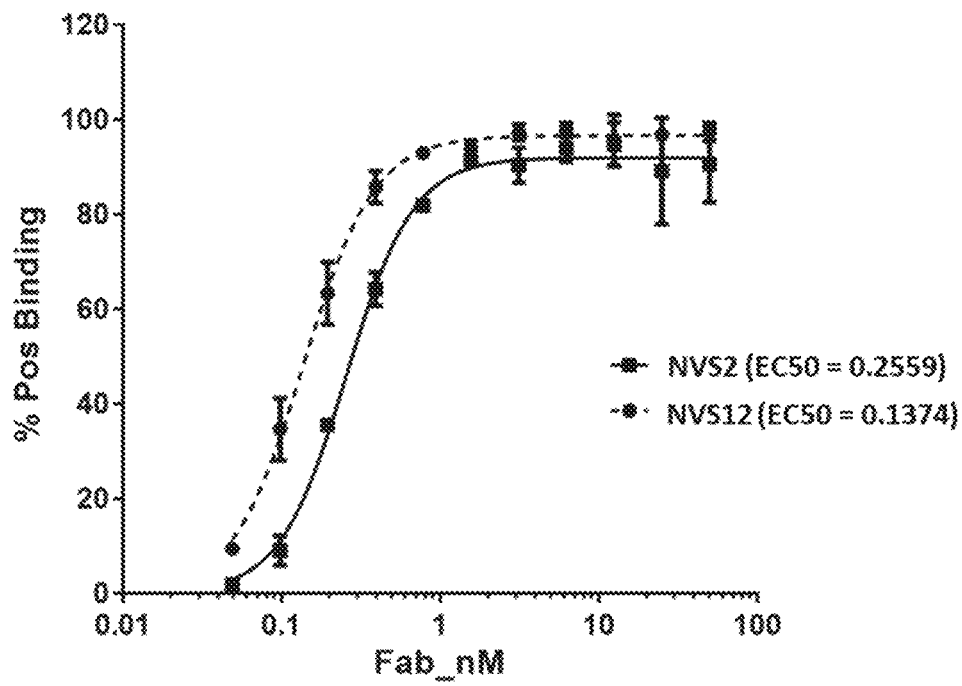

FIG. 6C-6D
FIG. 6C.
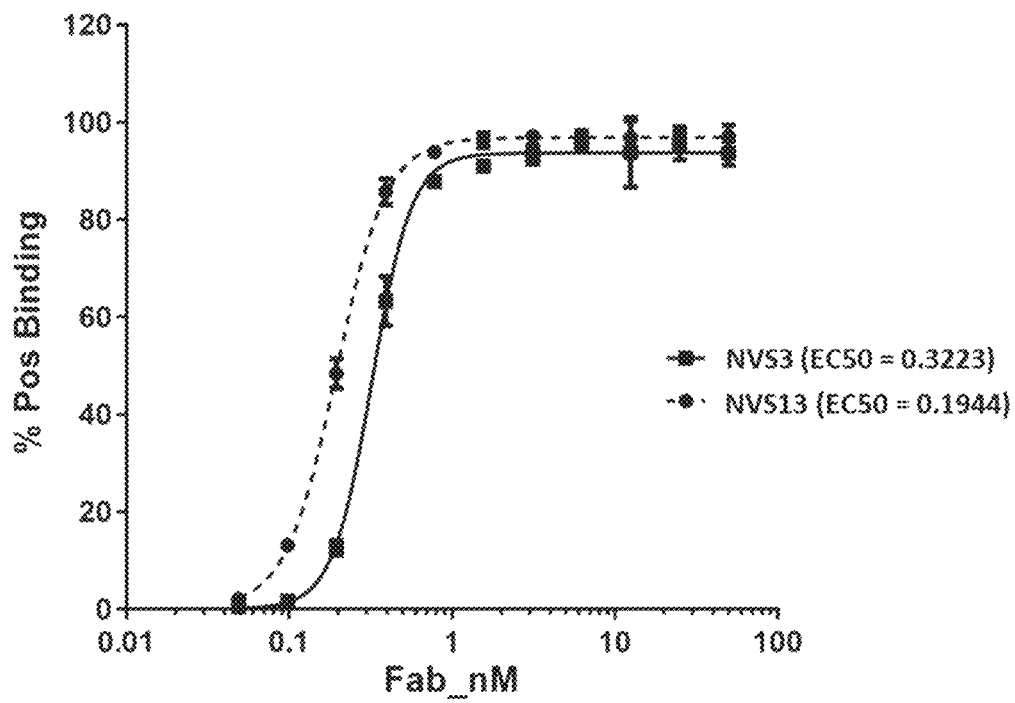
FIG. 6D.
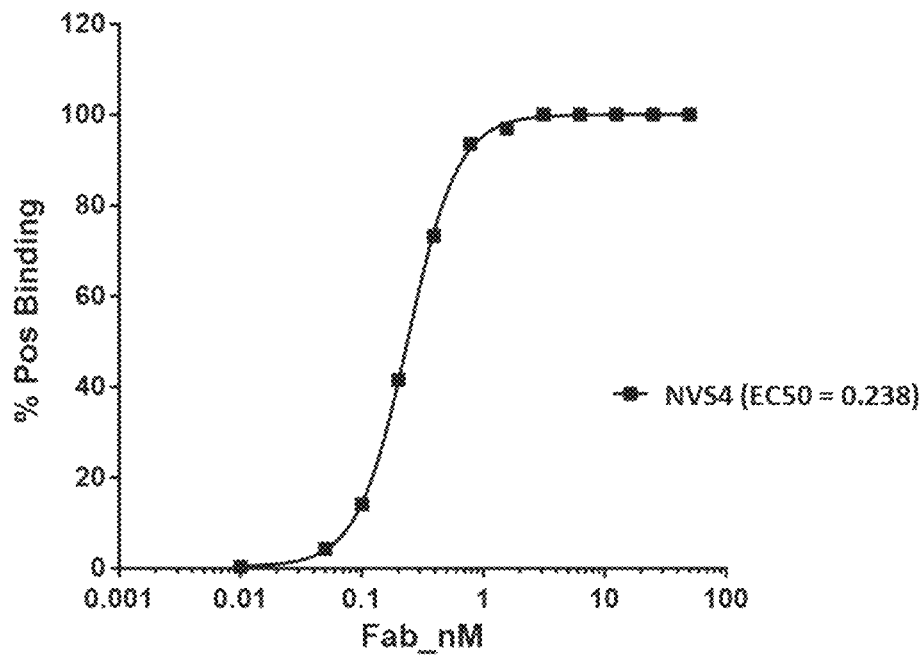

FIG. 6E-6F
FIG. 6E
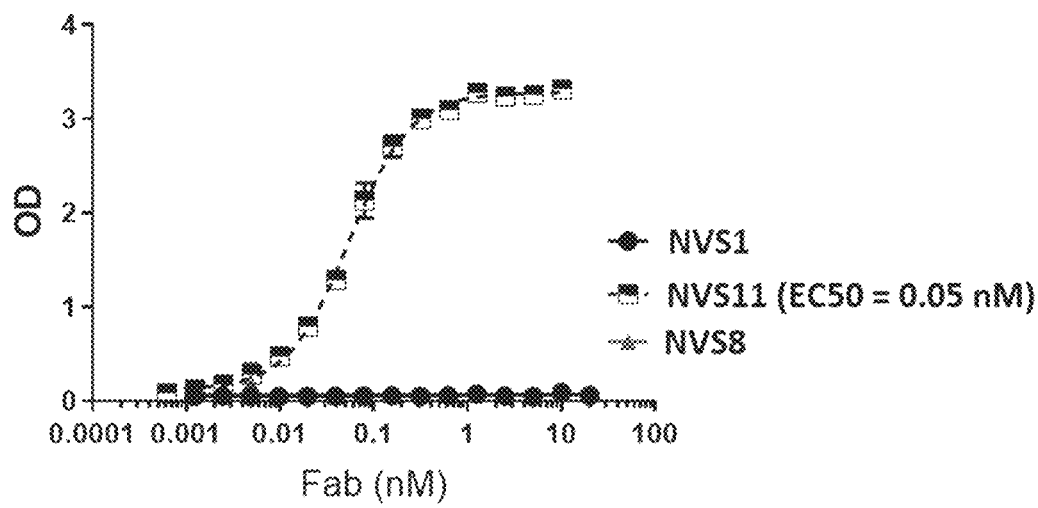
FIG. 6F
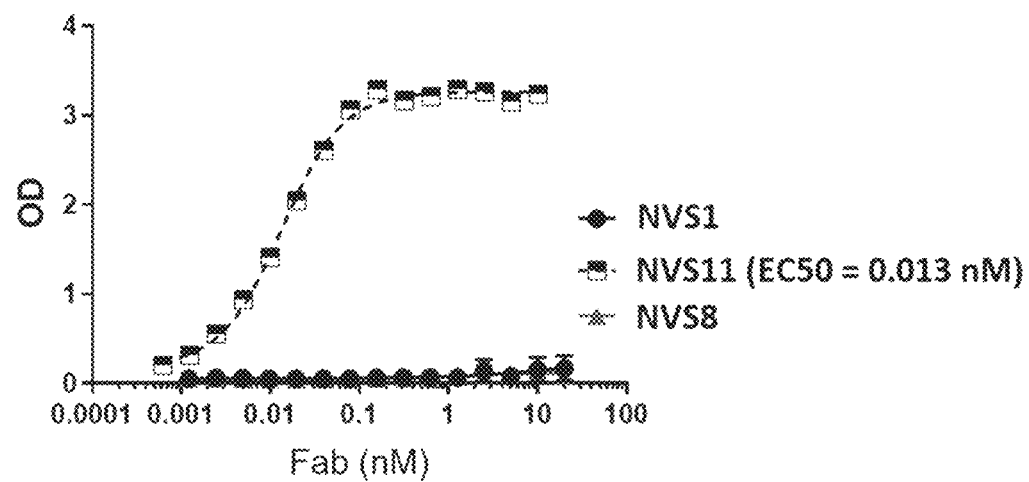

FIG. 7A-7B
FIG. 7A.
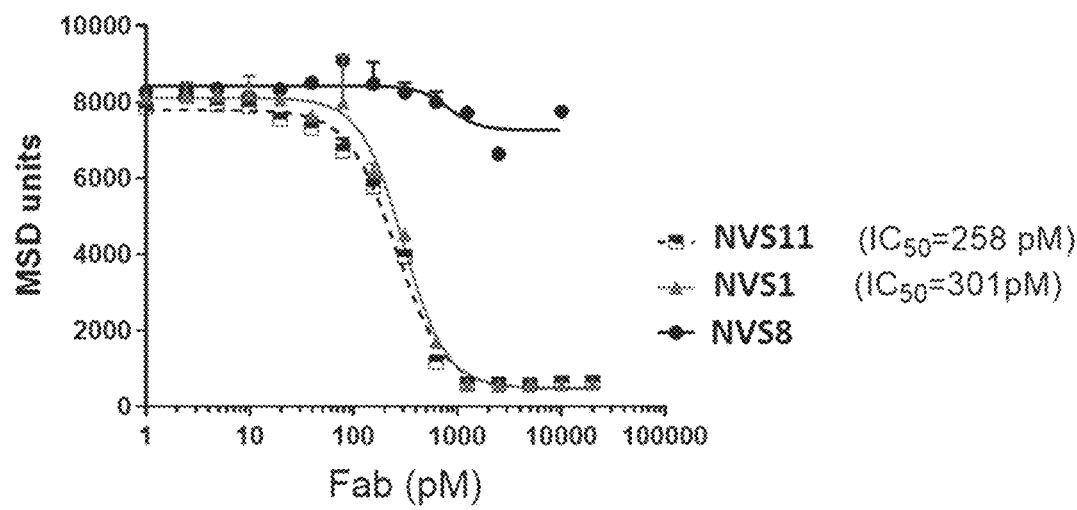
FIG. 7B.
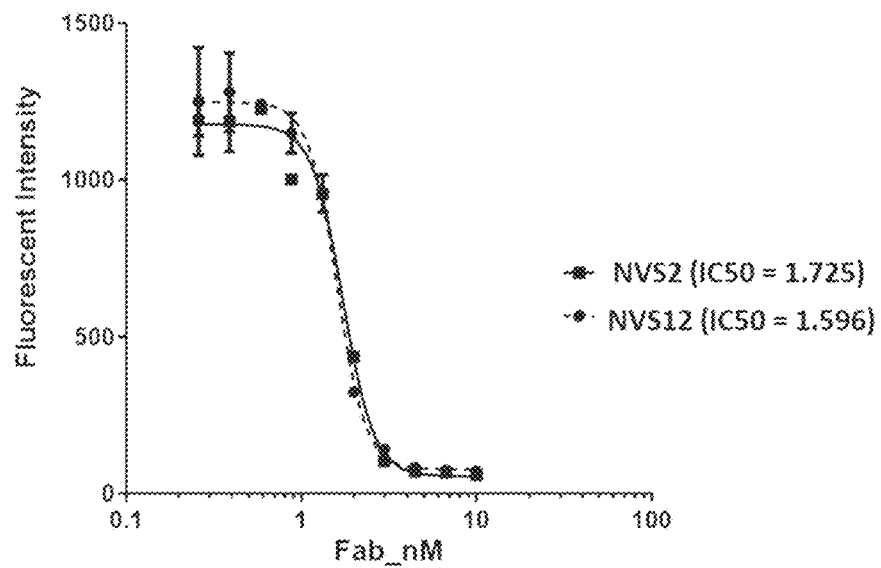

FIG. 7C-7D
FIG. 7C.
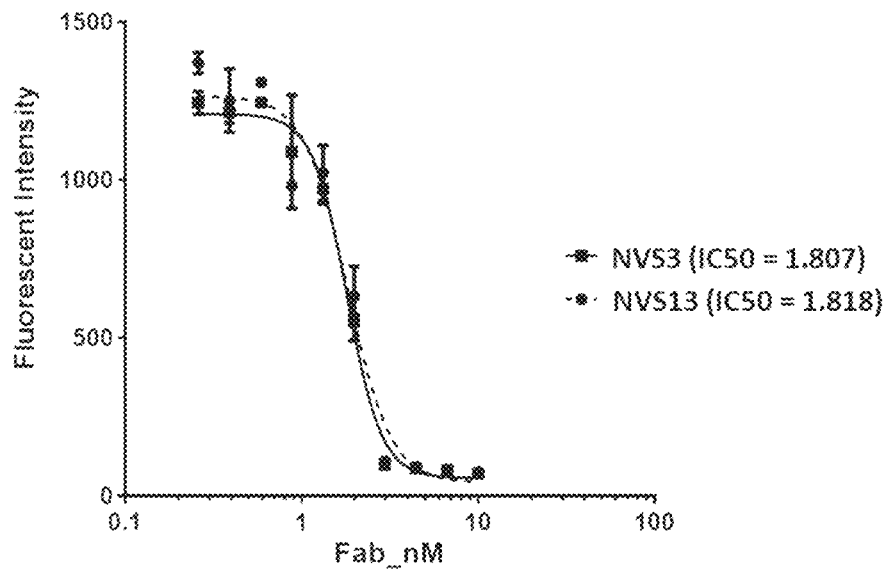
FIG. 7D.
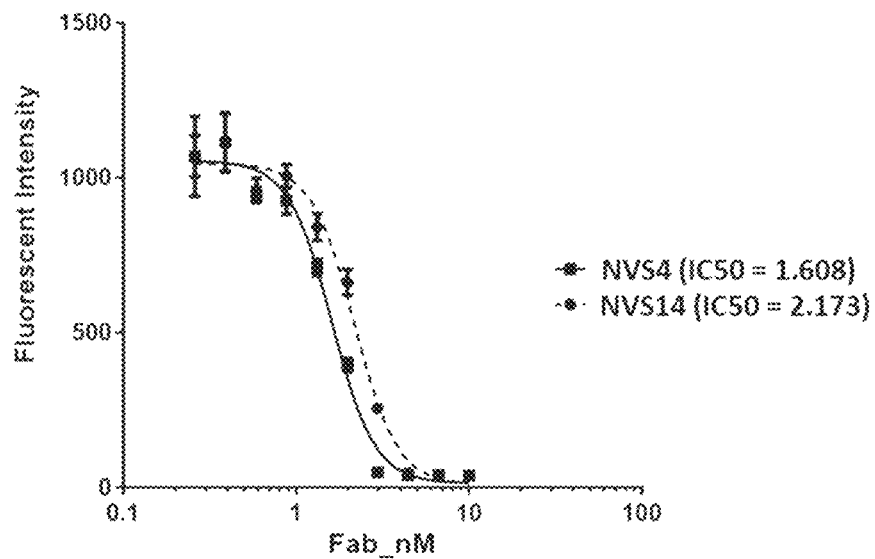

FIG. 8A-8B
FIG. 8A.
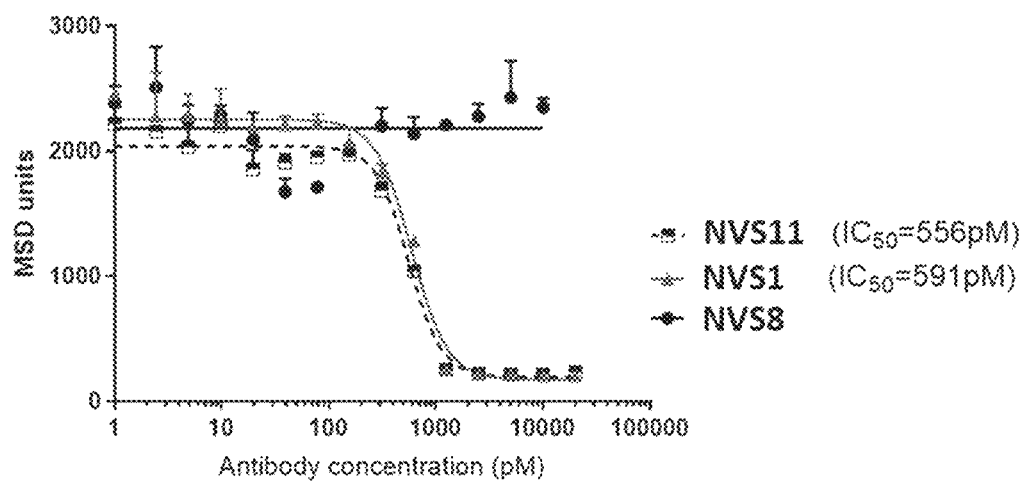
FIG. 8B.
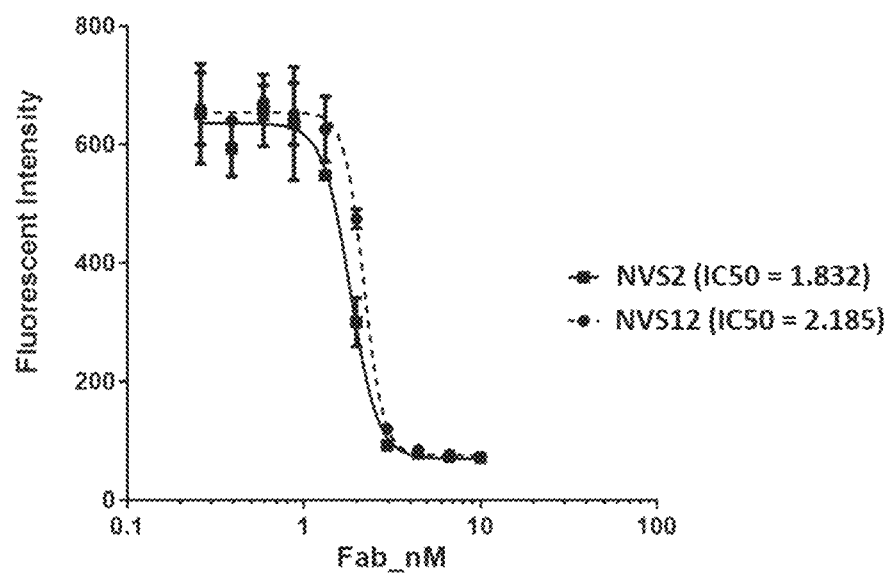

FIG. 8C-8D
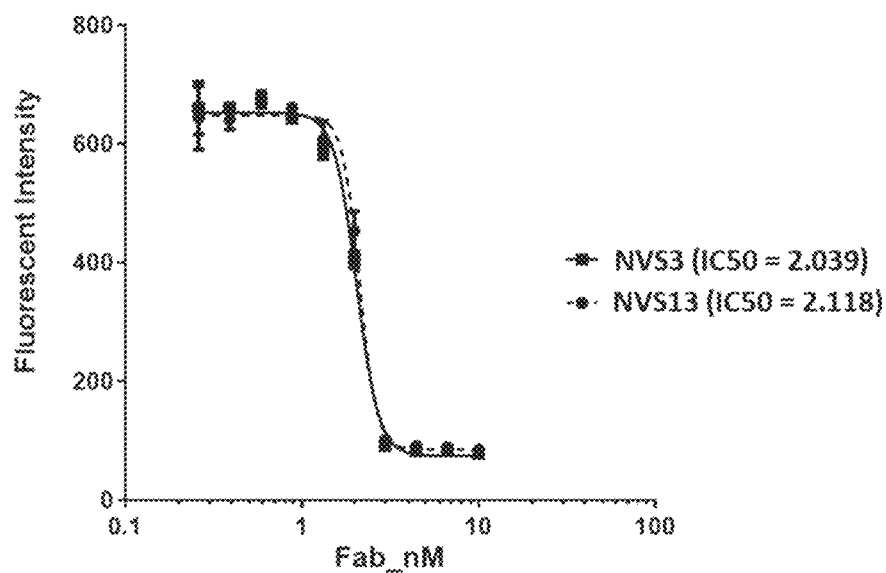
FIG. 8C.
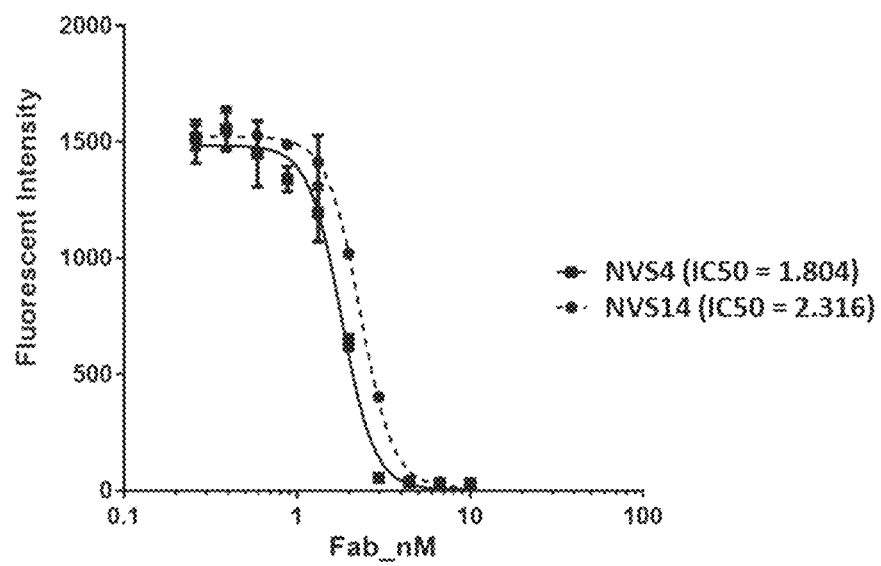
FIG. 8D.

FIG. 8E-8F
FIG. 8E.
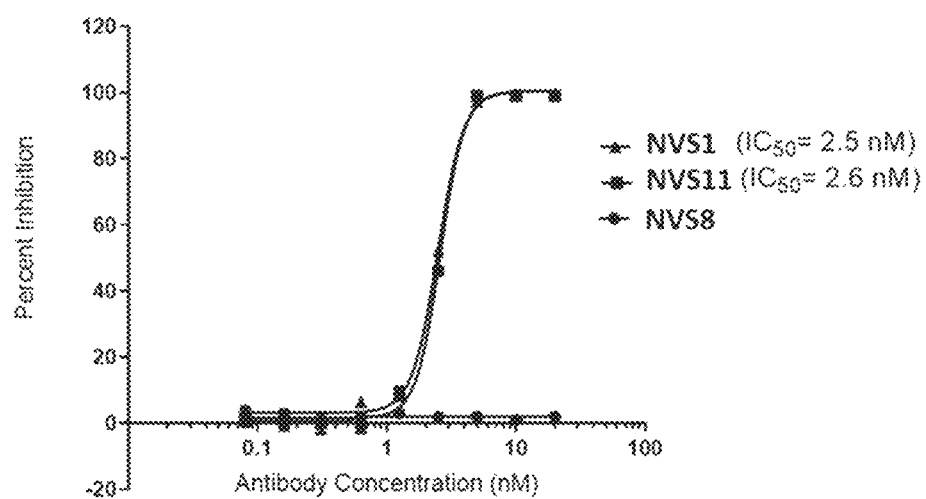
FIG. 8F.
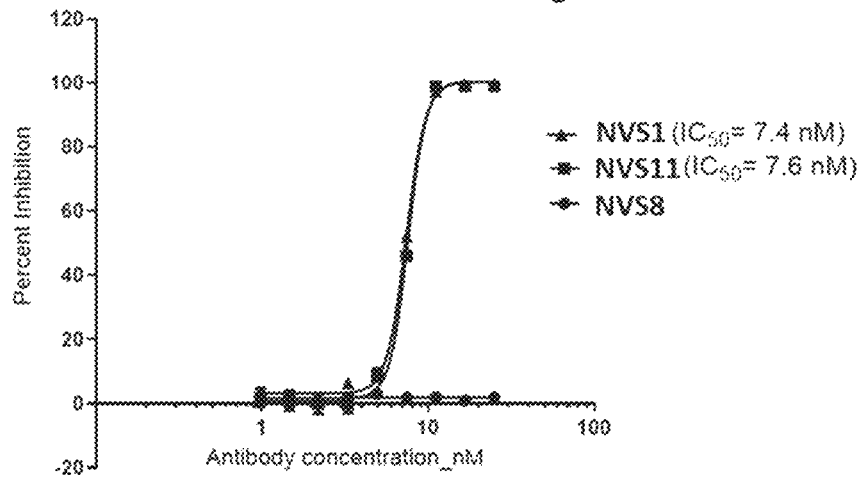

FIG. 9A-9B
FIG. 9A.
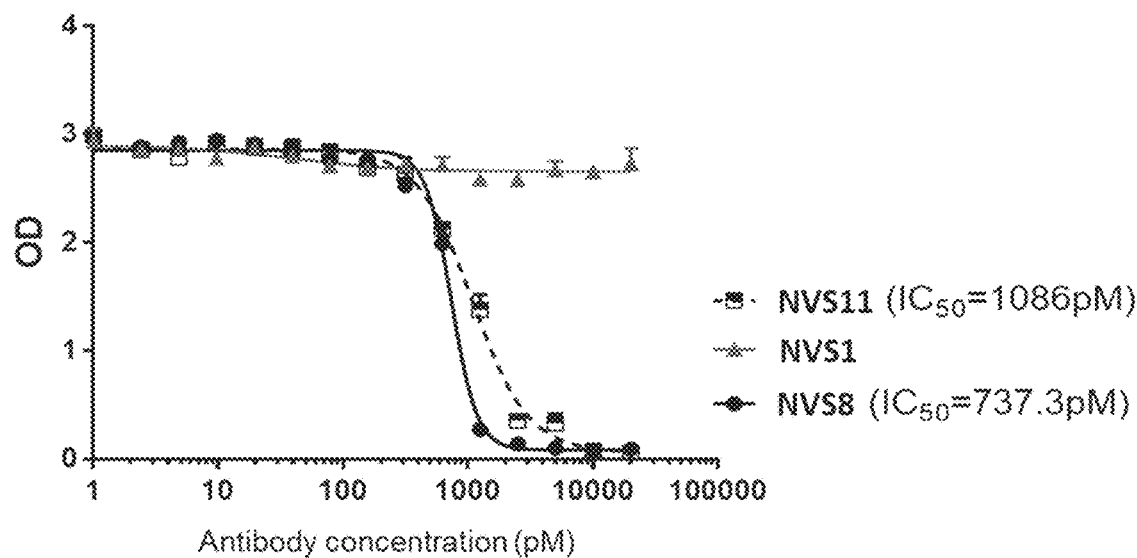
FIG. 9B.
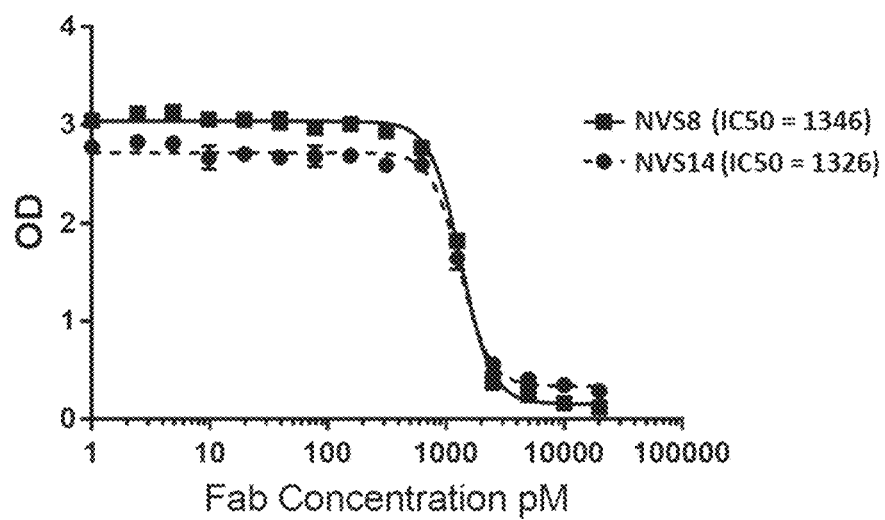

FIG. 10A-10B.
FIG. 10A.
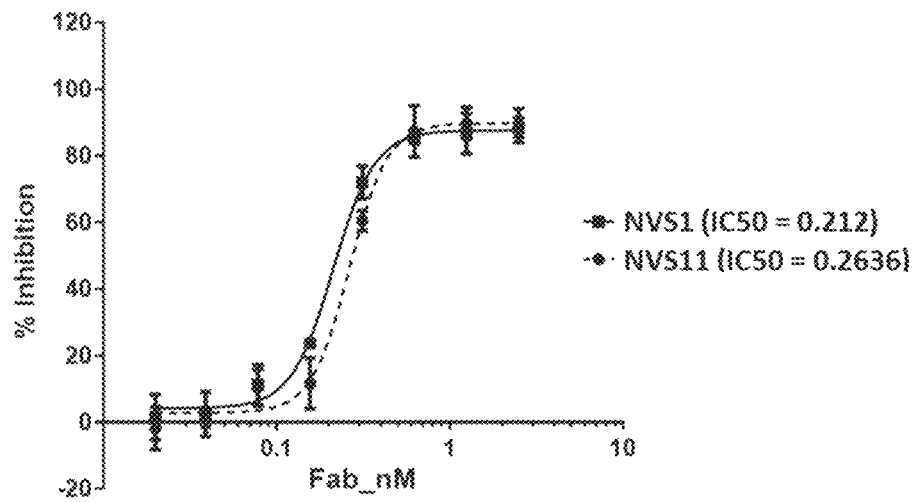
FIG. 10B.
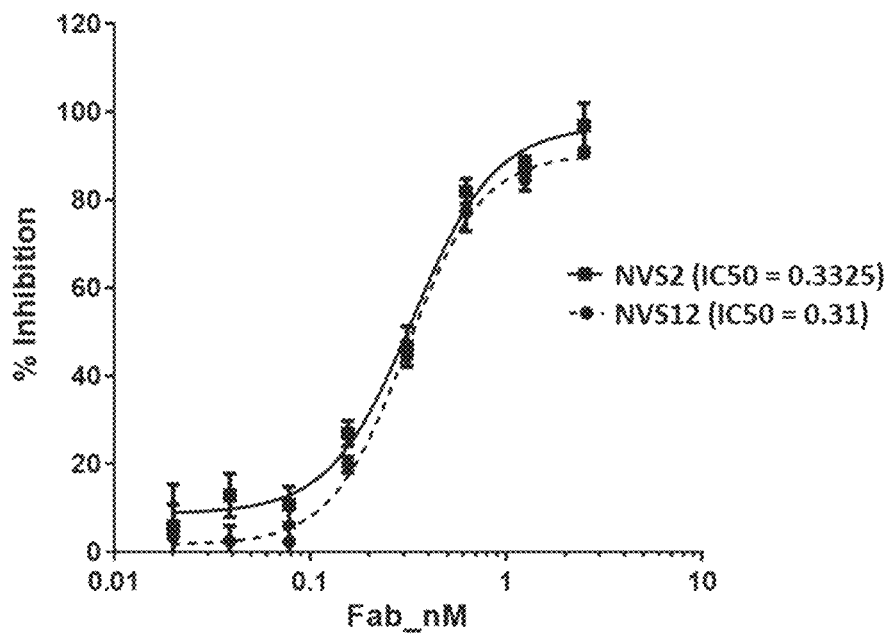

FIG. 10C-10D
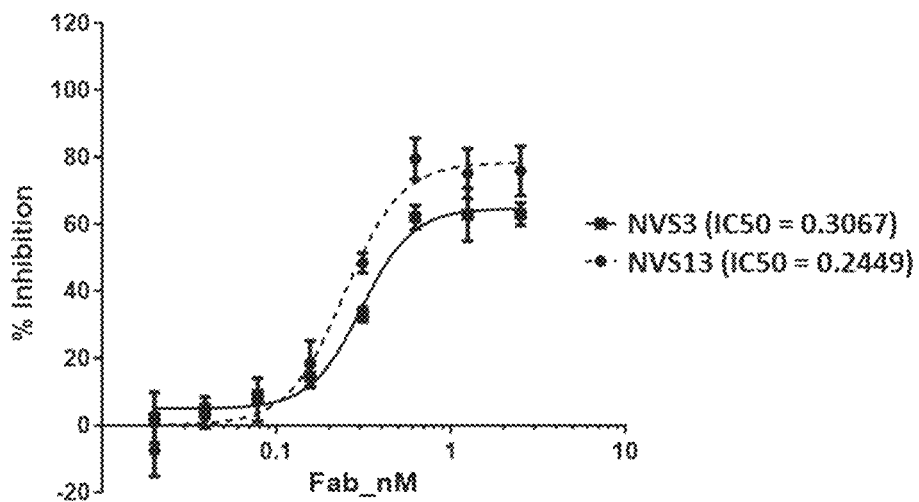
FIG. 10C.
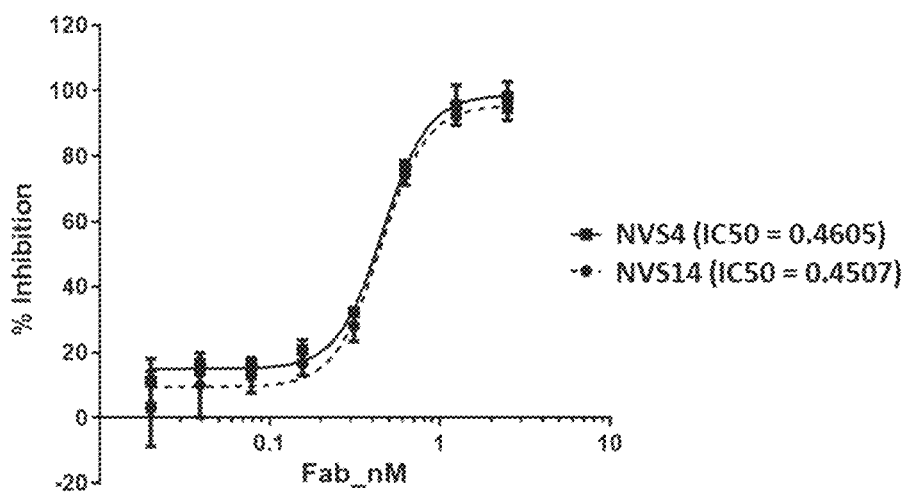
FIG. 10D.

FIG. 11A-11B
FIG. 11A.
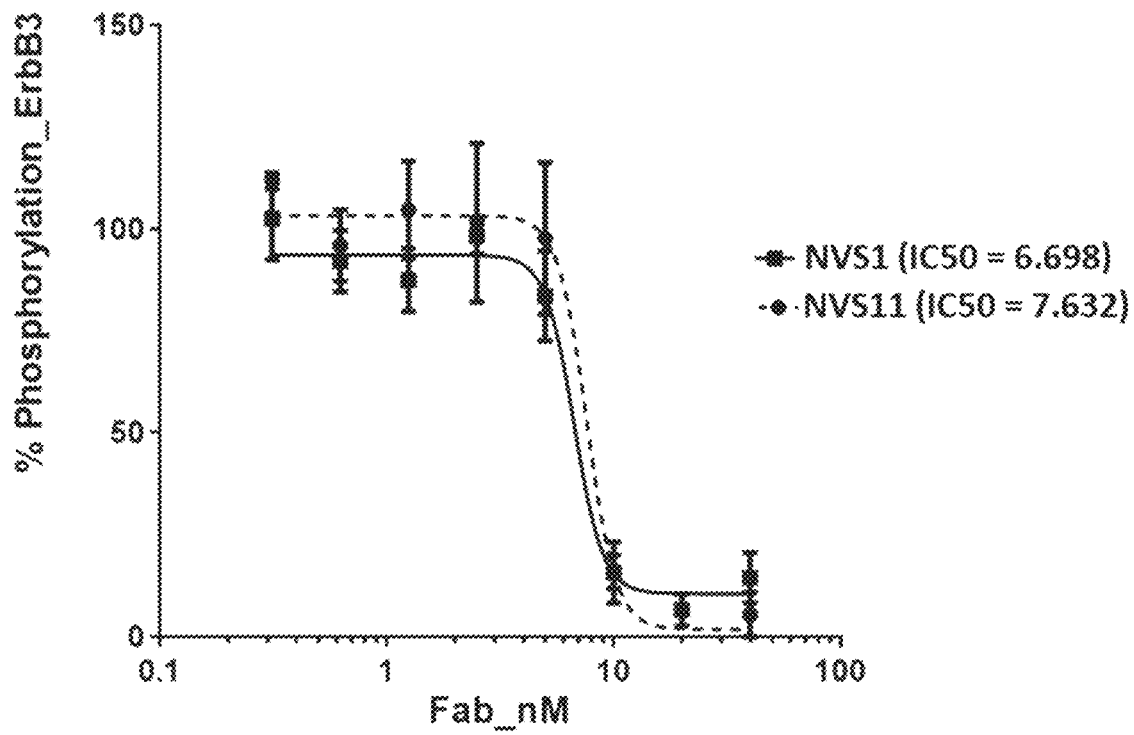
FIG. 11B.
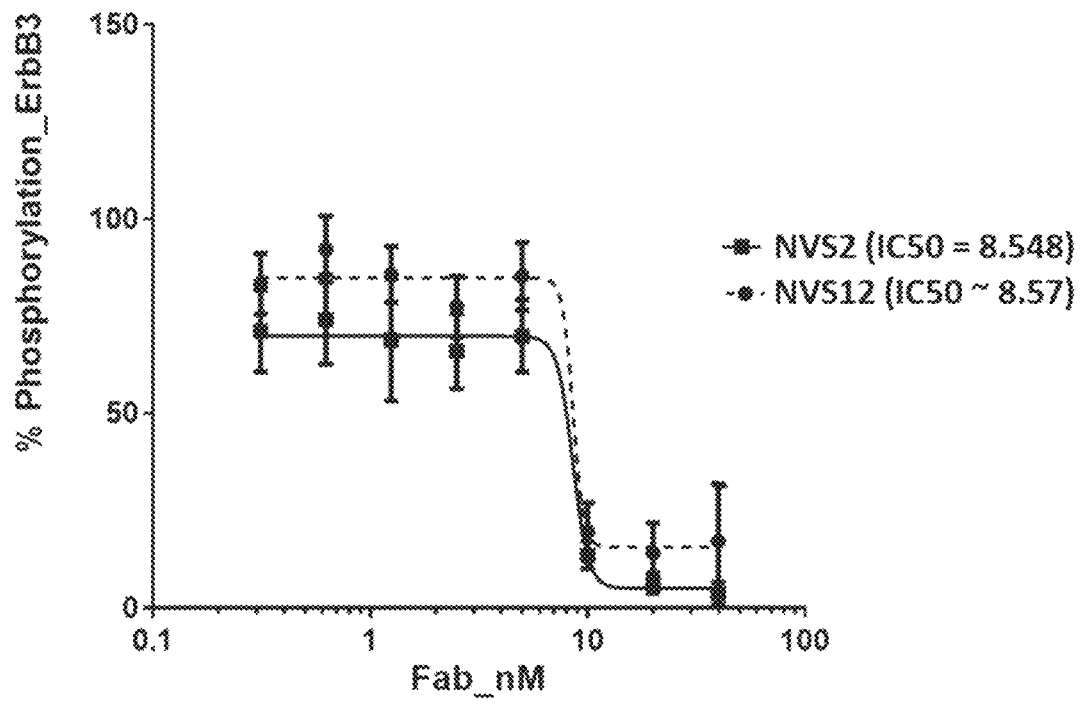

FIG. 11C-11D
FIG. 11C.
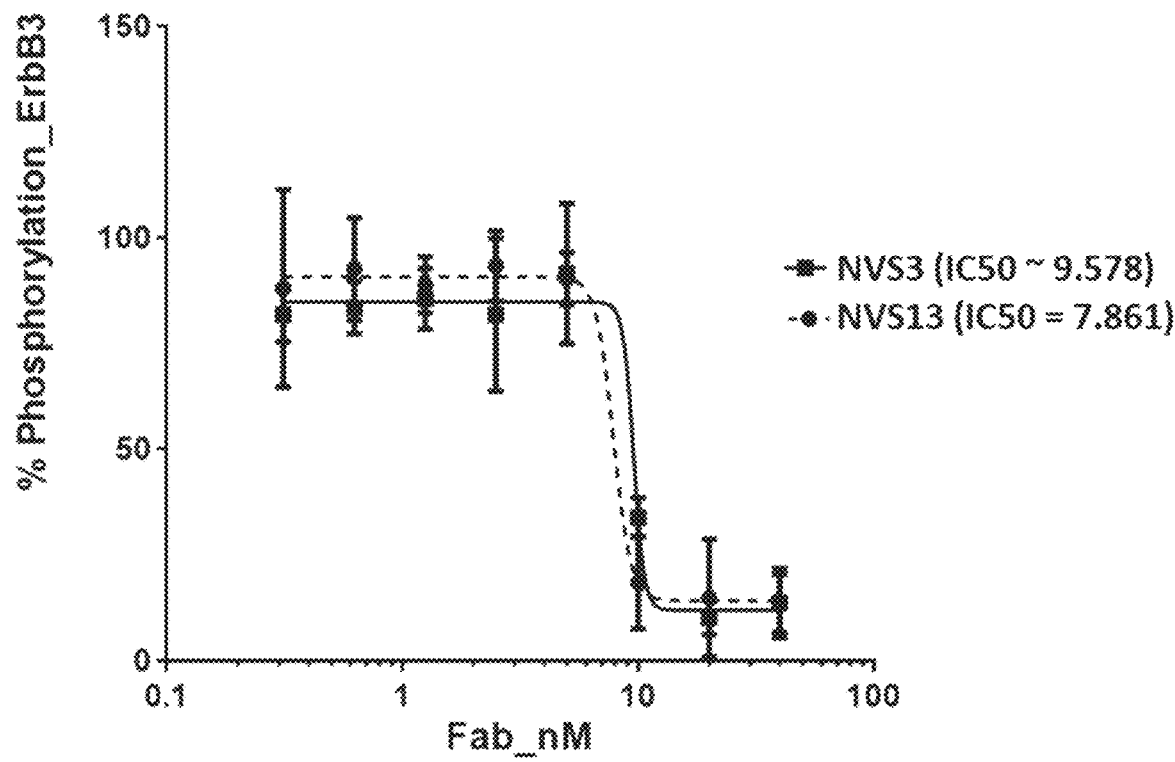
FIG. 11D.
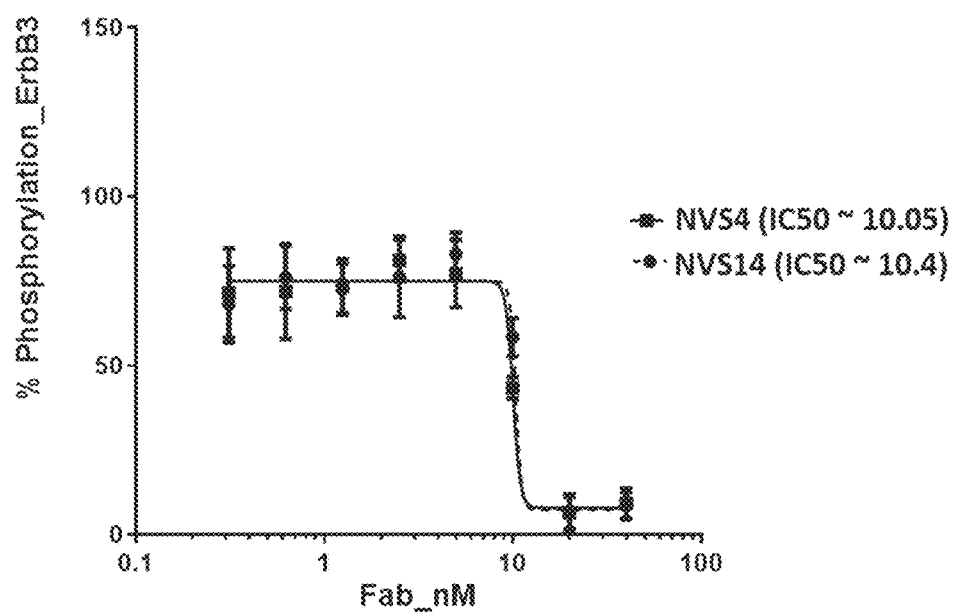

FIG. 12A-12B.
FIG. 12A.
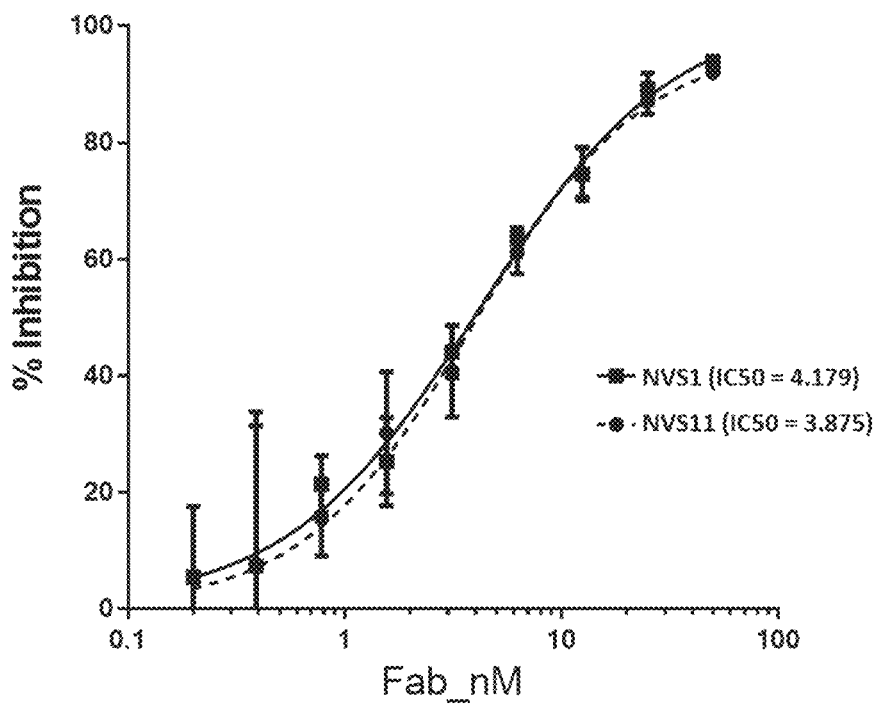
FIG. 12B.
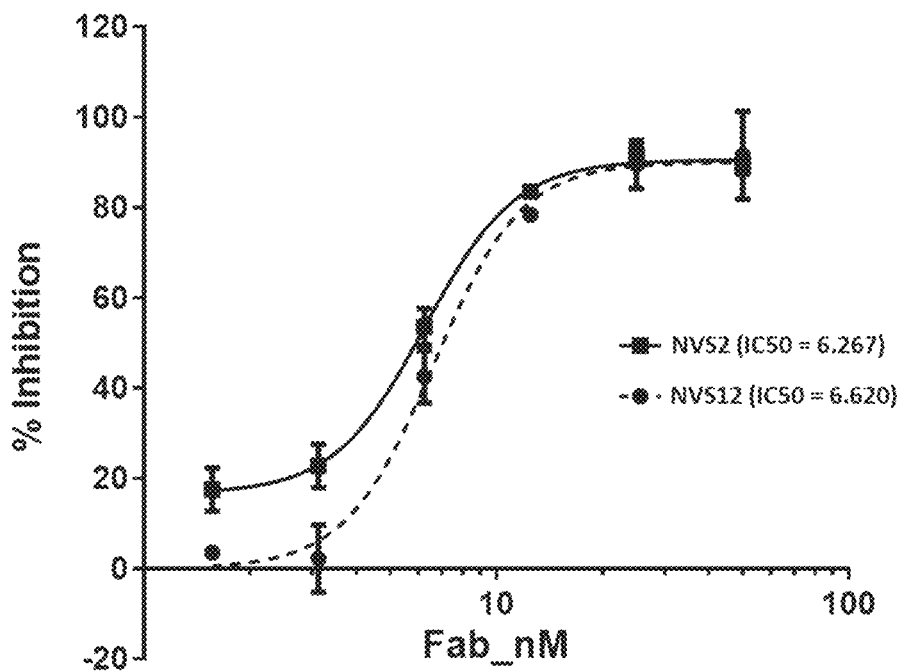

FIG. 12C-12D
FIG. 12C.
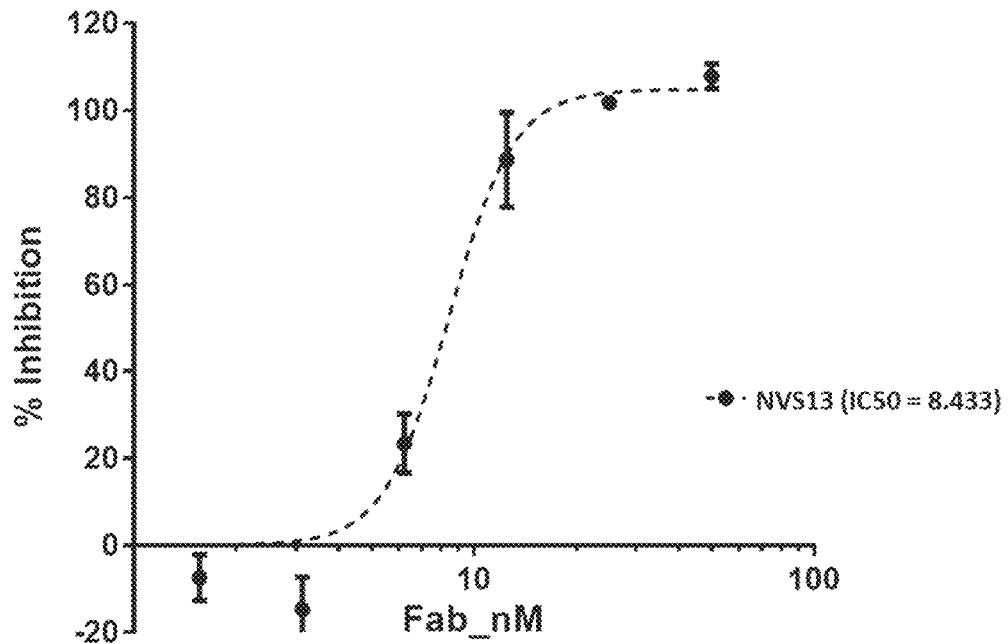
FIG. 12D.
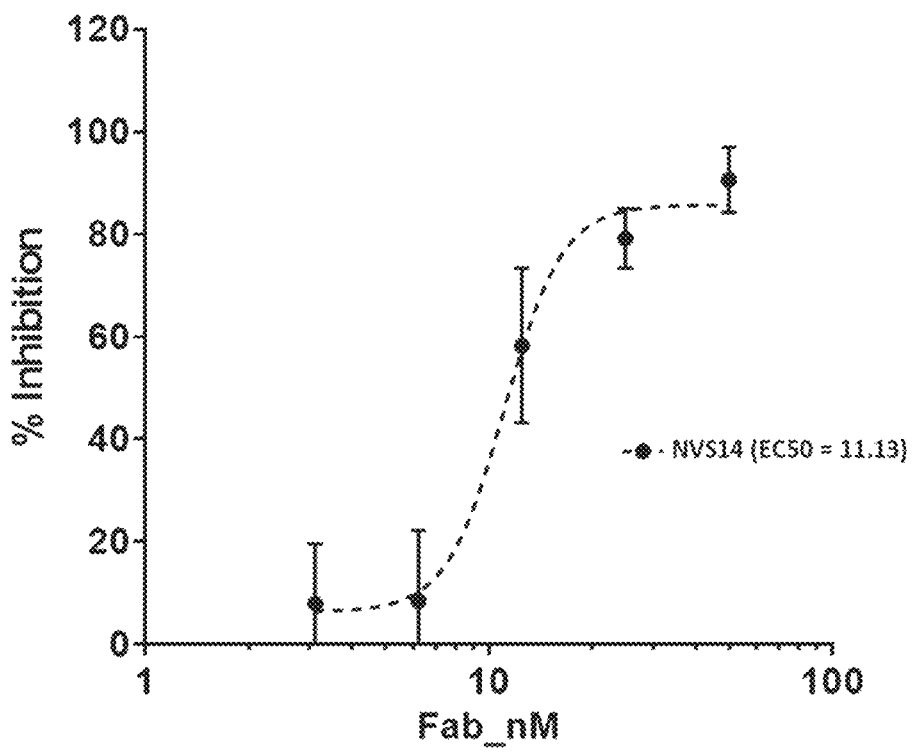

FIG. 13A-13B
FIG. 13A.
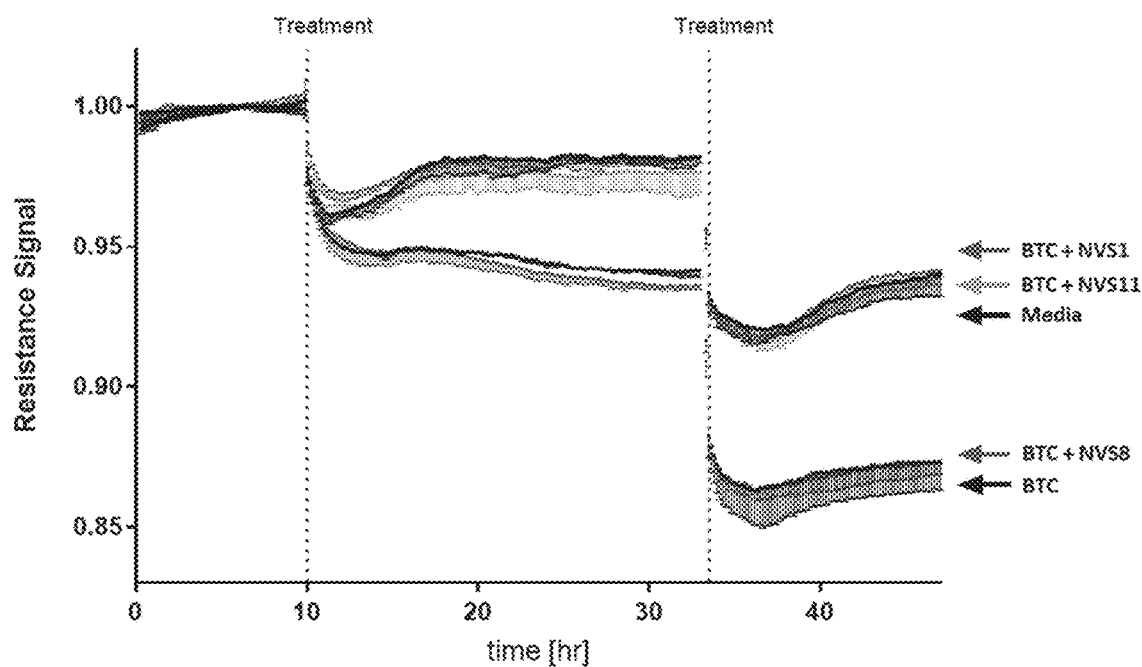
FIG. 13B.
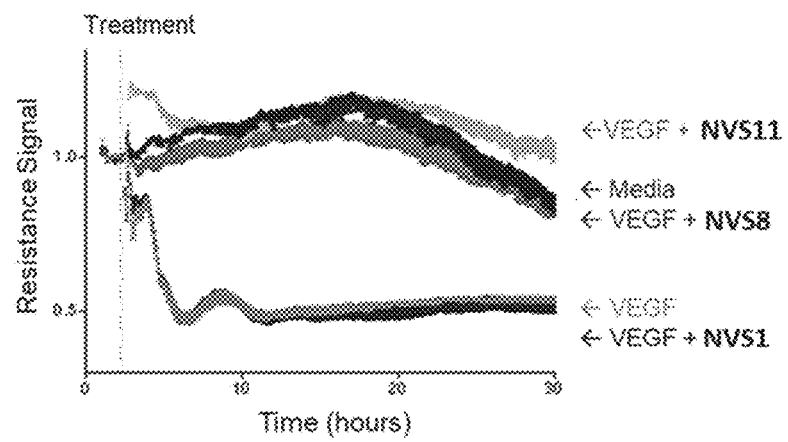

FIG. 18B-18C
FIG. 18B.
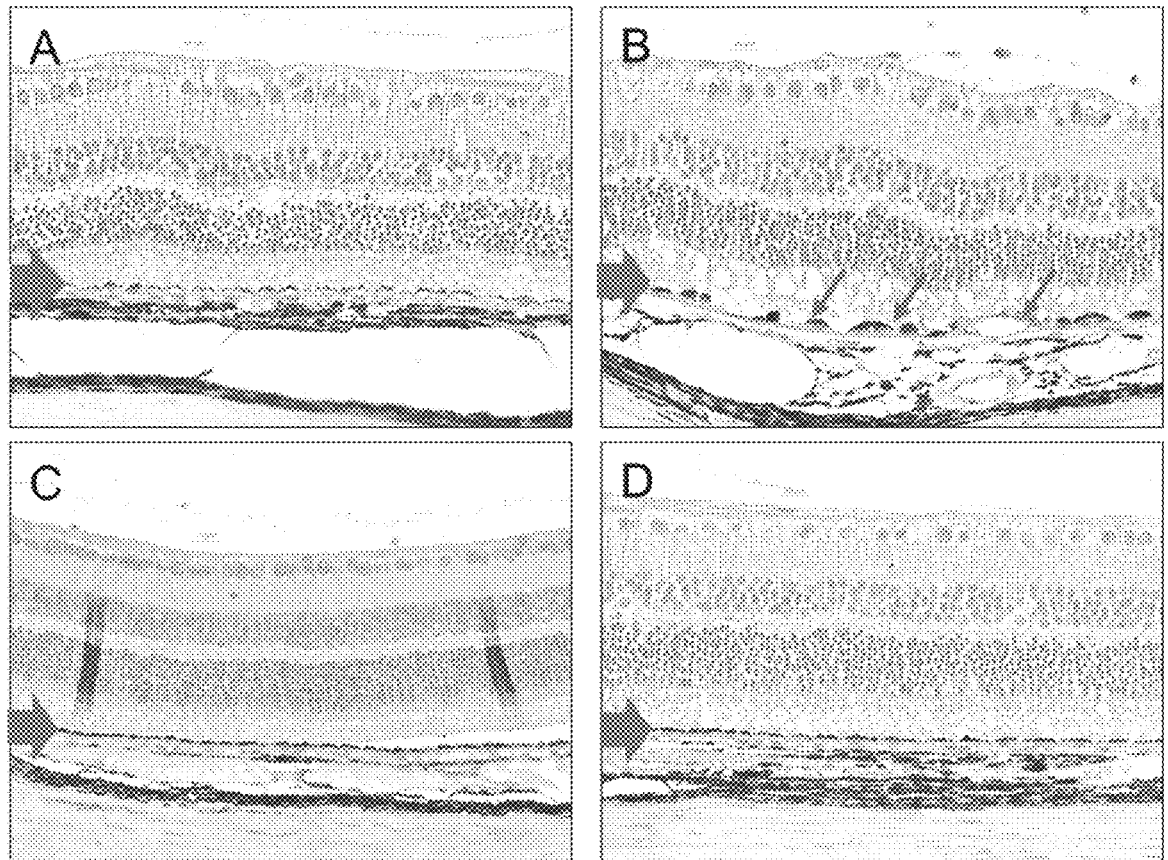
FIG. 18C.
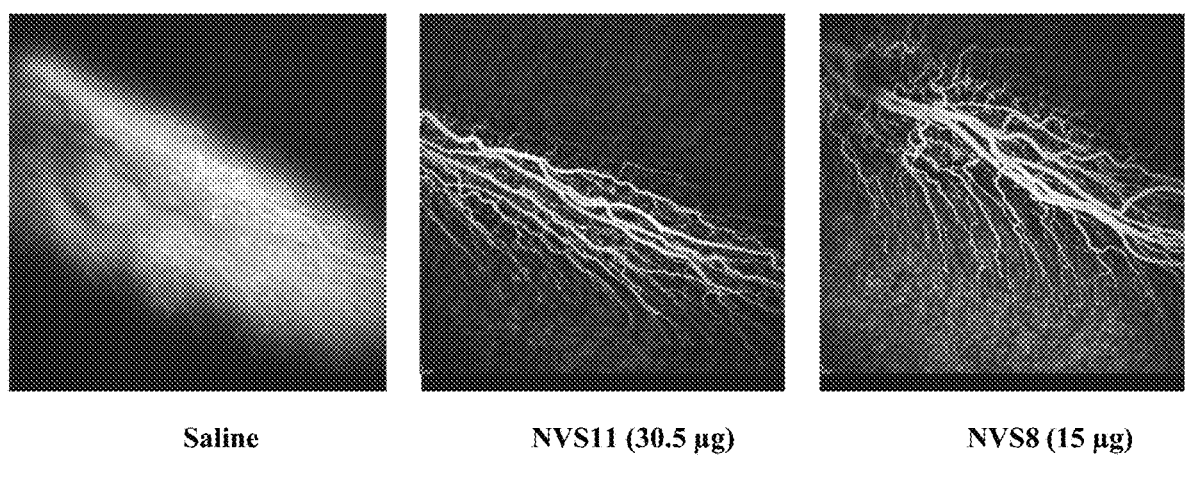
Saline          NVS11 (30.5 µg)          NVS8 (15 µg)

ANTI-BETACELLULIN ANTIBODIES, FRAGMENTS THEREOF, AND MULTI-SPECIFIC BINDING MOLECULES

CROSS-REFERENCE TO RELATED APPLICATION AND INCORPORATION OF SEQUENCE LISTING

This application claims priority to U.S. Provisional Patent Appln. No. 63/052,789 filed Jul. 16, 2020, and U.S. Provisional Patent Appln. No. 63/156,709 filed Mar. 4, 2021, which are incorporated into this application by reference in its entirety. The sequence listing that is contained in the filed named "PAT058888-US-NP SQL_ST25," which is 204,785 bytes (measured in operating system MS-Windows) and was created on Jun. 30, 2021, is filed herewith and incorporated herein by reference.

FIELD

The present invention relates to antibodies or antigen binding fragments thereof, methods of producing the same, pharmaceutical compositions comprising the same, and methods of using the same.

BACKGROUND

Betacellulin (BTC), a member of the epidermal growth factor (EGF) family, was originally isolated from the conditioned medium of a mouse pancreatic B-tumor cell line (Shing et al., Science, 259, 1604-1607, 1993). BTC is a ligand for the ErbB receptor tyrosine kinase family and mainly activates ErbB1 and ErbB4 homodimers triggering anti-apoptotic and pro-proliferative signaling pathway like the Ras/MAPK and the PL3K/AKT pathways.

BTC is initially expressed as a single-pass trans-membrane protein, and is subsequently cleaved (activated) into a 9 kDa secreted protein by members of the MMP family. Cleavage of the membrane-anchored forms of BTC to release a secreted form occurs principally by ADAM-10 (a disintegrin and metalloprotease-10) (Sahin et al., *J. CellBiol.* 164, 769-779, 2004; Sahin and Blobel, FEBS Lett 581, 41-44, 2007; and Sanderson et al., *J. Biol. Chem.* 280, 1826-1837, 2005). Mature, secreted human BTC is a 32-kDa glycoprotein composed of 80 amino acid residues (Asp1-Tyr80, residues 32 to 111 of the 178 residue, membrane-anchored precursor protein (pro-BTC) described as NP_001720.1 or SEQ ID NO: 156) generated by cleavage of the pro-BTC. The carboxyl terminus 50-residue region of BTC (Arg31-Tyr80) contains a conserved consensus sequence of the EGF family of proteins.

Strong BTC mRNA expression has been detected in a number of tissues including pancreas, liver, kidney, and small intestine in addition to somewhat lower expression in heart, lung, liver, skeletal muscle, kidney, prostate, testis, ovary, and colon (Sasada *et al., Biochem. Biophys. Res. Commun.* 190, 1173-1179, 1993; Sasada and Igarashi, *Nihon. Rinsho.* 51, 3308-3317, 1993; and Seno *et al., Growth Factors* 13, 181-191, 1996). BTC knock-out mice are viable and fertile, displaying no obvious phenotype.

High expression of BTC mRNA suggests that BTC may have a physiological role in the development and function of pancreas. BTC level was found to be elevated by 7.5-fold in 9 out of 10 pancreatic cancers compared to normal pancreas expression levels (*Yokoyama et al.,* 1995). In the pancreas, BTC expression has been localized to islet cell populations closely associated with insulin-producing B-cells (Miyagawa et al., *Endocr. J.* 46, 755-764, 1999). BTC can regulate pancreatic islet physiology and can induce the proliferation of fetal pancreatic cells and stimulate the conversion of non-β-cells into β-like insulin-producing cells. Moreover, overexpression of BTC has been reported in endometrial adenocarcinomas (Srinivasan et al., 1999); hepatocellular carcinomas (Moon et al., 2006); head and neck squamous cell carcinomas (O-charoenrat et al., 2000); and gastric carcinomas (Jemal et al., 2011).

In the eye of mammals, BTC protein is synthesized by retinal pigment epithelial (RPE), endothelial and Mueller cells (Anand-Apte et al., *PLoS One* 5, e13444, 2010), and is located in the outer blood retinal barrier.

While the general role of BTC in vascular endothelial functions has been studied, its specific role in the retina is currently unclear. Initial reports of the proliferative effect of BTC on RPE cells (Shing et al., 1993) and its proangiogenic functions suggested that it might play a role in proliferative diabetic retinopathy (PDR). While diabetic mice do not demonstrate PDR, they do show increased retinal vascular permeability (Poulaki et al., *J. Clin. Invest.* 109, 805-815, 2002). In addition, it has been determined that in a mouse model of diabetes, soluble cleaved BTC is increased in the retina and contributes to increased retinal vascular permeability (Anand-Apte et al., 2010).

Subretinal injection of an adeno-associated virus expressing soluble BTC resulted in a dramatic increase of retinal vascular permeability in mice. Overall, BTC appears as a potent permeability factor that could play a critical role in the development of increased retinal vascular permeability in diabetic retinopathy and be a potential therapeutic target in this disease.

Vascular endothelial growth factor (VEGF) has been shown to be a key mediator of neovascularization associated with tumors and intraocular disorders. VEGF is a potent vasopermeability factor and is essential in causing vascular leakage. In the eye of mammals, VEGF is located in the inner blood retinal barrier. VEGF levels are significantly elevated in vitreous of patients with diabetic macular edema (DME) when compared with non-diabetic eye conditions (Funatsu et al., *Ophthalmology* 2009 116:73-9).

Multiple anti-VEGF drugs are being used to treat ophthalmic disorders such as age-related macular degeneration (AMD) and/or DME, including pegaptanib (anti-VEGF aptamer; Macugen, OSI); ranibizumab (anti-VEGF Fab; Lucentis, Genentech); bevacizumab (full length humanized antibody; Avastin, Genentech); brolucizumab (anti-VEGF scFv; Beovu, Novartis); and aflibercept (anti-VEGF Fab; Eylea, Regeneron). Other anti-VEGF molecules include soluble VEGF receptor analogs, VEGF-Trap (Regeneron), small interfering RNAs (siRNAs) bevasiranib (Opko Health), and rapamycin (Sirolimus, MacuSight). Anti-VEGF drugs are delivered into the eye as intravitreal injections under topical anesthesia.

However, unmet need exists as anti-VEGF therapies alone exhibit suboptimal response in patients with ophthalmic disorders such as DME. Although anti-VEGF reagents reduce macular edema, inhibit angiogenesis, and improve vision, not all DME patients experience substantial prolonged improvements. For instance, approximately 25% of patients who receive anti-VEGF therapy do not show any improvement in visual acuity after 12 months of treatment, and nearly 50% of patients do not achieve legal driving vision of 20/40 (Mitchell et al., 2011). Alternative therapies such as laser photocoagulation or intravitreal steroids are less successful and have side effects (such as cataract with intraocular steroids (*Curr. Ophthalmol. Rep.* 2013 Sep 1(3)).

Therefore, there is a need to identify factors that could further enhance the response to anti-VEGF therapies to improve therapy for patients with a suboptimal response to anti-VEGF therapies.

BRIEF DESCRIPTION OF THE DRAWINGS

FIG. 1A) BTC/Fab NVS2 complex, FIG. 1B) BTC/Fab NVS3 complex, FIG. 1C) BTC/Fab NVS1 complex, and FIG. 1D) BTC/Fab NVS4 complex.

FIG. 2A-2D show the structural epitope residues of Fab binding to BTC. BTC is shown as a ribbon with varying orientations to highlight the epitope residues listed in Tables 12, 13, 14, and 15. The epitope residues are shown as ball and sticks and are labelled. FIG. 2A) BTC/Fab NVS2 complex, FIG. 2B) BTC/Fab NVS3 complex, FIG. 2C) BTC/Fab NVS1 complex, and FIG. 2D) BTC/Fab NVS4 complex.

FIG. 5A shows scanning laser ophthamoscopy (SLO) images of mice injected with a control vector (scAAV2-Null). FIG. 5B shows SLO images of mice injected with scAAV2-CMV-BTC vector.

FIG. 6A-6G show the binding of monospecific and bispecific antibodies to BTC and/or VEGF. FIG. 6A shows binding between NVS1, NVS11, or NVS8 and BTC. FIG. 6B shows binding between NVS2 or NVS12 and BTC. FIG. 6C shows binding between NVS3 or NVS13 and BTC.

FIG. 6D shows binding between NVS4 and BTC. FIG. 6E and FIG. 6F show binding of NVS11 to both BTC and VEGF. FIG. 6G shows inhibition of human VEGF binding to human VEGFR2-Fc by NVS11.

FIG. 7A-7D show the binding of BTC to ErbB1 in the presence of mono-(NVS1-4) and bispecific (NVS11-14) antibodies. FIG. 7A shows binding of BTC to ErbB1 in the presence of NVS1, NVS11, and NVS8. FIG. 7B shows binding of BTC to ErbB1 in the presence of NVS2 and NVS12. FIG. 7C shows binding of BTC to ErbB1 in the presence of NVS3 and NVS13. FIG. 7D shows binding of BTC to ErbB1 in the presence of NVS4 and NVS14.

FIG. 8A-8D show the binding of BTC to ErbB4 in the presence of mono-(NVS1-4) and bispecific (NVS 11-14) antibodies; FIG. 8A shows binding of BTC to ErbB4 in the presence of NVS1, NVS 11, and NVS8; FIG. 8B shows binding of BTC to ErbB4 in the presence of NVS2 and NVS12; FIG. 8C shows binding of BTC to ErbB4 in the presence of NVS3 and NVS13; and FIG. 8D shows binding of BTC to ErbB4 in the presence of NVS4 and NVS14. FIGS. 8E and 8F show the binding of BTC to ErbB1 or ErbB4 in the presence of NVS1, NVS 11, or NVS8; FIG. 8E shows binding of BTC to ErbB1 in the presence of NVS1, NVS11, and NVS8; and FIG. 8F shows binding of BTC to ErbB4 in the presence of NVS1, NVS 11, and NVS8.

FIG. 9A-9C show the binding of VEGF-A to VEGFR2 in the presence of mono-(NVS8) and bispecific (NVS11, NVS12, and NVS14) antibodies. FIG. 9A shows binding of VEGF-A to VEGFR2 in the presence of NVS1, NVS11, and NVS8. FIG. 9B shows binding of VEGF-A to VEGFR2 in the presence of NVS14 and NVS8. FIG. 9C shows binding of VEGF-A to VEGFR2 in the presence of NVS12 and NVS8.

FIG. 10A-10D show BTC-induced phosphorylation of ERK1/2 in the presence of mono-(NVS1-4) and bispecific (NVS11-14) antibodies. FIG. 10A shows BTC-induced phosphorylation of ERK1/2 in the presence of NVS1 and NVS11. FIG. 10B shows BTC-induced phosphorylation of ERK1/2 in the presence of NVS2 and NVS12. FIG. 10C shows BTC-induced phosphorylation of ERK1/2 in the presence of NVS3 and NVS13. FIG. 10D shows BTC-induced phosphorylation of ERK1/2 in the presence of NVS4 and NVS14.

FIG. 11A-11D show BTC-induced phosphorylation of ErbB3 in the presence of mono-(NVS1-4) and bispecific (NVS11-14) antibodies. FIG. 11A shows BTC-induced phosphorylation of ErbB3 in the presence of NVS1 and NVS11. FIG. 11B shows BTC-induced phosphorylation of ErbB3 in the presence of NVS2 and NVS12. FIG. 11C shows BTC-induced phosphorylation of ErbB3 in the presence of NVS3 and NVS13. FIG. 11D shows BTC-induced phosphorylation of ErbB3 in the presence of NVS4 and NVS14.

FIG. 12A-12D show BTC-induced phosphorylation of HER3 in the presence of mono-(NVS1-2) and bispecific (NVS11-14) antibodies. FIG. 12A shows BTC-induced phosphorylation of HER3 in the presence of NVS1 and NVS11. FIG. 12B shows BTC-induced phosphorylation of HER3 in the presence of NVS2 and NVS12. FIG. 12C shows BTC-induced phosphorylation of HER3 in the presence of NVS13. FIG. 12D shows BTC-induced phosphorylation of HER3 in the presence of NVS14.

FIGS. 13A and 13B show BTC-induced permeability of retinal pigment epithelial (RPE) (FIG. 13A) and human retinal microvascular endothelial (HREC) cells (FIG. 13B) in vitro in the presence of mono-(NVS1 or NVS8) and bispecific (NVS11) antibodies.

FIG. 18B shows BTC-induced RPE morphological changes in the presence of NVS11 or NVS1; FIG. 18C shows VEGF-induced retinal vessel leakage in rabbits (representative images) in the presence of NVS 11 or NVS8.

SUMMARY

Figure 1A:
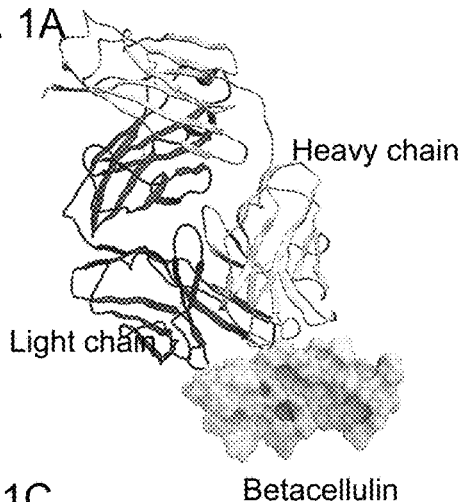
FIG. 1A-1D show the structure of Fab binding to BTC. BTC is shown as a solid surface and the Fab is shown as a ribbon. To illustrate the variance in binding modes with the Fabs, the BTC structure is in the same orientation in all panels.

The present disclosure provides an isolated antibody or antigen binding fragment thereof that binds specifically to betacellulin (BTC).

In one aspect, an antibody or antigen binding fragment thereof blocks BTC binding to ErbB1, ErbB4, or both.

In one aspect, an antibody or antigen binding fragment thereof blocks BTC-induced phospoh-ERK1/2 activation.

In one aspect, an antibody or antigen binding fragment thereof blocks BTC-induced phospoh-HER3 activation.

The present disclosure also provides an isolated antibody or antigen binding fragment thereof that binds specifically to BTC, where the antibody or antigen binding fragment has a dissociation constant (KD) of 5 pM or less.

In one aspect, an antibody or antigen binding fragment thereof binds to BTC comprising the amino acid sequence of SEQ ID NO: 157.

In one aspect, an antibody or antigen binding fragment thereof binds to at least one residue of SEQ ID NO: 157 selected from the group consisting of G34, H35, F36, S37, R38, C39, P40, K41, Q42, Y43, H45, Y46, R51, R53, F54, V56, A57, E58, Q59, T60, P61, A72, R73, E75, and R76.

In one aspect, an antibody or antigen binding fragment thereof binds to R38, C39, P40, K41, Q42, Y43, H45, Y46, F54, Q59, T60, P61, and R73 of SEQ ID NO: 157.

In one aspect, an antibody or antigen binding fragment thereof that binds specifically to BTC comprises heavy chain variable region complementarity determining region 1 (HCDR1), heavy chain variable region complementarity determining region 2 (HCDR2), and heavy chain variable region complementarity determining region 3 (HCDR3) as set forth in SEQ ID NOs: 1, 2, and 3, respectively, and light chain variable region complementarity determining region 1 (LCDR1), light chain variable region complementarity determining region 2 (LCDR2), and light chain variable region complementarity determining region 3 (LCDR3) as set forth in SEQ ID NOs: 14, 15, and 16, respectively.

In one aspect, an antibody or antigen binding fragment thereof that binds specifically to BTC comprises HCDR1, HCDR2, and HCDR3 as set forth in SEQ ID NOs: 4, 2, and 3, respectively, and LCDR1, LCDR2, and LCDR3 as set forth in SEQ ID NOs: 14, 15, and 16, respectively.

In one aspect, the HCDR1 comprises the consensus sequence XYAIS and/or the HCDR2 comprises the consensus sequence GIXPXXGXXXYAQKFQG, and where X is any amino acid and may not be the same in different positions.

In one aspect, an antibody or antigen binding fragment thereof that binds specifically to BTC comprises a heavy chain sequence of SEQ ID NO: 168 and a light chain sequence of SEQ ID NO: 169, or a heavy chain sequence of SEQ ID NO: 170 and a light chain sequence of SEQ ID NO: 171.

In one aspect, an antibody or antigen binding fragment thereof that binds specifically to BTC comprises HCDR1, HCDR2, and HCDR3 as set forth in SEQ ID NOs: 5, 6, and 3, respectively, and LCDR1, LCDR2, and LCDR3 as set forth in SEQ ID NOs: 17, 18, and 19, respectively.

In one aspect, an antibody or antigen binding fragment thereof that binds specifically to BTC comprises HCDR1, HCDR2, and HCDR3 as set forth in SEQ ID NOs: 7, 8, and 9, respectively, and LCDR1, LCDR2, and LCDR3 as set forth in SEQ ID NOs: 20, 18, and 16, respectively.

In one aspect, an antibody or antigen binding fragment thereof that binds specifically to BTC comprises a heavy chain variable region (VH) and a light chain variable region (VL) comprising an amino acid sequence with at least 90%, 95%, 96%, 97%, 98%, 99%, or 100% sequence identity to SEQ ID NOs: 10 and 21, respectively.

In one aspect, the differences in amino acid sequence is not within the complementary determining regions.

In one aspect, the differences in amino acid sequence are conservative substitutions.

In one aspect, an antibody or antigen binding fragment thereof that binds specifically to BTC comprises a VH and VL comprising amino acid sequence as set forth in SEQ ID NOs: 10 and 21, respectively.

In one aspect, the VH and VL are encoded by a nucleic acid sequence as set forth in SEQ ID NOs: 11 and 22, respectively.

In one aspect, an antibody or antigen binding fragment thereof that binds specifically to BTC comprises a heavy chain and a light chain with an amino acid sequence as set forth in SEQ ID NOs: 12 and 23, respectively.

In one aspect, the heavy chain and light chain are encoded by the nucleic acid sequence with at least 90%, 95%, 96%, 97%, 98%, 99%, or 100% sequence identity to SEQ ID NOs: 13 and 24, respectively.

In one aspect, an antibody or antigen binding fragment thereof that binds specifically to BTC comprises 1) HCDR1, HCDR2, and HCDR3 comprised in a VH with the amino acid sequence of SEQ ID NO: 10, and 2) LCDR1, LCDR2, and LCDR3 comprised in a VL with the amino acid sequence of SEQ ID NO: 21.

In one aspect, the HCDR1, HCDR2, HCDR3, LCDR1, LCDR2, and LCDR3 comprises: SEQ ID NOs: 1, 2, 3, 14, 15, and 16, respectively; SEQ ID NOs: 4, 2, 3, 14, 15, and 16, respectively; SEQ ID NOs: 5, 6, 3, 17, 18, and 19, respectively; or SEQ ID NOs: 7, 8, 9, 20, 18, and 16, respectively.

In one aspect, an antibody or antigen binding fragment thereof that binds specifically to BTC comprises HCDR1, HCDR2, HCDR3, LCDR1, LCDR2, and LCDR3, where a. the HCDR1 comprises the amino acid sequence selected from the group consisting of SEQ ID NOs: 1, 4, 5, and 7, the HCDR2 comprises the amino acid sequence selected from the group consisting of SEQ ID NOs: 2, 6, and 8, the HCDR3 comprises the amino acid sequence selected from the group consisting of SEQ ID NOs: 3 and 9, and b. the LCDR1 comprises the amino acid sequence selected from the group consisting of SEQ ID NOs: 14, 17, and 20, the LCDR2 comprises the amino acid sequence selected from the group consisting of SEQ ID NOs: 15 and 18, the LCDR3 comprises the amino acid sequence selected from the group consisting of SEQ ID NOs: 16 and 19.

In one aspect, an antibody or antigen binding fragment thereof that binds specifically to BTC comprises a VH and VL comprising the amino acid sequence of SEQ ID NOs: 10 and 21, respectively.

In one aspect, an antibody or antigen binding fragment thereof that binds specifically to BTC comprises a heavy chain and a light chain with the amino acid sequence as set forth in SEQ ID NOs: 12 and 23, respectively.

Also provided in the present disclosure is an isolated antibody or antigen binding fragment thereof that binds specifically to BTC, which comprises a VH and a VL with the amino acid sequence of SEQ ID NOs: 10 and 21, respectively.

In one aspect, an antibody or antigen binding fragment thereof binds to P40, K41, Q42, Y43, H45, Y46, E58, Q59, T60, P61, A72, R73, E75, and R76 of SEQ ID NO: 157.

In one aspect, an antibody or antigen binding fragment thereof that binds specifically to BTC comprises HCDR1, HCDR2, and HCDR3 as set forth in SEQ ID NOs: 25, 26, and 27, respectively, and LCDR1, LCDR2, and LCDR3 as set forth in SEQ ID NOs: 38, 39, and 40, respectively.

In one aspect, an antibody or antigen binding fragment thereof that binds specifically to BTC comprises HCDR1, HCDR2, and HCDR3 as set forth in SEQ ID NOs: 28, 26, and 27, respectively, and LCDR1, LCDR2, and LCDR3 as set forth in SEQ ID NOs: 38, 39, and 40, respectively.

In one aspect, an antibody or antigen binding fragment thereof that binds specifically to BTC comprises HCDR1, HCDR2, and HCDR3 as set forth in SEQ ID NOs: 29, 30, and 27, respectively, and LCDR1, LCDR2, and LCDR3 as set forth in SEQ ID NOs: 41, 42, and 43, respectively.

In one aspect, an antibody or antigen binding fragment thereof that binds specifically to BTC comprises HCDR1, HCDR2, and HCDR3 as set forth in SEQ ID NOs: 31, 32, and 33, respectively, and LCDR1, LCDR2, and LCDR3 as set forth in SEQ ID NOs: 44, 42, and 40, respectively.

In one aspect, an antibody or antigen binding fragment thereof that binds specifically to BTC comprises a VH and a VL comprising an amino acid sequence with at least 90%, 95%, 96%, 97%, 98%, 99%, or 100% sequence identity to SEQ ID NOs: 34 and 45, respectively.

In one aspect, the differences in amino acid sequence is not within the complementary determining regions.

In one aspect, the differences in amino acid sequence are conservative substitutions.

In one aspect, an antibody or antigen binding fragment thereof that binds specifically to BTC comprises a VH and VL comprising amino acid sequence as set forth in SEQ ID NOs: 34 and 45, respectively.

In one aspect, the VH and VL are encoded by a nucleic acid sequence as set forth in SEQ ID NOs: 35 and 46, respectively.

In one aspect, an antibody or antigen binding fragment thereof that binds specifically to BTC comprises a heavy chain and a light chain with an amino acid sequence as set forth in SEQ ID NOs: 36 and 47, respectively.

In one aspect, the heavy chain and light chain are encoded by a nucleic acid sequence with at least 90%, 95%, 96%, 97%, 98%, 99%, or 100% sequence identity to SEQ ID NOs: 37 and 48, respectively.

In one aspect, an antibody or antigen binding fragment thereof that binds specifically to BTC comprises 1) HCDR1, HCDR2, and HCDR3 comprised in a VH with the amino acid sequence of SEQ ID NO: 34, and 2) LCDR1, LCDR2, and LCDR3 comprised in a VL with the amino acid sequence of SEQ ID NO: 45.

In one aspect, the HCDR1, HCDR2, HCDR3, LCDR1, LCDR2, and LCDR3 comprises: SEQ ID NOs: 25, 26, 27, 38, 39, and 40, respectively; SEQ ID NOs: 28, 26, 27, 38, 39, and 40, respectively; SEQ ID NOs: 29, 30, 27, 41, 42, and 43, respectively; or SEQ ID NOs: 31, 32, 33, 44, 42, and 40, respectively.

In one aspect, an antibody or antigen binding fragment thereof that binds specifically to BTC comprises HCDR1, HCDR2, HCDR3, LCDR1, LCDR2, and LCDR3, where a. the HCDR1 comprises the amino acid sequence selected from the group consisting of SEQ ID NOs: 25, 28, 29, and 31, the HCDR2 comprises the amino acid sequence selected from the group consisting of SEQ ID NOs: 26, 30, and 32, the HCDR3 comprises the amino acid sequence selected from the group consisting of SEQ ID NOs: 27 and 33; and b. the LCDR1 comprises the amino acid sequence selected from the group consisting of SEQ ID NOs: 38, 41, and 44, the LCDR2 comprises the amino acid sequence selected from the group consisting of SEQ ID NOs: 39 and 42, the LCDR3 comprises the amino acid sequence selected from the group consisting of SEQ ID NOs: 40 and 43.

In one aspect, an antibody or antigen binding fragment thereof that binds specifically to BTC comprises a VH and VL comprising the amino acid sequence of SEQ ID NOs: 34 and 45, respectively.

In one aspect, an antibody or antigen binding fragment thereof that binds specifically to BTC comprises a heavy chain and a light chain with the amino acid sequence as set forth in SEQ ID NOs: 36 and 47, respectively.

The present disclosure further provides an isolated antibody or antigen binding fragment thereof that binds specifically to BTC, which comprises a VH and a VL with the amino acid sequence of SEQ ID NOs: 34 and 45, respectively.

In one aspect, an antibody or antigen binding fragment thereof binds to G34, H35, F36, S37, R38, C39, P40, K41, Q42, R51, R53, F54, and V56 of SEQ ID NO: 157.

In one aspect, an antibody or antigen binding fragment thereof that binds specifically to BTC comprises HCDR1, HCDR2, and HCDR3 as set forth in SEQ ID NOs: 25, 49, and 50, respectively, and LCDR1, LCDR2, and LCDR3 as set forth in SEQ ID NOs: 58, 59, and 60, respectively.

In one aspect, an antibody or antigen binding fragment thereof that binds specifically to BTC comprises HCDR1, HCDR2, and HCDR3 as set forth in SEQ ID NOs: 28, 49, and 50, respectively, and LCDR1, LCDR2, and LCDR3 as set forth in SEQ ID NOs: 58, 59, and 60, respectively.

In one aspect, the HCDR1 comprises the consensus sequence XXAMX, and/or the HCDR2 comprises the consensus sequence XXXX/-XXXXTXYXDSVKG, where X is any amino acid and may not be the same in different positions, and where X/-is any amino acid or a deletion.

In one aspect, an antibody or antigen binding fragment thereof that binds specifically to BTC comprises a heavy chain sequence of SEQ ID NO: 190 and a light chain sequence of SEQ ID NO: 191.

In one aspect, an antibody or antigen binding fragment thereof that binds specifically to BTC comprises HCDR1, HCDR2, and HCDR3 as set forth in SEQ ID NOs: 29, 51, and 50, respectively, and LCDR1, LCDR2, and LCDR3 as set forth in SEQ ID NOs: 61, 62, and 63, respectively.

In one aspect, an antibody or antigen binding fragment thereof that binds specifically to BTC comprises HCDR1, HCDR2, and HCDR3 as set forth in SEQ ID NOs: 31, 52, and 53, respectively, and LCDR1, LCDR2, and LCDR3 as set forth in SEQ ID NOs: 64, 62, and 60, respectively.

In one aspect, an antibody or antigen binding fragment thereof that binds specifically to BTC comprises a VH and a VL comprising an amino acid sequence with at least 90%, 95%, 96%, 97%, 98%, 99%, or 100% sequence identity to SEQ ID NOs: 54 and 65, respectively.

In one aspect, the differences in amino acid sequence is not within the complementary determining regions.

In one aspect, the differences in amino acid sequence are conservative substitutions.

In one aspect, an antibody or antigen binding fragment thereof that binds specifically to BTC comprises a VH and VL comprising amino acid sequence as set forth in SEQ ID NOs: 54 and 65, respectively.

In one aspect, the VH and VL are encoded by a nucleic acid sequence as set forth in SEQ ID NOs: 55 and 66, respectively.

In one aspect, an antibody or antigen binding fragment thereof that binds specifically to BTC comprises a heavy chain and a light chain with an amino acid sequence as set forth in SEQ ID NOs: 56 and 67, respectively.

In one aspect, the heavy chain and light chain are encoded by a nucleic acid sequence with at least 90%, 95%, 96%, 97%, 98%, 99%, or 100% sequence identity to SEQ ID NOs: 57 and 68, respectively.

In one aspect, an antibody or antigen binding fragment thereof that binds specifically to BTC comprises 1) HCDR1, HCDR2, and HCDR3 comprised in a VH with the amino acid sequence of SEQ ID NO: 54, and 2) LCDR1, LCDR2, and LCDR3 comprised in a VL with the amino acid sequence of SEQ ID NO: 65.

In one aspect, the HCDR1, HCDR2, HCDR3, LCDR1, LCDR2, and LCDR3 comprises: SEQ ID NOs: 25, 49, 50, 58, 59, and 60, respectively; SEQ ID NOs: 28, 49, 50, 58, 59, and 60, respectively; SEQ ID NOs: 29, 51, 50, 61, 62, and 63, respectively; or SEQ ID NOs: 31, 52, 53, 64, 62, and 60, respectively.

In one aspect, an antibody or antigen binding fragment thereof that binds specifically to BTC comprises HCDR1, HCDR2, HCDR3, LCDR1, LCDR2, and LCDR3, where a. the HCDR1 comprises the amino acid sequence selected from the group consisting of SEQ ID NOs: 25, 28, 29, and 31, the HCDR2 comprises the amino acid sequence selected from the group consisting of SEQ ID NOs: 49, 51, and 52, the HCDR3 comprises the amino acid sequence selected from the group consisting of SEQ ID NOs: 50 and 53; and b. the LCDR1 comprises the amino acid sequence selected from the group consisting of SEQ ID NOs: 58, 61, and 64, the LCDR2 comprises the amino acid sequence selected from the group consisting of SEQ ID NOs: 59 and 62, the LCDR3 comprises the amino acid sequence selected from the group consisting of SEQ ID NOs: 60 and 63.

In one aspect, an antibody or antigen binding fragment thereof that binds specifically to BTC comprises a VH and VL comprising the amino acid sequence of SEQ ID NOs: 54 and 65, respectively.

In one aspect, an antibody or antigen binding fragment thereof that binds specifically to BTC comprises a heavy chain and a light chain with the amino acid sequence as set forth in SEQ ID NOs: 56 and 67, respectively.

The present disclosure also provides an isolated antibody or antigen binding fragment thereof that binds specifically to BTC, which comprises a VH and a VL with the amino acid sequence of SEQ ID NOs: 54 and 65, respectively.

In one aspect, an antibody or antigen binding fragment thereof binds to S37, R38, C39, P40, K41, Q42, Y43, H45, Y46, F54, A57, Q59, T60, P61, A72, R73, and E75 of SEQ ID NO: 157.

In one aspect, an antibody or antigen binding fragment thereof that binds specifically to BTC comprises HCDR1, HCDR2, and HCDR3 as set forth in SEQ ID NOs: 69, 70, and 71, respectively, and LCDR1, LCDR2, and LCDR3 as set forth in SEQ ID NOs: 82, 83, and 84, respectively.

In one aspect, an antibody or antigen binding fragment thereof that binds specifically to BTC comprises HCDR1, HCDR2, and HCDR3 as set forth in SEQ ID NOs: 72, 70, and 71, respectively, and LCDR1, LCDR2, and LCDR3 as set forth in SEQ ID NOs: 82, 83, and 84, respectively.

In one aspect, the HCDR2 comprises the consensus sequence XIXXXXXXXXYADSVKG, and/or the LCDR3 comprises the consensus sequence QQYDXXXT, and where X is any amino acid and may not be the same in different positions.

In one aspect, an antibody or antigen binding fragment thereof that binds specifically to BTC comprises a heavy chain and a light chain sequence selected from the group consisting of: SEQ ID NOs: 194 and 195, respectively; SEQ ID NOs: 196 and 197, respectively; SEQ ID NOs: 198 and 199, respectively; SEQ ID NOs: 200 and 201, respectively; SEQ ID NOs: 202 and 203, respectively; SEQ ID NOs: 204 and 205, respectively; and SEQ ID NOs: 206 and 207, respectively.

In one aspect, an antibody or antigen binding fragment thereof that binds specifically to BTC comprises HCDR1, HCDR2, and HCDR3 as set forth in SEQ ID NOs: 73, 74, and 71, respectively, and LCDR1, LCDR2, and LCDR3 as set forth in SEQ ID NOs: 85, 18, and 86, respectively.

In one aspect, an antibody or antigen binding fragment thereof that binds specifically to BTC comprises HCDR1, HCDR2, and HCDR3 as set forth in SEQ ID NOs: 75, 76, and 77, respectively, and LCDR1, LCDR2, and LCDR3 as set forth in SEQ ID NOs: 87, 18, and 84, respectively.

In one aspect, an antibody or antigen binding fragment thereof that binds specifically to BTC comprises a VH and a VL comprising an amino acid sequence with at least 90%, 95%, 96%, 97%, 98%, 99%, or 100% sequence identity to SEQ ID NOs: 78 and 88, respectively.

In one aspect, the differences in amino acid sequence is not within the complementary determining regions.

In one aspect, the differences in amino acid sequence are conservative substitutions.

In one aspect, an antibody or antigen binding fragment thereof that binds specifically to BTC comprises a VH and VL comprising amino acid sequence as set forth in SEQ ID NOs: 78 and 88, respectively.

In one aspect, the VH and VL are encoded by a nucleic acid sequence as set forth in SEQ ID NOs: 79 and 89, respectively.

In one aspect, an antibody or antigen binding fragment thereof that binds specifically to BTC comprises a heavy chain and a light chain with an amino acid sequence as set forth in SEQ ID NOs: 80 and 90, respectively.

In one aspect, the heavy chain and light chain are encoded by a nucleic acid sequence with at least 90%, 95%, 96%, 97%, 98%, 99%, or 100% sequence identity to SEQ ID NOs: 81 and 91, respectively.

In one aspect, an antibody or antigen binding fragment thereof that binds specifically to BTC comprises 1) HCDR1, HCDR2, and HCDR3 comprised in a VH with the amino acid sequence of SEQ ID NO: 78, and 2) LCDR1, LCDR2, and LCDR3 comprised in a VL with the amino acid sequence of SEQ ID NO: 88.

In one aspect, the HCDR1, HCDR2, HCDR3, LCDR1, LCDR2, and LCDR3 comprise: SEQ ID NOs: 69, 70, 71, 82, 83, and 84, respectively; SEQ ID NOs: 72, 70, 71, 82, 83, and 84, respectively; SEQ ID NOs: 73, 74, 71, 85, 18, and 86, respectively; or SEQ ID NOs: 75, 76, 77, 87, 18, and 84, respectively.

In one aspect, an antibody or antigen binding fragment thereof that binds specifically to BTC comprises HCDR1, HCDR2, HCDR3, LCDR1, LCDR2, and LCDR3, where a. the HCDR1 comprises the amino acid sequence selected from the group consisting of SEQ ID NOs: 69, 72, 73, and 75, the HCDR2 comprises the amino acid sequence selected from the group consisting of SEQ ID NOs: 70, 74, and 76, the HCDR3 comprises the amino acid sequence selected from the group consisting of SEQ ID NOs: 71 and 77; and b. the LCDR1 comprises the amino acid sequence selected from the group consisting of SEQ ID NOs: 82, 85, and 87, the LCDR2 comprises the amino acid sequence selected from the group consisting of SEQ ID NOs: 83 and 18, the LCDR3 comprises the amino acid sequence selected from the group consisting of SEQ ID NOs: 84 and 86.

In one aspect, an antibody or antigen binding fragment thereof that binds specifically to BTC comprises a VH and VL comprising the amino acid sequence of SEQ ID NOs: 78 and 88, respectively.

In one aspect, an antibody or antigen binding fragment thereof that binds specifically to BTC comprises a heavy chain and a light chain with the amino acid sequence as set forth in SEQ ID NOs: 80 and 90, respectively.

The present disclosure also provides an isolated antibody or antigen binding fragment thereof that binds specifically to BTC, which comprises a VH and a VL with the amino acid sequence of SEQ ID NOs: 78 and 88, respectively.

In one aspect, an antibody or antigen binding fragment thereof that binds specifically to BTC is in a format selected from the group consisting of an isolated antibody, a Fab, a Fab', a F(ab')$_2$, a Fv, and a scFv.

In one aspect, an antibody or antigen binding fragment thereof that binds specifically to BTC is a Fab.

In one aspect, an antibody or antigen binding fragment thereof that binds specifically to BTC is a scFv.

In one aspect, an antibody or antigen binding fragment thereof that binds specifically to BTC is an isolated antibody.

In one aspect, an antibody or antigen binding fragment thereof that binds specifically to BTC is a monoclonal human antibody.

In one aspect, an antibody or antigen binding fragment thereof that binds specifically to BTC is a monoclonal humanized antibody.

In one aspect, the Fab comprises an Fc region.

In one aspect, the Fc region is selected from the group consisting of an Fc region from an IgG1, IgG2, IgG3, IgG4, IgA, IgM, IgE, and IgD.

In one aspect, the Fc region comprises human immunoglobulin Kappa chain constant region sequence as set forth in SEQ ID NO: 159.

In one aspect, the Fc region comprises human immunoglobulin first constant Ig domain of the heavy chain (CH1 domain) as set forth in SEQ ID NO: 160.

Provided in the present disclosure is an isolated antibody or antigen binding fragment thereof which is capable of competing with the antibody or antigen binding fragment thereof as described throughout for binding to BTC and reducing BTC-mediated signaling.

In one aspect, an antibody or antigen binding fragment thereof that binds specifically to BTC comprises a heavy chain and a light chain as set forth in SEQ ID NOs: 168 and 169, respectively; SEQ ID NOs: 170 and 171, respectively; SEQ ID NOs: 172 and 173, respectively; SEQ ID NOs: 174 and 175, respectively; SEQ ID NOs: 176 and 177, respectively; SEQ ID NOs: 178 and 179, respectively; SEQ ID NOs: 180 and 181, respectively; SEQ ID NOs: 182 and 183, respectively; SEQ ID NOs: 184 and 185, respectively; SEQ ID NOs: 186 and 187, respectively; or SEQ ID NOs: 188 and 189, respectively.

The present disclosure provides a polynucleotide comprising nucleotide sequences encoding the antibody or antigen binding fragment thereof as described throughout.

In one aspect, an expression cassette comprises the polynucleotide as described throughout.

In one aspect, a vector comprises the expression cassette as described throughout.

In one aspect, a host cell comprises the polynucleotide or the vector as described throughout.

Also provided in the present disclosure is a method of producing an antibody or antigen binding fragment thereof, comprising culturing the host cell under suitable conditions for expression of the antibody or antigen binding fragment thereof.

In one aspect, the method further comprises purifying the antibody or antigen binding fragment thereof.

Further provided in the present disclosure is a pharmaceutical composition comprising an effective amount of the antibody or antigen binding fragment thereof as described throughout.

In one aspect, the pharmaceutical composition comprises a pharmaceutically acceptable excipient, diluent, or carrier.

The present disclosure provides a method of treating a subject in need thereof, comprising administering to the subject an effective amount of the antibody or antigen binding fragment thereof or the pharmaceutical composition as described throughout.

In one aspect, the subject has a disease selected from the group consisting of pancreatic carcinoma, breast cancer, endometrial adenocarcinoma, hepatocellular carcinoma, head and neck squamous cell carcinoma, and gastric carcinoma.

In one aspect, the antibody or antigen binding fragment thereof or the pharmaceutical composition is administered via a route selected from the group consisting of intravenous administration, intramuscular administration, subcutaneous administration, parenteral administration, spinal administration, and epidermal administration.

In one aspect, the subject has an ophthalmic disorder.

In one aspect, the ophthalmic disorder is selected from the group consisting of diabetic macular edema, age-related macular degeneration, neovascular age-related macular degeneration, neovascular glaucoma, diabetic retinopathy, macular edema, pathologic myopia, retinal vein occlusions, retinopathy of prematurity, abnormal vascular proliferation associated with phakomatoses, central serous chorioretinopathy, and acute multifocal placoid pigment epitheliopathy.

In one aspect, the ophthalmic disorder is diabetic macular edema.

In one aspect, the administering is via subretinal injection.

In one aspect, the administering is via intravitreal injection.

In one aspect, the pharmaceutical composition further comprises an anti-VEGF antagonist.

In one aspect, the anti-VEGF antagonist is ranibizumab.
In one aspect, the anti-VEGF antagonist is bevacizumab.
In one aspect, the anti-VEGF antagonist is aflibercept.
In one aspect, the anti-VEGF antagonist is brolucizumab.
In one aspect, the anti-VEGF antagonist is pegaptanib.
In one aspect, the anti-VEGF antagonist comprises a heavy chain and a light chain as set forth in SEQ ID NOs: 103 and 114, respectively.

In one aspect, the anti-VEGF antagonist is encoded by a nucleic acid sequence as set forth in SEQ ID NOs: 104 and 115.

In one aspect, the method further comprises administering to the subject an anti-VEGF antagonist.

In one aspect, the anti-VEGF antagonist is ranibizumab.

In one aspect, the anti-VEGF antagonist is bevacizumab.

In one aspect, the anti-VEGF antagonist is aflibercept.

In one aspect, the anti-VEGF antagonist is brolucizumab.

In one aspect, the anti-VEGF antagonist is pegaptanib.

In one aspect, the anti-VEGF antagonist comprises a heavy chain and a light chain as set forth in SEQ ID NOs: 103 and 114.

In one aspect, the anti-VEGF antagonist is encoded by a nucleic acid sequence as set forth in SEQ ID NOs: 104 and 115.

The present disclosure provides a kit comprising the antibody or antigen binding fragment thereof or the pharmaceutical composition as described throughout.

In one aspect, the kit further comprises an instruction for use.

In one aspect, the kit further comprises a syringe.

The present disclosure provides a multi-specific binding molecule comprising 1) an anti-BTC binding moiety and 2) an anti-VEGF binding moiety.

In one aspect, the anti-BTC binding moiety binds to BTC comprising the amino acid sequence of SEQ ID NO: 157.

In one aspect, the anti-BTC binding moiety binds to at least one residue of SEQ ID NO: 157 selected from the group consisting of G34, H35, F36, S37, R38, C39, P40, K41, Q42, Y43, H45, Y46, R51, R53, F54, V56, A57, E58, Q59, T60, P61, A72, R73, E75, and R76.

In one aspect, the anti-BTC binding moiety binds to R38, C39, P40, K41, Q42, Y43, H45, Y46, F54, Q59, T60, P61, and R73 of SEQ ID NO: 157.

In one aspect, the anti-BTC binding moiety binds to P40, K41, Q42, Y43, H45, Y46, E58, Q59, T60, P61, A72, R73, E75, and R76 of SEQ ID NO: 157.

In one aspect, the anti-BTC binding moiety binds to G34, H35, F36, S37, R38, C39, P40, K41, Q42, R51, R53, F54, and V56 of SEQ ID NO: 157.

In one aspect, the anti-BTC binding moiety binds to S37, R38, C39, P40, K41, Q42, Y43, H45, Y46, F54, A57, Q59, T60, P61, A72, R73, and E75 of SEQ ID NO: 157.

In one aspect, the anti-BTC binding moiety is the antibody or antigen binding fragment thereof as described throughout.

In one aspect, the anti-VEGF binding moiety is an anti-VEGF antibody or antigen binding fragment thereof.

In one aspect, the anti-BTC binding moiety and the anti-VEGF binding moiety are in a format selected from the list consisting of an isolated antibody, a Fab, a Fab', a F(ab')$_2$, a Fv, and a scFv.

In one aspect, the anti-BTC binding moiety is an anti-BTC Fab and the anti-VEGF binding moiety is an anti-VEGF Fab.

In one aspect, the anti-BTC Fab comprises a heavy chain (HA) and a light chain (LA), and where the anti-VEGF Fab comprises a heavy chain (HB) and a light chain (LB).

In one aspect, the HA and the HB are linked in the format from the N-terminus to the C-terminus: N-HA-linker 1-HB-C, and where the LA and the LB are linked in the format from the N-terminus to the C-terminus: N-LA-linker 2-LB-C.

In one aspect, the HA and the HB is linked in the format from the N-terminus to the C-terminus: N-HB-linker 1-HA-C, and where the LA and the LB is linked in the format from the N-terminus to the C-terminus: N-LB-linker 2-LA-C.

In one aspect, the linker 1 and linker 2 comprise an amino sequence of SEQ ID NO: 118.

In one aspect, the linker 1 and linker 2 are encoded by a nucleic sequence of SEQ ID NO: 119.

In one aspect, the linker 1 and linker 2 comprise an amino sequence selected from the group consisting of SEQ ID NOs: 161-167.

In one aspect, the anti-BTC binding moiety comprises HCDR1, HCDR2, HCDR3, LCDR1, LCDR2, and LCDR3 as set forth in: SEQ ID NOs: 1, 2, 3, 14, 15, and 16, respectively; SEQ ID NOs: 4, 2, 3, 14, 15, and 16, respectively; SEQ ID NOs: 5, 6, 3, 17, 18, and 19, respectively; or SEQ ID NOs: 7, 8, 9, 20, 18, and 16, respectively.

In one aspect, the anti-BTC binding moiety comprises a VH and a VL with the amino acid sequence of SEQ ID NOs: 10 and 21, respectively.

In one aspect, the VH and VL is encoded by the nucleic acid sequence of SEQ ID NOs: 116 and 122, respectively.

In one aspect, the anti-BTC binding moiety comprises HCDR1, HCDR2, HCDR3, LCDR1, LCDR2, and LCDR3 as set forth in: SEQ ID NOs: 25, 26, 27, 38, 39, and 40, respectively; SEQ ID NOs: 28, 26, 27, 38, 39, and 40, respectively; SEQ ID NOs: 29, 30, 27, 41, 42, and 43, respectively; or SEQ ID NOs: 31, 32, 33, 44, 42, and 40, respectively.

In one aspect, the anti-BTC binding moiety comprises a VH and a VL with the amino acid sequence of SEQ ID NOs: 34 and 45, respectively.

In one aspect, the VH and VL is encoded by the nucleic acid sequence of SEQ ID NOs: 127 and 132, respectively.

In one aspect, the anti-BTC binding moiety comprises HCDR1, HCDR2, HCDR3, LCDR1, LCDR2, and LCDR3 as set forth in: SEQ ID NOs: 25, 49, 50, 58, 59, and 60, respectively; SEQ ID NOs: 28, 49, 50, 58, 59, and 60, respectively; SEQ ID NOs: 29, 51, 50, 61, 62, and 63, respectively; or SEQ ID NOs: 31, 52, 53, 64, 62, and 60, respectively.

In one aspect, the anti-BTC binding moiety comprises a VH and a VL with the amino acid sequence of SEQ ID NOs: 54 and 65, respectively.

In one aspect, the VH and VL is encoded by the nucleic acid sequence of SEQ ID NOs: 137 and 142, respectively.

In one aspect, the anti-BTC binding moiety comprises HCDR1, HCDR2, HCDR3, LCDR1, LCDR2, and LCDR3 as set forth in: SEQ ID NOs: 69, 70,71, 82, 83, and 84, respectively; SEQ ID NOs: 72, 70, 71, 82, 83, and 84, respectively; SEQ ID NOs: 73, 74, 71, 85, 18, and 86, respectively; or SEQ ID NOs: 75, 76, 77, 87, 18, and 84, respectively.

In one aspect, the anti-BTC binding moiety comprises a VH and a VL with the amino acid sequence of SEQ ID NOs: 78 and 88, respectively.

In one aspect, the VH and VL is encoded by the nucleic acid sequence of SEQ ID NOs: 147 and 151, respectively.

In one aspect, the anti-VEGF binding moiety comprises HCDR1, HCDR2, and HCDR3 as set forth in SEQ ID NOs: 92, 93, and 94, respectively, and LCDR1, LCDR2, and LCDR3 as set forth in SEQ ID NOs: 105, 106, and 107, respectively.

In one aspect, the anti-VEGF binding moiety comprises HCDR1, HCDR2, and HCDR3 as set forth in SEQ ID NOs: 95, 93, and 94, respectively, and LCDR1, LCDR2, and LCDR3 as set forth in SEQ ID NOs: 105, 106, and 107, respectively.

In one aspect, the anti-VEGF binding moiety comprises HCDR1, HCDR2, and HCDR3 as set forth in SEQ ID NOs: 96, 97, and 94, respectively, and LCDR1, LCDR2, and LCDR3 as set forth in SEQ ID NOs: 108, 109, and 110, respectively.

In one aspect, the anti-VEGF binding moiety comprises HCDR1, HCDR2, and HCDR3 as set forth in SEQ ID NOs:

98, 99, and 100, respectively, and LCDR1, LCDR2, and LCDR3 as set forth in SEQ ID NOs: 111, 109, and 107, respectively.

In one aspect, the anti-VEGF binding moiety comprises a VH and VL comprising an amino acid sequence with at least 90%, 95%, 96%, 97%, 98%, 99%, or 100% sequence identity to SEQ ID NOs: 101 and 112, respectively.

In one aspect, the differences in amino acid sequence is not within the complementary determining regions.

In one aspect, the differences in amino acid sequence are conservative substitutions.

In one aspect, the anti-VEGF binding moiety comprises a VH and VL comprising an amino acid sequence as set forth in SEQ ID NOs: 101 and 112, respectively.

In one aspect, the anti-VEGF binding moiety comprises a VH and VL encoded by the nucleic acid sequence as set forth in SEQ ID NOs: 102 and 113, respectively.

In one aspect, the anti-VEGF binding moiety comprises a VH and VL encoded by the nucleic acid sequence as set forth in SEQ ID NOs: 117 and 123, respectively.

In one aspect, the anti-VEGF binding moiety comprises a VH and VL encoded by the nucleic acid sequence as set forth in SEQ ID NOs: 128 and 133, respectively.

In one aspect, the anti-VEGF binding moiety comprises a VH and VL encoded by the nucleic acid sequence as set forth in SEQ ID NOs: 138 and 143, respectively.

In one aspect, the anti-VEGF binding moiety comprises a VH and VL encoded by the nucleic acid sequence as set forth in SEQ ID NOs: 148 and 152, respectively.

In one aspect, the anti-VEGF binding moiety comprises a heavy chain and a light chain with the amino acid sequence as set forth in SEQ ID NOs: 103 and 114, respectively.

In one aspect, the heavy chain and light chain are encoded by a nucleic acid sequence with at least 90%, 95%, 96%, 97%, 98%, 99%, or 100% sequence identity to SEQ ID NOs: 104 and 115, respectively.

Provided in the present disclosure is a multi-specific binding molecule comprising an anti-BTC binding moiety and an anti-VEGF binding moiety, where the anti-BTC binding moiety comprises a variable heavy chain domain (VHA) and a variable light chain domain (VLA) that bind to BTC, and where the anti-VEGF binding moiety comprises a variable heavy chain domain (VHB) and a variable light chain domain (VLB) that bind to VEGF, where:
  a. the VHA and VLA comprise the amino acid sequence as set forth in SEQ ID NOs: 10 and 21, respectively; and b. the VHB and VLB comprise the amino acid sequence as set forth in SEQ ID NOs: 101 and 112, respectively.

In one aspect, the anti-BTC binding moiety further comprises a heavy chain constant domain (CHIA) and a light chain constant domain (CKA), and where the anti-VEGF binding moiety further comprises a heavy chain constant domain (CHIB) and a light chain constant domain (CKB).

In one aspect, a multi-specific binding molecule is in the format from the N-terminus to C-terminus as: N-VHA-CH1A-linker-VHB-CH1B-C and N-VLA-CKA-linker-VLB-CKB-C.

In one aspect, a multi-specific binding molecule comprises a heavy chain comprising the VHA, CHIA, linker, VHB, and CHIB, where the heavy chain is as set forth in SEQ ID NO: 120.

In one aspect, the heavy chain is encoded by a nucleic acid sequence as set forth in SEQ ID NO: 121.

In one aspect, a multi-specific binding molecule comprises a light chain comprising the VLA, CKA, linker, VLB, and CKB, where the light chain is as set forth in SEQ ID NO: 125.

In one aspect, the light chain is encoded by a nucleic acid sequence as set forth in SEQ ID NO: 126.

Also provided in the present disclosure is a multi-specific binding molecule comprising an anti-BTC binding moiety and an anti-VEGF binding moiety, where the anti-BTC binding moiety comprises a variable heavy chain domain (VHA) and a variable light chain domain (VLA) that bind to BTC, and where the anti-VEGF binding moiety comprises a variable heavy chain domain (VHB) and a variable light chain domain (VLB) that bind to VEGF, where:
  a. the VHA and VLA comprise the amino acid sequence as set forth in SEQ ID NOs: 34 and 45, respectively; and
  b. the VHB and VLB comprise the amino acid sequence as set forth in SEQ ID NOs: 101 and 112, respectively.

In one aspect, the anti-BTC binding moiety further comprises a heavy chain constant domain (CHIA) and a light chain constant domain (CKA), and where the anti-VEGF binding moiety further comprises a heavy chain constant domain (CHIB) and a light chain constant domain (CKB).

In one aspect, a multi-specific binding molecule is in the format from the N-terminus to C-terminus as: N-VHA-CH1A-linker-VHB-CH1B-C and N-VLA-CKA-linker-VLB-CKB-C.

In one aspect, a multi-specific binding molecule comprises a heavy chain comprising the VHA, CHIA, linker, VHB, and CHIB, where the heavy chain is as set forth in SEQ ID NO: 130.

In one aspect, the heavy chain is encoded by a nucleic acid sequence as set forth in SEQ ID NO: 131.

In one aspect, a multi-specific binding molecule comprises a light chain comprising the VLA, CKA, linker, VLB, and CKB, where the light chain is as set forth in SEQ ID NO: 135.

In one aspect, the light chain is encoded by a nucleic acid sequence as set forth in SEQ ID NO: 136.

The present disclosure also provides a multi-specific binding molecule comprising an anti-BTC binding moiety and an anti-VEGF binding moiety, where the anti-BTC binding moiety comprises a variable heavy chain domain (VHA) and a variable light chain domain (VLA) that bind to BTC, and where the anti-VEGF binding moiety comprises a variable heavy chain domain (VHB) and a variable light chain domain (VLB) that bind to VEGF, where:
  a. the VHA and VLA comprise the amino acid sequence as set forth in SEQ ID NOs: 54 and 65, respectively; and
  b. the VHB and VLB comprise the amino acid sequence as set forth in SEQ ID NOs: 101 and 112, respectively.

In one aspect, the anti-BTC binding moiety further comprises a heavy chain constant domain (CHIA) and a light chain constant domain (CKA), and where the anti-VEGF binding moiety further comprises a heavy chain constant domain (CHIB) and a light chain constant domain (CKB).

In one aspect, a multi-specific binding molecule is in the format from the N-terminus to C-terminus as: N-VHA-CH1A-linker-VHB-CH1B-C and N-VLA-CKA-linker-VLB-CKB-C.

In one aspect, a multi-specific binding molecule comprises a heavy chain comprising the VHA, CHIA, linker, VHB, and CHIB, where the heavy chain is as set forth in SEQ ID NO: 140.

In one aspect, the heavy chain is encoded by a nucleic acid sequence as set forth in SEQ ID NO: 141.

In one aspect, a multi-specific binding molecule comprises a light chain comprising the VLA, CKA, linker, VLB, and CKB, where the light chain is as set forth in SEQ ID NO: 145.

In one aspect, the light chain is encoded by a nucleic acid sequence as set forth in SEQ ID NO: 146.

Further provided in the present disclosure is a multi-specific binding molecule comprising an anti-BTC binding moiety and an anti-VEGF binding moiety, where the anti-BTC binding moiety comprises a variable heavy chain domain (VHA) and a variable light chain domain (VLA) that bind to BTC, and where the anti-VEGF binding moiety comprises a variable heavy chain domain (VHB) and a variable light chain domain (VLB) that bind to VEGF, where:

a. the VHA and VLA comprise the amino acid sequence as set forth in SEQ ID NOs: 78 and 88, respectively; and b. the VHB and VLB comprise the amino acid sequence as set forth in SEQ ID NOs: 101 and 112, respectively.

In one aspect, the anti-BTC binding moiety further comprises a heavy chain constant domain (CHIA) and a light chain constant domain (CKA), and where the anti-VEGF binding moiety further comprises a heavy chain constant domain (CHIB) and a light chain constant domain (CKB).

In one aspect, a multi-specific binding molecule is in the format from the N-terminus to C-terminus as: N-VHA-CH1A-linker-VHB-CH1B-C and N-VLA-CKA-linker-VLB-CKB-C.

In one aspect, a multi-specific binding molecule comprises a heavy chain comprising the VHA, CHIA, linker, VHB, and CHIB, where the heavy chain is as set forth in SEQ ID NO: 149.

In one aspect, the heavy chain is encoded by a nucleic acid sequence as set forth in SEQ ID NO: 150.

In one aspect, a multi-specific binding molecule comprises a light chain comprising the VLA, CKA, linker, VLB, and CKB, where the light chain is as set forth in SEQ ID NO: 154.

In one aspect, the light chain is encoded by a nucleic acid sequence as set forth in SEQ ID NO: 155.

The present disclosure provides a multi-specific binding molecule, comprising a first polypeptide chain and a second polypeptide chain, where the first polypeptide chain comprises an amino acid sequence of SEQ ID NOs: 120, and the second polypeptide chain comprises an amino acid sequence of SEQ ID NOs: 125.

In one aspect, the first polypeptide chain is encoded by a nucleic acid sequence of SEQ ID NO: 121, and the second polypeptide chain is encoded by a nucleic acid sequence of SEQ ID NO: 126.

The present disclosure also provides a multi-specific binding molecule, comprising a first polypeptide chain and a second polypeptide chain, where the first polypeptide chain comprises an amino acid sequence of SEQ ID NOs: 130, and the second polypeptide chain comprises an amino acid sequence of SEQ ID NOs: 135.

In one aspect, the first polypeptide chain is encoded by a nucleic acid sequence of SEQ ID NO: 131, and the second polypeptide chain is encoded by a nucleic acid sequence of SEQ ID NO: 136.

The present disclosure further provides a multi-specific binding molecule, comprising a first polypeptide chain and a second polypeptide chain, where the first polypeptide chain comprises an amino acid sequence of SEQ ID NOs: 140, and the second polypeptide chain comprises an amino acid sequence of SEQ ID NOs: 145.

In one aspect, the first polypeptide chain is encoded by a nucleic acid sequence of SEQ ID NO: 141, and the second polypeptide chain is encoded by a nucleic acid sequence of SEQ ID NO: 146.

The present disclosure also provides a multi-specific binding molecule, comprising a first polypeptide chain and a second polypeptide chain, where the first polypeptide chain comprises an amino acid sequence of SEQ ID NOs: 149, and the second polypeptide chain comprises an amino acid sequence of SEQ ID NOs: 154.

In one aspect, the first polypeptide chain is encoded by a nucleic acid sequence of SEQ ID NO: 150, and the second polypeptide chain is encoded by a nucleic acid sequence of SEQ ID NO: 155.

The present disclosure provides a polynucleotide comprising a nucleotide sequences encoding the multi-specific binding molecule as described throughout.

The present disclosure also provides an expression cassette comprising the polynucleotide as described throughout.

Also provided in the present disclosure is a vector comprising the expression cassette as described throughout.

Further provided in the present disclosure is a host cell comprising the polynucleotide as described throughout.

The present disclosure provides a method of producing a multi-specific binding molecule, comprising culturing the host cell under suitable conditions for expression of the multi-specific binding molecule or a fragment thereof.

In one aspect, the method further comprises purifying the multi-specific binding molecule.

The present disclosure provides a pharmaceutical composition comprising an effective amount of the multi-specific binding molecule as described throughout.

In one aspect, the pharmaceutical composition further comprises a pharmaceutically acceptable excipient, diluent, or carrier.

In one aspect, the pharmaceutical composition further comprises one or more therapeutic agents.

Also provided in the present disclosure is a method of treating an ophthalmic disorder in a subject in need thereof, comprising administering to the subject an effective amount of the multi-specific binding molecule or the pharmaceutical composition as described throughout.

In one aspect, the multi-specific binding molecule or the pharmaceutical composition is administered intravitreally to the subject.

In one aspect, the multi-specific binding molecule or the pharmaceutical composition is administered via subretinal injection.

In one aspect, the ophthalmic disorder is selected from the group consisting of diabetic macular edema, age-related macular degeneration, neovascular age-related macular degeneration, neovascular glaucoma, diabetic retinopathy, macular edema, pathologic myopia, retinal vein occlusions, retinopathy of prematurity, and abnormal vascular proliferation associated with phakomatoses.

In one aspect, the ophthalmic disorder is diabetic macular edema.

Provided in the present disclosure is a method for preventing, treating, or managing an ophthalmic disorder comprising administering to a subject an effective amount of the multi-specific binding molecule as described in the present disclosure, where the multi-specific binding molecule reduces retinal leakage and/or retinal thickening in the subject relative to a control subject.

Further provided in the present disclosure is a kit comprising the multi-specific binding molecule or the pharmaceutical composition as described throughout.

In one aspect, the kit further comprise an instruction for use.

In one aspect, the kit further comprise a syringe.

Provided in the present disclosure is a method of preventing or treating macular edema, DME, AMD, neovascular AMD, or RVO in a subject in need thereof, comprising administering intravitreally to the subject a multi-specific binding molecule described herein, at a dose ranging from about 0.25 mg/eye to 7.5 mg/eye.

In one aspect, the dose is about 0.25 mg/eye, 0.75 mg/eye, 2.5 mg/eye, or 7.5 mg/eye.

In one aspect, the dose is 0.25 mg/eye.
In one aspect, the dose is 0.75 mg/eye.
In one aspect, the dose is 1 mg/eye.
In one aspect, the dose is 2.5 mg/eye.
In one aspect, the dose is 3 mg/eye.
In one aspect, the dose is 5 mg/eye.
In one aspect, the dose is 7.5 mg/eye.
In one aspect, the dose is 0.25 mg/eye, 0.3 mg/eye, 0.35 mg/eye, 0.4 mg/eye, 0.45 mg/eye, 0.5 mg/eye, 0.55 mg/eye, 0.6 mg/eye, 0.65 mg/eye, 0.7 mg/eye, 0.75 mg/eye, 0.8 mg/eye, 0.85 mg/eye, 0.9 mg/eye, 0.95 mg/eye, 1.0 mg/eye, 1.1 mg/eye, 1.2 mg/eye, 1.3 mg/eye, 1.4 mg/eye, 1.5 mg/eye, 1.6 mg/eye, 1.7 mg/eye, 1.8 mg/eye, 1.9 mg/eye, 2.0 mg/eye, 2.1 mg/eye, 2.2 mg/eye, 2.3 mg/eye, 2.4 mg/eye, 2.5 mg/eye, 2.6 mg/eye, 2.7 mg/eye, 2.8 mg/eye, 2.9 mg/eye, 3.0 mg/eye, 3.1 mg/eye, 3.2 mg/eye, 3.3 mg/eye, 3.4 mg/eye, 3.5 mg/eye, 3.6 mg/eye, 3.7 mg/eye, 3.8 mg/eye, 3.9 mg/eye, 4.0 mg/eye, 4.1 mg/eye, 4.2 mg/eye, 4.3 mg/eye, 4.4 mg/eye, 4.5 mg/eye, 4.6 mg/eye, 4.7 mg/eye, 4.8 mg/eye, 4.9 mg/eye, 5.0 mg/eye, 5.1 mg/eye, 5.2 mg/eye, 5.3 mg/eye, 5.4 mg/eye, 5.5 mg/eye, 5.6 mg/eye, 5.7 mg/eye, 5.8 mg/eye, 5.9 mg/eye, 6.0 mg/eye, 6.1 mg/eye, 6.2 mg/eye, 6.3 mg/eye, 6.4 mg/eye, 6.5 mg/eye, 6.6 mg/eye, 6.7 mg/eye, 6.8 mg/eye, 6.9 mg/eye, 7.0 mg/eye, 7.1 mg/eye, 7.2 mg/eye, 7.3 mg/eye, 7.4 mg/eye, or 7.5 mg/eye.

In one aspect, the multi-specific binding molecule comprises 1) the anti-BTC binding moiety comprising the amino acid sequence of SEQ ID NOs: 10 and 21, respectively; and 2) the anti-VEGF binding moiety comprising the amino acid sequence of SEQ ID NOs: 101 and 112, respectively.

In another aspect, the administration is once a month.

DETAILED DESCRIPTION

In general, the present disclosure is based in part on the discovery of antibodies specific for betacellulin (BTC). In particular, the inventors have discovered anti-BTC antibodies having properties compatible with therapeutic utility (i.e., the antibodies bind BTC with an affinity and specificity sufficient to achieve a desirable therapeutic effect). Based in part on this discovery, the present disclosure features therapeutic compositions including molecules including an antibody, or antibody fragment, specific for BTC attached to another therapeutic moiety, e.g., anti-VEGF antibody or antibody fragment. Such therapeutic moieties include antibodies, or fragments thereof, and proteins that bind to therapeutic targets in tissues having BTC (e.g., the vitreous) as well as compounds (e.g., low molecular weight compounds) that modulate therapeutic targets in such tissues. In cases where such therapeutic moieties include antibodies, the overall therapeutic composition can be a multispecific antibody (e.g., a bispecific antibody). In particular aspects, also provided herein are methods of treating an ocular disorder (e.g., AMD, e.g., neovascular AMD, DME, DR, etc.) by administering an anti-BTC antagonist and an anti-VEGF antagonist.

i. Terminology

Unless defined otherwise, all technical and scientific terms used herein have the same meaning as commonly understood by those of ordinary skill in the art to which this present disclosure pertains. Any references cited herein, including, e.g., all patents, published patent applications, and non-patent publications, are incorporated by reference in their entirety. To facilitate understanding of the disclosure, several terms and abbreviations as used herein are defined below as follows:

As used herein, the singular forms "a," "an," and "the" include plural references unless the content clearly dictates otherwise. Thus, for example, reference to "an antibody" includes a mixture of two or more such antibodies.

Unless otherwise specifically stated or clear from context, as used herein, the term "about" in relation to a numerical value is understood as being within the normal tolerance in the art, e.g., within two standard deviations of the mean. Thus, "about" can be within +/−10%, 9%, 8%, 7%, 6%, 5%, 4%, 3%, 2%, 1%, 0.1%, 0.05%, or 0.01% of the stated value, preferably +/−10% of the stated value. When used in front of a numerical range or list of numbers, the term "about" applies to each number in the series, e.g., the phrase "about 1-5" should be interpreted as "about 1—about 5", or, e.g., the phrase "about 1, 2, 3, 4" should be interpreted as "about 1, about 2, about 3, about 4, etc."

In all cases where the term "comprise", "comprises", "comprising" or the like are used in reference to a sequence (e.g., an amino acid sequence), it shall be understood that said sequence can also be limited by the term "consist", "consists", "consisting" or the like. As used herein, the phrase "consisting essentially of" refers to the genera or species of active pharmaceutical agents included in a method or composition, as well as any excipients inactive for the intended purpose of the methods or compositions. In some aspects, the phrase "consisting essentially of" expressly excludes the inclusion of one or more additional active agents other than a multi-specific binding molecule of the present disclosure. In some aspects, the phrase "consisting essentially of" expressly excludes the inclusion of one or more additional active agents other than a multi-specific binding molecule of the present disclosure and a second co-administered agent.

The term "betacellulin" or "BTC" refers to a growth factor of the EGF family in an organism. BTC activity can be measured by its binding to 1) ErbB1; 2) ErbB4; 3) ErbB homodimer (e.g., ErbB1/ErbB1 and ErbB4/ErB4) and/or 4) ErbB heterodimer (e.g., ErbB1/ErbB2, ErB1/ErB3, ErB1/ErB4, ErB2/ErB3, and ErB2/ErB4). See Dunbar and Goddard, *Int'l. J. Biochem. & CellBiol.*, 2000, 32: 805-815. BTC activity can also be measured by the level of phosphorylated ERK1/2. In humans, it is encoded by the BTC gene located on chromosome 4 at locus 4q13-q21. Human BTC is expressed as a 178-residuce protein as pro-BTC (e.g., NCBI: NP_001720.1 or SEQ ID NO: 156). The mature, secreted human BTC is composed of 80 amino acid residues, i.e., residues 32 to 111 of pro-BTC, as set forth in SEQ ID NO: 158. Mouse betacellulin is composed of 177 amino acid residuces (e.g., NCBI: NP_031594.1). Rat betacellulin is composed of 177 amino acid residuces (e.g., NCBI: GenBank: BAA96731.1).

The term "vascular endothelial growth factor" or "VEGF" refers to a protein having VEGF activity in an organism, e.g., induces proliferation and migration of vascular endothelial cells, and can be essential for both physiological and pathological angiogenesis. In mammals, the VEGF family comprises five members: VEGF-A, placenta growth factor (PGF), VEGF-B, VEGF-C and VEGF-D. Human VEGF exists as at least six isoforms (VEGF$_{121}$, VEGF$_{145}$, VEGF$_{165}$, VEGF$_{183}$, VEGF$_{189}$, and VEGF$_{206}$) that arise from alternative splicing of mRNA of a single gene (Ferrara N, Davis Smyth T. Endocr Rev 18:1-22 (1997)). VEGF$_{165}$, the most abundant isoform, is a basic, heparin binding, dimeric glycoprotein with a molecular mass of about 45,000 daltons. The term "human VEGF" as used herein refers to the 165-amino acid human vascular endothelial cell growth factor, and related 121-, 189-, and 206-, (and other isoforms) amino acid vascular endothelial cell growth factors, as described by Leung et al., Science 246:1306 (1989), and Houck et al., *Mol. Endocrin.* 5:1806 (1991) together with the naturally occurring allelic and processed forms of those growth factors.

The term "anti-BTC binding moiety," as used herein, means a polypeptide (e.g., an antibody, or antigen binding fragment thereof) that specifically binds to BTC. For the avoidance of any doubt, non-limiting examples of "anti-BTC binding moiety" include full length antibodies and antigen binding fragments thereof such as Fabs, scFvs, Fvs, single domain antibodies, etc. In a particular aspect, an anti-BTC antibody is a Fab or scFv. In a particular aspect, an anti-BTC binding moiety specifically binds to human BTC and/or cynomolgus BTC.

The term "anti-VEGF binding moiety," as used herein, means a polypeptide (e.g., an antibody, or antigen binding fragment thereof as set forth below), that specifically binds to VEGF (as defined below). For the avoidance of any doubt, non-limiting examples of "anti-VEGF binding moiety" include full length antibodies and antigen binding fragments thereof such as Fabs, scFvs, Fvs, single domain antibodies, etc., as set forth below. In a particular aspect, an anti-VEGF antibody is a Fab or scFv. In a particular aspect, an anti-VEGF binding moiety specifically binds to human VEGF-A.

The phrase "binds specifically", "specifically binds", or "selectively binds," when used in the context of describing the interaction between an antigen (e.g., a protein) and a multi-specific binding molecule of the disclosure, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the multi-specific binding molecule of the disclosure with a particular binding specificity bind to a particular antigen at least two times the background and do not substantially bind in a significant amount to other antigens present in the sample. In one aspect, under designated immunoassay conditions, the multi-specific binding molecule of the disclosure with a particular binding specificity binds to a particular antigen at least ten (10) times the background and does not substantially bind in a significant amount to other antigens present in the sample. Specific binding to an antibody or binding agent under such conditions can require the multi-specific binding molecule of the disclosure to have been selected for its specificity for a particular protein. As desired or appropriate, this selection can be achieved by subtracting out multi-specific binding molecules that cross-react with molecules from other species (e.g., mouse or rat) or other subtypes.

In some aspects, specific binding of a multi-specific binding molecule of the disclosure means binding with an equilibrium constant ($K^A$) ($k_{on}/k_{off}$) of at least $10^2 M^{-1}$, at least $5 \times 10^2 M^{-1}$, at least $10^3 M^{-1}$, at least $5 \times 10^3 M^{-1}$, at least $10^4 M^{-1}$, at least $5 \times 10^4 M^{-1}$, at least $10^5 M^{-1}$, at least $5 \times 10^5 M^{-1}$, at least $10^6 M^{-1}$, at least $5 \times 10^6 M^{-1}$, at least $10^7 M^{-1}$, at least $5 \times 10^7 M^{-1}$, at least $10^8 M^{-1}$, at least $5 \times 10^8 M^{-1}$, at least $10^9 M^{-1}$, at least $5 \times 10^9 M^{-1}$, at least $10^{10} M^{-1}$, at least $5 \times 10^{10} M^{-1}$, at least $10^{11} M^{-1}$, at least $5 \times 10^{11} M^{-1}$, at least $10^{12} M^{-1}$, at least $5 \times 10^{12} M^{-1}$, at least $10^{13} M^{-1}$, at least $5 \times 10^{13}$ $M^{-1}$, at least $10^{14} M^{-1}$, at least $5 \times 10^{14} M^{-1}$, at least $10^{15} M^{-1}$, or at least $5 \times 10^{15} M^{-1}$.

In some aspects, specific binding of a multi-specific binding molecule of the disclosure means a dissociation rate constant ($K_D$) ($k_{off}/k_{on}$) of less than $5 \times 10^{-2} M$, less than $10^{-2} M$, less than $5 \times 10^{-3} M$, less than $10^{-3} M$, less than $5 \times 10^{-4} M$, less than $10^{-4} M$, less than $5 \times 10^{-5} M$, less than $10^{-5} M$, less than $5 \times 10^{-6} M$, less than $10^{-6} M$, less than $5 \times 10^{-7} M$, less than $10^{-7} M$, less than $5 \times 10^{-8} M$, less than $10^{-8} M$, less than $5 \times 10^{-9} M$, less than $10^{-9} M$, less than $5 \times 10^{-10} M$, less than $10^{-10} M$, less than $5 \times 10^{-11}$ $M$, less than $10^{-11} M$, less than $5 \times 10^{-12} M$, less than $10^{-12} M$, less than $5 \times 10^{-13} M$, less than $10^{-13} M$, less than $5 \times 10^{-14} M$, less than $10^{-14} M$, less than $5 \times 10^{-15} M$, or less than $10^{-15} M$ or lower, and binds to the target antigen with an affinity that is at least two-fold greater than its affinity for binding to a non-specific antigen (e.g., HSA).

The term "$K_D$" or "Kd" refers to the dissociation equilibrium constant of a particular antibody-antigen interaction.

The term "therapeutic target binding moiety," as used herein, means a molecule that specifically binds a therapeutic target of interest. This molecule can be an antibody, or antigen binding fragment thereof (as set forth below), an antigen-specific binding moiety such as a DARPin, a Fynomer, an affibody, an adnectin, an affilin, an anticalin, an avimer, a centyrin or a RNA molecule such like an aptamer. This therapeutic target binding moiety can also be a polypeptide, such as a receptor or part of a receptor that specifically binds a therapeutic target of interest. For the avoidance of any doubt, non-limiting examples of "anti-BTC binding moiety" include full length antibodies and antigen binding fragments thereof such as Fabs, scFvs, Fvs, single domain antibodies, etc., as set forth below.

The term "antibody" as used herein refers to a whole antibody or antigen binding fragment thereof. A whole antibody is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2, and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. The term "antibody" includes, but is not limited to, monoclonal antibodies, human antibodies, humanized antibodies, camelised antibodies, chimeric antibodies, bispecific or multi-specific antibodies. The antibodies can be of any isotype/ class (e.g., IgG, IgE, IgM, IgD, IgA, and IgY) or subclass (e.g., $IgG_1$, $IgG_2$, $IgG_3$, $IgG_4$, $IgA_1$, and $IgA_2$).

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors. Antibodies can be of any isotype (e.g., immunoglobulin G (IgG), immunoglobulin E (IgE), immunoglobulin M (IgM), immunoglobulin D (IgD), immunoglobulin A (IgA) and immunoglobulin Y (IgY)), class (e.g., IgG1, IgG2, IgG3, IgG4, IgA1 and IgA2) or subclass. The term "IgG" or "IgG antibody" as used herein, and unless specified otherwise, means a type G whole antibody or Ig.

The term "light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, VH, and three constant region domains, $C_H1$, $C_H2$, and $C_H3$. The VH domain is at the amino-terminus of the polypeptide, and the CH domains are at the carboxyl-terminus, with the $C_H3$ being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain aspects, variable regions of different antibodies differ extensively in amino acid sequence even among antibodies of the same species. The variable region of an antibody typically determines specificity of a particular antibody for its target.

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme); Al-Lazikani et al., (1997) JMB 273,927-948 ("Chothia" numbering scheme); and Lefranc et al., (2003) Dev. Comp. Immunol., 27, 55-77 ("IMGT" numbering scheme). The Kabat definition is a standard for numbering the residues in an antibody and is typically used to identify CDR regions. See, e.g., Johnson & Wu, Nucleic Acids Res., 28: 214-8 (2000). The Chothia definition is similar to the Kabat definition, but the Chothia definition takes into account positions of certain structural loop regions. See, e.g., Chothia et al., J. Mol. Biol., 196: 901-17 (1986); Chothia et al., Nature, 342: 877-83 (1989).

Other methods for delineating the CDR regions can alternatively be used, for example, the CDR definitions of both Kabat and Chothia can be combined ("Combined" system). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia, the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the Combined CDRs consist of amino acid residues 26-35 (HCDR1), 50-65 (HCDR2), and 95-102 (HCDR3) in human VH, and amino acid residues 24-34 (LCDR1), 50-56 (LCDR2), and 89-97 (LCDR3) in human VL. As another example, under IMGT, the CDR amino acid residues in the heavy chain variable domain (VH) are numbered 26-33 (HCDR1), 51-58 (HCDR2), and 97-108 (HCDR3); and the CDR amino acid residues in the light chain variable domain (VL) are numbered 27-36 (LCDR1), 54-56 (LCDR2), and 93-101 (LCDR3).

The term "antibody framework" or "FR" as used herein refers to the part of the variable domain, either VL or VH, which serves as a scaffold for the antigen binding loops (CDRs) of this variable domain. In essence, it is the variable domain without the CDRs. Under IMGT, the CDR regions of an antibody can be determined using the program IMGT/DomainGap Align.

The term "antigen binding fragment" of an antibody, as used herein, refers to one or more fragments of an antibody, or one or more polypeptides including such a fragment, that retain the ability to specifically bind to a given antigen (e.g., BTC and VEGF). Antigen binding functions of an antibody can be performed by fragments of an intact antibody. Examples of binding fragments encompassed within the term antigen binding fragment of an antibody include, but are not limited to, a Fab fragment, a monovalent fragment consisting of the VL, VH, $C_L$ and CH1 domains; a F(ab)$_2$ fragment, a bivalent fragment comprising two Fab fragments linked by a disulfide bridge at the hinge region; an Fd fragment consisting of the VH and CH1 domains; an Fv fragment consisting of the $V_L$ and VH domains; a single chain Fv fragment (scFv) consisting of the $V_L$ and VH domains connected by a linker sequence; and a single domain antibody (dAb) fragment (Ward et al., 1989 Nature 341:544-546), which consists of a VH domain or a $V_L$ domain. Antigen binding fragments can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703,199, which describes fibronectin polypeptide monobodies). Antibody binding fragments can be incorporated into single chain molecules comprising a pair of tandem Fv segments (for example, VH-CH1-$V_H$-CH1) which, together with complementary light chain polypeptides (for example, $V_L$-VC-$V_L$-VC), form a pair of antigen binding regions (Zapata et al., (1995) Protein Eng. 8:1057-1062; and U.S. Pat. No. 5,641,870).

A "Fab" fragment as used herein comprises one constant and one variable domain of each of the heavy and the light chain. The heavy chain of a Fab molecule may not form a disulfide bond with another heavy chain molecule.

A "Fab' fragment" as used herein comprises one light chain and a portion of one heavy chain that contains the VH domain and the $C_H1$ domain and also the region between the $C_H1$ and $C_H2$ domains, such that an interchain disulfide bond can be formed between the two heavy chains of two Fab' fragments to form an $F(ab')_2$ molecule.

A "$F(ab')_2$ fragment" as used herein contains two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains.

The "Fv region" comprises the variable regions from both the heavy and light chains, but lacks the constant regions.

The term "single-chain Fv" or "scFv" as used herein refers to antibody fragments comprise the VH and VL domains of antibody, where these domains are present in a single polypeptide chain. Preferably, the Fv polypeptide further comprises an internal polypeptide linker between the VH and VL domains which enables the scFv to form the desired structure for antigen binding. An scFv can also have an engineered internal disulfide bridge that enhances stability. For a review of scFvs see Plückthun in *The Pharmacology of Monoclonal Antibodies*, vol. 113, Rosenburg and Moore eds., (1994) Springer-Verlag, New York, pp. 269-315. In preferred aspects, scFvs used in the multi-specific binding molecules of the disclosure have the general structures: $NH_2$-$V_L$-linker-$V_H$—COOH or $NH_2$-$V_H$-linker-$V_L$-COOH.

An "affinity matured" antibody as used herein is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "parent" or "parental" antibody as used herein is one which is encoded by an amino acid sequence used for the preparation of an affinity matured antibody or its variant. Preferably, the parent antibody has a human framework region and, if present, has human antibody constant region(s). For example, a parent antibody may be a humanized or human antibody.

The term "diabody" as used herein refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., (1993) Proc. Natl. Acad. Sci. USA 90:6444-6448.

The term "monospecific binding molecule" "or monospecific antibody" as used herein, refers to a molecule that binds to one epitope on a target antigen. In one aspect, a monospecific binding molecule or monospecific antibody of the present disclosure binds to BTC. In another aspect, a monospecific binding molecule or monospecific antibody of the present disclosure binds to VEGF.

The term "multi-specific binding molecule" or "multi-specific antibody" as used herein refers to a molecule that binds to two or more different antigens. Recognition of each antigen is generally accomplished via an "antigen-binding domain" (e.g., a "BTC antigen-binding domain", a "VEGF antigen-binding domain"). The term "multi-specific"includes "bispecific," i.e., a molecule that binds to two different antigens. In some aspects, a multi-specific binding molecule contains one or more polypeptide chains that each comprises one antigen binding domain. In one aspect, the multi-specific binding molecule contains a VH or a VL. In some aspects, a multi-specific binding molecule contains one or more polypeptide chains that each comprise more than one (e.g., two) antigen binding domains. In some aspects, the multi-specific binding molecules comprise two, three, four, or more polypeptide chains that together comprise a plurality, e.g., two or more, e.g., two, three, or four antigen binding domains.

The term "bispecific binding molecule" or "bispecific antibody" refer to molecules that combine the antigen binding sites of two antibodies within a single molecule. In one aspect, the bispecific binding molecule or bispecific antibody contains a single polypeptide. In another aspect, the bispecific binding molecule or bispecific antibody contains two polypeptides connected via disulfide brideges or any other covalent bonds. Thus, a bispecific antibody is able to bind two different antigens simultaneously or sequentially. Methods for making bispecific antibodies are well known in the art. Various formats for combining two antibodies are also known in the art. Forms of bispecific antibodies of the present disclosure include, but are not limited to, a diabody, a single-chain diabody, Fab dimerization (Fab-Fab), Fab-scFv, and a tandem antibody, as known to those of skill in the art.

The term "bivalent molecule" as used herein refers to a molecule that has two antigen-binding domains. The term "trivalent molecule" as used herein refers to a molecule that has three antigen-binding domains. In some aspects, a trivalent molecule of the present disclosure is a trivalent antibody-like molecule. In some aspects, a trivalent molecule can consist of two antigen-binding domains capable of binding to the same epitope of the same antigen, and a third antigen-binding domain that binds to a distinct-antigen. Such aspects are considered trivalent bispecific molecules.

The term "multivalent molecule" refers to a molecule that has at least two antigen binding sites, where the antigen binding sites can have specificity for the same antigen or different antigens. In some aspects, a multivalent molecule of the present disclosure is a multivalent antibody-like molecule. In some aspects, a multivalent molecule of the present disclosure is a multivalent antibody. In some aspects, a multivalent molecule is a bivalent molecule, trivalent molecule, or a tetravalent molecule. Trimerizing domain are described for example in EP 1 012 280B1. Pentamerizing modules are described for example in PCT/EP97/05897.

The term "substantially similar," or "substantially the same," as used herein refers to a sufficiently high degree of similarity between two numeric values (generally one associated with an antibody-like molecule of the disclosure and the other associated with a reference/comparator antibody or antibody-like molecule) such that one of skill in the art would consider the difference between the two values to be of little or no biological and/or statistical significance within the context of the biological characteristic measured by said values (e.g., Tm values or the amount of the assembled antibodies). The difference between said two values is preferably less than about 50%, preferably less than about 40%, preferably less than about 30%, preferably less than about 20%, preferably less than about 10% as a function of the value for the reference/comparator antibody.

The term "antigen" refers to a molecule or a portion of a molecule capable of being bound by a selective binding agent, such as an antigen binding protein (including, e.g., an antibody or immunological functional fragment thereof). In some aspects, the antigen is capable of being used in an animal to produce antibodies capable of binding to that antigen. An antigen can possess one or more epitopes that are capable of interacting with different antigen binding proteins, e.g., antibodies.

The term "epitope" or "antigenic determinant" as used herein refers to any determinant capable of binding with high affinity to an antibody or an antibody-like molecule. An epitope is a region of an antigen that is bound by an antibody (or an antibody-like molecule) that specifically targets that antigen, and when the antigen is a protein, includes specific amino acids that directly contact the antibody or the antibody-like molecule. Most often, epitopes reside on proteins, but in some instances, can reside on other kinds of molecules, such as nucleic acids. Epitope determinants can include chemically active surface groupings of molecules such as amino acids, sugar side chains, phosphoryl or sulfonyl groups, and can have specific three dimensional structural characteristics, and/or specific charge characteristics.

Generally, multi-specific binding molecules that are specific for a particular target antigen will preferentially recognize an epitope on that target antigen in a complex mixture of proteins and/or macromolecules.

Regions of a given polypeptide that include an epitope can be identified using any number of epitope mapping techniques, known in the art. See, e.g., Epitope Mapping Protocols in Methods in Molecular Biology, Vol. 66 (Glenn E. Morris, Ed., 1996) Humana Press, Totowa, N.J. For example, linear epitopes can be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., (1984) Proc. Natl. Acad. Sci. USA 8:3998-4002; Geysen et al., (1985) Proc. Natl. Acad. Sci. USA 82:78-182; Geysen et al., (1986) Mol. Immunol. 23:709-715. Similarly, conformational epitopes are readily identified by determining spatial conformation of amino acids such as by, e.g., x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., (1981) Proc. Natl. Acad. Sci USA 78:3824-3828; for determining antigenicity profiles, and the Kyte-Doolittle technique, Kyte et al., (1982) J.Mol. Biol. 157:105-132; for hydropathy plots.

The term "compete" when used in the context of antigen binding proteins that compete for the same epitope means competition between antigen binding proteins as determined by an assay in which the antigen binding protein (e.g., antibody or immunologically functional fragment thereof) being tested prevents or inhibits (e.g., reduces) specific binding of a reference antigen binding protein (e.g., a ligand, or a reference antibody) to a common antigen (e.g., BTC or a fragment thereof). Numerous types of competitive binding assays can be used to determine if one antigen binding protein competes with another, for example: solid phase direct or indirect radioimmunoassay (RIA), solid phase direct or indirect enzyme immunoassay (EIA), sandwich competition assay (see, e.g., Stahli et al., 1983, *Methods in Enzymology* 9:242-253); solid phase direct biotin-avidin EIA (see, e.g., Kirkland et al., 1986, *J. Immunol.* 137:3614-3619) solid phase direct labeled assay, solid phase direct labeled sandwich assay (see, e.g., Harlow and Lane, 1988, *Antibodies, A Laboratory Manual*, Cold Spring Harbor Press); solid phase direct label RIA using I-125 label (see, e.g., Morel et al., 1988, *Molec. Immunol.* 25:7-15); solid phase direct biotin-avidin EIA (see, e.g., Cheung, et al., 1990, *Virology* 176:546-552); and direct labeled RIA (Moldenhauer et al., 1990, *Scand. J. Immunol.* 32:77-82). Typically, such an assay involves the use of purified antigen bound to a solid surface or cells bearing either of these, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

The terms "polypeptide" and "protein" are used interchangeably herein to refer to a polymer of amino acid residues. The phrases also apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

As used herein, the term "polypeptide chain" refers to a complete amino acid chain of a multi-specific binding molecule of the disclosure having all the component regions and domains therein.

The terms "constant region" or "constant domain" refer to a carboxy terminal portion of the light and heavy chain which is not directly involved in binding of the antibody to antigen but exhibits various effector functions, such as interaction with the Fc receptor. The terms refer to the portion of an immunoglobulin molecule having a more conserved amino acid sequence relative to the other portion of the immunoglobulin, the variable domain, which contains the antigen binding site. The constant domain contains the CH1, CH2, and CH3 domains of the heavy chain and the $C_L$ domain of the light chain.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, pyroglutamate, c-terminal lysine cleavage, and O-phosphoserine, for example due to post-translational modifications. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known. Such conservatively modified variants are in addition to and do not exclude polymorphic variants, interspecies homologs, and alleles of the present disclosure. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some aspects, the term "conservative sequence modifications" or "conservative modifications" are used to refer to amino acid modifications that do not significantly affect or alter the binding characteristics of the antibody containing the amino acid sequence.

In certain aspects, the term "dose" refers to a quantity of therapeutic agent, which therapeutic agent can be a protein (e.g., an antibody or antigen-binding fragment) or a nucleic acid or a therapeutic target binding moiety can be a small molecule (e.g., <900 Daltons) therapeutic compound, administered to a subject all at one time (unit dose), or in two or more administrations over a defined time interval. For example, dose can refer to the quantity of protein (e.g., an anti-BTC antibody or functional fragment thereof conjugated to a molecule, for example, a protein comprising an anti-VEGF antibody or functional fragment thereof) administered to a subject over the course of three weeks or one, two, three, four, five, six, or more months (e.g., by a single administration, or by two or more administrations). The interval between doses can be any desired amount of time and is referred to as the "dosing interval."

The term "pharmaceutically effective" when referring to a dose means sufficient amount of the protein (e.g., antibody or antigen binding fragment) or other pharmaceutically active agent to provide the desired effect (e.g., improved vision or preventing further loss of vision). The amount that is "effective" will vary from subject to subject, depending on the age and general condition of the individual, the particular drug or pharmaceutically active agent and the like. Thus, it is not always possible to specify an exact "effective" amount applicable for all patients. However, an appropriate "effective" dose in any individual case can be determined by one of ordinary skill in the art using routine experimentation.

The term "human antibody," as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik, et al. (J. Mol. Biol. 296, 57-86, 2000). The human antibodies of the present disclosure can include amino acid residues not encoded by human sequences (e.g., mutations introduced by random or site-specific mutagenesis in vitro or by somatic mutation in vivo, or a conservative substitution to promote stability or manufacturing). However, the term "human antibody", as used herein, is not intended to include antibodies in which CDR sequences derived from the germline of another mammalian species, such as a mouse, have been grafted onto human framework sequences.

The term "monoclonal antibody" or "monoclonal antibody composition" as used herein refers to polypeptides, including antibodies and antigen-binding fragments that have substantially identical amino acid sequence or are derived from the same genetic source. This term also includes preparations of antibody molecules of single molecular composition. A monoclonal antibody composition displays a single binding specificity and affinity for a particular epitope. Methods for generation of monoclonal antibodies using phage display technology are known in the art (Proetzel, G., Ebersbach, H. (Eds.) Antibody Methods and Protocols. Humana Press ISBN 978-1-61779-930-3; 2012).

The term "humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin lo sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1: 105-115 (1998); Harris, Biochem. Soc. Transactions 23:1035-1038 (1995); Hurle and Gross, Curr. Op. Biotech. 5:428-433 (1994).

As used herein, "identity" refers to the sequence matching between two polypeptides, molecules or between two nucleic acids. When a position in both of the two compared sequences is occupied by the same base or amino acid (for instance, if a position in each of two polypeptides is occupied by a lysine), then the respective molecules are identical at that position. The "percentage identity" between two sequences is a function of the number of identical positions shared by the sequences, taking into account the number of gaps, and the length of each gap, which need to be introduced for optimal alignment of the two sequences. Generally, a comparison is made when two sequences are aligned to give maximum identity. Such alignment can be provided using, for instance, the method of the Needleman and Wunsch (J. Mol. Biol. (48):444-453 (1970)) algorithm which has been incorporated into the GAP program in the GCG software package, using either a Blosum 62 matrix or a PAM250 matrix, and a gap weight of 16, 14, 12, 10, 8, 6, or 4 and a length weight of 1, 2, 3, 4, 5, or 6. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. A comparison window can be used, where reference to a segment of any one of the number of contiguous positions selected from the group consisting of from 20 to 600, usually about 50 to about 200, more usually about 100 to about 150 in which a sequence can be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands. The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. The percent identity between two amino acid sequences can also be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available on the world wide web at gcg.com), using either a Blosum 62 matrix or a PAM250 matrix, and a gap weight of 16, 14, 12, 10, 8, 6, or 4 and a length weight of 1, 2, 3, 4, 5, or 6. Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the two nucleic acid sequences.

The terms "percent complementarity" or "percent complementary", as used herein in reference to two nucleotide sequences, is similar to the concept of percent identity but refers to the percentage of nucleotides of a query sequence that optimally base-pair or hybridize to nucleotides of a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" is calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen bonding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present disclosure, when two sequences (query and subject) are optimally base-paired (with allowance for mismatches or non-base-paired nucleotides but without folding or secondary structures), the "percent complementarity" for the query sequence is equal to the number of base-paired positions between the two sequences divided by the total number of positions in the query sequence over its length (or by the number of positions in the query sequence over a comparison window), which is then multiplied by 100%.

The term "isolated antibody" refers to an antibody that is substantially free of other antibodies or other proteins having different antigenic specificities. Moreover, an isolated antibody can be substantially free of other cellular material and/or chemicals, for example, an antibody isolated from a cell supernatant.

The term "linked" or "linking" in the context of anti-BTC multispecific binding molecules described herein refers to the attachment of an anti-BTC binding moiety, such as, for example, the anti-BTC antibodies or functional fragment thereof that bind BTC listed in Table 1, to a molecule. Attachment of the anti-BTC binding moiety to a protein can occur, for example, at the amino or carboxy terminus of the molecule, e.g., an anti-VEGF antibody or functional fragment thereof. The anti-BTC binding moiety can also be attached to both the amino and carboxy termini of a protein. The anti-BTC binding moiety can also be attached to one or more amino acids or nucleic acids within the protein or nucleic acid molecule, respectively. Linking of the anti-BTC binding moiety to a molecule can be accomplished by any method known in the art, including, but not limited to, expression of the anti-BTC binding moiety and molecule as a fusion protein, or by chemically joining an anti-BTC binding moiety to a molecule after translation, either directly to each other, or through a linker by disulfide bonds, etc.

The term "linker" or "linked" in the context of a multispecific binding molecule refers to one portion of a multispecific binding molecule being attached, directly or indirectly, to another portion of the molecule, e.g., an anti-BTC binding moiety to an anti-VEGF binding moiety. The linker can be covalently attached to one or both of the amino or carboxy termini of an anti-BTC binding moiety and/or a protein or nucleic acid molecule. The peptide linker can also be conjugated to an amino acid or nucleic acid within the sequence of a protein or nucleic acid molecule, respectively. It is contemplated that, in certain aspects, peptide linkers can be, for example, about 2 to 25 residues in length.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260: 2605-2608, 1985; and Rossolini et al., Mol. Cell. Probes 8:91-98, 1994).

The term "operably linked" refers to a functional relationship between two or more polynucleotide (e.g., DNA) segments. Typically, the term refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term, "optimized" or "codon optimization" means that a nucleotide sequence has been altered to encode an amino acid sequence using codons that are preferred in the production cell or organism, generally a eukaryotic cell, for example, a cell of *Pichia*, a Chinese Hamster Ovary cell (CHO), a human cell, or a prokaryotic cell, for example, an *Escherichia coli* cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, e.g., methods disclosed in at least U.S. Pat. Nos. 5,786,464 and 6,114,148. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

As used herein, the term "protein" refers to any organic compounds made of amino acids arranged in one or more linear chains and folded into a three-dimensional conformation. The amino acids in a polymer chain are joined together by the peptide bonds between the carboxyl and amino groups of adjacent amino acid residues. The term "protein" further includes, without limitation, peptides, single chain polypeptide or any complex molecules consisting primarily of two or more chains of amino acids. It further includes, without limitation, glycoproteins or other known post-translational modifications. It further includes known natural or artificial chemical modifications of natural proteins, such as without limitation, glycoengineering, pegylation, hesylation and the like, incorporation of non-natural amino acids, and amino acid modification for chemical conjugation with another molecule.

The terms "polypeptide" and "protein" are used interchangeably herein to refer to a polymer of amino acid residues. The phrases also apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "recombinant host cell" (or simply "host cell") refers to a cell into which one or more recombinant expression vectors have been introduced. It should be understood that such terms are intended to refer not only to the particular subject cell but to the progeny of such a cell. Because certain modifications can occur in succeeding generations due to either mutation or environmental influences, such progeny may not, in fact, be identical to the parent cell, but are still included within the scope of the term "host cell" as used herein.

The term "subject" includes human and non-human animals. Non-human animals include all vertebrates (e.g., mammals and non-mammals) such as, non-human primates (e.g., cynomolgus monkey), mice, rats, cats, rabbits, pigs, sheep, dog, cow, chickens, amphibians, and reptiles. Except when noted, the terms "patient" or "subject" are used herein interchangeably. As used herein, the terms "cyno" or "cynomolgus" refer to the cynomolgus monkey (*Macaca fascicularis*).

"Prevention" or "preventing" as it relates to indications described herein, such as ophthalmic conditions or disorders including, conditions or disorders associated with diabetic macular edema, retinal vascular disease, conditions or disorders associated with diabetic retinopathy, and/or conditions or disorders associated with macular edema, means any action that prevents or slows a worsening in visual function, retinal anatomy, retinal vascular disease parameter, diabetic retinopathy disease parameter, and/or macular edema disease parameter, as described below, in a patient at risk for said worsening. As used herein, "prevention" or "preventing" as it relates to non-ophthalmic conditions or disorders including pancreatic carcinoma, breast cancer, endometrial adenocarcinoma, hepatocellular carcinoma, head and neck squamous cell carcinoma, and gastric carcinoma, need not result in a complete prevention of the condition. Partial prevention or reduction of the condition or a symptom of the condition, or reduction of the risk of developing the condition is also encompassed by this term.

The term "treating" or "treatment" of conditions or disorders associated with diabetic macular edema, conditions or disorders associated with age-related macular degeneration, e.g., neovascular age-related macular degeneration, conditions or disorders associated with retinal vascular disease, conditions or disorders associated with diabetic retinopathy, and/or conditions or disorders associated with macular edema means any action that results in, or is contemplated to result in, the improvement or preservation of visual function and/or retinal anatomy. As used herein, "treating" or "treatment" of non-ophthalmic conditions or disorders including pancreatic carcinoma, breast cancer, endometrial adenocarcinoma, hepatocellular carcinoma, head and neck squamous cell carcinoma, and gastric carcinoma, refers to any action that results in, or is contemplated to result in, the improvement or reduction of the conditions or disorders. In another aspect, treatment includes reduction in the frequency of repeat administration and/or reduction in doctor/hospital visits. Also include an aspect/aspect where treatment involves chronic treatment, e.g., repeat administration over time indefinitely. Methods for assessing treatment and/or prevention of disease are known in the art and described herein below.

The term "therapeutically acceptable amount" or "therapeutically effective amount" or "therapeutically effective dose" interchangeably refer to an amount sufficient to effect the desired result (i.e., a reduction disease activity, reduction in disease progression, reduction in disease signs and/or symptoms, etc.). In some aspects, a therapeutically acceptable amount does not induce or cause undesirable side effects. A therapeutically acceptable amount can be determined by first administering a low dose, and then incrementally increasing that dose until the desired effect is achieved. A "prophylactically effective dosage," and a "therapeutically effective dosage," of the molecules of the present disclosure can prevent the onset of, or result in a decrease in severity of, respectively, disease symptoms, including symptoms associated with BTC activity and/or VEGF activity.

The term "vector" is intended to refer to a polynucleotide molecule capable of transporting another polynucleotide to which it has been linked. One type of vector is a "plasmid," which refers to a circular double stranded DNA loop into which additional DNA segments can be ligated. In another aspect, a polynucleotide sequence can be delivered to a subject using a viral vector, such as an adeno-associated viral vector (AAV, e.g., AAV1, AAV2, AAV3, AAV4, AAV5, AAV6, AAV7, AAV8, AAV9, AAV10, AAV 11, and AAV12), a lentiviral vector, or a retroviral vector, where additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" can be used interchangeably as the plasmid is the most commonly used form of vector. However, the present disclosure is intended to include such other forms of expression vectors, such as viral vectors (e.g., replication defective retroviruses, adenoviruses and adeno-associated viruses), which serve equivalent functions.

The term "recombinant" in reference to a polynucleotide (DNA or RNA) molecule, protein, construct, vector, etc., refers to a polynucleotide or protein molecule or sequence that is man-made and not normally found in nature, and/or is present in a context in which it is not normally found in nature, including a polynucleotide (DNA or RNA) molecule, protein, construct, etc., comprising a combination of two or more polynucleotide or protein sequences that would not naturally occur together in the same manner without human intervention, such as a polynucleotide molecule, protein, construct, etc., comprising at least two polynucleotide or protein sequences that are operably linked but heterologous with respect to each other. For example, the term "recombinant" can refer to any combination of two or more DNA or protein sequences in the same molecule (e.g., a plasmid, construct, vector, chromosome, protein, etc.) where such a combination is man-made and not normally found in nature. As used in this definition, the phrase "not normally found in nature" means not found in nature without human introduction. A recombinant polynucleotide or protein molecule, construct, etc., can comprise polynucleotide or protein sequence(s) that is/are (i) separated from other polynucleotide or protein sequence(s) that exist in proximity to each other in nature, and/or (ii) adjacent to (or contiguous with) other polynucleotide or protein sequence(s) that are not naturally in proximity with each other. Such a recombinant polynucleotide molecule, protein, construct, etc., can also refer to a polynucleotide or protein molecule or sequence that has been genetically engineered and/or constructed outside of a cell. For example, a recombinant DNA molecule can comprise any engineered or man-made plasmid, vector, etc., and can include a linear or circular DNA molecule. Such plasmids, vectors, etc., can contain various maintenance elements including a prokaryotic origin of replication and selectable marker, as well as one or more transgenes or expression cassettes perhaps in addition to a plant selectable marker gene, etc.

As used herein, an "encoding region" or "coding region" refers to a portion of a polynucleotide that encodes a functional unit or molecule (e.g., without being limiting, a mRNA, protein, or non-coding RNA sequence or molecule).

As used herein, the term "therapeutic protein" refers to a protein that is useful to treat, prevent or ameliorate a disease, condition or disorder.

A "modification" or "mutation" of an amino acid residue/position, as used herein, refers to a change of a primary amino acid sequence as compared to a starting amino acid sequence, where the change results from a sequence alteration involving said amino acid residue/positions. For example, typical modifications include substitution of the residue (or at said position) with another amino acid (e.g., a conservative or non-conservative substitution), insertion of one or more amino acids adjacent to said residue/position, and deletion of said residue/position. An "amino acid substitution," or variation thereof, refers to the replacement of an existing amino acid residue in a predetermined (starting) amino acid sequence with a different amino acid residue. Generally and preferably, the modification results in alteration in at least one physicobiochemical activity of the variant polypeptide compared to a polypeptide comprising the starting (or "wild type") amino acid sequence. For example, in the case of an antibody, a physicobiochemical activity that is altered can be binding affinity, binding capability and/or binding effect upon a target molecule.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As used herein, "C-terminus" refers to the carboxyl terminal amino acid of a polypeptide chain having a free carboxyl group (—COOH). As used herein, "N-terminus" refers to the amino terminal amino acid of a polypeptide chain having a free amine group (—NH$_2$).

As used herein, phrases such as "a patient in need of treatment" or "a subject in need of treatment" includes subjects, such as mammalian subjects, that would benefit from administration of molecule or pharmaceutical composition of the present disclosure used, e.g., for detection, for a diagnostic procedure and/or for treatment.

The phrase "pharmaceutically acceptable" means approved by a regulatory agency of a federal or a state government, or listed in the U.S. Pharmacopeia or other generally recognized pharmacopeia for use in animals, and more particularly, in humans.

The term "pharmaceutical composition" refers to a mixture of at least one active ingredient (e.g., an antibody or fragment of the disclosure) and at least one pharmaceutically-acceptable excipient, diluent or carrier.

A "medicament" refers to a substance used for medical treatment.

A "disorder mediated by BTC" encompasses all diseases and medical conditions in which BTC and/or VEGF, whether directly or indirectly, involves in the disease or medical condition, including the causation, development, progress, persistence or pathology of the disease or condition. A disorder mediated by BTC can include, but is not limited to, pancreatic carcinoma, breast cancer, endometrial adenocarcinoma, hepatocellular carcinoma, head and neck squamous cell carcinoma, gastric carcinoma, diabetic macular edema, age-related macular degeneration, neovascular age-related macular degeneration, neovascular glaucoma, diabetic retinopathy, macular edema, pathologic myopia, retinal vein occlusions, retinopathy of prematurity, abnormal vascular proliferation associated with phakomatoses, central serous chorioretiniopathy, and acute multifocal placoid pigment epitheliopathy.

A "disorder mediated by VEGF" encompasses all diseases and medical conditions in which VEGF, whether directly or indirectly, involves in the disease or medical condition, including the causation, development, progress, persistence or pathology of the disease or condition. A disorder mediated by VEGF can include, but is not limited to, central nervous system neoplasm, capillary hemangioblastoma, meningioma, cerebral edema, pituitary adenoma, nonastrocytic glioma, peritumoral edema, breast carcinoma, adenocarcinoma, lung carcinoma, diabetic macular edema, age-related macular degeneration, neovascular age-related macular degeneration, neovascular glaucoma, diabetic retinopathy, macular edema, pathologic myopia, retinal vein occlusions, retinopathy of prematurity, and abnormal vascular proliferation associated with phakomatoses.

ii. Anti-BTC Antibody or Anti-BTC Binding Moieties

BTC is a member of the EGF family. It is a ligand for the ErbB receptor tyrosine kinase family and mainly activates ErbB1 and ErbB4 homodimers triggering anti-apoptotic and pro-proliferative signaling pathway like the Ras/MAPK and the PL3K/AKT pathways. In the eye, BTC appears as a potent permeability factor that could play a critical role in the development of increased retinal vascular permeability in diabetic retinopathy and be a potential therapeutic target in this disease. An exemplary human pro-BTC amino acid sequence is presented as SEQ ID NO: 156. An exemplary human BTC amino acid sequence is presented as SEQ ID NO: 158. An exemplary human BTC amino acid sequence as expressed in the present disclosure is presented as SEQ ID NO: 157 (depicting residual amino acid residues in lower-case letters at N- and C-termini).

The structure of the human BTC protein bound to four anti-BTC Fab fragments has recently been solved by the applicant via X-ray crystallography. See Example 2. The human BTC structure is an EGF fold with five beta strands in a three-stranded and a two-stranded sheet. The structure is stabilized with three disulfide bonds.

Antibody or antigen binding fragments thereof that binds to BTC, including human BTC, are provided herein. In some aspects, an antibody or antigen binding fragments thereof provided are polypeptides which comprise one or more complementary determining regions (CDRs), as described herein. In some aspects, the CDRs are embedded into a "framework" region, which orients the CDR(s) such that the proper antigen binding properties of the CDR(s) is achieved. In some aspects, an antibody or antigen binding fragments thereof provided herein can interfere with, block, reduce, or modulate the interaction between BTC and ErbB receptor. In some aspects, antibody or antigen binding fragments thereof provided herein are capable of inhibiting BTC-mediated activity (including binding). In some aspects, antigen binding proteins binding to these epitopes inhibit, inter alia, interactions between BTC and ErbB receptor and other physiological effects mediated by BTC. In some aspects, the antigen binding proteins are human, such as fully human antibodies or a Fab to BTC.

In some aspects, an antibody or antigen binding fragments thereof binds to any one of the epitopes bound by the antibodies discussed herein. In some aspects, this can be determined by competition assays between the antibodies disclosed herein and other antibodies. In some aspects, an antibody or antigen binding fragments thereof binds to an epitope bound by one of the antibodies described in Table 1. In some aspects, an antibody or antigen binding fragments thereof binds to a specific conformational state of BTC so as to prevent BTC from interacting with ErbB receptor. In one aspect, an antibody or antigen binding fragments thereof of the present disclosure binds to one or more of the five beta strands of human BTC. In one aspect, an antibody or antigen binding fragments thereof binds to beta strand 1 of human BTC and prevents BTC from binding to ErbB receptor. In one aspect, an antibody or antigen binding fragments thereof binds to beta strand 2 of human BTC and prevents BTC from binding to ErbB receptor. In one aspect, an antibody or antigen binding fragments thereof binds to beta strand 3 of human BTC and prevents BTC from binding to ErbB receptor. In one aspect, an antibody or antigen binding fragments thereof binds to beta strand 4 of human BTC and prevents BTC from binding to ErbB receptor. In one aspect, an antibody or antigen binding fragments thereof binds to beta strand 5 of human BTC and prevents BTC from binding to ErbB receptor.

Disclosed herein are antibody or antigen binding fragment thereof that bind specifically to BTC. In some aspects, an anti-BTC antibody or antigen binding fragment thereof prevents BTC from functioning in various ways. In some aspects, an anti-BTC antibody or antigen binding fragment thereof blocks or reduces the ability of BTC to interact with other substances. For example, in some aspects, an anti-BTC antibody or antigen binding fragment thereof blocks or reduces the ability of BTC to bind to ErbB receptor. In other aspects, an anti-BTC antibody or antigen binding fragment thereof blocks BTC-induced phospoh-ERK1/2 activation. In some aspects, an anti-BTC antibody or antigen binding fragment thereof blocks BTC-induced phospoh-HER3 activation.

Certain of the antibody or antigen binding fragment thereof as provided herein specifically and/or selectively bind to human BTC as set forth in SEQ ID NO: 157 or 158. In some aspects, an antibody or antigen binding fragment thereof selectively binds to a human BTC protein as depicted in Example 2 and Table 1. In some aspects, an antibody or antigen binding fragment thereof specifically and/or selectively binds to at least one residue of SEQ ID NO: 157 selected from the group consisting of G34, H35, F36, S37, R38, C39, P40, K41, Q42, Y43, H45, Y46, R51, R53, F54, V56, A57, E58, Q59, T60, P61, A72, R73, E75, and R76. In some aspects, more than one (e.g., 2, 3, 4, 5, 6, 7, 8, 9. 10, 11, 12, 13, 14, 15, 16, 17, 18, 19, 20,21, 22, 23, 24, or 25) of the identified BTC residues are part of the region that is bound by an antibody or antigen binding fragment thereof.

In some aspects, an antibody or antigen binding fragment thereof specifically and/or selectively binds to R38, C39, P40, K41, Q42, Y43, H45, Y46, F54, Q59, T60, P61, and R73 of SEQ ID NO: 157, e.g., NVS1. In some aspects, an antibody or antigen binding fragment thereof specifically and/or selectively binds to P40, K41, Q42, Y43, H45, Y46, E58, Q59, T60, P61, A72, R73, E75, and R76 of SEQ ID NO: 157, e.g., NVS2. In some aspects, an antibody or antigen binding fragment thereof specifically and/or selectively binds to G34, H35, F36, S37, R38, C39, P40, K41, Q42, R51, R53, F54, and V56 of SEQ ID NO: 157, e.g., NVS3. In some aspects, an antibody or antigen binding fragment thereof specifically and/or selectively binds to S37, R38, C39, P40, K41, Q42, Y43, H45, Y46, F54, A57, Q59, T60, P61, A72, R73, and E75 of SEQ ID NO: 157, e.g., NVS4.

In aspects where an antibody or antigen binding fragment thereof is used for therapeutic applications, an antibody or antigen binding fragment thereof can inhibit, interfere with or modulate one or more biological activities of BTC. In one aspect, an antibody or antigen binding fragment thereof binds specifically to human BTC and/or substantially inhibits binding of human BTC to ErbB receptor by at least about 20%-40%, $_{40}$-60%, 60-80%, 80-85%, or more (for example, by measuring binding in an in vitro competitive binding assay). In some aspects, an antibody or antigen binding fragment thereof has a $K_d$ of less (binding more tightly) than 10-7, $10^{-1}$, 10, $10^{-10}$, $10^{-11}$, $10^{-12}$, $10^{-13}$ M. In some aspects, an antibody or antigen binding fragment thereof has an $IC_{50}$ for blocking the binding of ErbB receptor to BTC of less than 1 microM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM.

In some aspects, an antibody or antigen binding fragment thereof binds to variants of BTC that are at least 50%, 50-60%, 60-70%, 70-80%, 80-90%, 90-95%, 95-99%, or greater percent identity to the form of BTC as set forth in SEQ ID NO: 157 or 158. In some aspects, an antibody or antigen binding fragment thereof binds to an epitope bound by one of the antibodies described in Table 1. In some aspects, an antibody or antigen binding fragment thereof binds to a specific conformational state of BTC so as to prevent BTC from interacting with ErbB receptor.

An anti-BTC antibody or antigen binding fragment thereof of the present disclosure comprises heavy chain variable region complementarity determining region 1 (HCDR1), heavy chain variable region complementarity determining region 2 (HCDR2), heavy chain variable region complementarity determining region 3 (HCDR3), light chain variable region complementarity determining region 1 (LCDR1), light chain variable region complementarity determining region 2 (LCDR2), and light chain variable region complementarity determining region 3 (LCDR3). HCDR1, HCDR2, and HCDR3 are comprised in a heavy chain variable region (VH). LCDR1, LCDR2, and LCDR3 are comprised in a light chain variable region (VL). In one aspect an anti-BTC antibody or antigen binding fragment thereof comprises the heavy chain and light chain CDRs (e.g., Kabat, Chothia, IMGT, and/or combined CDRs) as set forth in Table 1 and described below.

In one aspect, an anti-BTC antibody or antigen binding fragment thereof comprises HCDR1, HCDR2, HCDR3, LCDR1, LCDR2, and LCDR3 as set forth in SEQ ID NOs: 4, 2, 3, 14, 15, and 16, respectively, according to the Kabat numbering scheme. In one aspect, an anti-BTC antibody or antigen binding fragment thereof comprises HCDR1, HCDR2, HCDR3, LCDR1, LCDR2, and LCDR3 as set forth in SEQ ID NOs: 5, 6, 3, 17, 18, and 19, respectively, according to the Chothia numbering scheme. In one aspect, an anti-BTC antibody or antigen binding fragment thereof comprises HCDR1, HCDR2, HCDR3, LCDR1, LCDR2, and LCDR3 as set forth in SEQ ID NOs: 1, 2, 3, 14, 15, and 16, respectively, according to the combined numbering scheme. In one aspect, an anti-BTC antibody or antigen binding fragment thereof comprises HCDR1, HCDR2, HCDR3, LCDR1, LCDR2, and LCDR3 as set forth in SEQ ID NOs: 7, 8, 9, 20, 18, and 16, respectively, according to the IMGT numbering scheme. In one aspect, an anti-BTC antibody or antigen binding fragment thereof is NVS1 as provided in Table 1. In a particular aspect, an anti-BTC antibody or antigen binding fragment thereof comprises the heavy chain and light chain CDRs (e.g., Kabat, Chothia, IMGT, and/or combined CDRs) of antibody NVS1 comprising a VH and a VL of SEQ ID NOs: 10 and 21, respectively.

In one aspect, an anti-BTC antibody or antigen binding fragment thereof comprises HCDR1, HCDR2, HCDR3, LCDR1, LCDR2, and LCDR3 as set forth in SEQ ID NOs: 28, 26, 27, 38, 39, and 40, respectively, according to the Kabat numbering scheme. In one aspect, an anti-BTC antibody or antigen binding fragment thereof comprises HCDR1, HCDR2, HCDR3, LCDR1, LCDR2, and LCDR3 as set forth in SEQ ID NOs: 29, 30, 27, 41, 42, and 43, respectively, according to the Chothia numbering scheme. In one aspect, an anti-BTC antibody or antigen binding fragment thereof comprises HCDR1, HCDR2, HCDR3, LCDR1, LCDR2, and LCDR3 as set forth in SEQ ID NOs: 25, 26, 27, 38, 39, and 40, respectively, according to the combined numbering scheme. In one aspect, an anti-BTC antibody or antigen binding fragment thereof comprises HCDR1, HCDR2, HCDR3, LCDR1, LCDR2, and LCDR3 as set forth in SEQ ID NOs: 31, 32, 33, 44, 42, and 40, respectively, according to the IMGT numbering scheme. In one aspect, an anti-BTC antibody or antigen binding fragment thereof is NVS2 as provided in Table 1. In a particular aspect, an anti-BTC antibody or antigen binding fragment thereof comprises the heavy chain and light chain CDRs (e.g., Kabat, Chothia, IMGT, and/or combined CDRs) of antibody NVS2 comprising a VH and a VL of SEQ ID NOs: 34 and 45, respectively.

In one aspect, an anti-BTC antibody or antigen binding fragment thereof comprises HCDR1, HCDR2, HCDR3, LCDR1, LCDR2, and LCDR3 as set forth in SEQ ID NOs: 28, 49, 50, 58, 59, and 60, respectively, according to the Kabat numbering scheme. In one aspect, an anti-BTC antibody or antigen binding fragment thereof comprises HCDR1, HCDR2, HCDR3, LCDR1, LCDR2, and LCDR3 as set forth in SEQ ID NOs: 29, 51, 50, 61, 62, and 63, respectively, according to the Chothia numbering scheme. In one aspect, an anti-BTC antibody or antigen binding fragment thereof comprises HCDR1, HCDR2, HCDR3, LCDR1, LCDR2, and LCDR3 as set forth in SEQ ID NOs: 25, 49, 50, 58, 59, and 60, respectively, according to the combined numbering scheme. In one aspect, an anti-BTC antibody or antigen binding fragment thereof comprises HCDR1, HCDR2, HCDR3, LCDR1, LCDR2, and LCDR3 as set forth in SEQ ID NOs: 31, 52, 53, 64, 62, and 60, respectively, according to the IMGT numbering scheme. In one aspect, an anti-BTC antibody or antigen binding fragment thereof is NVS3 as provided in Table 1. In a particular aspect, an anti-BTC antibody or antigen binding fragment thereof comprises the heavy chain and light chain CDRs (e.g., Kabat, Chothia, IMGT, and/or combined CDRs) of antibody NVS3 comprising a VH and a VL of SEQ ID NOs: 54 and 65, respectively.

In one aspect, an anti-BTC antibody or antigen binding fragment thereof comprises HCDR1, HCDR2, HCDR3, LCDR1, LCDR2, and LCDR3 as set forth in SEQ ID NOs: 72, 70, 71, 82, 83, and 84, respectively, according to the Kabat numbering scheme. In one aspect, an anti-BTC antibody or antigen binding fragment thereof comprises HCDR1, HCDR2, HCDR3, LCDR1, LCDR2, and LCDR3 as set forth in SEQ ID NOs: 73, 74, 71, 85, 18, and 86, respectively, according to the Chothia numbering scheme. In one aspect, an anti-BTC antibody or antigen binding fragment thereof comprises HCDR1, HCDR2, HCDR3, LCDR1, LCDR2, and LCDR3 as set forth in SEQ ID NOs: 69, 70, 71, 82, 83, and 84, respectively, according to the combined numbering scheme. In one aspect, an anti-BTC antibody or antigen binding fragment thereof comprises HCDR1, HCDR2, HCDR3, LCDR1, LCDR2, and LCDR3 as set forth in SEQ ID NOs: 75, 76, 77, 87, 18, and 84, respectively, according to the IMGT numbering scheme. In one aspect, an anti-BTC antibody or antigen binding fragment thereof is NVS4 as provided in Table 1. In a particular aspect, an anti-BTC antibody or antigen binding fragment thereof comprises the heavy chain and light chain CDRs (e.g., Kabat, Chothia, IMGT, and/or combined CDRs) of antibody NVS4 comprising a VH and a VL of SEQ ID NOs: 78 and 88, respectively.

In addition, the present disclosure also provides for an anti-BTC antibody or antigen binding fragment thereof comprising amino acid sequences that are homologous to the CDR sequences described throughout and in Table 1, and the anti-BTC antibody or antigen binding fragment thereof binds to BTC and retains the desired functional properties of those described herein. More specifically, the amino acid sequences of an anti-BTC antibody or antigen binding fragment thereof can have greater than or equal to 80%, 90%, 95%, 96%, 97%, 98%, or 99% identity to the CDR sequences as described throughout and set forth in Table 1 and retain the desired functional properties thereof.

The present disclosure also provides anti-BTC antibodies or antigen binding fragments thereof that are homologous to the VH and VL sequences described herein. More specifically, the present disclosure provides for a protein comprising amino acid sequences that are homologous to the sequences, such as those described in Table 1, and the anti-BTC antibodies or antigen binding fragments binds to a therapeutic target, e.g., an ophthalmic target, and retains the desired functional properties of those as described in Table 1 and the examples. An antibody or antigen binding fragment thereof having VH and VL regions with less than 100% sequence identity to the VH and VL regions of those described in Table 1 can be obtained by mutagenesis (e.g., site-directed or PCR-mediated mutagenesis) of nucleic acid molecules described in Table 1 followed by testing of the encoded altered antibody for retained function using the functional assays described herein and in US 20120014958. An antibody or antigen binding fragment thereof having a heavy chain and light chain with high (i.e., 80% or greater) identity to the heavy chains and light chains described in Table 1 can be obtained by mutagenesis (e.g., site-directed or PCR-mediated mutagenesis) of nucleic acid molecules encoding such polypeptides, followed by testing of the encoded altered antibody for retained function, e.g., by using the functional assays described herein.

An anti-BTC antibody or antigen binding fragment thereof of the present disclosure comprises a heavy chain variable region (VH) and a light chain variable region (VL) comprising an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 10 and 21, respectively. It is contemplated that the variability can be in the CDR or framework regions. In one aspect, an anti-BTC antibody or antigen binding fragment thereof comprising a VH and a VL comprising amino acid sequence as set forth in SEQ ID NOs: 10 and 21, respectively. In another aspect, an anti-BTC antibody or antigen binding fragment thereof is NVS1 as provided in Table 1. In another aspect, the VH and VL are encoded by a nucleic acid sequence as set forth in SEQ ID NOs: 11 and 22, respectively. In one aspect, an anti-BTC antibody or antigen binding fragment thereof comprises a VH and VL comprising an amino acid sequence having at least one, two or three modifications (e.g., substitutions, e.g., conservative substitutions), but not more than 10 modifications (e.g., substitutions, e.g., conservative substitutions) of an amino acid sequence of SEQ ID NOs: 10 and 21, respectively. In another aspect, the differences in amino acid sequence is not within the complementary determining regions.

In one aspect, an anti-BTC antibody or antigen binding fragment thereof of the present disclosure comprises a VH and a VL comprising an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 34 and 45, respectively. It is contemplated that the variability can be in the CDR or framework regions. In one aspect, an anti-BTC antibody or antigen binding fragment thereof comprising a VH and a VL comprising amino acid sequence as set forth in SEQ ID NOs: 34 and 45, respectively. In another aspect, an anti-BTC antibody or antigen binding fragment thereof is NVS2 as provided in Table 1. In another aspect, the VH and VL are encoded by a nucleic acid sequence as set forth in SEQ ID NOs: 35 and 46, respectively. In one aspect, an anti-BTC antibody or antigen binding fragment thereof comprises a VH and VL comprising an amino acid sequence having at least one, two or three modifications (e.g., substitutions, e.g., conservative substitutions), but not more than 10 modifications (e.g., substitutions, e.g., conservative substitutions) of an amino acid sequence of SEQ ID NOs: 34 and 45, respectively. In another aspect, the differences in amino acid sequence is not within the complementary determining regions.

In one aspect, an anti-BTC antibody or antigen binding fragment thereof of the present disclosure comprises a VH and a VL comprising an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 54 and 65, respectively. It is contemplated that the variability can be in the CDR or framework regions. In one aspect, an anti-BTC antibody or antigen binding fragment thereof comprising a VH and a VL comprising amino acid sequence as set forth in SEQ ID NOs: 54 and 65, respectively. In another aspect, an anti-BTC antibody or antigen binding fragment thereof is NVS3 as provided in Table 1. In another aspect, the VH and VL are encoded by a nucleic acid sequence as set forth in SEQ ID NOs: 55 and 66, respectively. In one aspect, an anti-BTC antibody or antigen binding fragment thereof comprises a VH and VL comprising an amino acid sequence having at least one, two or three modifications (e.g., substitutions, e.g., conservative substitutions), but not more than 10 modifications (e.g., substitutions, e.g., conservative substitutions) of an amino acid sequence of SEQ ID NOs: 54 and 65, respectively. In another aspect, the differences in amino acid sequence is not within the complementary determining regions.

In one aspect, an anti-BTC antibody or antigen binding fragment thereof of the present disclosure comprises a VH and a VL comprising an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 78 and 88, respectively. It is contemplated that the variability can be in the CDR or framework regions. In one aspect, an anti-BTC antibody or antigen binding fragment thereof comprising a VH and a VL comprising amino acid sequence as set forth in SEQ ID NOs: 78 and 88, respectively. In another aspect, an anti-BTC antibody or antigen binding fragment thereof is NVS4 as provided in Table 1. In another aspect, the VH and VL are encoded by a nucleic acid sequence as set forth in SEQ ID NOs: 79 and 89, respectively. In one aspect, an anti-BTC antibody or antigen binding fragment thereof comprises a VH and VL comprising an amino acid sequence having at least one, two or three modifications (e.g., substitutions, e.g., conservative substitutions), but not more than 10 modifications (e.g., substitutions, e.g., conservative substitutions) of an amino acid sequence of SEQ ID NOs: 78 and 88, respectively. In another aspect, the differences in amino acid sequence is not within the complementary determining regions.

An anti-BTC antibody or antigen binding fragment thereof of the present disclosure comprises a heavy chain and a light chain comprising an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 12 and 23, respectively. In one aspect, an anti-BTC antibody or antigen binding fragment thereof comprising a heavy chain and a light chain comprising amino acid sequence as set forth in SEQ ID NOs: 12 and 23, respectively. In one aspect, an anti-BTC antibody can inhibit BTC activity, e.g., BTC's binding to 1) ErbB1; 2) ErbB4; 3) ErbB homodimer (e.g., ErbB1/ErbB1 and ErbB4/ErbB4); 4) ErbB heterodimer (e.g., ErbB1/ErbB2, ErB1/ErB3, ErB1/ErB4, ErB2/ErB3, and ErB2/ErB4); and/or 5) can inhibit ERK1/2 phosphorylation. In another aspect, an anti-BTC antibody or antigen binding fragment thereof is NVS1 as provided in Table 1. In another aspect, the heavy chain and light chain are encoded by a nucleic acid sequence with about at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical or complementary to SEQ ID NOs: 13 and 24, respectively.

In one aspect, an anti-BTC antibody or antigen binding fragment thereof comprising a heavy chain and a light chain encoded by a nucleic acid sequence as set forth in SEQ ID NOs: 13 and 24, respectively, and is NVS1 as provided in Table 1.

In one aspect, an anti-BTC antibody or antigen binding fragment thereof of the present disclosure comprises a heavy chain and a light chain comprising an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 36 and 47, respectively. In one aspect, an anti-BTC antibody or antigen binding fragment thereof comprising a heavy chain and a light chain comprising amino acid sequence as set forth in SEQ ID NOs: 36 and 47, respectively. In one aspect, an anti-BTC antibody can inhibit BTC activity, e.g., BTC's binding to 1) ErbB1; 2) ErbB4; 3) ErbB homodimer (e.g., ErbB1/ErbB1 and ErbB4/ErbB4); 4) ErbB heterodimer (e.g., ErbB1/ErbB2, ErB1/ErB3, ErB1/ErB4, ErB2/ErB3, and ErB2/ErB4); and/or 5) can inhibit ERK1/2 phosphorylation. In another aspect, an anti-BTC antibody or antigen binding fragment thereof is NVS2 as provided in Table 1. In another aspect, the heavy chain and light chain are encoded by a nucleic acid sequence with about at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical or complementary to SEQ ID NOs: 37 and 48, respectively. In one aspect, an anti-BTC antibody or antigen binding fragment thereof comprising a heavy chain and a light chain encoded by a nucleic acid sequence as set forth in SEQ ID NOs: 37 and 48, respectively, and is NVS2 as provided in Table 1.

In one aspect, an anti-BTC antibody or antigen binding fragment thereof of the present disclosure comprises a heavy chain and a light chain comprising an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 56 and 67, respectively. In one aspect, an anti-BTC antibody or antigen binding fragment thereof comprising a heavy chain and a light chain comprising amino acid sequence as set forth in SEQ ID NOs: 56 and 67, respectively. In one aspect, an anti-BTC antibody can inhibit BTC activity, e.g., BTC's binding to 1) ErbB1; 2) ErbB4; 3) ErbB homodimer (e.g., ErbB1/ErbB1 and ErbB4/ErB4); 4) ErbB heterodimer (e.g., ErbB1/ErbB2, ErB1/ErB3, ErB1/ErB4, ErB2/ErB3, and ErB2/ErB4); and/or 5) can inhibit ERK1/2 phosphorylation. In another aspect, an anti-BTC antibody or antigen binding fragment thereof is NVS3 as provided in Table 1. In another aspect, the heavy chain and light chain are encoded by a nucleic acid sequence with about at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical or complementary to SEQ ID NOs: 57 and 68, respectively. In one aspect, an anti-BTC antibody or antigen binding fragment thereof comprising a heavy chain and a light chain encoded by a nucleic acid sequence as set forth in SEQ ID NOs: 57 and 68, respectively, and is NVS3 as provided in Table 1.

In one aspect, an anti-BTC antibody or antigen binding fragment thereof of the present disclosure comprises a heavy chain and a light chain comprising an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 80 and 90, respectively. In one aspect, an anti-BTC antibody or antigen binding fragment thereof comprising a heavy chain and a light chain comprising amino acid sequence as set forth in SEQ ID NOs: 80 and 90, respectively. In one aspect, an anti-BTC antibody can inhibit BTC activity, e.g., BTC's binding to 1) ErbB1; 2) ErbB4; 3) ErbB homodimer (e.g., ErbB1/ErbB1 and ErbB4/ErB4); 4) ErbB heterodimer (e.g., ErbB1/ErbB2, ErB1/ErB3, ErB1/ErB4, ErB2/ErB3, and ErB2/ErB4); and/or 5) can inhibit ERK1/2 phosphorylation. In another aspect, an anti-BTC antibody or antigen binding fragment thereof is NVS4 as provided in Table 1. In another aspect, the heavy chain and light chain are encoded by a nucleic acid sequence with about at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical or complementary to SEQ ID NOs: 81 and 91, respectively. In one aspect, an anti-BTC antibody or antigen binding fragment thereof comprising a heavy chain and a light chain encoded by a nucleic acid sequence as set forth in SEQ ID NOs: 81 and 91, respectively, and is NVS4 as provided in Table 1.

Further included within the scope of the present disclosure are isolated anti-BTC antibody or antigen binding fragment thereof with conservative modifications. More specifically, the present disclosure is related to anti-BTC binding moieties and molecules conjugated to anti-BTC binding moieties thereof with conservative modification to the anti-BTC binding moieties and molecules conjugated to anti-BTC binding moieties of Table 1. In certain aspects, the antibody conjugated to anti-BTC binding moieties of the present disclosure has a heavy chain variable region comprising CDR1, CDR2, and CDR3 sequences and a light chain variable region comprising CDR1, CDR2, and CDR3 sequences, where one or more of these CDR sequences have specified amino acid sequences based on the antibodies described herein or conservative modifications thereof, and where the antibody retains the desired functional properties of the antibodies of the present disclosure.

In specifif aspect, provided herein are polynucleotides whose sequence encode an anti-BTC antibody described herein (e.g., Table 1) or fragments thereof (e.g., VH or VL). In one aspect, an anti-BTC antibody or antigen binding fragment thereof is encoded by a polynucleotide whose sequence has been codon optimized for expression in a mammalian cell. In one aspect, the entire construct of the anti-BTC antibody or antigen binding fragment thereof is encoded by a polynucleotide whose entire sequence has been codon optimized for expression in a mammalian cell, e.g., a human cell. In other aspects, an anti-BTC antibody or antigen binding fragment thereof is optimized for expression in a mammalian cell and has a full length heavy chain sequence and a full length light chain sequence, where one or more of these sequences have specified amino acid sequences based on the antibodies described herein or conservative modifications thereof, and where the anti-BTC binding moieties retain the desired functional properties of the anti-BTC binding antibodies of the present disclosure. Accordingly, the present disclosure provides an isolated antibody or antigen binding fragment thereof optimized for expression in a mammalian cell comprising, for example, a VH and a VL where the VH comprises the amino acid sequence of SEQ ID NOs: 10, 34, 54, and 78, and conservative modifications thereof; and the VL comprises amino acid sequence of SEQ ID NO: 21, 45, 65, and 88, and conservative modifications thereof, which specifically bind to BTC.

The present disclosure provides anti-BTC binding moieties (e.g., BTC binding antibodies or fragments thereof) that bind to the same, or overlapping, epitope as the anti-BTC antibody or antigen binding fragment thereof described in Table 1. Additional antibodies can therefore be identified based on their ability to compete (e.g., to competitively inhibit the binding of, in a statistically significant manner) with other antibodies of the present disclosure in BTC binding assays. The ability of a test antibody to inhibit the binding of molecules of the present disclosure to BTC demonstrates that the test molecule can compete with that antibody for binding to BTC; such an antibody can, according to non-limiting theory, bind to the same or a related (e.g., a structurally similar or spatially proximal) epitope on BTC as the antibody with which it competes. In a certain aspect, the molecule that binds to the same epitope on BTC as the antibodies of the present disclosure is a human monoclonal antibody, a Fab, or a scFv. Such human monoclonal antibodies, Fabs, and scFvs can be prepared and isolated as described herein.

In one aspect, a molecule that competes with an anti-BTC antibody or antigen binding fragment thereof of the present disclosure binds to at least one residue of SEQ ID NO: 157 selected from the group consisting of G34, H35, F36, S37, R38, C39, P40, K41, Q42, Y43, H45, Y46, R51, R53, F54, V56, A57, E58, Q59, T60, P61, A72, R73, E75, and R76. In one aspect, the present disclosure provides an isolated antibody or antigen binding fragment thereof which is capable of competing with those as described in Table 1, e.g., NVS1, NVS2, NVS3, and NVS4, for binding to BTC and reducing BTC-mediated signaling. In another aspect, the competing antibody or antigen binding fragment thereof comprises a heavy chain and a light chain as set forth in SEQ ID NOs: 168-189, in Table 5.

An anti-BTC antibody or antigen binding fragment thereof of the present disclosure is in a format selected from the group consisting of an isolated antibody, a Fab, a Fab', a F(ab')$_2$, a Fv, and a scFv. In a preferred aspect, an anti-BTC antibody or antigen binding fragment thereof is a Fab, including a Fab comprising an Fc region. In another aspect, the Fc region is selected from the group consisting of an Fc region from an IgG1, IgG2, IgG3, IgG4, IgA, IgM, IgE, and IgD. In one aspect, the Fc region comprises human immunoglobulin Kappa chain constant region sequence as set forth in SEQ ID NO: 159. In another aspect, the Fe region comprises human immunoglobulin first constant Ig domain of the heavy chain (CH1 domain) as set forth in SEQ TD NO: 160. 03881 In one aspect, an ant-BTC antibody or antigen binding fragment thereof is an isolated antibody, e.g., a monoclonal human antibody or a monoclonal humanized antibody. In certain aspects, the anti-BTC antibodies can be in an scFv or Fab format. In certain aspects, the anti-BTC antibodies can be in an scFv or Fab format, D2,N,

TABLE 1

Exemplary anti-BTC Fabs

| NVS1 | | | |
|---|---|---|---|
| SEQ ID NO: 1 (Combined) | HCDR1 | | GGTFSSYAIS |
| SEQ ID NO: 2 (Combined) | HCDR2 | | GIVPWMGEAVYAQKFQG |
| SEQ ID NO: 3 (Combined) | HCDR3 | | SSSTYGIHAFDY |
| SEQ ID NO: 4 (Kabat) | HCDR1 | | SYAIS |
| SEQ ID NO: 2 (Kabat) | HCDR2 | | GIVPWMGEAVYAQKFQG |
| SEQ ID NO: 3 (Kabat) | HCDR3 | | SSSTYGIHAFDY |
| SEQ ID NO: 5 (Chothia) | HCDR1 | | GGTFSSY |
| SEQ ID NO: 6 (Chothia) | HCDR2 | | VPWMGE |
| SEQ ID NO: 3 (Chothia) | HCDR3 | | SSSTYGIHAFDY |
| SEQ ID NO: 7 (IMGT) | HCDR1 | | GGTFSSYA |
| SEQ ID NO: 8 (IMGT) | HCDR2 | | IVPWMGEA |
| SEQ ID NO: 9 (IMGT) | HCDR3 | | ARSSSTYGIHAFDY |
| SEQ ID NO: 10 | VH | | QVQLVQSGAEVKKPGSSVKVSCKASGGTFSSYAISWVRQAPG<br>QGLEWMGGIVPWMGEAVYAQKFQGRVTITADESTSTAYMELS<br>SLRSEDTAVYYCARSSSTYGIHAFDYWGQGTLVTVSS |
| SEQ ID NO: 11 | DNA VH | | CAGGTGCAATTGGTGCAGAGCGGTGCCGAAGTGAAAAACCG<br>GGCAGCAGCGTGAAAGTTAGCTGCAAAGCATCCGGAGGGACG<br>TTTAGCAGCTATGCGATTAGCTGGGTGCGCCAGGCCCCGGGC<br>CAGGGCCTCGAGTGGATGGGCGGTATCGTTCCGTGGATGGGC<br>GAAGCTGTTTACGCCCAGAAATTTCAGGGCCGGGTGACCATT<br>ACCGCCGATGAAAGCACCAGCACCGCCTATATGGAACTGAGC<br>AGCCTGCGCAGCGAAGATACGGCCGTGTATTATTGCGCGCGT<br>TCTTCTTCTACTTACGGTATCCATGCTTTCGATTACTGGGGC<br>CAAGGCACCCTGGTGACTGTTAGCTCA |
| SEQ ID NO: 12 | Heavy Chain | | QVQLVQSGAEVKKPGSSVKVSCKASGGTFSSYAISWVRQAPG<br>QGLEWMGGIVPWMGEAVYAQKFQGRVTITADESTSTAYMELS<br>SLRSEDTAVYYCARSSSTYGIHAFDYWGQGTLVTVSSASTKG<br>PSVFPLAPSSKSTSGGTAALGCLVKDYFPEPVTVSWNSGALT<br>SGVHTFPAVLQSSGLYSLSSVVTVPSSSLGTQTYICNVNHKP<br>SNTKVDKRVEPKSC |
| SEQ ID NO: 13 | DNA Heavy Chain | | CAGGTGCAATTGGTGCAGAGCGGTGCCGAAGTGAAAAACCG<br>GGCAGCAGCGTGAAAGTTAGCTGCAAAGCATCCGGAGGGACG<br>TTTAGCAGCTATGCGATTAGCTGGGTGCGCCAGGCCCCGGGC<br>CAGGGCCTCGAGTGGATGGGCGGTATCGTTCCGTGGATGGGC<br>GAAGCTGTTTACGCCCAGAAATTTCAGGGCCGGGTGACCATT<br>ACCGCCGATGAAAGCACCAGCACCGCCTATATGGAACTGAGC<br>AGCCTGCGCAGCGAAGATACGGCCGTGTATTATTGCGCGCGT<br>TCTTCTTCTACTTACGGTATCCATGCTTTCGATTACTGGGGC<br>CAAGGCACCCTGGTGACTGTTAGCTCAGCCTCCACCAAGGGC<br>CCCAGCGTGTTCCCCCTGGCCCCCAGCAGCAAGAGCACCAGC |

TABLE 1-continued

Exemplary anti-BTC Fabs

| | | |
|---|---|---|
| | | GGCGGCACAGCCGCCCTGGGCTGCCTGGTGAAGGACTACTTC CCCGAGCCCGTGACCGTGTCCTGGAACAGCGGAGCCCTGACC TCCGGCGTGCACACCTTCCCCGCCGTGCTGCAGAGCAGCGGC CTGTACAGCCTGAGCAGCGTGGTGACCGTGCCCAGCAGCAGC CTGGGCACCCAGACCTACATCTGTAACGTGAACCACAAGCCC AGCAACACCAAGGTGGACAAGAGAGTGGAGCCCAAGAGCTGT |
| SEQ ID NO: 14 (Combined) | LCDR1 | RASQSISNFLN |
| SEQ ID NO: 15 (Combined) | LCDR2 | AASNLQS |
| SEQ ID NO: 16 (Combined) | LCDR3 | QQYDDFPMT |
| SEQ ID NO: 14 (Kabat) | LCDR1 | RASQSISNFLN |
| SEQ ID NO: 15 (Kabat) | LCDR2 | AASNLQS |
| SEQ ID NO: 16 (Kabat) | LCDR3 | QQYDDFPMT |
| SEQ ID NO: 17 (Chothia) | LCDR1 | SQSISNF |
| SEQ ID NO: 18 (Chothia) | LCDR2 | AAS |
| SEQ ID NO: 19 (Chothia) | LCDR3 | YDDFPM |
| SEQ ID NO: 20 (IMGT) | LCDR1 | QSISNF |
| SEQ ID NO: 18 (IMGT) | LCDR2 | AAS |
| SEQ ID NO: 16 (IMGT) | LCDR3 | QQYDDFPMT |
| SEQ ID NO: 21 | VL | DIQMTQSPSSLSASVGDRVTITCRASQSISNFLNWYQQKPGK APKLLIYAASNLQSGVPSRFSGSGSGTDFTLTISSLQPEDFA TYYCQQYDDFPMTFGQGTKVEIK |
| SEQ ID NO: 22 | DNA VL | GATATCCAGATGACCCAGAGCCCGAGCAGCCTGAGCGCCAGC GTGGGCGATCGCGTGACCATTACCTGCAGAGCCAGCCAGTCT ATTTCTAACTTCCTGAACTGGTACCAGCAGAAACCGGGCAAA GCGCCGAAACTATTAATCTACGCTGCTTCTAACCTGCAAAGC GGCGTGCCGAGCCGCTTTAGCGGCAGCGGATCCGGCACCGAT TTCACCCTGACCATTAGCTCTCTGCAACCGGAAGACTTTGCG ACCTATTATTGCCAGCAGTACGACGACTTCCCGATGACCTTT GGCCAGGGCACGAAAGTTGAAATTAAA |
| SEQ ID NO: 23 | Light Chain | DIQMTQSPSSLSASVGDRVTITCRASQSISNFLNWYQQKPGK APKLLIYAASNLQSGVPSRFSGSGSGTDFTLTISSLQPEDFA TYYCQQYDDFPMTFGQGTKVEIKRTVAAPSVFIFPPSDEQLK SGTASVVCLLNNFYPREAKVQWKVDNALQSGNSQESVTEQDS KDSTYSLSSTLTLSKADYEKHKVYACEVTHQGLSSPVTKSFN RGEC |
| SEQ ID NO: 24 | DNA Light Chain | GATATCCAGATGACCCAGAGCCCGAGCAGCCTGAGCGCCAGC GTGGGCGATCGCGTGACCATTACCTGCAGAGCCAGCCAGTCT ATTTCTAACTTCCTGAACTGGTACCAGCAGAAACCGGGCAAA GCGCCGAAACTATTAATCTACGCTGCTTCTAACCTGCAAAGC GGCGTGCCGAGCCGCTTTAGCGGCAGCGGATCCGGCACCGAT TTCACCCTGACCATTAGCTCTCTGCAACCGGAAGACTTTGCG ACCTATTATTGCCAGCAGTACGACGACTTCCCGATGACCTTT GGCCAGGGCACGAAAGTTGAAATTAAACGTACGGTGGCCGCT CCCAGCGTGTTCATCTTCCCCCCCAGCGACGAGCAGCTGAAG AGCGGCACCGCCAGCGTGGTGTGCCTGCTGAACAACTTCTAC CCCCGGGAGGCCAAGGTGCAGTGGAAGGTGGACAACGCCCTG CAGAGCGGCAACAGCCAGGAAAGCGTCACCGAGCAGGACAGC AAGGACTCCACCTACAGCCTGAGCAGCACCCTGACCCTGAGC AAGGCCGACTACGAGAAGCACAAGGTGTACGCCTGCGAGGTG ACCCACCAGGGCCTGTCCAGCCCCGTGACCAAGAGCTTCAAC CGGGGCGAGTGT |

NVS2

| | | |
|---|---|---|
| SEQ ID NO: 25 (Combined) | HCDR1 | GFTFSSYAMS |
| SEQ ID NO: 26 (Combined) | HCDR2 | AISGSGGSTYYADSVKG |

TABLE 1-continued

Exemplary anti-BTC Fabs

| SEQ ID NO: 27 (Combined) | HCDR3 | QRYYFGEFDL |
|---|---|---|
| SEQ ID NO: 28 (Kabat) | HCDR1 | SYAMS |
| SEQ ID NO: 26 (Kabat) | HCDR2 | AISGSGGSTYYADSVKG |
| SEQ ID NO: 27 (Kabat) | HCDR3 | QRYYFGEFDL |
| SEQ ID NO: 29 (Chothia) | HCDR1 | GFTFSSY |
| SEQ ID NO: 30 (Chothia) | HCDR2 | SGSGGS |
| SEQ ID NO: 27 (Chothia) | HCDR3 | QRYYFGEFDL |
| SEQ ID NO: 31 (IMGT) | HCDR1 | GFTFSSYA |
| SEQ ID NO: 32 (IMGT) | HCDR2 | ISGSGGST |
| SEQ ID NO: 33 (IMGT) | HCDR3 | ARQRYYFGEFDL |
| SEQ ID NO: 34 | VH | EVQLLESGGGLVQPGGSLRLSCAASGFTFSSYAMSWVRQAPG KGLEWVSAISGSGGSTYYADSVKGRFTISRDNSKNTLYLQMN SLRAEDTAVYYCARQRYYFGEFDLWGQGTLVTVSS |
| SEQ ID NO: 35 | DNA VH | GAAGTGCAGCTGCTGGAAAGCGGTGGCGGTCTGGTGCAGCCA GGTGGTAGCCTGCGCCTGAGCTGTGCCGCAAGCGGCTTTACC TTTAGCAGCTATGCCATGAGCTGGGTGCGCCAAGCACCAGGC AAAGGCCTGGAATGGGTGAGCGCCATTAGCGGCAGCGGTGGC AGCACCTATTATGCCGATAGCGTGAAAGGTCGCTTTACCATT AGTCGCGATAACAGCAAAAACACCCTGTATCTGCAAATGAAC AGCCTGCGGGCAGAAGATACCGCAGTTTATTATTGCGCGCGA CAACGTTACTACTTCGGTGAGTTCGACCTGTGGGGCCAGGGC ACCCTGGTTACTGTCTCGAGC |
| SEQ ID NO: 36 | Heavy Chain | EVQLLESGGGLVQPGGSLRLSCAASGFTFSSYAMSWVRQAPG KGLEWVSAISGSGGSTYYADSVKGRFTISRDNSKNTLYLQMN SLRAEDTAVYYCARQRYYFGEFDLWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSN TKVDKRVEPKSC |
| SEQ ID NO: 37 | DNA Heavy Chain | GAAGTGCAGCTGCTGGAAAGCGGTGGCGGTCTGGTGCAGCCA GGTGGTAGCCTGCGCCTGAGCTGTGCCGCAAGCGGCTTTACC TTTAGCAGCTATGCCATGAGCTGGGTGCGCCAAGCACCAGGC AAAGGCCTGGAATGGGTGAGCGCCATTAGCGGCAGCGGTGGC AGCACCTATTATGCCGATAGCGTGAAAGGTCGCTTTACCATT AGTCGCGATAACAGCAAAAACACCCTGTATCTGCAAATGAAC AGCCTGCGGGCAGAAGATACCGCAGTTTATTATTGCGCGCGA CAACGTTACTACTTCGGTGAGTTCGACCTGTGGGGCCAGGGC ACCCTGGTTACTGTCTCGAGCGCCAGCACAAAGGGACCCAGC GTGTTCCCTCTGGCCCCCAGCAGCAAGTCTACATCTGGCGGA ACAGCCGCCCTGGGCTGCCTCGTGAAGGACTACTTTCCCGAG CCCGTGACCGTGTCCTGGAACTCTGGCGCTCTGACAAGCGGC GTGCACACCTTTCCAGCCGTGCTCCAGAGCAGCGGCCTGTAC TCTCTGAGCAGCGTCGTGACAGTGCCCAGCAGCTCTCTGGGC ACCCAGACCTACATCTGCAACGTGAACCACAAGCCCAGCAAC ACAAAGGTGGACAAGCGGGTGGAACCCAAGTCCTGC |
| SEQ ID NO: 38 (Combined) | LCDR1 | SGDKLGDKYAY |
| SEQ ID NO: 39 (Combined) | LCDR2 | QDSKRPS |
| SEQ ID NO: 40 (Combined) | LCDR3 | QAFDYLYSLGV |
| SEQ ID NO: 38 (Kabat) | LCDR1 | SGDKLGDKYAY |
| SEQ ID NO: 39 (Kabat) | LCDR2 | QDSKRPS |
| SEQ ID NO: 40 (Kabat) | LCDR3 | QAFDYLYSLGV |
| SEQ ID NO: 41 (Chothia) | LCDR1 | DKLGDKY |
| SEQ ID NO: 42 (Chothia) | LCDR2 | QDS |

TABLE 1-continued

Exemplary anti-BTC Fabs

| | | | |
|---|---|---|---|
| SEQ ID NO: 43 (Chothia) | LCDR3 | | FDYLYSLG |
| SEQ ID NO: 44 (IMGT) | LCDR1 | | KLGDKY |
| SEQ ID NO: 42 (IMGT) | LCDR2 | | QDS |
| SEQ ID NO: 40 (IMGT) | LCDR3 | | QAFDYLYSLGV |
| SEQ ID NO: 45 | VL | | SYELTQPPSVSVSPGQTASITCSGDKLGDKYAYWYQQKPGQS PVLVIYQDSKRPSGIPERFSGSNSGNTATLTISGTQAEDEAD YYCQAFDYLYSLGVEGGGTKLIVL |
| SEQ ID NO: 46 | DNA VL | | AGCTATGAACTGACCCAGCCGCCGAGCGTTAGCGTTAGCCCA GGCCAGACCGCCAGCATTACCTGTAGCGGCGACAAACTGGGC GACAAATACGCCTACTGGTATCAGCAGAAACCGGGCCAGAGC CCGGTGCTGGTTATCTATCAGGATAGCAAAGCCCGAGCGGC ATTCCAGAACGCTTTAGCGGCAGCAACAGCGGCAACACCGCC ACCCTGACCATTAGCGGCACCCAGGCCGAAGACGAAGCCGAT TATTACTGTCAGGCTTTCGACTACCTGTATTCCCTGGGTGTG TTTGGCGGCGGTACCAAGCTGACCGTGCTG |
| SEQ ID NO: 47 | Light Chain | | SYELTQPPSVSVSPGQTASITCSGDKLGDKYAYWYQQKPGQS PVLVIYQDSKRPSGIPERFSGSNSGNTATLTISGTQAEDEAD YYCQAFDYLYSLGVFGGGTKLTVLGQPKAAPSVTLFPPSSEE LQANKATLVCLISDFYPGAVTVAWKADSSPVKAGVETTTPSK QSNNKYAASSYLSLTPEQWKSHRSYSCQVTHEGSTVEKTVAP TECS |
| SEQ ID NO: 48 | DNA Light Chain | | AGCTATGAACTGACCCAGCCGCCGAGCGTTAGCGTTAGCCCA GGCCAGACCGCCAGCATTACCTGTAGCGGCGACAAACTGGGC GACAAATACGCCTACTGGTATCAGCAGAAACCGGGCCAGAGC CCGGTGCTGGTTATCTATCAGGATAGCAAAGCCCGAGCGGC ATTCCAGAACGCTTTAGCGGCAGCAACAGCGGCAACACCGCC ACCCTGACCATTAGCGGCACCCAGGCCGAAGACGAAGCCGAT TATTACTGTCAGGCTTTCGACTACCTGTATTCCCTGGGTGTG TTTGGCGGCGGTACCAAGCTGACCGTGCTGGGCCAGCCCAAA GCCGCCCCTAGCGTGACCCTGTTCCCCCCAAGCAGCGAGGAA CTCCAGGCCAACAAGGCCACCCTCGTGTGCCTGATCAGCGAC TTCTACCCTGGCGCCGTGACCGTGGCCTGGAAGGCCGATAGC AGCCCTGTGAAGGCCGGCGTGGAAACCACCACCCCCAGCAAG CAGAGCAACAACAAATACGCCGCCAGCAGCTACCTGAGCCTG ACCCCCGAGCAGTGGAAGTCCCACAGATCCTACAGCTGCCAG GTCACACACGAGGGCAGCACCGTGGAAAAGACCGTGGCCCCC ACCGAGTGCAGC |
| NVS3 | | | |
| SEQ ID NO: 25 (Combined) | HCDR1 | | GFTFSSYAMS |
| SEQ ID NO: 49 (Combined) | HCDR2 | | GLGHVGYTTYTDSVKG |
| SEQ ID NO: 50 (Combined) | HCDR3 | | DYLDFGYYFDV |
| SEQ ID NO: 28 (Kabat) | HCDR1 | | SYAMS |
| SEQ ID NO: 49 (Kabat) | HCDR2 | | GLGHVGYTTYTDSVKG |
| SEQ ID NO: 50 (Kabat) | HCDR3 | | DYLDFGYYFDV |
| SEQ ID NO: 29 (Chothia) | HCDR1 | | GFTFSSY |
| SEQ ID NO: 51 (Chothia) | HCDR2 | | GHVGY |
| SEQ ID NO: 50 (Chothia) | HCDR3 | | DYLDFGYYFDV |
| SEQ ID NO: 31 (IMGT) | HCDR1 | | GFTFSSYA |
| SEQ ID NO: 52 (IMGT) | HCDR2 | | LGHVGYT |
| SEQ ID NO: 53 (IMGT) | HCDR3 | | ARDYLDFGYYFDV |
| SEQ ID NO: 54 | VH | | QVQLLESGGGLVQPGGSLRLSCAASGFTFSSYAMSWVRQAPG KGLEWVSGLGHVGYTTYTDSVKGRFTISRDNSKNTLYLQMNS LRAEDTAVYYCARDYLDFGYYFDVWGQGTLVTVSS |

TABLE 1-continued

Exemplary anti-BTC Fabs

| | | |
|---|---|---|
| SEQ ID NO: 55 | DNA VH | CAGGTGCAGCTGCTGGAATCAGGCGGCGGACTGGTGCAGCCT GGCGGTAGCCTGAGACTGAGCTGCGCTGCTAGTGGCTTCACC TTCTCTAGCTACGCTATGAGCTGGGTCCGGCAGGCCCCTGGC AAAGGCCTGGAGTGGGTCTCCGGACTGGGTCACGTGGGCTAC ACTACCTACACCGATAGCGTGAAGGGCCGGTTCACTATCTCT AGGGATAACTCTAAGAACACCCTGTACCTGCAGATGAATAGC CTGAGAGCCGAGGACACCGCCGTCTACTACTGCGCTAGAGAC TACCTGGACTTCGGCTACTACTTCGACGTGTGGGGCCAGGGC ACCCTGGTCACCGTGTCTAGC |
| SEQ ID NO: 56 | Heavy Chain | QVQLLESGGGLVQPGGSLRLSCAASGFTFSSYAMSWVRQAPG KGLEWVSGLGHVGYTTYTDSVKGRFTISRDNSKNTLYLQMNS LRAEDTAVYYCARDYLDFGYYFDVWGQGTLVTVSSASTKGPS VFPLAPSSKSTSGGTAALGCLVKDYFPEPVTVSWNSGALTSG VHTEPAVLQSSGLYSLSSVVTVPSSSLGTQTYICNVNHKPSN TKVDKRVEPKSC |
| SEQ ID NO: 57 | DNA Heavy Chain | CAGGTGCAGCTGCTGGAATCAGGCGGCGGACTGGTGCAGCCT GGCGGTAGCCTGAGACTGAGCTGCGCTGCTAGTGGCTTCACC TTCTCTAGCTACGCTATGAGCTGGGTCCGGCAGGCCCCTGGC AAAGGCCTGGAGTGGGTCTCCGGACTGGGTCACGTGGGCTAC ACTACCTACACCGATAGCGTGAAGGGCCGGTTCACTATCTCT AGGGATAACTCTAAGAACACCCTGTACCTGCAGATGAATAGC CTGAGAGCCGAGGACACCGCCGTCTACTACTGCGCTAGAGAC TACCTGGACTTCGGCTACTACTTCGACGTGTGGGGCCAGGGC ACCCTGGTCACCGTGTCTAGCGCTAGCACTAAGGGCCCCTCC GTGTTCCCTCTGGCCCCTTCCAGCAAGTCTACCTCTGGCGGC ACCGCTGCTCTGGGCTGCCTGGTGAAGGACTACTTCCCTGAG CCTGTGACAGTGTCCTGGAACTCTGGCGCCCTGACCTCCGGC GTGCACACCTTCCCTGCCGTGCTGCAGTCCTCCGGCCTGTAC TCCCTGTCCTCCGTGGTGACAGTGCCTTCCTCCAGCCTGGGC ACCCAGACCTATATCTGCAACGTGAACCACAAGCCTTCCAAC ACCAAGGTGGACAAGCGGGTGGAGCCTAAGTCATGC |
| SEQ ID NO: 58 (Combined) | LCDR1 | SGDKIGKKYVH |
| SEQ ID NO: 59 (Combined) | LCDR2 | DDSDRPS |
| SEQ ID NO: 60 (Combined) | LCDR3 | QAWDMQSVV |
| SEQ ID NO: 58 (Kabat) | LCDR1 | SGDKIGKKYVH |
| SEQ ID NO: 59 (Kabat) | LCDR2 | DDSDRPS |
| SEQ ID NO: 60 (Kabat) | LCDR3 | QAWDMQSVV |
| SEQ ID NO: 61 (Chothia) | LCDR1 | DKIGKKY |
| SEQ ID NO: 62 (Chothia) | LCDR2 | DDS |
| SEQ ID NO: 63 (Chothia) | LCDR3 | WDMQSV |
| SEQ ID NO: 64 (IMGT) | LCDR1 | KIGKKY |
| SEQ ID NO: 62 (IMGT) | LCDR2 | DDS |
| SEQ ID NO: 60 (IMGT) | LCDR3 | QAWDMQSVV |
| SEQ ID NO: 65 | VL | SYELTQPLSVSVALGQTARITCSGDKIGKKYVHWYQQKPGQA PVLVIYDDSDRPSGIPERFSGSNSGNTATLTISRAQAGDEAD YYCQAWDMQSVVEGGGTKLTVL |
| SEQ ID NO: 66 | DNA VL | AGCTACGAGCTGACTCAGCCCCTGAGCGTCAGCGTGGCCCTG GGCCAGACCGCTAGAATCACCTGTAGCGGCGATAAGATCGGC AAGAAATACGTGCACTGGTATCAGCAGAAGCCCGGCCAGGCC CCCGTGCTGGTCATCTACGACGATAGCGATAGACCTAGCGGA ATCCCCGAGCGGTTTAGCGGCTCTAATAGCGGCAACACCGCT ACCCTGACTATCTCTAGGGCTCAGGCCGGCGACGAGGCCGAC TACTACTGTCAGGCCTGGGATATGCAGTCAGTGGTGTTCGGC GGAGGCACTAAGCTGACCGTGCTG |
| SEQ ID NO: 67 | Light Chain | SYELTQPLSVSVALGQTARITCSGDKIGKKYVHWYQQKPGQA PVLVIYDDSDRPSGIPERFSGSNSGNTATLTISRAQAGDEAD YYCQAWDMQSVVFGGGTKLTVLGQPKAAPSVTLFPPSSEELQ |

TABLE 1-continued

Exemplary anti-BTC Fabs

| | | |
|---|---|---|
| | | ANKATLVCLISDFYPGAVTVAWKADSSPVKAGVETTTPSKQS NNKYAASSYLSLTPEQWKSHRSYSCQVTHEGSTVEKTVAPTE CS |
| SEQ ID NO: 68 | DNA Light Chain | AGCTACGAGCTGACTCAGCCCCTGAGCGTCAGCGTGGCCCTG GGCCAGACCGCTAGAATCACCTGTAGCGGCGATAAGATCGGC AAGAAATACGTGCACTGGTATCAGCAGAAGCCCGGCCAGGCC CCCGTGCTGGTCATCTACGACGATAGCGATAGACCTAGCGGA ATCCCCGAGCGGTTTAGCGGCTCTAATAGCGGCAACACCGCT ACCCTGACTATCTCTAGGGCTCAGGCCGGCGACGAGGCCGAC TACTACTGTCAGGCCTGGGATATGCAGTCAGTGGTGTTCGGC GGAGGCACTAAGCTGACCGTGCTGGGCCAGCCTAAGGCTGCC CCCAGCGTGACCCTGTTCCCCCCCAGCAGCGAGGAGCTGCAG GCCAACAAGGCCACCCTGGTGTGCCTGATCAGCGACTTCTAC CCAGGCGCCGTGACCGTGGCCTGGAAGGCCGACAGCAGCCCC GTGAAGGCCGGCGTGGAGACCACCACCCCCAGCAAGCAGAGC AACAACAAGTACGCCGCCAGCAGCTACCTGAGCCTGACCCCC GAGCAGTGGAAGAGCCACAGGTCCTACAGCTGCCAGGTGACC CACGAGGGCAGCACCGTGGAAAAGACCGTGGCCCCAACCGAG TGCAGC |

NVS4

| | | |
|---|---|---|
| SEQ ID NO: 69 (Combined) | HCDR1 | GFTFSRYWIS |
| SEQ ID NO: 70 (Combined) | HCDR2 | YIDSTGTFINYADSVKG |
| SEQ ID NO: 71 (Combined) | HCDR3 | GGSLFDY |
| SEQ ID NO: 72 (Kabat) | HCDR1 | RYWIS |
| SEQ ID NO: 70 (Kabat) | HCDR2 | YIDSTGTFINYADSVKG |
| SEQ ID NO: 71 (Kabat) | HCDR3 | GGSLFDY |
| SEQ ID NO: 73 (Chothia) | HCDR1 | GFTFSRY |
| SEQ ID NO: 74 (Chothia) | HCDR2 | DSTGTF |
| SEQ ID NO: 71 (Chothia) | HCDR3 | GGSLFDY |
| SEQ ID NO: 75 (IMGT) | HCDR1 | GFTFSRYW |
| SEQ ID NO: 76 (IMGT) | HCDR2 | IDSTGTFI |
| SEQ ID NO: 77 (IMGT) | HCDR3 | ARGGSLFDY |
| SEQ ID NO: 78 | VH | QVQLLESGGGLVQPGGSLRLSCAASGFTFSRYWISWVRQAPG KGLEWVSYIDSTGTFINYADSVKGRFTISRDNSKNTLYLQMN SLRAEDTAVYYCARGGSLFDYWGQGTLVTVSS |
| SEQ ID NO: 79 | DNA VH | CAGGTGCAGCTGCTGGAATCAGGCGGCGGACTGGTGCAGCCT GGCGGTAGCCTGAGACTGAGCTGCGCTGCTAGTGGCTTCACC TTCTCTAGGTACTGGATTAGCTGGGTCCGGCAGGCCCCTGGC AAAGGCCTGGAGTGGGTCTCCTATATCGACTCTACCGGCACC TTTATTAACTACGCCGATAGCGTGAAGGGCCGGTTCACTATC TCTAGGGATAACTCTAAGAACACCCTGTACCTGCAGATGAAT AGCCTGAGAGCCGAGGACACCGCCGTCTACTACTGCGCTAGA GGCGGTAGTCTGTTCGACTACTGGGGCCAGGGCACCCTGGTC ACCGTGTCTAGC |
| SEQ ID NO: 80 | Heavy Chain | QVQLLESGGGLVQPGGSLRLSCAASGFTFSRYWISWVRQAPG KGLEWVSYIDSTGTFINYADSVKGRFTISRDNSKNTLYLQMN SLRAEDTAVYYCARGGSLFDYWGQGTLVTVSSASTKGPSVFP LAPSSKSTSGGTAALGCLVKDYFPEPVTVSWNSGALTSGVHT FPAVLQSSGLYSLSSVVTVPSSSLGTQTYICNVNHKPSNTKV DKRVEPKSC |
| SEQ ID NO: 81 | DNA Heavy Chain | CAGGTGCAGCTGCTGGAATCAGGCGGCGGACTGGTGCAGCCT GGCGGTAGCCTGAGACTGAGCTGCGCTGCTAGTGGCTTCACC TTCTCTAGGTACTGGATTAGCTGGGTCCGGCAGGCCCCTGGC AAAGGCCTGGAGTGGGTCTCCTATATCGACTCTACCGGCACC TTTATTAACTACGCCGATAGCGTGAAGGGCCGGTTCACTATC TCTAGGGATAACTCTAAGAACACCCTGTACCTGCAGATGAAT AGCCTGAGAGCCGAGGACACCGCCGTCTACTACTGCGCTAGA |

TABLE 1-continued

Exemplary anti-BTC Fabs

|  |  |  |
|---|---|---|
|  |  | GGCGGTAGTCTGTTCGACTACTGGGGCCAGGGCACCCTGGTC<br>ACCGTGTCTAGCGCTAGCACTAAGGGCCCCTCCGTGTTCCCT<br>CTGGCCCCTTCCAGCAAGTCTACCTCTGGCGGCACCGCTGCT<br>CTGGGCTGCCTGGTGAAGGACTACTTCCCTGAGCCTGTGACA<br>GTGTCCTGGAACTCTGGCGCCCTGACCTCCGGCGTGCACACC<br>TTCCCTGCCGTGCTGCAGTCCTCCGGCCTGTACTCCCTGTCC<br>TCCGTGGTGACAGTGCCTTCCTCCAGCCTGGGCACCCAGACC<br>TATATCTGCAACGTGAACCACAAGCCTTCCAACACCAAGGTG<br>GACAAGCGGGTGGAGCCTAAGTCATGC |
| SEQ ID NO: 82<br>(Combined) | LCDR1 | RASQGIISYLG |
| SEQ ID NO: 83<br>(Combined) | LCDR2 | AASSLQS |
| SEQ ID NO: 84<br>(Combined) | LCDR3 | QQYDALNT |
| SEQ ID NO: 82 (Kabat) | LCDR1 | RASQGIISYLG |
| SEQ ID NO: 83 (Kabat) | LCDR2 | AASSLQS |
| SEQ ID NO: 84 (Kabat) | LCDR3 | QQYDALNT |
| SEQ ID NO: 85 (Chothia) | LCDR1 | SQGIISY |
| SEQ ID NO: 18 (Chothia) | LCDR2 | AAS |
| SEQ ID NO: 86 (Chothia) | LCDR3 | YDALN |
| SEQ ID NO: 87 (IMGT) | LCDR1 | QGIISY |
| SEQ ID NO: 18 (IMGT) | LCDR2 | AAS |
| SEQ ID NO: 84 (IMGT) | LCDR3 | QQYDALNT |
| SEQ ID NO: 88 | VL | DIQMTQSPSSLSASVGDRVTITCRASQGIISYLGWYQQKPGK<br>APKLLIYAASSLQSGVPSRFSGSGSGTDFTLTISSLQPEDFA<br>TYYCQQYDALNTFGQGTKVEIK |
| SEQ ID NO: 89 | DNA VL | GATATTCAGATGACTCAGTCACCTAGTAGCCTGAGCGCTAGT<br>GTGGGCGATAGAGTGACTATCACCTGTAGAGCCTCTCAGGGG<br>ATTATTAGCTACCTGGGCTGGTATCAGCAGAAGCCCGGCAAA<br>GCCCCTAAGCTGCTGATCTACGCCGCCTCTAGCCTGCAGTCA<br>GGCGTGCCCTCTAGGTTTAGCGGTAGCGGTAGTGGCACCGAC<br>TTCACCCTGACTATTAGTAGCCTGCAGCCCGAGGACTTCGCT<br>ACCTACTACTGTCAGCAGTACGACGCCCTGAACACCTTCGGC<br>CAGGGCACTAAGGTCGAGATTAAG |
| SEQ ID NO: 90 | Light Chain | DIQMTQSPSSLSASVGDRVTITCRASQGIISYLGWYQQKPGK<br>APKLLIYAASSLQSGVPSRFSGSGSGTDFTLTISSLQPEDFA<br>TYYCQQYDALNTFGQGTKVEIKRTVAAPSVFIFPPSDEQLKS<br>GTASVVCLLNNFYPREAKVQWKVDNALQSGNSQESVTEQDSK<br>DSTYSLSSTLTLSKADYEKHKVYACEVTHQGLSSPVTKSFNR<br>GEC |
| SEQ ID NO: 91 | DNA Light<br>Chain | GATATTCAGATGACTCAGTCACCTAGTAGCCTGAGCGCTAGT<br>GTGGGCGATAGAGTGACTATCACCTGTAGAGCCTCTCAGGGG<br>ATTATTAGCTACCTGGGCTGGTATCAGCAGAAGCCCGGCAAA<br>GCCCCTAAGCTGCTGATCTACGCCGCCTCTAGCCTGCAGTCA<br>GGCGTGCCCTCTAGGTTTAGCGGTAGCGGTAGTGGCACCGAC<br>TTCACCCTGACTATTAGTAGCCTGCAGCCCGAGGACTTCGCT<br>ACCTACTACTGTCAGCAGTACGACGCCCTGAACACCTTCGGC<br>CAGGGCACTAAGGTCGAGATTAAGCGTACGGTGGCCGCTCCC<br>AGCGTGTTCATCTTCCCCCCCAGCGACGAGCAGCTGAAGAGC<br>GGCACCGCCAGCGTGGTGTGCCTGCTGAACAACTTCTACCCC<br>CGGGAGGCCAAGGTGCAGTGGAAGGTGGACAACGCCCTGCAG<br>AGCGGCAACAGCCAGGAGAGCGTCACCGAGCAGGACAGCAAG<br>GACTCCACCTACAGCCTGAGCAGCACCCTGACCCTGAGCAAG<br>GCCGACTACGAGAAGCATAAGGTGTACGCCTGCGAGGTGACC<br>CACCAGGGCCTGTCCAGCCCCGTGACCAAGAGCTTCAACAGG<br>GGCGAGTGC | iii. Binding Partner of Anti-BTC Antibody

As noted above, the present disclosure features compositions including one or more anti-BTC antibody or antigen binding fragment thereof conjugated (e.g., covalently-linked, non-covalently, or fused) to a therapeutic target binding moiety specific to a target located in or near a tissue having BTC (e.g., substantial levels of BTC, e.g., the eye, the pancreas, etc.). For example, the present disclosure features compositions with one or more anti-BTC antibody or antigen binding fragment thereof attached to a therapeutic target binding moiety relevant for the treatment of BTC-associated conditions or diseases (e.g., DR, DME, AMD, e.g., neovascular AMD, and/or RVO). In another aspect, the present disclosure features a pharmaceutical composition comprising an anti-BTC antibody or antigen binding fragment thereof and a therapeutic target binding moiety, and the pharmaceutical composition can be used in the treatment of BTC-mediated conditions or diseases. In yet another aspect, the present disclosure features a method of treating a subject in need thereof, comprising administering to the subject an effective amount of an anti-BTC antibody or antigen binding fragment thereof of the present disclosure, followed by administering to the subject a therapeutic target binding moiety (e.g., VEGF inhibitor), where the subject has BTC-mediated conditions or diseases.

In certain preferred aspects, the therapeutic target binding moiety is an antibody, or antigen binding fragment thereof, that binds a therapeutic target (e.g., in the format of a scFv, Fab, single domain antibody, or a diabody) or a polypeptide that binds a therapeutic target (e.g. a soluble receptor). Such therapeutic targets can be, e.g., associated with an ophthalmic disorder, e.g., VEGF, PDGF, PDGF-BB, angiopoietin, Angiopoetin-2, SiP, integrins $\alpha v \beta$, $\alpha v \beta 5$, $\alpha 5 \beta 1$, apelin/APJ, erythropoietin, complement factor D, TNF$\alpha$, C2, Factor B, Factor H, Factor P, CFHR3, Clq, C3, C3b, C5, C5a, C3a, HtrA1, ARMS2, EPO, EPOR, TIMP3, HLA, IL8, CX3CR1, TLR3, TLR4, CETP, LIPC, COL10A1, IL-1$\beta$, IL-17A, FGFR2, and TNFRSF1OA. Additional therapeutic targets include, Factor P, Factor D, IL-6, IL-12, IL-18, bFGF, MCP-1, CD132, IL-6R, CD20, and IGF-1.

In one aspect, the present disclosure features multi-specific binding molecules having at least one of each of an anti-BTC binding moiety and one or more therapeutic target binding moiety. Accordingly, in one aspect, the present disclosure features, e.g., bispecific molecules (e.g., bispecific antibodies) having combinations of binding selectivities selected from the following: BTC and VEGF, BTC and PDGF, BTC and PDGF-BB, BTC and angiopoietin, BTC and Angiopoetin-2, BTC and SIP, BTC and integrins $\alpha v \beta$, BTC and $\alpha v \beta 5$, BTC and $\alpha 5 \beta 1$, BTC and apelin/APJ, BTC and erythropoietin, BTC and complement factor D, BTC and TNF$\alpha$, BTC and C2, BTC and Factor B, BTC and Factor H, BTC and CFHR3, BTC and Clq, BTC and C3, BTC and C3b, BTC and C5, BTC and C5a, BTC and C3a, BTC and HtrA1, BTC and ARMS2, BTC and EPO, BTC and EPOR, BTC and TIMP3, BTC and HLA, BTC and IL8, BTC and CX3CR1, BTC and TLR3, BTC and TLR4, BTC and CETP, BTC and LIPC, BTC and COL10A1, BTC and IL-1$\beta$, BTC and IL-17A, BTC and FGFR2, BTC and TNFRSF1OA, BTC and Factor P, BTC and Factor D, BTC and IL-6, BTC and IL-12, BTC and IL-18, BTC and bFG, BTC and MCP-1, BTC and CD132, BTC and IL-6R, BTC and CD20, or BTC and IGF-1.

In one aspect, a therapeutic target binding moiety can be an anti-VEGF antagonist. In one aspect, an anti-VEGF antagonist is ranibizumab (LUCENTIS®; WO 98/45331; WO 98/45331; U.S. Pat. Nos. 6,884,879; 6,407,213; 7,060, 269; 7,365,166). In one aspect, an anti-VEGF antagonist is bevacizumab (AVASTIN®; U.S. Pat. Nos. 6,054,297; 7,169, 901; 7,375,193; 7,297,334). In one aspect, an anti-VEGF antagonist is aflibercept (EYLEA®; U.S. Pat. No. 7,279, 159). In one aspect, an anti-VEGF antagonist is brolucizumab (BEOVU®; WO 2009/155724; U.S. Pat. Nos. 8,349, 322; 9,090,684; 9,873,737; WO 03/097697; WO 2016/073915; WO/2016/073918). In one aspect, an anti-VEGF antagonist is pegaptanib (MACUGEN®). In one aspect, an anti-VEGF antagonist is KH902 (WO2005/121176; U.S. Pat. No. 7,750,138). In one aspect, an anti-VEGF antagonist comprises a heavy chain and a light chain as set forth in SEQ ID NOs: 103 and 114, respectively. In one aspect, an anti-VEGF antagonist is encoded by a nucleic acid sequence as set forth in SEQ ID NOs: 104 and 115.

iv. Multi-Specific Binding Molecule

Also provided in the present disclosure is a multi-specific binding molecule comprising 1) an anti-BTC binding moiety and 2) an anti-VEGF binding moiety.

a) Anti-BTC Binding Moiety

In one aspect, an anti-BTC binding moiety binds to human BTC as set forth in SEQ ID NO: 157 or 158. In some aspects, an anti-BTC binding moiety selectively binds to a human BTC protein as depicted in Example 2 and Table 4. In some aspects, an anti-BTC binding moiety specifically and/or selectively binds to at least one residue of SEQ ID NO: 157 selected from the group consisting of G34, H35, F36, S37, R38, C39, P40, K41, Q42, Y43, H45, Y46, R51, R53, F54, V56, A57, E58, Q59, T60, P61, A72, R73, E75, and R76. In some aspects, more than one (e.g., 2, 3, 4, 5, 6, 7, 8, 9. 10, 11, 12, 13, 14, 15, 16, 17, 18, 19, 20,21, 22, 23, 24, or 25) of the identified BTC residues are part of the region that is bound by an anti-BTC binding moiety. In specific aspects, such an anti-BTC binding moiety selectively binds to a human BTC protein and inhibits BTC activity (e.g., partially inhibits).

In some aspects, an anti-BTC binding moiety specifically and/or selectively binds to R38, C39, P40, K41, Q42, Y43, H45, Y46, F54, Q59, T60, P61, and R73 of SEQ ID NO: 157, e.g., NVS11. In some aspects, an antibody or antigen binding fragment thereof specifically and/or selectively binds to P40, K41, Q42, Y43, H45, Y46, E58, Q59, T60, P61, A72, R73, E75, and R76 of SEQ ID NO: 157, e.g., NVS12. In some aspects, an antibody or antigen binding fragment thereof specifically and/or selectively binds to G34, H35, F36, S37, R38, C39, P40, K41, Q42, R51, R53, F54, and V56 of SEQ ID NO: 157, e.g., NVS13. In some aspects, an antibody or antigen binding fragment thereof specifically and/or selectively binds to S37, R38, C39, P40, K41, Q42, Y43, H45, Y46, F54, A57, Q59, T60, P61, A72, R73, and E75 of SEQ ID NO: 157, e.g., NVS14. In one aspect, an anti-BTC binding moiety is the anti-BTC antibody or antigen binding fragment thereof as described throughout. In specific aspects, such an anti-BTC binding moiety selectively binds to a human BTC protein and inhibits BTC activity (e.g., partially inhibits).

In aspects where an anti-BTC binding moiety is used for therapeutic applications, an anti-BTC binding moiety can inhibit, interfere with or modulate one or more biological activities of BTC. In one aspect, an anti-BTC binding moiety binds specifically to human BTC and/or substantially inhibits binding of human BTC to ErbB receptor by at least about 20%-40%, 40-60%, 60-80%, 80-85%, or more (for example, by measuring binding in an in vitro competitive binding assay). In some aspects, an anti-BTC binding moiety thereof has a $K_d$ of less (binding more tightly) than $10^{-7}$, $10^{-8}$, 10, $10^{-10}$, $10^{-11}$, $10^{-12}$, $10^{-13}$ M. In some aspects, an anti-BTC binding moiety has an $IC_{50}$ for blocking the binding of ErbB receptor to BTC of less than 1 microM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM. In specific aspects, such an anti-BTC binding moiety selectively binds to a human BTC protein and inhibits BTC activity (e.g., partially inhibits).

In some aspects, an anti-BTC binding moiety binds to variants of BTC that are about at least 50%, 50-60%, 60-70%, 70-80%, 80-90%, 90-95%, 95-99%, or greater percent identity to the form of BTC as set forth in SEQ ID NO: 157 or 158. In some aspects, an anti-BTC binding moiety binds to an epitope bound by one of the antibodies described in Table 3. In some aspects, an anti-BTC binding moiety binds to a specific conformational state of BTC so as to prevent BTC from interacting with ErbB receptor.

An anti-BTC binding moiety of a multi-specific binding molecule of the present disclosure comprises heavy chain variable region complementarity determining region 1 (HCDR1), heavy chain variable region complementarity determining region 2 (HCDR2), heavy chain variable region complementarity determining region 3 (HCDR3), light chain variable region complementarity determining region 1 (LCDR1), light chain variable region complementarity determining region 2 (LCDR2), and light chain variable region complementarity determining region 3 (LCDR3). HCDR1, HCDR2, and HCDR3 are comprised in a heavy chain variable region (VH). LCDR1, LCDR2, and LCDR3 are comprised in a light chain variable region (VL). In one aspect an anti-BTC antibody or antigen binding fragment thereof comprise the heavy chain and light chain CDRs (e.g., Kabat, Chothia, IMGT, and/or combined CDRs) as set forth in Table 3 and described below.

In one aspect, an anti-BTC binding moiety comprises HCDR1, HCDR2, HCDR3, LCDR1, LCDR2, and LCDR3 as set forth in SEQ ID NOs: 4, 2, 3, 14, 15, and 16, respectively, according to the Kabat numbering scheme. In one aspect, an anti-BTC binding moiety comprises HCDR1, HCDR2, HCDR3, LCDR1, LCDR2, and LCDR3 as set forth in SEQ ID NOs: 5, 6, 3, 17, 18, and 19, respectively, according to the Chothia numbering scheme. In one aspect, an anti-BTC binding moiety comprises HCDR1, HCDR2, HCDR3, LCDR1, LCDR2, and LCDR3 as set forth in SEQ ID NOs: 1, 2, 3, 14, 15, and 16, respectively, according to the combined numbering scheme. In one aspect, an anti-BTC binding moiety comprises HCDR1, HCDR2, HCDR3, LCDR1, LCDR2, and LCDR3 as set forth in SEQ ID NOs: 7, 8, 9, 20, 18, and 16, respectively, according to the IMGT numbering scheme. In one aspect, an anti-BTC binding moiety is comprised in NVS11 as provided in Table 3.

In one aspect, an anti-BTC binding moiety comprises HCDR1, HCDR2, HCDR3, LCDR1, LCDR2, and LCDR3 as set forth in SEQ ID NOs: 28, 26, 27, 38, 39, and 40, respectively, according to the Kabat numbering scheme. In one aspect, an anti-BTC binding moiety comprises HCDR1, HCDR2, HCDR3, LCDR1, LCDR2, and LCDR3 as set forth in SEQ ID NOs: 29, 30, 27, 41, 42, and 43, respectively, according to the Chothia numbering scheme. In one aspect, an anti-BTC binding moiety comprises HCDR1, HCDR2, HCDR3, LCDR1, LCDR2, and LCDR3 as set forth in SEQ ID NOs: 25, 26, 27, 38, 39, and 40, respectively, according to the combined numbering scheme. In one aspect, an anti-BTC binding moiety comprises HCDR1, HCDR2, HCDR3, LCDR1, LCDR2, and LCDR3 as set forth in SEQ ID NOs: 31, 32, 33, 44, 42, and 40, respectively, according to the IMGT numbering scheme. In one aspect, an anti-BTC binding moiety is comprised in NVS12 as provided in Table 3.

In one aspect, an anti-BTC binding moiety comprises HCDR1, HCDR2, HCDR3, LCDR1, LCDR2, and LCDR3 as set forth in SEQ ID NOs: 28, 49, 50, 58, 59, and 60, respectively, according to the Kabat numbering scheme. In one aspect, an anti-BTC binding moiety comprises HCDR1, HCDR2, HCDR3, LCDR1, LCDR2, and LCDR3 as set forth in SEQ ID NOs: 29, 51, 50, 61, 62, and 63, respectively, according to the Chothia numbering scheme. In one aspect, an anti-BTC binding moiety comprises HCDR1, HCDR2, HCDR3, LCDR1, LCDR2, and LCDR3 as set forth in SEQ ID NOs: 25, 49, 50, 58, 59, and 60, respectively, according to the combined numbering scheme. In one aspect, an anti-BTC binding moiety comprises HCDR1, HCDR2, HCDR3, LCDR1, LCDR2, and LCDR3 as set forth in SEQ ID NOs: 31, 52, 53, 64, 62, and 60, respectively, according to the IMGT numbering scheme. In one aspect, an anti-BTC binding moiety is comprised in NVS13 as provided in Table 3.

In one aspect, an anti-BTC binding moiety comprises HCDR1, HCDR2, HCDR3, LCDR1, LCDR2, and LCDR3 as set forth in SEQ ID NOs: 72, 70, 71, 82, 83, and 84, respectively, according to the Kabat numbering scheme. In one aspect, an anti-BTC binding moiety comprises HCDR1, HCDR2, HCDR3, LCDR1, LCDR2, and LCDR3 as set forth in SEQ ID NOs: 73, 74, 71, 85, 18, and 86, respectively, according to the Chothia numbering scheme. In one aspect, an anti-BTC binding moiety comprises HCDR1, HCDR2, HCDR3, LCDR1, LCDR2, and LCDR3 as set forth in SEQ ID NOs: 69, 70, 71, 82, 83, and 84, respectively, according to the combined numbering scheme. In one aspect, an anti-BTC binding moiety comprises HCDR1, HCDR2, HCDR3, LCDR1, LCDR2, and LCDR3 as set forth in SEQ ID NOs: 75, 76, 77, 87, 18, and 84, respectively, according to the IMGT numbering scheme. In one aspect, an anti-BTC binding moiety is comprised in NVS14 as provided in Table 3.

In addition, the present disclosure also provides for an anti-BTC binding moiety comprising amino acid sequences that are homologous to the CDR sequences described throughout and in Table 3, and the anti-BTC binding moiety binds to BTC and retains the desired functional properties of those described herein. More specifically, the amino acid sequences of an anti-BTC binding moiety can have greater than or equal to 80%, 90%, 95%, 96%, 97%, 98%, or 99% identity to the CDR sequences as described throughout and set forth in Table 3 and retain the desired functional properties thereof.

The present disclosure also provides anti-BTC binding moieties that are homologous to the VH and VL sequences described herein. More specifically, the present disclosure provides for a protein comprising amino acid sequences that are homologous to the sequences, such as those described in Table 3, and the anti-BTC binding moieties binds to the ophthalmic target, and retains the desired functional properties of those as described in Table 3 and the examples. An anti-BTC binding moiety having VH and VL regions with less than 100% sequence identity to the VH and VL regions of those described in Table 3 can be obtained by mutagenesis (e.g., site-directed or PCR-mediated mutagenesis) of nucleic acid molecules described in Table 3 followed by testing of the encoded altered antibody for retained function using the functional assays described herein and in US 20120014958. An anti-BTC binding moiety having a heavy chain and light chain with high (i.e., 80% or greater) identity to the heavy chains and light chains described in Table 3 can be obtained by mutagenesis (e.g., site-directed or PCR-mediated mutagenesis) of nucleic acid molecules encoding such polypeptides, followed by testing of the encoded altered antibody for retained function using the functional assays described herein.

An anti-BTC binding moiety of the present disclosure comprises a heavy chain variable region (VH) and a light chain variable region (VL) comprising an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 10 and 21, respectively. It is contemplated that the variability can be in the CDR or framework regions. In one aspect, an anti-BTC binding moiety comprising a VH and a VL comprising amino acid sequence as set forth in SEQ ID NOs: 10 and 21, respectively. In another aspect, an anti-BTC binding moiety is NVS11 as provided in Table 3. In another aspect, the VH and VL are encoded by a nucleic acid sequence as set forth in SEQ ID NOs: 116 and 122, respectively. In one aspect, an anti-BTC binding moiety comprises a VH and VL comprising an amino acid sequence having at least one, two or three modifications (e.g., substitutions, e.g., conservative substitutions), but not more than 10 modifications (e.g., substitutions, e.g., conservative substitutions) of an amino acid sequence of SEQ ID NOs: 10 and 21, respectively. In another aspect, the differences in amino acid sequence is not within the complementary determining regions.

In one aspect, an anti-BTC binding moiety of the present disclosure comprises a $V_H$ and a VL comprising an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 34 and 45, respectively. It is contemplated that the variability can be in the CDR or framework regions. In one aspect, an anti-BTC binding moiety comprising a VH and a VL comprising amino acid sequence as set forth in SEQ ID NOs: 34 and 45, respectively. In another aspect, an anti-BTC binding moiety is NVS12 as provided in Table 3. In another aspect, the VH and VL are encoded by a nucleic acid sequence as set forth in SEQ ID NOs: 127 and 132, respectively. In one aspect, an anti-BTC binding moiety comprises a VH and VL comprising an amino acid sequence having at least one, two or three modifications (e.g., substitutions, e.g., conservative substitutions), but not more than 10 modifications (e.g., substitutions, e.g., conservative substitutions) of an amino acid sequence of SEQ ID NOs: 34 and 45, respectively. In another aspect, the differences in amino acid sequence is not within the complementary determining regions.

In one aspect, an anti-BTC binding moiety of the present disclosure comprises a $V_H$ and a $V_L$ comprising an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 54 and 65, respectively. It is contemplated that the variability can be in the CDR or framework regions. In one aspect, an anti-BTC binding moiety comprising a VH and a VL comprising amino acid sequence as set forth in SEQ ID NOs: 54 and 65, respectively. In another aspect, an anti-BTC binding moiety is NVS13 as provided in Table 3. In another aspect, the VH and VL are encoded by a nucleic acid sequence as set forth in SEQ ID NOs: 137 and 142, respectively. In one aspect, an anti-BTC binding moiety comprises a VH and VL comprising an amino acid sequence having at least one, two or three modifications (e.g., substitutions, e.g., conservative substitutions), but not more than 10 modifications (e.g., substitutions, e.g., conservative substitutions) of an amino acid sequence of SEQ ID NOs: 54 and 65, respectively. In another aspect, the differences in amino acid sequence is not within the complementary determining regions.

In one aspect, an anti-BTC binding moiety of the present disclosure comprises a VH and a VL comprising an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 78 and 88, respectively. It is contemplated that the variability can be in the CDR or framework regions. In one aspect, an anti-BTC binding moiety comprising a VH and a VL comprising amino acid sequence as set forth in SEQ ID NOs: 78 and 88, respectively. In another aspect, an anti-BTC binding moiety is NVS14 as provided in Table 3. In another aspect, the VH and VL are encoded by a nucleic acid sequence as set forth in SEQ ID NOs: 147 and 151, respectively. In one aspect, an anti-BTC binding moiety comprises a VH and VL comprising an amino acid sequence having at least one, two or three modifications (e.g., substitutions, e.g., conservative substitutions), but not more than 10 modifications (e.g., substitutions, e.g., conservative substitutions) of an amino acid sequence of SEQ ID NOs: 78 and 88, respectively. In another aspect, the differences in amino acid sequence is not within the complementary determining regions.

In one aspect, an anti-BTC binding moiety of the present disclosure comprises 1) an HCDR1, an HCDR2, an HCDR3, an LCDR1, an LCDR2, and an LCDR3 comprising SEQ ID NOs: 1, 2, 3, 14, 15, and 16, respectively (combined numbering scheme); SEQ ID NOs: 4, 2, 3, 14, 15, and 16, respectively (Kabat numbering scheme); SEQ ID NOs: 5, 6, 3, 17, 18, and 19, respectively (Chothia numbering scheme); or SEQ ID NOs: 7, 8, 9, 20, 18, and 16, respectively (IMGT numbering scheme); and 2) a VH and a VL comprising amino acid sequence as set forth in SEQ ID NOs: 10 and 21, respectively. In another aspect, an anti-BTC binding moiety is comprised in NVS11 as provided in Table 3.

In one aspect, an anti-BTC binding moiety of the present disclosure comprises 1) an HCDR1, an HCDR2, an HCDR3, an LCDR1, an LCDR2, and an LCDR3 comprising SEQ ID NOs: 25, 26, 27, 38, 39, and 40, respectively (combined numbering scheme); SEQ ID NOs: 28, 26, 27, 38, 39, and 40, respectively (Kabat numbering scheme); SEQ ID NOs: 29, 30, 27, 41, 42, and 43, respectively (Chothia numbering scheme); or SEQ ID NOs: 31, 32, 33, 44, 42, and 40, respectively (IMGT numbering scheme); and 2) a VH and a VL comprising amino acid sequence as set forth in SEQ ID NOs: 34 and 45, respectively. In another aspect, an anti-BTC binding moiety is comprised in NVS12 as provided in Table 3.

In one aspect, an anti-BTC binding moiety of the present disclosure comprises 1) an HCDR1, an HCDR2, an HCDR3, an LCDR1, an LCDR2, and an LCDR3 comprising SEQ ID NOs: 25, 49, 50, 58, 59, and 60, respectively (combined numbering scheme); SEQ ID NOs: 28, 49, 50, 58, 59, and 60, respectively (Kabat numbering scheme); SEQ ID NOs: 29, 51, 50, 61, 62, and 63, respectively (Chothia numbering scheme); or SEQ ID NOs: 31, 52, 53, 64, 62, and 60, respectively (IMGT numbering scheme); and 2) a VH and a VL comprising amino acid sequence as set forth in SEQ ID NOs: 54 and 65, respectively. In another aspect, an anti-BTC binding moiety is comprised in NVS13 as provided in Table 3.

In one aspect, an anti-BTC binding moiety of the present disclosure comprises 1) an HCDR1, an HCDR2, an HCDR3, an LCDR1, an LCDR2, and an LCDR3 comprising SEQ ID NOs: 69, 70, 71, 82, 83, and 84, respectively (combined numbering scheme); SEQ ID NOs: 72, 70, 71, 82, 83, and 84, respectively (Kabat numbering scheme); SEQ ID NOs: 73, 74, 71, 85, 18, and 86, respectively (Chothia numbering scheme); or SEQ ID NOs: 75, 76, 77, 87, 18, and 84, respectively (IMGT numbering scheme); and 2) a VH and a VL comprising amino acid sequence as set forth in SEQ ID NOs: 78 and 88, respectively. In another aspect, an anti-BTC binding moiety is comprised in NVS14 as provided in Table 3.

b) Anti-VEGF Binding Moiety

Also provided in the present disclosure is an anti-VEGF binding moiety comprised in a multi-specific binding molecule. In specific aspects, an anti-VEGF binding moiety comprises heavy chain variable region complementarity determining region 1 (HCDR1), heavy chain variable region complementarity determining region 2 (HCDR2), heavy chain variable region complementarity determining region 3 (HCDR3), light chain variable region complementarity determining region 1 (LCDR1), light chain variable region complementarity determining region 2 (LCDR2), and light chain variable region complementarity determining region 3 (LCDR3). HCDR1, HCDR2, and HCDR3 are comprised in a heavy chain variable region (VH). LCDR1, LCDR2, and LCDR3 are comprised in a light chain variable region (VL). In one aspect an anti-VEGF binding moiety comprise the heavy chain and light chain CDRs (e.g., Kabat, Chothia, IMGT, and/or combined CDRs) as set forth in Table 2 or 3 and described below. In one aspect, an anti-VEGF binding moiety is an anti-VEGF antibody or antigen binding fragment thereof. In one aspect, an anti-VEGF binding moiety is an anti-VEGF antibody or antigen binding fragment thereof that inhibits (e.g., partially inhibits) VEGF activity.

In one aspect, an anti-VEGF binding moiety comprises HCDR1, HCDR2, HCDR3, LCDR1, LCDR2, and LCDR3 as set forth in SEQ ID NOs: 95, 93, 94, 105, 106, and 107, respectively, according to the Kabat numbering scheme. In one aspect, an anti-VEGF binding moiety comprises HCDR1, HCDR2, HCDR3, LCDR1, LCDR2, and LCDR3 as set forth in SEQ ID NOs: 96, 97, 94, 108, 109, and 110, respectively, according to the Chothia numbering scheme. In one aspect, an anti-VEGF binding moiety comprises HCDR1, HCDR2, HCDR3, LCDR1, LCDR2, and LCDR3 as set forth in SEQ ID NOs: 92, 93, 94, 105, 106, and 107, respectively, according to the combined numbering scheme. In one aspect, an anti-VEGF binding moiety comprises HCDR1, HCDR2, HCDR3, LCDR1, LCDR2, and LCDR3 as set forth in SEQ ID NOs: 98, 99, 100, 111, 109, and 107, respectively, according to the IMGT numbering scheme. In one aspect, an anti-VEGF binding moiety is NVS8 as provided in Table 2 or comprised in anyone of NVS11-NVS14 as provided in Table 3. In another aspect, an anti-VEGF binding moiety is brolucizumab (BEOVU®).

In addition, the present disclosure also provides for an anti-VEGF binding moiety comprising amino acid sequences that are homologous to the CDR sequences described throughout and in Table 2 or 3, and the anti-VEGF binding moiety binds to VEGF and retains the desired functional properties of those described herein. More specifically, the amino acid sequences of an anti-VEGF binding moiety can have greater than or equal to 80%, 90%, 95%, 96%, 97%, 98%, or 99% identity to the CDR sequences as described throughout and set forth in Table 2 or 3 and retain the desired functional properties thereof.

The present disclosure also provides anti-VEGF binding moieties that are homologous to the VH and VL sequences described herein. More specifically, the present disclosure provides for a protein comprising amino acid sequences that are homologous to the sequences, such as those described in Table 2 or 3, and the anti-VEGF binding moieties binds to an ophthalmic target, and retains the desired functional properties of those as described in Table 2 or 3 and the examples. An anti-VEGF binding moiety having VH and VL regions with less than 100% sequence identity to the VH and VL regions of those described in Table 2 or 3 can be obtained by mutagenesis (e.g., site-directed or PCR-mediated mutagenesis) of nucleic acid molecules described in Table 2 or 3 followed by testing of the encoded altered antibody for retained function using the functional assays described herein and in US 20120014958. An anti-VEGF binding moiety having a heavy chain and light chain with high (i.e., 80% or greater) identity to the heavy chains and light chains described in Table 2 or 3 can be obtained by mutagenesis (e.g., site-directed or PCR-mediated mutagenesis) of nucleic acid molecules encoding such polypeptides, followed by testing of the encoded altered antibody for retained function using the functional assays described herein.

An anti-VEGF binding moiety of the present disclosure comprises a heavy chain variable region (VH) and a light chain variable region (VL) comprising an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 101 and 112, respectively. It is contemplated that the variability can be in the CDR or framework regions. In one aspect, an anti-VEGF binding moiety comprising a VH and a VL comprising amino acid sequence as set forth in SEQ ID NOs: 101 and 112, respectively. In another aspect, an anti-VEGF binding moiety is NVS8 as provided in Table 2 or comprised in anyone of NVS11-NVS14 as provided in Table 3. In one aspect, an anti-VEGF binding moiety comprises a VH and VL comprising an amino acid sequence having at least one, two or three modifications (e.g., substitutions, e.g., conservative substitutions), but not more than 10 modifications (e.g., substitutions, e.g., conservative substitutions) of an amino acid sequence of SEQ ID NOs: 101 and 112, respectively. In another aspect, the differences in amino acid sequence is not within the complementary determining regions.

In one aspect, the VH and VL of an anti-VEGF binding moiety are encoded by a nucleic acid sequence as set forth in SEQ ID NOs: 102 and 113, respectively. In one aspect, an anti-VEGF binding moiety is NVS8 as provided in Table 2.

In one aspect, the VH and VL of an anti-VEGF binding moiety are encoded by a nucleic acid sequence as set forth in SEQ ID NOs: 117 and 123, respectively. In one aspect, an anti-VEGF binding moiety is comprised in NVS11 as provided in Table 3.

In one aspect, the VH and VL of an anti-VEGF binding moiety are encoded by a nucleic acid sequence as set forth in SEQ ID NOs: 128 and 133, respectively. In one aspect, an anti-VEGF binding moiety is comprised in NVS12 as provided in Table 3.

In one aspect, the VH and VL of an anti-VEGF binding moiety are encoded by a nucleic acid sequence as set forth in SEQ ID NOs: 138 and 143, respectively. In one aspect, an anti-VEGF binding moiety is comprised in NVS13 as provided in Table 3.

In one aspect, the VH and VL of an anti-VEGF binding moiety are encoded by a nucleic acid sequence as set forth in SEQ ID NOs: 148 and 152, respectively. In one aspect, an anti-VEGF binding moiety is comprised in NVS14 as provided in Table 3.

In one aspect, an anti-VEGF binding moiety of the present disclosure comprises 1) an HCDR1, an HCDR2, an HCDR3, an LCDR1, an LCDR2, and an LCDR3 comprising SEQ ID NOs: 92, 93, 94, 105, 106, and 107, respectively (combined numbering scheme); SEQ ID NOs: 95, 93, 94, 105, 106, and 107, respectively (Kabat numbering scheme); SEQ ID NOs: 96, 97, 94, 108, 109, and 110, respectively (Chothia numbering scheme); or SEQ ID NOs: 98, 99, 100, 111, 109, and 107, respectively (IMGT numbering scheme); and 2) a VH and a VL comprising amino acid sequence as set forth in SEQ ID NOs: 101 and 112, respectively. In another aspect, an anti-VEGF binding moiety is NVS8 as provided in Table 2 or comprised in anyone of NVS11-NVS14 as provided in Table 3. In one aspect, an anti-VEGF binding moiety inhibits (e.g., partially inhibits) VEGF activity.

In one aspect, an anti-VEGF binding moiety of the present disclosure (e.g., anti-VEGF binding moiety that inhibits VEGF activity) comprises a heavy chain and a light chain comprising an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 103 and 114, respectively. In one aspect, an anti-VEGF binding moiety comprising a heavy chain and a light chain comprising amino acid sequence as set forth in SEQ ID NOs: 103 and 114, respectively. In another aspect, an anti-VEGF binding moiety is NVS8 as provided in Table 2. In another aspect, the heavy chain and light chain are encoded by a nucleic acid sequence with about at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical or complementary to SEQ ID NOs: 104 and 115, respectively. In one aspect, an anti-VEGF binding moiety comprising a heavy chain and a light chain encoded by a nucleic acid sequence as set forth in SEQ ID NOs: 104 and 115, respectively, and is NVS8 as provided in Table 2.

c) Bi-Specific Binding Molecule

In specific aspects, the present invention is a multi-specific binding molecule comprising an anti-BTC binding moiety and an anti-VEGF binding moiety. Provided in the present disclosure is a multi-specific binding molecule comprising an anti-BTC binding moiety and an anti-VEGF binding moiety, 1) where the anti-BTC binding moiety comprises HCDR1, HCDR2, HCDR3, LCDR1, LCDR2, and LCDR3 of an anti-BTC antibody as set forth in Table 1 (e.g., NVS1, NVS2, NVS3, or NVS4); and 2) where the anti-VEGF binding moiety comprises HCDR1, HCDR2, HCDR3, LCDR1, LCDR2, and LCDR3 of an anti-VEGF antibody as set forth in Table 2 or 3. In one aspect, a multi-specific binding molecule is NVS11 as provided in Table 3.

Provided in the present disclosure is a multi-specific binding molecule comprising an anti-BTC binding moiety and an anti-VEGF binding moiety, 1) where the anti-BTC binding moiety comprises 1) HCDR1, HCDR2, HCDR3, LCDR1, LCDR2, and LCDR3 comprising SEQ ID NOs: 1, 2, 3, 14, 15, and 16, respectively (combined numbering scheme); SEQ ID NOs: 4, 2, 3, 14, 15, and 16, respectively (Kabat numbering scheme); SEQ ID NOs: 5, 6, 3, 17, 18, and 19, respectively (Chothia numbering scheme); or SEQ ID NOs: 7, 8, 9, 20, 18, and 16, respectively (IMGT numbering scheme); and 2) where the anti-VEGF binding moiety comprises SEQ ID NOs: 92, 93, 94, 105, 106, and 107, respectively (combined numbering scheme); SEQ ID NOs: 95, 93, 94, 105, 106, and 107, respectively (Kabat numbering scheme); SEQ ID NOs: 96, 97, 94, 108, 109, and 110, respectively (Chothia numbering scheme); or SEQ ID NOs: 98, 99, 100, 111, 109, and 107, respectively (IMGT numbering scheme). In one aspect, a multi-specific binding molecule is NVS11 as provided in Table 3. In one aspect, such a multi-specific binding molecule 1) selectively binds to a human BTC protein and inhibits BTC activity (e.g., partially inhibits) and 2) selectively binds to a human VEGF protein and inhibits VEGF activity (e.g., partially inhibits).

Also provided in the present disclosure is a multi-specific binding molecule comprising an anti-BTC binding moiety and an anti-VEGF binding moiety, 1) whrein the anti-BTC binding moiety comprises 1) HCDR1, HCDR2, HCDR3, LCDR1, LCDR2, and LCDR3 comprising SEQ ID NOs: 25, 26, 27, 38, 39, and 40, respectively (combined numbering scheme); SEQ ID NOs: 28, 26, 27, 38, 39, and 40, respectively (Kabat numbering scheme); SEQ ID NOs: 29, 30, 27, 41, 42, and 43, respectively (Chothia numbering scheme); or SEQ ID NOs: 31, 32, 33, 44, 42, and 40, respectively (IMGT numbering scheme); and 2) where the anti-VEGF binding moiety comprises SEQ ID NOs: 92, 93, 94, 105, 106, and 107, respectively (combined numbering scheme); SEQ ID NOs: 95, 93, 94, 105, 106, and 107, respectively (Kabat numbering scheme); SEQ ID NOs: 96, 97, 94, 108, 109, and 110, respectively (Chothia numbering scheme); or SEQ ID NOs: 98, 99, 100, 111, 109, and 107, respectively (IMGT numbering scheme). In one aspect, a multi-specific binding molecule is NVS12 as provided in Table 3.

Also provided in the present disclosure is a multi-specific binding molecule comprising an anti-BTC binding moiety and an anti-VEGF binding moiety, 1) where the anti-BTC binding moiety comprises 1) HCDR1, HCDR2, HCDR3, LCDR1, LCDR2, and LCDR3 comprising SEQ ID NOs: 25, 49, 50, 58, 59, and 60, respectively (combined numbering scheme); SEQ ID NOs: 28, 49, 50, 58, 59, and 60, respectively (Kabat numbering scheme); SEQ ID NOs: 29, 51, 50, 61, 62, and 63, respectively (Chothia numbering scheme); or SEQ ID NOs: 31, 52, 53, 64, 62, and 60, respectively (IMGT numbering scheme); and 2) where the anti-VEGF binding moiety comprises SEQ ID NOs: 92, 93, 94, 105, 106, and 107, respectively (combined numbering scheme); SEQ ID NOs: 95, 93, 94, 105, 106, and 107, respectively (Kabat numbering scheme); SEQ ID NOs: 96, 97, 94, 108, 109, and 110, respectively (Chothia numbering scheme); or SEQ ID NOs: 98, 99, 100, 111, 109, and 107, respectively (IMGT numbering scheme). In one aspect, a multi-specific binding molecule is NVS13 as provided in Table 3.

Also provided in the present disclosure is a multi-specific binding molecule comprising an anti-BTC binding moiety and an anti-VEGF binding moiety, 1) where the anti-BTC binding moiety comprises 1) HCDR1, HCDR2, HCDR3, LCDR1, LCDR2, and LCDR3 comprising SEQ ID NOs: 69, 70, 71, 82, 83, and 84, respectively (combined numbering scheme); SEQ ID NOs: 72, 70, 71, 82, 83, and 84, respectively (Kabat numbering scheme); SEQ ID NOs: 73, 74, 71, 85, 18, and 86, respectively (Chothia numbering scheme); or SEQ ID NOs: 75, 76, 77, 87, 18, and 84, respectively (IMGT numbering scheme); and 2) where the anti-VEGF binding moiety comprises SEQ ID NOs: 92, 93, 94, 105, 106, and 107, respectively (combined numbering scheme); SEQ ID NOs: 95, 93, 94, 105, 106, and 107, respectively (Kabat numbering scheme); SEQ ID NOs: 96, 97, 94, 108, 109, and 110, respectively (Chothia numbering scheme); or SEQ ID NOs: 98, 99, 100, 111, 109, and 107, respectively (IMGT numbering scheme). In one aspect, a multi-specific binding molecule is NVS14 as provided in Table 3.

In one aspect, a multi-specific binding molecule of the present disclosure comprises 1) a VHA and a VLA that bind to BTC, where the VHA and VLA comprises an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 10 and 21, respectively; and 2) a VHB and a VLB that bind to VEGF, where the VHB and VLB comprises an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 101 and 112, respectively. In another aspect, a multi-specific binding molecule of the present disclosure comprises 1) a VHA and a VLA that bind to BTC comprising an amino acid sequence of SEQ ID NOs: 10 and 21, respectively; and 2) a VHB and a VLB that bind to VEGF comprising an amino acid sequence of SEQ ID NOs: 101 and 112, respectively. In another aspect, the VHA and VLA is encoded by a nucleic acid sequence about at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 116 and 122, respectively. In another aspect, the VHB and VLB is encoded by a nucleic acid sequence about at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 117 and 123, respectively. In one aspect, a multi-specific binding molecule is NVS11 as provided in Table 3. In one aspect, such a multi-specific binding molecule 1) selectively binds to a human BTC protein and inhibits BTC activity (e.g., partially inhibits) and 2) selectively binds to a human VEGF protein and inhibits VEGF activity (e.g., partially inhibits).

In one aspect, a multi-specific binding molecule of the present disclosure comprises 1) a VHA and a VLA that bind to BTC, where the VHA and VLA comprises an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 34 and 45, respectively; and 2) a VHB and a VLB that bind to VEGF, where the VHB and VLB comprises an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 101 and 112, respectively. In another aspect, a multi-specific binding molecule of the present disclosure comprises 1) a VHA and a VLA that bind to BTC comprising an amino acid sequence of SEQ ID NOs: 34 and 45, respectively; and 2) a VHB and a VLB that bind to VEGF comprising an amino acid sequence of SEQ ID NOs: 101 and 112, respectively. In another aspect, the VHA and VLA is encoded by a nucleic acid sequence about at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 127 and 132, respectively. In another aspect, the VHB and VLB is encoded by a nucleic acid sequence about at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 128 and 133, respectively. In one aspect, a multi-specific binding molecule is NVS12 as provided in Table 3. In one aspect, such a multi-specific binding molecule 1) selectively binds to a human BTC protein and inhibits BTC activity (e.g., partially inhibits) and 2) selectively binds to a human VEGF protein and inhibits VEGF activity (e.g., partially inhibits).

In one aspect, a multi-specific binding molecule of the present disclosure comprises 1) a VHA and a VLA that bind to BTC, where the VHA and VLA comprises an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 54 and 65, respectively; and 2) a VHB and a VLB that bind to VEGF, where the VHB and VLB comprises an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 101 and 112, respectively. In another aspect, a multi-specific binding molecule of the present disclosure comprises 1) a VHA and a VLA that bind to BTC comprising an amino acid sequence of SEQ ID NOs: 54 and 65, respectively; and 2) a VHB and a VLB that bind to VEGF comprising an amino acid sequence of SEQ ID NOs: 101 and 112, respectively. In another aspect, the VHA and VLA is encoded by a nucleic acid sequence about at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 137 and 142, respectively. In another aspect, the VHB and VLB is encoded by a nucleic acid sequence about at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 138 and 143, respectively. In one aspect, a multi-specific binding molecule is NVS13 as provided in Table 3. In one aspect, such a multi-specific binding molecule 1) selectively binds to a human BTC protein and inhibits BTC activity (e.g., partially inhibits) and 2) selectively binds to a human VEGF protein and inhibits VEGF activity (e.g., partially inhibits).

In one aspect, a multi-specific binding molecule of the present disclosure comprises 1) a VHA and a VLA that bind to BTC, wherein the VHA and VLA comprises an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 78 and 88, respectively; and 2) a VHB and a VLB that bind to VEGF, where the VHB and VLB comprises an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 101 and 112, respectively. In another aspect, a multi-specific binding molecule of the present disclosure comprises 1) a VHA and a VLA that bind to BTC comprising an amino acid sequence of SEQ ID NOs: 78 and 88, respectively; and 2) a VHB and a VLB that bind to VEGF comprising an amino acid sequence of SEQ ID NOs: 101 and 112, respectively. In another aspect, the VHA and VLA is encoded by a nucleic acid sequence about at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 147 and 151, respectively. In another aspect, the VHB and VLB is encoded by a nucleic acid sequence about at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 148 and 152, respectively. In one aspect, a multi-specific binding molecule is NVS14 as provided in Table 3. In one aspect, such a multi-specific binding molecule 1) selectively binds to a human BTC protein and inhibits BTC activity (e.g., partially inhibits) and 2) selectively binds to a human VEGF protein and inhibits VEGF activity (e.g., partially inhibits).

A multi-specific binding molecule of the present disclosure comprises 1) a heavy chain comprising the VHA, CH1A, linker, VHB, and CH1B, where the heavy chain comprises an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 120; and 2) a light chain comprising the VLA, CKA, linker, VLB, and CKB, where the light chain comprises an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 125. In one aspect, the heavy chain and light chain are encoded by a nucleic acid sequence about at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 121 and 126, respectively. In one aspect, a multi-specific binding molecule comprises a first polypeptide chain and a second polypeptide chain, where the first polypeptide chain comprises an amino acid sequence of SEQ ID NOs: 120, and the second polypeptide chain comprises an amino acid sequence of SEQ ID NOs: 125, as set forth in NVS11 as provided in Table 3. In one aspect, such a multi-specific binding molecule 1) selectively binds to a human BTC protein and inhibits BTC activity (e.g., partially inhibits) and 2) selectively binds to a human VEGF protein and inhibits VEGF activity (e.g., partially inhibits).

A multi-specific binding molecule of the present disclosure comprises 1) a heavy chain comprising the VHA, CH1A, linker, VHB, and CH1B, where the heavy chain comprises an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 130; and 2) a light chain comprising the VLA, CKA, linker, VLB, and CKB, where the light chain comprises an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 135. In one aspect, the heavy chain and light chain are encoded by a nucleic acid sequence about at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 131 and 136, respectively. In one aspect, a multi-specific binding molecule comprises a first polypeptide chain and a second polypeptide chain, where the first polypeptide chain comprises an amino acid sequence of SEQ ID NOs: 130, and the second polypeptide chain comprises an amino acid sequence of SEQ ID NOs: 135, as set forth in NVS12 as provided in Table 3. In one aspect, such a multi-specific binding molecule 1) selectively binds to a human BTC protein and inhibits BTC activity (e.g., partially inhibits) and 2) selectively binds to a human VEGF protein and inhibits VEGF activity (e.g., partially inhibits).

A multi-specific binding molecule of the present disclosure comprises 1) a heavy chain comprising the VHA, CH1A, linker, VHB, and CH1B, where the heavy chain comprises an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 140; and 2) a light chain comprising the VLA, CKA, linker, VLB, and CKB, where the light chain comprises an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 145. In one aspect, the heavy chain and light chain are encoded by a nucleic acid sequence about at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 141 and 146, respectively. In one aspect, a multi-specific binding molecule comprises a first polypeptide chain and a second polypeptide chain, where the first polypeptide chain comprises an amino acid sequence of SEQ ID NOs: 140, and the second polypeptide chain comprises an amino acid sequence of SEQ ID NOs: 145, as set forth in NVS13 as provided in Table 3. In one aspect, such a multi-specific binding molecule 1) selectively binds to a human BTC protein and inhibits BTC activity (e.g., partially inhibits) and 2) selectively binds to a human VEGF protein and inhibits VEGF activity (e.g., partially inhibits).

A multi-specific binding molecule of the present disclosure comprises 1) a heavy chain comprising the VHA, CH1A, linker, VHB, and CH1B, where the heavy chain comprises an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 149; and 2) a light chain comprising the VLA, CKA, linker, VLB, and CKB, where the light chain comprises an amino acid sequence with about at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 154. In one aspect, the heavy chain and light chain are encoded by a nucleic acid sequence about at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 150 and 155, respectively. In one aspect, a multi-specific binding molecule comprises a first polypeptide chain and a second polypeptide chain, where the first polypeptide chain comprises an amino acid sequence of SEQ ID NOs: 149, and the second polypeptide chain comprises an amino acid sequence of SEQ ID NOs: 154, as set forth in NVS14 as provided in Table 3. In one aspect, such a multi-specific binding molecule 1) selectively binds to a human BTC protein and inhibits BTC activity (e.g., partially inhibits) and 2) selectively binds to a human VEGF protein and inhibits VEGF activity (e.g., partially inhibits).

A multi-specific binding molecule of the present disclosure (e.g., NVS11-NVS14) can:
 a. bind simultaneously to BTC and VEGF;
 b. inhibit binding of soluble BTC to ErbB1 or ErB4 and subsequent phosphorylation of Erb receptors;
 c. inhibit soluble BTC-induced phosphorylation of ERK1/2;
 d. bind to membrane bound BTC and inhibit juxtacrine activation of membrane-bound BTC induced phosphorylation of ErbB1;
 e. inhibit binding of soluble VEGF-A165 to soluble VEGFR2;
 f. inhibit BTC-induced human iPSC-derived RPE permeability in an in vitro outer BRB model;
 g. inhibit VEGF-induced human retinal endothelial cells (HREC) permeability in an in vitro inner BRB model;
 h. inhibit BTC-induced retinal thickening; and/or
 i. inhibit VEGF-induced retinal vessel leakage.

TABLE 2

Exemplary anti-VEGF Fab

NVS8

| | | |
|---|---|---|
| SEQ ID NO: 92 (Combined) | HCDR1 | GFSLTDYYYMT |
| SEQ ID NO: 93 (Combined) | HCDR2 | FIDPDDDPYYATWAKG |
| SEQ ID NO: 94 (Combined) | HCDR3 | GDHNSGWGLDI |
| SEQ ID NO: 95 (Kabat) | HCDR1 | DYYYMT |
| SEQ ID NO: 93 (Kabat) | HCDR2 | FIDPDDDPYYATWAKG |
| SEQ ID NO: 94 (Kabat) | HCDR3 | GDHNSGWGLDI |
| SEQ ID NO: 96 (Chothia) | HCDR1 | GFSLTDYY |
| SEQ ID NO: 97 (Chothia) | HCDR2 | DPDDD |
| SEQ ID NO: 94 (Chothia) | HCDR3 | GDHNSGWGLDI |
| SEQ ID NO: 98 (IMGT) | HCDR1 | GFSLTDYY |
| SEQ ID NO: 99 (IMGT) | HCDR2 | IDPDDDP |
| SEQ ID NO: 100 (IMGT) | HCDR3 | AGGDHNSGWGLDI |
| SEQ ID NO: 101 | VH | EVQLVESGGGLVQPGGSLRLSCTASGFSLTDYYYMTWVRQAPGK GLEWVGFIDPDDDPYYATWAKGRFTISRDNSKNTLYLQMNSLRA EDTAVYYCAGGDHNSGWGLDIWGQGTLVTVSS |
| SEQ ID NO: 102 | DNA VH | GAGGTGCAATTGGTTGAATCTGGGGGCGGACTGGTGCAGCCCGG TGGATCTTTGCGCCTGTCCTGTACAGCTTCTGGCTTCTCCTTGA CCGACTACTATTACATGACTTGGGTTCGCCAAGCCCCAGGCAAA GGGCTTGAATGGGTGGGGTTCATTGACCCCGACGATGATCCTTA CTACGCCACATGGGCAAAGGGCCGTTTACTATCAGCCGGGATA ATTCCAAAAACACATTGTATTTGCAAATGAACTCACTGAGAGCA GAAGATACGGCTGTGTACTATTGCGCAGGCGGCGATCATAACTC CGGCTGGGGCCTGGACATCTGGGGGCAGGGGACCCTGGTGACAG TCAGCTCA |
| SEQ ID NO: 103 | Heavy Chain | EVQLVESGGGLVQPGGSLRLSCTASGFSLTDYYYMTWVRQAPGK GLEWVGFIDPDDDPYYATWAKGRFTISRDNSKNTLYLQMNSLRA EDTAVYYCAGGDHNSGWGLDIWGQGTLVTVSSASTKGPSVFPLA PSSKSTSGGTAALGCLVKDYFPEPVTVSWNSGALTSGVHTFPAV LQSSGLYSLSSVVTVPSSSLGTQTYICNVNHKPSNTKVDKRVEP KSC |

TABLE 2-continued

Exemplary anti-VEGF Fab

NVS8

| | | |
|---|---|---|
| SEQ ID NO: 104 | DNA Heavy Chain | GAGGTGCAATTGGTTGAATCTGGGGGCGGACTGGTGCAGCCCGG TGGATCTTTGCGCCTGTCCTGTACAGCTTCTGGCTTCTCCTTGA CCGACTACTATTACATGACTTGGGTTCGCCAAGCCCCAGGCAAA GGGCTTGAATGGGTGGGGTTCATTGACCCCGACGATGATCCTTA CTACGCCACATGGGCAAAGGGCCGGTTTACTATCAGCCGGGATA ATTCCAAAAACACATTGTATTTGCAAATGAACTCACTGAGAGCA GAAGATACGGCTGTGTACTATTGCGCAGGCGGCGATCATAACTC CGGCTGGGGCCTGGACATCTGGGGGCAGGGGACCCTGGTGACAG TCAGCTCAGCCTCAACGAAGGGGCCCAGCGTGTTTCCTTTGGCC CCAAGCAGCAAGTCCACGTCCGGTGGGACTGCAGCTCTTGGTTG TCTGGTCAAGGATTATTTCCCAGAACCCGTGACCGTGTCTTGGA ACAGTGGTGCATTGACATCAGGAGTGCATACATTCCCAGCTGTG CTGCAGAGCTCTGGCCTGTATAGCCTTTCCTCTGTTGTCACGGT GCCCAGCTCCAGCCTGGGGACGCAGACCTATATTTGTAACGTGA ACCATAAACCCTCCAACACCAAGGTTGATAAAGAGTGGAGCCC AAGTCTTGT |
| SEQ ID NO: 105 (Combined) | LCDR1 | QASEIIHSWLA |
| SEQ ID NO: 106 (Combined) | LCDR2 | LASTLAS |
| SEQ ID NO: 107 (Combined) | LCDR3 | QNVYLASTNGAN |
| SEQ ID NO: 105 (Kabat) | LCDR1 | QASEIIHSWLA |
| SEQ ID NO: 106 (Kabat) | LCDR2 | LASTLAS |
| SEQ ID NO: 107 (Kabat) | LCDR3 | QNVYLASTNGAN |
| SEQ ID NO: 108 (Chothia) | LCDR1 | SEIIHSW |
| SEQ ID NO: 109 (Chothia) | LCDR2 | LAS |
| SEQ ID NO: 110 (Chothia) | LCDR3 | VYLASTNGA |
| SEQ ID NO: 111 (IMGT) | LCDR1 | EIIHSW |
| SEQ ID NO: 109 (IMGT) | LCDR2 | LAS |
| SEQ ID NO: 107 (IMGT) | LCDR3 | QNVYLASTNGAN |
| SEQ ID NO: 112 | VL | EIVMTQSPSTLSASVGDRVIITCQASEIIHSWLAWYQQKPGKAP KLLIYLASTLASGVPSRFSGSGSGAEFTLTISSLQPDDFATYYC QNVYLASTNGANFGQGTKLTVLK |
| SEQ ID NO: 113 | DNA VL | GAGATTGTGATGACTCAGAGCCCTTCAACGCTGTCTGCATCCGT AGGTGATCGCGTCATTATTACCTGTCAAGCCTCAGAGATCATTC ACTCTTGGCTCGCCTGGTATCAGCAGAAGCCCGGTAAGGCCCCC AAGCTGCTGATCTATCTTGCTTCAACCCTCGCGAGCGGGGTGCC CTCCCGCTTCAGCGGCTCCGGCTCTGGTGCCGAATTTACCCTGA CAATCAGCTCTCTCCAACCCGATGATTTCGCGACTTACTACTGT CAGAATGTCTACTTGGCCTCAACCAACGGAGCCAACTTCGGCCA GGGGACCAAACTGACCGTCCTTAAG |
| SEQ ID NO: 114 | Light Chain | EIVMTQSPSTLSASVGDRVIITCQASEIIHSWLAWYQQKPGKAP KLLIYLASTLASGVPSRFSGSGSGAEFTLTISSLQPDDFATYYC QNVYLASTNGANFGQGTKLTVLKRTVAAPSVFIFPPSDEQLKSG TASVVCLLNNFYPREAKVQWKVDNALQSGNSQESVTEQDSKDST YSLSSTLTLSKADYEKHKVYACEVTHQGLSSPVTKSENRGEC |
| SEQ ID NO: 115 | DNA Light Chain | GAGATTGTGATGACTCAGAGCCCTTCAACGCTGTCTGCATCCGT AGGTGATCGCGTCATTATTACCTGTCAAGCCTCAGAGATCATTC ACTCTTGGCTCGCCTGGTATCAGCAGAAGCCCGGTAAGGCCCCC AAGCTGCTGATCTATCTTGCTTCAACCCTCGCGAGCGGGGTGCC CTCCCGCTTCAGCGGCTCCGGCTCTGGIGCCGAATTTACCCTGA CAATCAGCTCTCTCCAACCCGATGATTTCGCGACTTACTACTGT CAGAATGTCTACTTGGCCTCAACCAACGGAGCCAACTTCGGCCA GGGGACCAAACTGACCGTCCTTAAGCGTACGGIGGCAGCTCCGT CTGTTTTCATCTTTCCACCTAGCGACGAGCAACTCAAAAGTGGT ACAGCATCCGTGGTTTGTCTGCTGAACAATTTTTACCCCAGGGA GGCTAAGGTCCAGTGGAAAGTCGATAACGCTCTTCAGTCTGGCA ACAGTCAGGAGAGCGTCACAGAGCAGGACTCTAAGGATAGCACT |

TABLE 2-continued

Exemplary anti-VEGF Fab

NVS8

TATAGTCTGTCCTCCACGCTGACACTGTCTAAAGCGGATTATGA
GAAGCACAAGGTTTACGCCTGTGAGGTAACGCACCAAGGACTCT
CCTCCCCAGTTACCAAATCTTTCAACAGAGGAGAATGT

TABLE 3

Exemplary anti-BTC/anti-VEGF bispecific Fabs

NVS11

| | | | |
|---|---|---|---|
| SEQ ID NO: 1 (Combined) | 1 | HCDR1 | GGTFSSYAIS |
| SEQ ID NO: 2 (Combined) | 1 | HCDR2 | GIVPWMGEAVYAQKFQG |
| SEQ ID NO: 3 (Combined) | 1 | HCDR3 | SSSTYGIHAFDY |
| SEQ ID NO: 4 (Kabat) | 1 | HCDR1 | SYAIS |
| SEQ ID NO: 2 (Kabat) | 1 | HCDR2 | GIVPWMGEAVYAQKFQG |
| SEQ ID NO: 3 (Kabat) | 1 | HCDR3 | SSSTYGIHAFDY |
| SEQ ID NO: 5 (Chothia) | 1 | HCDR1 | GGTFSSY |
| SEQ ID NO: 6 (Chothia) | 1 | HCDR2 | VPWMGE |
| SEQ ID NO: 3 (Chothia) | 1 | HCDR3 | SSSTYGIHAFDY |
| SEQ ID NO: 7 (IMGT) | 1 | HCDR1 | GGTFSSYA |
| SEQ ID NO: 8 (IMGT) | 1 | HCDR2 | IVPWMGEA |
| SEQ ID NO: 9 (IMGT) | 1 | HCDR3 | ARSSSTYGIHAFDY |
| SEQ ID NO: 10 | 1 | VH | QVQLVQSGAEVKKPGSSVKVSCKASGGTFSSYAISWVRQAPGQG LEWMGGIVPWMGEAVYAQKFQGRVTITADESTSTAYMELSSLRS EDTAVYYCARSSSTYGIHAFDYWGQGTLVTVSS |
| SEQ ID NO: 116 | 1 | DNA VH | CAAGTGCAGCTGGTGCAGTCTGGCGCCGAAGTGAAGAAACCCGG CTCCTCCGTGAAAGTGTCCTGCAAGGCCTCCGGCGGCACCTTCT CCAGCTACGCCATCTCCTGGGTCCGACAGGCCCCAGGCCAGGGC CTGGAGTGGATGGGCGGCATCGTGCCTTGGATGGGCGAGGCCGT GTACGCCCAGAAATTCCAGGGCAGAGTGACCATCACCGCCGACG AGTCCACCTCCACCGCCTACATGGAACTGTCCTCCCTGAGGAGC GAGGACACCGCCGTGTACTACTGCGCCCGGTCCTCCTCCACCTA CGGCATCCACGCCTTCGACTACTGGGGCCAGGGCACCCTGGTCA CCGTGTCCTCC |
| SEQ ID NO: 92 (Combined) | 2 | HCDR1 | GFSLTDYYMT |
| SEQ ID NO: 93 (Combined) | 2 | HCDR2 | FIDPDDDPYYATWAKG |
| SEQ ID NO: 94 (Combined) | 2 | HCDR3 | GDHNSGWGLDI |
| SEQ ID NO: 95 (Kabat) | 2 | HCDR1 | DYYMT |
| SEQ ID NO: 93 (Kabat) | 2 | HCDR2 | FIDPDDDPYYATWAKG |
| SEQ ID NO: 94 (Kabat) | 2 | HCDR3 | GDHNSGWGLDI |
| SEQ ID NO: 96 (Chothia) | 2 | HCDR1 | GFSLTDYY |
| SEQ ID NO: 97 (Chothia) | 2 | HCDR2 | DPDDD |
| SEQ ID NO: 94 (Chothia) | 2 | HCDR3 | GDHNSGWGLDI |
| SEQ ID NO: 98 (IMGT) | 2 | HCDR1 | GFSLTDYY |
| SEQ ID NO: 99 (IMGT) | 2 | HCDR2 | IDPDDDP |

TABLE 3-continued

Exemplary anti-BTC/anti-VEGF bispecific Fabs

| | | | |
|---|---|---|---|
| SEQ ID NO: 100 (IMGT) | 2 | HCDR3 | AGGDHNSGWGLDI |
| SEQ ID NO: 101 | 2 | VH | EVQLVESGGGLVQPGGSLRLSCTASGFSLTDYYYMTWVRQAPGK GLEWVGFIDPDDDPYYATWAKGRFTISRDNSKNTLYLQMNSLRA EDTAVYYCAGGDHNSGWGLDIWGQGTLVTVSS |
| SEQ ID NO: 117 | 2 | DNA VH | GAAGTCCAGCTGGTGGAATCCGGCGGAGGCCTGGTGCAGCCAGG CGGATCCCTGAGGCTGTCTTGCACCGCCTCCGGCTTCTCCCTGA CCGACTACTACTACATGACTTGGGTCCGCCAGGCTCCCGGAAAA GGACTGGAGTGGGTCGGATTCATCGACCCCGACGACGACCCCTA CTACGCCACCTGGGCCAAGGGCCGGTTCACCATCTCCCGGGACA ACTCCAAGAACACCCTGTACCTGCAGATGAACTCCCTGAGGGCC GAAGATACAGCTGTGTACTATTGCGCTGGCGGCGACCACAACTC CGGCTGGGGCCTGGATATCTGGGGACAGGGAACACTCGTGACAG TGTCCAGC |
| SEQ ID NO: 118 | | HC linker | GSGGGGSGGGGSGGG |
| SEQ ID NO: 119 | | DNA HC linker | GGCTCTGGCGGCGGAGGATCTGGCGGAGGCGGTAGCGGAGGCGG A |
| SEQ ID NO: 120 | | Heavy Chain | QVQLVQSGAEVKKPGSSVKVSCKASGGTFSSYAISWVRQAPGQG LEWMGGIVPWMGEAVYAQKFQGRVTITADESTSTAYMELSSLRS EDTAVYYCARSSSTYGIHAFDYWGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKRVE PKSCGSGGGGSGGGGSGGGEVQLVESGGGLVQPGGSLRLSCTAS GFSLTDYYYMTWVRQAPGKGLEWVGE1DPDDDPYYATWAKGRFT ISRDNSKNTLYLQMNSLRAEDTAVYYCAGGDHNSGWGLDIWQQG TLVTVSSASTKGPSVFPLAPSSKSTSGGTAALGCLVKDYFPEPV TVSWNSGALTSGVHTFPAVLQSSGLYSLSSVVTVPSSSLGTQTY ICNVNHKPSNTKVDKRVEPKSC |
| SEQ ID NO: 121 | | DNA Heavy Chain | CAAGTGCAGCTGGTGCAGTCTGGCGCCGAAGTGAAGAAACCCGG CTCCTCCGTGAAAGTGTCCTGCAAGGCCTCCGGCGGCACCTTCT CCAGCTACGCCATCTCCTGGGTCCGACAGGCCCCAGGCCAGGGC CTGGAGTGGATGGGCGGCATCGTGCCTTGGATGGGCGAGGCCGT GTACGCCCAGAAATTCCAGGGCAGAGTGACCATCACCGCCGACG AGTCCACCTCCACCGCCTACATGGAACTGTCCTCCCTGAGGAGC GAGGACACCGCCGTGTACTACTGCGCCCGGTCCTCCTCCACCTA CGGCATCCACGCCTTCGACTACTGGGGCCAGGGCACCCTGGTCA CCGTGTCCTCCGCCTCCACCAAGGGACCCTCCGTGTTCCCTCTG GCCCCTTCCAGCAAGTCCACCTCTGGCGGCACCGCCGCTCTGGG CTGCCTGGTCAAGGACTACTTCCCCGAGCCCGTGACCGTGTCCT GGAACTCTGGCGCCCTGACCTCCGGCGTGCACACCTTCCCTGCC GTGCTGCAGTCCTCCGGCCTGTACTCCCTGTCCTCCGTCGTGAC CGTGCCCTCCAGCTCTCTGGGCACCCAGACCTACATCTGCAACG TGAACCACAAGCCCTCCAACACCAAAGTGGACAAGCGGGTGGAA CCCAAGTCCTGCGGCTCTGGCGGCGGAGGATCTGGCGGAGGCGG TAGCGGAGGCGGAGAAGTCCAGCTGGTGGAATCCGGCGGAGGCC TGGTGCAGCCAGGCGGATCCCTGAGGCTGTCTTGCACCGCCTCC GGCTTCTCCCTGACCGACTACTACTACATGACTTGGGTCCGCCA GGCTCCCGGAAAAGGACTGGAGTGGGTCGGATTCATCGACCCCG ACGACGACCCCTACTACGCCACCTGGGCCAAGGGCCGGTTCACC ATCTCCCGGGACAACTCCAAGAACACCCTGTACCTGCAGATGAA CTCCCTGAGGGCCGAAGATACAGCTGTGTACTATTGCGCTGGCG GCGACCACAACTCCGGCTGGGGCCTGGATATCTGGGGACAGGGA ACACTCGTGACAGTGTCCAGCGCCAGCACCAAGGGCCCCTCCGT GTTCCCTCTGGCCCCTTCCAGCAAGTCTACCTCTGGCGGCACCG CTGCTCTGGGCTGCCTGGTGAAGGACTACTTCCCTGAGCCTGTG ACAGTGTCCTGGAACTCTGGCGCCCTGACCTCCGGCGTGCACAC CTTCCCTGCCGTGCTGCAGTCCTCCGGCCTGTACTCCCTGTCCT CCGTGGTGACAGTGCCTTCCTCCAGCCTGGGCACCCAGACCTAT ATCTGCAACGTGAACCACAAGCCTTCCAACACCAAGGTGGACAA GCGGGTGGAGCCTAAGTCATGC |
| SEQ ID NO: 14 (Combined) | 1 | LCDR1 | RASQSISNFLN |
| SEQ ID NO: 15 (Combined) | 1 | LCDR2 | AASNLQS |
| SEQ ID NO: 16 (Combined) | 1 | LCDR3 | QQYDDFPMT |
| SEQ ID NO: 14 (Kabat) | 1 | LCDR1 | RASQSISNFLN |
| SEQ ID NO: 15 (Kabat) | 1 | LCDR2 | AASNLQS |

TABLE 3-continued

Exemplary anti-BTC/anti-VEGF bispecific Fabs

| | | | |
|---|---|---|---|
| SEQ ID NO: 16 (Kabat) | 1 | LCDR3 | QQYDDFPMT |
| SEQ ID NO: 17 (Chothia) | 1 | LCDR1 | SQSISNF |
| SEQ ID NO: 18 (Chothia) | 1 | LCDR2 | AAS |
| SEQ ID NO: 19 (Chothia) | 1 | LCDR3 | YDDFPM |
| SEQ ID NO: 20 (IMGT) | 1 | LCDR1 | QSISNF |
| SEQ ID NO: 18 (IMGT) | 1 | LCDR2 | AAS |
| SEQ ID NO: 16 (IMGT) | 1 | LCDR3 | QQYDDFPMT |
| SEQ ID NO: 21 | 1 | VL | DIQMTQSPSSLSASVGDRVTITCRASQSISNFLNWYQQKPGKAP KLLIYAASNLQSGVPSRFSGSGSGTDFTLTISSLQPEDFATYYC QQYDDFPMTFGQGTKVEIK |
| SEQ ID NO: 122 | 1 | DNA VL | GACATCCAGATGACCCAGAGCCCCTCCAGCCTGTCCGCCTCCGT GGGCGACAGAGTGACCATCACCTGTCGGGCCTCCCAGTCTATCT CCAACTTCCTGAACTGGTATCAGCAGAAGCCCGGCAAGGCCCCT AAGCTGCTGATCTACGCCGCCTCCAACCTGCAGTCCGGCGTGCC CTCCAGATTCTCCGGCTCTGGCTCCGGCACCGACTTCACCCTGA CCATCTCCAGCCTGCAGCCCGAGGACTTCGCCACCTACTACTGC CAGCAGTACGACGACTTCCCCATGACCTTCGGCCAGGGCACCAA AGTGGAAATCAAG |
| SEQ ID NO: 105 (Combined) | 2 | LCDR1 | QASEIIHSWLA |
| SEQ ID NO: 106 (Combined) | 2 | LCDR2 | LASTLAS |
| SEQ ID NO: 107 (Combined) | 2 | LCDR3 | QNVYLASTNGAN |
| SEQ ID NO: 105 (Kabat) | 2 | LCDR1 | QASEIIHSWLA |
| SEQ ID NO: 106 (Kabat) | 2 | LCDR2 | LASTLAS |
| SEQ ID NO: 107 (Kabat) | 2 | LCDR3 | QNVYLASTNGAN |
| SEQ ID NO: 108 (Chothia) | 2 | LCDR1 | SEIIHSW |
| SEQ ID NO: 109 (Chothia) | 2 | LCDR2 | LAS |
| SEQ ID NO: 110 (Chothia) | 2 | LCDR3 | VYLASTNGA |
| SEQ ID NO: 111 (IMGT) | 2 | LCDR1 | EIIHSW |
| SEQ ID NO: 109 (IMGT) | 2 | LCDR2 | LAS |
| SEQ ID NO: 107 (IMGT) | 2 | LCDR3 | QNVYLASTNGAN |
| SEQ ID NO: 112 | 2 | VL | EIVMTQSPSTLSASVGDRVIITCQASEIIHSWLAWYQQKPGKAP KLLIYLASTLASGVPSRFSGSGSGAEFTLTISSLQPDDFATYYC QNVYLASTNGANFGQGTKLTVLK |
| SEQ ID NO: 123 | 2 | DNA VL | GAGATCGTGATGACCCAGTCCCCTAGCACCCTGAGCGCCAGCGT GGGAGATCGCGTGATCATCACATGCCAGGCCTCCGAGATCATCC ACAGCTGGCTGGCTTGGTATCAGCAGAAACCTGGAAAAGCTCCC AAGCTCCTGATCTATCTGGCCAGCACCCTGGCCTCTGGCGTGCC CAGCAGATTCAGCGGCTCCGGCAGCGGCGCTGAGTTTACCCTGA CAATCAGCTCCCTGCAGCCTGACGATTTTGCTACCTACTATTGT CAGAACGTGTACCTGGCCTCCACCAACGGCGCCAACTTTGGCCA GGGAACAAAGCTGACCGTGCTGAAG |
| SEQ ID NO: 118 | | LC linker | GSGGGGSGGGGSGGG |
| SEQ ID NO: 124 | | DNA LC linker | GGCTCCGGCGGAGGCGGATCTGGTGGCGGAGGATCTGGCGGTGG C |
| SEQ ID NO: 125 | | Light Chain | DIQMTQSPSSLSASVGDRVTITCRASQSISNFLNWYQQKPGKAP KLLIYAASNLQSGVPSRFSGSGSGTDFTLTISSLQPEDFATYYC QQYDDFPMTFGQGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGECGSGGGG |

TABLE 3-continued

Exemplary anti-BTC/anti-VEGF bispecific Fabs

| | | | |
|---|---|---|---|
| | | | SGGGGSGGGEIVMTQSPSTLSASVGDRVIITCQASEIIHSWLAW
YQQKPGKAPKLLIYLASTLASGVPSRFSGSGSGAEFTLTISSLQ
PDDFATYYCQNVYLASTNGANFGQGTKLTVLKRTVAAPSVFIFP
PSDEQLKSGTASVVCLLNNFYPREAKVQWKVDNALQSGNSQESV
TEQDSKDSTYSLSSTLTLSKADYEKHKVYACEVTHQGLSSPVTK
SFNRGEC |
| SEQ ID NO: 126 | | DNA Light Chain | GACATCCAGATGACCCAGAGCCCCTCCAGCCTGTCCGCCTCCGT
GGGCGACAGAGTGACCATCACCTGTCGGGCCTCCCAGTCTATCT
CCAACTTCCTGAACTGGTATCAGCAGAAGCCCGGCAAGGCCCCT
AAGCTGCTGATCTACGCCGCCTCCAACCTGCAGTCCGGCGTGCC
CTCCAGATTCTCCGGCTCTGGCTCCGGCACCGACTTCACCCTGA
CCATCTCCAGCCTGCAGCCCGAGGACTTCGCCACCTACTACTGC
CAGCAGTACGACGACTTCCCCATGACCTTCGGCCAGGGCACCAA
AGTGGAAATCAAGCGGACCGTGGCCGCTCCCTCCGTGTTCATCT
TCCCACCCTCCGACGAGCAGCTGAAGTCCGGCACCGCCTCCGTC
GTGTGCCTGCTGAACAACTTCTACCCTCGCGAGGCCAAAGTGCA
GTGGAAAGTGGACAACGCCCTGCAGAGCGGCAACTCCCAGGAAT
CCGTCACCGAGCAGGACTCCAAGGACAGCACCTACTCCCTGTCC
TCCACCCTGACCCTGTCCAAGGCCGACTACGAGAAGCACAAAGT
GTACGCCTGCGAAGTGACCCACCAGGGCCTGTCCAGCCCCGTGA
CCAAGTCCTTCAACCGGGGCGAGTGTGGCTCCGGCGGAGGCGGA
TCTGGTGGCGGAGGATCTGGCGGTGGCGGAGATCGTGATGACCA
GTCCCCTAGCACCCTGAGCGCCAGCGTGGGAGATCGCGTGATCA
TCACATGCCAGGCCTCCGAGATCATCCACAGCTGGCTGGCTGGT
ATCAGCAGAAACCTGGAAAAGCTCCCAAGCTCCTGATCTATCTG
GCCAGCACCCTGGCCTCTGGCGTGCCCAGCAGATTCAGCGGCTC
CGGCAGCGGCGCTGAGTTTACCCTGACAATCAGCTCCCTGCAGC
CTGACGATTTTGCTACCTACTATTGTCAGAACGTGTACCTGGCC
TCCACCAACGGCGCCAACTTTGGCCAGGGAACAAAGCTGACCGT
GCTGAAGCGTACGGTGGCCGCTCCCAGCGTGTTCATCTTCCCC
CCAGCGACGAGCAGCTGAAGAGCGGCACCGCCAGCGTGGTGTGC
CTGCTGAACAACTTCTACCCCGGGAGGCCAAGGTGCAGTGGAA
GGTGGACAACGCCCTGCAGAGCGGCAACAGCCAGGAGAGCGTCA
CCGAGCAGGACAGCAAGGACTCCACCTACAGCCTGAGCAGCACC
CTGACCCTGAGCAAGGCCGACTACGAGAAGCATAAGGTGTACGC
CTGCGAGGTGACCCACCAGGGCCTGTCCAGCCCCGTGACCAAGA
GCTTCAACAGGGGCGAGTGC |
| NVS12 | | | |
| SEQ ID NO: 25 (Combined) | | 1 HCDR1 | GFTFSSYAMS |
| SEQ ID NO: 26 (Combined) | | 1 HCDR2 | AISGSGGSTYYADSVKG |
| SEQ ID NO: 27 (Combined) | | 1 HCDR3 | QRYYFGEFDL |
| SEQ ID NO: 28 (Kabat) | | 1 HCDR1 | SYAMS |
| SEQ ID NO: 26 (Kabat) | | 1 HCDR2 | AISGSGGSTYYADSVKG |
| SEQ ID NO: 27 (Kabat) | | 1 HCDR3 | QRYYFGEFDL |
| SEQ ID NO: 29 (Chothia) | | 1 HCDR1 | GFTFSSY |
| SEQ ID NO: 30 (Chothia) | | 1 HCDR2 | SGSGGS |
| SEQ ID NO: 27 (Chothia) | | 1 HCDR3 | QRYYFGEFDL |
| SEQ ID NO: 31 (IMGT) | | 1 HCDR1 | GFTFSSYA |
| SEQ ID NO: 32 (IMGT) | | 1 HCDR2 | ISGSGGST |
| SEQ ID NO: 33 (IMGT) | | 1 HCDR3 | ARQRYYFGEFDL |
| SEQ ID NO: 34 | | 1 VH | EVQLLESGGGLVQPGGSLRLSCAASGFTFSSYAMSWVRQAPGKG
LEWVSAISGSGGSTYYADSVKGRFTISRDNSKNTLYLQMNSLRA
EDTAVYYCARQRYYFGEFDLWGQGTLVTVSS |
| SEQ ID NO 127 | | 1 DNA VH | GAAGTGCAGCTGCTGGAATCTGGCGGCGGACTGGTGCAGCCTGG
CGGCTCCCTGAGGCTGTCTTGTGCCGCCTCCGGCTTCACCTTCT
CCAGCTACGCCATGTCCTGGGTCCGACAGGCCCCTGGCAAGGGC
CTGGAGTGGGTGTCCGCCATCTCCGGCTCCGGCGGCTCTACCTA
CTACGCCGACTCCGTGAAGGGCCGGTTCACCATCTCCGGGACA
ACTCCAAGAACACCCTGTACCTGCAGATGAACTCCCTGAGGGCC
GAGGACACCGCCGTGTACTACTGCGCCAGACAGCGGTACTACTT |

TABLE 3-continued

| | | | |
|---|---|---|---|
| Exemplary anti-BTC/anti-VEGF bispecific Fabs | | | |
| | | | CGGCGAGTTCGACCTGTGGGGCCAGGGCACCCTGGTCACCGTGT<br>CCTCC |
| SEQ ID NO: 92<br>(Combined) | | 2 HCDR1 | GFSLTDYYYMT |
| SEQ ID NO: 93<br>(Combined) | | 2 HCDR2 | FIDPDDDPYYATWAKG |
| SEQ ID NO: 94<br>(Combined) | | 2 HCDR3 | GDHNSGWGLDI |
| SEQ ID NO: 95 (Kabat) | | 2 HCDR1 | DYYYMT |
| SEQ ID NO: 93 (Kabat) | | 2 HCDR2 | FIDPDDDPYYATWAKG |
| SEQ ID NO: 94 (Kabat) | | 2 HCDR3 | GDHNSGWGLDI |
| SEQ ID NO: 96 (Chothia) | | 2 HCDR1 | GFSLTDYY |
| SEQ ID NO: 97 (Chothia) | | 2 HCDR2 | DPDDD |
| SEQ ID NO: 94 (Chothia) | | 2 HCDR3 | GDHNSGWGLDI |
| SEQ ID NO: 98 (IMGT) | | 2 HCDR1 | GFSLTDYYY |
| SEQ ID NO: 99 (IMGT) | | 2 HCDR2 | IDPDDDP |
| SEQ ID NO: 100 (IMGT) | | 2 HCDR3 | AGGDHNSGWGLDI |
| SEQ ID NO: 101 | | 2 VH | EVQLVESGGGLVQPGGSLRLSCTASGFSLTDYYYMTWVRQAPGK<br>GLEWVGFIDPDDDPYYATWAKGRFTISRDNSKNTLYLQMNSLRA<br>EDTAVYYCAGGDHNSGWGLDIWGQGTLVTVSS |
| SEQ ID NO: 128 | | 2 DNA VH | GAAGTCCAGCTGGTGGAAAGCGGCGGAGGCCTGGTCCAGCCAGG<br>CGGATCCCTGAGGCTCAGCTGCACCGCCTCTGGCTTCTCCCTGA<br>CCGACTACTACTATATGACTTGGGTCCGCCAGGCTCCCGGAAAA<br>GGACTCGAATGGGTCGGATTCATCGACCCCGACGACGACCCTTA<br>CTACGCCACCTGGGCCAAGGGCAGATTCACCATCAGCAGAGACA<br>ACAGCAAGAACACACTCTATCTCCAGATGAACTCCCTGAGGGCT<br>GAAGATACCGCTGTCTATTACTGCGCTGGCGGCGACCACAACTC<br>CGGCTGGGGCCTGGATATCTGGGGACAGGGCACACTCGTGACAG<br>TGTCCAGC |
| SEQ ID NO: 118 | | HC linker | GSGGGGSGGGGSGGG |
| SEQ ID NO: 129 | | DNA HC<br>linker | GGCTCTGGCGGAGGCGGAAGTGGTGGCGGAGGATCAGGCGGCGG<br>A |
| SEQ ID NO: 130 | | Heavy<br>Chain | EVQLLESGGGLVQPGGSLRLSCAASGFTFSSYAMSWVRQAPGKG<br>LEWVSAISGSGGSTYYADSVKGRFTISRDNSKNTLYLQMNSLRA<br>EDTAVYYCARQRYYFGEFDLWGQGTLVTVSSASTKGPSVFPLAP<br>SSKSTSGGTAALGCLVKDYFPEPVTVSWNSGALTSGVHTFPAVL<br>QSSGLYSLSSVVTVPSSSLGTQTYICNVNHKPSNTKVDKRVEPK<br>SCGSGGGGSGGGGSGGGEVQLVESGGGLVQPGGSLRLSCTASGF<br>SLTDYYYMTWVRQAPGKGLEWVGFIDPDDDPYYATWAKGRFTIS<br>RDNSKNTLYLQMNSLRAEDTAVYYCAGGDHNSGWGLDIWGQGTL<br>VTVSSASTKGPSVFPLAPSSKSTSGGTAALGCLVKDYEPEPVTV<br>SWNSGALTSGVHTFPAVLQSSGLYSLSSVVTVPSSSLGTQTYIC<br>NVNHKPSNTKVDKRVEPKSC |
| SEQ ID NO: 131 | | DNA Heavy<br>Chain | GAAGTGCAGCTGCTGGAATCTGGCGGCGGACTGGTGCAGCCTGG<br>CGGCTCCCTGAGGCTGTCTTGTGCCGCCTCCGGCTTCACCTTCT<br>CCAGCTACGCCATGTCCTGGGTCCGACAGGCCCCTGGCAAGGGC<br>CTGGAGTGGGTGTCCGCCATCTCCGGCTCCGGCGGCTCTACCTA<br>CTACGCCGACTCCGTGAAGGGCCGGTTCACCATCTCCCGGGACA<br>ACTCCAAGAACACCCTGTACCTGCAGATGAACTCCCTGAGGGCC<br>GAGGACACCGCCGTGTACTACTGCGCCAGACAGCGGTACTACTT<br>CGGCGAGTTCGACCTGTGGGGCCAGGGCACCCTGGTCACCGTGT<br>CCTCCGCCTCCACCAAGGGACCCTCCGTGTTCCCTCTGGCCCCT<br>TCCAGCAAGTCCACCTCTGGCGGCACCGCCGCTCTGGGCTGCCT<br>GGTCAAGGACTACTTCCCCGAGCCCGTGACCGTGTCCTGGAACT<br>CCGGCGCTCTGACCTCCGGCGTGCACACCTTCCCTGCCGTGCTG<br>CAGTCCTCCGGCCTGTACTCCCTGTCCTCCGTCGTGACCGTGCC<br>CTCCAGCTCTCTGGGCACCCAGACCTACATCTGCAACGTGAACC<br>ACAAGCCCTCCAACACCAAAGTGGACAAGCGGGTGGAACCCAAG<br>TCCTGCGGCTCTGGCGGAGGCGGAAGTGGTGGCGGAGGATCAGG<br>CGGCGGAGAAGTCCAGCTGGTGGAAAGCGGCGGAGGCCTGGTCC |

TABLE 3-continued

Exemplary anti-BTC/anti-VEGF bispecific Fabs

| | | | |
|---|---|---|---|
| | | | AGCCAGGCGGATCCCTGAGGCTCAGCTGCACCGCCTCTGGCTTC<br>TCCCTGACCGACTACTACTATATGACTTGGGTCCGCCAGGCTCC<br>CGGAAAAGGACTCGAATGGGTCGGATTCATCGACCCCGACGACG<br>ACCCTTACTACGCCACCTGGGCCAAGGGCAGATTCACCATCAGC<br>AGAGACAACAGCAAGAACACACTCTATCTCCAGATGAACTCCCT<br>GAGGGCTGAAGATACCGCTGTCTATTACTGCGCTGGCGGCGACC<br>ACAACTCCGGCTGGGGCCTGGATATCTGGGGACAGGGCACACTC<br>GTGACAGTGTCCAGCGCCAGCACCAAGGGCCCCTCCGTGTTCCC<br>TCTGGCCCCTTCCAGCAAGTCTACCTCTGGCGGCACCGCTGCTC<br>TGGGCTGCCTGGTAAGGACTACTTCCCTGAGCCTGTGACAGTG<br>TCCTGGAACTCTGGCGCCCTGACCTCCGGCGTGCACACCTTCCC<br>TGCCGTGCTGCAGTCCTCCGGCCTGTACTCCCTGTCCTCCGTGG<br>TGACAGTGCCTTCCTCAGCCTGGGCACCCAGACCTATATCTGC<br>AACGTGAACCACAAGCCTTCCAACACCAAGGTGGACAAGCGGGT<br>GGAGCCTAAGTCATGC |
| SEQ ID NO: 38<br>(Combined) | 1 | LCDR1 | SGDKLGDKYAY |
| SEQ ID NO: 39<br>(Combined) | 1 | LCDR2 | QDSKRPS |
| SEQ ID NO: 40<br>(Combined) | 1 | LCDR3 | QAFDYLYSLGV |
| SEQ ID NO: 38 (Kabat) | 1 | LCDR1 | SGDKLGDKYAY |
| SEQ ID NO: 39 (Kabat) | 1 | LCDR2 | QDSKRPS |
| SEQ ID NO: 40 (Kabat) | 1 | LCDR3 | QAFDYLYSLGV |
| SEQ ID NO: 41 (Chothia) | 1 | LCDR1 | DKLGDKY |
| SEQ ID NO: 42 (Chothia) | 1 | LCDR2 | QDS |
| SEQ ID NO: 43 (Chothia) | 1 | LCDR3 | FDYLYSLG |
| SEQ ID NO: 44 (IMGT) | 1 | LCDR1 | KLGDKY |
| SEQ ID NO: 42 (IMGT) | 1 | LCDR2 | QDS |
| SEQ ID NO: 40 (IMGT) | 1 | LCDR3 | QAFDYLYSLGV |
| SEQ ID NO: 45 | 1 | VL | SYELTQPPSVSVSPGQTASITCSGDKLGDKYAYWYQQKPGQSPV<br>LVIYQDSKRPSGIPERFSGSNSGNTATLTISGTQAEDEADYYCQ<br>AFDYLYSLGVEGGGTKLIVL |
| SEQ ID NO: 132 | 1 | DNA VL | TCCTACGAGCTGACCCAGCCTCCCTCCGTGTCCGTGTCTCCTGG<br>CCAGACCGCCTCCATCACCTGTTCCGGCGACAAGCTGGGCGATA<br>AGTACGCCTACTGGTATCAGCAGAAGCCCGGCCAGTCCCCTGTG<br>CTGGTCATCTACCAGGACTCCAAGCGGCCCTCCGGCATCCCTGA<br>GCGGTTCTCCGGCTCCAACTCCGGCAACACCGCCACCCTGACCA<br>TCTCCGGCACCCAGGCCGAGGACGAGGCCGACTACTACTGCCAG<br>GCCTTCGACTACCTGTACTCCCTGGGCGTGTTCGGCGGAGGCAC<br>CAAGCTGACCGTGCTG |
| SEQ ID NO: 105<br>(Combined) | 2 | LCDR1 | QASEIIHSWLA |
| SEQ ID NO: 106<br>(Combined) | 2 | LCDR2 | LASTLAS |
| SEQ ID NO: 107<br>(Combined) | 2 | LCDR3 | QNVYLASTNGAN |
| SEQ ID NO: 105 (Kabat) | 2 | LCDR1 | QASEIIHSWLA |
| SEQ ID NO: 106 (Kabat) | 2 | LCDR2 | LASTLAS |
| SEQ ID NO: 107 (Kabat) | 2 | LCDR3 | QNVYLASTNGAN |
| SEQ ID NO: 108 (Chothia) | 2 | LCDR1 | SEIIHSW |
| SEQ ID NO: 109 (Chothia) | 2 | LCDR2 | LAS |
| SEQ ID NO: 110 (Chothia) | 2 | LCDR3 | VYLASTNGA |
| SEQ ID NO: 111 (IMGT) | 2 | LCDR1 | EIIHSW |

TABLE 3-continued

Exemplary anti-BTC/anti-VEGF bispecific Fabs

| SEQ ID NO: 109 (IMGT) | 2 LCDR2 | LAS |
|---|---|---|
| SEQ ID NO: 107 (IMGT) | 2 LCDR3 | QNVYLASTNGAN |
| SEQ ID NO: 112 | 2 VL | EIVMTQSPSTLSASVGDRVIITCQASEIIHSWLAWYQQKPGKAP KLLIYLASTLASGVPSRFSGSGSGAEFTLTISSLQPDDFATYYC QNVYLASTNGANFGQGTKLTVLK |
| SEQ ID NO: 133 | 2 DNA VL | GAGATCGTGATGACCCAGTCCCCTTCCACCCTGTCCGCCTCCGT GGGCGACAGAGTGATCATCACCTGTCAGGCCTCCGAGATCATCC ACAGCTGGCTGGCTTGGTATCAGCAGAAACCTGGCAAGGCCCCT AAGCTGCTGATCTACCTGGCCTCCACCCTGGCCTCCGGCGTGCC CTCCAGATTCTCCGGATCTGGCTCTGGCGCCGAGTTCACCCTGA CAATCAGCTCCCTGCAGCCCGACGACTTCGCCACCTACTACTGT CAGAACGTGTACCTGGCCAGCACCAACGGCGCCAACTTCGGCCA GGGCACAAAACTGACAGTGCTGAAG |
| SEQ ID NO: 118 | LC linker | GSGGGGSGGGGSGGG |
| SEQ ID NO: 134 | DNA LC linker | GGCTCTGGTGGCGGAGGATCTGGCGGAGGCGGTTCTGGCGGCGG A |
| SEQ ID NO: 135 | Light Chain | SYELTQPPSVSVSPGQTASITCSGDKLGDKYAYWYQQKPGQSPV LVIYQDSKRPSGIPERFSGSNSGNTATLTISGTQAEDEADYYCQ AFDYLYSLGVFGGGTKLTVLGQPKAAPSVTLFPPSSEELQANKA TLVCLISDFYPGAVTVAWKADSSPVKAGVETTTPSKQSNNKYAA SSYLSLTPEQWKSHRSYSCQVTHEGSTVEKTVAPTECSGSGGGG SGGGGSGGGEIVMTQSPSTLSASVGDRVIITCQASEIIHSWLAW YQQKPGKAPKLLIYLASTLASGVPSRFSGSGSGAEFTLTISSLQ PDDFATYYCQNVYLASTNGANFGQGTKLTVLKRTVAAPSVFIFP PSDEQLKSGTASVVCLLNNFYPREAKVQWKVDNALQSGNSQESV TEQDSKDSTYSLSSTLTLSKADYEKHKVYACEVTHQGLSSPVTK SFNRGEC |
| SEQ ID NO: 136 | DNA Light Chain | TCCTACGAGCTGACCCAGCCTCCCTCCGTGTCCGTGTCTCCTGG CCAGACCGCCTCCATCACCTGTTCCGGCGACAAGCTGGGCGATA AGTACGCCTACTGGTATCAGCAGAAGCCCGGCCAGTCCCCTGTG CTGGTCATCTACCAGGACTCCAAGCGGCCCTCCGGCATCCCTGA GCGGTTCTCCGGCTCCAACTCCGGCAACACCGCCACCCTGACCA TCTCCGGCACCCAGGCCGAGGACGAGGCCGACTACTACTGCCAG GCCTTCGACTACCTGTACTCCCTGGGCGTGTTCGGCGGAGGCAC CAAGCTGACCGTGCTGGGCCAGCCCAAGGCCGCTCCTTCCGTGA CCCTGTTCCCTCCATCCTCCGAGGAACTGCAGGCCAACAAGGCC ACCCTCGTGTGCCTGATCTCCGACTTCTACCCTGGCGCCGTGAC CGTGGCCTGGAAGGCCGACAGCTCTCCTGTGAAGGCCGGCGTGG AAACCACCACCCCTTCCAAGCAGTCCAACAACAAATACGCCGCC TCCTCCTACCTGTCCCTGACCCCTGAGCAGTGGAAGTCCCACCG GTCCTACAGCTGCCAAGTCACACACGAGGGCTCCACCGTGGAAA AGACCGTGGCCCCTACCGAGTGCTCCGGCTCTGGTGGCGGAGGA TCTGGCGGAGGCGGTTCTGGCGGCGGAGAGATCGTGATGACCCA GTCCCCTTCCACCCTGTCCGCCTCCGTGGGCGACAGAGTGATCA TCACCTGTCAGGCCTCCGAGATCATCCACAGCTGGCTGGCTTGG TATCAGCAGAAACCTGGCAAGGCCCCTAAGCTGCTGATCTACCT GGCCTCCACCCTGGCCTCCGGCGTGCCCTCCAGATTCTCCGGAT CTGGCTCTGGCGCCGAGTTCACCCTGACAATCAGCTCCCTGCAG CCCGACGACTTCGCCACCTACTACTGTCAGAACGTGTACCTGGC CAGCACCAACGGCGCCAACTTCGGCCAGGGCACAAAACTGACAG TGCTGAAGCGTACGGTGGCCGCTCCCAGCGTGTTCATCTTCCCC CCCAGCGACGAGCAGCTGAAGAGCGGCACCGCCAGCGTGGTGTG CCTGCTGAACAACTTCTACCCCCGGGAGGCCAAGGTGCAGTGGA AGGTGGACAACGCCCTGCAGAGCGGCAACAGCCAGGAGAGCGTC ACCGAGCAGGACAGCAAGGACTCCACCTACAGCCTGAGCAGCAC CCTGACCCTGAGCAAGGCCGACTACGAGAAGCATAAGGTGTACG CCTGCGAGGTGACCCACCAGGGCCTGTCCAGCCCCGTGACCAAG AGCTTCAACAGGGGCGAGTGC |

NVS13

| SEQ ID NO: 25 (Combined) | 1 HCDR1 | GFTFSSYAMS |
|---|---|---|
| SEQ ID NO: 49 (Combined) | 1 HCDR2 | GLGHVGYTTYTDSVKG |
| SEQ ID NO: 50 (Combined) | 1 HCDR3 | DYLDFGYYFDV |

TABLE 3-continued

Exemplary anti-BTC/anti-VEGF bispecific Fabs

| SEQ ID NO: 28 (Kabat) | 1 HCDR1 | SYAMS |
|---|---|---|
| SEQ ID NO: 49 (Kabat) | 1 HCDR2 | GLGHVGYTTYTDSVKG |
| SEQ ID NO: 50 (Kabat) | 1 HCDR3 | DYLDFGYYFDV |
| SEQ ID NO: 29 (Chothia) | 1 HCDR1 | GFTFSSY |
| SEQ ID NO: 51 (Chothia) | 1 HCDR2 | GHVGY |
| SEQ ID NO: 50 (Chothia) | 1 HCDR3 | DYLDFGYYFDV |
| SEQ ID NO: 31 (IMGT) | 1 HCDR1 | GFTFSSYA |
| SEQ ID NO: 52 (IMGT) | 1 HCDR2 | LGHVGYT |
| SEQ ID NO: 53 (IMGT) | 1 HCDR3 | ARDYLDFGYYFDV |
| SEQ ID NO: 54 | 1 VH | QVQLLESGGGLVQPGGSLRLSCAASGFTFSSYAMSWVRQAPGKG LEWVSGLGHVGYTTYTDSVKGRFTISRDNSKNTLYLQMNSLRAE DTAVYYCARDYLDFGYYFDVWGQGTLVTVSS |
| SEQ ID NO: 137 | 1 DNA VH | CAAGTGCAGCTGCTGGAATCTGGCGGCGGACTGGTGCAGCCTGG CGGCTCCCTGAGGCTGTCTTGTGCCGCCTCCGGCTTCACCTTCT CCAGCTACGCCATGTCCTGGGTCCGACAGGCCCCTGGCAAGGGC CTGGAGTGGGTGTCCGGCCTGGGCCACGTGGGCTACACCACCTA CACCGACTCCGTGAAGGGCCGGTTCACCATCTCCCGGGACAACT CCAAGAACACCCTGTACCTGCAGATGAACTCCCTGAGGGCCGAG GACACCGCCGTGTACTACTGCGCCAGAGACTACCTGGACTTCGG CTACTACTTCGACGTGTGGGGCCAGGGCACCCTGGTCACCGTGT CCTCC |
| SEQ ID NO: 92 (Combined) | 2 HCDR1 | GFSLTDYYYMT |
| SEQ ID NO: 93 (Combined) | 2 HCDR2 | FIDPDDDPYYATWAKG |
| SEQ ID NO: 94 (Combined) | 2 HCDR3 | GDHNSGWGLDI |
| SEQ ID NO: 95 (Kabat) | 2 HCDR1 | DYYYMT |
| SEQ ID NO: 93 (Kabat) | 2 HCDR2 | FIDPDDDPYYATWAKG |
| SEQ ID NO: 94 (Kabat) | 2 HCDR3 | GDHNSGWGLDI |
| SEQ ID NO: 96 (Chothia) | 2 HCDR1 | GFSLTDYY |
| SEQ ID NO: 97 (Chothia) | 2 HCDR2 | DPDDD |
| SEQ ID NO: 94 (Chothia) | 2 HCDR3 | GDHNSGWGLDI |
| SEQ ID NO: 98 (IMGT) | 2 HCDR1 | GFSLTDYYY |
| SEQ ID NO: 99 (IMGT) | 2 HCDR2 | IDPDDDP |
| SEQ ID NO: 100 (IMGT) | 2 HCDR3 | AGGDHNSGWGLDI |
| SEQ ID NO: 101 | 2 VH | EVQLVESGGGLVQPGGSLRLSCTASGFSLTDYYYMTWVRQAPGK GLEWVGFIDPDDDPYYATWAKGRFTISRDNSKNTLYLQMNSLRA EDTAVYYCAGGDHNSGWGLDIWGQGTLVTVSS |
| SEQ ID NO: 138 | 2 DNA VH | GAAGTGCAGCTGGTCGAGAGTGGCGGAGGCCTCGTCCAGCCAGG CGGATCCCTGAGGCTCAGCTGCACCGCCTCTGGCTTCTCCCTGA CCGACTACTACTATATGACTTGGGTCCGCCAGGCTCCCGGAAAA GGACTCGAATGGGTCGGATTCATCGACCCCGACGACGACCCCTA CTACGCCACCTGGGCCAAGGGCAGATTCACCATCAGCAGAGACA ACAGCAAGAACACACTCTATCTCCAGATGAACTCCCTGAGGGCT GAAGATACCGCTGTCTATTACTGCGCTGGCGGCGACCACAACTC CGGCTGGGGCCTGGATATCTGGGGACAGGGCACACTCGTGACAG TGTCCAGC |
| SEQ ID NO: 118 | HC linker | GSGGGGSGGGGSGGG |
| SEQ ID NO: 139 | DNA HC linker | GGCTCTGGCGGAGGCGGAAGTGGTGGCGGAGGATCAGGCGGCGG A |

TABLE 3-continued

Exemplary anti-BTC/anti-VEGF bispecific Fabs

| SEQ ID NO: 140 | Heavy Chain | QVQLLESGGGLVQPGGSLRLSCAASGFTFSSYAMSWVRQAPGKG<br>LEWVSGLGHVGYTTYTDSVKGRFTISRDNSKNTLYLQMNSLRAE<br>DTAVYYCARDYLDFGYYFDVWGQGTLVTVSSASTKGPSVFPLAP<br>SSKSTSGGTAALGCLVKDYFPEPVTVSWNSGALTSGVHTFPAVL<br>QSSGLYSLSSVVTVPSSSLGTQTYICNVNHKPSNTKVDKRVEPK<br>SCGSGGGSGGGGSGGGEVQLVESGGGLVQPGGSLRLSCTASGF<br>SLTDYYYMTWVRQAPGKGLEWVGElDPDDDPYYATWAKGRFTIS<br>RDNSKNTLYLQMNSLRAEDTAVYYCAGGDHNSGWGLDIWGQGTL<br>VTVSSASTKGPSVFPLAPSSKSTSGGTAALGCLVKDYEPEPVTV<br>SWNSGALTSGVHTFPAVLQSSGLYSLSSVVTVPSSSLGTQTYIC<br>NVNHKPSNTKVDKRVEPKSC |
| --- | --- | --- |
| SEQ ID NO: 141 | DNA Heavy Chain | CAAGTGCAGCTGCTGGAATCTGGCGGCGGACTGGTGCAGCCTGG<br>CGGCTCCCTGAGGCTGTCTTGTGCCGCCTCCGGCTTCACCTTCT<br>CCAGCTACGCCATGTCCTGGGTCCGACAGGCCCCTGGCAAGGGC<br>CTGGAGTGGGTGTCCGGCCTGGGCCACGTGGGCTACACCACCTA<br>CACCGACTCCGTGAAGGGCCGGTTCACCATCTCCCGGGACAACT<br>CCAAGAACACCCTGTACCTGCAGATGAACTCCCTGAGGGCCGAG<br>GACACCGCCGTGTACTACTGCGCCAGAGACTACCTGGACTTCGG<br>CTACTACTTCGACGTGTGGGGCCAGGGCACCCTGGTCACCGTGT<br>CCTCCGCCTCCACCAAGGGACCCTCCGTGTTCCCTCTGGCCCCT<br>TCCAGCAAGTCCACCTCTGGCGGCACCGCCGCTCTGGGCTGCCT<br>GGTCAAGGACTACTTCCCCGAGCCCGTGACCGTGTCCTGGAACT<br>CTGGCGCCCTGACCTCCGGCGTGCACACCTTCCCTGCCGTGCTG<br>CAGTCCTCCGGCCTGTACTCCCTGTCCTCCGTCGTGACCGTGCC<br>CTCCAGCTCTCTGGGCACCCAGACCTACATCTGCAACGTGAACC<br>ACAAGCCCTCCAACACCAAAGTGGACAAGCGGGTGGAACCCAAG<br>TCCTGCGGCTCTGGCGGAGGCGGAAGTGGTGGCGGAGGATCAGG<br>CGGCGGAGAAGTGCAGCTGGTCGAGAGTGGCGGAGGCCTCGTCC<br>AGCCAGGCGGATCCCTGAGGCTCAGCTGCACCGCCTCTGGCTTC<br>TCCCTGACCGACTACTACTATATGACTTGGGTCCGCCAGGCTCC<br>CGGAAAAGGACTCGAATGGGTCGGATTCATCGACCCCGACGACG<br>ACCCCTACTACGCCACCTGGGCCAAGGGCAGATTCACCATCAGC<br>AGAGACAACAGCAAGAACACACTCTATCTCCAGATGAACTCCCT<br>GAGGGCTGAAGATACCGCTGTCTATTACTGCGCTGGCGGCGACC<br>ACAACTCCGGCTGGGGCCTGGATATCTGGGGACAGGGCACACTC<br>GTGACAGTGTCCAGCGCCAGCACCAAGGGCCCCTCCGTGTTCCC<br>TCTGGCCCCTTCCAGCAAGTCTACCTCTGGCGGCACCGCTGCTC<br>TGGGCTGCCTGGTGAAGGACTACTTCCCTGAGCCTGTGACAGTG<br>TCCTGGAACTCTGGCGCCCTGACCTCCGGCGTGCACACCTTCCC<br>TGCCGTGCTGCAGTCCTCCGGCCTGTACTCCCTGTCCTCCGTGG<br>TGACAGTGCCTTCCTCCAGCCTGGGCACCCAGACCTATATCTGC<br>AACGTGAACCACAAGCCTTCCAACACCAAGGTGGACAAGCGGGT<br>GGAGCCTAAGTCATGC |
| SEQ ID NO: 58 (Combined) | 1 LCDR1 | SGDKIGKKYVH |
| SEQ ID NO: 59 (Combined) | 1 LCDR2 | DDSDRPS |
| SEQ ID NO: 60 (Combined) | 1 LCDR3 | QAWDMQSVV |
| SEQ ID NO: 58 (Kabat) | 1 LCDR1 | SGDKIGKKYVH |
| SEQ ID NO: 59 (Kabat) | 1 LCDR2 | DDSDRPS |
| SEQ ID NO: 60 (Kabat) | 1 LCDR3 | QAWDMQSVV |
| SEQ ID NO: 61 (Chothia) | 1 LCDR1 | DKIGKKY |
| SEQ ID NO: 62 (Chothia) | 1 LCDR2 | DDS |
| SEQ ID NO: 63 (Chothia) | 1 LCDR3 | WDMQSV |
| SEQ ID NO: 64 (IMGT) | 1 LCDR1 | KIGKKY |
| SEQ ID NO: 62 (IMGT) | 1 LCDR2 | DDS |
| SEQ ID NO: 60 (IMGT) | 1 LCDR3 | QAWDMQSVV |
| SEQ ID NO: 65 | 1 VL | SYELTQPLSVSVALGQTARITCSGDKIGKKYVHWYQQKPGQAPV<br>LVIYDDSDRPSGIPERFSGSNSGNTATLTISRAQAGDEADYYCQ<br>AWDMQSVVEGGGTKLTVL |
| SEQ ID NO: 142 | 1 DNA VL | TCCTACGAGCTGACCCAGCCCCTGTCCGTGTCTGTGGCTCTGGG<br>CCAGACCGCCCGGATCACCTGTTCCGGCGACAAGATCGGCAAGA |

TABLE 3-continued

Exemplary anti-BTC/anti-VEGF bispecific Fabs

| | | | |
|---|---|---|---|
| | | | AATACGTGCACTGGTATCAGCAGAAGCCCGGCCAGGCCCCTGTG<br>CTGGTCATCTACGACGACTCCGACCGGCCCTCCGGCATCCCTGA<br>GCGGTTCTCCGGCTCCAACTCCGGCAACACCGCCACCCTGACCA<br>TCTCCAGAGCCCAGGCCGGCGACGAGGCCGACTACTACTGCCAG<br>GCCTGGGACATGCAGTCCGTGGTGTTCGGCGGAGGCACCAAGCT<br>GACCGTGCTG |
| SEQ ID NO: 105 (Combined) | | 2 LCDR1 | QASEIIHSWLA |
| SEQ ID NO: 106 (Combined) | | 2 LCDR2 | LASTLAS |
| SEQ ID NO: 107 (Combined) | | 2 LCDR3 | QNVYLASTNGAN |
| SEQ ID NO: 105 | (Kabat) | 2 LCDR1 | QASEIIHSWLA |
| SEQ ID NO: 106 | (Kabat) | 2 LCDR2 | LASTLAS |
| SEQ ID NO: 107 | (Kabat) | 2 LCDR3 | QNVYLASTNGAN |
| SEQ ID NO: 108 | (Chothia) | 2 LCDR1 | SEIIHSW |
| SEQ ID NO: 109 | (Chothia) | 2 LCDR2 | LAS |
| SEQ ID NO: 110 | (Chothia) | 2 LCDR3 | VYLASTNGA |
| SEQ ID NO: 111 | (IMGT) | 2 LCDR1 | EIIHSW |
| SEQ ID NO: 109 | (IMGT) | 2 LCDR2 | LAS |
| SEQ ID NO: 107 | (IMGT) | 2 LCDR3 | QNVYLASTNGAN |
| SEQ ID NO: 112 | | 2 VL | EIVMTQSPSTLSASVGDRVIITCQASEIIHSWLAWYQQKPGKAP<br>KLLIYLASTLASGVPSRFSGSGSGAEFTLTISSLQPDDFATYYC<br>QNVYLASTNGANFGQGTKLTVLK |
| SEQ ID NO: 143 | | 2 DNA VL | GAGATCGTGATGACCCAGTCCCCTTCCACCCTGTCCGCCTCCGT<br>GGGCGACAGAGTGATCATCACCTGTCAGGCCTCCGAGATCATCC<br>ACAGCTGGCTGGCTTGGTATCAGCAGAAACCTGGCAAGGCTCCC<br>AAGCTGCTGATCTACCTGGCCTCCACCCTGGCCTCCGGCGTGCC<br>CTCCAGATTCTCCGGATCTGGCTCTGGCGCCGAGTTCACCCTGA<br>CAATCAGCTCCCTGCAGCCCGACGACTTCGCCACCTACTACTGT<br>CAGAACGTGTACCTGGCCAGCACCAACGGCGCCAACTTCGGCCA<br>GGGCACAAAACTGACAGTGCTGAAG |
| SEQ ID NO: 118 | | LC linker | GSGGGGSGGGGSGGG |
| SEQ ID NO: 144 | | DNA LC linker | GGCTCTGGTGGCGGAGGATCTGGCGGAGGCGGTTCTGGCGGCGG<br>A |
| SEQ ID NO: 145 | | Light Chain | SYELTQPLSVSVALGQTARITCSGDKIGKKYVHWYQQKPGQAPV<br>LVIYDDSDRPSGIPERFSGSNSGNTATLTISRAQAGDEADYYCQ<br>AWDMQSVVFGGGTKLTVLGQPKAAPSVTLFPPSSEELQANKATL<br>VCLISDFYPGAVTVAWKADSSPVKAGVETTTPSKQSNNKYAASS<br>YLSLTPEQWKSHRSYSCQVTHEGSTVEKTVAPTECSGSGGGGSG<br>GGGSGGGEIVMTQSPSTLSASVGDRVIITCQASEIIHSWLAWYQ<br>QKPGKAPKLLIYLASTLASGVPSRFSGSGSGAEFTLTISSLQPD<br>DFATYYCQNVYLASTNGANFGQGTKLTVLKRTVAAPSVFIFPPS<br>DEQLKSGTASVVCLLNNFYPREAKVQWKVDNALQSGNSQESVTE<br>QDSKDSTYSLSSTLTLSKADYEKHKVYACEVTHQGLSSPVTKSF<br>NRGEC |
| SEQ ID NO: 146 | | DNA Light Chain | TCCTACGAGCTGACCCAGCCCCTGTCCGTGTCTGTGGCTCTGGG<br>CCAGACCGCCCGGATCACCTGTTCCGGCGACAAGATCGGCAAGA<br>AATACGTGCACTGGTATCAGCAGAAGCCCGGCCAGGCCCCTGTG<br>CTGGTCATCTACGACGACTCCGACCGGCCCTCCGGCATCCCTGA<br>GCGGTTCTCCGGCTCCAACTCCGGCAACACCGCCACCCTGACCA<br>TCTCCAGAGCCCAGGCCGGCGACGAGGCCGACTACTACTGCCAG<br>GCCTGGGACATGCAGTCCGTGGTGTTCGGCGGAGGCACCAAGCT<br>GACCGTGCTGGGCCAGCCCAAGGCCGCTCCCTCTGTGACCCTGT<br>TCCCTCCATCCTCCGAGGAACTGCAGGCCAACAAGGCCACCCTC<br>GTGTGCCTGATCTCCGACTTCTACCCTGGCGCCGTGACCGTGGC<br>CTGGAAGGCCGACAGCTCTCCTGTGAAGGCCGGCGTGGAAACCA<br>CCACCCCTTCCAAGCAGTCCAACAACAAATACGCCGCCTCCTCC<br>TACCTGTCCCTGACCCCTGAGCAGTGGAAGTCCCACCGGTCCTA<br>CAGCTGCCAAGTCACACACGAGGGCTCCACCGTGGAAAAGACCG |

TABLE 3-continued

Exemplary anti-BTC/anti-VEGF bispecific Fabs

|  |  |  |  |
|---|---|---|---|
|  |  |  | TGGCCCCTACCGAGTGCTCCGGCTCTGGTGGCGGAGGATCTGGC<br>GGAGGCGGTTCTGGCGGCGGAGAGATCGTGATGACCCAGTCCCC<br>TTCCACCCTGTCCGCCTCCGTGGGCGACAGAGTGATCATCACCT<br>GTCAGGCCTCCGAGATCATCCACAGCTGGCTGGCTTGGTATCAG<br>CAGAAACCTGGCAAGGCTCCCAAGCTGCTGATCTACCTGGCCTC<br>CACCCTGGCCTCCGGCGTGCCCTCCAGATTCTCCGGATCTGGCT<br>CTGGCGCCGAGTTCACCCTGACAATCAGCTCCCTGCAGCCCGAC<br>GACTTCGCCACCTACTACTGTCAGAACGTGTACCTGGCCAGCAC<br>CAACGGCGCCAACTTCGGCCAGGGCACAAAACTGACAGTGCTGA<br>AGCGTACGGTGGCCGCTCCCAGCGTGTTCATCTTCCCCCCCAGC<br>GACGAGCAGCTGAAGAGCGGCACCGCCAGCGTGGTGTGCCTGCT<br>GAACAACTTCTACCCCGGGAGGCCAAGGTGCAGTGGAAGGTGG<br>ACAACGCCCTGCAGAGCGGCAACAGCCAGGAGAGCGTCACCGAG<br>CAGGACAGCAAGGACTCCACCTACAGCCTGAGCAGCACCCTGAC<br>CCTGAGCAAGGCCGACTACGAGAAGCATAAGGTGTACGCCTGCG<br>AGGTGACCCACCAGGGCCTGTCCAGCCCCGTGACCAAGAGCTTC<br>AACAGGGGCGAGTGC |

NVS14

| SEQ ID NO: 69 (Combined) | 1 HCDR1 | GFTFSRYWIS |
|---|---|---|
| SEQ ID NO: 70 (Combined) | 1 HCDR2 | YIDSTGTFINYADSVKG |
| SEQ ID NO: 71 (Combined) | 1 HCDR3 | GGSLFDY |
| SEQ ID NO: 72 (Kabat) | 1 HCDR1 | RYWIS |
| SEQ ID NO: 70 (Kabat) | 1 HCDR2 | YIDSTGTFINYADSVKG |
| SEQ ID NO: 71 (Kabat) | 1 HCDR3 | GGSLFDY |
| SEQ ID NO: 73 (Chothia) | 1 HCDR1 | GFTFSRY |
| SEQ ID NO: 74 (Chothia) | 1 HCDR2 | DSTGTF |
| SEQ ID NO: 71 (Chothia) | 1 HCDR3 | GGSLFDY |
| SEQ ID NO: 75 (IMGT) | 1 HCDR1 | GFTFSRYW |
| SEQ ID NO: 76 (IMGT) | 1 HCDR2 | IDSTGTFI |
| SEQ ID NO: 77 (IMGT) | 1 HCDR3 | ARGGSLFDY |
| SEQ ID NO: 78 | 1 VH | QVQLLESGGGLVQPGGSLRLSCAASGFTFSRYWISWVRQAPGKG<br>LEWVSYIDSTGTFINYADSVKGRFTISRDNSKNTLYLQMNSLRA<br>EDTAVYYCARGGSLFDYWGQGTLVTVSS |
| SEQ ID NO: 147 | 1 DNA VH | CAAGTGCAGCTGCTGGAATCTGGCGGCGGACTGGTGCAGCCTGG<br>CGGCTCCCTGAGGCTGTCTTGTGCCGCCTCCGGCTTCACCTTCT<br>CCCGGTACTGGATCTCCTGGGTCCGACAGGCCCCTGGCAAGGGC<br>CTGGAGTGGGTGTCCTACATCGACTCCACCGGCACCTTCATCAA<br>CTACGCCGACTCCGTGAAGGGCCGGTTCACCATCAGCCGGGACA<br>ACTCCAAGAACACCCTGTACCTGCAGATGAACTCCCTGAGGGCC<br>GAGGACACCGCCGTGTACTACTGCGCCAGAGGCGGCAGCCTGTT<br>CGACTACTGGGGCCAGGGCACCCTGGTCACCGTGTCCTCC |
| SEQ ID NO: 92 (Combined) | 2 HCDR1 | GFSLTDYYYMT |
| SEQ ID NO: 93 (Combined) | 2 HCDR2 | FIDPDDDPYYATWAKG |
| SEQ ID NO: 94 (Combined) | 2 HCDR3 | GDHNSGWGLDI |
| SEQ ID NO: 95 (Kabat) | 2 HCDR1 | DYYYMT |
| SEQ ID NO: 93 (Kabat) | 2 HCDR2 | FIDPDDDPYYATWAKG |
| SEQ ID NO: 94 (Kabat) | 2 HCDR3 | GDHNSGWGLDI |
| SEQ ID NO: 96 (Chothia) | 2 HCDR1 | GFSLTDYY |
| SEQ ID NO: 97 (Chothia) | 2 HCDR2 | DPDDD |

TABLE 3-continued

Exemplary anti-BTC/anti-VEGF bispecific Fabs

| | | | |
|---|---|---|---|
| SEQ ID NO: 94 (Chothia) | 2 | HCDR3 | GDHNSGWGLDI |
| SEQ ID NO: 98 (IMGT) | 2 | HCDR1 | GFSLTDYYY |
| SEQ ID NO: 99 (IMGT) | 2 | HCDR2 | IDPDDDP |
| SEQ ID NO: 100 (IMGT) | 2 | HCDR3 | AGGDHNSGWGLDI |
| SEQ ID NO: 101 | 2 | VH | EVQLVESGGGLVQPGGSLRLSCTASGFSLTDYYYMTWVRQAPGK GLEWVGFIDPDDDPYYATWAKGRFTISRDNSKNTLYLQMNSLRA EDTAVYYCAGGDHNSGWGLDIWGQGTLVTVSS |
| SEQ ID NO: 148 | 2 | DNA VH | GAAGTGCAGCTGGTCGAGAGTGGCGGAGGCCTCGTCCAGCCAGG CGGATCCCTGAGGCTCAGCTGCACCGCCTCTGGCTTCTCCCTGA CCGACTACTACTACATGACATGGGTCCGCCAGGCTCCCGGAAAA GGACTCGAATGGGTCGGATTCATCGACCCCGACGACGACCCCTA CTACGCCACCTGGGCCAAGGGCAGATTCACCATCTCCAGAGATA ACAGCAAGAACACACTCTATCTCCAGATGAACTCCCTGAGGGCT GAAGATACCGCTGTCTATTACTGCGCTGGCGGCGACCACAACTC CGGCTGGGGCCTGGATATCTGGGACAGGGAACACTCGTGACAG TGTCCAGC |
| SEQ ID NO: 118 | | HC linker | GSGGGGSGGGGSGGG |
| SEQ ID NO: 139 | | DNA HC linker | GGCTCTGGCGGAGGCGGAAGTGGTGGCGGAGGATCAGGCGGCGG A |
| SEQ ID NO: 149 | | Heavy Chain | QVQLLESGGGLVQPGGSLRLSCAASGFTFSRYWISWVRQAPGKG LEWVSYIDSTGTFINYADSVKGRFTISRDNSKNTLYLQMNSLRA EDTAVYYCARGGSLFDYWGQGTLVTVSSASTKGPSVFPLAPSSK STSGGTAALGCLVKDYFPEPVTVSWNSGALTSGVHTFPAVLQSS GLYSLSSVVTVPSSSLGTQTYICNVNHKPSNTKVDKRVEPKSCG SGGGGSGGGGSGGGEVQLVESGGGLVQPGGSLRLSCTASGFSLT DYYYMTWVRQAPGKGLEWVGFIDPDDDPYYATWAKGRFTISRDN SKNTLYLQMNSLRAEDTAVYYCAGGDHNSGWGLDIWGQGTLVTV SSASTKGPSVFPLAPSSKSTSGGTAALGCLVKDYFPEPVTVSWN SGALTSGVHTFPAVLQSSGLYSLSSVVTVPSSSLGTQTYICNVN HKPSNTKVDKRVEPKSC |
| SEQ ID NO: 150 | | DNA Heavy Chain | CAAGTGCAGCTGCTGGAATCTGGCGGCGGACTGGTGCAGCCTGG CGGCTCCCTGAGGCTGTCTTGTGCCGCCTCCGGCTTCACCTTCT CCCGGTACTGGATCTCCTGGGTCCGACAGGCCCCTGGCAAGGGC CTGGAGTGGGTGTCCTACATCGACTCCACCGGCACCTTCATCAA CTACGCCGACTCCGTGAAGGGCCGGTTCACCATCAGCCGGGACA ACTCCAAGAACACCCTGTACCTGCAGATGAACTCCCTGAGGGCC GAGGACACCGCCGTGTACTACTGCGCCAGAGGCGGCAGCCTGTT CGACTACTGGGGCCAGGGCACCCTGGTCACCGTGTCCTCCGCCT CCACCAAGGGACCCTCCGTGTTCCCTCTGGCCCCTTCCAGCAAG TCCACCTCTGGCGGCACCGCCGCTCTGGGCTGCCTGGTCAAGGA CTACTTCCCCGAGCCCGTGACCGTGTCCTGGAACTCTGGCGCCC TGACCTCCGGCGTGCACACCTTCCCTGCCGTGCTGCAGTCCTCC GGCCTGTACTCCCTGTCCTCCGTCGTGACCGTGCCCTCCAGCTC TCTGGGCACCCAGACCTACATCTGCAACGTGAACCACAAGCCCT CCAACACCAAAGTGGACAAGCGGGTGGAACCCAAGTCCTGCGGC TCTGGCGGAGGCGGAAGTGGTGGCGGAGGATCAGGCGGCGGAGA AGTGCAGCTGGTCGAGAGTGGCGGAGGCCTCGTCCAGCCAGGCG GATCCCTGAGGCTCAGCTGCACCGCCTCTGGCTTCTCCCTGACC GACTACTACTACATGACATGGGTCCGCCAGGCTCCCGGAAAAGG ACTCGAATGGGTCGGATTCATCGACCCCGACGACGACCCCTACT ACGCCACCTGGGCCAAGGGCAGATTCACCATCTCCAGAGATAAC AGCAAGAACACACTCTATCTCCAGATGAACTCCCTGAGGGCTGA AGATACCGCTGTCTATTACTGCGCTGGCGGCGACCACAACTCCG GCTGGGGCCTGGATATCTGGGACAGGGAACACTCGTGACAGTG TCCAGCGCCAGCACCAAGGGCCCCTCCGTGTTCCCTCTGGCCCC TTCCAGCAAGTCTACCTCTGGCGGCACCGCTGCTCTGGGCTGCC TGGTGAAGGACTACTTCCCTGAGCCTGTGACAGTGTCCTGGAAC TCTGGCGCCCTGACCTCCGGCGTGCACACCTTCCCTGCCGTGCT GCAGTCCTCCGGCCTGTACTCCCTGTCCTCCGTGGTGACAGTGC CTTCCTCCAGCCTGGGCACCCAGACCTATATCTGCAACGTGAAC CACAAGCCTTCCAACACCAAGGTGGACAAGCGGGTGGAGCCTAA GTCATGC |
| SEQ ID NO: 82 (Combined) | 1 | LCDR1 | RASQGIISYLG |
| SEQ ID NO: 83 (Combined) | 1 | LCDR2 | AASSLQS |

TABLE 3-continued

Exemplary anti-BTC/anti-VEGF bispecific Fabs

| SEQ ID NO: 84 (Combined) | 1 LCDR3 | QQYDALNT |
|---|---|---|
| SEQ ID NO: 82 (Kabat) | 1 LCDR1 | RASQGIISYLG |
| SEQ ID NO: 83 (Kabat) | 1 LCDR2 | AASSLQS |
| SEQ ID NO: 84 (Kabat) | 1 LCDR3 | QQYDALNT |
| SEQ ID NO: 85 (Chothia) | 1 LCDR1 | SQGIISY |
| SEQ ID NO: 18 (Chothia) | 1 LCDR2 | AAS |
| SEQ ID NO: 86 (Chothia) | 1 LCDR3 | YDALN |
| SEQ ID NO: 87 (IMGT) | 1 LCDR1 | QGIISY |
| SEQ ID NO: 18 (IMGT) | 1 LCDR2 | AAS |
| SEQ ID NO: 84 (IMGT) | 1 LCDR3 | QQYDALNT |
| SEQ ID NO: 88 | 1 VL | DIQMTQSPSSLSASVGDRVTITCRASQGIISYLGWYQQKPGKAP KLLIYAASSLQSGVPSRFSGSGSGTDFTLTISSLQPEDFATYYC QQYDALNTFGQGTKVEIK |
| SEQ ID NO: 151 | 1 DNA VL | GACATCCAGATGACCCAGAGCCCCTCCAGCCTGTCCGCCTCCGT GGGCGACAGAGTGACCATCACCTGTCGGGCCTCCCAGGGCATCA TCTCCTACCTGGGCTGGTATCAGCAGAAGCCCGGCAAGGCCCCT AAGCTGCTGATCTACGCCGCCAGCTCCCTGCAGTCCGGCGTGCC CTCCAGATTCTCCGGCTCTGGCTCCGGCACCGACTTCACCCTGA CCATCTCCAGCCTGCAGCCCGAGGACTTCGCCACCTACTACTGC CAGCAGTACGACGCCCTGAACACCTTCGGCCAGGGCACCAAAGT GGAAATCAAG |
| SEQ ID NO: 105 (Combined) | 2 LCDR1 | QASEIIHSWLA |
| SEQ ID NO: 106 (Combined) | 2 LCDR2 | LASTLAS |
| SEQ ID NO: 107 (Combined) | 2 LCDR3 | QNVYLASTNGAN |
| SEQ ID NO: 105 (Kabat) | 2 LCDR1 | QASEIIHSWLA |
| SEQ ID NO: 106 (Kabat) | 2 LCDR2 | LASTLAS |
| SEQ ID NO: 107 (Kabat) | 2 LCDR3 | QNVYLASTNGAN |
| SEQ ID NO: 108 (Chothia) | 2 LCDR1 | SEIIHSW |
| SEQ ID NO: 109 (Chothia) | 2 LCDR2 | LAS |
| SEQ ID NO: 110 (Chothia) | 2 LCDR3 | VYLASTNGA |
| SEQ ID NO: 111 (IMGT) | 2 LCDR1 | EIIHSW |
| SEQ ID NO: 109 (IMGT) | 2 LCDR2 | LAS |
| SEQ ID NO: 107 (IMGT) | 2 LCDR3 | QNVYLASTNGAN |
| SEQ ID NO: 112 | 2 VL | EIVMTQSPSTLSASVGDRVIITCQASEIIHSWLAWYQQKPGKAP KLLIYLASTLASGVPSRFSGSGSGAEFTLTISSLQPDDFATYYC QNVYLASTNGANFGQGTKLTVLK |
| SEQ ID NO: 152 | 2 DNA VL | GAGATCGTGATGACCCAGTCCCCTAGCACCCTGAGCGCCAGCGT GGGAGATCGCGTGATCATCACATGCCAGGCCTCCGAGATCATCC ACAGCTGGCTGGCTTGGTATCAGCAGAAACCTGGAAAGCTCCC AAGCTCCTGATCTATCTGGCCAGCACCCTGGCCTCTGGCGTGCC CAGCAGATTCAGCGGCTCCGGCAGCGGCGCTGAGTTTACCCTGA CAATCAGCTCTCTGCAGCCTGACGATTTTGCTACCTACTATTGT CAGAACGTGTACCTGGCCTCCACCAACGGCGCCAACTTTGGCCA GGGAACAAAGCTGACCGTGCTGAAG |
| SEQ ID NO: 118 | LC linker | GSGGGGSGGGGSGGG |

TABLE 3-continued

Exemplary anti-BTC/anti-VEGF bispecific Fabs

| SEQ ID NO: 153 | DNA LC linker | GGCTCCGGCGGAGGCGGATCTGGTGGCGGAGGATCTGGCGGTGG<br>C |
|---|---|---|
| SEQ ID NO: 154 | Light Chain | DIQMTQSPSSLSASVGDRVTITCRASQGIISYLGWYQQKPGKAP<br>KLLIYAASSLQSGVPSRFSGSGSGTDFTLTISSLQPEDFATYYC<br>QQYDALNTFGQGTKVEIKRTVAAPSVFIFPPSDEQLKSGTASVV<br>CLLNNFYPREAKVQWKVDNALQSGNSQESVTEQDSKDSTYSLSS<br>TLTLSKADYEKHKVYACEVTHQGLSSPVTKSFNRGECGSGGGGS<br>GGGGSGGGEIVMTQSPSTLSASVGDRVIITCQASEIIHSWLAWY<br>QQKPGKAPKLLIYLASTLASGVPSRFSGSGSGAEFTLTISSLQP<br>DDFATYYCQNVLASTNGANFGQGTKLTVLKRTVAAPSVFIFPP<br>SDEQLKSGTASVVCLLNNFYPREAKVQWKVDNALQSGNSQESVT<br>EQDSKDSTYSLSSTLTLSKADYEKHKVYACEVTHQGLSSPVTKS<br>FNRGEC |
| SEQ ID NO: 155 | DNA Light Chain | GACATCCAGATGACCCAGAGCCCCTCCAGCCTGTCCGCCTCCGT<br>GGGCGACAGAGTGACCATCACCTGTCGGGCCTCCCAGGGCATCA<br>TCTCCTACCTGGGCTGGTATCAGCAGAAGCCCGGCAAGGCCCCT<br>AAGCTGCTGATCTACGCCGCCAGCTCCCTGCAGTCCGGCGTGCC<br>CTCCAGATTCTCCGGCTCTGGCTCCGGCACCGACTTCACCCTGA<br>CCATCTCCAGCCTGCAGCCCGAGGACTTCGCCACCTACTACTGC<br>CAGCAGTACGACGCCCTGAACACCTTCGGCCAGGGCACCAAAGT<br>GGAAATCAAGCGGACCGTGGCCGCTCCCTCCGTGTTCATCTTCC<br>CACCCTCCGACGAGCAGCTGAAGTCCGGCACCGCCTCCGTCGTG<br>TGCCTGCTGAACAACTTCTACCCTCGCGAGGCCAAAGTGCAGTG<br>GAAAGTGGACAACGCCCTGCAGAGCGGCAACTCCCAGGAATCCG<br>TCACCGAGCAGGACTCCAAGGACAGCACCTACTCCCTGTCCTCC<br>ACCCTGACCCTGTCCAAGGCCGACTACGAGAAGCACAAAGTGTA<br>CGCCTGCGAAGTGACCCACCAGGGCCTGTCCAGCCCCGTGACCA<br>AGTCCTTCAACCGGGGCGAGTGTGGCTCCGGCGGAGGCGGATCT<br>GGTGGCGGAGGATCTGGCGGTGGCGAGATCGTGATGACCCAGTC<br>CCCTAGCACCCTGAGCGCCAGCGTGGGAGATCGCGTGATCATCA<br>CATGCCAGGCCTCCGAGATCATCCACAGCTGGCTGGCTTGGTAT<br>CAGCAGAAACCTGGAAAAGCTCCCAAGCTCCTGATCTATCTGGC<br>CAGCACCCTGGCCTCTGGCGTGCCCAGCAGATTCAGCGGCTCCG<br>GCAGCGGCGCTGAGTTTACCCTGACAATCAGCTCTCTGCAGCCT<br>GACGATTTTGCTACCTACTATTGTCAGAACGTGTACCTGGCCTC<br>CACCAACGGCGCCAACTTTGGCCAGGGAACAAAGCTGACCGTGC<br>TGAAGCGTACGGTGGCCGCTCCCAGCGTGTTCATCTTCCCCCCC<br>AGCGACGAGCAGCTGAAGAGCGGCACCGCCAGCGTGGTGTGCCT<br>GCTGAACAACTTCTACCCCGGGAGGCCAAGGTGCAGTGGAAGG<br>TGGACAACGCCCTGCAGAGCGGCAACAGCCAGGAGAGCGTCACC<br>GAGCAGGACAGCAAGGACTCCACCTACAGCCTGAGCAGCACCCT<br>GACCCTGAGCAAGGCCGACTACGAGAAGCATAAGGTGTACGCCT<br>GCGAGGTGACCCACCAGGGCCTGTCCAGCCCCGTGACCAAGAGC<br>TTCAACAGGGGCGAGTGC | v. Linkers

In certain aspects of the present disclosure an anti-BTC binding moiety can be linked to a molecule, e.g., an anti-VEGF binding moiety, by a linker. More specifically, an anti-BTC binding moieties may be linked to a protein or a nucleic acid, by a peptide linker (e.g., a $(Gly_n-Ser_n)_n$ or $(Ser_n-Gly_n)_n$ linker) with an optimized length and/or amino acid composition. It is known that peptide linker length can greatly affect how the connected proteins fold and interact. For examples of linker orientation and size See, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, which are incorporated herein by reference.

The peptide linker sequence can be at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, or more amino acid residues in length. The peptide linker sequence can be comprised of a naturally, or non-naturally, occurring amino acids. In some aspects, the linker is a glycine polymer. In some aspects, the amino acids glycine and serine comprise the amino acids within the linker sequence. In certain aspects, a linker region comprises sets of glycine repeats $(GlySerGly_3)_n$, where n is a positive integer equal to or greater than 1, e.g., n=3 (SEQ ID NO: 118). More specifically, the linker sequence can be GlySerGlyGlyGly (SEQ ID NO: 165). Alternatively, a linker sequence can be GlySerGlyGly (SEQ ID NO: 166). In certain other aspects, a linker region orientation comprises sets of glycine repeats $(SerGly_3)_n$, where n is a positive integer equal to or greater than 1, e.g., n=3 (SEQ ID NO: 167).

The peptide linkers can also include, but are not limited to, $(Gly4 Ser)_4$ (SEQ ID NO: 161) or $(Gly_4 Ser)_3$ (SEQ ID NO: 162). The amino acid residues Glu and Lys can be interspersed within the Gly-Ser peptide linkers for better solubility. In certain aspects, the peptide linkers can include multiple repeats of $(Gly_3Ser)$, $(Gly_2Ser)$, or $(GlySer)$. In certain aspects, the peptide linkers can include multiple repeats of $(SerGly_3)$, $(SerGly_2)$, or $(SerGly)$. In other aspects, the peptide linkers can include combinations and multiples of $(Gly_3Ser)+(Gly_4Ser)+(GlySer)$ (SEQ ID NO: 163). In still other aspects, Ser can be replaced with Ala, e.g., $(Gly_4Ala)$ or $(Gly_3Ala)$. In yet other aspects, the linker comprises the motif $(GluAlaAlaAlaLys)_n$(SEQ ID NO: 164), where n is a positive integer equal to or greater than 1. In certain aspects, peptide linkers can also include cleavable linkers.

Peptide linkers can be of varying lengths. In particular, a peptide linker is from about 5 to about 50 amino acids in length; from about 10 to about 40 amino acids in length; from about 15 to about 30 amino acids in length; or from about 15 to about 20 amino acids in length. Variation in peptide linker length can retain or enhance activity, giving rise to superior efficacy in activity studies. Peptide linkers can be introduced into polypeptide and protein sequences using techniques known in the art. For example, PCR mutagenesis can be used. Modifications can be confirmed by DNA sequence analysis. Plasmid DNA can be used to transform host cells for stable production of the polypeptides produced.

Peptide linkers, anti-BTC binding moieties and proteins, e.g., an anti-VEGF binding moiety, can be encoded in the same vector and expressed and assembled in the same host cell. Alternatively, each peptide linker, anti-BTC binding moiety, anti-VEGF binding moiety, and protein or nucleic acid can be generated separately and then conjugated to one another. Peptide linkers, anti-BTC binding moieties and proteins or nucleic acids can be prepared by conjugating the constituent components, using methods known in the art. Site-specific conjugation can be achieved using sortase-mediated enzymatic conjugation (Mao H, et al., J. Am. Chem. Soc. 2004 Mar 10;126(9):2670-1). A variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyl-dithio)propionate (SPDP), and sulfosuccinimidyl 4-(N-maleimidomethyl) cyclohexane-1-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78,118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

vi. Formats and Types of Multi-Specific Binding Molecules

In some aspects a multi-specific binding molecule is a bispecific antibody or bispecific antibody-like molecule. In some aspects, the bispecific antibody or antibody-like molecule can be multivalent, e.g., bivalent, with respect to one antigen and monovalent with respect to the other antigen. An exemplary bispecific antibody molecule or bispecific antibody-like molecule is characterized by a first antigen binding domain (e.g., comprising a first heavy chain and a first light chain) which has binding specificity for a first antigen or epitope (e.g., BTC) and a second antigen binding domain (e.g., comprising a second heavy chain and a second light chain) that has binding specificity for a second antigen or epitope (e.g., VEGF).

In some aspects the first and second epitopes are on the same antigen, e.g., the same protein (or subunit of a multimeric protein). In aspects a bispecific antibody molecule or bispecific antibody-like molecule comprises a heavy chain variable domain sequence and a light chain variable domain sequence that have binding specificity for a first epitope or antigen, and a heavy chain variable domain sequence and a light chain variable domain sequence which have binding specificity for a second epitope or antigen.

In some aspects a bispecific antibody molecule or antibody-like molecule comprises a half antibody having binding specificity for a first epitope or antigen; and a half antibody having binding specificity for a second epitope or antigen. In an aspect a bispecific antibody molecule or antibody-like molecule comprises a half antibody, or fragment thereof, having binding specificity for a first epitope or antigen; and a half antibody, or fragment thereof, having binding specificity for a second epitope or antigen.

In aspects a bispecific antibody molecule or bispecific antibody-like molecule comprises an scFv or Fab, or fragment thereof, having binding specificity for a first epitope or antigen; and an antibody, or fragment thereof, have binding specificity for a second epitope or antigen. In aspects a bispecific antibody molecule or bispecific antibody-like molecule comprises two scFvs or Fabs, or fragment thereof, having binding specificity for a first epitope or antigen; and an antibody, or fragment thereof, have binding specificity for a second epitope or antigen. In aspects a bispecific antibody molecule or bispecific antibody-like molecule comprises an scFv, or fragment thereof, having binding specificity for a first epitope or antigen; and a Fab, or fragment thereof, have binding specificity for a second epitope or antigen.

In certain aspects, the antibody or antibody-like molecule is a multi-specific (e.g., a bispecific or a trispecific) antibody or antibody-like molecule. Protocols for generating bispecific or heterodimeric antibody or antibody-like molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody or antibody-like molecule determinants generated by recombining half antibodies (heavy-light chain pairs or Fabs) from different antibodies or antibody-like molecules through cycle of reduction and oxidation of disulfide bonds between the two heavy chains, as described in, e.g., U.S. Pat. No. 4,444,878; trifunctional antibodies, e.g., three Fab' fragments cross-linked through sulfhdryl reactive groups, as described in, e.g., U.S. Pat. No. 5,273, 743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono—and oligovalent receptors, e.g., $V_H$-CH1 regions (Fd regions) of two antibodies (two Fab fragments) linked through a polypeptide spacer between the CH1 region of one antibody and the $V_H$ region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multi-specific binding proteins, e.g., dimer of polypeptides having first domain with binding region of Ig heavy chain variable region, and second domain with binding region of Ig light chain variable region, generally termed diabodies (higher order structures are also encompassed creating for bispecific, trispecific, or tetraspecific molecules, as described in, e.g., U.S. Pat. No. 5,837,242; minibody constructs with linked $V_L$ and $V_H$ chains further connected with peptide spacers to an antibody hinge region and CH3 region, which can be dimerized to form bispecific/multivalent molecules, as described in, e.g., U.S. Pat. No. 5,837,821; $V_L$ and $V_H$ domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; string of $V_H$ domains (or $V_L$ domains in family members) connected by peptide linkages with crosslinkable groups at the C-terminus further associated with $V_L$ domains to form a series of FVs (or scFvs), as described in, e.g., U.S. Pat. No. 5,864,019; $V_L$ and $V_H$ domains, scFvs, or Fabs where one of the antigens is bound monovalently and one of the antigens is bound bivalently, optionally comprising heterodimeric Fc regions, as described in, e.g., WO2011/028952; and single chain binding polypeptides with both a $V_L$ and $V_H$ domain linked through a peptide linker are combined into multivalent structures through non-covalent or chemical crosslinking to form, e.g., homobivalent, heterobivalent, trivalent, and tetravalent structures using both scFv or diabody type format, as described in, e.g., U.S. Pat. No. 5,869,620.

Additional exemplary multi-specific and bispecific molecules and methods of making the same are found, for example, in U.S. Pat. Nos. 5,910,573, 5,932,448, 5,959,083, 5,989,830, 6,005,079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

Accordingly, in some aspects, BTC/VEGF multi-specific binding molecules of the present disclosure comprises a BTC binding domain and a VEGF binding domain in any one of the multi-specific or bispecific formats known in the art and described throughout. Preferred formats for the multi-specific binding molecules of the present disclosure are described in more detail below.

A multi-specific binding molecule of the present disclosure comprises an anti-BTC binding moiety and an anti-VEGF binding moiety, where the anti-BTC binding moiety comprises a variable heavy chain domain (VHA) and a variable light chain domain (VLA) that bind to BTC, and where the anti-VEGF binding moiety comprises a variable heavy chain domain (VHB) and a variable light chain domain (VLB) that bind to VEGF. In one aspect, the VHA and the VLA are linked via a covalent bond, e.g., a disulfide bond. In one aspect, the VHB and the VLB are linked via a covalent bond, e.g., a disulfide bond. In one aspect, a multi-specific binding molecule is in the format from the N-terminus to C-terminus as: N-VHA-linker 1-VHB-C and N-VLA-linker 2-VLB-C. In another aspect, a multi-specific binding molecule is in the format from the N-terminus to C-terminus as: N-VHB-linker 1-VHA-C and N-VLB-linker 2-VLA-C. The linker 1 and linker 2 can be the same or different.

In one aspect, the anti-BTC binding moiety further comprises a heavy chain constant domain (CHIA) and a light chain constant domain (CKA), and where the anti-VEGF binding moiety further comprises a heavy chain constant domain (CHIB) and a light chain constant domain (CKB). In one aspect, a multi-specific binding molecule is in the format from the N-terminus to C-terminus as: N-VHA-CH1A-linker-VHB-CH1B-C and N-VLA-CKA-linker-VLB-CKB-C, e.g., NVS11, NVS12, NVS13, and NVS14 as provided in Table 3. In another aspect, a multi-specific binding molecule is in the format from the N-terminus to C-terminus as: N—VHB-CH1B-linker-VHA-CH1A-C and N-VLB-CKB-linker-VLA-CKA-C. In one aspect, the two linkers are the same. In another aspect, the two linkers are different.

In certain aspects, a CH1 constant region is present with a VH and a $C_\kappa$ constant region is present with a VL, such that a Fab fragment is formed by dimerization of the respective light and heavy chains (i.e., VHA-CH1 will form a Fab fragment with a VLA-$C_\kappa$, and VHB-CH1 will form a Fab fragment with VLB-$C_\kappa$). In certain aspects, a multi-specific binding molecule of the present disclosure is a Fab-Fab format, in which an anti-BTC binding moiety and an anti-VEGF binding moiety both form Fab fragments. In another aspect, a CH1 constant region is present with a $V_H$ and a Cλ constant region is present with a VL, such that a Fab fragment is formed by dimerization of the respective light and heavy chains (i.e., VHA-CH1 will form a Fab fragment with a VLA-Cλ, and VHB-CH1 will form a Fab fragment with VLB-Cλ).

A multi-specific binding molecule of the present disclosure comprises an anti-BTC binding moiety and an anti-VEGF binding moiety, where the anti-BTC binding moiety is a Fab and comprises a heavy chain (HA) and a light chain (LA), and where the the anti-VEGF is a Fab and comprises a heavy chain (HB) and a light chain (LB). In one aspect, the HA and the HB are linked in the format from the N-terminus to the C-terminus: N-HA-linker 1-HB-C, and where the LA and the LB are linked in the format from the N-terminus to the C-terminus: N-LA-linker 2-LB-C. In another aspect, the HA and the HB is linked in the format from the N-terminus to the C-terminus: N-HB-linker 1-HA-C, and where the LA and the LB is linked in the format from the N-terminus to the C-terminus: N-LB-linker 2-LA-C. The linker 1 and linker 2 can be the same or different. In one aspect, the linker 1 and the linker 2 comprise an amino sequence of SEQ ID NO: 118, or are encoded by a nucleic sequence of SEQ ID NO: 119. In another aspect, the linker 1 and linker 2 comprise an amino sequence selected from the group consisting of SEQ ID NOs: 161-167.

In one aspect, a Fab multi-specific binding molecule of the present disclosure has the structure depicted in FIG. 1-2.

In one aspect, a bispecific antibody of the present disclosure comprises two polypeptide chains, one chain comprising an anti-VEGF scFv and the light chain variable domain of an anti-BTC antibody (VLB) also having a light chain constant region CL (VLB-CL), linked together by a linker peptide, and the other chain comprising a heavy chain variable domain of an anti-BTC antibody (VHB) also having a heavy chain constant region CH1 (VHB-CH1). In another aspect, a bispecific antibody of the present disclosure comprises two polypeptide chains, one chain comprising an anti-VEGF scFv and a heavy chain variable domain of an anti-BTC antibody (VHB) also having a heavy chain constant region CH1 (VHB-CH1), linked together by a linker peptide, and the other chain comprising a light chain variable domain of an anti-BTC antibody (VLB) also having a light chain constant region CL (VLB-CL).

In certain aspects, the orientation of scFv on one polypeptide chain of a bispecific antibody of the present disclosure can be NH2-VLB-CL-Linker 2-scFv-COOH or NH2-VHB-CH1-Linker 2-scFv-COOH. In one aspect, the linker sequence between the VL and VH domains on the scFv has the sequence of (GGGGS)$_4$ (SEQ ID NO: 63), the VL and VH being in the NH2-VLA-Linker 2-VHA-COOH format.

In other aspects, one of the binding domains of a bispecific antibody of the present disclosure forms a Fab and the other binding domain forms a single-chain (scFv) antibody fragment. One of skill in the art will recognize other orientations are possible in addition to those shown. For example, scFv-Fab format is possible, or binding specificities can be rearranged.

In some aspects a multi-specific binding molecule is a bispecific antibody or bispecific antibody-like molecule. In another aspect, the present disclosure features multi-specific molecules comprising a domain with specificity to BTC (i.e., an anti-BTC binding moiety) and another domain with specificity to another therapeutic target (a therapeutic target binding moiety), e.g., VEGF. For example, a multi-specific molecule can comprise an anti-BTC binding moiety, an antibody, or antigen binding fragment thereof, and a nucleic acid molecule of the present disclosure. Anti-BTC antibodies are known in the art, e.g., as described in U.S. Pat. No. 6,183,971 and WO 2004/083241 A2.

An antibody of the present disclosure, or antigen binding fragment thereof, can be derivatized or linked to another functional molecule, e.g., another peptide or protein (e.g., another antibody or ligand for a receptor) to generate a bispecific molecule that binds to at least two different binding sites or target molecules. The antibody of the present disclosure can in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the present disclosure, an antibody of the present disclosure can be functionally linked (e.g., by chemical coupling, genetic fusion, non-covalent association or otherwise) to one or more other binding molecules, such as another antibody, antigen binding fragment, peptide, or binding mimetic, such that a bispecific molecule results.

Accordingly, the present disclosure includes bispecific molecules comprising at least one first binding specificity for BTC and a second binding specificity for a second target epitope, e.g., another therapeutic target. For example, the second target epitope is an epitope of VEGF.

In one aspect, an anti-BTC binding moiety and an anti-VEGF binding moiety comprised in a multi-specific binding molecule are in a format, including, e.g., a Fab, a Fab', a F(ab')$_2$, a Fv, or a single chain Fv (scFv). In another aspect, the anti-BTC binding moiety is an anti-BTC Fab and the anti-VEGF binding moiety is an anti-VEGF Fab. In another aspect, the anti-BTC binding moiety is an scFv and the anti-VEGF binding moiety is an scFV. An anti-BTC binding moiety and an anti-VEGF binding moiety comprised in a multi-specific binding molecule can also be a light chain or heavy chain dimer, or any minimal fragment thereof such as a Fv or a single chain construct as described in Ladner et al. U.S. Pat. No. 4,946,778.

In one aspect, a multi-specific binding molecule of the present disclosure can be a diabody. Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen binding sites (see e.g., Holliger et al., 1993 Proc. Natl. Acad. Sci. USA 90:6444-6448; Poljak et al., 1994 Structure 2:1121-1123). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer *Immunol. Immunother.*, 45(3-4):128-30; Wu et al., 1996 *Immunotechnology*, 2(1):21-36). scDb can be expressed in bacteria in soluble, active monomeric form (see Holliger and Winter, 1997 Cancer *Immunol. Immunother.*, 45(34): 128-30; Wu et al., 1996 *Immunotechnology*, 2(1):21-36; Pluckthun and Pack, 1997 Immunotechnology, 3(2): 83-105; Ridgway et al., 1996 *Protein Eng.*, 9(7):617-21). A diabody can be fused to Fc to generate a "di-diabody" (see Lu et al., 2004 *J. Biol. Chem.*, 279(4):2856-65). Other antibodies which can be employed in the bispecific molecules of the present disclosure are murine, chimeric and humanized monoclonal antibodies.

Protocols for generating bispecific or heterodimeric antibody or antibody-like molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bispecific structure using a heterobifunctional reagent having an amine-reactive group and a sulfhydryl reactive group as described in, e.g., U.S. Pat. No. 4,433,059; bispecific antibody or antibody-like molecule determinants generated by recombining half antibodies (heavy-light chain pairs or Fabs) from different antibodies or antibody-like molecules through cycle of reduction and oxidation of disulfide bonds between the two heavy chains, as described in, e.g., U.S. Pat. No. 4,444,878; trifunctional antibodies, e.g., three Fab' fragments cross-linked through sulfhdryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono—and oligovalent receptors, e.g., VH-CH1 regions (Fd regions) of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multi-specific binding proteins, e.g., dimer of polypeptides having first domain with binding region of Ig heavy chain variable region, and second domain with binding region of Ig light chain variable region, generally termed diabodies (higher order structures are also encompassed creating for bispecific, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VL and VH domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; string of VH domains (or VL domains in family members) connected by peptide linkages with cross-linkable groups at the C-terminus further associated with VL domains to form a series of FVs (or scFvs), as described in, e.g., U.S. Pat. No. 5,864,019; VL and VH domains, scFvs, or Fabs where one of the antigens is bound monovalently and one of the antigens is bound bivalently, optionally comprising heterodimeric Fc regions, as described in, e.g., WO 2011/028952; and single chain binding polypeptides with both a VL and VH domain linked through a peptide linker are combined into multivalent structures through non-covalent or chemical crosslinking to form, e.g., homo-bivalent, heterobivalent, trivalent, and tetravalent structures using both scFv or diabody type format, as described in, e.g., U.S. Pat. No. 5,869,620.

Additional exemplary multi-specific and bispecific molecules and methods of making the same are found, for example, in U.S. Pat. Nos. 5,910,573, 5,932,448, 5,959,083, 5,989,830, 6,005,079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US 2002004587A1, US 2002076406A1, US 2002103345A1, US 2003207346A1, US 2003211078A1, US2004219643A1, US 2004220388A1, US 2004242847A1, US 2005003403A1, US2005004352A1, US 2005069552A1, US 2005079170A1, US 2005100543A1, US2005136049A1, US 2005136051A1, US 2005163782A1, US 2005266425A1, US2006083747A1, US 2006120960A1, US 2006204493A1, US 2006263367A1, US2007004909A1, US 2007087381A1, US 2007128150A1, US 2007141049A1, US2007154901A1, US 2007274985A1, US 2008050370A1, US 2008069820A1, US 2008152645A1, US 2008171855A1, US 2008241884A1, US 2008254512A1, US 2008260738A1, US 2009130106A1, US 2009148905A1, US 2009155275A1, US 2009162359A1, US 2009162360A1, US 2009175851A1, US 2009175867A1, US 2009232811A1, US 2009234105A1, US 2009263392A1, US 2009274649A1, EP 346087A2, WO 0006605A2, WO 02072635A2, WO 04081051A1, WO 06020258A2, WO 2007044887A2, WO 2007095338A2, WO 2007137760A2, WO 2008119353A1, WO 2009021754A2, WO 2009068630A1, WO 9103493A1, WO 9323537A1, WO 9409131A1, WO 9412625A2, WO 9509917A1, WO 9637621A2, WO 9964460A1. The contents of the above-referenced applications are incorporated herein by reference in their entireties.

Bispecific molecules can be prepared by conjugating the constituent binding specificities, using methods known in the art. For example, each binding specificity of the bispecific molecule can be generated separately and then conjugated to one another.

When the binding specificities are antibodies, they can be conjugated by sulfhydryl bonding of the C-terminus hinge regions of the two heavy chains. In a particular aspect, the hinge region is modified to contain an odd number of sulfhydryl residues, for example one, prior to conjugation. Alternatively, both binding specificities can be encoded in the same vector and expressed and assembled in the same host cell. This method is particularly useful where the bispecific molecule is a mAb×mAb, mAb×Fab, Fab×F(ab')$_2$, ligand×Fab, anti-BTC antibody or functional fragment thereof ×mAb, Crossmab format, BITE format, anti-BTC antibody or functional fragment thereof x Fab fusion protein. A bispecific molecule of the present disclosure can be a single chain molecule comprising one single chain antibody and a binding determinant, or a single chain bispecific molecule comprising two binding determinants. Bispecific molecules can comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the multi-specific binding or multivalent molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present disclosure provides multivalent molecules comprising at least two identical or different antigen binding portions of the antibodies of the present disclosure binding to a target, such as BTC. In a further aspect, the present disclosure provides multivalent compounds comprising at least two identical or different antigen binding portions of the BTC binding moieties and/or a therapeutic target binding moieties. The antigen binding portions can be linked together via protein fusion or covalent or non-covalent linkage. Alternatively, methods of linkage have been described for the multi-specific molecules. Tetravalent compounds can be obtained for example by crosslinking antibodies of the antibodies of the present disclosure with an antibody that binds to the constant regions of the antibodies of the present disclosure, for example the Fc or hinge region.

vii. Modification of the Molecules of the Present Disclosure

The present application includes variants of the molecules described herein and/or fragments thereof having various modifications in variable regions and/or constant regions, as well as fusions and conjugates of the disclosed molecules. For example, the Fc region of the disclosed multi-specific binding molecules, e.g., CH1 and/or $C_\kappa$, can be wild-type, or it can be modified to achieve various outcomes. Preferred modifications to the Fc include the "LS" mutation (M428L, N434S, (EU numbering)) and the "YTE" mutation (M252Y, S254T, T256E (EU Numbering)) for half-life extension, the "DAPA" mutation (D265A, P329A (EU Numbering)) for effector silencing, and knob-in-hole mutations (e.g., knob S354C, T366W; hole Y349C, T366S, L368A, Y407V (EU Numbering)) that facilitate proper chain pairing.

Fc regions can also be modified to "silence" the effector function, for example, to reduce or eliminate the ability of a BTC binding molecule to mediate antibody dependent cellular cytotoxicity (ADCC) and/or antibody dependent cellular phagocytosis (ADCP). This can be achieved, for example, by introducing a mutation in an Fc region. Such mutations have been described in the art: LALA and N297A (Strohl, 2009, Curr. Opin. Biotechnol. 20(6):685-691); and D265A (Baudino et al., 2008, J. Immunol. 181: 6664-69; Strohl, supra). Examples of silent Fc igG1 antibodies comprise the so-called LALA mutant comprising L234A and L235A mutation in the lgG1 Fc amino acid sequence. Another example of a silent lgG1 antibody comprises the D265A mutation. Another silent lgG1 antibody comprises the so-called DAPA mutant comprising D265A and P329A mutations in the lgG1 Fc amino acid sequence. Another silent lgG1 antibody comprises the N297A mutation, which results in aglycosylated/non-glycosylated antibodies.

Each of the VH and VL domains of an anti-BTC antibody or antigent binding fragment thereof and/or a multi-specific binding molecule of the present disclosure comprises hypervariable regions CDR1, CDR2, and CDR3 sequences. In certain aspects, one or more of these CDR sequences have conservative modifications of the amino acid sequences, and where the modified molecules retain or have enhanced binding properties as compared to the parent antibodies.

In addition, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.). The molecules of the present disclosure can be modified by introducing such mutations to its variable region frameworks in order to improve the binding properties.

Another type of variable region modification is to mutate amino acid residues within the VH and/or VL CDR1, CDR2 and/or CDR3 domains to thereby improve one or more binding properties (e.g., affinity) of the molecule (e.g., antibody or antibody-like molecule) of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein. Conservative modifications (as discussed above) can be introduced. The mutations can be amino acid substitutions, additions or deletions. Moreover, typically no more than one, two, three, four or five residues within a CDR region are altered.

Amino acid sequence variants of the present molecules can be prepared by introducing appropriate nucleotide changes into the encoding DNAs, or by synthesis of the desired variants. Such variants include, for example, deletions from, or insertions or substitutions of, residues within the amino acid sequences of present molecules. Any combination of deletion, insertion, and substitution is made to arrive at the final construct, provided that the final construct possesses the desired antigen-binding characteristics. The amino acid changes also can alter post-translational processes of the molecules, such as changing the number or position of glycosylation sites.

The present application includes variants of the molecules described herein and/or fragments thereof having amino acid conservative modifications in variable regions and/or constant regions.

viii. Nucleic Acids, Expression Vectors, and Host Cells

The present disclosure provides purified nucleic acid molecules (e.g., substantially purified nucleic acid molecules) which encode an anti-BTC antibodies or antigen binding fragment thereof, and/or a multi-specific binding molecule comprising a BTC-binding moiety and another binding moiety (e.g., an anti-VEGF binding moiety) described herein. In certain aspects the present disclosure provides purified nucleic acid molecules (e.g., substantially purified nucleic acid molecules) which encode an anti-BTC binding moiety described in Table 1. In another aspect, the present disclosure provides purified nucleic acid molecules (e.g., substantially purified nucleic acid molecules) which encode a multi-specific binding molecule comprising a BTC-binding moiety and an anti-VEGF binding moiety described in Table 3.

The nucleic acid molecules of the present disclosure can encode both a variable region and a constant region of the antibody. Some of the nucleic acid sequences of the present disclosure comprise nucleotides encoding a modified heavy chain sequence that has substantial identity (e.g., at least 80%, 90%, 95%, or 99%) to the original heavy chain sequence (e.g., substantial identity to the heavy chain of NVS1, NVS2, NVS3, NVS4, NVS11, NVS12, NVS13, or NVS14). Some other nucleic acid sequences comprising nucleotides encoding a modified light chain sequence that has substantial identity (e.g., at least 80%, 90%, 95%, or 99%) to the original light chain sequence (e.g., substantial identity to the light chain of NVS1, NVS2, NVS3, NVS4, NVS11, NVS12, NVS13, or NVS14).

The polynucleotide sequences can be produced by de novo solid-phase DNA synthesis or by PCR mutagenesis of an existing sequence (e.g., sequences as described in the Examples below) encoding an anti-BTC antibody or its binding fragment. Direct chemical synthesis of nucleic acids can be accomplished by methods known in the art, such as the phosphotriester method of Narang et al., 1979, *Meth. Enzymol.* 68:90; the phosphodiester method of Brown et al., *Meth. Enzymol.* 68:109, 1979; the diethylphosphoramidite method of Beaucage et al., *Tetra. Lett.*, 22:1859, 1981; and the solid support method of U.S. Pat. No. 4,458,066. Introducing mutations to a polynucleotide sequence by PCR can be performed as described in, e.g., PCR Technology: *Principles and Applications for DNA Amplification*, H. A. Erlich (Ed.), Freeman Press, NY, NY, 1992; *PCR Protocols: A Guide to Methods and Applications*, Innis et al. (Ed.), Academic Press, San Diego, Calif., 1990; Mattila et al., *Nucleic Acids Res.* 19:967, 1991; and Eckert et al., *PCR Methods and Applications* 1:17, 1991.

Also provided in the present disclosure are expression cassettes, vectors, and host cells for producing an anti-BTC binding moiety and/or a multi-specific binding molecule comprising a BTC-binding moiety and an anti-VEGF binding moiety. More specifically, the present disclosure provides an expression cassette and/or a vector comprising a nucleic acid encoding an anti-BTC binding moiety having the sequences as set forth in Table 1, or alternatively, an expression cassette and/or a vector comprising a nucleic acid encoding an anti-BTC binding moiety conjugated to a molecule as described herein. In certain aspects the expression cassette and/or vector comprises a nucleic acid encoding any one of the molecules conjugated to anti-BTC anti-BTC binding moiety thereof described in Table 1. In another aspect, the present disclosure provides an expression cassette and/or vector comprising a nucleic acid encoding a multi-specific binding molecule comprising a BTC-binding moiety and an anti-VEGF binding moiety as set forth in Table 3.

In one aspect, the present disclosure provides an expression cassette and/or a vector comprising a nucleic acid molecule encoding a VH and a VL of an anti-BTC antibody or antigen binding fragment thereof, where the nucleic acid molecule is about at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical or complementary to SEQ ID NOs: 11 and 22, respectively; SEQ ID NOs: 35 and 46, respectively; SEQ ID NOs: 55 and 66, respectively; or SEQ ID NOs: 79 and 89, respectively.

In one aspect, the present disclosure provides an expression cassette and/or a vector comprising a nucleic acid molecule encoding a heavy chain and a light chain of an anti-BTC antibody or antigen binding fragment thereof, where the nucleic acid molecule is about at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical or complementary to SEQ ID NOs: 13 and 24, respectively; SEQ ID NOs: 37 and 48, respectively; SEQ ID NOs: 57 and 68, respectively; or SEQ ID NOs: 81 and 91, respectively.

In one aspect, the present disclosure provides an expression cassette and/or a vector comprising a nucleic acid molecule encoding a multi-specific binding molecule comprising 1) a VHA and a VLA that bind to BTC, where the VHA and VLA is encoded by a nucleic acid sequence about at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical or complementary to SEQ ID NOs: 116 and 122, respectively; and 2) a VHB and a VLB that bind to VEGF, where the VHB and VLB is encoded by a nucleic acid sequence about at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical or complementary to SEQ ID NOs: 117 and 123, respectively.

In one aspect, the present disclosure provides an expression cassette and/or a vector comprising a nucleic acid molecule encoding a multi-specific binding molecule comprising 1) a VHA and a VLA that bind to BTC, where the VHA and VLA is encoded by a nucleic acid sequence about at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical or complementary to SEQ ID NOs: 127 and 132, respectively; and 2) a VHB and a VLB that bind to VEGF, where the VHB and VLB is encoded by a nucleic acid sequence about at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical or complementary to SEQ ID NOs: 128 and 133, respectively.

In one aspect, the present disclosure provides an expression cassette and/or a vector comprising a nucleic acid molecule encoding a multi-specific binding molecule comprising 1) a VHA and a VLA that bind to BTC, where the VHA and VLA is encoded by a nucleic acid sequence about at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical or complementary to SEQ ID NOs: 137 and 142, respectively; and 2) a VHB and a VLB that bind to VEGF, where the VHB and VLB is encoded by a nucleic acid sequence about at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical or complementary to SEQ ID NOs: 138 and 143, respectively.

In one aspect, the present disclosure provides an expression cassette and/or a vector comprising a nucleic acid molecule encoding a multi-specific binding molecule comprising 1) a VHA and a VLA that bind to BTC, where the VHA and VLA is encoded by a nucleic acid sequence about at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical or complementary to SEQ ID NOs: 147 and 151, respectively; and 2) a VHB and a VLB that bind to VEGF, where the VHB and VLB is encoded by a nucleic acid sequence about at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical or complementary to SEQ ID NOs: 148 and 152, respectively.

In one aspect, the present disclosure provides an expression cassette and/or a vector comprising a nucleic acid molecule encoding a multi-specific binding molecule comprising a heavy chain and a light chain encoded by a nucleic acid sequence about at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical or complementary to SEQ ID NOs: 121 and 126, respectively; SEQ ID NOs: 131 and 136, respectively; SEQ ID NOs: 141 and 146, respectively; or SEQ ID NOs: 150 and 155, respectively.

In one aspect, the present application provides a method of producing the one or more main polypeptide chains of the multi-specific binding molecule recombinantly, comprising: 1) producing one or more DNA constructs comprising a nucleic acid molecule encoding each of the polypeptide chains of the multi-specific binding molecule; 2) introducing said DNA construct(s) into one or more expression vectors; 3) co-transfecting said expression vector(s) in one or more host cells; and 4) expressing and assembling the molecule in a host cell or in solution.

In this respect, the disclosure provides isolated nucleic acids, e.g., one or more polynucleotides, encoding the multi-specific binding molecule described herein, for example a multi-specific binding molecule that includes a BTC binding domain and a VEGF binding domain, e.g., as described herein. In some aspects, the isolated nucleic acid is disposed on a single continuous polynucleotide. In other aspects, the isolated polynucleotide is disposed on two or more continuous nucleic acid includes sequences. In some aspects, the isolated nucleic acid molecule is complementary DNA (cDNA) or messenger RNA (mRNA).

In aspects, the isolated nucleic acid includes a sequence encoding a BTC binding domain or fragment thereof and/or a sequence encoding a VEGF binding domain or fragment thereof. In aspects, the sequence encoding a BTC binding domain or fragment thereof and the sequence encoding the VEGF binding domain are disposed on separate polynucleotides. In aspects, the sequence encoding a BTC binding domain or fragment thereof and the sequence encoding the VEGF binding domain are disposed on a single polynucleotide.

In an exemplary aspect, a DNA sequence encoding the light chain of a multi-specific binding molecule and a DNA sequence encoding the heavy chain of the multi-specific binding molecule are placed in separate expression vectors. The expression vectors are then co-transfected into a host cell at a ratio giving rise to optimal assembly. The encoded heavy chains and light chains are expressed in the host cell and assemble into functional molecules. Provided herein are host cells comprising these cloning and expression vectors.

In another exemplary aspect, the DNA sequences encoding a heavy and a light chain of multi-specific binding molecule are placed in one expression vector. The expression vector can then be transfected into a host cell. The encoded heavy chains and light chains are expressed in the host cell and assemble into functional molecules. Alternatively, the expression vectors can be transfected into different host cell populations, and the multi-specific binding molecule assembled in solution.

Provided herein are cloning and expression vectors comprising one or more nucleic acid molecules or a set of nucleic acid molecules that encode a multi-specific binding molecule as described herein, where the vector is suitable for the recombinant production of a multi-specific binding molecule. Provided herein are processes for the production of a multi-specific binding molecule as described herein, comprising culturing a host cell as disclosed herein under conditions sufficient to express the multi-specific binding molecule, and thereafter purifying and recovering the multi-specific binding molecule from the host cell culture.

The nucleic acid sequences coding for the desired molecules of the present disclosure can be obtained using recombinant methods known in the art, such as, for example by screening libraries from cells expressing the gene, by deriving the gene from a vector known to include the same, or by isolating directly from cells and tissues containing the same, using standard techniques. Alternatively, the nucleic acid of interest can be produced synthetically, rather than cloned. The present disclosure also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length. RNA so produced can efficiently transfect different kinds of cells. In one aspect, the template includes sequences for the polypeptides of the multi-specific binding molecule, e.g., bispecific molecule, e.g., bispecific antibody or bispecific antibody-like molecule. In an aspect, an RNA vector is transduced into a cell by electroporation.

Various vectors can be employed to express the desired molecules of the present disclosure. Both viral-based and non-viral expression vectors can be used to produce the proteins in a mammalian host cell. Non-viral vectors and systems include plasmids, episomal vectors, typically with an expression cassette for expressing a protein or RNA, and human artificial chromosomes (see, e.g., Harrington et al., Nat Genet 15:345, 1997). For example, non-viral vectors useful for expression of an anti-BTC binding moiety and/or a multi-specific binding molecule comprising a BTC-binding moiety and an anti-VEGF binding moiety in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adeno-associated viruses (AAV), herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992. Methods for generating virus vectors are well known in the art and would allow for the skilled artisan to generate the virus vectors of the present disclosure (See, e.g., U.S. Pat. No. 7,465,583).

AAVs are small, single-stranded DNA viruses which require helper virus to facilitate efficient replication. A viral vector comprises a vector genome and a protein capsid. The viral vector capsid can be supplied from any one of the AAV serotypes known in the art, including presently identified human and non-human AAV serotypes and AAV serotypes yet to be identified, e.g., AAV1, AAV2, AAV3, AAV4, AAV5, AAV6, AAV7, AAV8, AAV9, AAV10, AAV 11, and AAV12. Virus capsids can be mixed and matched with other vector components to form a hybrid viral vector. For example, the ITRs and capsid of the viral vector can come from different AAV serotypes. In one aspect, the ITRs can be from an AAV2 serotype while the capsid is from, for example, an AAV2 or AAV8 serotype. In addition, one of skill in the art would recognize that the vector capsid can also be a mosaic capsid (e.g., a capsid composed of a mixture of capsid proteins from different serotypes), or even a chimeric capsid (e.g., a capsid protein containing a foreign or unrelated protein sequence for generating markers and/or altering tissue tropism). It is contemplated that the viral vector of the present disclosure can comprise an AAV2, AAV5, AAV8, or AAV9 capsid. It is further contemplated that the present disclosure provides methods for producing a molecule of the present disclosure by a viral vector comprising an AAV8 capsid. In another aspect, the present disclosure provides methods for producing a molecule of the present disclosure by a viral vector comprising an AAV9 capsid. In certain aspects, the present disclosure provides methods producing a molecule of the present disclosure by a viral vector comprising an AAV5 capsid or AA6 capsid. In one aspect, an anti-BTC antibody or antigen binding fragment thereof can be expressed using an AAV vector. In one aspect, an anti-BTC binding moiety of a multi-specific binding molecule can be expressed using an AAV vector. In another aspect, an anti-VEGF binding moiety of a multi-specific binding molecule can be expressed using an AAV vector.

The choice of expression vector depends on the intended host cells in which the vector is to be expressed. Typically, the expression vectors contain a promoter and other regulatory sequences (e.g., enhancers) that are operably linked to the polynucleotides encoding an antibody chain or fragment, or an antibody chain or fragment conjugated to anti-BTC binding moieties. In some aspects, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under non-inducing conditions without biasing the population for coding sequences whose expression products are better tolerated by the host cells. In addition to promoters, other regulatory elements can also be required or desired for efficient expression of an antibody chain or fragment, or an antibody chain or fragment conjugated to anti-BTC binding moieties. These elements typically include an ATG initiation codon and adjacent ribosome binding site or other sequences. In addition, the efficiency of expression can be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer can be used to increase expression in mammalian host cells.

The expression vectors can also provide a secretion signal sequence positioned to form a fusion protein or bispecific antibody with sequences of polypeptides or sequences of antibodies conjugated to anti-BTC binding moieties. More often, such inserted sequences are linked to a signal sequences before inclusion in the vector. Vectors to be used to receive sequences encoding antibody light and heavy chain variable domains, or antibody conjugated to anti-BTC binding moieties, sometimes also encode constant regions or parts thereof. Such vectors allow expression of the variable regions as fusion proteins or bispecific antibodies with the constant regions thereby leading to production of intact antibodies or antigen binding fragments. Typically, such constant regions are human.

Provided in the present disclosure is a method of producing an antibody or antigen binding fragment thereof, comprising culturing host cells as described below under suitable conditions for expression of an anti-BTC antibody or antigen binding fragment thereof and/or a multi-specific binding molecule comprising a BTC-binding moiety and an anti-VEGF binding moiety. In one aspect, the method further comprises purifying the anti-BTC antibody or antigen binding fragment thereof and/or the multi-specific binding molecule comprising a BTC-binding moiety and an anti-VEGF binding moiety.

The host cells for harboring and expressing an anti-BTC binding moiety and/or a multi-specific binding molecule comprising a BTC-binding moiety and an anti-VEGF binding moiety, can be either prokaryotic or eukaryotic. *E. coli* is one prokaryotic host useful for cloning and expressing the polynucleotides of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express an anti-BTC binding moiety and/or a multi-specific binding molecule comprising a BTC-binding moiety and an anti-VEGF binding moiety described herein. Insect cells in combination with baculovirus vectors can also be used.

In some preferred aspects, mammalian host cells are used to express and produce an anti-BTC binding moiety and/or a multi-specific binding molecule comprising a BTC-binding moiety and an anti-VEGF binding moiety of the present disclosure. For example, they can be either a hybridoma cell line expressing endogenous immunoglobulin genes or a mammalian cell line harboring an exogenous expression vector. These include any normal mortal or normal or abnormal immortal animal or human cell. For example, a number of suitable host cell lines capable of secreting intact immunoglobulins have been developed, are known to those of skill in the art, and include CHO cell lines, various Cos cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen, et al., *Immunol*. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters can be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MIRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation can be used for other cellular hosts. (See generally Sambrook, et al.). Other methods include, e.g., electroporation, calcium phosphate treatment, liposome-mediated transformation, injection and microinjection, ballistic methods, virosomes, immunoliposomes, polycation: nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired.

For example, cell lines which stably express an anti-BTC binding moiety and/or a multi-specific binding molecule comprising a BTC-binding moiety and an anti-VEGF binding moiety can be prepared using expression vectors of the present disclosure which contain viral origins of replication or endogenous expression elements and a selectable marker gene. Following the introduction of the vector, cells can be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type. The present disclosure further provides for process for producing the anti-BTC binding moieties and/or molecules conjugated to anti-BTC binding moieties described herein, where a host cell capable of producing an anti-BTC binding moiety or molecules conjugated to anti-BTC binding moieties as described herein is cultured under appropriate conditions for the production of one or more anti-BTC binding moieties and/or molecules conjugated to anti-BTC binding moieties. The process can further include isolating the anti-BTC binding moieties and/or molecules conjugated to anti-BTC binding moieties of the present disclosure.

Expression vectors containing nucleic acid sequences encoding an anti-BTC binding moiety and/or a multi-specific binding molecule comprising a BTC-binding moiety and an anti-VEGF binding moiety of the present disclosure can be used for delivering a gene to the eye. In certain aspects of the present disclosure, the expression vector encodes an antibody is linked to one or more anti-BTC binding moieties of the present disclosure and is suitable for delivery to the eye. In other aspects of the present disclosure, the therapeutic binding moiety and anti-BTC binding moiety are encoded in one or more expression vectors suitable for delivery to the eye. Methods for delivering a gene product to the eye are known in the art.

ix. Antibody Production

Polypeptides and antibodies and fragments thereof can be produced by a variety of techniques, including conventional monoclonal antibody methodology e.g., the standard somatic cell hybridization technique of Kohler and Milstein, (1975) *Nature* 256: 495.

Chimeric or humanized antibodies of the present disclosure can be prepared based on the sequence of a murine monoclonal antibody prepared as described throughout. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

In a certain aspect, antibodies of the present disclosure are human monoclonal antibodies. Such human monoclonal antibodies directed against BTC and/or VEGF can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice." In another aspect, human antibodies of the present disclosure can be raised using a mouse that carries human immunoglobulin sequences on transgenes and transchromosomes such as a mouse that carries a human heavy chain transgene and a human light chain transchromosome. Such mice, referred to herein as "KM mice," are described in detail in PCT Publication WO 02/43478 to Ishida et al.

Still further, alternative transgenic animal systems expressing human immunoglobulin genes are available in the art and can be used to raise antibodies of the present disclosure. For example, an alternative transgenic system referred to as the Xenomouse (Abgenix, Inc.) can be used. Such mice are described in, e.g., U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise the antibodies of the present disclosure. For example, mice carrying both a human heavy chain transchromosome and a human light chain transchromosome, referred to as "TC mice" can be used; such mice are described in Tomizuka et al., 2000 *Proc. Natl. Acad. Sci. USA* 97:722-727. Furthermore, cows carrying human heavy and light chain transchromosomes have been described in the art (Kuroiwa et al., 2002 *Nature* Biotechnology 20:889-894) and can be used to raise antibodies of the present disclosure.

Human monoclonal antibodies of the present disclosure can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the present disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Standard molecular biology techniques can be used to prepare and express the sequence of the altered anti-BTC binding moieties and/or anti-VEGF binding moieties. The altered anti-BTC binding moieties or anti-VEGF binding moieties encoded by the altered sequence(s) is one that retains one, some or all of the functional properties of the altered anti-BTC binding moieties or anti-VEGF binding moieties.

In certain aspects of the methods of engineering anti-BTC binding moieties or anti-VEGF binding moieties, mutations can be introduced randomly or selectively along all or part of an anti-BTC antibody or anti-VEGF antibody coding sequence and the resulting modified anti-BTC antibodies or anti-VEGF antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

In certain aspects of the present disclosure antibodies can be engineered to remove sites of deamidation. Deamidation is known to cause structural and functional changes in a peptide or protein. Deamindation can result in decreased bioactivity, as well as alterations in pharmacokinetics and antigenicity of the protein pharmaceutical (*Anal Chem.* 2005 Mar 1;77(5):1432-9). In certain other aspects of the present disclosure, antibodies and anti-BTC antibodies or functional fragments thereof can be engineered to add or remove sites of protease cleavage.

Antibody proteins obtained from members of the camel and dromedary (*Camelus bactrianus* and *Camelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 *J. Biol. Chem.* 279: 1256-1261; Dumoulin, M. et al., 2003 *Nature* 424: 783-788; Pleschberger, M. et al. 2003 *Bioconjugate Chem.* 14: 440-448; Cortez-Retamozo, V. et al. 2002 *Int. J. Cancer.* 89: 456-62; and Lauwereys, M. et al. 1998 *EMBO J.* 17: 3512-3520. Engineered libraries of camelid antibodies and antigen binding fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized."

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents to detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues. Nanobodies can further facilitate drug transport across the blood brain barrier. See U.S. Patent Application 20040161738 published Aug. 19, 2004. Further, these molecules can be fully expressed in prokaryotic cells such as *E. coli* and are expressed as bispecific antibodies or fusion proteins with bacteriophage and are functional.

Accordingly, a feature of the present disclosure is a camelid antibody or nanobody having, for example, high affinity for BTC (i.e., in cases where the anti-BTC binding moiety is in the format of a camelid antibody or nanobody). In certain aspects herein, the camelid antibody or nanobody is naturally produced in the camelid animal, i.e., is produced by the camelid following immunization with BTC or a peptide fragment thereof, using techniques described herein for other antibodies. Alternatively, a camelid nanobody is engineered (i.e., produced by selection, for example) from a library of phage displaying appropriately mutagenized camelid nanobody proteins using panning procedures with an appropriate target. Engineered nanobodies can further be customized by genetic engineering. The camelid nanobody can be, e.g., specific for a therapeutic target, and linked to an anti-BTC binding moiety as described herein. In a specific aspects, the camelid antibody or nanobody is obtained by grafting the CDRs sequences of the heavy or light chain of the human antibodies of the present disclosure into nanobody or single domain antibody framework sequences, as described for example in PCT/EP93/02214.

x. Pharmaceutical Compositions

The present disclosure provides pharmaceutical compositions comprising an effective amount of an anti-BTC antibody or antigen binding fragment as described herein. The present disclosure also provides pharmaceutical compositions comprising an effective amount of an anti-BTC antibody or an antigen binding fragment thereof or a multispecific binding molecule as described herein (e.g., those described in Tables 1 and 3).

Pharmaceutical compositions of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: eral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

In certain specific aspects, an anti-BTC binding moiety according to Table 1 can be formulated together, or separately, with a pharmaceutically acceptable excipient, diluent, or carrier. The present disclosure also provides compositions comprising an anti-BTC binding moiety formulated together, or separately, with a pharmaceutically acceptable excipient, diluent, or carrier.

In certain aspects, the present disclosure provides compositions comprising multi-specific binding molecule comprising 1) an anti-BTC binding moiety and 2) an anti-VEGF binding moiety, e.g., an anti-BTC antibody, or antigen binding fragment thereof, linked to an anti-VEGF antibody, or antigen binding fragment thereof. A composition can be in a lyophilized dose form and can be reconstituted with water for injection. A composition can comprise at least 10 mg, at least 12 mg, at least 14 mg, at least 16 mg, at least 18 mg, at least 20 mg, at least 22 mg, at least 24 mg, at least 26 mg, at least 28 mg, at least 30 mg, at least 35 mg, at least 40 mg, at least 45 mg, or at least 50 mg of a bispecific antibody (e.g., comprising an anti-BTC binding moiety and an anti-VEGF binding moiety). A composition can further comprise at least 10 mM, at least 15 mM, at least 20 mM, at least 25 mM, at least 30 mM, at least 35 mM, at least 40 mM, at least 45 mM, or at least 50 mM histidine, at least 200 mM, at least 210 mM, at least 220 mM, at least 230 mM, at least 240 mM, or at least 250 mM sucrose, and/or at least 0.01%, at least 0.02%, at least 0.04%, at least 0.06%, at least 0.08%, at least 0.1%, at least 0.2%, or at least 0.5% polysorbate 20.

The compositions described herein can be formulated together with a pharmaceutically acceptable excipient, diluent, or carrier. The compositions can additionally contain one or more other therapeutic agents that are suitable for treating or preventing, for example, conditions or disorders associated with ophthalmic conditions or disorders. Pharmaceutically acceptable carriers enhance or stabilize the composition, or can be used to facilitate preparation of the composition. Pharmaceutically acceptable carriers include solvents, dispersion media, coatings, antibacterial and antifungal agents, isotonic and absorption delaying agents, and the like that are physiologically compatible.

A molecule of the present disclosure can also be administered via one or more routes of administration using one or more of a variety of methods known in the art. As will be appreciated by the skilled artisan, the route and/or mode of administration will vary depending upon the desired results. Selected routes of administration for the antibodies include intravenous, intramuscular, intradermal, intraperitoneal, subcutaneous, spinal or other parenteral routes of administration, for example by injection or infusion. Parenteral administration can represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the present disclosure can be administered via a non-parenteral route, such as a topical, epidermal or mucosal route of administration, for example, intranasally, orally, vaginally, rectally, sublingually, or topically.

In certain aspects, the pharmaceutical composition is administered systemically and allowed to localize to the tissue of interest based on its affinity for BTC. It is preferred that the composition be suitable for administration to the eye directly, more specifically, the composition can be suitable for intravitreal and/or subretinal administration. The pharmaceutically acceptable excipient, diluent or carrier should be suitable for administration to the eye. (e.g., by injection or sub-conjunctival administration), more specifically, for intravitreal administration and/or subretinal administration.

The composition should be sterile and fluid. Proper fluidity can be maintained, for example by use of surfactants. In many cases, it is preferable to include isotonic agents, for example, sugars, polyalcohols such as mannitol or sorbitol, and sodium chloride in the composition.

Pharmaceutical compositions of the present disclosure can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the molecule employed in the pharmaceutical compositions of the present disclosure.

The molecules conjugated to anti-BTC or anti-VEGF binding moieties are formulated into pharmaceutically acceptable dosage forms by conventional methods known to those of skill in the art. Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The composition should be sterile and fluid. In many cases, it is preferable to include isotonic agents, for example, sugars, polyalcohols such as mannitol or sorbitol, and sodium chloride in the composition.

In certain aspects, the molecules or fragments thereof of the present disclosure can be formulated to ensure proper distribution in vivo.

The present disclosure provides a kit comprising a pharmaceutical composition comprising an anti-BTC antibody or antigen binding fragment thereof and/or a multi-specific binding molecule, e.g., a multi-specific binding molecule comprising an anti-BTC binding moiety and an anti-VEGF binding moiety.

In one aspect, a kit further comprises an instruction for use, which can provide the dose, route of administration, regimen, and total treatment. In another aspect, a kit further comprises means for administering the molecule of the present disclosure, e.g., an autoinjector, a syringe, a vial, a prefilled syringe, and/or a prefilled pen.

These kits can contain additional therapeutic agents for treating a subject having a pathological disorder mediated by BTC and/or VEGF, e.g., DME. In one aspect, additional therapeutic agents include, but are not limited to, Beovu/brolucizumab, Lucentis/ranibizumab, Avastin/bevicizumab, Eylea/aflibercept, pegaptanib, pazopanib, sorafinib, sunitinib, and/or rapamycin.

xi. Diagnostic and Therapeutic Uses

The present molecules have many diagnostic and therapeutic applications. For instance, they can be used for enzyme immunoassay, with arms binding a specific epitope on an enzyme and other portions of the molecule binding an immobilizing matrix. The enzyme immunoassay using antibody-like molecules is discussed by Nolan et al. (Nolan et al., (1990) Biochem. Biophys. Acta. 1040:1-11). The multi-specific binding molecules can also be used for diagnosis of various diseases, e.g., pancreatic carcinoma, breast cancer, endometrial adenocarcinoma, hepatocellular carcinoma, head and neck squamous cell carcinoma, gastric carcinoma, diabetic macular edema, age-related macular degeneration, neovascular age-related macular degeneration, neovascular glaucoma, diabetic retinopathy, macular edema, pathologic myopia, retinal vein occlusions, retinopathy of prematurity, abnormal vascular proliferation associated with phakomatoses, central serous chorioretiniopathy, and acute multifocal placoid pigment epitheliopathy.

The present molecules have in vitro and in vivo diagnostic and therapeutic utilities. For example, these molecules can be administered to cells in culture, e.g., in vitro or in vivo, or in a subject, e.g., in vivo, to treat, prevent or diagnose a variety of disorders.

In one aspect, the molecules of the disclosure are useful for detecting the presence of BTC and/or VEGF in a biological sample. The term "detecting" as used herein encompasses quantitative or qualitative detection. In certain aspects, a biological sample comprises a cell or tissue. In certain aspects, such tissues include normal and/or cancerous tissues that express BTC and/or VEGF at higher levels relative to other tissues.

In one aspect, the present disclosure provides a method of detecting the presence of BTC and/or VEGF in a biological sample. In certain aspects, the method comprises contacting the biological sample with a multi-specific molecule of the disclosure under conditions permissive for binding of the antibody to the antigen, and detecting whether a complex is formed between the antibody and the antigen. The biological sample can include, without limitation, urine or blood samples.

Also included is a method of diagnosing a disorder associated with expression of BTC and/or VEGF. In certain aspects, the method comprises contacting a test cell with a multi-specific molecule of the disclosure; determining the level of expression (either quantitatively or qualitatively) of BTC and/or VEGF in the test cell by detecting binding of the a multi-specific molecule of the disclosure; and comparing the level of expression of BTC and/or VEGF in the test cell with the level of expression of BTC and/or VEGF in a control cell (e.g., a normal cell of the same tissue origin as the test cell or a non-virus infected cell), where a higher level of presence of BTC and/or VEGF in the test cell as compared to the control cell indicates the presence of a disorder associated with BTC and/or VEGF. In certain aspects, the test cell is obtained from an individual suspected of having a pathological disorder mediated by BTC and/or VEGF.

The molecules described herein can be used as a medicament. As provided below (e.g., in Example 13), a combined treatment of an anti-BTC antibody and an anti-VEGF antibody surprisingly led to a reduction of retinal leakage in animal models by 77% relative to control animals.

In particular, an anti-BTC antibody or antigen binding fragment thereof and/or a multi-specific binding molecule of the present disclosure can be used for treating pancreatic carcinoma, breast cancer, endometrial adenocarcinoma, hepatocellular carcinoma, head and neck squamous cell carcinoma, and gastric carcinoma. In another aspect, an anti-BTC antibody or antigen binding fragment thereof and/or a multi-specific binding molecule of the present disclosure can be used for treating ophthalmic conditions or disorders, e.g., conditions or disorders associated with retinal vascular disease in a subject.

The present disclosure provides a method of treating pathological disorders mediated by BTC and/or VEGF by administering to a subject in need thereof an effective amount of the molecules of the present disclosure. Pathological disorders mediated by BTC and/or VEGF include conditions associated with or characterized by aberrant BTC and/or VEGF levels and/or diseases or conditions that can be treated by reducing or suppressing BTC and/or VEGF-induced activity in target cells or tissues, e.g., retinal cells. In one aspect, the present disclosure provides a method of treating a disease or disorder associated with increased BTC and/or VEGF levels and/or activity. In one aspect, the disease or disorder is a retinal disease or disorder, e.g., DME.

Patients with diabetes often face ophthalmic complications affecting various parts of the eye, including the retina (DR or diabetic retinopathy), the macula (DME), the lens (cataract), and the optic nerve (glaucoma). The prevalence of DME among those with type 1 diabetes (T1D) and type 2 diabetes (T2D) varies by region. Prevalence rates range from 11% in Europe to 7.5% in some African countries. More than 31 million people are affected worldwide. Approximately one in 14 people with diabetes has some degree of DME. An estimated 20% of people living with T1D, and 25% of those with T2D, can expect to develop DME. DME is the leading cause of blindness in the working age population in developed countries.

DME is a subtype of DR that occurs most frequently in patients with progressive diabetic retinopathy (PDR) but can occur at any stage of the disease. It is caused by the progressive growth of new blood vessels under the retina that leak fluid and lipids, leading to swelling of the macula, which can result in significant blurring of vision and contribute to the risk of blindness from DR. DME leads to significant visual impairment including blurred vision and image distortion, as well as changes in color vision and scotomas (Yau et al., *Diabetes Care* 35:556-564, 2012; Ting et al., *Clin. Exp. Ophthalmol.* 2016: 209-22). DME is a major cause of reduced visual acuity in diabetic retinopathy (20% in T1D and 40% in T2D). The pathophysiology of DR/DME is complex given the interplay between various biochemical pathways, inflammatory mediators, and angiogenic factors.

VEGF inhibitors are the first-line treatment of diffuse, center-involved DME. Although anti-VEGF agents reduce macular edema, inhibit angiogenesis, and improve vision, not all DME patients experience substantial prolonged improvements in vision or respond adequately to treatment, indicating the role of other mediators in the disease's pathology.

The present disclosure provides a method of treating an ophthalmic disorder, e.g., DME, by administering to a subject in need thereof an effective amount of the molecules of the present disclosure, e.g., an anti-BTC antibody or antigen binding fragment thereof or a multi-specific binding molecule comprising an anti-BTC binding moiety and an anti-VEGF binding moiety. The present disclosure also provides a method of preventing the progression of an ophthalmic disorder, e.g., DME, by administering to a subject in need thereof an effective amount of the molecules of the present disclosure, e.g., an anti-BTC antibody or antigen binding fragment thereof or a multi-specific binding molecule comprising an anti-BTC binding moiety and an anti-VEGF binding moiety.

The present disclosure further provides a method of treating diabetic retinopathy (DR) or proliferative diabetic retinopathy (PDR) by administering to a subject in need thereof an effective amount of the molecules of the present disclosure.

The present disclosure further provides a method of treating age-related macular degeneration (AMD, e.g., neovascular AMD) by administering to a subject in need thereof an effective amount of the molecules of the present disclosure.

Still further, the present disclosure provides methods for treating retinal vein occlusion (RVO) including Central Retinal Vein Occlusion (CRVO), Branch Retinal Vein Occlusion (BRVO), and macular edema secondary to CRVO or BRVO, angioedema, multifocal choroiditis, myopic choroidal neovascularization, and/or retinopathy of prematurity, choroidal neovascularization (CNV), retinal vascular permeability, and/or including CNV associated with nAMD (neovascular AMD), sequela associated with retinal ischemia, by administering to a subject in need thereof an effective amount of the molecules of the present disclosure.

Treatment and/or prevention of retinal disease, e.g., macular edema, DME, PDR or DR, and AMD, e.g., neovascular AMD, can be determined by an ophthalmologist or health care professional using clinically relevant measurements of visual function and/or retinal anatomy. Treatment of conditions or disorders associated with retinal vascular disease means any action (e.g., administration of a BTC antibody or antigen binding fragment thereof and/or a multi-specific binding molecule described herein) that results in, or is contemplated to result in, the improvement or preservation of visual function and/or retinal anatomy. In addition, prevention as it relates to conditions or disorders associated with retinal vascular disease means any action (e.g., administration of a BTC antibody or antigen binding fragment thereof and/or a multi-specific binding molecule described herein) that prevents or slows a worsening in visual function, retinal anatomy, and/or a retinal vascular disease parameter, as defined herein, in a patient at risk for said worsening.

Visual function can include, for example, visual acuity, visual acuity with low illumination, visual field, central visual field, peripheral vision, contrast sensitivity, dark adaptation, photostress recovery, color discrimination, reading speed, dependence on assistive devices (e.g., large typeface, magnifying devices, telescopes), facial recognition, proficiency at operating a motor vehicle, ability to perform one or more activities of daily living, and/or patient-reported satisfaction related to visual function.

The present disclosure further provides a method of improving visual function or preventing further decline of visual functions by administering to a subject in need thereof an effective amount of the molecules of the present disclosure.

Exemplary measures of visual function include Snellen visual acuity, ETDRS visual acuity, low-luminance visual acuity, Amsler grid, Goldmann visual field, Humphrey visual field, microperimetry, Pelli-Robson charts, SKILL card, Ishihara color plates, Farnsworth D15 or D100 color test, standard electroretinography, multifocal electroretinography, validated tests for reading speed, facial recognition, driving simulations, and patient reported satisfaction. Thus, treatment of vascular disease and/or macular edema can be said to be achieved upon a gain of or failure to lose 2 or more lines (or 10 letters) of vision on an ETDRS scale. In addition, treatment of vascular disease and/or macular edema can be said to occur where a subject exhibits at least a 10% an increase or lack of 10% decrease in reading speed (words per minute). In addition, treatment of vascular disease and/or macular edema can be said to occur where a subject exhibits at least a 20% increase or lack of a 20% decrease in the proportion of correctly identified plates on an Ishihara test or correctly sequenced disks on a Farnsworth test. Further, treatment of retinal vascular disease and/or macular edema, can be said to occur if a subject has, for example, at least 10% decrease or lack of a 10% or more increase in time to a pre-specified degree of dark adaptation. In addition, treatment of retinal vascular disease and/or macular edema can be said to occur where a subject exhibits, for example, at least a 10% reduction or lack of a 10% or more increase in total area of visual scotoma expressed as a visual angle determined by a qualified health care professional (i.e., ophthalmologist).

Undesirable aspects of retinal anatomy that can be treated or prevented include, for example, microaneurysm, macular edema, cotton-wool spot, intraretinal microvascular abnormality (IRMA), capillary dropout, leukocyte adhesion, retinal ischemia, neovascularization of the optic disk, neovascularization of the posterior pole, iris neovascularization, intraretinal hemorrhage, vitreous hemorrhage, macular scar, subretinal fibrosis, and retinal fibrosis, venous dilation, vascular tortuosity, vascular leakage. Thus, treatment of, for example, macular edema can be determined by a 20% or more reduction in thickness of the central retinal sub-field as measured by optical coherence tomography.

Exemplary means of assessing retinal anatomy include funduscopy, fundus photography, fluorescein angiography, indocyanine green angiography, optical coherence tomography (OCT), spectral domain optical coherence tomography, scanning laser ophthalmoscopy, confocal microscopy, adaptive optics, fundus autofluorescence, biopsy, necropsy, and immunohistochemistry. Thus, vascular disease and/or macular edema can be said to be treated in a subject upon a 10% reduction in leakage area as determined by fluorescein angiography. Subjects to be treated with therapeutic agents of the present disclosure can also be administered other therapeutic agents with known methods of treating conditions associated with diabetes mellitus, such as all forms of insulin and anti-hypertensive medications.

Treatment and/or prevention of ocular disease such as macular edema, DME, AMD, e.g., neovascular AMD, retinal vein occlusion (RVO), angioedema, multifocal choroiditis, myopic choroidal neovascularization, and/or retinopathy of prematurity can be determined by an ophthalmologist or health care professional using clinically relevant measurements of visual function and/or retinal anatomy by any of the measures described throughout. Although the measures described herein do not apply to each and every ocular disease herein, one of skill in the art would recognize the clinically relevant measurement of visual function and/or retinal anatomy that could be used to treat the given ocular disease.

When an anti-BTC antibody or antigen binding fragment thereof of the present disclosure is administered together with another agent, the two can be administered sequentially in either order or simultaneously. In some aspects, an anti-BTC antibody or antigen binding fragment thereof of the present disclosure is administered to a subject who is also receiving therapy with a second agent (e.g., BEOVU/brolucizumab, LUCENTIS/ranibizumab, AVASTIN/bevicizumab, EYLEA/aflibercept, pegaptanib, pazopanib, sorafinib, sunitinib, and rapamycin). A combination therapy regimen can be additive, or it can produce synergistic results (e.g., reductions in retinopathy severity more than expected for the combined use of the two agents).

Further still, the present disclosure relates to a method of treating a disorder (e.g., ocular disorder) by administering to a subject in need thereof an effective amount of a therapeutic molecule conjugated to an anti-BTC binding moiety. It is contemplated that the molecules are conjugated to anti-BTC binding moieties that bind BTC in the eye with a KD of less than or equal to 100 µM. For example, the anti-BTC binding moieties can bind BTC with a KD of less than or equal to, 50 µM, 40 µM, 30 µM, 20 µM, 10 µM, 5 µM, 4 µM, 3 µM, 2 µM, 1 µM, 0.5 µM, 0.1 µM, 0.05 µM, 0.01 µM, or 0.005 µM. In one aspect, the molecule conjugated to an anti-BTC binding moiety that binds BTC with a KD of less than or equal to 100.0 µM. In one aspect, the molecule is conjugated to an anti-BTC binding moiety that binds BTC with a KD of less than or equal to 10 µM. In one aspect, the molecule conjugated to an anti-BTC binding moiety comprises an anti-BTC binding moiety that binds BTC with a KD of less than or equal to 5.0 µM. In one aspect, the molecule conjugated to an anti-BTC antibody or functional fragment thereof comprises anti-BTC binding moiety that binds BTC with a KD of less than or equal to 1.0 µM. In a further aspect, the foregoing methods further comprise, prior to the step of administering, the step of diagnosing a subject with such condition or disorder.

xii. Dosing

Selecting an administration regimen for a therapeutic depends on several factors, including the serum or tissue turnover rate of the entity, the level of signs or symptoms, the immunogenicity of the entity, and the accessibility of the target cells in the biological matrix. In certain aspects, an administration regimen maximizes the amount of therapeutic delivered to the patient consistent with an acceptable level of side effects.

The dosage and frequency of administration can vary depending on whether the treatment is prophylactic or therapeutic. Administration of an anti-BTC binding moiety and/or a multi-specific binding molecule comprising a BTC-binding moiety and an anti-VEGF binding moiety described herein leads to a clinically meaningful improvement of dose and dosing frequency, e.g., decreased dosing and/or decreased dosing frequency. Achieving a clinically meaningful improvement in dose and dosing frequency can vary depending on the initial starting dose of a composition.

A composition of a multi-specific binding molecule comprising a BTC-binding moiety and an anti-VEGF binding moiety described herein can be administered on multiple occasions. Intervals between single dosages can be weekly or monthly. Intervals can also be irregular as indicated by the need for retreatment in the patient, based for example on visual acuity or disease activity. In addition, alternative dosing intervals can be determined by a physician and administered monthly or as necessary to be efficacious.

In one aspect, efficacy of of a multi-specific binding molecule comprising a BTC-binding moiety and an anti-VEGF binding moiety described herein, e.g., NVS11, in treating an ocular disease, e.g., macular edema, DME, AMD, neovascular AMD, and/or RVO, is based on reduction of central retinal thickness (CRT, in µm), e.g., as measured in the central ETDRS subfield Spectral-Domain Optical coherence tomography (SD-OCT). In another aspect, efficacy of of a multi-specific binding molecule comprising a BTC-binding moiety and an anti-VEGF binding moiety described herein, e.g., NVS11, in treating an ocular disease, e.g., macular edema, DME, AMD, neovascular AMD, and/or RVO, is based on improvement in best-corrected visual acuity (BCVA), e.g., as measured in letters.

The dosage and frequency of administration can vary depending on, for example, whether the treatment is prophylactic or therapeutic and is affected by the half-life of the molecule dosed. Administration of the molecules described herein leads to a clinically meaningful improvement of dose and dosing frequency. For example, the molecules can be dosed at lower frequency compared to unconjugated molecules. Achieving a clinically meaningful improvement in dose and dosing frequency can vary depending on the initial starting dose of a composition.

An effective amount for a particular patient can vary depending on factors such as the condition being treated, the overall health of the patient, the method route and dose of administration and the severity of side effects (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

Described herein is a method of preventing or treating an ocular disease, e.g., macular edema, DME, AMD, neovascular AMD, or RVO, comprising administering intravitreally a multi-specific binding molecule comprising an anti-BTC binding moiety and an anti-VEGF binding moiety described herein, at a dose ranging from about 0.25 to 7.5 mg/eye or from about 7.5 to 15 mg/eye, e.g., at a dose of 0.25 mg/eye, 0.75 mg/eye, 2.5 mg/eye, or 7.5 mg/eye; or at a dose of 8 mg/eye, 8.5 mg/eye, 9 mg/eye, 9.5 mg/eye, 10 mg/eye, 10.5 mg/eye, 11 mg/eye, 11.5 mg/eye, 12 mg/eye, 12.5 mg/eye, 13 mg/eye, 13.5 mg/eye, 14 mg/eye, 14.5 mg/eye, or 15 mg/eye. An exemplary treatment regimen entails intravitreal administration once every week, once every two weeks, once a month, once every 2 months, once every 3 months, once every 4 months, once every 5 months, once every 6 months, or as needed (PRN). In one aspect, 7.5 mg/eye is the maximum feasible dose. In another aspect, 7.5 mg/eye is the maximum feasible safe dose.

In one aspect, a multi-specific binding molecule comprising an anti-BTC binding moiety and an anti-VEGF binding moiety described herein can be administered, e.g., intravitreally, at a dose of 0.25 mg/eye, 0.3 mg/eye, 0.35 mg/eye, 0.4 mg/eye, 0.45 mg/eye, 0.5 mg/eye, 0.55 mg/eye, 0.6 mg/eye, 0.65 mg/eye, 0.7 mg/eye, 0.75 mg/eye, 0.8 mg/eye, 0.85 mg/eye, 0.9 mg/eye, 0.95 mg/eye, 1.0 mg/eye, 1.1 mg/eye, 1.2 mg/eye, 1.3 mg/eye, 1.4 mg/eye, 1.5 mg/eye, 1.6 mg/eye, 1.7 mg/eye, 1.8 mg/eye, 1.9 mg/eye, 2.0 mg/eye, 2.1 mg/eye, 2.2 mg/eye, 2.3 mg/eye, 2.4 mg/eye, 2.5 mg/eye, 2.6 mg/eye, 2.7 mg/eye, 2.8 mg/eye, 2.9 mg/eye, 3.0 mg/eye, 3.1 mg/eye, 3.2 mg/eye, 3.3 mg/eye, 3.4 mg/eye, 3.5 mg/eye, 3.6 mg/eye, 3.7 mg/eye, 3.8 mg/eye, 3.9 mg/eye, 4.0 mg/eye, 4.1 mg/eye, 4.2 mg/eye, 4.3 mg/eye, 4.4 mg/eye, 4.5 mg/eye, 4.6 mg/eye, 4.7 mg/eye, 4.8 mg/eye, 4.9 mg/eye, 5.0 mg/eye, 5.1 mg/eye, 5.2 mg/eye, 5.3 mg/eye, 5.4 mg/eye, 5.5 mg/eye, 5.6 mg/eye, 5.7 mg/eye, 5.8 mg/eye, 5.9 mg/eye, 6.0 mg/eye, 6.1 mg/eye, 6.2 mg/eye, 6.3 mg/eye, 6.4 mg/eye, 6.5 mg/eye, 6.6 mg/eye, 6.7 mg/eye, 6.8 mg/eye, 6.9 mg/eye, 7.0 mg/eye, 7.1 mg/eye, 7.2 mg/eye, 7.3 mg/eye, 7.4 mg/eye, or 7.5 mg/eye.

In another aspect, a multi-specific binding molecule comprising an anti-BTC binding moiety and an anti-VEGF binding moiety described herein can be administered, e.g., intravitreally, at a dose between 0.25 and 0.75 mg/eye, 0.3 and 0.75 mg/eye, 0.35 and 0.75 mg/eye, 0.4 and 0.75 mg/eye, 0.45 and 0.75 mg/eye, 0.5 and 0.75 mg/eye, 0.55 and 0.75 mg/eye, 0.6 and 0.75 mg/eye, 0.65 and 0.75 mg/eye, 0.7 and 0.75 mg/eye, 0.25 and 0.7 mg/eye, 0.25 and 0.65 mg/eye, 0.25 and 0.6 mg/eye, 0.25 and 0.55 mg/eye, 0.25 and 0.5 mg/eye, 0.25 and 0.45 mg/eye, 0.25 and 0.4 mg/eye, 0.25 and 0.35 mg/eye, 0.25 and 0.3 mg/eye, 0.3 and 0.7 mg/eye, 0.35 and 0.65 mg/eye, 0.4 and 0.6 mg/eye, 0.45 and 0.55 mg/eye, 0.35 and 0.45 mg/eye, 0.45 and 0.55 mg/eye, or 0.55 and 0.65 mg/eye.

In another aspect, a multi-specific binding molecule comprising an anti-BTC binding moiety and an anti-VEGF binding moiety described herein can be administered, e.g., intravitreally, at a dose between 0.75 and 2.5 mg/eye, 0.8 and 2.5 mg/eye, 0.85 and 2.5 mg/eye, 0.9 and 2.5 mg/eye, 0.95 and 2.5 mg/eye, 1 and 2.5 mg/eye, 1.25 and 2.5 mg/eye, 1.5 and 2.5 mg/eye, 1.75 and 2.5 mg/eye, 2 and 2.5 mg/eye, 2.25 and 2.5 mg/eye, 0.75 and 2.25 mg/eye, 0.75 and 2 mg/eye, 0.75 and 1.75 mg/eye, 0.75 and 1.5 mg/eye, 0.75 and 1.25 mg/eye, 0.75 and 1 mg/eye, 0.8 and 2.25 mg/eye, 0.85 and 2 mg/eye, 0.9 and 1.75 mg/eye, 0.95 and 1.5 mg/eye, 1 and 1.25 mg/eye, 0.8 and 0.9 mg/eye, 0.9 and 1 mg/eye, 1 and 1.25 mg/eye, 1.25 and 1.5 mg/eye, 1.5 and 1.75 mg/eye, 1.75 and 2 mg/eye, 2 and 2.25 mg/eye, or 2.25 and 2.5 mg/eye.

In one aspect, a multi-specific binding molecule comprising an anti-BTC binding moiety and an anti-VEGF binding moiety described herein can be administered, e.g., intravitreally, at a dose between 2.5 and 7.5 mg/eye, 2.75 and 7.5 mg/eye, 3 and 7.5 mg/eye, 3.25 and 7.5 mg/eye, 3.5 and 7.5 mg/eye, 3.75 and 7.5 mg/eye, 4 and 7.5 mg/eye, 4.25 and 7.5 mg/eye, 4.5 and 7.5 mg/eye, 4.75 and 7.5 mg/eye, 5 and 7.5 mg/eye, 5.25 and 7.5 mg/eye, 5.5 and 7.5 mg/eye, 5.75 and 7.5 mg/eye, 6 and 7.5 mg/eye, 6.25 and 7.5 mg/eye, 6.5 and 7.5 mg/eye, 6.75 and 7.5 mg/eye, 7 and 7.5 mg/eye, 7.25 and 7.5 mg/eye, 2.5 and 7.25 mg/eye, 2.5 and 7 mg/eye, 2.5 and 6.75 mg/eye, 2.5 and 6.5 mg/eye, 2.5 and 6.25 mg/eye, 2.5 and 6 mg/eye, 2.5 and 5.75 mg/eye, 2.5 and 5.5 mg/eye, 2.5 and 5.25 mg/eye, 2.5 and 5 mg/eye, 2.5 and 4.75 mg/eye, 2.5 and 4.5 mg/eye, 2.5 and 4.25 mg/eye, 2.5 and 4 mg/eye, 2.5 and 3.75 mg/eye, 2.5 and 3.5 mg/eye, 2.5 and 3.25 mg/eye, 2.5 and 3 mg/eye, 2.5 and 2.75 mg/eye, 2.75 and 7.25 mg/eye, 3 and 7 mg/eye, 3.25 and 6.75 mg/eye, 3.5 and 6.5 mg/eye, 3.75 and 6.25 mg/eye, 4 and 6 mg/eye, 4.25 and 5.75 mg/eye, 4.5 and 5.5 mg/eye, 4.75 and 5.25 mg/eye, 2.75 and 3 mg/eye, 3 and 3.25 mg/eye, 3.25 and 3.5 mg/eye, 3.5 and 3.75 mg/eye, 3.75 and 4 mg/eye, 4 and 4.25 mg/eye, 4.25 and 4.5 mg/eye, 4.5 and 4.75 mg/eye, 4.75 and 5 mg/eye, 5 and 5.25 mg/eye, 5.25 and 5.5 mg/eye, 5.5 and 5.75 mg/eye, 5.75 and 6 mg/eye, 6 and 6.25 mg/eye, 6.25 and 6.5 mg/eye, 6.5 and 6.75 mg/eye, 6.75 and 7 mg/eye, 7 and 7.25 mg/eye, or 7.25 and 7.5 mg/eye.

In one aspect, a multi-specific binding molecule comprising an anti-BTC binding moiety and an anti-VEGF binding moiety described herein can be administered, e.g., intravitreally, at a dose between 7.5 and 15 mg/eye, 8 and 15 mg/eye, 8.5 and 15 mg/eye, 9 and 15 mg/eye, 9.5 and 15 mg/eye, 10 and 15 mg/eye, 10.5 and 15 mg/eye, 11 and 15 mg/eye, 11.5 and 15 mg/eye, 12 and 15 mg/eye, 12.5 and 15 mg/eye, 13 and 15 mg/eye, 13.5 and 15 mg/eye, 14 and 15 mg/eye, 14.5 and 15 mg/eye, 7.5 and 14.5 mg/eye, 7.5 and 14 mg/eye, 7.5 and 13.5 mg/eye, 7.5 and 13 mg/eye, 7.5 and 12.5 mg/eye, 7.5 and 12 mg/eye, 7.5 and 11.5 mg/eye, 7.5 and 11 mg/eye, 7.5 and 10.5 mg/eye, 7.5 and 10 mg/eye, 7.5 and 9.5 mg/eye, 7.5 and 9 mg/eye, 7.5 and 8.5 mg/eye, 7.5 and 8 mg/eye, 8 and 14.5 mg/eye, 8.5 and 14 mg/eye, 9 and 13.5 mg/eye, 9.5 and 13 mg/eye, 10 and 12.5 mg/eye, 10.5 and 12 mg/eye, 11 and 11.5 mg/eye, 8 and 8.5 mg/eye, 8.5 and 9 mg/eye, 9 and 9.5 mg/eye, 9.5 and 10 mg/eye, 10 and 10.5 mg/eye, 10.5 and 11 mg/eye, 11 and 11.5 mg/eye, 11.5 and 12 mg/eye, 12 and 12.5 mg/eye, 12.5 and 13 mg/eye, 13 and 13.5 mg/eye, 13.5 and 14 mg/eye, 14 and 14.5 mg/eye, or 14.5 and 15 mg/eye.

In a certain aspect, a multi-specific binding molecule comprising an anti-BTC binding moiety and an anti-VEGF binding moiety described herein (e.g., as described in Table 3, such as NVS 11 or an antibody comprising LCDRs and HCDRs of NVS 11) for use in methods provided herein (e.g., methods for preventing or treating macular edema, DME, AMD, e.g., neovascular AMD, and/or RVO) is administered, for example by intravitreal administration, at a dose of 0.25 mg/eye.

In another aspect, a multi-specific binding molecule comprising an anti-BTC binding moiety and an anti-VEGF binding moiety described herein (e.g., as described in Table 3, such as NVS 11 or an antibody comprising LCDRs and HCDRs of NVS 11) for use in methods provided herein (e.g., methods for preventing or treating macular edema, DME, AMD, e.g., neovascular AMD, and/or RVO) is administered, for example by intravitreal administration, at a dose of 0.75 mg/eye.

In another aspect, a multi-specific binding molecule comprising an anti-BTC binding moiety and an anti-VEGF binding moiety described herein (e.g., as described in Table 3, such as NVS 11 or an antibody comprising LCDRs and HCDRs of NVS 11) for use in methods provided herein (e.g., methods for preventing or treating macular edema, DME, AMD, e.g., neovascular AMD, and/or RVO) is administered, for example by intravitreal administration, at a dose of 1 mg/eye.

In another aspect, a multi-specific binding molecule comprising an anti-BTC binding moiety and an anti-VEGF binding moiety described herein (e.g., as described in Table 3, such as NVS 11 or an antibody comprising LCDRs and HCDRs of NVS 11) for use in methods provided herein (e.g., methods for preventing or treating macular edema, DME, AMD, e.g., neovascular AMD, and/or RVO) is administered, for example by intravitreal administration, at a dose of 1.5 mg/eye.

In another aspect, a multi-specific binding molecule comprising an anti-BTC binding moiety and an anti-VEGF binding moiety described herein (e.g., as described in Table 3, such as NVS 11 or an antibody comprising LCDRs and HCDRs of NVS 11) for use in methods provided herein (e.g., methods for preventing or treating macular edema, DME, AMD, e.g., neovascular AMD, and/or RVO) is administered, for example by intravitreal administration, at a dose of 2 mg/eye.

In another aspect, a multi-specific binding molecule comprising an anti-BTC binding moiety and an anti-VEGF binding moiety described herein (e.g., as described in Table 3, such as NVS 11 or an antibody comprising LCDRs and HCDRs of NVS 11) for use in methods provided herein (e.g., methods for preventing or treating macular edema, DME, AMD, e.g., neovascular AMD, and/or RVO) is administered, for example by intravitreal administration, at a dose of 2.5 mg/eye.

In another aspect, a multi-specific binding molecule comprising an anti-BTC binding moiety and an anti-VEGF binding moiety described herein (e.g., as described in Table 3, such as NVS 11 or an antibody comprising LCDRs and HCDRs of NVS 11) for use in methods provided herein (e.g., methods for preventing or treating macular edema, DME, AMD, e.g., neovascular AMD, and/or RVO) is administered, for example by intravitreal administration, at a dose of 3 mg/eye.

In another aspect, a multi-specific binding molecule comprising an anti-BTC binding moiety and an anti-VEGF binding moiety described herein (e.g., as described in Table 3, such as NVS 11 or an antibody comprising LCDRs and HCDRs of NVS 11) for use in methods provided herein (e.g., methods for preventing or treating macular edema, DME, AMD, e.g., neovascular AMD, and/or RVO) is administered, for example by intravitreal administration, at a dose of 5 mg/eye.

In another aspect, a multi-specific binding molecule comprising an anti-BTC binding moiety and an anti-VEGF binding moiety described herein (e.g., as described in Table 3, such as NVS 11 or an antibody comprising LCDRs and HCDRs of NVS 11) for use in methods provided herein (e.g., methods for preventing or treating macular edema, DME, AMD, e.g., neovascular AMD, and/or RVO) is administered, for example by intravitreal administration, at a dose of 7.5 mg/eye.

In another aspect, a multi-specific binding molecule comprising an anti-BTC binding moiety and an anti-VEGF binding moiety described herein (e.g., as described in Table 3, such as NVS 11 or an antibody comprising LCDRs and HCDRs of NVS 11) for use in methods provided herein (e.g., methods for preventing or treating macular edema, DME, AMD, e.g., neovascular AMD, and/or RVO) is administered, for example by intravitreal administration, at a dose of 10 mg/eye.

In another aspect, a multi-specific binding molecule comprising an anti-BTC binding moiety and an anti-VEGF binding moiety described herein (e.g., as described in Table 3, such as NVS 11 or an antibody comprising LCDRs and HCDRs of NVS 11) for use in methods provided herein (e.g., methods for preventing or treating macular edema, DME, AMD, e.g., neovascular AMD, and/or RVO) is administered, for example by intravitreal administration, at a dose of 15 mg/eye. Described herein is a method of preventing or treating an ocular disease, e.g., macular edema, DME, AMD, neovascular AMD, or RVO, comprising administering intravitreally an anti-BTC antibody described herein, e.g., NVS1, at a dosage ranging from about 0.125 to 3.75 mg/eye or from about 3.75 to 7.5 mg/eye, e.g, at a dose of 0.125 mg/eye, 0.375 mg/eye, 1.25 mg/eye, or 3.75 mg/eye; or at a dose of 4 mg/eye, 4.25 mg/eye, 4.5 mg/eye, 4.75 mg/eye, 5 mg/eye, 5.25 mg/eye, 5.5 mg/eye, 5.75 mg/eye, 6 mg/eye, 6.25 mg/eye, 6.5 mg/eye, 6.75 mg/eye, 7 mg/eye, 7.25 mg/eye, or 7.5 mg/eye. An exemplary treatment regimen entails intravitreal administration once every week, once every two weeks, once a month, once every 2 months, once every 3 months, once every 4 months, once every 5 months, once every 6 months, or as needed (PRN).

Various (enumerated) aspects of the present disclosure are described herein. It will be recognized that features specified in each aspect can be combined with other specified features to provide further aspects of the present disclosure. When an aspect is described as being "according to" a previous aspect, the previous aspect includes sub-aspects thereof. The contents of any patents, patent applications, and references cited throughout this specification are hereby incorporated by reference in their entireties. Unless otherwise required by context, singular terms used herein shall include pluralities and plural terms shall include the singular.

EXAMPLES

The present disclosure is further illustrated by the following examples, which should not be construed as further limiting.

Example 1. Screening of Affinity Matured BTC Antibodies

Anti-BTC Fabs were isolated in vitro using the MorphoSys' HUCAL® (Human Combinatorial Antibody Library) technology, where purified human and mouse Betacellulin antigens were used to identify specific anti-BTC binding antibodies.

A fully human phage display library was used to generate the Betacellulin binding antibodies described herein. Biotinylated and non-biotinylated human and cynomolgus Betacellulin were used in solution and solid phase pannings. Standard panning was performed as well as RAPMAT (rapid maturation antibody technology) approaches (Prassler et al., (2009) *Immunotherapy* 1(4):571-583). Following secondary screening and RAPMAT panning, clones were selected for sequence analysis and a set of four antibodies were selected for conversion to a FabCys format, germlining, pI optimization and removal of deamidation sites. FabCys generation was accomplished with a proprietary RAPCLONE® method (conversion of Fab fragments into IgG antibodies in a single step). RAPCLONE® was performed as a two-step method for convenient and efficient conversion of a large amount of Fab clones into the IgG and FabCys format. In a first cloning step, a eukaryotic expression cassette was introduced into the expression vectors PMORPH®xl1 (for HUCAL PLATINUM®—a DNA library of different Fab fragments) via BsiWI/MfeI (for K pools) or HpaI/MfeI (for X pools) digestion and subsequent ligation. This was followed by a second cloning step, in which the Fab pools containing the expression cassette were digested using EcoRV/BlpI (x and X pools) and subsequently cloned into the PMORPH@4_IgGlf or PMORPH@4_h_FabCys acceptor vector for expression in mammalian cells. For this project, RAPCLONE® was applied only on unique, sequenced and characterized Fab. Therefore all clones were recovered after RAPCLONE®.

The following sections provide further details of the screening of affinity matured BTC antibodies.

a) Solid Phase Panning Against Betacellulin

The HUCAL® phagemid library (Knappik et al., J Mol Biol 296, 57-86, 2000) was used along with the CYSDISPLAY™ technology for displaying the Fab on the phage surface (Lohning, 2001 WO 01/05950).

96-well MAXISORP™ plates were coated with 300 µl of antigen (soluble processed) Betacellulin species o/n (overnight) at 4° C. The coated wells were blocked with PBS (phosphate buffered saline)/5% milk powder. For each panning, about $4\times10^{13}$ HUCAL PLATINUM® phage-antibodies were blocked with an equal volume of PBS/0.05% TWEEN20 (surfactant)/5% milk powder/5% BSA (bovine serum albumin). During phage blocking, additional blocking reagents were coated on MAXISORP™ plate and blocked phage preparations were additionally pre-cleared on the coated reagents to avoid selection of antibodies against the tag of the antigen. After the blocking procedure, 300 µl of pre-blocked phage mix was added to each antigen coated and blocked well and incubated for 2 h (hours) at RT (room temperature) on a microtiter plate shaker. Afterwards, unspecific bound phage was washed off by several washing steps using first PBS/0.05% TWEEN20 and then PBS. For elution of specifically bound phage, 300 µl 25 mM DTT (dithiothreitol) in 10 mM TRIS (tris(hydroxymethyl)aminomethane)/HCl (hydrochloric acid) pH 8 per well were added for 10 min at RT. The DTT eluate was transferred into 14 ml of E. coli TG1, which were grown to an OD (optical density) 600 of 0.6-0.8. The mix of E. coli (Escherichia co/i) TG1 and DTT eluate was incubated for 45 min (minutes) in a water bath at 37° C. (Celsius) for phage infection. The bacterial pellets were resuspended in 2xYT (Yeast Extract Tryptone) medium, plated on LB/Cam (chloramphenicol) agar plates and incubated o/n at 30° C. Colonies were scraped off the plates and were used for phage rescue, polyclonal amplification of selected clones, and phage production. With purified phage the next panning round was started.

The second and third round of solid phase panning was performed according to the protocol of the first round except for more stringent washing conditions.

b) Solution Panning Against Betacellulin

Prerequisite for a solution panning was biotinylation of the antigen and confirmation of retained activity of biotinylated antigen. During solution panning, the Fab displaying phage and the biotinylated antigen were incubated in solution which facilitated the accessibility of the antigen by the phage.

c) Solution Panning Protocol with Streptavidin-Coupled Magnetic Beads

Per phage pool, 4 mg Streptavidin beads (DYNABEADS® M-280 Streptavidin; Invitrogen) were blocked in 1×CHEMIBLOCKER (membrane-blocking agent). In parallel, for each panning, about $4\times10^{13}$ HUCAL PLATINUM® phage-antibodies were blocked with an equal volume of 2x CHEMIBLOCKER/0.1% TWEEN20. For removal of bead-binding phage, pre-adsorption of blocked phage particles was performed twice using 1 mg blocked Streptavidin beads each. In order to avoid selection of antibodies against biotin, 1 mg Streptavidin beads per subcode and selection round were coated with an irrelevant biotinylated antigen which was used for phage pre-adsorption. During phage blocking, additional non biotinylated blocking reagents were added to the blocking buffer to avoid selection of antibodies against the tag (e.g. irrelevant FLAG_6×His antigen). Subsequently, biotinylated Betacellulin species (e.g. 100 nM) was added to the pre-adsorbed and blocked phage particles and incubated for 1-2 hours at RT on a rotator. The phage-antigen complexes were captured using 2 mg blocked Streptavidin beads and phage particles bound to the Streptavidin beads were collected with a magnetic separator. Unspecific bound phage was washed off by several washing steps using PBS/0.05% TWEEN20 and PBS. For elution of specifically bound phage from Streptavidin beads, 200 µl 25 mM DTT in 10 mM TRIS/HCl pH 8 per well were added for 10 min at RT. The DTT eluate was then transferred into 14 ml of E. coli TG1, which were grown to an OD600 of 0.6-0.8. The mix of TG1 and DTT eluate was incubated for 45 min in a water bath at 37° C. for phage infection. The bacterial pellets were resuspended in 2xYT medium, plated on LB/Cam agar plates and incubated o/n at 30° C. Colonies were scraped off the plates and were used for phage rescue, polyclonal amplification of selected clones, and phage production. With purified phage the next panning round was started. The second and third round of the solution panning was performed according to the protocol of the first round except for decreased amounts of antigen and more stringent washing conditions. In one strategy, off-rate selections (Hawkins et al., J Mol Biol 226, 889-896, 1992) were performed in the $3^{rd}$ panning round.

d) Screening of Fab Containing Bacterial Lysates for ELISA (Binding, Potency) and FACS Screening 5 µl of each o/n culture were transferred to a sterile 384-well microtiter plate pre-filled with 40 µl 2×YT medium (34 pg/ml chloramphenicol (Cam); 0.1% Glucose) per well. Plates were incubated at 37° C. until the cultures were slightly turbid. To these expression plates, 10 µl 2×YT medium (34 pg/ml Cam and 2.5-5 mM IPTG)) was added per well. Plates were sealed with a gas-permeable tape, and incubated o/n at 22° C. To each well of the expression plates, 15 µl BEL buffer (2.5 mg/ml lysozyme, 4 mM EDTA, 10 U/µl Benzonase) was added and plates were incubated for 1 h. Fab containing E. co/i lysates were used for screening purposes. The method was slightly modified for FACS screening e) Subcloning of HuCAL PLATINUM® Fab Fragments To facilitate rapid expression of soluble Fab, the Fab encoding inserts of the selected HUCAL PLATINUM®phage were subcloned from PMORPH®30 display vector into PMORPH®x11 expression vector PMORPH®x11_FH. Subcloning was performed by triple digest via EcoRI/XbaI/BmtI. After transformation of E. coli TG1-F-single clone expression and preparation of periplasmatic extracts containing HUCAL®-Fab fragments were performed as described previously (Rauchenberger et al., J Biol Chem 278, 38194-38205, 2003).

f) Generation of Masterplates

Chloramphenicol resistant single clones were picked into the wells of a sterile 384-well microtiter plate pre-filled with 60 µl 2×YT-CG (34 pg/ml chloramphenicol (Cam); 0.1% Glucose) medium and grown o/n at 37° C. Next morning, 100 µl sterile 2×YT media containing 30% glycerol was added into each well of the masterplates; plates were sealed with aluminum foil and stored at −80° C.

The following two sections describe the preparation of lysates from Fab-expressing E. co/i in 384- and 96-well format, respectively. These expression plates were later used for ELISA and/or FACS screening approaches.

g) Expression and Purification of His-tagged Fab Fragments in E. coli (mg scale)

Expression of Fab fragments encoded by PMORPH®11_Fab_FH and PYBEX10®_Fab_FH in E. co/i TG1 F cells was carried out in shake flask cultures using 500 ml of 2×YT medium supplemented with 0.1% glucose and 34 pg/ml chloramphenicol. Cultures were shaken at 30° C. (PMORPH®×11_Fab_FH) or 22° C. (PYBEX10®_Fab_FH) until the OD60o reached a value of 0.5. Fab expression was induced by adding IPTG (isopropyl-β-D-thiogalactopyranoside) at a final concentration of 0.75 mM (PMORPH®×11_Fab_FH) or 0.5 mM (PYBEX10®_Fab_FH) and further cultivation for 20 h at 30° C. (PMORPH®×111_Fab_FH) or 22° C. (PYBEX10®_Fab_FH). Cells were harvested and disrupted using lysozyme. His$_6$-tagged Fab fragments were isolated via IMAC (Bio-Rad, Germany) and eluted using imidazole. Buffer exchange to 1× Dulbecco's PBS (pH 7.2) was performed using PD10 columns (GE Healthcare, Germany). Samples were sterile filtered (0.2 µm). Protein concentrations were determined by UV-spectrophotometry. The purity of the samples was analyzed in denaturing, non-reducing 15% SDS-PAGE. The homogeneity of Fab preparations was determined in native state by size exclusion chromatography (HP-SEC) with calibration standards.

h) Conversion to Mammalian IgG and FabCys Format

RAPCLONE® was performed as a two-step method for a convenient and efficient conversion of a large amount of Fab clones into the FabCys format. In a first cloning step, a eukaryotic expression cassette was introduced into the expression vector PMORPH®×111 via BsiWI/MfeI(for κpools) or HpaI/MfeI (for λ pools) digestion and subsequent ligation. This was followed by a second cloning step, in which the Fab pools containing the expression cassette were digested using EcoRV/BlpI (x and λ pools) and subsequently cloned into the PMORPH®4_FabCys acceptor vector for expression in mammalian cells.

i) Expression and Purification of Human FabCys using pMORPH®4 Vector System

Eukaryotic HKB11 cells were transfected with PMORPH®4 or PYMEX expression vector DNA encoding both heavy and light chains of FabCys. Cell culture supernatant was harvested on day 3 post-transfection and subjected to Capture Select IgG-CH1 (Life Technologies) for purification of FabCys. If not stated otherwise, buffer exchange was performed to 1× Dulbecco's PBS (pH 7.2, Invitrogen) and samples were sterile filtered (0.2 µm pore size). Purity of FabCys was analyzed under denaturing, reducing and non-reducing conditions using CE-SDS (LABCHIP GXII, Perkin Elmer, USA; protein characterization system). Protein concentrations were determined by UV-spectrophotometry and HP-SEC was performed to analyze protein preparations in native state.

Parental anti-BTC Fabs were generated. Following affinity maturation (Knappik et al., (2000) J. Mol. Biol., 296: 57-86) a set of four antibodies were subsequently chosen for conversion to a disulfide-bridged Fab format. The resulting disulfide bridged Fabs are designated as NVS1, NVS2, NVS3, and NVS4.

The binding affinity of NVS1-NVS4 to the BTC protein from a variety of species was measured in a Biacore assay. The result is as provided in Table 6 below.

TABLE 6

Binding affinity of NVS1-NVS4 to BTC

Biacore/ProteOno (Affinity in pM)

| | Human BTC | Mouse BTC | Cyno BTC | Rat BTC | Rabbit BTC |
|---|---|---|---|---|---|
| NVS1 | 6 | 4 | 8 | 7 | 4 |
| NVS2 | 14 | 9 | 16 | 21 | 5 |
| NVS3 | 1.4 | <1 | 5.4 | 20 | 17 |
| NVS4 | 5 | 5 | 12 | 8 | 1 |

Table 5 lists the sequences of parental and affinity matured variants for each of NVS1, NVS2, NVS3, and NVS4.

j) Epitope Binning via Competition ELISA

For epitope binning, Fab A was coated at a constant amount on MAXISORP plates and tested for competition with increasing amounts of Fab B in solution. As positive control, the coated Fab was analyzed for competition with itself in solution. All tested Fabs were incubated in 10 fold molar excess with biotinylated human BTC for 1 h at RT in solution. Antigen/antibody complexes were then added to the coated antibodies and detection of bound complexes occurred via the biotinylated antigen. In general, signals at high Fab concentration could only be obtained when the coated Fab was able to bind to accessible epitopes on the antigen different to the tested Fab in solution (i.e. a non-competitive antibody). In contrast, for competitive antibodies, antibodies with partially overlapping epitopes or antibodies that block the epitope by steric hindrance, binding signals at high Fab concentration were significantly decreased in contrast to controls. Respective wells of MAXISORP plates were coated with 20 µl/well of Fab A at a concentration of 1 pg/ml in PBS, incubated overnight at 4° C. and then washed 3x with PBST. Plates were blocked with 90 µl 5% MPBST well for 2 h at RT and washed 3x with PBST. For antigen/antibody pre-incubation, anti-BTC antibodies (Fab B) were titrated in 1:3 steps (starting at a final conc. of 25 pg/ml and incubated with a final conc. of 0.6 pg/ml biotinylated BTC for 1 h at RT. 20 µl/well pre-incubated BTC/antibody complex was added to the blocked and washed MAXISORP plates and incubated for 20 min at RT shaking gently. Plates were washed 3x with PBST and incubated for 1 h with 20 µl/well Streptavidin-AP (AbD Serotec, Cat# Star6b) diluted 1:5000 in 1% BSA/0,05% TWEEN20/PBS. Plates were washed 5x with PBST, 20 µl ATTOPHOS (fluorescent substrate system) solution (1:10 diluted in ddH$_2$O) were added and plates were measured at the Tecan Reader.

k) ELISA based Epitope Binning

One affinity matured variant per family was tested against other representatives in a competition ELISA. Affinity maturation was mainly performed by varying sequences in HCDR3. Each tested candidate (TC) was derived from different parental families, with the exception that TC12 is from the same family as NVS3, TC15 and TC16 are from the same family as NVS2, and TC23 is from the same family as NVS4. TC1-TC8 and TC10-TC30 represent the affinity matured candidates identified from either HUCAL or YLANTHIA (antibody library) as described throughout.

As shown in Table 7 below, one major bin E and one small bin B (only target by TC11) were clearly identified.

TABLE 7

Binning of affinity matured anti-BTC Fabs

| | | | Bin E<br>Pre-incubated with ligand in solution | | | | | | | | | Bin B |
|---|---|---|---|---|---|---|---|---|---|---|---|---|
| | Tested | | | | | | | | | | | |
| | Candidate | TC1 | TC2 | TC3 | TC4 | TC5 | TC6 | TC7 | TC8 | NVS1 | TC10 | TC11 |
| Bin E Coated | TC1 | N/A | 1 | 1 | 1 | 1 | 1 | | | | | 2 |
| on | TC2 | 1 | N/A | 1 | 1 | 1 | 1 | | | | | 2 |
| plate | TC3 | 1 | 1 | N/A | 1 | 1 | 1 | | | | | 3 |
| | TC4 | 1 | 1 | 1 | N/A | 1 | 1 | | | | | 2 |
| | TC5 | 1 | 1 | 1 | 1 | N/A | 1 | | | | | 2 |
| | TC6 | 1 | 1 | 1 | 1 | 1 | N/A | 1 | 1 | 1 | 1 | 2 |
| | TC7 | | | | | | 1 | N/A | 1 | 1 | 1 | 2 |
| | TC8 | | | | | | 1 | 1 | N/A | 1 | 1 | 2 |
| | NVS1 | | | | | | 1 | 1 | 1 | N/A | 1 | 2 |
| | TC10 | | | | | | 1 | 1 | 1 | 2 | N/A | 2 |
| | TC12 | | | | | | 1 | | | | | 2 |
| | TC13 | | | | | | 1 | | | | | 2 |
| | TC14 | | | | | | 1 | | | | | 2 |
| Bin B | TC11 | 2 | 2 | 2 | 2 | 2 | 2 | 2 | 2 | 2 | 2 | N/A |

1: >70% signal reduction, i.e., same bin
2: <30% signal reduction, i.e., distinct bin
3: 30-70% signal reduction, i.e., intermediate
Blank: data unavailable As shown in Table 8 below, two major bins (bin A and bin E) and three smaller bins (bin B, C, D) were identified.

TABLE 8

Binning of affinity matured anti-BTC Fabs

| | | | Bin A<br>Pre-incubated with ligand in solution | | | | | | | Bin B | Bin C |
|---|---|---|---|---|---|---|---|---|---|---|---|
| | Tested | | | | | | | | | | |
| | Candidate | TC15/16 | TC17 | TC18 | TC19 | TC20 | TC21 | TC22 | TC11 | TC23 |
| Bin A Coated | TC15/16 | N/A | 1 | 1 | 1 | 1 | 1 | 1 | 1 | 1 |
| on | TC17 | 1 | N/A | 1 | 1 | 1 | 1 | 1 | 1 | |
| plate | TC18 | 1 | 1 | N/A | 1 | 1 | 1 | 1 | 1 | 1 |
| | TC19 | 1 | 1 | 1 | N/A | 1 | 1 | 1 | 1 | |
| | TC20 | 1 | 1 | 1 | 1 | N/A | 1 | 1 | | |
| | TC21 | 1 | 1 | 1 | 1 | 1 | N/A | 1 | 1 | |
| | TC22 | 1 | 1 | 1 | 1 | 1 | 1 | N/A | 1 | |
| Bin B | TC11 | 1 | 1 | 1 | 1 | 1 | 1 | 1 | N/A | 1 |
| Bin C | TC23 | 1 | 1 | 1 | 1 | 1 | 1 | 1 | 1 | N/A |
| Bin D | TC24 | 1 | 1 | 1 | 1 | 1 | 3 | 1 | 2 | 1 |
| | TC25 | 1 | 1 | 1 | 1 | 1 | 1 | 1 | 2 | 1 |
| Bin E | TC26 | 3 | 3 | 1 | 1 | 2 | 3 | 2 | 1 | 1 |
| | TC27 | 2 | 2 | 2 | 2 | 2 | 2 | 3 | | |
| | TC28 | 2 | 2 | 2 | 2 | 3 | 3 | 3 | 2 | 1 |
| | TC29 | 2 | 3 | 2 | 2 | 2 | 2 | 3 | | |
| | TC30 | 2 | 2 | 2 | 2 | 3 | 2 | 3 | | |
| | TC6 | | 2 | | 3 | | | | 2 | 1 |

| | | | Bin D | | Bin E<br>Pre-incubated with ligand in solution | | | | | |
|---|---|---|---|---|---|---|---|---|---|---|
| | | Tested | | | | | | | | |
| | | Candidate | TC24 | TC25 | TC26 | TC27 | TC28 | TC29 | TC30 | TC6 |
| Bin A | Coated | TC15/16 | 1 | 3 | 1 | 3 | 2 | 2 | 2 | 2 |
| | on | TC17 | 1 | 1 | 3 | 3 | 2 | 2 | 3 | |
| | plate | TC18 | 1 | 1 | 3 | 2 | 2 | 2 | 2 | 2 |
| | | TC19 | 1 | 1 | 3 | 3 | 2 | 2 | 2 | |
| | | TC20 | 1 | 1 | 3 | 2 | 2 | 3 | 3 | |
| | | TC21 | 1 | 1 | 3 | 3 | 2 | 2 | 2 | |
| | | TC22 | 1 | 3 | 3 | 3 | 2 | 2 | 2 | |
| Bin B | | TC11 | 2 | 2 | 1 | | 2 | | | 2 |
| Bin C | | TC23 | 1 | 1 | 3 | | 2 | | | 3 |
| Bin D | | TC24 | N/A | 1 | 1 | 1 | 1 | 1 | 1 | 1 |
| | | TC25 | 1 | N/A | 1 | 1 | 2 | 1 | 1 | 3 |
| Bin E | | TC26 | 1 | 1 | N/A | 1 | 1 | 1 | 1 | 1 |
| | | TC27 | 1 | 1 | 1 | N/A | 1 | 1 | 1 | |
| | | TC28 | 1 | 1 | 1 | 1 | N/A | 1 | 1 | 1 |

TABLE 8-continued

| Binning of affinity matured anti-BTC Fabs | | | | | | | | |
|---|---|---|---|---|---|---|---|---|
| TC29 | 1 | 1 | 1 | 1 | 1 | N/A | 1 | |
| TC30 | 1 | 1 | 1 | 1 | 1 | 1 | N/A | |
| TC6 | 1 | 1 | 1 | | 1 | | | N/A |

1: >70% signal reduction, i.e., same bin
2: <30% signal reduction, i.e., distinct bin
3: 30-70% signal reduction, i.e., intermediate
Blank: data unvailable l) Characterization of NVS1-NVS4

The four affinity matured candidates, NVS1-NVS4, were subject to characterization (e.g., potency and affinity) in assays as provided in the examples below. The results are as provided in Table 9 below.

TABLE 9

Characterization of NVS1-NVS4

| | MSD-based binding inhibition | | Cell-based binding inhibition | | Binding to membraine-Anchored BTC (median. X above 293F) | ADR/Res pErbB3 (IC50 in nM) | A431 pERK (IC50 in nM) | MCF10A pERK | Epitope mapping/ binning (ELISA) | Neutral-ization of juxtacrine signaling |
|---|---|---|---|---|---|---|---|---|---|---|
| | BTC/ErbB1 | BTC/ErbB4 | BTC/ErbB1 | BTC/ErbB4 | | | | | | |
| NVS1 | >90% | >90% | >90% | >90% | >10X | 5.7 | 0.25 | 99.7 | E | 89% |
| NVS2 | >90% | >90% | >90% | >90% | >10X | 6.3 | 0.37 | 99.7 | A | 90% |
| NVS3 | >90% | >90% | >90% | >90% | >10X | 7.89 | >90% | >90% | E | 99% |
| NVS4 | >90% | >90% | >90% | >90% | >10X | 6.1 | 0.49 | 99.4 | C | 87% |

Example 2. Crystallographic Epitope of Anti-BTC Antibodies a) X-Ray Crystallographic Structure Determination of the Human Betacellulin/Fab Complexes The crystal structures of a human BTC (SEQ ID NO: 157) bound to four Fab fragments of antibodies NVS1, NVS2, NVS3, and NVS4 were determined. As detailed below, Fab fragments were expressed and purified. The insoluble, *E. coli* expressed, mature form of BTC was refolded and purified. The purified BTC and Fab proteins were mixed and the resulting complexes were purified and crystallized. To define the epitope, atomic-resolution structure of BTC bound to Fab fragments were determined by using X-ray crystallography.

b) Protein Production

The sequences of BTC and Fabs (NVS1, NVS2, NVS3, and NVS4) produced for crystallography are shown in Table 1. The expression construct of BTC comprises residues 32 to 111 (underlined) of human protein Probetacellulin (UniProt identifier P35070, SEQ ID NO: 156), along with N- and C-terminal residues from recombinant expression vector (shown in lower case letters, SEQ ID NO: 157). An N-terminal start codon resulted in the addition of the amino acid MET prior to the beginning residue of the mature BTC sequence. The C-terminus of the mature BTC sequence was fused with a hexa-histidine purification tag. For the Fabs (NVS 1, NVS2, NVS3, and NVS), the sequences of heavy and light chains are shown in Table 10 below.

TABLE 10

Proteins used for crystal structure determination

| Construct | Amino acid sequence in one letter code | SEQ ID NO. |
|---|---|---|
| Human Pro-BTC (P35070) | MDRAARCSGASSLPLLLALALGLVILHCVVA<u>DGNSTRSPET NGLLCGDPEENCAATTTQSKRKGHFSRCPKQYKHYCIKGRC RFVVAEQTPSCVCDEGYIGARCERVDLFYLRGDRGQILVIC</u>LIAVMVVFIILVIGVCTCCHPLRKRRKRKKKEEEMETLGKD ITPINEDIEETNIA | 156 |
| Human BTC expressed | mDGNSTRSPETNGLLCGDPEENCAATTTQSKRKGHFSRCPK QYKHYCIKGRCRFVVAEQTPSCVCDEGYIGARCERVDLFYh hhhhh | 157 |
| Human BTC | DGNSTRSPETNGLLCGDPEENCAATTTQSKRKGHFSRCPKQ YKHYCIKGRCRFVVAEQTPSCVCDEGYIGARCERVDLFY | 164 |
| NVS2 Fab heavy chain | EVQLLESGGGLVQPGGSLRLSCAASGFTFSSYAMSWVRQAP GKGLEWVSAISGSGGSTYYADSVKGRFTISRDNSKNTLYLQ | 36 |

TABLE 10-continued

Proteins used for crystal structure determination

| Construct | Amino acid sequence in one letter code | SEQ ID NO. |
|---|---|---|
| | MNSLRAEDTAVYYCARQRYYFGEFDLWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKRVEPKSC | |
| NVS2 Fab light chain | SYELTQPPSVSVSPGQTASITCSGDKLGDKYAYWYQQKPGQ SPVLVIYQDSKRPSGIPERFSGSNSGNTATLTISGTQAEDE ADYYCQAFDYLYSLGVFGGGTKLTVLGQPKAAPSVTLFPPS SEELQANKATLVCLISDFYPGAVTVAWKADSSPVKAGVETT TPSKQSNNKYAASSYLSLTPEQWKSHRSYSCQVTHEGSTVE KTVAPTECS | 47 |
| NVS3 Fab heavy chain | QVQLLESGGGLVQPGGSLRLSCAASGFTFSSYAMSWVRQAP GKGLEWVSGLGHVGYTTYTDSVKGRFTISRDNSKNTLYLQM NSLRAEDTAVYYCARDYLDFGYYFDVWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKRVEPKSC | 56 |
| NVS3 Fab light chain | SYELTQPLSVSVALGQTARITCSGDKIGKKYVHWYQQKPGQ APVLVIYDDSDRPSGIPERFSGSNSGNTATLTISRAQAGDE ADYYCQAWDMQSVVFGGGTKLTVLGQPKAAPSVTLFPPSSE ELQANKATLVCLISDFYPGAVTVAWKADSSPVKAGVETTTP SKQSNNKYAASSYLSLTPEQWKSHRSYSCQVTHEGSTVEKT VAPTECS | 67 |
| NVS1 Fab heavy chain | QVQLVQSGAEVKKPGSSVKVSCKASGGTFSSYAISWVRQAP GQGLEWMGGIVPWMGEAVYAQKFQGRVTITADESTSTAYME LSSLRSEDTAVYYCARSSSTYGIHAFDYWGQGTLVTVSSAS TKGPSVFPLAPSSKSTSGGTAALGCLVKDYFPEPVTVSWNS GALTSGVHTFPAVLQSSGLYSLSSVVTVPSSSLGTQTYICN VNHKPSNTKVDKRVEPKSC | 12 |
| NVS1 Fab light chain | DIQMTQSPSSLSASVGDRVTITCRASQSISNFLNWYQQKPG KAPKLLIYAASNLQSGVPSRFSGSGSGTDFTLTISSLQPED FATYYCQQYDDFPMTFGQGTKVEIKRTVAAPSVFIFPPSDE QLKSGTASVVCLLNNFYPREAKVQWKVDNALQSGNSQESVT EQDSKDSTYSLSSTLTLSKADYEKHKVYACEVTHQGLSSPV TKSFNRGEC | 23 |
| NVS4 Fab heavy chain | QVQLLESGGGLVQPGGSLRLSCAASGFTFSRYWISWVRQAP GKGLEWVSYIDSTGTFINYADSVKGRFTISRDNSKNTLYLQ MNSLRAEDTAVYYCARGGSLFDYWGQGTLVTVSSASTKGPS VFPLAPSSKSTSGGTAALGCLVKDYFPEPVTVSWNSGALTS GVHTFPAVLQSSGLYSLSSVVTVPSSSLGTQTYICNVNHKP SNTKVDKRVEPKSC | 80 |
| NVS4 Fab light chain | DIQMTQSPSSLSASVGDRVTITCRASQGIISYLGWYQQKPG KAPKLLIYAASSLQSGVPSRFSGSGSGTDFTLTISSLQPED FATYYCQQYDALNTFGQGTKVEIKRTVAAPSVFIFPPSDEQ LKSGTASVVCLLNNFYPREAKVQWKVDNALQSGNSQESVTE QDSKDSTYSLSSTLTLSKADYEKHKVYACEVTHQGLSSPVT KSFNRGEC | 90 |

BTC was expressed in E. coli strain BL21(DE3)STAR (Invitrogen). Following four hours of induction with 1 mM TPTG at 37° C., cells were harvested and lysed. The insoluble pellet was washed 2 × in 50 mM 2 M Urea, 100 mM TRIS pH 8.0, 5 mM DTT, 200 TRITON X-100 (surfactant), followed by Ix wash with 100 mM TRIS pH 8.0. The washed inclusion bodies were solubilized in 8 M urea, 50 mM NaPhosphate pH 8.0, 0.3 M NaCl, followed by centrifugation at 15,000×g for 10 minutes. To the supernatant Ni-NTA agarose (Qiagen) equilibrated in the same buffer was added and mixture was rotated at 4 C for 1 hour. The resin was collected in a gravity flow column, washed with equilibration buffer, followed by a wash with the same buffer containing 25 mM imidazole. Protein was eluted with same buffer containing 300 mM imidazole. To the eluate, 0.1 M reduced glutathione was added then incubated for 2 hours at room temperature, after which 0.5 mM oxidized glutathione was added. The protein solution was then dialyzed using 3500 Da mwco against 5M Urea, 100 mM TRIS pH 7.5, 0.5 mM oxidized glutathione for approximately 4 hours at room temperature, uncovered. Dialysis tubing was next transferred to 8L of 2.5 M Urea, 100 mM TRIS pH 7.5, 0.5 mM oxidized glutathione and dialyzed overnight. Dialysis tubing was then transferred to 8 L of 1 M Urea, 100 mM TRIS pH 7.5, 0.5 mM oxidized glutathione and dialyzed for approximately 4 hours. The final transfer was into 50 mM TRIS pH 7.5, 100 mM NaCl, 0.5 mM oxidized glutathione, which was left to dialyzed overnight. Dialysate was filtered through 0.22 μm filter to remove visible precipitate. Refolded betacellulin protein was concentrated and applied to a SUPERDEX75 column (GE Healthcare Life Sciences) equilibrated in 25 mM HEPES pH 7.5, 150 mM NaCl. Fractions containing monomeric BTChis were pooled.

BTC/Fab complexes were prepared by mixing purified BTC was mixed with purified Fab at a 2:1 molar ratio. The complex was incubated at room temperature for 1 hour, then concentrated and applied to a SUPERDEX200 column (GE Healthcare Life Sciences) equilibrated in 25 mM HEPES pH 7.5, 150 mM NaCl. Peak fractions were analyzed by SDS-PAGE and LCMS. Fractions containing BTC/Fab complex were pooled.

c) Crystallization and Structure Determination

BTC/NVS1 crystals for data collection were grown by sitting drop vapor diffusion at 20° C. The BTC/NVS1 complex was concentrated to 7 mg/ml. Crystals were grown by mixing 0.5 μl complex with 0.5 μl reservoir solution containing 27% PEG 4000, 0.17 M ammonium sulfate, 5% glycerol, and equilibrating the drop against 1000 μl of the same reservoir solution. Before data collection, several μl of 29% PEG 4000, 12% ethylene glycol, 10% glycerol, 0.17 M ammonium sulfate were added to the crystal containing drop, then the crystals were flash cooled in liquid nitrogen.

BTC/NVS2 crystals for data collection were grown by sitting drop vapor diffusion at 4° C. The BTC/NVS2 complex was concentrated to approximately 25 mg/ml. Crystals were grown by mixing 150 nl of complex with 150 nl of reservoir solution containing 5% PEG 1000, 40% ethanol, 0.1 M phosphate/citrate pH 4.2, and equilibrating the drop against 40 μl of the same reservoir solution. For data collection, crystals were flash cooled in liquid nitrogen.

BTC/NVS3 crystals for data collection were grown by sitting drop vapor diffusion at 4° C. The BTC/NVS3 complex was concentrated to 12 mg/ml. Crystals were gown by mixing 150 nl of complex with 150 nl of reservoir solution containing 30% PEG 400, 0.1 M sodium acetate trihydrate pH 4.5, 0.2 M calcium acetate hydrate, and equilibrating the drop against 40 μl of the same reservoir solution. For data collection, crystals were flash frozen in liquid nitrogen.

BTC/NVS4 crystals for data collection were grown by sitting drop vapor diffusion at 20° C. The BTC/NVS4 complex was concentrated to 13 mg/ml. Crystals were grown by mixing 150 nl of complex with 150 nl of reservoir solution containing 0.2 M magnesium chloride hexahydrate, 0.1 M TRIS hydrochloride pH 8.5, 20% PEG 8000 and equilibrating the drop against 40 μl of the same reservoir solution. Before data collection, several μl of 22% PEG 8000, 12% ethylene glycol, 10% glycerol, 0.1 M TRIS pH 8.5, 0.2 M magnesium chloride were added to the drop, then the crystals were flash cooled in liquid nitrogen.

Diffraction data were collected at beamline 17-ID at the Advanced Photon Source (Argonne National Laboratory, USA). Data were processed and scaled using Autoproc (version 1.1.7. Global Phasing, LTD). The resolution limit, space group, and unit cell dimensions are summarized in Table 2. The structure of the complexes were solved by molecular replacement using PHENIX (v. 1.12_2829, Adams et. al., (2010) Acta. Cryst. D66:213-221) using in-house Fab structures as search models. The BTC structure was built directly into the partially refined Fab model using COOT (v. 0.8.8) (Emsley & Cowtan (2004) Acta Cryst. D60:2126-2132). The final model was iteratively built and refined using COOT and PHENIX. The number of copies of the BTC/Fab model in the asymmetric unit of the unit cell, Rwork and Rfree values, root-mean-square (r.m.s) deviation values of bond lengths and bond angles are summarized in Table 11.

The structural epitope was defined as residues of BTC that contain atoms within 5 Å of any atom in the Fab. These residues were identified by the ACT program in the CCP4 program suite (v. 7.0.045 Winn et al., (2011) Acta. Cryst. D67:235-242). When multiple copies of the complex exist in the asymmetric unit, only those antibody-contacting residues that are common in all copies are considered to be structural epitope residues. The epitope residues and the corresponding contact Fab residues identified in the structures of the Fab complexes NVS1, NVS2, NVS3, and NVS4 are listed in Tables 12, 13, 14, and 15; respectively (chains H for heavy chain, and L light chains).

TABLE 11

Diffraction data and structure refinement summary

| Parameters | BTC/NVS2 | BTC/NVS3 | BTC/NVS1 | BTC/NVS4 |
|---|---|---|---|---|
| Resolution | 2.7 Å | 1.7 Å | 2.8 Å | 3.0 Å |
| Space group | P2$_1$ | P4$_2$2$_1$2 | P3$_2$ | P2$_1$2$_1$2$_1$ |
| Unit Cell (a b c alpha beta 90.00 gamma) | 44.8 Å 201.3 Å 67.1 Å 90.0° 92.4 ° 90.0° 90.0° | 123.8 Å 123.8 Å 125.1 Å 90.0° 90.0° 90.0° | 176.5 Å 176.5 Å 186.6 Å 90.0° 90.0° 120.0° | 70.5 Å 158.7 Å 200.4 Å 90.0° |
| # complexes/a.s.u. | 2 | 1 | 12 | 4 |
| R$_{work}$ R$_{free}$ | 23.4%, 30.5% | 15.6%, 17.2% | 19.0%, 27.4% | 19.8%, 28.3% |
| r.m.s. deviation bond lengths, angles | 0.011 Å, 1.374° | 0.009 Å, 0.990° | 0.009 Å, 1.184° | 0.010 Å, 1.22° | d) BTC Epitope Structure

The BTC structure is an EGF fold with five beta strands in a three-stranded and a two-stranded sheet. The structure is stabilized with three disulfide bonds. The observed BTC structure is well conserved in all of the crystal structures. The structure is similar to the previously reported NMR structure (pdb: 1IPO, Miura, K. et. al. (2002) Biochem.Biophys. Res. Comm 294 1040-1046) with the exception of a significant shift of the two C-terminal beta strands. As illustrated in FIGS. 1 and 2, both the epitopes and overall orientation of the Fabs vary between the complexes.

The crystal structure of Fab NVS2 bound to human BTC was used to identify the structural epitope on BTC. The interaction surface is formed by several continuous and discontinuous (i.e. noncontiguous) sequences: namely residues (40-43, 45-46, 58-61, 72-73, 75-76), as detailed in Table 12. These residues form the three-dimensional conformational epitope that is recognized by Fab NVS2 (FIGS. 1A and 2A).

Figure 1B:
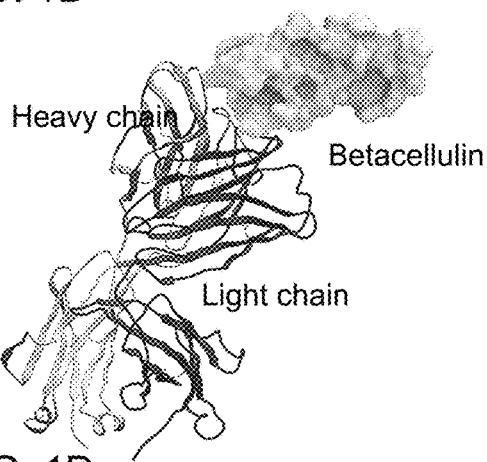

The crystal structure of Fab NVS3 bound to human BTC was used to identify the structural epitope on BTC. The interaction surface is formed by several continuous and discontinuous (i.e. noncontiguous) sequences: namely residues (34-42, 51, 53-54, 56), as detailed in Table 13. These residues form the three-dimensional conformational epitope that is recognized by Fab NVS3 (FIGS. 1B and 2B).

Figure 1C:
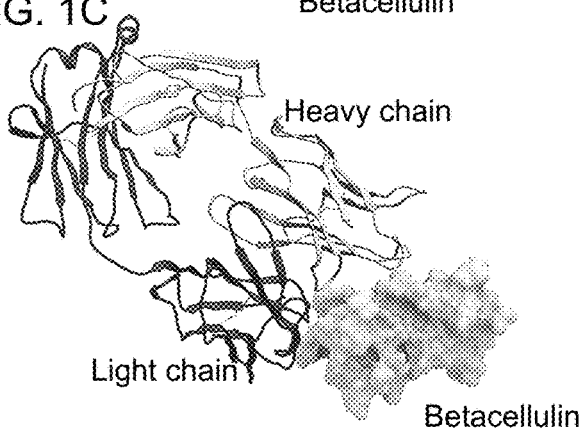

The crystal structure of Fab NVS1 bound to human BTC was used to identify the structural epitope on BTC. The interaction surface is formed by several continuous and discontinuous (i.e. noncontiguous) sequences: namely residues (38-43, 45-46, 54, 59-71, 73), as detailed in Table 14. These residues form the three-dimensional conformational epitope that is recognized by Fab NVS1 (FIGS. 1C and 2C).

Figure 1D:
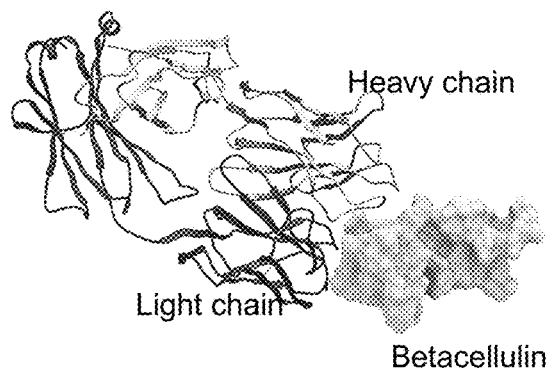

The crystal structure of Fab NVS4 bound to human BTC was used to identify the structural epitope on BTC. The interaction surface is formed by several continuous and discontinuous (i.e. noncontiguous) sequences: namely residues (37-43, 45-46, 54, 57, 59-61, 72-73, 75), as detailed in Table 15. These residues form the three-dimensional conformational epitope that is recognized by Fab NVS4 (FIGS. 1D and 2D).

Interactions between human BTC and Fab NVS2. BTC residues are numbered based upon SEQ ID NO: 157. Fab residues are numbered based upon their linear amino acid sequence (SEQ ID NOs: 36 and 47). BTC residues shown have at least one atom within 5 Å of an atom in the Fab NVS2, to account for potential water mediated interactions. The interactions are in common between the two copies of the complex in the asymmetric unit.

TABLE 12

Interactions between
human BTC and Fab NVS2

| BTC | | Fab NVS2 | | |
|---|---|---|---|---|
| Amino acid | Number | Amino acid | Number | Chain |
| PRO | 40 | TYR | 32 | L |
| LYS | 41 | GLY | 29 | L |
|  |  | ASP | 30 | L |
| GLN | 42 | GLY | 29 | L |
|  |  | ASP | 30 | L |
|  |  | LYS | 31 | L |
|  |  | TYR | 32 | L |
|  |  | ASP | 51 | L |
|  |  | TYR | 93 | L |
| TYR | 43 | TYR | 101 | H |
|  |  | GLU | 105 | H |
|  |  | TYR | 32 | L |
|  |  | TYR | 34 | L |
|  |  | GLN | 50 | L |
|  |  | TYR | 93 | L |
| HIS | 45 | TYR | 93 | L |
|  |  | LEU | 94 | L |
| TYR | 46 | TYR | 101 | H |
|  |  | TYR | 102 | H |
|  |  | PHE | 103 | H |
|  |  | TYR | 93 | L |
| GLU | 58 | ARG | 100 | H |
| GLN | 59 | ARG | 100 | H |
|  |  | GLN | 50 | L |
|  |  | LYS | 53 | L |
| THR | 60 | ARG | 100 | H |
|  |  | TYR | 101 | H |
| PRO | 61 | TYR | 101 | H |
| ALA | 72 | TYR | 102 | H |
| ARG | 73 | TYR | 102 | H |
|  |  | PHE | 103 | H |
|  |  | TYR | 93 | L |
|  |  | LEU | 94 | L |
|  |  | SER | 96 | L |
| GLU | 75 | TYR | 102 | H |
| ARG | 76 | SER | 57 | H |

Interactions between human BTC and Fab NVS3. BTC residues are numbered based upon SEQ ID NO: 157. Fab residues are numbered based upon their linear amino acid sequence (SEQ TD NOs: 56 and 67). BTC residues shown have at least one atom within 5 Å of an atom in the Fab NVS3, to account for potential water mediated interactions. IDC-31 1T1,M

TABLE 13

Interactions between
human BTC and Fab NVS3

| BTC | | Fab NVS3 | | |
|---|---|---|---|---|
| Amino acid | Number | Amino acid | Number | Chain |
| GLY | 34 | HIS | 53 | L |
|  |  | VAL | 54 | L |
| HIS | 35 | HIS | 53 | L |
|  |  | VAL | 54 | L |
|  |  | GLY | 55 | L |
|  |  | TYR | 56 | L |
| PHE | 36 | HIS | 53 | L |
|  |  | TYR | 56 | L |
|  |  | ASP | 101 | L |
|  |  | PHE | 102 | L |
| SER | 37 | GLN | 93 | H |
|  |  | TYR | 56 | L |
|  |  | ASP | 101 | L |
|  |  | PHE | 102 | L |
| ARG | 38 | TYR | 31 | H |
|  |  | ASP | 49 | H |
|  |  | ASP | 101 | L |
|  |  | PHE | 102 | L |
|  |  | GLY | 103 | L |
|  |  | TYR | 104 | L |
|  |  | TYR | 105 | L |
| CYS | 39 | TYR | 31 | H |
| PRO | 40 | TYR | 31 | H |
| LYS | 41 | ILE | 27 | H |
|  |  | GLY | 28 | H |
|  |  | LYS | 29 | H |
|  |  | LYS | 30 | H |
|  |  | TYR | 31 | H |
|  |  | ASP | 50 | H |
|  |  | ASN | 65 | H |
| GLN | 42 | LYS | 29 | H |
| ARG | 51 | TYR | 99 | L |
|  |  | LEU | 100 | L |
|  |  | ASP | 101 | L |
|  |  | TYR | 104 | L |
| ARG | 53 | HIS | 53 | L |
|  |  | ASP | 101 | L |
| PHE | 54 | GLN | 93 | H |
| VAL | 56 | GLN | 93 | H |
|  |  | TYR | 56 | L |

Interactions between human BTC and NVS1 Fab. BTC residues are numbered based upon SEQ ID NO: 157. Fab residues are numbered based upon their linear amino acid sequence (SEQ ID NOs: 12 and 23). BTC residues shown have at least one atom within 5 Å of an atom in the Fab NVS1, to account for potential water mediated interactions. The interactions are in common between the 12 copies of the complex in the asymmetric unit.

TABLE 14

Interactions between human BTC and NVS1 Fab

| BTC | | Fab NVS1 | | |
|---|---|---|---|---|
| Amino acid | Number | Amino acid | Number | Chain |
| ARG | 38 | SER | 28 | L |
| | | ILE | 29 | L |
| | | SER | 30 | L |
| | | PHE | 32 | L |
| | | ASP | 92 | L |
| CYS | 39 | PHE | 32 | L |
| | | ASP | 92 | L |
| PRO | 40 | PHE | 32 | L |
| | | TYR | 91 | L |
| | | ASP | 92 | L |
| LYS | 41 | SER | 28 | L |
| | | ASP | 92 | L |
| | | ASP | 93 | L |
| GLN | 42 | VAL | 52 | H |
| | | TRP | 54 | H |
| | | GLY | 104 | H |
| | | ILE | 105 | H |
| | | HIS | 106 | H |
| | | TYR | 91 | L |
| | | ASP | 92 | L |
| | | PHE | 94 | L |
| | | MET | 96 | L |
| TYR | 43 | TRP | 54 | H |
| | | SER | 101 | H |
| | | TYR | 103 | H |
| | | GLY | 104 | H |
| | | ILE | 105 | H |
| | | HIS | 106 | H |
| HIS | 45 | TRP | 54 | H |
| TYR | 46 | TRP | 54 | H |
| | | TYR | 103 | H |
| PHE | 54 | HIS | 106 | H |
| | | PHE | 32 | L |
| GLN | 59 | SER | 101 | H |
| | | HIS | 106 | H |
| | | ALA | 50 | L |
| | | TYR | 91 | L |
| THR | 60 | TYR | 103 | H |
| PRO | 61 | TYR | 103 | H |
| ARG | 73 | TRP | 54 | H |

Interactions between human BTC and NVS4 Fab. BTC residues are numbered based upon SEQ ID NO: 157. Fab residues are numbered based upon their linear amino acid sequence (SEQ TD NOs: 80 and 90). BTC residues shown have at least one atom within 5 Å of an atom in the NVS4 Fab, to account for potential water mediated interactions. The interactions are in common between the 4 copies of the complex in the asymmetric unit.

TABLE 15

Interactions between human BTC and NVS4 Fab

| BTC | | Fab NVS4 | | |
|---|---|---|---|---|
| Amino acid | Number | Amino acid | Number | Chain |
| SER | 37 | TYR | 32 | L |
| ARG | 38 | TYR | 32 | L |
| CYS | 39 | TYR | 32 | L |
| PRO | 40 | TYR | 32 | L |
| | | ASP | 92 | L |
| LYS | 41 | ILE | 2 | L |
| | | GLN | 27 | L |
| | | GLY | 28 | L |

TABLE 15-continued

Interactions between human BTC and NVS4 Fab

| BTC | | Fab NVS4 | | |
|---|---|---|---|---|
| Amino acid | Number | Amino acid | Number | Chain |
| | | ASP | 92 | L |
| | | ALA | 93 | L |
| GLN | 42 | TYR | 50 | H |
| | | PHE | 57 | H |
| | | ASN | 59 | H |
| | | SER | 101 | H |
| | | TYR | 91 | L |
| | | ASP | 92 | L |
| | | ALA | 93 | L |
| | | LEU | 94 | L |
| | | ASN | 95 | L |
| TYR | 43 | TRP | 33 | H |
| | | TYR | 50 | H |
| | | PHE | 57 | H |
| | | GLY | 100 | H |
| | | SER | 101 | H |
| | | TYR | 91 | L |
| HIS | 45 | PHE | 57 | H |
| TYR | 46 | TRP | 33 | H |
| | | ASP | 52 | H |
| | | SER | 53 | H |
| | | THR | 54 | H |
| | | PHE | 57 | H |
| PHE | 54 | SER | 101 | H |
| | | TYR | 32 | L |
| | | TYR | 91 | L |
| ALA | 57 | TYR | 49 | L |
| GLN | 59 | SER | 101 | H |
| | | LEU | 102 | H |
| | | TYR | 32 | L |
| | | ALA | 50 | L |
| | | TYR | 91 | L |
| THR | 60 | TRP | 33 | H |
| PRO | 61 | TRP | 33 | H |
| ALA | 72 | THR | 54 | H |
| ARG | 73 | ASP | 52 | H |
| | | THR | 54 | H |
| | | PHE | 57 | H |
| GLU | 75 | THR | 54 | H |

Example 3. Generation of Anti-BTC/Anti-VEGF Bispecific Fab

The anti-VEGF Fab portion of the bispecific molecule was derived from anti-VEGF scFv (1008 scFv) previously disclosed in US 20120014958 and identified as 578minimaxT84N_V89L or Protein No: 1008, which is incorporated by reference in its entirety. To convert the 1008 scFv to its Fab version, the amino acid sequence of the 1008 scFv was aligned with published human IgG framework sequences and determined to have high homology with the Kappa framework.

Consequently, the 1008 scFv was converted by adding 1) human immunoglobulin Kappa chain constant region sequence (SEQ ID NO: 159) to the C-terminal end of the $V_L$ of 1008 scFv, and 2) human immunoglobulin first constant Ig domain of the heavy chain (CH1 domain) sequence (SEQ ID NO: 160) to the C-terminal end of $V_H$ of 1008 scFv.

Figure 3:
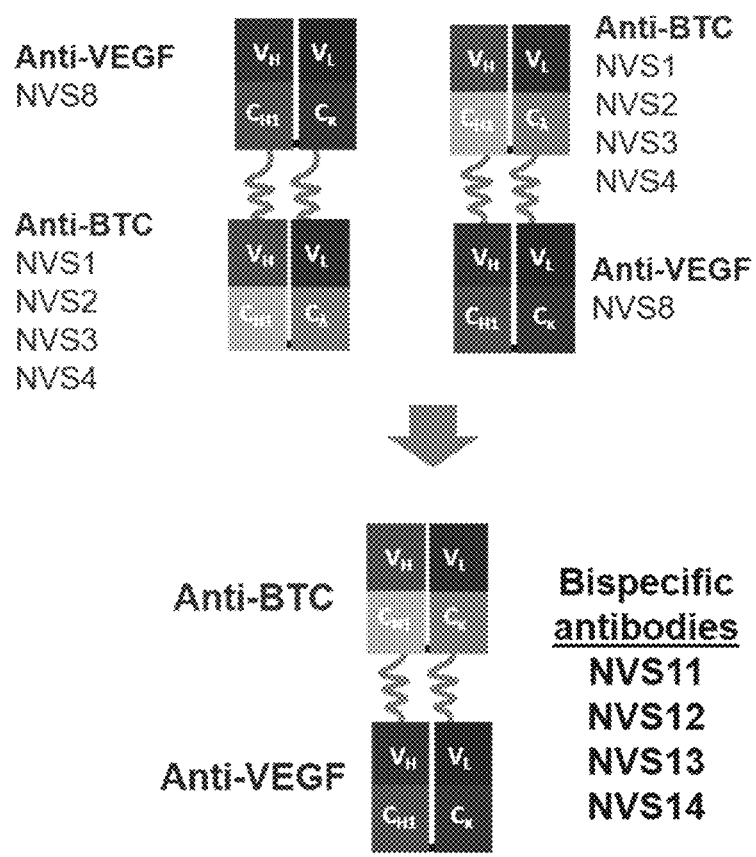
FIG. 3 provides the graphical representation of the monospecific and bispecific antibodies.

Two orientations were generated for the bispecific molecules (FIG. 3). In orientation 1, the anti-BTC Fab was at the N-terminus while the anti-VEGF Fab was at the C-terminus of the molecule. In orientation 2, the anti-VEGF Fab was at the N-terminus while the anti-BTC Fab was at the C-terminus of the molecule. The heavy chains of the two Fabs were joined by a (GSGGG)$_3$ (SEQ ID NO: 118) linker, and the two light chains are joined by a (GSGGG)$_3$ (SEQ ID NO: 118) linker.

Nucleotides encoding amino acids of light and heavy chains of the anti-BTC and anti-VEGF were synthesized by Genewiz, LLC and delivered in a pUC57 vector. To clone into an expression vector, 4 pg of the plasmid DNA was digested overnight with restriction enzymes HindIII and XbaI at 37° C. Digested plasmids were ran on 1% agarose gel for 40 minutes at 100 volts. A band corresponding to the size of digested DNA fragment of interest was gel extracted, and DNA was recovered the using QIAQUICK Gel Extraction Kit (Qiagen, Cat. #28704) according to the manufacturer's protocol. The HindIII/XbaI digested anti-BTC/anti-VEGF fragment was cloned into a HindIII/XbaI digested pRS5a expression vector according to the manufacturer's protocol using LIGAFAST™ Rapid DNA Ligation System (Promega Cat. No. M8225). The ligation product was transformed into ONESHOT TOP10 chemically competent E. coli (Invitrogen Cat. No. C4040-10), plated on LB-agar plate containing 100 pg/mL carbenicillin, and incubated at 37° C. overnight. Four colonies were picked, grew overnight in LB medium containing 100 pg/mL carbenicillin at 37° C. With QIAPREP Spin Miniprep Kit (Qiagen Cat. No. 27104), DNA from these bacterial cultures was extracted following the manufacturer's protocol. The extracted DNA was sent for sequencing to screen and select for a correct ligated product. Upon confirmation of correct clones, the DNA was re-transformed into ONESHOT TOP10 chemically competent E. coli, and a single colony was picked and grown to scale up DNA using HIPURE Plasmid Megaprep Kit (Invitrogen Cat. No. K57010) according to the manufacturer's protocol to obtain sufficient DNA for transient HEK293 protein expression.

$0.5 \times 10^6$ HEK293FREESTYLE cells/mL were seeded a day before transfection in 1 L of FREESTYLE 293 Expression Medium (Invitrogen Cat. No. 12338018) in a 3 L Erlenmeyer flask (Corning Cat. No. 431252) so that the cells reached density of approximately $1 \times 10^6$ cells/mL and >95% viability on the day of transfection. For a 1 L transfection culture, in one tube, 2 mL of 1 mg/ml polyethylenimine solution (PEI) was added into 23 mL of FREESTYLE 293 Expression Medium, and in another tube containing 25 mL FREESTYLE 293 Expression Medium, 0.5 mg of the light chain and 0.5 mg of the heavy chain expression vector DNA was added. Both tubes were incubated for 5-10 minutes. The tube containing plasmid DNA was filtered through a 0.22 μm membrane STERIFLIP (Millipore Cat. #SCGP00525) to prevent potential contamination. This DNA mixture was then added to the other tube containing PEI and incubated at room temperature for 20-30 minutes. After incubation, the transfection mixture was added to the $1 \times 10^6$ cells/mL culture and cultivated for 5 days at 37° C., 125 rpm shaking, and with 5-10% $CO_2$. The culture was harvested, centrifuged, and the supernatant was filtered through a 0.22 μm membrane STERICUP (Millipore Cat. No. SCGU1 IRE) before purification using standard affinity resins, for example, GE Healthcare Life Science's ATKA system.

The harvested culture containing the anti-BTC/anti-VEGF bispecific Fab was purified by flowing over the 5 mL prepacked CAPTURESELECT IgG-CH1 affinity column (Life Technologies Cat. No. 494320005) using GE's ATKA system. Once the loading was completed, 20-50 column volumes (CV) of PBS, pH 7.4 wash buffer was flowed over the resin to remove any non-specific binding components, followed by 16-20 CV of a low pH elution gradient of 100 mM citrate buffer, pH 3.0 (Teknova Cat. No. Q2445). The eluted fraction containing the bispecific Fab was further polished for improved purity using a multimodal chromatography resin, a 5 mL prepacked HITRAP CAPTOAD-HERE column (GE Healthcare Life Sciences Cat. No. 28405846). The CAPTOADHERE column is a strong anion exchanger with multimodal functionality that can remove aggregates, host cell proteins, nucleic acids, and viruses. The pH of the previously eluted protein solution was raised above its isoelectric point (pI) with 1 M TRIS-HCl, pH 9.5 (Teknova Cat. No. T1095) to get a net negative charge for the protein to bind to the resin. Once loaded onto the column, it was washed with PBS, pH 7.4, and eluted with a gradient of 100 mM citrate buffer, pH 3.0. The eluted fractions were analyzed on SDS-PAGE gel to select for fractions with high purity. The pooled fractions were concentrated as well as buffer exchanged into PBS, pH 7.4, using a 10 kD molecular weight cutoff VIVASPIN20 protein concentrator (Sartorius Cat. No. VS2001). Finally, additional characterizations of the protein were done to determine concentration using UV absorption at 280 nm, for purity by SDS-PAGE gel, for aggregation and purity with SEC-HPLC, to confirm correct molecular weight by LC/MS, and for endotoxin level via Charles River LAL cartridge using the ENDOSAFE (endotoxin testing equipment) system.

Example 4. Prolonged BTC Expression in Mice Causes Vessel Dilation and Vascular Leakage Resulting in Retinal Edema Animal model and study design. In vivo studies were performed in female C57/B16J mice (8-10 weeks old) acquired from Jackson Laboratories (Bar Harbor, Me.). The effect of BTC overexpression in the mouse retina was investigated by injecting (subretinal, s.r.) self-complementary adeno-associated viruses, serotype 2 (scAAV2) that expressed BTC under the control of the cytomegalovirus (CMV) promoter. Both eyes in a single animal were injected with the same dose of scAAV2-CMV-BTC, and two different doses were tested. Control eyes (naive, formulation buffer or injected with a null scAAV2) and test eyes were imaged (color fundus photography, fundus fluorescence angiography (FFA), scanning laser ophthalmoscopy (SLO), and optical coherence tomography (OCT)) 4-6 weeks after delivery. Details for each of the studies performed are described in the Table 16 below.

TABLE 16

Summary of subretinal treatment of mice with BTC

| Study #1 | | | |
|---|---|---|---|
| Subretinal Treatment | Volume/ Dose (vg/eye) | Eyes recorded for OCT | Eyes recorded for SLO |
| Naive | N/A | 10 | N/A |
| scAAV2-CMV-BTC | 1 μL/1 × $10^8$ | 8 | N/A |
| Formulation Buffer | 1 μL | 8 | N/A |
| scAAV2-null | 1 μL/1 × $10^8$ | 8 | N/A |

| Study #2 | | | |
|---|---|---|---|
| Subretinal treatment | Volume/ Dose (vg/eye) | Eyes recorded for $1^{st}$ OCT/ $2^{nd}$ OCT | Eyes recorded for SLO |
| scAAV2-CMV-BTC | 1 μL/5 × $10^8$ | 10/20 | 10 |
| scAAV2-null | 1 μL/5 × $10^8$ | 10/8* | 10 |

*One mouse died prior to imaging

Animal preparation for subretinal injections or imaging. Murine eyes were dilated with cyclopentolate (1%, topical)

and phenylephrine (2.5% or 10% depending on availability, topical). The cornea was desensitized with proparacaine (0.5%, topical). The mice also received an intraperitoneal (i.p.) injection of ketamine/xylazine cocktail (100-150 mg/kg and 5-10 mg/kg, respectively) for sedation.

Subretinal delivery of scAAV2-CMV-BTC. The anesthetized animals were positioned under a surgical microscope. A blunt-ended needle attached to a 10 μL Hamilton syringe was inserted through a small scleral incision. The needle was directed posterior to the lens, towards the temporal retina until resistance was felt. 1 μL of scAAV2-CMV-BTC (containing 200 pg/mL of sodium fluorescein) was slowly injected into the subretinal space. Two doses were tested: $1\times10^8$ viral genomes (vg)/eye or $5\times 10^8$ vg/eye. Successful injections were confirmed by visualization of the fluorescein containing bleb through the previously dilated pupil. Eyes with significant hemorrhage or leakage of vector solution from the subretinal space into the vitreous were excluded from further study. After the procedure, 0.3% tobramycin ophthalmic ointment was applied to the eyes and the mouse was allowed to recover from the anesthesia prior to being returned to its cage in the housing room. Animal health was monitored as described in the protocols cited.

Fundus photography and fundus fluorescence angiography (FFA). Anesthetized mice were placed on a heated stage. The imaged eye (usually the right eye, OD) was kept moist with ocular lubricant (GENTEAL or equivalent), and the retina was photographed with a MICRON III system (retinal imaging platform; Phoenix Research Laboratories, Pleasanton, Calif.) FFFA was performed only in study 1. The procedure is the same as fundus photography, the only difference being that fluorescein (100 mg/kg) was injected (i.p.) before anesthesia. The mice were imaged 2-3 minutes after injection of the fluorescent dye. 1-3 photographs were obtained from each imaged eye.

Scanning laser ophthalmoscopy imaging (SLO). Mice were anesthetized and their pupils were dilated as described. Moisture was maintained with hypromellose lubricant drops. 15 mg/kg of 2.9 mg/mL indocyanine green (ICG) and 50 mg/kg of 20 mg/mL sodium fluorescein solution were injected i.p. into the mouse to label the vessels and assess retinal leakage. Three minutes after the dyes were injected; mice were subsequently anesthetized with an intraperitoneal injection of a ketamine/xylazine cocktail (100-150/5-10 mg/kg). Proparacaine (0.5%) was also applied as a topical corneal anesthetic.

BTC-induced retinal vessel permeability changes were assessed using the fluorescein and ICG channels of an SLO-based fluorescence angiography system. ICG binds plasma proteins, creating a high molecular weight structure that remains in the vessels and therefore allows a map of vessel architecture to be captured. Retinal vessel permeability was subsequently assessed via the injection of low molecular weight sodium fluorescein dye that is known to leak from retinal vessels after BTC injection.

Exported images were an average of up to 40 registered SLO images acquired with a 55 degree lens centered on the optic nerve.

Optical coherence tomography (OCT). For the first time point in study 2, OCT images were taken in conjunction with SLO images, making the preparation for imaging the same. SLO imaging was not acquired for study 1, therefore animal preparation was the same as described throughout. OCT images were acquired using a spectral domain OCT system (ENVISU R2200, Bioptigen, Morrisville, N.C.). Volumetric scans were centered on the optic nerve and consisted of 400×400 a-scans distributed across a 1.7×1.7 mm field of view. Horizontal and vertical 1.8 mm linear b-scans. The acquisition of b-scans intersecting the optic nerve were also acquired. These consisted of an average of approximately 10 b-scans at each location that were aligned and processed using a script in MATLAB® (programing platform; Mathworks, Natick, Mass., USA).

Retinal thickness quantification from OCT images. Retinal thickness quantification was performed only in study 1. Morphometric analysis was performed on the extracted images (excluding the optic nerve) in MATLAB® by manually delineating the nerve fiber layer and Bruch's membrane to calculate total retinal thickness. Quantification consisted of values acquired across the scan as well as measurements of the thickest 10% of the retina in order to capture focal changes that could be obscured by data from a large region of the retina.

Statistical analysis. GRAPHPAD PRISM (software; La Jolla, Calif., USA) was used to plot morphometric data and perform statistical analyses. When comparing thickness changes a one-way ANOVA with Tukey's posttest was used to compare between groups with each treated as an independent data point. Error bars are reported as standard error with significance as $P<0.05$ unless otherwise stated.

Figure 4:
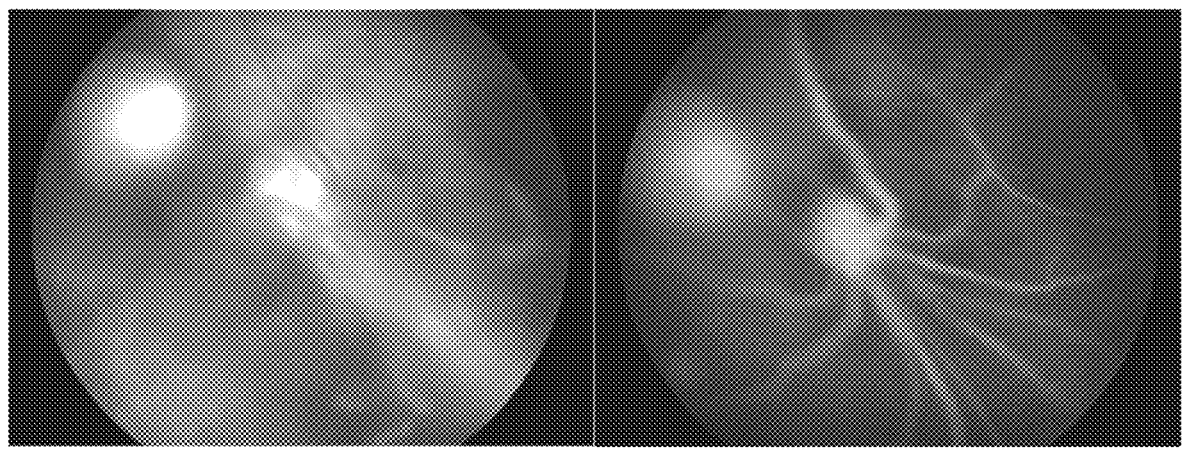
FIG. 4 shows retinal images of mice injected with scAAV2-CMV-BTC from fundus photography (left panel) and FFA visualization (right panel).

Results—Fundus photography and FFA. Study #1. Mice were injected (s.r.) with scAAV2-CMV-BTC, and imaged four weeks later. Fundus photography (FIG. 4, left panel) showed retinal vessel tortuosity, vascular leakage, and possible retinal detachments. Potential retinal hemorrhages were also observed. When visualized by FFA (FIG. 4, right panel), retinal tortuosity and vascular leakage were evident.

Figures 5A, 5B:
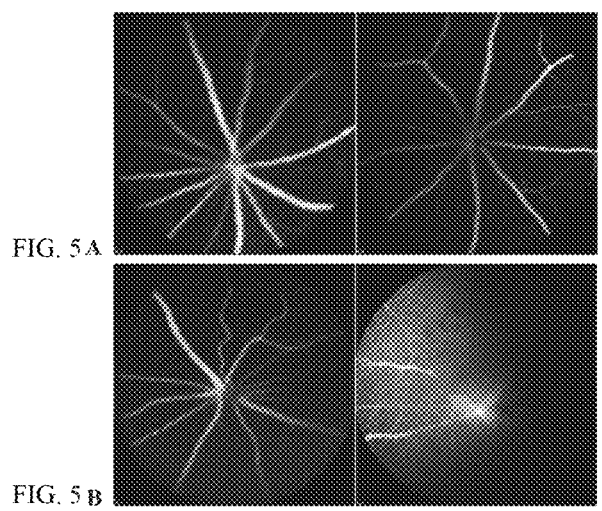
FIG. 5A-5B show retinal images of mice injected with scAAV2-CMV-BTC from scanning laser ophthalmoscopy.

Results—Scanning laser ophthalmoscopy (SLO). SLO images were only acquired in study #2. Images obtained from control mice injected with a null AAV2 were normal and did not reveal vascular leakage. Retinas injected with scAAV2-CMV-BTC exhibited increased vessel tortuosity and vascular leakage. In some eyes, the retinal detachment detected by OCT prevented the acquisition of high quality SLO images from the retinal vessels. Representative SLO images are shown in FIG. 5A of mice injected (s.r.) with a control vector (scAAV2-Null, 5×108 vg/eye). Clearly defined vessels are observed with no vascular leakage. In contrast, mice injected (s.r.) with scAAV2-CMV-BTC presented tortuous vessels and fluorescein leakage (FIG. 5B).

Example 5. FACS Binding Assay Assessing Binding of Antibodies to Membrane-Bound BTC First 293F cells which did not express BTC on the surface and a stable cell 293F-hBTC which expressed BTC on the cell surface were plated until a confluent monolayer was formed. After washing the cells, the cells were dissociated using Versene at 37° C. The cells were washed with FACS buffer and plated at 100 μl in a 96 well plate using cells at $1\times10^6$ cells/ml. Then 100 μl of a serial dilution of antibodies starting at 50 nM was used. The cells were incubated, washed and then treated with the secondary anti-human Fab-FITC antibody. The antibodies only bound to the cells expressing BTC. After which the cells were washed and analyzed on the Attune Flow Cytometry. All data analysis was carried out using Flow Jo software.

FIG. 6A-6D shows that both the bispecific Fab-Fabs (NVS11, NVS12, and NVS13) and their corresponding anti-BTC Fabs (NVS1, NVS2, and NVS3) showed comparable binding to membrane bound BTC. In FIG. 6A, Flow cytometry was used to assess the binding of NVS11 to membrane-bound BTC using an anti-human Fab antibody for detection. NVS11 binds to membrane-bound BTC over-expressed on 293F cells with an average EC50 of 93+42PM (9.0+4.0 ng/mL)

A sandwich enzyme linked immunosorbent assay (ELISA) was performed by coating either BTC or VEGF, then adding a titration of NVS 11 followed by detection with the second target, either biotinylated BTC or biotinylated VEGF. As shown in FIGS. 6E and 6F, in both formats, NVS11 can bind to both BTC and VEGF simultaneously. Neither of the single Fabs, NVS1 or NVS8, could bind to both BTC and VEGF at the same time.

Figure 6G:
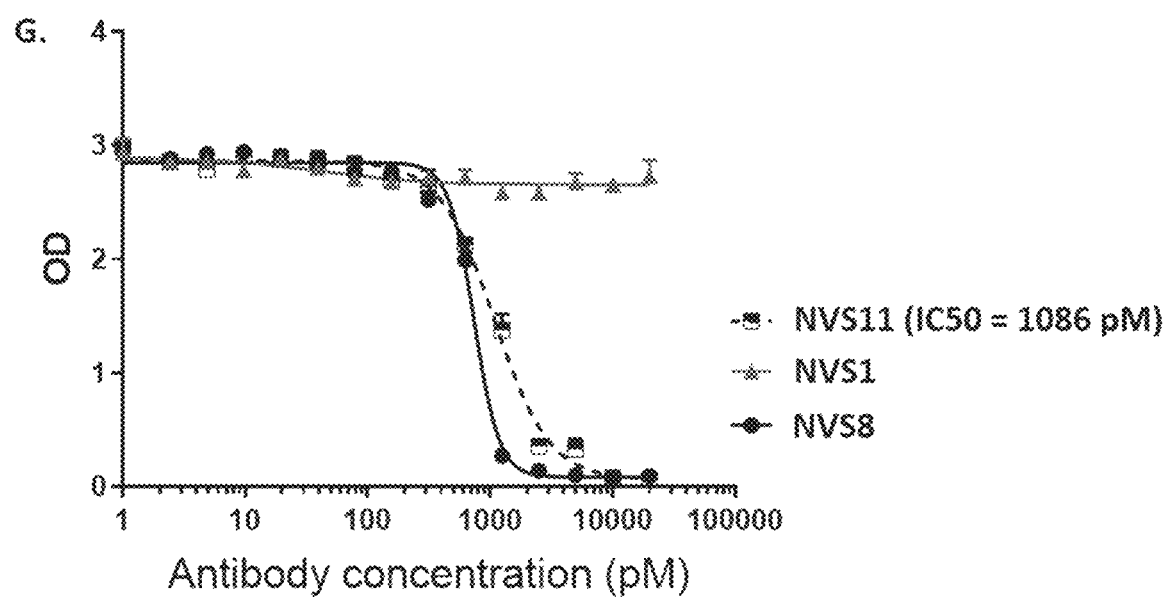

NVS11 neutralization of VEGF was determined by ELISA. Various concentrations of NVS11 was pre-incubated with biotinylated human VEGF and added to VEGFR2-Fc coated plates. As shown in FIG. 6G, bound VEGF-biotin to VEGFR2 was detected with streptavidin-HRP. NVS11 inhibited human VEGF binding to human VEGFR2-Fc with an average IC50 value of 1300+200 µM (127+19 ng/mL).

Example 6. Biacore Kn Determination

First, surface plasmon resonance used for affinity measurements of BTC or VEGF binding to NVS11 was captured on the chip. NVS11 binds to human and cyno BTC with $K_D$s of 5.8 and 7.2 pM respectively, and to human VEGF-A with 18.6 pM. Sequences of human and cyno isoforms VEGF-A198, -165, -121 and -111 are 100% identical. Hence affinity to cyno VEGF-A is identical to human VEGF-A. Association and dissociation rate constants and affinities are listed in Table 17 below.

TABLE 17

Average kinetic rate constants and affinities for NVS11 to human and cynomolgus BTC and human VEGF-A

| Antibody | Ligand species | $k_{ass}$ (1/Ms) average | $k_{diss}$ (1/s) average | KD (M) average |
|---|---|---|---|---|
| NVS11 | Human BTC | 5.1E+06 | 3.0E-05 | 5.8E-12 |
| NVS11 | Cyno BTC | 4.2E+06 | 3.0E-05 | 7.2E-12 |
| NVS11 | Human VEGF$_{165}$ (100% identical to cyno) | 1.3E+06 | 2.4E-05 | 1.86E-11 |

The average values for human VEGF are calculated from 5 individual experiments. The average values for human and cyno BTC are calculated from 7 individual experiments.

In order to assess if binding to BTC or VEGF was affected when the Fabs were presented in the bispecific form, affinity determinations were generated using BIACORE assays. Kinetic rate constants was performed via SPR using the BIACORE T200 instrument (surface plasmon resonance system; Biacore, GE Healthcare) as described below. The anti-Fab capture method was utilized in order to determine kinetics for the Fabs and bispecifics to BTC. A commercially available anti-Fab capture IgG (Jackson Immuno research) was immobilized on the chip surface using the provided amine coupling protocol from GE. This immobilized antibody captured the single Fabs and bispecifics. The goal was to capture Fab amounts to achieve an $R_{max}$ of 20. Then the BTC flowed over the Fabs as the analyte. The BTC concentration started at 5 nM and was serially diluted at 1:2 for seven concentrations. Regeneration was performed at the end of each concentration cycle using a final 1% phosphoric acid with 1:10 of 5 mM NaOH flowing at 60pl/min for 1 minute.

Double reference subtraction was completed to generate the final data. The raw data was fitted to a 1:1 binding model, with parameter(s) $R_{max}$ set to local.

Table 18 below shows that the affinity is comparable for BTC and VEGF between the Fabs and its corresponding bispecific.

TABLE 18

Affinity of mono- and bispecific antibodies

| | Human BTC | | | Human VEGF | | |
|---|---|---|---|---|---|---|
| Construct | Ka | Kd | KD (pM) | Ka | Kd | KD (pM) |
| NVS1 | 1.98E+07 | 3.39E-05 | 1.7 | NO binding detected | | |
| NVS11 | 2.47E+07 | 4.41E-05 | 1.8 | 1.54E+06 | 3.81E-05 | 2.5 |
| NVS2 | 1.12E+07 | 5.26E-05 | 4.7 | NO binding detected | | |
| NVS12 | 1.11E+07 | 6.67E-05 | 6.0 | 1.46E+06 | 2.46E-05 | 17.0 |
| NVS4 | 1.14E+07 | 4.86E-05 | 4.3 | (non-specific binding) | | |
| NVS14 | 1.67E+07 | 3.22E-05 | 2.0 | 1.48E+06 | 2.40E-05 | 16.0 |
| NVS3 | 1.35E+07 | 5.98E-05 | 4.4 | NO binding detected | | |
| NVS13 | 1.33E+07 | 2.40E-05 | 1.8 | 1.55E+06 | 1.01E-05 | 6.5 |
| NVS8 | NO binding detected | | | 5.26E+06 | 1.52E-05 | 3.0 |

Example 7. Neutralization Potency of the Antibodies for Blocking BTC Binding to ErbB1 or ErbB4

In order to assess potency of the Fabs and bispecific in neutralizing binding of BTC to its receptor Erb1 or ErbB4, the following assay was performed. HKB11 over-expressing either ErbB1 or ErbB4 cells were plated 1×10$^5$ cells/well. Cells were washed once with FACS buffer by spun down at 1200 rpm for 5 minutes and supernatant removed. Next, the Fab sample dilutions and BTC were prepared in FACS buffer. Human BTC-avitag-biotin was diluted to a fixed concentration of 15 nM. The test Fab samples were prepared at a starting concentration of 40 nM and titrated for 9 points at a serial dilution of 1:2. Both biotin-BTC and the test Fab samples are incubated for 30 minutes at room temperature. The pre-incubated samples were then added to the cell plate at 100 µl per well in duplicate and incubated for 1 hour on ice. The plate was then washed once in FACS buffer and spun down at 1200 rpm for 5 minutes and supernatant removed. After suspending the cell pellet with 100 µl/well of diluted secondary antibody streptavidin-ALEXA FLUOR488 (fluorescent compound; 1:2000) in FACS buffer, the cells were then incubated for 60 min on ice. The cells were washed once with FACS buffer and re-suspended in 120 µl of FACS buffer for flow cytometric analysis..

Measurements were performed on Attune Flow Cytometry machine. Data were analysed using the Flow Jo software. The live cell populations analysed were gated in forward and side scattering (FSC-A/SSC-A dot plot). The interval gate was established on the control histogram, which was obtained with sample incubated in streptavidin-ALEXA FLUOR488 only, and subsequently, determined percent of positive binding events of cells carrying membrane-bound receptor ErbB1 or ErbB4 and biotin-BTC. The median of fluorescence intensity (MFI) value was also derived for the live cell population. MFI values were then used to calculate for percent inhibition of test sample and subsequently plotted in GRAPHPAD PRISM 7.03 using nonlinear regression (curve fit) model to generate IC50 value.

FIG. 7 shows the inhibition of 2 nM BTC binding to ErbB1; and FIG. 8 shows the inhibition of 2 nM BTC binding to ErbB4. FIGS. 7 and 8 show that both the bispecific Fab-Fabs and their corresponding anti-BTC Fabs showed comparable potency for inhibition of BTC to either ErbB1 or ErbB4.

Flow cytometry cellular potency assay was conducted using HKB11 cells over expressing human ErbB1 or ErbB4 on the cell surface. NVS11 was pre-incubated at varying concentrations with 15 nM soluble human BTC-avitag-biotin, to assess NVS11 binding to BTC. As shown in FIGS. 8E and 8F, NVS11 blocked soluble BTC from binding to human ErbB1 and ErbB4 with an average IC50 of 2.9+0.3 nM (279±29 ng/ml) for ErbB1 and 4.6+2.7 nM (443+260 ng/ml) for ErbB4.

Figure 8G:
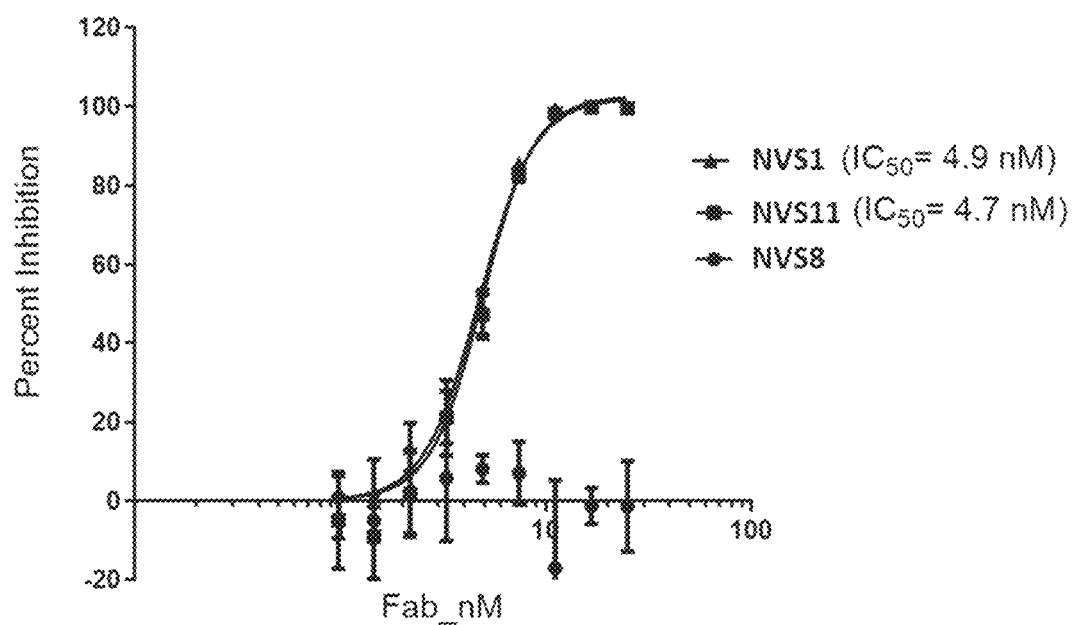
FIG. 8G shows BTC-induced EGFR phosphrylation in the presence of NVS1, NVS11, or NVS8.

As shown in FIG. 8G, an ELISA format using specific antibodies to detect phosphorylated EGFR confirmed that pre-incubation of soluble BTC with NVS1 or NVS11 prevented the BTC induced phosphorylation of EGFR endogenously expressed on the human ovarian carcinoma cell line NCI/ADR-RES.

Example 8. Neutralization Potency of the Antibodies for Blocking VEGF-A Binding to VEGFR2

VEGF-A regulates angiogenesis and vascular permeability by binding and activating through VEGFR2. Over expression of VEGF-A has been implicated with increased microvascular permeability and angiogenesis in ocular conditions such as DR and AMD. The purpose of the following experiment was to test the potency of the antibodies in neutralizing the binding of VEGF-A to VEGFR2.

VEGF-R2 (R&D systems #357-$K_D$/CF) was coated at 4ug/ml in 1XPBS at 20 µl/well overnight at 4° C. on 384 MAXISORP plates. The plates were then washed 3 times using 1XTBST. The plates were blocked in 2% BSA diluent (0.1% Tween 20/0.1% TirtonX100) overnight. After blocking, the plates were washed 3 times using TBST and then the sample mixture was added at 20 µl/well. The sample mixture consisted a final fixed concentration of VEGF-biotin (in-house) at 400 µM and a 15 point 1:2 serial dilution of the antibody starting at 20 nM. The sample mixture was pre-incubated for 1 hour prior to adding to the plate and then incubated for another hour at room temperature on the plate. Afterwards, the plate was washed 3 times using TBST and 20 µl/well of Streptavidin-TRP diluted at 1:5000 was added for an incubation time of 1 hour. The plates were washed 3 times in TBST and then 20 µl/well of TMB substrate was added. TMB is a chromogen that yields a blue color when oxidized. TMB was incubated for 10 minutes until the signal saturated in the no antibody samples, and then 10 µl/well of 2N sulfuric acid was added which then changes the blue color to yellow and this now has a maximum absorbance at 450 nm.

Figure 9C:
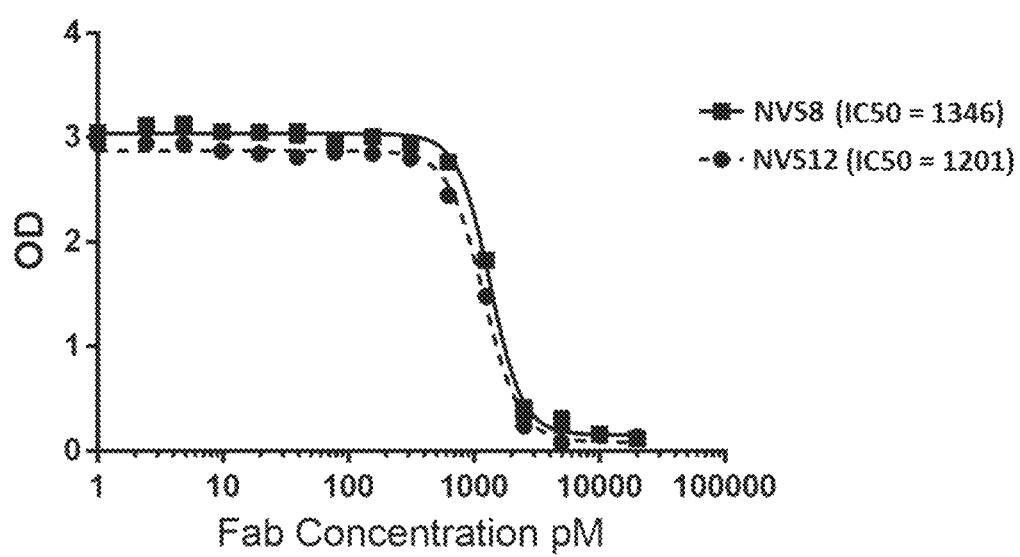

FIG. 9A-C show that both the bispecific Fab-Fabs and their corresponding anti-VEGF Fab showed comparable potency for inhibition of VEGF-A to VEGFR2.

Example 9. Neutralization Potency of the Antibodies for Blocking BTC Induced Phospho-ERK1/2 Activation Using Alpha Screen Assay BTC can bind to receptors ErbB1 or ErbB4 which can then form homodimers or heterodimers with the other ErbB receptors. Upon dimerization, the receptors will trans-phosphorylate and can signal through the MAPK/ERK pathway. A431 (ATCC# CRL-1555) is a human epidermoid carcinoma cell line which has high expression of ErbB1I and has some expression of ErbB3 and ErbB4. These cells were plated in a 384-well plate 17,500 cells/well in growth media in tissue culture incubator at 37° C., 5% $CO_2$. After 24 hours, the media was removed and replaced with 30 µl serum-free media DMEM supplement with 0.05% BSA and cells were then serum-starved for 5 hours. Next the sample dilutions were prepared in serum-free media. Human BTC was diluted to a concentration of 4 nM. The test samples were prepared at starting concentration of 80 nM and titrated for 9 points of 1:2 dilutions. Control samples were serum-free medium and 4 nM BTC plus 0 nM test sample. Both BTC and the test samples were pre-incubated for 30 minutes at room temperature at a 1:1 mixture. 10 µl of the mixture was added to each well containing the cells and treated for 5 minutes at 37° C. Treatment was immediately removed and then 30 µl of 1× SureFire Ultra lysis buffer was added to each well, incubated plate for 10 minutes at room temperature with gentle shaking.

The quantification of phosphorylated ERK1/2 level was evaluated using ALPHALISA SUREFIRE ULTRA pERK kit (immunoassay for detection of phospho-ERK). The assay was performed in 384-well white PROXIPLATE microplates according to the manufacturer's instructions. 10 µl of samples were incubated with 5 µl of acceptor mix and 5 µl of donor mix for at least two hours at room temperature in the dark. Plate was then read with Envision system using ALPHASCREEN (bead-based assay) settings. Data analysis of percent inhibition was calculated on Excel file. IC50 values were generated in GRAPHPAD PRISM 7.03 using a non-linear regression (curve fit) model.

Raw data of untreated (A0) and ligand BTC treated control (A100) from each assay plate were used to calculate % of inhibition of the test agents (A) based on the formula: % Inhibition=(1-(A-A0)/(A100-A0))*100). In this formula, % inhibition of a test agent is linear scaled between untreated control (0%) and treated control (100%).

FIG. 10A-D show that both the bispecific Fab-Fabs and their corresponding anti-BTC Fabs showed comparable potency for inhibition of pERK activation.

Example 10. Neutralization Potency of the Antibodies for Blocking BTC Induced Phospho-HER3 Activation BTC can bind to receptors ErbB1 or ErbB4 which can then form homodimers or heterodimers with the other ErbB receptors. Upon dimerization, the receptors will trans-phosphorylate and can signal through the MAPK/ERK pathway. NCI/ADR-RES cells (NCI) are an ovarian cancer cell line.

These cells express all 4 of the ErbB receptors. ErbB3 (HER3) is catalytically inactive and cannot trans-activate the other receptors. It does undergo trans-activation by the other receptors.

In the pHER3 assay, serial dilutions of the Fabs with a starting concentration of 20 nM were made at 1:2. This was pre-incubated with 5 nM soluble human BTC in order to form a Fab-BTC complex. The cells were seeded in a 48 well tissue culture plate and incubated for 24 hours and serum starved for 5 hours prior to antibody-BTC complex addition. The culturing media was 10% FBS in RPMI and the serum starving condition was Optimem media. The BTC-antibody complex was then added to the 48 well tissue culture plate which had been serum starved for 5 hours and the complex-cells were treated for 8 minutes. After the treatment, the supernatant was removed and the cells were washed once with cold 1X PBS. Then the cells were lysed and phosphorylation of ErbB3 assessed by MSD. The MSD method consisted of first plating a total HER3 capture antibody at 2 pg/ml at 10 µl per well for 2 hours at room temperature. The plate was then washed once with 1XTBST and then blocked in 5% BSA (1XTBST) for 2 hours. The plate was then washed and the test lysate was added at 10ul/well and incubated for 1 hour room temperature. The plate was then washed and the detection antibodyanti-pHER3 antibody diluted 1:1000 was added at 10 µl/well and incubated 1 hour at room temperature. The plate was then washed once and the rabbit sulfotag antibody was added at 1:5000 dilution at 10 µl/well. The plate was washed, MSD Read buffer added and the plate was read on the MSD instrument.

FIG. 11A-D show that the inhibition of 5 nM BTC induces phosphorylation of ErbB3 in ADR-RES cells. Both the bispecific Fab-Fabs and their corresponding anti-BTC Fabs showed comparable potency for inhibition of ErbB3 phosphorylation.

Example 11. Neutralization Potency of the Antibodies for Blocking Membrane-Bound BTC Induction of Phospho-HER3 Activation in a Juxacrine Manner BTC is a member of the EGF family that can exist as a soluble or precursor transmembrane form. Its transmembrane form can undergo proteolytic cleavage by the metalloproteinase ADAM10. Both the soluble and transmembrane forms can bind and signal through ErbB1 and ErbB4. The purpose of the following experiment is to assess potency of the bispecific Fab-Fabs compared to its anti-BTC single Fabs in inhibiting binding and activation of the membrane-bound BTC to NCI/ADR-RES (NCI) cells which contain the ErbB receptors.

Neutralization of surface bound BTC to its receptors was carried out using NCI/ADR-RES cells which expressed the ErbB receptors and the stable cell line 293F-human BTC which expressed membrane bound BTC. Serial dilutions of the Fabs with a starting concentration of 20 nM were made at 1:2. Next the Fab dilutions and the 293-BTC cells were pre-incubated in order to enable complex formation. This complex was then added to the ADR/RES cells and incubated for 10 minutes at 37° C. After the treatment, the supernatant was removed and the cells were washed once with cold 1X PBS. Then the cells were lysed and phosphorylation of ErbB3 assessed by MSD. The MSD method consisted of first plating a total HER3 capture antibody at 2 pg/ml at 10 µl per well for 2 hours at room temperature. The plate was then washed once with 1XTBST and then blocked in 5% BSA (1XTBST) for 2 hours. The plate was then washed and the test lysate was added at 10ul/well and incubated for 1 hour room temperature. The plate was then washed and the detection antibody anti-pHER3 antibody diluted 1:1000 was added at 10 µl/well and incubated 1 hour at room temperature. The plate was then washed once and the rabbit sulfotag antibody was added at 1:5000 dilution at 10 µl/well. The plate was washed, MSD Read buffer added and the plate was read on the MSD instrument.

FIG. 12A-D show that both the bispecific Fab-Fabs and their corresponding anti-BTC Fabs showed comparable potency for inhibition of membrane bound BTC to NCI/ADR-RES cells which contain the ErbB receptors.

Example 12. Inhibition of BTC Induced Permeability in an In Vitro Model Using RPE Integrity Tight junction formation of the retinal pigment epithelium (RPE) cells forms the outer blood retinal barrier (BRB) which regulates the movement of solutes and nutrients from the choroid to the sub-retinal space. It prevents leakage of fluid from the choroid into the retina. In the following assay, the potency of the antibodies were tested for their ability to neutralize BTC induced permeability of RPE cells.

RPE cells differentiated from human iPS cells have high expression of ErbB1 receptor. Treatment of RPE cells with BTC was able to induce permeability, as measured by a drop in the resistance signal of the cell monolayer. An XCELLIGENCE 384-well E-PLATE (#5867681001; microplate) was initialized by taking a resistance signal measurement (cell index) prior to addition of cells. RPE cells were plated at 10,000 cells/well in growth media (Lonza #195406, 2% FBS, 1X anti-anti #15240062, 20 ng/ml FGF #PHG6015), and cultured in a tissue culture incubator at 37° C., 5% $CO_2$. The cells were allowed to differentiate by culturing for 2-3 weeks, changing growth media every 2-3 days. Prior to start of an experiment, cells were cultured overnight in basal media (Lonza #195406). Resistance signal in each well was normalized to 1 prior to treatment. BTC and BTC/antibody complex [5 nM/42.5 nM] treatments in fresh basal media were added to the RPE cells daily, with resistance measured every 10 minutes. Normalized resistance signal over time was plotted.

FIG. 13A shows that both the bispecific Fab-Fab and its corresponding anti-BTC Fab showed comparable potency for inhibition of BTC-induced permeability of RPE cells in vitro.

For inner BRB integrity, HREC were cultured until formation of tight junctions. VEGF treatment decreased HREC resistance, whereas BTC did not. As shown in FIG. 13B, NVS11 pre-incubated with VEGF inhibited the VEGF-induced permeability of HREC cells.

Example 13. Anti-BTC and Anti-VEGF Combination Therapy Reduces Retinal Leakage Compared To Monotherapies in Diabetic Rats This example describes the use of the pancreatic toxin STZ (streptozotocin) to induce hyperglycemia in rats. After six weeks of hyperglycemia, retinal leakage is increased in these animals. Two antibodies were tested in their ability to reduce retinal leakage: an anti-VEGF antibody (4G3) and an anti-BTC antibody (LZR230).

4G3 was identified by panning biotinylated mouse VEGF with Morphosys HUCAL GOLD. The Fab was also found to bind and neutralize human VEGF and human/mouse crossreactivity made it useful in various mouse models. 4G3 is a VH5/V13 antibody that has been reformatted as a human and mouse IgG1 and mouse IgG2a. The mouse IgG1 was used in the rat STZ models. 4G3 is a primary isolate and not affinity matured.

LZR230 is a full-length IgG version of an anti-BTC Fab (SEQ ID NOs: 180 and 181; or "TC16").

Two weeks of systemic dosing of either anti-BTC (LZR230) or anti-VEGF (4G3) antibodies at 3 mg/kg inhibits retinal leakage when compared to IgG control hyperglycemic animals. Combining anti-BTC with anti-VEGF at 3 mg/kg leads to further reductions in retinal leakage.

Brown Norway rats were selected between 8 to 10 weeks old, or >200 grams in weight. Hyperglycemia was induced by destruction of insulin producing pancreatic beta cells with a single injection of 65 mg/kg (ip) STZ. Animals were considered diabetic and included in the study when blood glucose levels were >250 mg/dL 7 days after STZ injection. STZ is prepared in 0.1M sodium citrate buffer at pH 4.5. Control animals were injected with 0.1 M sodium citrate buffer at pH 4.5.

To assess retinal leakage, rats are injected IV via tail vein with FITC-dextran (4.4 kDa, 50 mg/mL in PBS pH 7.4, 50 mg/kg body weight). After 25 min., rats are euthanized with $CO_2$. Blood samples were collected (0.5-1 mL) via heart puncture in EDTA-coated tubes. Next, 20 mL of PBS was perfused throughout the systemic vasculature through the left ventricle. This step facilitated removal of blood that contains FITC-dextran, thus allowing quantitation of FITC-dextran that leaked from the blood into retinal tissue.

Eyes were enucleated and immediately snap-frozen on dry ice before storage at −80° C. Retinas are dissected from each eye, weighed, and homogenized in 150 µL of PBS containing 2% TRITON X-100. To account for variations in tail-vein injections, plasma FITC-dextran levels were factored into the calculation to determine levels of FITC-dextran in retinal tissue (pg/g tissue). Spectrophotometer excitation wavelength was 483 nm and emission wavelength was 538 nm. The amount of FITC-dextran leakage into the ocular tissue was calculated using the following equation, after correcting for dilutions:

$$\text{Retinal leakage (µL/g/min)} = \frac{\text{Retinal } FITC\text{-dextran (µg)/retinal weight (g)}}{\text{Plasma } FITC\text{-dextran (µg/µl)} \times \text{circulation time (min)}}$$

For assessment of the role of BTC and VEGF in retinal leakage, anti-BTC (LZR230) and/or anti-VEGF (4G3) antibodies were injected IP on 5 days over 2 weeks prior to the end of the experiment. Control animals received 6 mg/kg control IgG. Anti-BTC (LZR230) and anti-VEGF (4G3) were injected 3 mg/kg alone or in combination.

Results. Four independent experiments assessed the effects of 3 mg/kg anti-BTC (LZR230), 3 mg/kg anti-VEGF (4G3), and 3 mg/kg anti-BTC (LZR230)+3 mg/kg anti-VEGF (4G3), compared to IgG control on retinal leakage in hyperglycemic rats. In all four studies, retinal leakage was significantly increased in hyperglycemic animals compared to controls. In two of four studies, anti-BTC (LZR230) alone or anti-VEGF (4G3) alone significantly reduced retinal leakage. In all four studies, the combination treatment of anti-BTC (LZR230) and anti-VEGF (4G3) significantly inhibited retinal leakage as compared to IgG control. GRAPHPAD PRISM (La Jolla, Calif., USA) was used to plot data and perform statistical analyses. Each eye was treated as an independent data point. Comparisons were made to the STZ control control (IgG) by one-way analysis of variance (ANOVA) with a Dunnett's multiple comparison test. Significance was P<0.05 unless otherwise stated. Induction of hyperglycemia with STZ led to a significant increase in retinal leakage compared to normoglycemic animals. Treatment with anti-VEGF (4G3) led to a 32% reduction in retinal leakage. Treatment with anti-BTC (LZR230) led to a 41% reduction in retinal leakage. Combination of anti-BTC (LZR230) and anti-VEGF (4G3) surprisingly led to a 77% reduction in retinal leakage.

Figure 14:
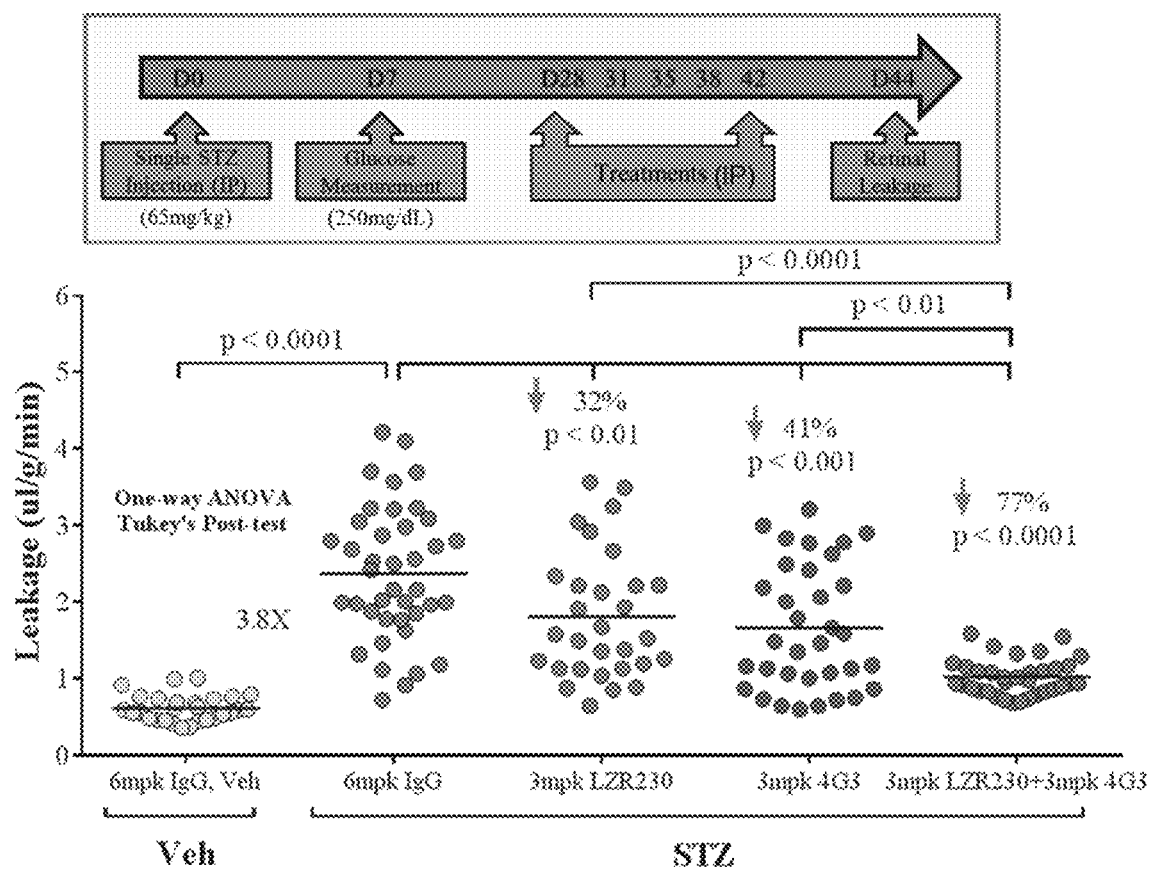
FIG. 14 shows hyperglycemia-induced retinal leakage in diabetic rats in the presence of anti-BTC (LZR230) and/or anti-VEGF (4G3) antibodies.

FIG. 14 shows that hyperglycemia induced retinal leakage is driven by both BTC and VEGF, and targeting both BTC and VEGF clinically will lead to greater efficacy than targeting VEGF alone.

Example 14. Efficacy of Anti-BTC/Anti-VEGF Bispecific Fabs in BTC or VEGF Challenges Methods and Animal model. In vivo studies were performed in male Dutch Belted rabbits weighing approximately 1.6-2.2 kg.

Animal preparation for intravitreal injections or imaging. Rabbit eyes were dilated with topical 1% cyclopentolate and phenylephrine (2.5 or 10% concentration used depending on availability), and the cornea anesthetized with topical 0.5% proparacaine. Rabbits were then anesthetized with an i.m. injection of a cocktail containing ketamine (17.5-35 mg/kg) and xylazine (2.5-5 mg/kg).

Intravitreal test article injection in rabbits. Under direct visualization with a surgical microscope, 50 µL of the test article was injected into the vitreous with a 30 gauge needle inserted superotemporally −2 mm from the limbus into the middle of the vitreous. Any injection-related complications were recorded during the injection (hemorrhage, retinal detachment, lens injury, or regurgitation of fluid), and then the procedure was repeated on the fellow eye. In studies where a VEGF injection occurred less than two weeks later, ointment containing 0.3% tobramycin was applied to both eyes following the procedure. If VEGF injection occurred more than two weeks after test article injection, ointment containing 0.3% tobramycin and 0.1% dexamethasone was applied to both eyes following the procedure.

Intravitreal VEGF/BTC injections in rabbits. Retinal vessel or morphological changes were induced using a 50 µL intravitreal (IVT) injection containing 400 ng human VEGF-A (165 isoform) in saline (Peprotech, catalog number AF-100-20) or using a 50 µL intravitreal (IVT) injection containing 0.75 pg human BTC in saline, respectively. The procedure was the same as that outlined in the previous section except that ointment containing 0.3% tobramycin was applied to both eyes following the procedure (no dexamethasone).

Efficacy of Anti-BTC/Anti-VEGF Bispecific Fabs in BTC Challenge

Retinal thickness image acquisition and quantification assessed by Optical Coherence Tomography (OCT). OCT images of the rabbit retina were acquired using a Heidelberg SPECTRALIS® OCT system (Heidelberg Engineering; Franklin, MA, USA). The OCT acquisition consisted of seven high resolution b-scans with 30 frames averaged per b-scan (30×10 degrees). The scan was centered inferior to the optic nerve head and rotated vertically until the long axis of the scan was aligned perpendicular to the medullary rays. The location described encompasses the rabbit visual streak, which is known to have high m-cone and ganglion cell density (Juliusson et al., 1994). The instrument automatically registers the OCT scan region for each retina so follow-up images are acquired in the same location.

Quantifying retinal thickness from OCT images. Images were exported from the Heidelberg software in .tif format. A custom-written algorithm was created in MATLAB® (Natick, Mass.) to crop and extract the OCT images from the .tif file. Morphometric analysis was performed on extracted OCT images in MATLAB® by manual segmentation of the retinal layers. Lines were traced along the inner retinal membrane, Bruch's membrane, and at the interface of the choroid and sclera. The proximal difference between these lines was used to generate retinal and choroidal thickness values (retinal thickness includes RPE). The edges of the OCT images often captured a small portion of the nerve head, or had imaging-related artifacts, so the code was written to crop the outside 25% of each image, leaving the middle 50% to be exported for analysis. Values were converted from pixels to µm for final output. While IVT injection of BTC induces both retinal and RPE thickening, in the studies described here, only retinal thickness was measured and quantified.

Efficacy studies. Test article was injected on day 0 immediately following acquisition of a pre-injection baseline OCT. Another OCT image was subsequently acquired on day 7 immediately preceding injection of BTC to induce retinal/RPE thickening. Final OCT was acquired on day 14. Change in retinal thickness (difference between day 14 and day 0) was measured and compared between groups. Percent inhibition was calculated for each treatment group by taking the difference in mean change in retinal thickness between that treatment group and saline (negative control) group.

Efficacy of Anti-BTC/Anti-VEGF Bispecific Fabs in VEGF Challenge

Image acquisition. VEGF-induced retinal vessel permeability changes were assessed with scanning laser ophthalmoscope (SLO)-based fluorescence angiography. Images were acquired for two fluorescent dyes selected to either label the vessel architecture (FITC conjugated dextran) or determine vessel permeability (fluorescein). The fluorescein channel from a 6-mode SPECTRALIS® system (Heidelberg Engineering) was used for image acquisition. Approximately 5 minutes before image acquisition, an i.v. injection of 1 mL of a solution of FITC-conjugated 2000 kDa dextran was delivered into the marginal ear vein. This high molecular weight dye remains in the vessels and therefore allows a map of vessel architecture to be captured. The concentration of FITC-dextran used (35-70 mg/mL) was chosen empirically for each lot based on the fluorescence signal necessary to generate high quality images (Sigma, FD2000s). Images of the labeled retinal vasculature in both eyes were acquired prior to the next step. Retinal vessel permeability was subsequently assessed via injection of 0.3 mL of a low molecular weight dye that was known to leak from the vessels after VEGF injection (10% sodium fluorescein solution). The dye was delivered i.v. into the marginal ear vein with images acquired at approximately 3 minutes post-injection for one eye and approximately 4-6 minutes post-injection for the fellow eye. Exported images were an average of up to 40 registered SLO images acquired with a 30 degree lens on the nasal medullary ray adjacent to the optic nerve.

Quantification of retinal vessel permeability. Image analysis was performed on masked, randomized data. Vascular permeability was quantified by processing the 48 hour post-VEGF FITC-dextran image in conjunction with the corresponding fluorescein image taken on the same day from the same eye. Image processing was accomplished using a software routine developed in MATLAB®. Images were first registered to each other. The region containing the optic nerve and the area outside of the medullary ray were then cropped out of the co-registered images along with any localized regions with insufficient image quality for analysis. The normalized, co-registered images were then subtracted from each other on a pixel-by-pixel basis. Since the FITC-dextran image contained only labeled vessels and the fluorescein image contained signal in the vessels as well as extravasated dye, subtraction of the FITC-dextran image from the fluorescein image produced an image containing just the extravasated fluorescein. The resulting fluorescein intensity per unit area from the calculated image was reported as "fluorescein leakage" for that eye. Average fluorescein leakage values for groups where no inhibition is present are typically in the range from 0.3 to 0.5. Significant inhibition of fluorescein leakage results in values closer to 0.

Efficacy studies. Efficacy arising from anti-VEGF test articles is assessed at a single time point (Day N) referenced to the day IVT injections of test articles are performed (Day 0). Leakage is induced with IVT VEGF delivered several days later (Day N-2). The interval between test article injection and VEGF injection varies, depending on the study needs. However, fluorescein leakage assessment imaging always occurs two days post-VEGF injection, regardless of study duration.

Statistical Analysis. GRAPHPAD PRISM (La Jolla, Calif. USA) was used to plot data and perform statistical analyses. Each eye was treated as an independent data point. Error bars are standard error unless otherwise stated. Significance was $P<0.05$ unless otherwise stated. Retinal thickness was measured for the central line scan (4 out of 7 scans) for all time points. Change in retinal thickness between day 0 (baseline before IVT of test article) and day 14 (14 days after test article injection and 7 days post-BTC injection) was measured for antibodies and saline (negative control). If a subject's data points were not available for all time-points, that subject was removed from the analysis. Calculations of average fluorescein leakage or retinal thickening, inhibition relative to controls (%) and statistics are performed on groups composed of individual eyes. Comparisons are made to the negative control by one-way analysis of variance (ANOVA) with a Dunnett's multiple comparison test.

Figure 15A:
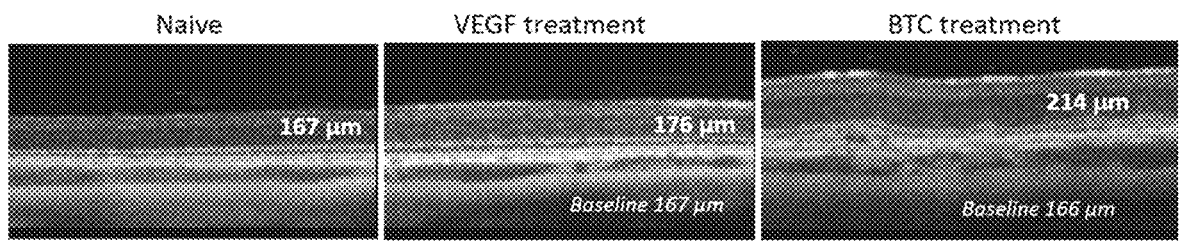
FIG. 15A shows optical coherence tomography (OCT) and histological images from rabbit eyes after treatment with VEGF or BTC.
Figure 15A:
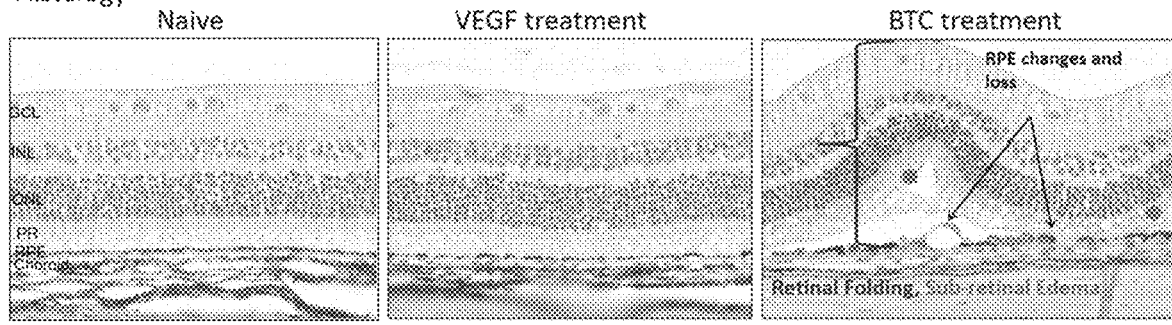
Figure 15B:
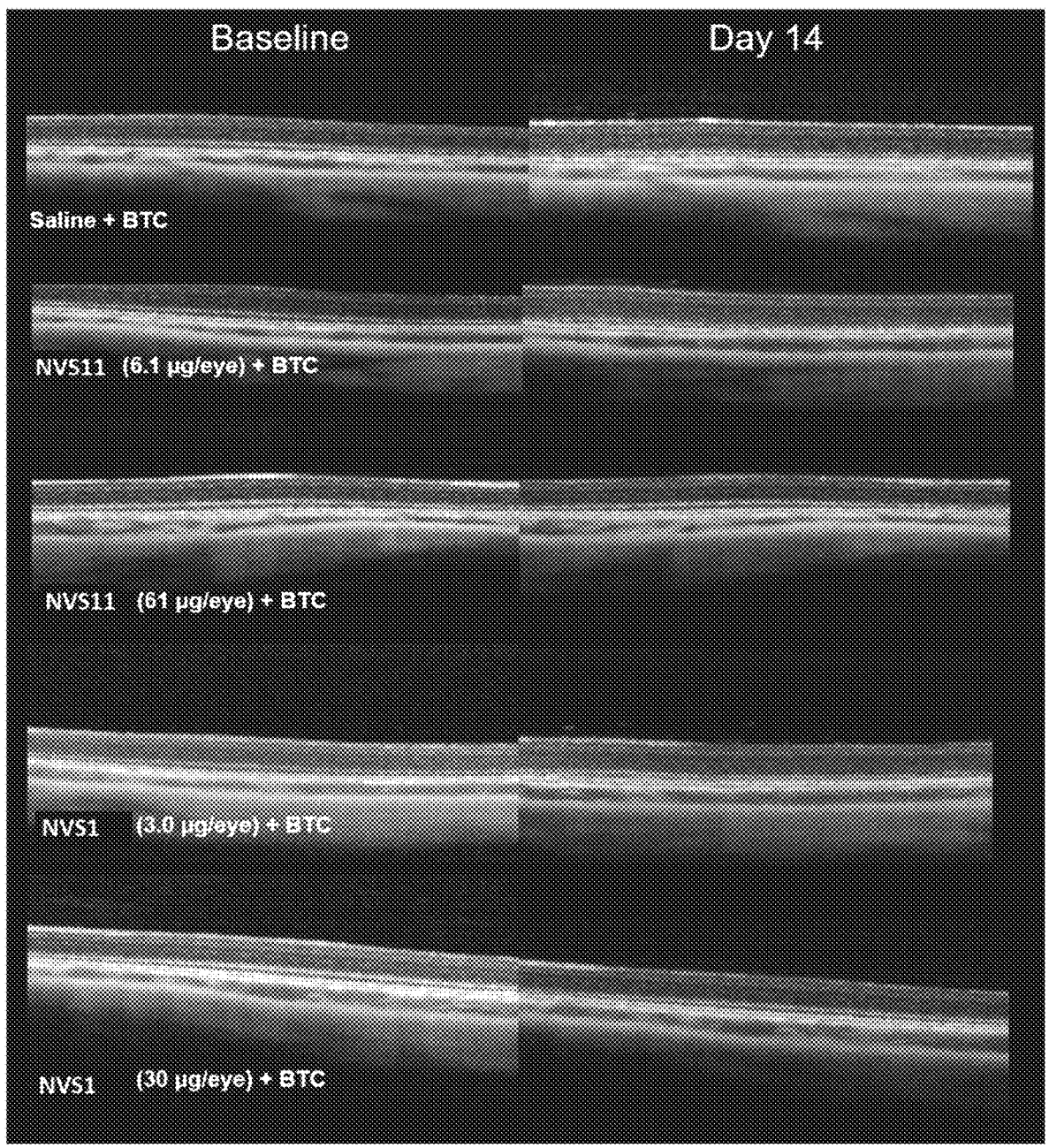
FIG. 15B shows representative OCT images demonstrating the effect of intravitreal betacellulin on rabbit retinas after intravitreal injection of NVS1 or NVS11.

FIG. 15A shows representative OCT images from a rabbit eye acquired at baseline (left), 2 days after treatment of 400 ng of VEGF (middle), and 7 days after 750 ng of BTC (right). 750 ng of BTC induced significant retinal thickening (48 microns) at day 7, and 400 ng of VEGF induced minimal retinal thickening (9 microns) 2 days post-injection. Retinal sections in the bottom from the same eyes show the pathology. Intravitreal BTC induces subretinal edema and RPE changes in rabbits whereas VEGF does not. In order to evaluate the effectiveness of NVS1 blocking BTC effects in vivo, NVS1 was injected IVT 7 days prior to IVT injection of BTC. Changes in retinal thickness were assessed 7 days after BTC injection. NVS1 significantly inhibited retinal thickening in BTC challenged eyes (85-87% with 61 pg/eye NVS11 (~40 pg/ml in 1.5 ml rabbit vitreous), $p<0.0001$, n=2; 30% with 6.1 pg/eye NVS11, $p<0.01$, n=1 study) (FIG. 15B).

Figure 16:
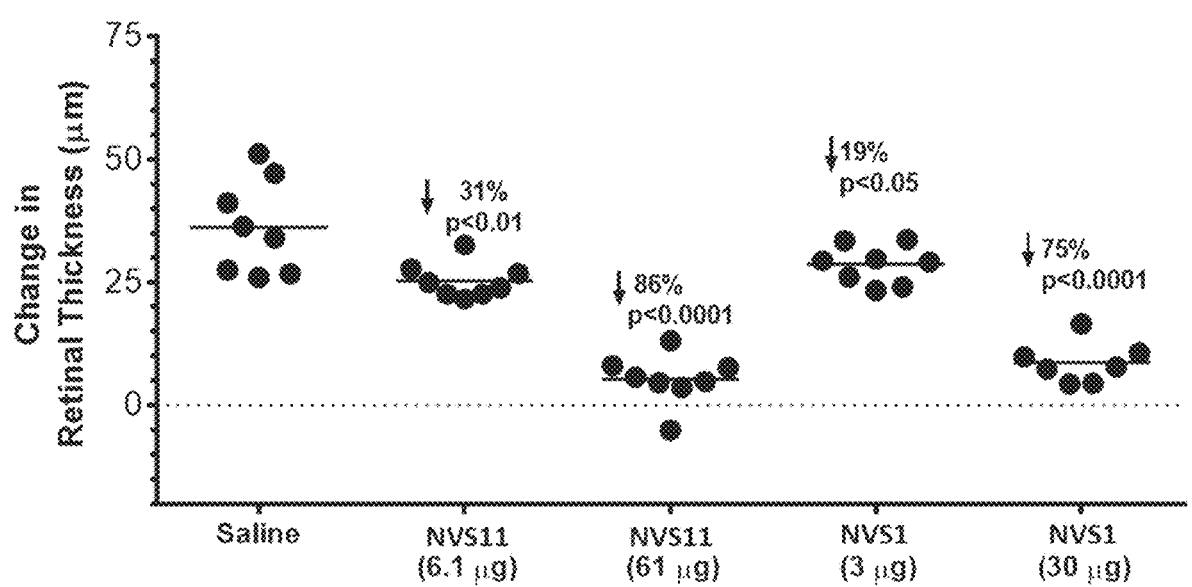
FIG. 16 shows change in retinal thickness of rabbit eyes after treatment with NVS1 or NVS11.

FIG. 16 shows change in retinal thickness values for each eye (total thickness between day 14 and day 0) for each treatment group (BTC alone, two doses of NVS1-3 and 30 pg, molar equivalent doses of 6.1 and 61 pg of NVS11). Both doses of NVS11 and NVS1 significantly reduced retinal thickening in a dose-dependent manner. The reduction in retinal thickening observed in eyes receiving the bispecific molecule NVS11 was comparable to that achieved by an equimolar dose of NVS1.

Figure 17:
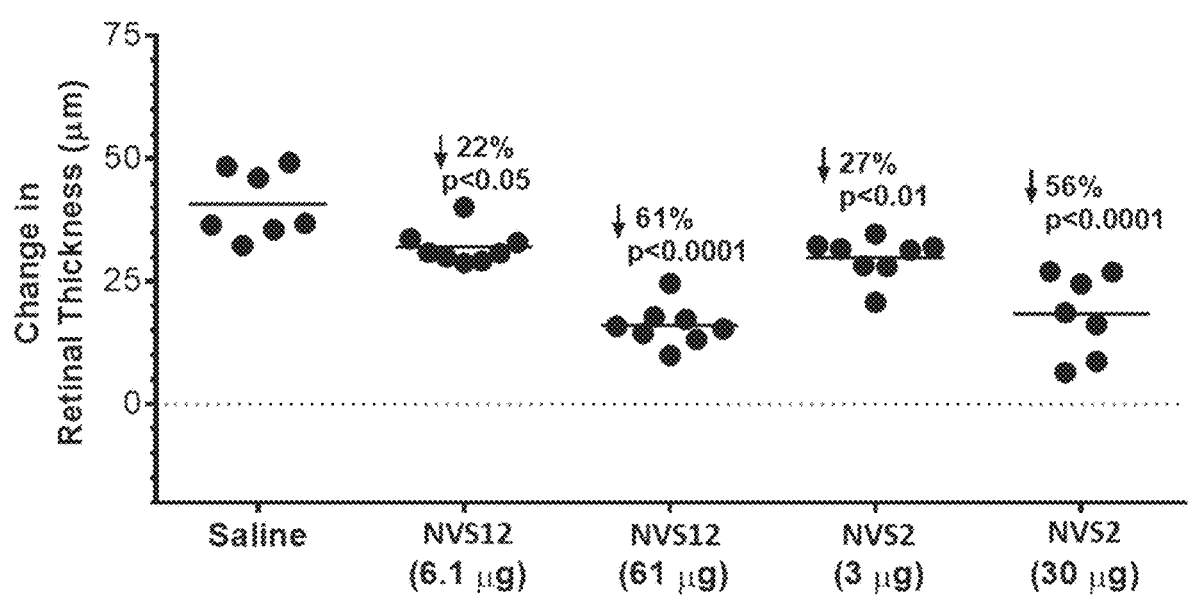
FIG. 17 shows change in retinal thickness of rabbit eyes after treatment with NVS2 or NVS12.

FIG. 17 shows the change in retinal thickness for each eye (total thickness between day 14 and day 0) for each treatment group (BTC alone, two doses of NVS2-3 and 30 pg, molar equivalent doses of 6.1 and 61 pg of NVS12). BTC-induced retinal thickening was significantly inhibited by bispecific molecule, NVS12, in a dose-dependent manner. The reduction seen in the bispecific group was comparable to that observed in the corresponding anti-BTC treated groups.

Figure 18A:
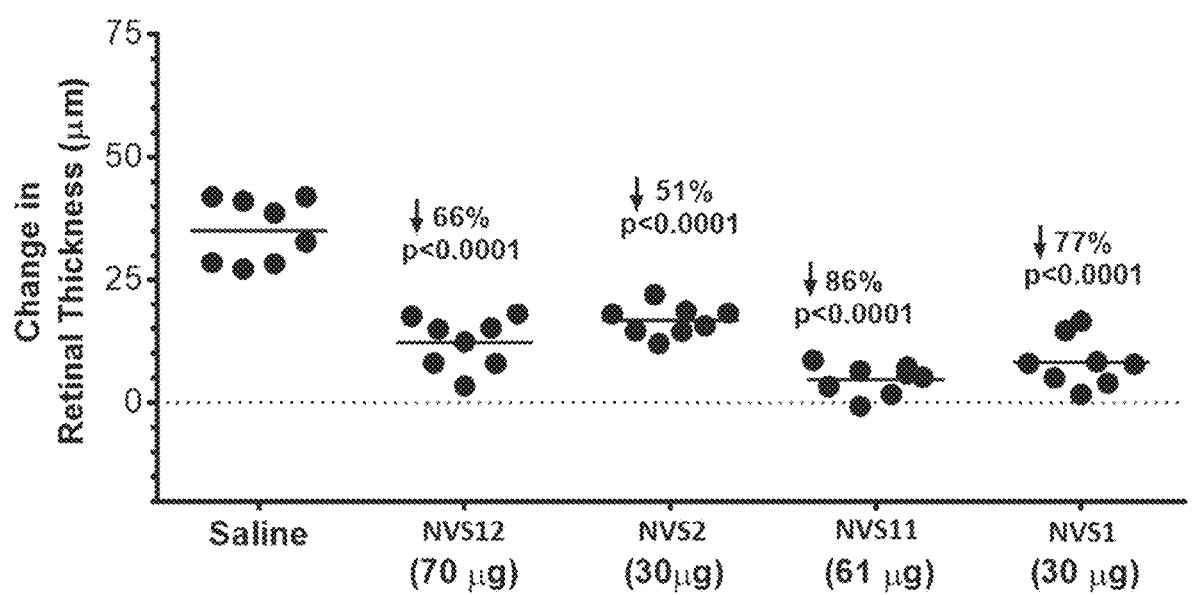
FIG. 18A shows change in retinal thickness of rabbit eyes after treatment with NVS1, NVS11, NVS2, or NVS12.

FIG. 18A shows change in retinal thickness for each rabbit eye (day 14-day 0) for the different treatment groups (BTC alone, 30 pg molar equivalent doses of NVS 11, NVS12, and their corresponding molecules, NVS1 and NVS2, respectively). Both bispecific antibodies, 70 pg of NVS12 and 61 pg of NVS 11, significantly inhibited BTC-induced retinal thickening in rabbit eyes, comparable to approximately equimolar doses of their corresponding molecule, 30 pg of NVS1 and NVS2, respectively.

IVT injection of 0.75 pg/eye human BTC increased retinal thickness by ~36 µm after 7 days (RD-2017-00326, p<0.0001). Histological examination revealed BTC-induced RPE changes including hypertrophy, vacuolation, pigmentary changes, retinal folding and subretinal edema (FIG. 18B, (compare saline injected rabbit in panel A vs BTC injected rabbit in panel B)). BTC-induced histological changes were prevented in rabbits administered 61 pg NVS 11 (FIG. 18B panel C). The histology of rabbit retina shown in FIG. 18B B-D correspond to the rabbit OCT images shown in FIG. 15B. FIG. 18B: panels of retinal histology from rabbits injected IVT with A) saline. B) BTC. C) BTC+61 µg of NVS11. D) BTC+30 µg of NVS1 (positive control). The RPE layer is indicated in each panel by a thick horizontal red arrow. BTC-induced RPE changes denoted by thin red arrows.

Figure 18D:
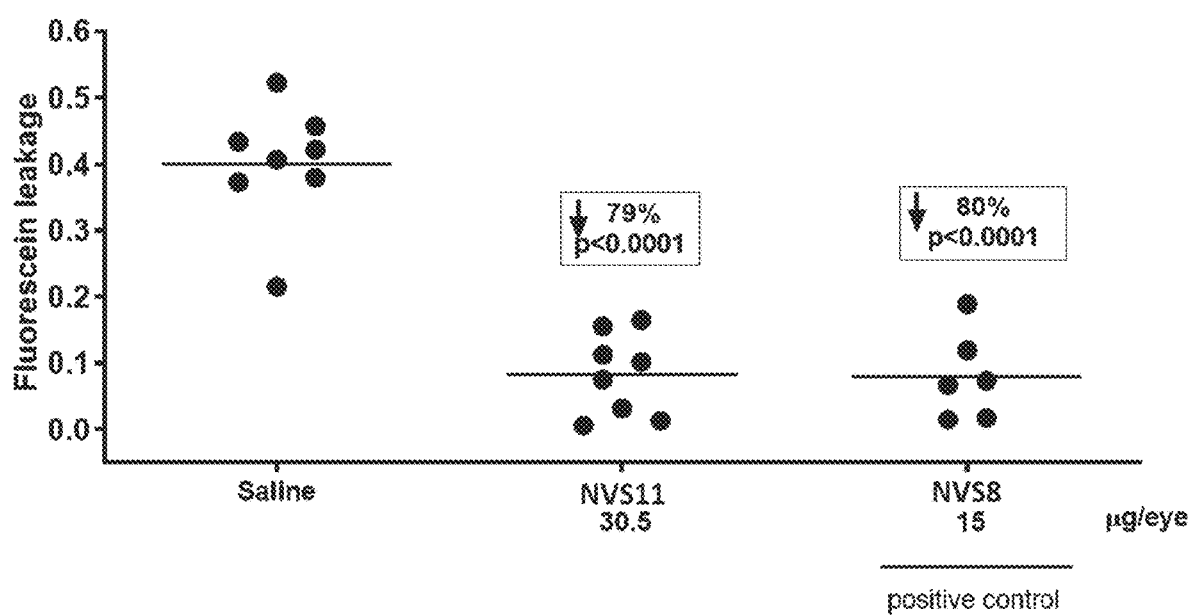
FIG. 18D shows VEGF-induced retinal vessel leakage in rabbits (fluorescein antiography quantitation) in the presence of NVS 11 or NVS8.

IVT human VEGF-A injection (400 ng/eye) induces retinal vascular leakage evident by fluorescein angiography (FIG. 18C). In order to evaluate the effectiveness of NVS 11 blocking VEGF effects in vivo, rabbits were injected IVT with NVS11 14 days prior to a 400 ng/eye IVT VEGF-A challenge. Changes in retinal leakage were assessed 2 days after the VEGF challenge. NVS11 effectively reduced VEGF-induced retinal vascular leakage (79% reduction, p<0.0001, n=2 studies), similar to equimolar dose of the corresponding anti-VEGF Fab (NVS8) reducing fluorescein leakage by 80% (p<0.0001) (FIG. 18D).

Figure 19:
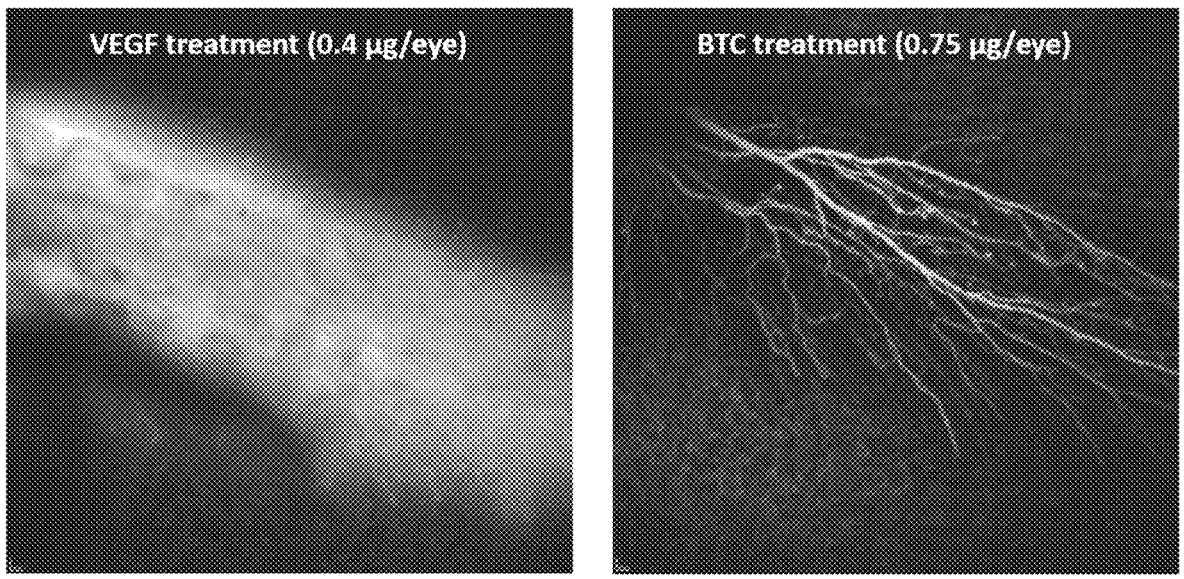
FIG. 19 shows fluorescein angiography images of rabbit eyes after IVT delivery of VEGF or BTC.

FIG. 19 shows representative fluorescein angiography images obtained 2 days after IVT delivery of 400 ng of VEGF (left) and 7 days after 750 ng of BTC (right). VEGF injection causes retinal vascular leakage in rabbits while BTC does not.

Figure 20:
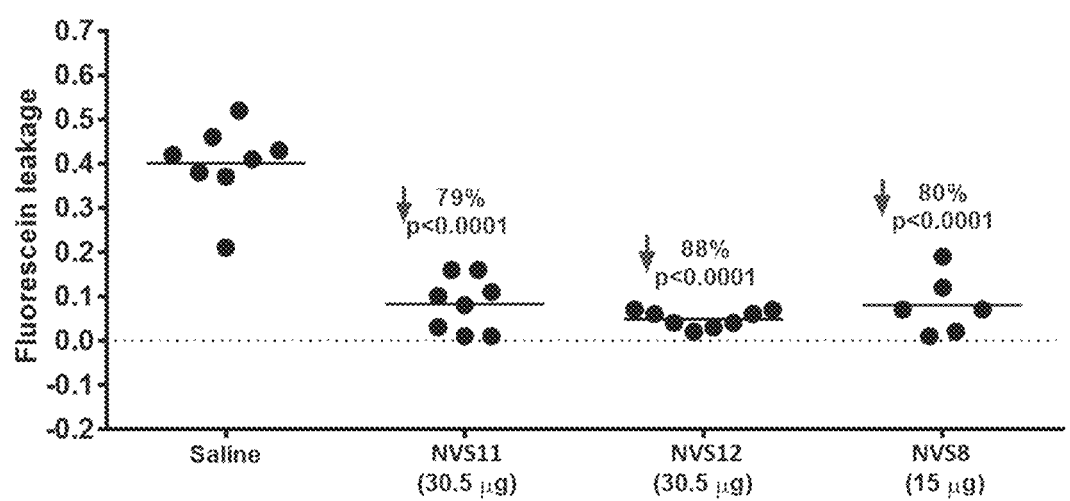
FIG. 20 shows fluorescein vascular leakage values from individual rabbit eyes after treatment with NVS8, NVS11, or NVS12.

FIG. 20 shows fluorescein leakage (t=3-5 min) values from individual eyes from different treatment groups (VEGF alone, or treated with equimolar doses of NVS 11, NVS12, and NVS8). IVT administration is as follows: Day 0: bispecific (30.5ug per eye) and single fab (15ug per eye); Day 14: VEGF (0.4 µg per eye); Day 16: imaging with Scanning Laser Ophthalmoscopy was done to assess fluorescein leakage induced by VEGF injection. Two images were taken per eye. Fluorescein Angiography (FA) was the technique used to image. FD (refers to the image taken before fluorescein injection)—FITC Dextran labeled image provided the architecture of the blood vessels and FA was done following fluorescein injection to determine the leakage. Terminal drugs refers to PK collection to determine drug levels in the eye. Retinal vascular leakage was significantly inhibited by both bispecific molecules and their corresponding anti-VEGF molecule, NVS8. This result was confirmed in two studies.

Figure 21:
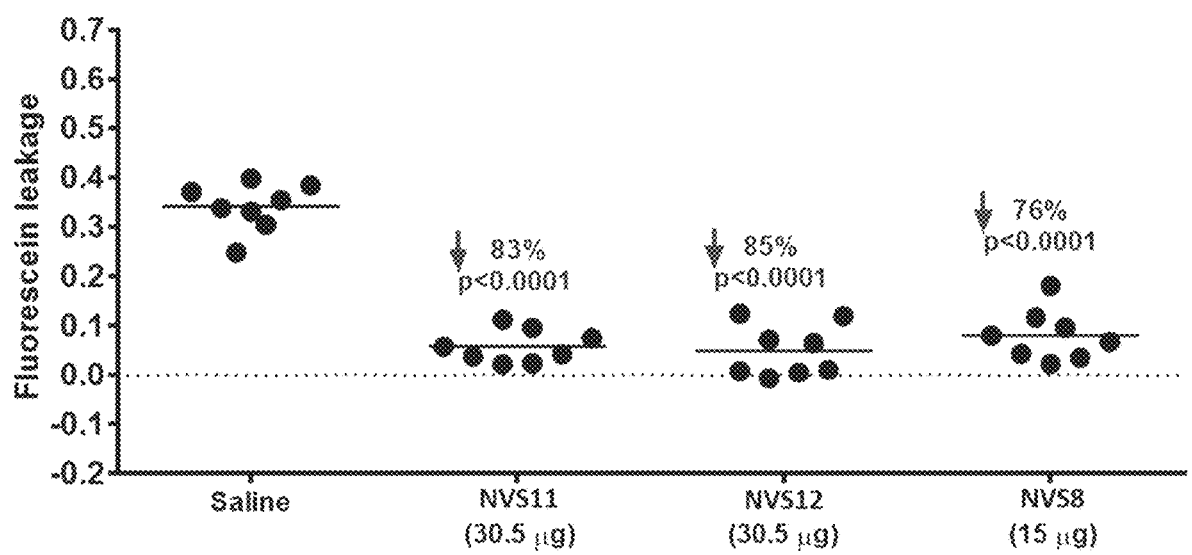
FIG. 21 shows fluorescein vascular leakage values from individual rabbit eyes after treatment with NVS 11, NVS12, or NVS8.

FIG. 21 shows fluorescein leakage (t=3-5 min) of individual eyes injected with saline, 30.5 µg of NVS11, 30.5 µg of NVS12, and 15 µg of NVS8. Although all three Fabs show a decrease in fluorescein leakage, the two bispecifics, NVS 11 and NVS12, exhibit more decrease than NVS8, an anti-VEGF Fab.

Figure 22:
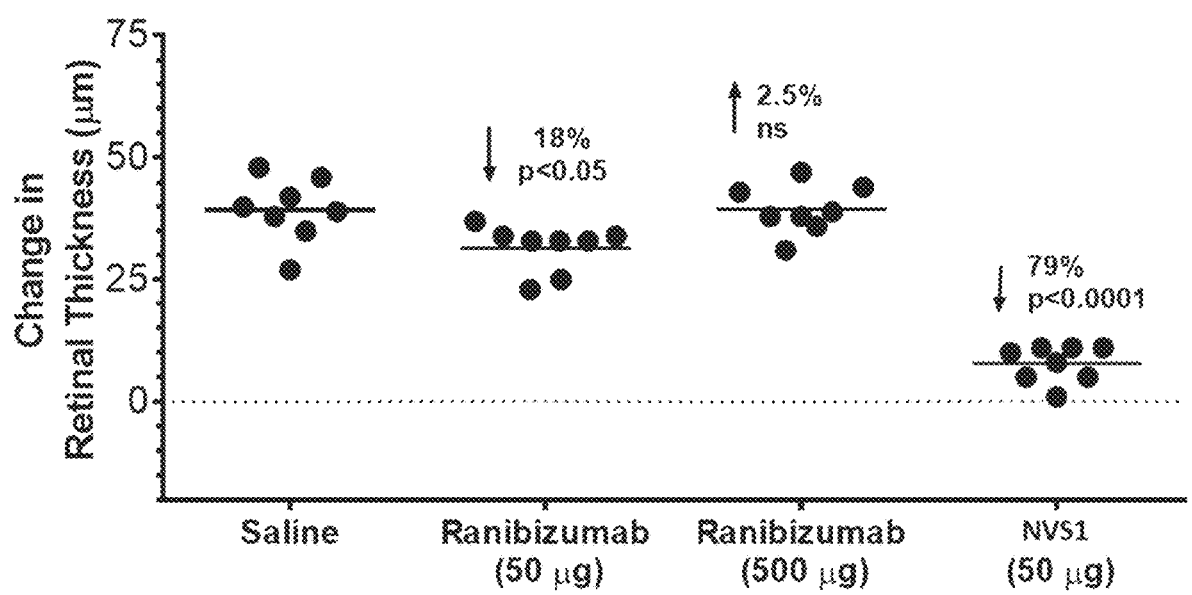
FIG. 22 shows change in total retinal thickness values from individual rabbit eyes after treatment with ranibizumab or NVS1.

FIG. 22 shows change in total retinal thickness values from individual eyes treated with saline, 50 and 500 µg of Lucentis (ranibizumab; anti-VEGF Fab) or 50 µg of NVS1 (anti-BTC Fab). 50 µg of NVS1 significantly inhibited BTC-induced retinal thickening, while both doses of anti-VEGF Fab were unable to inhibit BTC-induced retinal thickening. This result was confirmed in two studies.

Example 15. In Vivo PD Model: BTC Induced Retinal Thickening in Rabbit

Intravitreal (IVT) injection of BTC in rabbits leads to retinal thickening, as detected by optical coherence tomography (OCT). Antibodies tested in the study included: NVS1, parental to NVS1 ("PNVS1"; SEQ ID NOs: 168 and 169), Mor3207 negative control. Briefly, on Day 0, baseline OCT measurements were determined prior to IVT injection of BTC and/or compound.

The study included 6 groups of rabbits: 1) 0.75 µg rhBTC/eye (n=4); 2) 500 µg NVS1/eye (n=3); 3) 0.75 µg rhBTC+500 µg NVS1/eye (n=4); 4) 500 µg PNVS1 (n=3); 5) 0.75 µg rh BTC+500 µg PNVS1/eye (n=4); 6) 0.75 µg rhBTC+500 µg Mor3207/eye (n=4).

On day 7, OCT analysis was performed prior to euthanasia and collection of ocular tissues for histological and PK analysis. Rabbits injected with NVS1 or PNVS1 pre-incubated with BTC exhibited significantly less BTC-induced retinal thickening (both p<0.001) compared to BTC alone. Mean retinal thickness was similar to baseline values after injection of NVS1 or PNVS1 alone. Rabbits injected with Mor3207 pre-incubated with BTC exhibited significantly more retinal thickening (p<0.01) compared to BTC alone. Retinal thickness changes are relative to each animal's retinal thickness prior to IVT injection.

Figure 23:
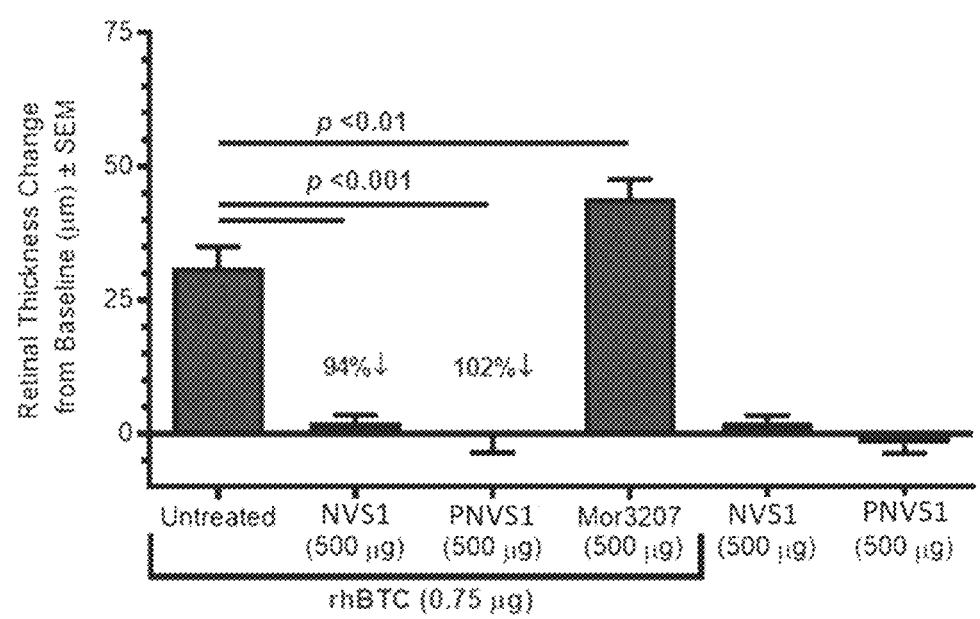
FIG. 23 shows change in retinal thickness in rabbits following treatment with NVS1 or PNVS1.

FIG. 23 shows that both NVS1 and PNVS1 significantly reduced retinal thickness in rabbits relative to untreated control and negative control. Groups were compared by One-Way ANOVA with Dunnett's posttest (P<0.05=significant).

Having described the present disclosure in detail, it will be apparent that modifications, variations, and equivalent aspects are possible without departing from the spirit and scope of the present disclosure as described herein and in the appended claims. Furthermore, it should be appreciated that all examples in the present disclosure are provided as non-limiting examples Example 16. Study in Humans Human study is carried out to assess the safety and tolerability of anti-BTC/anti-VEGF multispecific antibodies described herein, e.g., NVS11-NVS14, following a single intravitreal (IVT) dose in up to 24 participants with DME, RVO, and/or neovascular AMD. Participants eligible for inclusion in this study meet all of the following criteria:

1) Participants with macular edema, in at least one eye, including those with focal or diffuse DME, neovascular AMD, or RVO;
2) Early Treatment Diabetic Retinopathy (ETDRS) letter score in the study eye is worse than 60 letters (20/63) but better than 24 letters (20/320) at screening and baseline; the ETDRS score in the non-study eye is >60 letters at screening and baseline;
3) Sufficiently clear ocular media and adequate pupil dilation to permit fundus photographs of adequate clarity to measure diameters of retinal arteries and veins;
4) Vital signs are within the normal ranges in the sitting position at screening and baseline (pre-injection): oral body temperature between 35.0 and 37.5° C.; systolic blood pressure between 90-160 mmHg; diastolic blood pressure between 50-100 mmHg; pand ulse rate between 40-90 bpm; and Key exclusion criteria of this study include proliferative diabetic retinopathy in the study eye. The following are permitted as an exception:
  a. Tufts of neovascularization less than one disc area with no vitreous hemorrhage; and
  b. Focal, peripheral retinal areas treated with photocoagulation with fewer than 30 laser burns performed at least six months preceding Day 1.

Other exclusion criteria include:
  a. Patients with type 1 or type 2 diabetes who have hemoglobin AlC of >12 at screening;
  b. Other ocular and systemic conditions.

This is an open-label study. No subjects, sponsor personnel, or investigators are masked to treatment assignment or dose level. This study enrolls up to a total of 24 participants, with the possible addition of participants of Japanese ancestry as needed in the highest tolerated dose level. The sample size (N) is based on feasibility considerations and standard practice in first in human studies to characterize safety and pharmacokinetics (PK).

A total of up to four cohorts are enrolled, with an additional optional lower or intermediate cohort of six participants. In one aspect, a dose escalation design of the study comprises the following cohorts:
  a. Cohort 1: 0.25 mg/eye, N=3;
  b. Cohort 2: 0.75 mg/eye, N=3;
  c. Cohort 3: 2.5 mg/eye, N=6;
  d. Cohort 4: 7.5 mg/eye, N=6; and
  e. Cohort 5: optional cohort with intermediate dosing.

In one aspect, a single dose of an anti-BTC/anti-VEGF multispecific antibody described herein, e.g., NVS11-NVS14, is administered intravitreally at Baseline/Day 1 in the study eye. A follow up period lasts until Day 60/end of study (EOS).

As provided above, in one aspect, four dose levels/cohorts of 0.25, 0.75, 2.5, and 7.5 mg/eye are tested. In one aspect, IVT doses are delivered in a volume of 50 µL.

A review of all safety and tolerability data is performed prior to escalation to a higher dose. The time point for dose escalation is chosen at Day 15 when all three participants in cohort 1, two out of three participants in cohort 2, and four out of six participants in cohorts 3 and 4 have reached Day 15. The following datasets are evaluated including the following-up to Day 15 at the dose escalation review: vital signs (body temperature, blood pressure, and pulse rate), ECGs, safety labs, visual acuity, IOP, adverse events, retinal thickness changes, and fluorescein angiography.

In case of notable adverse events or safety concerns during dose escalation of the study, the following changes to the next planned dose level are considered: administration of an intermediate dose between the current and preceding dose; additional participant recruitment for current or previous lower dose; and/or termination of any further dose escalation.

Primary outcome measures of this study include the determination of the number of participants with ocular and nonocular adverse events (from Day 1 through Day 60). The evaluation includes the safety and tolerability of a single IVT dose over two months by reviewing ophthalmic, medical examination, and safety laboratories. Endpoints for the primary outcome measures include:
  a. Characterization of ocular and non-ocular safety by the incidence of treatment-emergent adverse events (AEs) (new or worsening from baseline) summarized categorically by system organ class and/or preferred term; and
  b. Measurement of changes compared to baseline in the following: vital signs, ECG, safety laboratories, IOP, BCVA, and macular thickness as measured by SD-OCT.

Secondary outcome measures of this study include PK profile of an anti-BTC/anti-VEGF multispecific antibody described herein (e.g., NVS11-NVS14) following a single IVT dose, the endpoints of which include serum concentration of total antibody as described by PK parameters including but not limited to Cmax, Tmax, T1/2, AUClast, and AUCinf, all of which are within time frame of Days 1, 2, 5, 15, 29, 43 and 60.

TABLE 4

| | | MISCELLANEOUS SEQUENCES |
|---|---|---|
| SEQ ID NO: 156 | Human ProBTC | MDRAARCSGASSLPLLLALALGLVILHCVVA<u>DGNSTRSPETNGLLC GDPEENCAATTTQSKRKGHFSRCPKQYKHYCIKGRCRFVVAEQTPS CVCDEGYIGARCERVDLFYLRGDRGQILVICLIAVMVVFIILVIGV</u>CTCCHPLRKRRKRKKKEEEMETLGKDITPINEDIEETNIA |
| SEQ ID NO: 157 | Human BTC expressed (D32- Y111) | MDGNSTRSPETNGLLCGDPEENCAATTTQSKRKGHFSRCPKQYKHY CIKGRCRFVVAEQTPSCVCDEGYIGARCERVDLFYhhhhhh |
| SEQ ID NO: 158 | Human BTC | DGNSTRSPETNGLLCGDPEENCAATTTQSKRKGHFSRCPKQYKHYC IKGRCRFVVAEQTPSCVCDEGYIGARCERVDLFY |
| SEQ ID NO: 159 | human immunoglobulin Kappa chain constant region | KRTVAAPSVFIFPPSDEQLKSGTASVVCLLNNFYPREAKVQWKVDN ALQSGNSQESVTEQDSKDSTYSLSSTLTLSKADYEKHKVYACEVTH QGLSSPVTKSFNRGEC |

TABLE 4-continued

MISCELLANEOUS SEQUENCES

| | | |
|---|---|---|
| SEQ ID NO: 160 | human immunoglobulin first constant Ig domain of the heavy chain | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSC |
| SEQ ID NO: 161 | Linker | GGGGSGGGGSGGGGSGGGGS |
| SEQ ID NO: 162 | Linker | GGGGSGGGGSGGGGS |
| SEQ ID NO: 163 | Linker | GGGSGGGGSGS |
| SEQ ID NO: 164 | Linker | EAAAK |
| SEQ ID NO: 165 | Linker | GSGGG |
| SEQ ID NO: 166 | Linker | GSGG |
| SEQ ID NO: 167 | Linker | SGGGSGGGSGGG |

TABLE 5

PARENTAL AND AFFINITY MATURED ANTI-BTC ANTIBODY SEQUENCES

Parental to NVS1

| | | |
|---|---|---|
| SEQ ID NO: 168 | Heavy chain (CDR1, CDR2 CDR3) | QVQLVQSGAEVKKPGSSVKVSCKASGGTFNDYAISWVRQAPGGL EWMGGIIPIFGNANYAQKFQGRVTITADESTSTAYMELSSLRSE DTAVYYCARSSSTYGIHAFDYWGQGTLVTVSSASTKGPSVFPLA PSSKSTSGGTAALGCLVKDYFPEPVTVSWNSGALTSGVHTFPAV LQSSGLYSLSSVVTVPSSSLGTQTYICNVNHKPSNTKVDKKVEP KS |
| SEQ ID NO: 169 | Light chain (CDR1, CDR2 CDR3) | DIQMTQSPSSLSASVGDRVTITCRASQSISNFLNWYQQKPGKAP KLLIYAASNLQSGVPSRFSGSGSGTDFTLTISSLQPEDFATYYC QQYDDFPMTFGQGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |

Affinity matured NVS1 variant

| | | |
|---|---|---|
| SEQ ID NO: 170 | Heavy chain (CDR1, CDR2 CDR3) | QVQLVQSGAEVKKPGSSVKVSCKASGGTFSSYAISWVRQAPGQG LEWMGGIVPWMGIPVYAQKFQGRVTITADESTSTAYMELSSLRS EDTAVYYCARSSSTYGIHAFDYWGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKRV |
| SEQ ID NO: 171 | Light chain (CDR1, CDR2 CDR3) | DIQMTQSPSSLSASVGDRVTITCRASQSISNFLNWYQQKPGKAP KLLIYAASNLQSGVPSRFSGSGSGTDFTLTISSLQPEDFATYYC QQYDDFPMTFGQGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |

Parental to NVS2

| | | |
|---|---|---|
| SEQ ID NO: 172 | Heavy chain (CDR1, CDR2 CDR3) | EVQLLESGGGLVQPGGSLRLSCAASGFTFSSYAMSWVRQAPGKG LEWVSAISGSGGSTYYADSVKGRFTISRDNSKNTLYLQMNSLRA EDTAVYYCARQRYYFGEFDLWGQGTLVTVSSASTKGPSVFPLAP SSKSTSGGTAALGCLVKDYFPEPVTVSWNSGALTSGVHTFPAVL QSSGLYSLSSVVTVPSSSLGTQTYICNVNHKPSNTKVDKKVEPK S |
| SEQ ID NO: 173 | Light chain (CDR1, CDR2 CDR3) | SYELTQPPSVSVSPGQTASITCSGDKLGDKYAYWYQQKPGQSPV LVIYQDSKRPSGIPERFSGSNSGNTATLTISGTQAEDEADYYCQ LYDYLSSTGVFGGGTKLTVLGQPKAAPSVTLFPPSSEELQANKA TLVCLISDFYPGAVTVAWKADSSPVKAGVETTTPSKQSNNKYAA SSYLSLTPEQWKSHRSYSCQVTHEGSTVEKTVAPTEA |

Affinity matured NVS2 variant (TC15)

| | | |
|---|---|---|
| SEQ ID NO: 174 | Heavy chain (CDR1, CDR2 CDR3) | EVQLLESGGGLVQPGGSLRLSCAASGFTFSSYAMSWVRQAPGKG LEWVSAISGSGGSTYYADSVKGRFTISRDNSKNTLYLQMNSLRA EDTAVYYCARQRYYFGEFDLWGQGTLVTVSSASTKGPSVFPLAP |

TABLE 5-continued

PARENTAL AND AFFINITY MATURED ANTI-BTC ANTIBODY SEQUENCES

|  |  |  |
|---|---|---|
|  |  | SSKSTSGGTAALGCLVKDYFPEPVTVSWNSGALTSGVHTFPAVL<br>QSSGLYSLSSVVTVPSSSLGTQTYICNVNHKPSNTKVDKRVEPK<br>SC |
| SEQ ID NO: 175 | Light chain<br>(CDR1, CDR2<br>CDR3) | SYELTQPPSVSVSPGQTASITC<u>SGDKLGDKYAY</u>WYQQKPGQSPV<br>LVIY<u>QDSKRPS</u>GIPERFSGSNSGNTATLTISGTQAEDEADYYC<u>S</u><br><u>TFDYKLSLGV</u>FGGGTKLTVLGQPKAAPSVTLFPPSSEELQANKA<br>TLVCLISDFYPGAVTVAWKADSSPVKAGVETTTPSKQSNNKYAA<br>SSYLSLTPEQWKSHRSYSCQVTHEGSTVEKTVAPTECS |

Affinity matured NVS2 variant

| SEQ ID NO: 176 | Heavy chain<br>(CDR1, CDR2<br>CDR3) | EVQLLESGGGLVQPGGSLRLSCAASGFTFS<u>SYAMS</u>WVRQAPGKG<br>LEWVS<u>AISGSGGSTYYADSVK</u>GRFTISRDNSKNTLYLQMNSLRA<br>EDTAVYYCAR<u>QRYYFGEFDL</u>WGQGTLVTVSSASTKGPSVFPLAP<br>SSKSTSGGTAALGCLVKDYFPEPVTVSWNSGALTSGVHTFPAVL<br>QSSGLYSLSSVVTVPSSSLGTQTYICNVNHKPSNTKVDKRVEPK<br>SC |
|---|---|---|
| SEQ ID NO: 177 | Light chain<br>(CDR1, CDR2<br>CDR3) | SYELTQPPSVSVSPGQTASITC<u>SGDKLGDKYAY</u>WYQQKPGQSPV<br>LVIY<u>QDSKRPS</u>GIPERFSGSNSGNTATLTISGTQAEDEADYYC<u>Q</u><br><u>AFDYYRSSGV</u>FGGGTKLTVLGQPKAAPSVTLFPPSSEELQANKA<br>TLVCLISDFYPGAVTVAWKADSSPVKAGVETTTPSKQSNNKYAA<br>SSYLSLTPEQWKSHRSYSCQVTHEGSTVEKTVAPTECS |

Affinity matured NVS2 variant

| SEQ ID NO: 178 | Heavy chain<br>(CDR1, CDR2<br>CDR3) | EVQLLESGGGLVQPGGSLRLSCAASGFTFS<u>SYAMS</u>WVRQAPGKG<br>LEWVS<u>AISGSGGSTYYADSVK</u>GRFTISRDNSKNTLYLQMNSLRA<br>EDTAVYYCAR<u>QRYYFGEFDL</u>WGQGTLVTVSSASTKGPSVFPLAP<br>SSKSTSGGTAALGCLVKDYFPEPVTVSWNSGALTSGVHTFPAVL<br>QSSGLYSLSSVVTVPSSSLGTQTYICNVNHKPSNTKVDKRVEPK<br>SC |
|---|---|---|
| SEQ ID NO: 179 | Light chain<br>(CDR1, CDR2<br>CDR3) | SYELTQPPSVSVSPGQTASITC<u>SGDKLGDKYAY</u>WYQQKPGQSPV<br>LVIY<u>QDSKRPS</u>GIPERFSGSNSGNTATLTISGTQAEDEADYYC<u>Q</u><br><u>AFDYKSDVGV</u>EGGGTKLTVLGQPKAAPSVTLFPPSSEELQANKA<br>TLVCLISDFYPGAVTVAWKADSSPVKAGVETTTPSKQSNNKYAA<br>SSYLSLTPEQWKSHRSYSCQVTHEGSTVEKTVAPTECS |

Affinity matured NVS2 variant (TC16)

| SEQ ID NO: 180 | Heavy chain<br>(CDR1, CDR2<br>CDR3) | EVQLLESGGGLVQPGGSLRLSCAASGFTFS<u>SYAMS</u>WVRQAPGKG<br>LEWVS<u>AISGSGGSTYYADSVK</u>GRFTISRDNSKNTLYLQMNSLRA<br>EDTAVYYCAR<u>QRYYFGEFDL</u>WGQGTLVTVSSASTKGPSVFPLAP<br>SSKSTSGGTAALGCLVKDYFPEPVTVSWNSGALTSGVHTFPAVL<br>QSSGLYSLSSVVTVPSSSLGTQTYICNVNHKPSNTKVDKRVEPK<br>SC |
|---|---|---|
| SEQ ID NO: 181 | Light chain<br>(CDR1, CDR2<br>CDR3) | SYELTQPPSVSVSPGQTASITC<u>SGDKLGDKYAY</u>WYQQKPGQSPV<br>LVIY<u>QDSKRPS</u>GIPERFSGSNSGNTATLTISGTQAEDEADYYC<u>Q</u><br><u>AFSYLTSGV</u>FGGGTKLTVLGQPKAAPSVTLFPPSSEELQANKA<br>TLVCLISDFYPGAVTVAWKADSSPVKAGVETTTPSKQSNNKYAA<br>SSYLSLTPEQWKSHRSYSCQVTHEGSTVEKTVAPTECS |

Affinity matured NVS2 variant

| SEQ ID NO: 182 | Heavy chain<br>(CDR1, CDR2<br>CDR3) | EVQLLESGGGLVQPGGSLRLSCAASGFTFS<u>SYAMS</u>WVRQAPGKG<br>LEWVS<u>AISGSGGSTYYADSVK</u>GRFTISRDNSKNTLYLQMNSLRA<br>EDTAVYYCAR<u>QRYYFGEFDL</u>WGQGTLVTVSSASTKGPSVFPLAP<br>SSKSTSGGTAALGCLVKDYFPEPVTVSWNSGALTSGVHTFPAVL<br>QSSGLYSLSSVVTVPSSSLGTQTYICNVNHKPSNTKVDKRVEPK<br>SC |
|---|---|---|
| SEQ ID NO: 183 | Light chain<br>(CDR1, CDR2<br>CDR3) | SYELTQPPSVSVSPGQTASITC<u>SGDKLGDKYAY</u>WYQQKPGQSPV<br>LVIY<u>QDSKRPS</u>GIPERFSGSNSGNTATLTISGTQAEDEADYYC<u>Q</u><br><u>SFDYLYSSGV</u>FGGGTKLTVLGQPKAAPSVTLFPPSSEELQANKA<br>TLVCLISDFYPGAVTVAWKADSSPVKAGVETTTPSKQSNNKYAA<br>SSYLSLTPEQWKSHRSYSCQVTHEGSTVEKTVAPTECS |

Affinity matured NVS2 variant

| SEQ ID NO: 184 | Heavy chain<br>(CDR1, CDR2 | EVQLLESGGGLVQPGGSLRLSCAASGFTFS<u>SYAMS</u>WVRQAPGKG<br>LEWVS<u>AISGSGGSTYYADSVK</u>GRFTISRDNSKNTLYLQMNSLRA<br>EDTAVYYCAR<u>QRYYFGEFDL</u>WGQGTLVTVSSASTKGPSVFPLAP<br>SSKSTSGGTAALGCLVKDYFPEPVTVSWNSGALTSGVHTFPAVL |
|---|---|---|
| SEQ ID NO: 185 |  | QSSGLYSLSSVVTVPSSSLGTQTYICNVNHKPSNTKVDKRVEPK<br>SC |

TABLE 5-continued

PARENTAL AND AFFINITY MATURED ANTI-BTC ANTIBODY SEQUENCES

|  | Light chain (CDR1, CDR2 CDR3) | SYELTQPPSVSVSPGQTASITC<u>SGDKLGDKYAY</u>WYQQKPGQSPV LVIY<u>QDSKRPS</u>GIPERFSGSNSGNTATLTISGTQAEDEADYYC<u>Q <br>TFYYLSSLGV</u>FGGGTKLTVLGQPKAAPSVTLFPPSSEELQANKA TLVCLISDFYPGAVTVAWKADSSPVKAGVETTTPSKQSNNKYAA SSYLSLTPEQWKSHRSYSCQVTHEGSTVEKTVAPTECS |

Affinity matured NVS2 variant

| SEQ ID NO: 186 | Heavy chain (CDR1, CDR2 CDR3) | EVQLLESGGGLVQPGGSLRLSCAASGFTFS<u>SYAMS</u>WVRQAPGKG LEWVS<u>AISGSGGSTYYADSVKG</u>RFTISRDNSKNTLYLQMNSLRA EDTAVYYCAR<u>QRYYFGEFDL</u>WGQGTLVTVSSASTKGPSVFPLAP SSKSTSGGTAALGCLVKDYFPEPVTVSWNSGALTSGVHTFPAVL QSSGLYSLSSVVTVPSSSLGTQTYICNVNHKPSNTKVDKRVEPK SC |
| --- | --- | --- |
| SEQ ID NO: 187 | Light chain (CDR1, CDR2 CDR3) | SYELTQPPSVSVSPGQTASITC<u>SGDKLGDKYAY</u>WYQQKPGQSPV LVIY<u>QDSKRPS</u>GIPERFSGSNSGNTATLTISGTQAEDEADYYC<u>Q AFDYLASSGV</u>FGGGTKLTVLGQPKAAPSVTLFPPSSEELQANKA TLVCLISDFYPGAVTVAWKADSSPVKAGVETTTPSKQSNNKYAA SSYLSLTPEQWKSHRSYSCQVTHEGSTVEKTVAPTECS |

Affinity matured NVS2 variant

| SEQ ID NO: 188 | Heavy chain (CDR1, CDR2 CDR3) | EVQLLESGGGLVQPGGSLRLSCAASGFTFS<u>SYAMS</u>WVRQAPGKG LEWVS<u>AISGSGGSTYYADSVKG</u>AISGSGGSTYYADSVKG<u>QRYYF GEFDL</u>WGQGTLVTVSSASTKGPSVFPLAPSSKSTSGGTAALGCL VKDYEPEPVTVSWNSGALTSGVHTFPAVLQSSGLYSLSSVVTVP SSSLGTQTYICNVNHKPSNTKVDKRVEPKSC |
| --- | --- | --- |
| SEQ ID NO: 189 | Light chain (CDR1, CDR2 CDR3) | SYELTQPPSVSVSPGQTASITC<u>SGDKLGDKYAY</u>WYQQKPGQSPV LVIY<u>QDSKRPS</u>GIPERFSGSNSGNTATLTISGTQAEDEADYYC<u>Q AFDYLHSIGV</u>FGGGTKLTVLGQPKAAPSVTLFPPSSEELQANKA TLVCLISDFYPGAVTVAWKADSSPVKAGVETTTPSKQSNNKYAA SSYLSLTPEQWKSHRSYSCQVTHEGSTVEKTVAPTECS |

Parental to NVS3

| SEQ ID NO: 190 | Heavy chain (CDR1, CDR2 CDR3) | EVQLLESGGGLVQPGGSLRLSCAASGFTFS<u>DHAMH</u>WVRQAPGKG LEWVS<u>SIVYDGSNTFYADSVKG</u>RFTISRDNSKNTLYLQMNSLRA EDTAVYYCAR<u>DYLDFGYYFDV</u>WGQGTLVTVSSASTKGPSVFPLA PSSKSTSGGTAALGCLVKDYFPEPVTVSWNSGALTSGVHTFPAV LQSSGLYSLSSVVTVPSSSLGTQTYICNVNHKPSNTKVDKKVEP KS |
| --- | --- | --- |
| SEQ ID NO: 191 | Light chain (CDR1, Q3, CDR3) | DlELTQPPSVSVSPGQTASITC<u>SGDKIGKKYVH</u>WYQQKPGQAPV LVIY<u>DDSDRPS</u>GIPERFSGSNSGNTATLTISGTQAEDEADYYC<u>Q AWDMQSVV</u>FGGGTKLTVLGQPKAAPSVTLFPPSSEELQANKATL VCLISDFYPGAVTVAWKADSSPVKAGVETTTPSKQSNNKYAASS YLSLTPEQWKSHRSYSCQVTHEGSTVEKTVAPTEC |

Affinity matured NVS3 variant (TC12)

| SEQ ID NO: 192 | Heavy chain (CDR1, CDR2 CDR3) | QVQLLESGGGLVQPGGSLRLSCAASGFTFS<u>SYAMS</u>WVRQAPGKG LEWVS<u>GLGHVGYTTYTDSVKG</u>RFTISRDNSKNTLYLQMNSLRAE DTAVYYCAR<u>DYLDFGYYFDV</u>WGQGTLVTVSSASTKGPSVFPLAP SSKSTSGGTAALGCLVKDYFPEPVTVSWNSGALTSGVHTFPAVL QSSGLYSLSSVVTVPSSSLGTQTYICNVNHKPSNTKVDKRVEPK SC |
| --- | --- | --- |
| SEQ ID NO: 193 | Light chain (CDR1, CDR2 CDR3) | DIELTQPPSVSVSPGQTASITC<u>SGDKIGKKYVH</u>WYQQKPGQAPV LVIY<u>DDSDRPS</u>GIPERFSGSNSGNTATLTISGTQAEDEADYYC<u>Q AWDMQSVV</u>FGGGTKLTVLGQPKAAPSVTLFPPSSEELQANKATL VCLISDFYPGAVTVAWKADSSPVKAGVETTTPSKQSNNKYAASS YLSLTPEQWKSHRSYSCQVTHEGSTVEKTVAPTECS |

Parental to NVS4

| SEQ ID NO: 194 | Heavy chain (CDR1, CDR2 CDR3) | EVQLLESGGGLVQPGGSLRLSCAASGFTFS<u>RYWIS</u>WVRQAPGKG LEWVS<u>YIDSWGSYTNYADSVKG</u>RFTISRDNSKNTLYLQMNSLRA EDTAVYYCAR<u>GGSLFDY</u>WGQGTLVTVSSASTKGPSVFPLAPSSK STSGGTAALGCLVKDYFPEPVTVSWNSGALTSGVHTFPAVLQSS GLYSLSSVVTVPSSSLGTQTYICNVNHKPSNTKVDKKVEPKS |
| --- | --- | --- |
| SEQ ID NO: 195 | Light chain (CDR1, CDR2 CDR3) | DIQMTQSPSSLSASVGDRVTITC<u>RASQGIISYLGW</u>YQQKPGKAP KLLIY<u>AASSLQS</u>GVPSRFSGSGSGTDFTLTISSLQPEDFATYYC <u>QQYDALNT</u>FGQGTKVEIKRTVAAPSVFIFPPSDEQLKSGTASVV |

TABLE 5-continued

PARENTAL AND AFFINITY MATURED ANTI-BTC ANTIBODY SEQUENCES

CLLNNFYPREAKVQWKVDNALQSGNSQESVTEQDSKDSTYSLSS
TLTLSKADYEKHKVYACEVTHQGLSSPVTKSFNRGEA

Affinity matured NVS4 variant

SEQ ID NO: 196 Heavy chain (CDR1, CDR2 CDR3)
QVQLLESGGGLVQPGGSLRLSCAASGFTFS<u>RYWIS</u>WVRQAPGKG
LEWVS<u>YIDSWGSYTNYADSVKG</u>RFTISRDNSKNTLYLQMNSLRA
EDTAVYYCAR<u>GGSLFDY</u>WGQGTLVTVSSASTKGPSVFPLAPSSK
STSGGTAALGCLVKDYFPEPVTVSWNSGALTSGVHTFPAVLQSS
GLYSLSSVVTVPSSSLGTQTYICNVNHKPSNTKVDKRVEPKSC SEQ ID NO: 197 Light chain (CDR1, CDR2 CDR3)
DIQMTQSPSSLSASVGDRVTITC<u>RASQGIISYLG</u>WYQQKPGKAP
KLLIY<u>AASSLQS</u>GVPSRFSGSGSGTDFTLTISSLQPEDFATYYC
<u>QQYDDWDT</u>FGQGTKVEIKRTVAAPSVFIFPPSDEQLKSGTASVV
CLLNNFYPREAKVQWKVDNALQSGNSQESVTEQDSKDSTYSLSS
TLTLSKADYEKHKVYACEVTHQGLSSPVTKSFNRGEC

Affinity matured NVS4 variant

SEQ ID NO: 198 Heavy chain (CDR1, CDR2 CDR3)
QVQLLESGGGLVQPGGSLRLSCAASGFTFS<u>RYWIS</u>WVRQAPGKG
LEWVS<u>YIDSWGSYTNYADSVKG</u>RFTISRDNSKNTLYLQMNSLRA
EDTAVYYCAR<u>GGSLFDY</u>WGQGTLVTVSSASTKGPSVFPLAPSSK
STSGGTAALGCLVKDYFPEPVTVSWNSGALTSGVHTFPAVLQSS
GLYSLSSVVTVPSSSLGTQTYICNVNHKPSNTKVDKRVEPKSC SEQ ID NO: 199 Light chain (CDR1, CDR2 CDR3)
DIQMTQSPSSLSASVGDRVTITC<u>RASQGIISYLG</u>WYQQKPGKAP
KLLIY<u>AASSLQS</u>GVPSRFSGSGSGTDFTLTISSLQPEDFATYYC
<u>QQYDDFDT</u>FGQGTKVEIKRTVAAPSVFIFPPSDEQLKSGTASVV
CLLNNFYPREAKVQWKVDNALQSGNSQESVTEQDSKDSTYSLSS
TLTLSKADYEKHKVYACEVTHQGLSSPVTKSFNRGEC

Affinity matured NVS4 variant

SEQ ID NO: 200 Heavy chain (CDR1, CDR2 CDR3)
QVQLLESGGGLVQPGGSLRLSCAASGFTFS<u>RYWIS</u>WVRQAPGKG
LEWVS<u>YIDSGGTFINYADSVKG</u>RFTISRDNSKNTLYLQMNSLRA
EDTAVYYCAR<u>GGSLFDY</u>WGQGTLVTVSSASTKGPSVFPLAPSSK
STSGGTAALGCLVKDYFPEPVTVSWNSGALTSGVHTFPAVLQSS
GLYSLSSVVTVPSSSLGTQTYICNVNHKPSNTKVDKRVEPKSC SEQ ID NO: 201 Light chain (CDR1, CDR2 CDR3)
DIQMTQSPSSLSASVGDRVTITC<u>RASQGIISYLG</u>WYQQKPGKAP
KLLIY<u>AASSLQS</u>GVPSRFSGSGSGTDFTLTISSLQPEDFATYYC
<u>QQYDALNT</u>FGQGTKVEIKRTVAAPSVFIFPPSDEQLKSGTASVV
CLLNNFYPREAKVQWKVDNALQSGNSQESVTEQDSKDSTYSLSS
TLTLSKADYEKHKVYACEVTHQGLSSPVTKSFNRGEC

Affinity matured NVS4 variant (1C23)

SEQ ID NO: 202 Heavy chain (CDR1, CDR2 CDR3)
QVQLLESGGGLVQPGGSLRLSCAASGFTFS<u>RYWIS</u>WVRQAPGKG
LEWVS<u>YIDSTGTFIHYADSVKG</u>RFTISRDNSKNTLYLQMNSLRA
EDTAVYYCAR<u>GGSLFDY</u>WGQGTLVTVSSASTKGPSVFPLAPSSK
STSGGTAALGCLVKDYFPEPVTVSWNSGALTSGVHTFPAVLQSS
GLYSLSSVVTVPSSSLGTQTYICNVNHKPSNTKVDKRVEPKSC SEQ ID NO: 203 Light chain (CDR1, CDR2 CDR3)
DIQMTQSPSSLSASVGDRVTITC<u>RASQGIISYLG</u>WYQQKPGKAP
KLLIY<u>AASSLQS</u>GVPSRFSGSGSGTDFTLTISSLQPEDFATYYC
<u>QQYDALNT</u>FGQGTKVEIKRTVAAPSVFIFPPSDEQLKSGTASVV
CLLNNFYPREAKVQWKVDNALQSGNSQESVTEQDSKDSTYSLSS
TLTLSKADYEKHKVYACEVTHQGLSSPVTKSFNRGEC

Affinity matured NVS4 variant

SEQ ID NO: 204 Heavy chain (CDR1, CDR2 CDR3)
QVQLLESGGGLVQPGGSLRLSCAASGFTFS<u>RYWIS</u>WVRQAPGKG
LEWVS<u>HIDSNSDWTSYADSVKG</u>RFTISRDNSKNTLYLQMNSLRA
EDTAVYYCAR<u>GGSLFDY</u>WGQGTLVTVSSASTKGPSVFPLAPSSK
STSGGTAALGCLVKDYFPEPVTVSWNSGALTSGVHTFPAVLQSS
GLYSLSSVVTVPSSSLGTQTYICNVNHKPSNTKVDKRVEPKSC SEQ ID NO: 205 Light chain (CDR1, CDR2 CDR3)
DIQMTQSPSSLSASVGDRVTITC<u>RASQGIISYLG</u>WYQQKPGKAP
KLLIY<u>AASSLQS</u>GVPSRFSGSGSGTDFTLTISSLQPEDFATYYC
<u>QQYDALNT</u>FGQGTKVEIKRTVAAPSVFIFPPSDEQLKSGTASVV
CLLNNFYPREAKVQWKVDNALQSGNSQESVTEQDSKDSTYSLSS
TLTLSKADYEKHKVYACEVTHQGLSSPVTKSFNRGEC

Affinity matured NVS4 variant

SEQ ID NO: 206 Heavy chain (CDR1, CDR2 CDR3)
QVQLLESGGGLVQPGGSLRLSCAASGFTFS<u>RYWIS</u>WVRQAPGKG
LEWVS<u>HINYEGTWTLYADSVKG</u>RFTISRDNSKNTLYLQMNSLRA
EDTAVYYCAR<u>GGSLFDY</u>WGQGTLVTVSSASTKGPSVFPLAPSSK

TABLE 5-continued

PARENTAL AND AFFINITY MATURED ANTI-BTC ANTIBODY SEQUENCES

| | | |
|---|---|---|
| | | STSGGTAALGCLVKDYFPEPVTVSWNSGALTSGVHTFPAVLQSS<br>GLYSLSSVVTVPSSSLGTQTYICNVNHKPSNTKVDKRVEPKSC |
| SEQ ID NO: 207 | Light chain<br>(CDR1, CDR2<br>CDR3) | DIQMTQSPSSLSASVGDRVTITC<u>RASQGIISYL</u>GWYQQKPGKAP<br>KLLIY<u>AASSLQS</u>GVPSRFSGSGSGTDFTLTISSLQPEDFATYYC<br><u>QQYDALNT</u>FGQGTKVEIKRTVAAPSVFIFPPSDEQLKSGTASVV<br>CLLNNFYPREAKVQWKVDNALQSGNSQESVTEQDSKDSTYSLSS<br>TLTLSKADYEKHKVYACEVTHQGLSSPVTKSFNRGEC |

Enumerated Embodiments

1. An isolated antibody or antigen binding fragment thereof that binds specifically to betacellulin (BTC).

2. The antibody or antigen binding fragment thereof of embodiment 1, which blocks BTC binding to ErbB1, ErbB4, or both.

3. The antibody or antigen binding fragment thereof of embodiment 1 or 2, which blocks BTC-induced phospoh-ERK1/2 activation.

4. The antibody or antigen binding fragment thereof of any one of embodiments 1 to 3, which blocks BTC-induced phospoh-HER3 activation.

5. An isolated antibody or antigen binding fragment thereof that binds specifically to BTC, wherein the antibody or antigen binding fragment has a dissociation constant (KD) of 5 pM or less.

6. The antibody or antigen binding fragment thereof of any one of embodiments 1 to 5, which binds to BTC comprising the amino acid sequence of SEQ ID NO: 157.

7. The antibody or antigen binding fragment thereof of embodiment 6, which binds to at least one residue of SEQ ID NO: 157 selected from the group consisting of G34, H35, F36, S37, R38, C39, P40, K41, Q42, Y43, H45, Y46, R51, R53, F54, V56, A57, E58, Q59, T60, P61, A72, R73, E75, and R76.

8. The antibody or antigen binding fragment thereof of any one of embodiments 1 to 7, which binds to R38, C39, P40, K41, Q42, Y43, H45, Y46, F54, Q59, T60, P61, and R73 of SEQ ID NO: 157.

9. The antibody or antigen binding fragment thereof of any one of embodiments 1 to 8, which comprises heavy chain variable region complementarity determining region 1 (HCDR1), heavy chain variable region complementarity determining region 2 (HCDR2), and heavy chain variable region complementarity determining region 3 (HCDR3) as set forth in SEQ ID NOs: 1, 2, and 3, respectively, and light chain variable region complementarity determining region 1 (LCDR1), light chain variable region complementarity determining region 2 (LCDR2), and light chain variable region complementarity determining region 3 (LCDR3) as set forth in SEQ ID NOs: 14, 15, and 16, respectively.

10. The antibody or antigen binding fragment thereof of any one of embodiments 1 to 9, which comprises HCDR1, HCDR2, and HCDR3 as set forth in SEQ ID NOs: 4, 2, and 3, respectively, and LCDR1, LCDR2, and LCDR3 as set forth in SEQ ID NOs: 14, 15, and 16, respectively.

11. The antibody or antigen binding fragment thereof of any one of embodiments 1 to 9, wherein the HCDR1 comprises the consensus sequence XYAIS and/or the HCDR2 comprises the consensus sequence GIXPXXGXXXYAQKFQG, and wherein X is any amino acid and may not be the same in different positions.

12. The antibody or antigen binding fragment thereof of embodiment 11, which comprises a heavy chain sequence of SEQ ID NO: 168 and a light chain sequence of SEQ ID NO: 169, or a heavy chain sequence of SEQ ID NO: 170 and a light chain sequence of SEQ ID NO: 171.

13. The antibody or antigen binding fragment thereof of any one of embodiments 1 to 9, which comprises HCDR1, HCDR2, and HCDR3 as set forth in SEQ ID NOs: 5, 6, and 3, respectively, and LCDR1, LCDR2, and LCDR3 as set forth in SEQ ID NOs: 17, 18, and 19, respectively.

14. The antibody or antigen binding fragment thereof of any one of embodiments 1 to 9, which comprises HCDR1, HCDR2, and HCDR3 as set forth in SEQ ID NOs: 7, 8, and 9, respectively, and LCDR1, LCDR2, and LCDR3 as set forth in SEQ ID NOs: 20, 18, and 16, respectively.

15. The antibody or antigen binding fragment thereof of any one of embodiments 9 to 14, which comprises a heavy chain variable region (VH) and a light chain variable region (VL) comprising an amino acid sequence with at least about 90%, 95%, 96%, 97%, 98%, 99%, or 100% sequence identity to SEQ ID NOs: 10 and 21, respectively.

16. The antibody or antigen binding fragment thereof of embodiment 15, wherein the differences in amino acid sequence is not within the complementary determining regions.

17. The antibody or antigen binding fragment thereof of embodiment 15, wherein the differences in amino acid sequence are conservative substitutions.

18. The antibody or antigen binding fragment thereof of embodiment 15, which comprises a VH and VL comprising amino acid sequence as set forth in SEQ ID NOs: 10 and 21, respectively.

19. The antibody or antigen binding fragment thereof of embodiment 18, wherein the $V_H$ and $V_L$ are encoded by a nucleic acid sequence as set forth in SEQ ID NOs: 11 and 22, respectively.

20. The antibody or antigen binding fragment thereof of any one of embodiments 1 to 19, which comprises a heavy chain and a light chain with an amino acid sequence as set forth in SEQ ID NOs: 12 and 23, respectively.

21. The antibody or antigen binding fragment thereof of embodiment 20, wherein the heavy chain and light chain are encoded by the nucleic acid sequence with at least 90%, 95%, 96%, 97%, 98%, 99%, or 100% sequence identity to SEQ ID NOs: 13 and 24, respectively.

22. The antibody or antigen binding fragment thereof of any one of embodiments 9 to 21, which comprises 1) HCDR1, HCDR2, and HCDR3 comprised in a $V_H$ with the amino acid sequence of SEQ ID NO: 10, and 2) LCDR1, LCDR2, and LCDR3 comprised in a $V_L$ with the amino acid sequence of SEQ ID NO: 21.

23. The antibody or antigen binding fragment thereof of embodiment 22, wherein the HCDR1, HCDR2, HCDR3, LCDR1, LCDR2, and LCDR3 comprises:

a. SEQ ID NOs: 1, 2, 3, 14, 15, and 16, respectively;
b. SEQ ID NOs: 4, 2, 3, 14, 15, and 16, respectively;
c. SEQ ID NOs: 5, 6, 3, 17, 18, and 19, respectively; or
d. SEQ ID NOs: 7, 8, 9, 20, 18, and 16, respectively.

24. The antibody or antigen binding fragment thereof of any one of embodiments 1 to 8, which comprises HCDR1, HCDR2, HCDR3, LCDR1, LCDR2, and LCDR3, wherein a. the HCDR1 comprises the amino acid sequence selected from the group consisting of SEQ ID NOs: 1, 4, 5, and 7, the HCDR2 comprises the amino acid sequence selected from the group consisting of SEQ ID NOs: 2, 6, and 8, the HCDR3 comprises the amino acid sequence selected from the group consisting of SEQ ID NOs: 3 and 9, and b. the LCDR1 comprises the amino acid sequence selected from the group consisting of SEQ ID NOs: 14, 17, and 20, the LCDR2 comprises the amino acid sequence selected from the group consisting of SEQ ID NOs: 15 and 18, the LCDR3 comprises the amino acid sequence selected from the group consisting of SEQ ID NOs: 16 and 19.

25. The antibody or antigen binding fragment thereof of embodiment 24, which comprises a VH and VL comprising the amino acid sequence of SEQ ID NOs: 10 and 21, respectively.

26. The antibody or antigen binding fragment thereof of embodiment 25, which comprises a heavy chain and a light chain with the amino acid sequence as set forth in SEQ ID NOs: 12 and 23, respectively.

27. An isolated antibody or antigen binding fragment thereof that binds specifically to BTC, which comprises a VH and a VL with the amino acid sequence of SEQ ID NOs: 10 and 21, respectively.

28. The antibody or antigen binding fragment thereof of any one of embodiments 1 to 7, which binds to P40, K41, Q42, Y43, H45, Y46, E58, Q59, T60, P61, A72, R73, E75, and R76 of SEQ ID NO: 157.

29. The antibody or antigen binding fragment thereof of any one of embodiments 1 to 7 and 28, which comprises HCDR1, HCDR2, and HCDR3 as set forth in SEQ ID NOs: 25, 26, and 27, respectively, and LCDR1, LCDR2, and LCDR3 as set forth in SEQ ID NOs: 38, 39, and 40, respectively.

30. The antibody or antigen binding fragment thereof of any one of embodiments 1 to 7 and 28, which comprises HCDR1, HCDR2, and HCDR3 as set forth in SEQ ID NOs: 28, 26, and 27, respectively, and LCDR1, LCDR2, and LCDR3 as set forth in SEQ ID NOs: 38, 39, and 40, respectively.

31. The antibody or antigen binding fragment thereof of any one of embodiments 1 to 7 and 28, which comprises HCDR1, HCDR2, and HCDR3 as set forth in SEQ ID NOs: 29, 30, and 27, respectively, and LCDR1, LCDR2, and LCDR3 as set forth in SEQ ID NOs: 41, 42, and 43, respectively.

32. The antibody or antigen binding fragment thereof of any one of embodiments 1 to 7 and 28, which comprises HCDR1, HCDR2, and HCDR3 as set forth in SEQ ID NOs: 31, 32, and 33, respectively, and LCDR1, LCDR2, and LCDR3 as set forth in SEQ ID NOs: 44, 42, and 40, respectively.

33. The antibody or antigen binding fragment thereof of any one of embodiments 28 to 32, which comprises a VH and a VL comprising an amino acid sequence with at least about 90%, 95%, 96%, 97%, 98%, 99%, or 100% sequence identity to SEQ ID NOs: 34 and 45, respectively.

34. The antibody or antigen binding fragment thereof of embodiment 33, wherein the differences in amino acid sequence is not within the complementary determining regions.

35. The antibody or antigen binding fragment thereof of embodiment 33, wherein the differences in amino acid sequence are conservative substitutions.

36. The antibody or antigen binding fragment thereof of embodiment 33, which comprises a VH and VL comprising amino acid sequence as set forth in SEQ ID NOs: 34 and 45, respectively.

37. The antibody or antigen binding fragment thereof of embodiment 36, wherein the VH and VL are encoded by a nucleic acid sequence as set forth in SEQ ID NOs: 35 and 46, respectively.

38. The antibody or antigen binding fragment thereof of any one of embodiments 28 to 37, which comprises a heavy chain and a light chain with an amino acid sequence as set forth in SEQ ID NOs: 36 and 47, respectively.

39. The antibody or antigen binding fragment thereof of embodiment 38, wherein the heavy chain and light chain are encoded by a nucleic acid sequence with at least about 90%, 95%, 96%, 97%, 98%, 99%, or 100% sequence identity to SEQ ID NOs: 37 and 48, respectively.

40. The antibody or antigen binding fragment thereof of any one of embodiments 28 to 39, which comprises 1) HCDR1, HCDR2, and HCDR3 comprised in a VH with the amino acid sequence of SEQ ID NO: 34, and 2) LCDR1, LCDR2, and LCDR3 comprised in a VL with the amino acid sequence of SEQ ID NO: 45.

41. The antibody or antigen binding fragment thereof of embodiment 40, wherein the HCDR1, HCDR2, HCDR3, LCDR1, LCDR2, and LCDR3 comprises:
a. SEQ ID NOs: 25, 26, 27, 38, 39, and 40, respectively;
b. SEQ ID NOs: 28, 26, 27, 38, 39, and 40, respectively;
c. SEQ ID NOs: 29, 30, 27, 41, 42, and 43, respectively; or
d. SEQ ID NOs: 31, 32, 33, 44, 42, and 40, respectively.

42. The antibody or antigen binding fragment thereof of any one of embodiments 1 to 7 and 28, which comprises HCDR1, HCDR2, HCDR3, LCDR1, LCDR2, and LCDR3, wherein
a. the HCDR1 comprises the amino acid sequence selected from the group consisting of SEQ ID NOs: 25, 28, 29, and 31, the HCDR2 comprises the amino acid sequence selected from the group consisting of SEQ ID NOs: 26, 30, and 32, the HCDR3 comprises the amino acid sequence selected from the group consisting of SEQ ID NOs: 27 and 33; and
b. the LCDR1 comprises the amino acid sequence selected from the group consisting of SEQ ID NOs: 38, 41, and 44, the LCDR2 comprises the amino acid sequence selected from the group consisting of SEQ ID NOs: 39 and 42, the LCDR3 comprises the amino acid sequence selected from the group consisting of SEQ ID NOs: 40 and 43.

43. The antibody or antigen binding fragment thereof of embodiment 42, which comprises a VH and VL comprising the amino acid sequence of SEQ ID NOs: 34 and 45, respectively.

44. The antibody or antigen binding fragment thereof of embodiment 43, which comprises a heavy chain and a light chain with the amino acid sequence as set forth in SEQ ID NOs: 36 and 47, respectively.

45. An isolated antibody or antigen binding fragment thereof that binds specifically to BTC, which comprises a VH and a VL with the amino acid sequence of SEQ ID NOs: 34 and 45, respectively.

46. The antibody or antigen binding fragment thereof of any one of embodiments 1 to 7, which binds to G34, H35, F36, S37, R38, C39, P40, K41, Q42, R51, R53, F54, and V56 of SEQ ID NO: 157.

47. The antibody or antigen binding fragment thereof of any one of embodiments 1 to 7 and 46, which comprises HCDR1, HCDR2, and HCDR3 as set forth in SEQ ID NOs: 25, 49, and 50, respectively, and LCDR1, LCDR2, and LCDR3 as set forth in SEQ ID NOs: 58, 59, and 60, respectively.

48. The antibody or antigen binding fragment thereof of any one of embodiments 1 to 7 and 46, which comprises HCDR1, HCDR2, and HCDR3 as set forth in SEQ ID NOs: 28, 49, and 50, respectively, and LCDR1, LCDR2, and LCDR3 as set forth in SEQ ID NOs: 58, 59, and 60, respectively.

49. The antibody or antigen binding fragment thereof of any one of embodiments 1 to 7 and 46, wherein the HCDR1 comprises the consensus sequence XXAMX, and/or the HCDR2 comprises the consensus sequence XXXX/-XXXXTXYXDSVKG, wherein X is any amino acid and may not be the same in different positions, and wherein X/- is any amino acid or a deletion.

50. The antibody or antigen binding fragment thereof of embodiment 49, which comprises a heavy chain sequence of SEQ ID NO: 190 and a light chain sequence of SEQ ID NO: 191.

51. The antibody or antigen binding fragment thereof of any one of embodiments 1 to 7 and 46, which comprises HCDR1, HCDR2, and HCDR3 as set forth in SEQ ID NOs: 29, 51, and 50, respectively, and LCDR1, LCDR2, and LCDR3 as set forth in SEQ ID NOs: 61, 62, and 63, respectively.

52. The antibody or antigen binding fragment thereof of any one of embodiments 1 to 7 and 46, which comprises HCDR1, HCDR2, and HCDR3 as set forth in SEQ ID NOs: 31, 52, and 53, respectively, and LCDR1, LCDR2, and LCDR3 as set forth in SEQ ID NOs: 64, 62, and 60, respectively.

53. The antibody or antigen binding fragment thereof of any one of embodiments 46 to 52, which comprises a VH and a VL comprising an amino acid sequence with at least 90%, 95%, 96%, 97%, 98%, 99%, or 100% sequence identity to SEQ ID NOs: 54 and 65, respectively.

54. The antibody or antigen binding fragment thereof of embodiment 53, wherein the differences in amino acid sequence is not within the complementary determining regions.

55. The antibody or antigen binding fragment thereof of embodiment 53, wherein the differences in amino acid sequence are conservative substitutions.

56. The antibody or antigen binding fragment thereof of embodiment 53, which comprises a VH and VL comprising amino acid sequence as set forth in SEQ ID NOs: 54 and 65, respectively.

57. The antibody or antigen binding fragment thereof of embodiment 56, wherein the VH and VL are encoded by a nucleic acid sequence as set forth in SEQ ID NOs: 55 and 66, respectively.

58. The antibody or antigen binding fragment thereof of any one of embodiments 46 to 57, which comprises a heavy chain and a light chain with an amino acid sequence as set forth in SEQ ID NOs: 56 and 67, respectively.

59. The antibody or antigen binding fragment thereof of embodiment 58, wherein the heavy chain and light chain are encoded by a nucleic acid sequence with at least 90%, 95%, 96%, 97%, 98%, 99%, or 100% sequence identity to SEQ ID NOs: 57 and 68, respectively.

60. The antibody or antigen binding fragment thereof of any one of embodiments 46 to 59, which comprises 1) HCDR1, HCDR2, and HCDR3 comprised in a $V_H$ with the amino acid sequence of SEQ ID NO: 54, and 2) LCDR1, LCDR2, and LCDR3 comprised in a $V_L$ with the amino acid sequence of SEQ ID NO: 65.

61. The antibody or antigen binding fragment thereof of embodiment 60, wherein the HCDR1, HCDR2, HCDR3, LCDR1, LCDR2, and LCDR3 comprises:
  a. SEQ ID NOs: 25, 49, 50, 58, 59, and 60, respectively;
  b. SEQ ID NOs: 28, 49, 50, 58, 59, and 60, respectively;
  c. SEQ ID NOs: 29, 51, 50, 61, 62, and 63, respectively; or
  d. SEQ ID NOs: 31, 52, 53, 64, 62, and 60, respectively.

62. The antibody or antigen binding fragment thereof of any one of embodiments 1 to 7 and 46, which comprises HCDR1, HCDR2, HCDR3, LCDR1, LCDR2, and LCDR3, wherein
  a. the HCDR1 comprises the amino acid sequence selected from the group consisting of SEQ ID NOs: 25, 28, 29, and 31, the HCDR2 comprises the amino acid sequence selected from the group consisting of SEQ ID NOs: 49, 51, and 52, the HCDR3 comprises the amino acid sequence selected from the group consisting of SEQ ID NOs: 50 and 53; and
  b. the LCDR1 comprises the amino acid sequence selected from the group consisting of SEQ ID NOs: 58, 61, and 64, the LCDR2 comprises the amino acid sequence selected from the group consisting of SEQ ID NOs: 59 and 62, the LCDR3 comprises the amino acid sequence selected from the group consisting of SEQ ID NOs: 60 and 63.

63. The antibody or antigen binding fragment thereof of embodiment 62, which comprises a VH and VL comprising the amino acid sequence of SEQ ID NOs: 54 and 65, respectively.

64. The antibody or antigen binding fragment thereof of embodiment 63, which comprises a heavy chain and a light chain with the amino acid sequence as set forth in SEQ ID NOs: 56 and 67, respectively.

65. An isolated antibody or antigen binding fragment thereof that binds specifically to BTC, which comprises a VH and a VL with the amino acid sequence of SEQ ID NOs: 54 and 65, respectively.

66. The antibody or antigen binding fragment thereof of any one of embodiments 1 to 7, which binds to S37, R38, C39, P40, K41, Q42, Y43, H45, Y46, F54, A57, Q59, T60, P61, A72, R73, and E75 of SEQ ID NO: 157.

67. The antibody or antigen binding fragment thereof of any one of embodiments 1 to 7 and 66, which comprises HCDR1, HCDR2, and HCDR3 as set forth in SEQ ID NOs: 69, 70, and 71, respectively, and LCDR1, LCDR2, and LCDR3 as set forth in SEQ ID NOs: 82, 83, and 84, respectively.

68. The antibody or antigen binding fragment thereof of any one of embodiments 1 to 7 and 66, which comprises HCDR1, HCDR2, and HCDR3 as set forth in SEQ ID NOs: 72, 70, and 71, respectively, and LCDR1, LCDR2, and LCDR3 as set forth in SEQ ID NOs: 82, 83, and 84, respectively.

69. The antibody or antigen binding fragment thereof of any one of embodiments 1 to 7 and 66, wherein the HCDR2 comprises the consensus sequence XIXXXXXXXXY-ADSVKG, and/or the LCDR3 comprises the consensus sequence QQYDXXXT, and wherein X is any amino acid and may not be the same in different positions.

70. The antibody or antigen binding fragment thereof of embodiment 69, which comprises a heavy chain and a light chain sequence selected from the group consisting of: a. SEQ ID NOs: 194 and 195, respectively;
   b. SEQ ID NOs: 196 and 197, respectively;
   c. SEQ ID NOs: 198 and 199, respectively;
   d. SEQ ID NOs: 200 and 201, respectively;
   e. SEQ ID NOs: 202 and 203, respectively;
   f. SEQ ID NOs: 204 and 205, respectively; and
   g. SEQ ID NOs: 206 and 207, respectively.

71. The antibody or antigen binding fragment thereof of any one of embodiments 1 to 7 and 66, which comprises HCDR1, HCDR2, and HCDR3 as set forth in SEQ ID NOs: 73, 74, and 71, respectively, and LCDR1, LCDR2, and LCDR3 as set forth in SEQ ID NOs: 85, 18, and 86, respectively.

72. The antibody or antigen binding fragment thereof of any one of embodiments 1 to 7 and 66, which comprises HCDR1, HCDR2, and HCDR3 as set forth in SEQ ID NOs: 75, 76, and 77, respectively, and LCDR1, LCDR2, and LCDR3 as set forth in SEQ ID NOs: 87, 18, and 84, respectively.

73. The antibody or antigen binding fragment thereof of any one of embodiments 66 to 72, which comprises a VH and a VL comprising an amino acid sequence with at least 90%, 95%, 96%, 97%, 98%, 99%, or 100% sequence identity to SEQ ID NOs: 78 and 88, respectively.

74. The antibody or antigen binding fragment thereof of embodiment 73, wherein the differences in amino acid sequence is not within the complementary determining regions.

75. The antibody or antigen binding fragment thereof of embodiment 73, wherein the differences in amino acid sequence are conservative substitutions.

76. The antibody or antigen binding fragment thereof of embodiment 73, which comprises a VH and VL comprising amino acid sequence as set forth in SEQ ID NOs: 78 and 88, respectively.

77. The antibody or antigen binding fragment thereof of embodiment 76, wherein the $V_H$ and $V_L$ are encoded by a nucleic acid sequence as set forth in SEQ ID NOs: 79 and 89, respectively.

78. The antibody or antigen binding fragment thereof of any one of embodiments 66 to 77, which comprises a heavy chain and a light chain with an amino acid sequence as set forth in SEQ ID NOs: 80 and 90, respectively.

79. The antibody or antigen binding fragment thereof of embodiment 78, wherein the heavy chain and light chain are encoded by a nucleic acid sequence with at least 90%, 95%, 96%, 97%, 98%, 99%, or 100% sequence identity to SEQ ID NOs: 81 and 91, respectively.

80. The antibody or antigen binding fragment thereof of any one of embodiments 66 to 79, which comprises 1) HCDR1, HCDR2, and HCDR3 comprised in a $V_H$ with the amino acid sequence of SEQ ID NO: 78, and 2) LCDR1, LCDR2, and LCDR3 comprised in a $V_L$ with the amino acid sequence of SEQ ID NO: 88.

81. The antibody or antigen binding fragment thereof of embodiment 80, wherein the HCDR1, HCDR2, HCDR3, LCDR1, LCDR2, and LCDR3 comprises:
   a. SEQ ID NOs: 69, 70,71, 82, 83, and 84, respectively;
   b. SEQ ID NOs: 72, 70, 71, 82, 83, and 84, respectively;
   c. SEQ ID NOs: 73, 74, 71, 85, 18, and 86, respectively; or
   d. SEQ ID NOs: 75, 76, 77, 87, 18, and 84, respectively.

82. The antibody or antigen binding fragment thereof of any one of embodiments 1 to 7 and 66, which comprises HCDR1, HCDR2, HCDR3, LCDR1, LCDR2, and LCDR3, wherein
   a. the HCDR1 comprises the amino acid sequence selected from the group consisting of SEQ ID NOs: 69, 72, 73, and 75, the HCDR2 comprises the amino acid sequence selected from the group consisting of SEQ ID NOs: 70, 74, and 76, the HCDR3 comprises the amino acid sequence selected from the group consisting of SEQ ID NOs: 71 and 77; and
   b. the LCDR1 comprises the amino acid sequence selected from the group consisting of SEQ ID NOs: 82, 85, and 87, the LCDR2 comprises the amino acid sequence selected from the group consisting of SEQ ID NOs: 83 and 18, the LCDR3 comprises the amino acid sequence selected from the group consisting of SEQ ID NOs: 84 and 86.

83. The antibody or antigen binding fragment thereof of embodiment 82, which comprises a VH and VL comprising the amino acid sequence of SEQ ID NOs: 78 and 88, respectively.

84. The antibody or antigen binding fragment thereof of embodiment 83, which comprises a heavy chain and a light chain with the amino acid sequence as set forth in SEQ ID NOs: 80 and 90, respectively.

85. An isolated antibody or antigen binding fragment thereof that binds specifically to BTC, which comprises a VH and a VL with the amino acid sequence of SEQ ID NOs: 78 and 88, respectively.

86. The antibody or antigen binding fragment thereof of any one of embodiments 1 to 85, which is in a format selected from the group consisting of an isolated antibody, a Fab, a Fab', a F(ab')$_2$, a Fv, and a scFv.

87. The antibody or antigen binding fragment thereof of embodiment 86, which is a Fab.

88. The antibody or antigen binding fragment thereof of embodiment 86, which is a scFv.

89. The antibody or antigen binding fragment thereof of embodiment 86, which is an isolated antibody.

90. The antibody or antigen binding fragment thereof of embodiment 89, wherein the isolated antibody is a monoclonal human antibody.

91. The antibody or antigen binding fragment thereof of embodiment 89, wherein the isolated antibody is a monoclonal humanized antibody.

92. The antibody or antigen binding fragment thereof of any one of embodiments 1 to 90, wherein the Fab comprises an Fc region.

93. The antibody or antigen binding fragment thereof of embodiment 92, wherein the Fc region is selected from the group consisting of an Fc region from an IgG1, IgG2, IgG3, IgG4, IgA, IgM, IgE, and IgD.

94. The antibody or antigen binding fragment thereof of embodiment 92, wherein the Fc region comprises human immunoglobulin Kappa chain constant region sequence as set forth in SEQ ID NO: 159.

95. The antibody or antigen binding fragment thereof of embodiment 92, wherein the Fc region comprises human immunoglobulin first constant Ig domain of the heavy chain (CH1 domain) as set forth in SEQ ID NO: 160.

96. An isolated antibody or antigen binding fragment thereof which is capable of competing with the antibody or antigen binding fragment thereof of any one of embodiments 1 to 95 for binding to BTC and reducing BTC-mediated signaling.

97. The antibody or antigen binding fragment thereof of embodiment 96, which comprises a heavy chain and a light chain as set forth in SEQ ID NOs: 168 and 169, respectively; SEQ ID NOs: 170 and 171, respectively; SEQ ID NOs: 172 and 173, respectively; SEQ ID NOs: 174 and 175, respectively; SEQ ID NOs: 176 and 177, respectively; SEQ ID NOs: 178 and 179, respectively; SEQ ID NOs: 180 and 181, respectively; SEQ ID NOs: 182 and 183, respectively; SEQ ID NOs: 184 and 185, respectively; SEQ ID NOs: 186 and 187, respectively; or SEQ ID NOs: 188 and 189, respectively.

98. A polynucleotide comprising nucleotide sequences encoding the antibody or antigen binding fragment thereof of any one of embodiments 1 to 97.

99. An expression cassette comprising the polynucleotide of embodiment 98.

100. A vector comprising the expression cassette of embodiment 99.

101. A host cell comprising the polynucleotide of embodiment 98 or the vector of embodiment 100.

102. A method of producing an antibody or antigen binding fragment thereof, comprising culturing the host cell of embodiment 101 under suitable conditions for expression of the antibody or antigen binding fragment thereof.

103. The method of embodiment 102, which further comprises purifying the antibody or antigen binding fragment thereof.

104. A pharmaceutical composition comprising an effective amount of the antibody or antigen binding fragment thereof of any one of embodiments 1 to 97.

105. The pharmaceutical composition of embodiment 104, further comprising a pharmaceutically acceptable excipient, diluent, or carrier.

106. A method of treating a subject in need thereof, comprising administering to the subject an effective amount of the antibody or antigen binding fragment thereof of any one of embodiments 1 to 95 or the pharmaceutical composition of embodiment 104 or 105.

107. The method of embodiment 106, wherein the subject has a disease selected from the group consisting of pancreatic carcinoma, breast cancer, endometrial adenocarcinoma, hepatocellular carcinoma, head and neck squamous cell carcinoma, and gastric carcinoma.

108. The method of embodiment 107, wherein the antibody or antigen binding fragment thereof or the pharmaceutical composition is administered via a route selected from the group consisting of intravenous administration, intramuscular administration, subcutaneous administration, parenteral administration, spinal administration, and epidermal administration.

109. The method of embodiment 106, wherein the subject has an ophthalmic disorder.

110. The method of embodiment 109, wherein the ophthalmic disorder is selected from the group consisting of diabetic macular edema, age-related macular degeneration, neovascular age-related macular degeneration, neovascular glaucoma, diabetic retinopathy, macular edema, pathologic myopia, retinal vein occlusions, retinopathy of prematurity, abnormal vascular proliferation associated with phakomatoses, central serous chorioretiniopathy, and acute multifocal placoid pigment epitheliopathy.

111. The method of embodiment 110, wherein the ophthalmic disorder is diabetic macular edema.

112. The method of any one of embodiments 109 to 111, wherein the administering is via subretinal injection.

113. The method of any one of embodiments 109 to 111, wherein the administering is via intravitreal injection.

114. The method of any one of embodiments 109 to 113, wherein the pharmaceutical composition further comprises an anti-VEGF antagonist.

115. The method of embodiment 114, wherein the anti-VEGF antagonist is ranibizumab.

116. The method of embodiment 114, wherein the anti-VEGF antagonist is bevacizumab.

117. The method of embodiment 114, wherein the anti-VEGF antagonist is aflibercept.

118. The method of embodiment 114, wherein the anti-VEGF antagonist is brolucizumab.

119. The method of embodiment 114, wherein the anti-VEGF antagonist is pegaptanib.

120. The method of embodiment 114, wherein the anti-VEGF antagonist comprises a heavy chain and a light chain as set forth in SEQ ID NOs: 103 and 114, respectively.

121. The method of embodiment 120, wherein the anti-VEGF antagonist is encoded by a nucleic acid sequence as set forth in SEQ ID NOs: 104 and 115.

122. The method of any one of embodiments 109 to 113, further comprises administering to the subject an anti-VEGF antagonist.

123. The method of embodiment 122, wherein the anti-VEGF antagonist is ranibizumab.

124. The method of embodiment 122, wherein the anti-VEGF antagonist is bevacizumab.

125. The method of embodiment 122, wherein the anti-VEGF antagonist is aflibercept.

126. The method of embodiment 122, wherein the anti-VEGF antagonist is brolucizumab.

127. The method of embodiment 122, wherein the anti-VEGF antagonist is pegaptanib.

128. The method of embodiment 122, wherein the anti-VEGF antagonist comprises a heavy chain and a light chain as set forth in SEQ ID NOs: 103 and 114.

129. The method of embodiment 128, wherein the anti-VEGF antagonist is encoded by a nucleic acid sequence as set forth in SEQ ID NOs: 104 and 115.

130. A kit comprising the antibody or antigen binding fragment thereof of any one of embodiments 1 to 97 or the pharmaceutical composition of embodiment 104 or 105.

131. The kit of embodiment 130, further comprising an instruction for use.

132. The kit of embodiment 131, further comprising a syringe.

133. A multi-specific binding molecule comprising 1) an anti-BTC binding moiety and 2) an anti-VEGF binding moiety.

134. The multi-specific binding molecule of embodiment 133, wherein the anti-BTC binding moiety binds to BTC comprising the amino acid sequence of SEQ ID NO: 157.

135. The multi-specific binding molecule of embodiment 134, wherein the anti-BTC binding moiety binds to at least one residue of SEQ ID NO: 157 selected from the group consisting of G34, H35, F36, S37, R38, C39, P40, K41, Q42, Y43, H45, Y46, R51, R53, F54, V56, A57, E58, Q59, T60, P61, A72, R73, E75, and R76.

136. The multi-specific binding molecule of embodiment 135, wherein the anti-BTC binding moiety binds to R38, C39, P40, K41, Q42, Y43, H45, Y46, F54, Q59, T60, P61, and R73 of SEQ ID NO: 157.

137. The multi-specific binding molecule of embodiment 135, wherein the anti-BTC binding moiety binds to P40, K41, Q42, Y43, H45, Y46, E58, Q59, T60, P61, A72, R73, E75, and R76 of SEQ ID NO: 157.

138. The multi-specific binding molecule of embodiment 135, wherein the anti-BTC binding moiety binds to G34, H35, F36, S37, R38, C39, P40, K41, Q42, R51, R53, F54, and V56 of SEQ ID NO: 157.

139. The multi-specific binding molecule of embodiment 135, wherein the anti-BTC binding moiety binds to S37, R38, C39, P40, K41, Q42, Y43, H45, Y46, F54, A57, Q59, T60, P61, A72, R73, and E75 of SEQ ID NO: 157.

140. The multi-specific binding molecule of embodiment 133, wherein the anti-BTC binding moiety is the antibody or antigen binding fragment thereof of any one of embodiments 1 to 95.

141. The multi-specific binding molecule of embodiment 133, wherein the anti-VEGF binding moiety is an anti-VEGF antibody or antigen binding fragment thereof.

142. The multi-specific binding molecule of any one of embodiments 133 to 141, wherein the anti-BTC binding moiety and the anti-VEGF binding moiety are in a format selected from the list consisting of an isolated antibody, a Fab, a Fab', a F(ab')₂, a Fv, and a scFv.

143. The multi-specific binding molecule of embodiment 142, wherein the anti-BTC binding moiety is an anti-BTC Fab and the anti-VEGF binding moiety is an anti-VEGF Fab.

144. The multi-specific binding molecule of embodiment 143, wherein the anti-BTC Fab comprises a heavy chain (HA) and a light chain (LA), and wherein the anti-VEGF Fab comprises a heavy chain (HB) and a light chain (LB).

145. The multi-specific binding molecule of embodiment 144, wherein the HA and the HB are linked in the format from the N-terminus to the C-terminus: N-HA-linker 1-HB-C, and wherein the LA and the LB are linked in the format from the N-terminus to the C-terminus: N-LA-linker 2-LB-C.

146. The multi-specific binding molecule of embodiment 144 wherein the HA and the HB is linked in the format from the N-terminus to the C-terminus: N-HB-linker 1-HA-C, and wherein the LA and the LB is linked in the format from the N-terminus to the C-terminus: N-LB-linker 2-LA-C.

147. The multi-specific binding molecule of embodiment 145 or 146, wherein the linker 1 and linker 2 comprise an amino sequence of SEQ ID NO: 118.

148. The multi-specific binding molecule of embodiment 147, wherein the linker 1 and linker 2 are encoded by a nucleic sequence of SEQ ID NO: 119.

149. The multi-specific binding molecule of embodiment 145 or 146, wherein the linker 1 and linker 2 comprise an amino sequence selected from the group consisting of SEQ ID NOs: 161-167.

150. The multi-specific binding molecule of any one of embodiments 133 to 149, wherein the anti-BTC binding moiety comprises HCDR1, HCDR2, HCDR3, LCDR1, LCDR2, and LCDR3 as set forth in:
  a. SEQ ID NOs: 1, 2, 3, 14, 15, and 16, respectively;
  b. SEQ ID NOs: 4, 2, 3, 14, 15, and 16, respectively;
  c. SEQ ID NOs: 5, 6, 3, 17, 18, and 19, respectively; or
  d. SEQ ID NOs: 7, 8, 9, 20, 18, and 16, respectively.

151. The multi-specific binding molecule of embodiment 150, wherein the anti-BTC binding moiety comprises a VH and a VL with the amino acid sequence of SEQ ID NOs: 10 and 21, respectively.

152. The multi-specific binding molecule of embodiment 151, wherein the VH and VL is encoded by the nucleic acid sequence of SEQ ID NOs: 116 and 122, respectively.

153. The multi-specific binding molecule of any one of embodiments 133 to 148, wherein the anti-BTC binding moiety comprises HCDR1, HCDR2, HCDR3, LCDR1, LCDR2, and LCDR3 as set forth in:
  a. SEQ ID NOs: 25, 26, 27, 38, 39, and 40, respectively;
  b. SEQ ID NOs: 28, 26, 27, 38, 39, and 40, respectively;
  c. SEQ ID NOs: 29, 30, 27, 41, 42, and 43, respectively; or
  d. SEQ ID NOs: 31, 32, 33, 44, 42, and 40, respectively.

154. The multi-specific binding molecule of embodiment 153, wherein the anti-BTC binding moiety comprises a VH and a VL with the amino acid sequence of SEQ ID NOs: 34 and 45, respectively.

155. The multi-specific binding molecule of embodiment 153, wherein the VH and VL is encoded by the nucleic acid sequence of SEQ ID NOs: 127 and 132, respectively.

156. The multi-specific binding molecule of any one of embodiments 133 to 148, wherein the anti-BTC binding moiety comprises HCDR1, HCDR2, HCDR3, LCDR1, LCDR2, and LCDR3 as set forth in:
  a. SEQ ID NOs: 25, 49, 50, 58, 59, and 60, respectively;
  b. SEQ ID NOs: 28, 49, 50, 58, 59, and 60, respectively;
  c. SEQ ID NOs: 29, 51, 50, 61, 62, and 63, respectively; or
  d. SEQ ID NOs: 31, 52, 53, 64, 62, and 60, respectively.

157. The multi-specific binding molecule of embodiment 156, wherein the anti-BTC binding moiety comprises a VH and a VL with the amino acid sequence of SEQ ID NOs: 54 and 65, respectively.

158. The multi-specific binding molecule of embodiment 157, wherein the VH and VL is encoded by the nucleic acid sequence of SEQ ID NOs: 137 and 142, respectively.

159. The multi-specific binding molecule of any one of embodiments 133 to 148, wherein the anti-BTC binding moiety comprises HCDR1, HCDR2, HCDR3, LCDR1, LCDR2, and LCDR3 as set forth in:
  a. SEQ ID NOs: 69, 70, 71, 82, 83, and 84, respectively;
  b. SEQ ID NOs: 72, 70, 71, 82, 83, and 84, respectively;
  c. SEQ ID NOs: 73, 74, 71, 85, 18, and 86, respectively; or
  d. SEQ ID NOs: 75, 76, 77, 87, 18, and 84, respectively.

160. The multi-specific binding molecule of embodiment 159, wherein the anti-BTC binding moiety comprises a VH and a VL with the amino acid sequence of SEQ ID NOs: 78 and 88, respectively.

161. The multi-specific binding molecule of embodiment 160, wherein the VH and VL is encoded by the nucleic acid sequence of SEQ ID NOs: 147 and 151, respectively.

162. The multi-specific binding molecule of any one of embodiments 133 to 161, wherein the anti-VEGF binding moiety comprises HCDR1, HCDR2, and HCDR3 as set forth in SEQ ID NOs: 92, 93, and 94, respectively, and LCDR1, LCDR2, and LCDR3 as set forth in SEQ ID NOs: 105, 106, and 107, respectively.

163. The multi-specific binding molecule of any one of embodiments 133 to 161, wherein the anti-VEGF binding moiety comprises HCDR1, HCDR2, and HCDR3 as set forth in SEQ ID NOs: 95, 93, and 94, respectively, and LCDR1, LCDR2, and LCDR3 as set forth in SEQ ID NOs: 105, 106, and 107, respectively.

164. The multi-specific binding molecule of any one of embodiments 133 to 161, wherein the anti-VEGF binding moiety comprises HCDR1, HCDR2, and HCDR3 as set forth in SEQ ID NOs: 96, 97, and 94, respectively, and LCDR1, LCDR2, and LCDR3 as set forth in SEQ ID NOs: 108, 109, and 110, respectively.

165. The multi-specific binding molecule of any one of embodiments 133 to 161, wherein the anti-VEGF binding moiety comprises HCDR1, HCDR2, and HCDR3 as set forth in SEQ ID NOs: 98, 99, and 100, respectively, and LCDR1, LCDR2, and LCDR3 as set forth in SEQ ID NOs: 111, 109, and 107, respectively.

166. The multi-specific binding molecule of any one of embodiments 133 to 165, wherein the anti-VEGF binding moiety comprises a VH and VL comprising an amino acid sequence with at least 90%, 95%, 96%, 97%, 98%, 99%, or 100% sequence identity to SEQ ID NOs: 101 and 112, respectively.

167. The multi-specific binding molecule of embodiment 166, wherein the differences in amino acid sequence is not within the complementary determining regions.

168. The multi-specific binding molecule of embodiment 166, wherein the differences in amino acid sequence are conservative substitutions.

169. The multi-specific binding molecule of embodiment 166, wherein the anti-VEGF binding moiety comprises a VH and VL comprising an amino acid sequence as set forth in SEQ ID NOs: 101 and 112, respectively.

170. The multi-specific binding molecule of embodiment 169, wherein the anti-VEGF binding moiety comprises a VH and VL encoded by the nucleic acid sequence as set forth in SEQ ID NOs: 102 and 113, respectively.

171. The multi-specific binding molecule of embodiment 169, wherein the anti-VEGF binding moiety comprises a VH and VL encoded by the nucleic acid sequence as set forth in SEQ ID NOs: 117 and 123, respectively.

172. The multi-specific binding molecule of embodiment 169, wherein the anti-VEGF binding moiety comprises a VH and VL encoded by the nucleic acid sequence as set forth in SEQ ID NOs: 128 and 133, respectively.

173. The multi-specific binding molecule of embodiment 169, wherein the anti-VEGF binding moiety comprises a VH and VL encoded by the nucleic acid sequence as set forth in SEQ ID NOs: 138 and 143, respectively.

174. The multi-specific binding molecule of embodiment 169, wherein the anti-VEGF binding moiety comprises a VH and VL encoded by the nucleic acid sequence as set forth in SEQ ID NOs: 148 and 152, respectively.

175. The multi-specific binding molecule of any one of embodiments 133 to 174, wherein the anti-VEGF binding moiety comprises a heavy chain and a light chain with the amino acid sequence as set forth in SEQ ID NOs: 103 and 114, respectively.

176. The multi-specific binding molecule of embodiment 175, wherein the heavy chain and light chain are encoded by a nucleic acid sequence with at least 90%, 95%, 96%, 97%, 98%, 99%, or 100% sequence identity to SEQ ID NOs: 104 and 115, respectively.

177. A multi-specific binding molecule comprising an anti-BTC binding moiety and an anti-VEGF binding moiety, wherein the anti-BTC binding moiety comprises a variable heavy chain domain (VHA) and a variable light chain domain (VLA) that bind to BTC, and wherein the anti-VEGF binding moiety comprises a variable heavy chain domain (VHB) and a variable light chain domain (VLB) that bind to VEGF, wherein:
  a. the VHA and VLA comprise the amino acid sequence as set forth in SEQ ID NOs: 10 and 21, respectively; and
  b. the VHB and VLB comprise the amino acid sequence as set forth in SEQ ID NOs: 101 and 112, respectively.

178. The multi-specific binding molecule of embodiment 177, wherein the anti-BTC binding moiety further comprises a heavy chain constant domain (CHIA) and a light chain constant domain (CKA), and wherein the anti-VEGF binding moiety further comprises a heavy chain constant domain (CH1B) and a light chain constant domain (CKB).

179. The multi-specific binding molecule of embodiment 178, which is in the format from the N-terminus to C-terminus as: N-VHA-CH1A-linker-VHB-CH1B-C and N-VLA-CKA-linker-VLB-CKB-C.

180. The multi-specific binding molecule of embodiment 179, which comprises a heavy chain comprising the VHA, CHIA, linker, VHB, and CHIB, wherein the heavy chain is as set forth in SEQ ID NO: 120.

181. The multi-specific binding molecule of embodiment 180, wherein the heavy chain is encoded by a nucleic acid sequence as set forth in SEQ ID NO: 121.

182. The multi-specific binding molecule of embodiment 179, which comprises a light chain comprising the VLA, CKA, linker, VLB, and CKB, wherein the light chain is as set forth in SEQ ID NO: 125.

183. The multi-specific binding molecule of embodiment 182, wherein the light chain is encoded by a nucleic acid sequence as set forth in SEQ ID NO: 126.

184. A multi-specific binding molecule comprising an anti-BTC binding moiety and an anti-VEGF binding moiety, wherein the anti-BTC binding moiety comprises a variable heavy chain domain (VHA) and a variable light chain domain (VLA) that bind to BTC, and wherein the anti-VEGF binding moiety comprises a variable heavy chain domain (VHB) and a variable light chain domain (VLB) that bind to VEGF, wherein:
  a. the VHA and VLA comprise the amino acid sequence as set forth in SEQ ID NOs: 34 and 45, respectively; and
  b. the VHB and VLB comprise the amino acid sequence as set forth in SEQ ID NOs: 101 and 112, respectively.

185. The multi-specific binding molecule of embodiment 184, wherein the anti-BTC binding moiety further comprises a heavy chain constant domain (CHIA) and a light chain constant domain (CKA), and wherein the anti-VEGF binding moiety further comprises a heavy chain constant domain (CHIB) and a light chain constant domain (CKB).

186. The multi-specific binding molecule of embodiment 185, which is in the format from the N-terminus to C-terminus as: N-VHA-CH1A-linker-VHB-CH1B-C and N-VLA-CKA-linker-VLB-CKB-C.

187. The multi-specific binding molecule of embodiment 186, which comprises a heavy chain comprising the VHA, CHIA, linker, VHB, and CHIB, wherein the heavy chain is as set forth in SEQ ID NO: 130.

188. The multi-specific binding molecule of embodiment 187, wherein the heavy chain is encoded by a nucleic acid sequence as set forth in SEQ ID NO: 131.

189. The multi-specific binding molecule of embodiment 186, which comprises a light chain comprising the VLA, CKA, linker, VLB, and CKB, wherein the light chain is as set forth in SEQ ID NO: 135.

190. The multi-specific binding molecule of embodiment 189, wherein the light chain is encoded by a nucleic acid sequence as set forth in SEQ ID NO: 136.

191. A multi-specific binding molecule comprising an anti-BTC binding moiety and an anti-VEGF binding moiety, wherein the anti-BTC binding moiety comprises a variable heavy chain domain (VHA) and a variable light chain domain (VLA) that bind to BTC, and wherein the anti-VEGF binding moiety comprises a variable heavy chain domain (VHB) and a variable light chain domain (VLB) that bind to VEGF, wherein:

a. the VHA and VLA comprise the amino acid sequence as set forth in SEQ ID NOs: 54 and 65, respectively; and
b. the VHB and VLB comprise the amino acid sequence as set forth in SEQ ID NOs: 101 and 112, respectively.

192. The multi-specific binding molecule of embodiment 191, wherein the anti-BTC binding moiety further comprises a heavy chain constant domain (CHIA) and a light chain constant domain (CKA), and wherein the anti-VEGF binding moiety further comprises a heavy chain constant domain (CHIB) and a light chain constant domain (CKB).

193. The multi-specific binding molecule of embodiment 192, which is in the format from the N-terminus to C-terminus as: N-VHA-CH1A-linker-VHB-CH1B-C and N-VLA-CKA-linker-VLB-CKB-C.

194. The multi-specific binding molecule of embodiment 193, which comprises a heavy chain comprising the VHA, CHIA, linker, VHB, and CHIB, wherein the heavy chain is as set forth in SEQ ID NO: 140.

195. The multi-specific binding molecule of embodiment 194, wherein the heavy chain is encoded by a nucleic acid sequence as set forth in SEQ ID NO: 141.

196. The multi-specific binding molecule of embodiment 193, which comprises a light chain comprising the VLA, CKA, linker, VLB, and CKB, wherein the light chain is as set forth in SEQ ID NO: 145.

197. The multi-specific binding molecule of embodiment 196, wherein the light chain is encoded by a nucleic acid sequence as set forth in SEQ ID NO: 146.

198. A multi-specific binding molecule comprising an anti-BTC binding moiety and an anti-VEGF binding moiety, wherein the anti-BTC binding moiety comprises a variable heavy chain domain (VHA) and a variable light chain domain (VLA) that bind to BTC, and wherein the anti-VEGF binding moiety comprises a variable heavy chain domain (VHB) and a variable light chain domain (VLB) that bind to VEGF, wherein:
a. the VHA and VLA comprise the amino acid sequence as set forth in SEQ ID NOs: 78 and 88, respectively; and
b. the VHB and VLB comprise the amino acid sequence as set forth in SEQ ID NOs: 101 and 112, respectively.

199. The multi-specific binding molecule of embodiment 198, wherein the anti-BTC binding moiety further comprises a heavy chain constant domain (CHIA) and a light chain constant domain (CKA), and wherein the anti-VEGF binding moiety further comprises a heavy chain constant domain (CHIB) and a light chain constant domain (CKB).

200. The multi-specific binding molecule of embodiment 199, which is in the format from the N-terminus to C-terminus as: N-VHA-CH1A-linker-VHB-CH1B-C and N-VLA-CKA-linker-VLB-CKB-C.

201. The multi-specific binding molecule of embodiment 200, which comprises a heavy chain comprising the VHA, CHIA, linker, VHB, and CHIB, wherein the heavy chain is as set forth in SEQ ID NO: 149.

202. The multi-specific binding molecule of embodiment 201, wherein the heavy chain is encoded by a nucleic acid sequence as set forth in SEQ ID NO: 150.

203. The multi-specific binding molecule of embodiment 200, which comprises a light chain comprising the VLA, CKA, linker, VLB, and CKB, wherein the light chain is as set forth in SEQ ID NO: 154.

204. The multi-specific binding molecule of embodiment 203, wherein the light chain is encoded by a nucleic acid sequence as set forth in SEQ ID NO: 155.

205. A multi-specific binding molecule, comprising a first polypeptide chain and a second polypeptide chain, wherein the first polypeptide chain comprises an amino acid sequence of SEQ ID NOs: 120, and the second polypeptide chain comprises an amino acid sequence of SEQ ID NOs: 125.

206. The multi-specific binding molecule of embodiment 205, wherein the first polypeptide chain is encoded by a nucleic acid sequence of SEQ ID NO: 121, and the second polypeptide chain is encoded by a nucleic acid sequence of SEQ ID NO: 126.

207. A multi-specific binding molecule, comprising a first polypeptide chain and a second polypeptide chain, wherein the first polypeptide chain comprises an amino acid sequence of SEQ ID NOs: 130, and the second polypeptide chain comprises an amino acid sequence of SEQ ID NOs: 135.

208. The multi-specific binding molecule of embodiment 207, wherein the first polypeptide chain is encoded by a nucleic acid sequence of SEQ ID NO: 131, and the second polypeptide chain is encoded by a nucleic acid sequence of SEQ ID NO: 136.

209. A multi-specific binding molecule, comprising a first polypeptide chain and a second polypeptide chain, wherein the first polypeptide chain comprises an amino acid sequence of SEQ ID NOs: 140, and the second polypeptide chain comprises an amino acid sequence of SEQ ID NOs: 145.

210. The multi-specific binding molecule of embodiment 209, wherein the first polypeptide chain is encoded by a nucleic acid sequence of SEQ ID NO: 141, and the second polypeptide chain is encoded by a nucleic acid sequence of SEQ ID NO: 146.

211. A multi-specific binding molecule, comprising a first polypeptide chain and a second polypeptide chain, wherein the first polypeptide chain comprises an amino acid sequence of SEQ ID NOs: 149, and the second polypeptide chain comprises an amino acid sequence of SEQ ID NOs: 154.

212. The multi-specific binding molecule of embodiment 211, wherein the first polypeptide chain is encoded by a nucleic acid sequence of SEQ ID NO: 150, and the second polypeptide chain is encoded by a nucleic acid sequence of SEQ ID NO: 155.

213. A polynucleotide comprising a nucleotide sequences encoding the multi-specific binding molecule of any one of embodiments 133 to 212.

214. An expression cassette comprising the polynucleotide of embodiment 213.

215. A vector comprising the expression cassette of embodiment 214.

216. A host cell comprising the polynucleotide of embodiment 213 or the vector of embodiment 215.

217. A method of producing a multi-specific binding molecule, comprising culturing the host cell of embodiment 216 under suitable conditions for expression of the multi-specific binding molecule or a fragment thereof.

218. The method of embodiment 217, which further comprises purifying the multi-specific binding molecule.

219. A pharmaceutical composition comprising an effective amount of the multi-specific binding molecule of any one of embodiments 133 to 212.

220. The pharmaceutical composition of embodiment 219, further comprising a pharmaceutically acceptable excipient, diluent, or carrier.

221. The pharmaceutical composition of embodiment 220, further comprising one or more therapeutic agents.

222. A method of treating an ophthalmic disorder in a subject in need thereof, comprising administering to the subject an effective amount of the multi-specific binding molecule of any one of embodiments 133 to 212 or the pharmaceutical composition of embodiment 219 or 220.

223. The method of embodiment 222, wherein the multi-specific binding molecule or the pharmaceutical composition is administered intravitreally to the subject.

224. The method of embodiment 222, wherein the multi-specific binding molecule or the pharmaceutical composition is administered via subretinal injection.

225. The method of any one of embodiments 222 to 224, wherein the ophthalmic disorder is selected from the group consisting of diabetic macular edema, age-related macular degeneration, neovascular age-related macular degeneration, neovascular glaucoma, diabetic retinopathy, macular edema, pathologic myopia, retinal vein occlusions, retinopathy of prematurity, and abnormal vascular proliferation associated with phakomatoses.

226. The method of embodiment 222, wherein the ophthalmic disorder is diabetic macular edema.

227. A method comprising administering to a subject an effective amount of the multi-specific binding molecule of any one of embodiments 133 to 212, wherein the multi-specific binding molecule reduces retinal leakage and/or retinal thickening in the subject relative to a control subject.

228. A kit comprising the multi-specific binding molecule of any one of embodiments 133 to 204 or the pharmaceutical composition of embodiment 219 or 220.

229. The kit of embodiment 228, further comprising an instruction for use.

230. The kit of embodiment 229, further comprising a syringe.

231. A method of preventing or treating macular edema, DME, AMD, neovascular AMD, or RVO in a subject in need thereof, comprising administering intravitreally to the subject the multi-specific binding molecule of any one of embodiments 133 to 212, at a dose ranging from about 0.25 mg/eye to 7.5 mg/eye.

232. The method of embodiment 231, wherein the dose is about 0.25 mg/eye, 0.75 mg/eye, 2.5 mg/eye, or 7.5 mg/eye.

233. The method of embodiment 231, wherein the dose is 0.25 mg/eye.

234. The method of embodiment 231, wherein the dose is 0.75 mg/eye.

235. The method of embodiment 231, wherein the dose is 1 mg/eye.

236. The method of embodiment 231, wherein the dose is 2.5 mg/eye.

237. The method of embodiment 231, wherein the dose is 3 mg/eye.

238. The method of embodiment 231, wherein the dose is 5 mg/eye.

239. The method of embodiment 231, wherein the dose is 7.5 mg/eye.

240. The method of embodiment 231, wherein the dose is 0.25 mg/eye, 0.3 mg/eye, 0.35 mg/eye, 0.4 mg/eye, 0.45 mg/eye, 0.5 mg/eye, 0.55 mg/eye, 0.6 mg/eye, 0.65 mg/eye, 0.7 mg/eye, 0.75 mg/eye, 0.8 mg/eye, 0.85 mg/eye, 0.9 mg/eye, 0.95 mg/eye, 1.0 mg/eye, 1.1 mg/eye, 1.2 mg/eye, 1.3 mg/eye, 1.4 mg/eye, 1.5 mg/eye, 1.6 mg/eye, 1.7 mg/eye, 1.8 mg/eye, 1.9 mg/eye, 2.0 mg/eye, 2.1 mg/eye, 2.2 mg/eye, 2.3 mg/eye, 2.4 mg/eye, 2.5 mg/eye, 2.6 mg/eye, 2.7 mg/eye, 2.8 mg/eye, 2.9 mg/eye, 3.0 mg/eye, 3.1 mg/eye, 3.2 mg/eye, 3.3 mg/eye, 3.4 mg/eye, 3.5 mg/eye, 3.6 mg/eye, 3.7 mg/eye, 3.8 mg/eye, 3.9 mg/eye, 4.0 mg/eye, 4.1 mg/eye, 4.2 mg/eye, 4.3 mg/eye, 4.4 mg/eye, 4.5 mg/eye, 4.6 mg/eye, 4.7 mg/eye, 4.8 mg/eye, 4.9 mg/eye, 5.0 mg/eye, 5.1 mg/eye, 5.2 mg/eye, 5.3 mg/eye, 5.4 mg/eye, 5.5 mg/eye, 5.6 mg/eye, 5.7 mg/eye, 5.8 mg/eye, 5.9 mg/eye, 6.0 mg/eye, 6.1 mg/eye, 6.2 mg/eye, 6.3 mg/eye, 6.4 mg/eye, 6.5 mg/eye, 6.6 mg/eye, 6.7 mg/eye, 6.8 mg/eye, 6.9 mg/eye, 7.0 mg/eye, 7.1 mg/eye, 7.2 mg/eye, 7.3 mg/eye, 7.4 mg/eye, or 7.5 mg/eye.

241. The method of any one of embodiments 231 to 240, wherein the multi-specific binding molecule comprises 1) the anti-BTC binding moiety comprising the amino acid sequence of SEQ ID NOs: 10 and 21, respectively; and 2) the anti-VEGF binding moiety comprising the amino acid sequence of SEQ ID NOs: 101 and 112, respectively.

242. The method of any one of embodiments 231 to 241, wherein the administration is once a month.

The invention claimed is:

1. A multi-specific binding molecule comprising 1) an anti-betacellulin (BTC) binding moiety and 2) an anti-vascular endothelial growth factor (VEGF) binding moiety, wherein the anti-BTC binding moiety comprises HCDR1, HCDR2, HCDR3, LCDR1, LCDR2, and LCDR3 as set forth in:
   a. SEQ ID NOs: 1, 2, 3, 14, 15, and 16, respectively; SEQ ID NOs: 4, 2, 3, 14, 15, and 16, respectively; SEQ ID NOs: 5, 6, 3, 17, 18, and 19, respectively; or SEQ ID NOs: 7, 8, 9, 20, 18, and 16, respectively;
   b. SEQ ID NOs: 25, 26, 27, 38, 39, and 40, respectively; SEQ ID NOs: 28, 26, 27, 38, 39, and 40, respectively; SEQ ID NOs: 29, 30, 27, 41, 42, and 43, respectively; or SEQ ID NOs: 31, 32, 33, 44, 42, and 40, respectively;
   c. SEQ ID NOs: 25, 49, 50, 58, 59, and 60, respectively; SEQ ID NOs: 28, 49, 50, 58, 59, and 60, respectively; SEQ ID NOs: 29, 51, 50, 61, 62, and 63, respectively; or SEQ ID NOs: 31, 52, 53, 64, 62, and 60, respectively; or
   d. SEQ ID NOs: 69, 70, 71, 82, 83, and 84, respectively; SEQ ID NOs: 72, 70, 71, 82, 83, and 84, respectively; SEQ ID NOs: 73, 74, 71, 85, 18, and 86, respectively; or SEQ ID NOs: 75, 76, 77, 87, 18, and 84, respectively,
   wherein the anti-BTC binding moiety and the anti-VEGF binding moiety are an antibody or antigen binding fragment thereof.

2. The multi-specific binding molecule of claim 1, wherein the anti-VEGF binding moiety is an anti-VEGF antibody or antigen binding fragment thereof in a format selected from the group consisting of an isolated antibody, a Fab, a Fab', a F(ab')$_2$, a Fv, and a scFv.

3. The multi-specific binding molecule of claim 1, wherein the anti-BTC binding moiety is an anti-BTC Fab and the anti-VEGF binding moiety is an anti-VEGF Fab, wherein the anti-BTC Fab comprises a heavy chain (HA) and a light chain (LA), and wherein the anti-VEGF Fab comprises a heavy chain (HB) and a light chain (LB).

4. The multi-specific binding molecule of claim 3, wherein the HA and the HB are linked in the format from the N-terminus to the C-terminus: N-HA-linker 1-HB-C, and wherein the LA and the LB are linked in the format from the N-terminus to the C-terminus: N-LA-linker 2-LB-C.

5. The multi-specific binding molecule of claim 1, wherein the anti-BTC binding moiety comprises a VH and a VL comprising an amino acid sequence with at least 90% sequence identity to:
   a. SEQ ID NOs: 10 and 21, respectively;
   b. SEQ ID NOs: 34 and 45, respectively;
   c. SEQ ID NOs: 54 and 65, respectively; or
   d. SEQ ID NOs: 78 and 88, respectively.

6. The multi-specific binding molecule of claim 5, wherein the anti-BTC binding moiety comprises a heavy chain and a light chain with an amino acid sequence as set forth in:
   a. SEQ ID NOs: 12 and 23, respectively;
   b. SEQ ID NOs: 36 and 47, respectively;
   c. SEQ ID NOs: 56 and 67, respectively; or
   d. SEQ ID NOs: 80 and 90, respectively.

7. The multi-specific binding molecule of claim 1, wherein the anti-VEGF binding moiety comprises HCDR1, HCDR2, HCDR3, LCDR1, LCDR2, and LCDR3 as set forth in:
   a. SEQ ID NOs: 92, 93, 94, 105, 106, and 107 respectively;
   b. SEQ ID NOs: 95, 93, 94, 105, 106, and 107, respectively;
   c. SEQ ID NOs: 96, 97, 94, 108, 109, and 110, respectively; or
   d. SEQ ID NOs: 98, 99, 100, 111, 109, and 107, respectively.

8. The multi-specific binding molecule of claim 7, wherein the anti-VEGF binding moiety comprises a VH and VL comprising an amino acid sequence with at least 90% sequence identity to SEQ ID NOs: 101 and 112, respectively.

9. The multi-specific binding molecule of claim 7, wherein the anti-VEGF binding moiety comprises a VH and VL encoded by the nucleic acid sequence as set forth in:
   a. SEQ ID NOs: 102 and 113, respectively;
   b. SEQ ID NOs: 117 and 123, respectively;
   c. SEQ ID NOs: 128 and 133, respectively;
   d. SEQ ID NOs: 138 and 143, respectively; or
   e. SEQ ID NOs: 148 and 152, respectively.

10. The multi-specific binding molecule of claim 7, wherein the anti-VEGF binding moiety comprises a heavy chain and a light chain with the amino acid sequence as set forth in SEQ ID NOs: 103 and 114, respectively, or wherein the heavy chain and light chain are encoded by a nucleic acid sequence with 100% sequence identity to SEQ ID NOs: 104 and 115, respectively.

11. The multi-specific binding molecule of claim 1, wherein the anti-BTC binding moiety comprises a variable heavy chain domain (VHA) and a variable light chain domain (VLA) that bind to BTC, and wherein the anti-VEGF binding moiety comprises a variable heavy chain domain (VHB) and a variable light chain domain (VLB) that bind to VEGF, wherein the multi-specific binding molecule is in the format from the N-terminus to C-terminus as: N-VHA-heavy chain constant domain (CH1A)-linker 1-VHB-heavy chain constant domain (CH1B)-C and N-VLA-light chain constant domain (CKA)-linker 2-VLB-light chain constant domain (CKB)-C, which comprises a heavy chain comprising the VHA, CH1A, linker 1, VHB, and CH1B, and which comprises a light chain comprising the VLA, CKA, linker 2, VLB, and CKB, wherein the heavy chain and the light chain is as set forth in:
   a. SEQ ID NOs: 120 and 125, respectively;
   b. SEQ ID NOs: 130 and 135, respectively;
   c. SEQ ID NOs: 140 and 145, respectively; or
   d. SEQ ID NOs: 149 and 154, respectively.

12. The multi-specific binding molecule of claim 1, wherein the anti-BTC binding moiety comprises HCDR1, HCDR2, HCDR3, LCDR1, LCDR2, and LCDR3 and the anti-VEGF binding moiety comprises HCDR1, HCDR2, HCDR3, LCDR1, LCDR2, and LCDR3, which are as set forth in:
   a. SEQ ID NOs: 1, 2, 3, 14, 15, 16, 92, 93, 94, 105, 106, and 107, respectively;
   b. SEQ ID NOs: 4, 2, 3, 14, 15, 16, 95, 93, 94, 105, 106, and 107, respectively;
   c. SEQ ID NOs: 5, 6, 3, 17, 18, 19, 96, 97, 94, 108, 109, and 110, respectively; or
   d. SEQ ID NOs: 7, 8, 9, 20, 18, 16, 98, 99, 100, 111, 109, and 107, respectively.

13. The multi-specific binding molecule of claim 1, wherein the anti-BTC binding moiety comprises HCDR1, HCDR2, HCDR3, LCDR1, LCDR2, and LCDR3 and the anti-VEGF binding moiety comprises HCDR1, HCDR2, HCDR3, LCDR1, LCDR2, and LCDR3, which are as set forth in:
   a. SEQ ID NOs: 25, 26, 27, 38, 39, 40, 92, 93, 94, 105, 106, and 107, respectively;
   b. SEQ ID NOs: 28, 26, 27, 38, 39, 40, 95, 93, 94, 105, 106, and 107, respectively;
   c. SEQ ID NOs: 29, 30, 27, 41, 42, 43, 96, 97, 94, 108, 109, and 110, respectively; or
   d. SEQ ID NOs: 31, 32, 33, 44, 42, 40, 98, 99, 100, 111, 109, and 107, respectively.

14. The multi-specific binding molecule of claim 1, wherein the anti-BTC binding moiety comprises HCDR1, HCDR2, HCDR3, LCDR1, LCDR2, and LCDR3 and the anti-VEGF binding moiety comprises HCDR1, HCDR2, HCDR3, LCDR1, LCDR2, and LCDR3, which are as set forth in:
   a. SEQ ID NOs: 25, 49, 50, 58, 59, 60, 92, 93, 94, 105, 106, and 107, respectively;
   b. SEQ ID NOs: 28, 49, 50, 58, 59, 60, 95, 93, 94, 105, 106, and 107, respectively;
   c. SEQ ID NOs: 29, 51, 50, 61, 62, 63, 96, 97, 94, 108, 109, and 110, respectively; or
   d. SEQ ID NOs: 31, 52, 53, 64, 62, 60, 98, 99, 100, 111, 109, and 107, respectively.

15. The multi-specific binding molecule of claim 1, wherein the anti-BTC binding moiety comprises HCDR1, HCDR2, HCDR3, LCDR1, LCDR2, and LCDR3 and the anti-VEGF binding moiety comprises HCDR1, HCDR2, HCDR3, LCDR1, LCDR2, and LCDR3, which are as set forth in:
   a. SEQ ID NOs: 69, 70, 71, 82, 83, 84, 92, 93, 94, 105, 106, and 107, respectively;
   b. SEQ ID NOs: 72, 70, 71, 82, 83, 84, 95, 93, 94, 105, 106, and 107, respectively;
   c. SEQ ID NOs: 73, 74, 71, 85, 18, 86, 96, 97, 94, 108, 109, and 110, respectively; or
   d. SEQ ID NOs: 75, 76, 77, 87, 18, 84, 98, 99, 100, 111, 109, and 107, respectively.

16. A polynucleotide comprising a nucleotide sequence encoding the anti-BTC binding moiety of the multi-specific binding molecule of claim 1.

17. An expression cassette or a vector comprising the polynucleotide of claim 16.

18. A pharmaceutical composition comprising an effective amount of the multi-specific binding molecule of claim 1.

19. A kit comprising the pharmaceutical composition of claim 18.

20. A polynucleotide comprising a nucleotide sequence encoding the multi-specific binding molecule of claim 11.

* * * * *

SEQUENCE LISTING

<160> NUMBER OF SEQ ID NOS: 207

<210> SEQ ID NO 1
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 1

Gly Gly Thr Phe Ser Ser Tyr Ala Ile Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 2

Gly Ile Val Pro Trp Met Gly Glu Ala Val Tyr Ala Gln Lys Phe Gln
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 3

Ser Ser Ser Thr Tyr Gly Ile His Ala Phe Asp Tyr
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 4

Ser Tyr Ala Ile Ser
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 5

Gly Gly Thr Phe Ser Ser Tyr
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 6

Val Pro Trp Met Gly Glu
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 7

Gly Gly Thr Phe Ser Ser Tyr Ala
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 8

Ile Val Pro Trp Met Gly Glu Ala

<210> SEQ ID NO 9
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 9

Ala Arg Ser Ser Ser Thr Tyr Gly Ile His Ala Phe Asp Tyr
1               5                   10

<210> SEQ ID NO 10
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Val Pro Trp Met Gly Glu Ala Val Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Ser Thr Tyr Gly Ile His Ala Phe Asp Tyr Trp Gly
            100                 105                 110

Gln Gly Thr Leu Val Thr Val Ser Ser
        115                 120

<210> SEQ ID NO 11
<211> LENGTH: 363
<212> TYPE: DNA
<213> ORGANISM: Artificial Sequence
<220> FEATURE:
<223> OTHER INFORMATION: Synthetic polynucleotide

<400> SEQUENCE: 11
caggtgcaat tggtgcagag cggtgccgaa gtgaaaaaac cgggcagcag cgtgaaagtt      60
agctgcaaag catccggagg gacgtttagc agctatgcga ttagctgggt gcgccaggcc     120
ccgggccagg gcctcgagtg gatgggcggt atcgttccgt ggatgggcga agctgtttac     180
gcccagaaat tcagggccgg ggtgaccatt accgccgatg aaagcaccag caccgcctat     240
atggaactga gcagcctgcg cagcgaagat acggccgtgt attattgcgc gcgttcttct     300
tctacttacg gtatccatgc tttcgattac tggggccaag gcaccctggt gactgttagc     360
tca                                                                   363

<210> SEQ ID NO 12
<211> LENGTH: 224
<212> TYPE: PRT
<213> ORGANISM: Artificial Sequence
<220> FEATURE:

<223> OTHER INFORMATION: Synthetic polypeptide

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Val Pro Trp Met Gly Glu Ala Val Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Ser Thr Tyr Gly Ile His Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

<210> SEQ ID NO 13
<211> LENGTH: 672
<212> TYPE: DNA
<213> ORGANISM: Artificial Sequence
<220> FEATURE:
<223> OTHER INFORMATION: Synthetic polynucleotide

<400> SEQUENCE: 13
caggtgcaat tggtgcagag cggtgccgaa gtgaaaaaac cgggcagcag cgtgaaagtt      60
agctgcaaag catccggagg gacgtttagc agctatgcga ttagctgggt gcgccaggcc     120
ccgggccagg gcctcgagtg gatgggcggt atcgttccgt ggatgggcga agctgtttac     180
gcccagaaat tcagggccg ggtgaccatt accgccgatg aaagcaccag caccgcctat     240
atggaactga gcagcctgcg cagcgaagat acggccgtgt attattgcgc gcgttcttct     300
tctacttacg gtatccatgc tttcgattac tggggccaag gcaccctggt gactgttagc     360
tcagcctcca ccaagggccc cagcgtgttc cccctggccc ccagcagcaa gagcaccagc     420
ggcggcacag ccgccctggg ctgcctggtg aaggactact ccccgagcc cgtgaccgtg     480
tcctggaaca gcggagccct gacctccggc gtgcacacct tccccgccgt gctgcagagc     540
agcggcctgt acagcctgag cagcgtggtg accgtgccca gcagcagcct gggcacccag     600
acctacatct gtaacgtgaa ccacaagccc agcaacacca aggtggacaa gagagtggag     660
cccaagagct gt                                                        672

```
<210> SEQ ID NO 14
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 14

Arg Ala Ser Gln Ser Ile Ser Asn Phe Leu Asn
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 15

Ala Ala Ser Asn Leu Gln Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 16

Gln Gln Tyr Asp Asp Phe Pro Met Thr
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 17

Ser Gln Ser Ile Ser Asn Phe
1               5

<210> SEQ ID NO 18
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 18

Ala Ala Ser
1

<210> SEQ ID NO 19
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 19

Tyr Asp Asp Phe Pro Met
1               5
```

<210> SEQ ID NO 20
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 20

Gln Ser Ile Ser Asn Phe
1               5

<210> SEQ ID NO 21
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Phe
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Asp Phe Pro Met
                85                  90                  95

Thr Phe Gly Gln Gly Thr Lys Val Glu Ile Lys
            100                 105

<210> SEQ ID NO 22
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 22
gatatccaga tgacccagag cccgagcagc ctgagcgcca gcgtgggcga tcgcgtgacc      60
attacctgca gagccagcca gtctatttct aacttcctga actggtacca gcagaaaccg     120
ggcaaagcgc cgaaactatt aatctacgct gcttctaacc tgcaaagcgg cgtgccgagc     180
cgctttagcg gcagcggatc cggcaccgat ttcaccctga ccattagctc tctgcaaccg     240
gaagactttg cgacctatta ttgccagcag tacgacgact cccgatgac ctttggccag     300 ggcacgaaag ttgaaattaa a                                               321

<210> SEQ ID NO 23
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Phe
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Asp Phe Pro Met
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 24
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 24
gatatccaga tgacccagag cccgagcagc ctgagcgcca gcgtgggcga tcgcgtgacc      60
attacctgca gagccagcca gtctatttct aacttcctga actggtacca gcagaaaccg     120
ggcaaagcgc cgaaactatt aatctacgct gcttctaacc tgcaaagcgg cgtgccgagc     180
cgctttagcg gcagcggatc cggcaccgat ttcaccctga ccattagctc tctgcaaccg     240
gaagactttg cgacctatta ttgccagcag tacgacgact cccgatgac ctttggccag     300 ggcacgaaag ttgaaattaa acgtacggtg gccgctccca gcgtgttcat cttcccccc      360 agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gaaagcgtca ccgagcagga cagcaaggac tccacctaca gcctgagcag caccctgacc     540
ctgagcaagg ccgactacga gaagcacaag gtgtacgcct gcgaggtgac ccaccagggc     600
ctgtccagcc ccgtgaccaa gagcttcaac cggggcgagt gt                        642

<210> SEQ ID NO 25
<211> LENGTH: 10
<212> TYPE: PRT
<213> ORGANISM: Artificial Sequence
<220> FEATURE:
<223> OTHER INFORMATION: Synthetic polypeptide

```
<400> SEQUENCE: 25

Gly Phe Thr Phe Ser Ser Tyr Ala Met Ser
1               5                   10

<210> SEQ ID NO 26
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 26

Ala Ile Ser Gly Ser Gly Gly Ser Thr Tyr Tyr Ala Asp Ser Val Lys
1               5                   10                  15

Gly

<210> SEQ ID NO 27
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 27

Gln Arg Tyr Tyr Phe Gly Glu Phe Asp Leu
1               5                   10

<210> SEQ ID NO 28
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 28

Ser Tyr Ala Met Ser
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 29

Gly Phe Thr Phe Ser Ser Tyr
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 30

Ser Gly Ser Gly Gly Ser
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic polypeptide
```

<400> SEQUENCE: 31

Gly Phe Thr Phe Ser Ser Tyr Ala
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 32

Ile Ser Gly Ser Gly Gly Ser Thr
1               5

<210> SEQ ID NO 33
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 33

Ala Arg Gln Arg Tyr Tyr Phe Gly Glu Phe Asp Leu
1               5                   10

<210> SEQ ID NO 34
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Arg Tyr Tyr Phe Gly Glu Phe Asp Leu Trp Gly Gln Gly
            100                 105                 110

Thr Leu Val Thr Val Ser Ser
        115

<210> SEQ ID NO 35
<211> LENGTH: 357
<212> TYPE: DNA
<213> ORGANISM: Artificial Sequence
<220> FEATURE:
<223> OTHER INFORMATION: Synthetic polynucleotide

<400> SEQUENCE: 35
gaagtgcagc tgctggaaag cggtggcggt ctggtgcagc caggtggtag cctgcgcctg      60
agctgtgccg caagcggctt tacctttagc agctatgcca tgagctgggt gcgccaagca     120

```
ccaggcaaag gcctggaatg ggtgagcgcc attagcggca gcggtggcag cacctattat    180
gccgatagcg tgaaaggtcg ctttaccatt agtcgcgata cagcaaaaa cccctgtat     240 ctgcaaatga acagcctgcg ggcagaagat accgcagttt attattgcgc gcgacaacgt    300
tactacttcg gtgagttcga cctgtggggc cagggcaccc tggttactgt ctcgagc      357
```

<210> SEQ ID NO 36
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 36

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Arg Tyr Tyr Phe Gly Glu Phe Asp Leu Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys
    210                 215                 220
```

<210> SEQ ID NO 37
<211> LENGTH: 666
<212> TYPE: DNA
<213> ORGANISM: Artificial Sequence
<220> FEATURE:
<223> OTHER INFORMATION: Synthetic polynucleotide

<400> SEQUENCE: 37

```
gaagtgcagc tgctggaaag cggtggcggt ctggtgcagc aggtggtag cctgcgcctg    60 agctgtgccg caagcggctt tacctttagc agctatgcca tgagctgggt gcgccaagca    120
ccaggcaaag gcctggaatg ggtgagcgcc attagcggca gcggtggcag cacctattat    180
gccgatagcg tgaaaggtcg ctttaccatt agtcgcgata cagcaaaaa cccctgtat     240
```

```
ctgcaaatga acagcctgcg ggcagaagat accgcagttt attattgcgc gcgacaacgt    300
tactacttcg gtgagttcga cctgtggggc cagggcaccc tggttactgt ctcgagcgcc    360
agcacaaagg gacccagcgt gttccctctg cccccagca gcaagtctac atctggcgga    420
acagccgccc tgggctgcct cgtgaaggac tactttcccg agcccgtgac cgtgtcctgg    480
aactctggcg ctctgacaag cggcgtgcac acctttccag ccgtgctcca gagcagcggc    540
ctgtactctc tgagcagcgt cgtgacagtg cccagcagct ctctgggcac ccagacctac    600
atctgcaacg tgaaccacaa gcccagcaac acaaaggtgg acaagcgggt ggaacccaag    660
tcctgc                                                              666
```

```
<210> SEQ ID NO 38
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 38

Ser Gly Asp Lys Leu Gly Asp Lys Tyr Ala Tyr
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 39

Gln Asp Ser Lys Arg Pro Ser
1               5

<210> SEQ ID NO 40
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 40

Gln Ala Phe Asp Tyr Leu Tyr Ser Leu Gly Val
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 41

Asp Lys Leu Gly Asp Lys Tyr
1               5

<210> SEQ ID NO 42
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 42

Gln Asp Ser
1
```

```
<210> SEQ ID NO 43
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 43

Phe Asp Tyr Leu Tyr Ser Leu Gly
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 44

Lys Leu Gly Asp Lys Tyr
1               5

<210> SEQ ID NO 45
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 45

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
                20                  25                  30

Tyr Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ala Phe Asp Tyr Leu Tyr Ser Leu
                85                  90                  95

Gly Val Phe Gly Gly Gly Thr Lys Leu Thr Val Leu
            100                 105

<210> SEQ ID NO 46
<211> LENGTH: 324
<212> TYPE: DNA
<213> ORGANISM: Artificial Sequence
<220> FEATURE:
<223> OTHER INFORMATION: Synthetic polynucleotide

<400> SEQUENCE: 46
agctatgaac tgacccagcc gccgagcgtt agcgttagcc caggccagac cgccagcatt    60
acctgtagcg gcgacaaact gggcgacaaa tacgcctact ggtatcagca gaaaccgggc   120
cagagcccgg tgctggttat ctatcaggat agcaaacgcc cgagcggcat tccagaacgc   180
tttagcggca gcaacagcgg caacaccgcc accctgacca ttagcggcac ccaggccgaa   240
gacgaagccg attattactg tcaggctttc gactacctgt attccctggg tgtgtttggc   300
```
ggcggtacca agctgaccgt gctg 324

<210> SEQ ID NO 47
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 47

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Tyr Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ala Phe Asp Tyr Leu Tyr Ser Leu
                85                  90                  95

Gly Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 48
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 48
agctatgaac tgacccagcc gccgagcgtt agcgttagcc caggccagac cgccagcatt      60
acctgtagcg gcgacaaact gggcgacaaa tacgcctact ggtatcagca gaaaccgggc     120
cagagcccgg tgctggttat ctatcaggat agcaaacgcc cgagcggcat tccagaacgc     180
tttagcggca gcaacagcgg caacaccgcc accctgacca ttagcggcac ccaggccgaa     240
gacgaagccg attattactg tcaggctttc gactacctgt attccctggg tgtgtttggc     300
ggcggtacca agctgaccgt gctgggccag cccaaagccg cccctagcgt gaccctgttc     360
ccccaagcag cgaggaact ccaggccaac aaggccaccc tcgtgtgcct gatcagcgac     420
ttctaccctg gcgccgtgac cgtggcctgg aaggccgata gcagccctgt gaaggccggc     480

```
gtggaaacca ccacccccag caagcagagc aacaacaaat acgccgccag cagctacctg        540
agcctgaccc ccgagcagtg gaagtcccac agatcctaca gctgccaggt cacacacgag        600
ggcagcaccg tggaaaagac cgtggccccc accgagtgca gc                           642
```

```
<210> SEQ ID NO 49
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 49

Gly Leu Gly His Val Gly Tyr Thr Thr Tyr Thr Asp Ser Val Lys Gly
1               5                   10                  15

<210> SEQ ID NO 50
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 50

Asp Tyr Leu Asp Phe Gly Tyr Tyr Phe Asp Val
1               5                   10

<210> SEQ ID NO 51
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 51

Gly His Val Gly Tyr
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 52

Leu Gly His Val Gly Tyr Thr
1               5

<210> SEQ ID NO 53
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 53

Ala Arg Asp Tyr Leu Asp Phe Gly Tyr Tyr Phe Asp Val
1               5                   10

<210> SEQ ID NO 54
<211> LENGTH: 119
<212> TYPE: PRT
<213> ORGANISM: Artificial Sequence
<220> FEATURE:
<223> OTHER INFORMATION: Synthetic polypeptide
```

<400> SEQUENCE: 54

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Leu Gly His Val Gly Tyr Thr Thr Tyr Thr Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Tyr Leu Asp Phe Gly Tyr Tyr Phe Asp Val Trp Gly Gln Gly
            100                 105                 110

Thr Leu Val Thr Val Ser Ser
        115

<210> SEQ ID NO 55
<211> LENGTH: 357
<212> TYPE: DNA
<213> ORGANISM: Artificial Sequence
<220> FEATURE:
<223> OTHER INFORMATION: Synthetic polynucleotide

<400> SEQUENCE: 55
caggtgcagc tgctggaatc aggcggcgga ctggtgcagc ctggcggtag cctgagactg    60
agctgcgctg ctagtggctt caccttctct agctacgcta tgagctgggt ccggcaggcc   120
cctggcaaag gcctggagtg gtctccggac tgggtcacg tgggctacac tacctacacc    180
gatagcgtga agggccggtt cactatctct agggataact ctaagaacac cctgtacctg   240
cagatgaata gcctgagagc cgaggacacc gccgtctact actgcgctag agactacctg   300
gacttcggct actacttcga cgtgtggggc cagggcaccc tggtcaccgt gtctagc      357

<210> SEQ ID NO 56
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 56

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Leu Gly His Val Gly Tyr Thr Thr Tyr Thr Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Tyr Leu Asp Phe Gly Tyr Tyr Phe Asp Val Trp Gly Gln Gly
            100                 105                 110

```
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys
        210                 215                 220
```

<210> SEQ ID NO 57
<211> LENGTH: 666
<212> TYPE: DNA
<213> ORGANISM: Artificial Sequence
<220> FEATURE:
<223> OTHER INFORMATION: Synthetic polynucleotide

<400> SEQUENCE: 57

```
caggtgcagc tgctggaatc aggcggcgga ctggtgcagc ctggcggtag cctgagactg      60
agctgcgctg ctagtggctt caccttctct agctacgcta tgagctgggt ccggcaggcc     120
cctggcaaag cctggagtg gtctccgga ctgggtcacg tgggctacac tacctacacc      180
gatagcgtga agggccggtt cactatctct aggataact ctaagaacac cctgtacctg      240
cagatgaata gcctgagagc cgaggacacc gccgtctact actgcgctag agactacctg      300
gacttcggct actacttcga cgtgtggggc cagggcaccc tggtcaccgt gtctagcgct     360
agcactaagg gccctccgt gttccctctg gccccttcca gcaagtctac ctctggcggc     420
accgctgctc tgggctgcct ggtgaaggac tacttccctg agcctgtgac agtgtcctgg     480
aactctggcg ccctgaccctc cggcgtgcac accttccctg ccgtgctgca gtcctccggc     540
ctgtactccc tgtcctccgt ggtgacagtg ccttcctcca gcctgggcac ccagacctat     600
atctgcaacg tgaaccacaa gccttccaac accaaggtgg acaagcgggt ggagcctaag     660
tcatgc                                                                666
```

<210> SEQ ID NO 58
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 58

```
Ser Gly Asp Lys Ile Gly Lys Lys Tyr Val His
1               5                   10
```

<210> SEQ ID NO 59
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 59

```
Asp Asp Ser Asp Arg Pro Ser
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 60

Gln Ala Trp Asp Met Gln Ser Val Val
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 61

Asp Lys Ile Gly Lys Lys Tyr
1               5

<210> SEQ ID NO 62
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 62

Asp Asp Ser
1

<210> SEQ ID NO 63
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 63

Trp Asp Met Gln Ser Val
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 64

Lys Ile Gly Lys Lys Tyr
1               5

<210> SEQ ID NO 65
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 65

Ser Tyr Glu Leu Thr Gln Pro Leu Ser Val Ser Val Ala Leu Gly Gln
```

```
1               5                   10                  15
Thr Ala Arg Ile Thr Cys Ser Gly Asp Lys Ile Gly Lys Lys Tyr Val
                20                  25                  30

His Trp Tyr Gln Gln Lys Pro Gly Gln Ala Pro Val Leu Val Ile Tyr
                35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ala Trp Asp Met Gln Ser Val Val
                85                  90                  95

Phe Gly Gly Gly Thr Lys Leu Thr Val Leu
                100                 105

<210> SEQ ID NO 66
<211> LENGTH: 318
<212> TYPE: DNA
<213> ORGANISM: Artificial Sequence
<220> FEATURE:
<223> OTHER INFORMATION: Synthetic polynucleotide

<400> SEQUENCE: 66
agctacgagc tgactcagcc cctgagcgtc agcgtggccc tgggccagac cgctagaatc      60
acctgtagcg gcgataagat cggcaagaaa tacgtgcact ggtatcagca gaagcccggc     120
caggcccccg tgctggtcat ctacgacgat agcgatagac ctagcggaat ccccgagcgg     180
tttagcggct ctaatagcgg caacaccgct accctgacta tctctagggc tcaggccggc     240
gacgaggccg actactactg tcaggcctgg gatatgcagt cagtggtgtt cggcggaggc     300
actaagctga ccgtgctg                                                   318

<210> SEQ ID NO 67
<211> LENGTH: 212
<212> TYPE: PRT
<213> ORGANISM: Artificial Sequence
<220> FEATURE:
<223> OTHER INFORMATION: Synthetic polypeptide

<400> SEQUENCE: 67

Ser Tyr Glu Leu Thr Gln Pro Leu Ser Val Ser Val Ala Leu Gly Gln
1               5                   10                  15

Thr Ala Arg Ile Thr Cys Ser Gly Asp Lys Ile Gly Lys Lys Tyr Val
                20                  25                  30

His Trp Tyr Gln Gln Lys Pro Gly Gln Ala Pro Val Leu Val Ile Tyr
                35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ala Trp Asp Met Gln Ser Val Val
                85                  90                  95

Phe Gly Gly Gly Thr Lys Leu Thr Val Leu Gly Gln Pro Lys Ala Ala
                100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140
```

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 68
<211> LENGTH: 636
<212> TYPE: DNA
<213> ORGANISM: Artificial Sequence
<220> FEATURE:
<223> OTHER INFORMATION: Synthetic polynucleotide

<400> SEQUENCE: 68
agctacgagc tgactcagcc cctgagcgtc agcgtggccc tgggccagac cgctagaatc      60
acctgtagcg gcgataagat cggcaagaaa tacgtgcact ggatcagca gaagcccggc     120 caggcccccg tgctggtcat ctacgacgat agcgatagac ctagcggaat ccccgagcgg    180
tttagcggct ctaatagcgg caacaccgct accctgacta tctctagggc tcaggccggc    240
gacgaggccg actactactg tcaggcctgg gatatgcagt cagtggtgtt cggcggaggc    300
actaagctga ccgtgctggg ccagcctaag gctgccccca gcgtgaccct gttcccccc    360 agcagcgagg agctgcaggc caacaaggcc accctggtgt gcctgatcag cgacttctac    420
ccaggcgccg tgaccgtggc ctggaaggcc gacagcagcc ccgtgaaggc cggcgtggag    480
accaccaccc ccagcaagca gagcaacaac aagtacgccg ccagcagcta cctgagcctg    540 accccgagc agtggaagag ccacaggtcc tacagctgcc aggtgaccca cgagggcagc    600
accgtggaaa agaccgtggc cccaaccgag tgcagc                              636

<210> SEQ ID NO 69
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 69

Gly Phe Thr Phe Ser Arg Tyr Trp Ile Ser
1               5                   10

<210> SEQ ID NO 70
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 70

Tyr Ile Asp Ser Thr Gly Thr Phe Ile Asn Tyr Ala Asp Ser Val Lys
1               5                   10                  15

Gly

<210> SEQ ID NO 71
<211> LENGTH: 7
<212> TYPE: PRT

```
<213> ORGANISM: Artificial Sequence
<220> FEATURE:
<223> OTHER INFORMATION: Synthetic polypeptide

<400> SEQUENCE: 71

Gly Gly Ser Leu Phe Asp Tyr
1               5

<210> SEQ ID NO 72
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 72

Arg Tyr Trp Ile Ser
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 73

Gly Phe Thr Phe Ser Arg Tyr
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 74

Asp Ser Thr Gly Thr Phe
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 75

Gly Phe Thr Phe Ser Arg Tyr Trp
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 76

Ile Asp Ser Thr Gly Thr Phe Ile
1               5

<210> SEQ ID NO 77
<211> LENGTH: 9
<212> TYPE: PRT
<213> ORGANISM: Artificial Sequence
```

```
<220> FEATURE:
<223> OTHER INFORMATION: Synthetic polypeptide

<400> SEQUENCE: 77

Ala Arg Gly Gly Ser Leu Phe Asp Tyr
1               5

<210> SEQ ID NO 78
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 78

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Ile Ser Trp Val Arg Gln Ala Pro Gly Lys Gly Leu Glu Trp Val
        35                  40                  45

Ser Tyr Ile Asp Ser Thr Gly Thr Phe Ile Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Leu Phe Asp Tyr Trp Gly Gln Gly Thr Leu Val
            100                 105                 110

Thr Val Ser Ser
        115

<210> SEQ ID NO 79
<211> LENGTH: 348
<212> TYPE: DNA
<213> ORGANISM: Artificial Sequence
<220> FEATURE:
<223> OTHER INFORMATION: Synthetic polynucleotide

<400> SEQUENCE: 79
caggtgcagc tgctggaatc aggcggcgga ctggtgcagc ctggcggtag cctgagactg      60
agctgcgctg ctagtggctt caccttctct aggtactgga ttagctgggt ccggcaggcc     120
cctggcaaag gcctggagtg gtctcctat atcgactcta ccggcacctt tattaactac     180
gccgatagcg tgaagggccg gttcactatc tctagggata actctaagaa caccctgtac     240
ctgcagatga atagcctgag agccgaggac accgccgtct actactgcgc tagaggcggt     300
agtctgttcg actactgggg ccagggcacc ctggtcaccg tgtctagc                   348

<210> SEQ ID NO 80
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 80

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30
```

Trp Ile Ser Trp Val Arg Gln Ala Pro Gly Lys Gly Leu Glu Trp Val
            35                  40                  45
Ser Tyr Ile Asp Ser Thr Gly Thr Phe Ile Asn Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Gly Ser Leu Phe Asp Tyr Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Arg Val Glu Pro Lys Ser Cys
    210                 215

<210> SEQ ID NO 81
<211> LENGTH: 657
<212> TYPE: DNA
<213> ORGANISM: Artificial Sequence
<220> FEATURE:
<223> OTHER INFORMATION: Synthetic polynucleotide

<400> SEQUENCE: 81
caggtgcagc tgctggaatc aggcggcgga ctggtgcagc ctggcggtag cctgagactg     60
agctgcgctg ctagtggctt caccttctct aggtactgga ttagctgggt ccggcaggcc    120
cctggcaaag cctggagtg gtctcctat atcgactcta ccggcacctt tattaactac    180
gccgatagcg tgaagggccg gttcactatc tctagggata ctctaagaa caccctgtac    240
ctgcagatga atagcctgag agccgaggac accgccgtct actactgcgc tagaggcggt    300
agtctgttcg actactgggg ccagggcacc tggtcaccg tgtctagcgc tagcactaag    360
ggcccctccg tgttccctct ggccccttcc agcaagtcta cctctggcgg caccgctgct    420
ctgggctgcc tggtgaagga ctacttccct gagcctgtga cagtgtcctg gaactctggc    480
gccctgacct ccggcgtgca caccttccct gccgtgctgc agtcctccgg cctgtactcc    540
ctgtcctccg tggtgacagt gccttcctcc agcctgggca cccagaccta tatctgcaac    600
gtgaaccaca gccttccaa caccaaggtg acaagcggg tggagcctaa gtcatgc       657

<210> SEQ ID NO 82
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 82

Arg Ala Ser Gln Gly Ile Ile Ser Tyr Leu Gly
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 83

Ala Ala Ser Ser Leu Gln Ser
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 84

Gln Gln Tyr Asp Ala Leu Asn Thr
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 85

Ser Gln Gly Ile Ile Ser Tyr
1               5

<210> SEQ ID NO 86
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 86

Tyr Asp Ala Leu Asn
1               5

<210> SEQ ID NO 87
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 87

Gln Gly Ile Ile Ser Tyr
1               5

<210> SEQ ID NO 88
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 88

Asp Ile Gln Met Thr Gln Ser Pro Ser Ser Leu Ser Ala Ser Val Gly

```
                1               5              10              15
Asp Arg Val Thr Ile Thr Cys Arg Ala Ser Gln Gly Ile Ile Ser Tyr
                20              25              30

Leu Gly Trp Tyr Gln Gln Lys Pro Gly Lys Ala Pro Lys Leu Leu Ile
        35              40              45

Tyr Ala Ala Ser Ser Leu Gln Ser Gly Val Pro Ser Arg Phe Ser Gly
        50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Tyr Asp Ala Leu Asn Thr
                85              90              95

Phe Gly Gln Gly Thr Lys Val Glu Ile Lys
                100             105
```

<210> SEQ ID NO 89
<211> LENGTH: 318
<212> TYPE: DNA
<213> ORGANISM: Artificial Sequence
<220> FEATURE:
<223> OTHER INFORMATION: Synthetic polynucleotide

<400> SEQUENCE: 89

```
gatattcaga tgactcagtc acctagtagc ctgagcgcta gtgtgggcga tagagtgact      60
atcacctgta gagcctctca ggggattatt agctacctgg gctggtatca gcagaagccc     120
ggcaaagccc ctaagctgct gatctacgcc gcctctagcc tgcagtcagg cgtgccctct     180
aggtttagcg gtagcggtag tggcaccgac ttcaccctga ctattagtag cctgcagccc     240
gaggacttcg ctacctacta ctgtcagcag tacgacgccc tgaacacctt cggccagggc     300
actaaggtcg agattaag                                                   318
```

<210> SEQ ID NO 90
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 90

```
Asp Ile Gln Met Thr Gln Ser Pro Ser Ser Leu Ser Ala Ser Val Gly
1               5              10              15

Asp Arg Val Thr Ile Thr Cys Arg Ala Ser Gln Gly Ile Ile Ser Tyr
                20              25              30

Leu Gly Trp Tyr Gln Gln Lys Pro Gly Lys Ala Pro Lys Leu Leu Ile
        35              40              45

Tyr Ala Ala Ser Ser Leu Gln Ser Gly Val Pro Ser Arg Phe Ser Gly
        50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Tyr Asp Ala Leu Asn Thr
                85              90              95

Phe Gly Gln Gly Thr Lys Val Glu Ile Lys Arg Thr Val Ala Ala Pro
                100             105             110

Ser Val Phe Ile Phe Pro Pro Ser Asp Glu Gln Leu Lys Ser Gly Thr
        115             120             125

Ala Ser Val Val Cys Leu Leu Asn Asn Phe Tyr Pro Arg Glu Ala Lys
    130             135             140
```

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 91
<211> LENGTH: 639
<212> TYPE: DNA
<213> ORGANISM: Artificial Sequence
<220> FEATURE:
<223> OTHER INFORMATION: Synthetic polynucleotide

<400> SEQUENCE: 91
gatattcaga tgactcagtc acctagtagc ctgagcgcta gtgtgggcga tagagtgact      60
atcacctgta gagcctctca ggggattatt agctacctgg ctggtatca gcagaagccc     120 ggcaaagccc ctaagctgct gatctacgcc gcctctagcc tgcagtcagg cgtgccctct    180
aggtttagcg gtagcggtag tggcaccgac ttcaccctga ctattagtag cctgcagccc    240
gaggacttcg ctacctacta ctgtcagcag tacgacgccc tgaacaccttc ggccagggc    300 actaaggtcg agattaagcg tacggtggcc gctcccagcg tgttcatctt ccccccccagc   360 gacgagcagc tgaagagcgg caccgccagc gtggtgtgcc tgctgaacaa cttctacccc    420
cgggaggcca aggtgcagtg gaaggtggac aacgccctgc agagcggcaa cagccaggag    480
agcgtcaccg agcaggacag caaggactcc acctacagcc tgagcagcac cctgaccctg    540
agcaaggccg actacgagaa gcataaggtg tacgcctgcg aggtgaccca ccagggcctg    600
tccagccccg tgaccaagag cttcaacagg ggcgagtgc                           639

<210> SEQ ID NO 92
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 92

Gly Phe Ser Leu Thr Asp Tyr Tyr Tyr Met Thr
1               5                   10

<210> SEQ ID NO 93
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 93

Phe Ile Asp Pro Asp Asp Asp Pro Tyr Tyr Ala Thr Trp Ala Lys Gly
1               5                   10                  15

<210> SEQ ID NO 94
<211> LENGTH: 11
<212> TYPE: PRT
<213> ORGANISM: Artificial Sequence
<220> FEATURE:

<223> OTHER INFORMATION: Synthetic polypeptide

<400> SEQUENCE: 94

Gly Asp His Asn Ser Gly Trp Gly Leu Asp Ile
1               5                   10

<210> SEQ ID NO 95
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 95

Asp Tyr Tyr Tyr Met Thr
1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 96

Gly Phe Ser Leu Thr Asp Tyr Tyr
1               5

<210> SEQ ID NO 97
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 97

Asp Pro Asp Asp Asp
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 98

Gly Phe Ser Leu Thr Asp Tyr Tyr Tyr
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 99

Ile Asp Pro Asp Asp Asp Pro
1               5

<210> SEQ ID NO 100
<211> LENGTH: 13
<212> TYPE: PRT
<213> ORGANISM: Artificial Sequence
<220> FEATURE:
<223> OTHER INFORMATION: Synthetic polypeptide -continued

<400> SEQUENCE: 100

Ala Gly Gly Asp His Asn Ser Gly Trp Gly Leu Asp Ile
1               5                   10

<210> SEQ ID NO 101
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Asp His Asn Ser Gly Trp Gly Leu Asp Ile Trp Gly Gln
            100                 105                 110

Gly Thr Leu Val Thr Val Ser Ser
        115                 120

<210> SEQ ID NO 102
<211> LENGTH: 360
<212> TYPE: DNA
<213> ORGANISM: Artificial Sequence
<220> FEATURE:
<223> OTHER INFORMATION: Synthetic polynucleotide

<400> SEQUENCE: 102
gaggtgcaat tggttgaatc tggggggcgga ctggtgcagc ccggtggatc tttgcgcctg      60
tcctgtacag cttctggctt ctccttgacc gactactatt acatgacttg ggttcgccaa     120
gccccaggca aagggcttga atgggtgggg ttcattgacc ccgacgatga tccttactac     180
gccacatggg caaagggccg gtttactatc agccgggata attccaaaaa cacattgtat     240
ttgcaaatga actcactgag agcagaagat acggctgtgt actattgcgc aggcggcgat     300
cataactccg gctggggcct ggacatctgg gggcagggga ccctggtgac agtcagctca     360

<210> SEQ ID NO 103
<211> LENGTH: 223
<212> TYPE: PRT
<213> ORGANISM: Artificial Sequence
<220> FEATURE:
<223> OTHER INFORMATION: Synthetic polypeptide

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp

```
                35                  40                  45
Val Gly Phe Ile Asp Pro Asp Asp Pro Tyr Tyr Ala Thr Trp Ala
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Gly Asp His Asn Ser Gly Trp Gly Leu Asp Ile Trp Gly Gln
                100                 105                 110

Gly Thr Leu Val Thr Val Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Arg Val Glu Pro Lys Ser Cys
210                 215                 220

<210> SEQ ID NO 104
<211> LENGTH: 669
<212> TYPE: DNA
<213> ORGANISM: Artificial Sequence
<220> FEATURE:
<223> OTHER INFORMATION: Synthetic polynucleotide

<400> SEQUENCE: 104
gaggtgcaat tggttgaatc tgggggcgga ctggtgcagc ccggtggatc tttgcgcctg      60
tcctgtacag cttctggctt ctccttgacc gactactatt acatgacttg ggttcgccaa     120
gccccaggca aagggcttga atgggtgggg ttcattgacc ccgacgatga tccttactac     180
gccacatggg caaagggccg gtttactatc agccgggata attccaaaaa cacattgtat     240
ttgcaaatga actcactgag agcagaagat acggctgtgt actattgcgc aggcggcgat     300
cataactccg ctggggcct ggacatctgg ggcagggga ccctggtgac agtcagctca      360
gcctcaacga aggggcccag cgtgtttcct ttggccccaa gcagcaagtc cacgtccggt     420
gggactgcag ctcttggttg tctggtcaag gattatttcc cagaacccgt gaccgtgtct     480
tggaacagtg gtgcattgac atcaggagtg catacattcc cagctgtgct gcagagctct     540
ggcctgtata gcctttcctc tgttgtcacg gtgcccagct ccagcctggg gacgcagacc     600
tatatttgta acgtgaacca taaaccctcc aacaccaagg ttgataaaag agtggagccc     660
aagtcttgt                                                             669

<210> SEQ ID NO 105
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 105
```

Gln Ala Ser Glu Ile Ile His Ser Trp Leu Ala
1               5                   10

<210> SEQ ID NO 106
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 106

Leu Ala Ser Thr Leu Ala Ser
1               5

<210> SEQ ID NO 107
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 107

Gln Asn Val Tyr Leu Ala Ser Thr Asn Gly Ala Asn
1               5                   10

<210> SEQ ID NO 108
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 108

Ser Glu Ile Ile His Ser Trp
1               5

<210> SEQ ID NO 109
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 109

Leu Ala Ser
1

<210> SEQ ID NO 110
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 110

Val Tyr Leu Ala Ser Thr Asn Gly Ala
1               5

<210> SEQ ID NO 111
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 111

Glu Ile Ile His Ser Trp

<210> SEQ ID NO 112
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 112

```
Glu Ile Val Met Thr Gln Ser Pro Ser Thr Leu Ser Ala Ser Val Gly
1               5                   10                  15
Asp Arg Val Ile Ile Thr Cys Gln Ala Ser Glu Ile Ile His Ser Trp
            20                  25                  30
Leu Ala Trp Tyr Gln Gln Lys Pro Gly Lys Ala Pro Lys Leu Leu Ile
        35                  40                  45
Tyr Leu Ala Ser Thr Leu Ala Ser Gly Val Pro Ser Arg Phe Ser Gly
    50                  55                  60
Ser Gly Ser Gly Ala Glu Phe Thr Leu Thr Ile Ser Ser Leu Gln Pro
65                  70                  75                  80
Asp Asp Phe Ala Thr Tyr Tyr Cys Gln Asn Val Tyr Leu Ala Ser Thr
                85                  90                  95
Asn Gly Ala Asn Phe Gly Gln Gly Thr Lys Leu Thr Val Leu Lys
            100                 105                 110
```

<210> SEQ ID NO 113
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 113

```
gagattgtga tgactcagag cccttcaacg ctgtctgcat ccgtaggtga tcgcgtcatt    60
attacctgtc aagcctcaga gatcattcac tcttggctcg cctggtatca gcagaagccc   120
ggtaaggccc ccaagctgct gatctatctt gcttcaaccc tcgcgagcgg ggtgccctcc   180
cgcttcagcg gctccggctc tggtgccgaa tttaccctga caatcagctc tctccaaccc   240
gatgatttcg cgacttacta ctgtcagaat gtctacttgg cctcaaccaa cggagccaac   300
ttcggccagg gaccaaaact gaccgtcctt aag                                333
```

<210> SEQ ID NO 114
<211> LENGTH: 218
<212> TYPE: PRT
<213> ORGANISM: Artificial Sequence
<220> FEATURE:
<223> OTHER INFORMATION: Synthetic polypeptide

<400> SEQUENCE: 114

```
Glu Ile Val Met Thr Gln Ser Pro Ser Thr Leu Ser Ala Ser Val Gly
1               5                   10                  15
Asp Arg Val Ile Ile Thr Cys Gln Ala Ser Glu Ile Ile His Ser Trp
            20                  25                  30
Leu Ala Trp Tyr Gln Gln Lys Pro Gly Lys Ala Pro Lys Leu Leu Ile
        35                  40                  45
Tyr Leu Ala Ser Thr Leu Ala Ser Gly Val Pro Ser Arg Phe Ser Gly
    50                  55                  60
Ser Gly Ser Gly Ala Glu Phe Thr Leu Thr Ile Ser Ser Leu Gln Pro
65                  70                  75                  80
```

```
Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 115
<211> LENGTH: 654
<212> TYPE: DNA
<213> ORGANISM: Artificial Sequence
<220> FEATURE:
<223> OTHER INFORMATION: Synthetic polynucleotide

<400> SEQUENCE: 115

```
gagattgtga tgactcagag cccttcaacg ctgtctgcat ccgtaggtga tcgcgtcatt     60
attacctgtc aagcctcaga gatcattcac tcttggctcg cctggtatca gcagaagccc    120
ggtaaggccc ccaagctgct gatctatctt gcttcaaccc tcgcgagcgg ggtgccctcc    180
cgcttcagcg gctccggctc tggtgccgaa tttacccctga caatcagctc tctccaaccc   240
gatgatttcg cgacttacta ctgtcagaat gtctacttgg cctcaaccaa cggagccaac    300
ttcggccagg ggaccaaact gaccgtcctt aagcgtacgg tggcagctcc gtctgttttc    360
atctttccac ctagcgacga gcaactcaaa agtggtacag catccgtggt ttgtctgctg    420
aacaattttt accccaggga ggctaaggtc cagtggaaag tcgataacgc tcttcagtct    480
ggcaacagtc aggagagcgt cacagagcag gactctaagg atagcactta tagtctgtcc    540
tccacgctga cactgtctaa agcggattat gagaagcaca aggtttacgc ctgtgaggta    600
acgcaccaag gactctcctc cccagttacc aaatctttca cagaggaga atgt           654
```

<210> SEQ ID NO 116
<211> LENGTH: 363
<212> TYPE: DNA
<213> ORGANISM: Artificial Sequence
<220> FEATURE:
<223> OTHER INFORMATION: Synthetic polynucleotide

<400> SEQUENCE: 116

```
caagtgcagc tggtgcagtc tggcgccgaa gtgaagaaac ccggctcctc cgtgaaagtg     60
tcctgcaagg cctccggcgg caccttctcc agctacgcca tctcctgggt ccgacaggcc    120
ccaggccagg gctggagtg gatgggcggc atcgtgcctt ggatgggcga ggccgtgtac    180
gcccagaaat tccagggcag agtgaccatc accgccgacg agtccacctc caccgcctac    240
atggaactgt cctccctgag gagcgaggac accgccgtgt actactgcgc ccggtcctcc    300
```

```
tccacctacg gcatccacgc cttcgactac tggggccagg gcaccctggt caccgtgtcc    360
tcc                                                                 363

<210> SEQ ID NO 117
<211> LENGTH: 360
<212> TYPE: DNA
<213> ORGANISM: Artificial Sequence
<220> FEATURE:
<223> OTHER INFORMATION: Synthetic polynucleotide

<400> SEQUENCE: 117
gaagtccagc tggtggaatc cggcggaggc ctggtgcagc caggcggatc cctgaggctg     60
tcttgcaccg cctccggctt ctccctgacc gactactact acatgacttg ggtccgccag    120
gctcccggaa aaggactgga gtgggtcgga ttcatcgacc ccgacgacga cccctactac    180
gccacctggg ccaagggccg gttcaccatc tcccgggaca actccaagaa caccctgtac    240
ctgcagatga actccctgag ggccgaagat acagctgtgt actattgcgc tggcggcgac    300
cacaactccg gctggggcct ggatatctgg ggacaggaa cactcgtgac agtgtccagc    360

<210> SEQ ID NO 118
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 118

Gly Ser Gly Gly Gly Gly Ser Gly Gly Gly Gly Ser Gly Gly Gly
 1               5                  10                  15

<210> SEQ ID NO 119
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 119
ggctctggcg gcggaggatc tggcggaggc ggtagcggag gcgga                    45

<210> SEQ ID NO 120
<211> LENGTH: 462
<212> TYPE: PRT
<213> ORGANISM: Artificial Sequence
<220> FEATURE:
<223> OTHER INFORMATION: Synthetic polypeptide

<400> SEQUENCE: 120

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Val Pro Trp Met Gly Glu Ala Val Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Ser Ser Ser Thr Tyr Gly Ile His Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Gly Ser Gly Gly Gly Gly Ser Gly Gly Gly Gly Ser Gly Gly Gly Glu
225                 230                 235                 240

Val Gln Leu Val Glu Ser Gly Gly Gly Leu Val Gln Pro Gly Gly Ser
                245                 250                 255

Leu Arg Leu Ser Cys Thr Ala Ser Gly Phe Ser Leu Thr Asp Tyr Tyr
            260                 265                 270

Tyr Met Thr Trp Val Arg Gln Ala Pro Gly Lys Gly Leu Glu Trp Val
        275                 280                 285

Gly Phe Ile Asp Pro Asp Asp Asp Pro Tyr Tyr Ala Thr Trp Ala Lys
    290                 295                 300

Gly Arg Phe Thr Ile Ser Arg Asp Asn Ser Lys Asn Thr Leu Tyr Leu
305                 310                 315                 320

Gln Met Asn Ser Leu Arg Ala Glu Asp Thr Ala Val Tyr Tyr Cys Ala
                325                 330                 335

Gly Gly Asp His Asn Ser Gly Trp Gly Leu Asp Ile Trp Gly Gln Gly
            340                 345                 350

Thr Leu Val Thr Val Ser Ser Ala Ser Thr Lys Gly Pro Ser Val Phe
        355                 360                 365

Pro Leu Ala Pro Ser Ser Lys Ser Thr Ser Gly Gly Thr Ala Ala Leu
    370                 375                 380

Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu
                405                 410                 415

Gln Ser Ser Gly Leu Tyr Ser Leu Ser Ser Val Val Thr Val Pro Ser
            420                 425                 430

Ser Ser Leu Gly Thr Gln Thr Tyr Ile Cys Asn Val Asn His Lys Pro
        435                 440                 445

Ser Asn Thr Lys Val Asp Lys Arg Val Glu Pro Lys Ser Cys
    450                 455                 460

<210> SEQ ID NO 121
<211> LENGTH: 1386
<212> TYPE: DNA
<213> ORGANISM: Artificial Sequence
<220> FEATURE:
<223> OTHER INFORMATION: Synthetic polynucleotide

<400> SEQUENCE: 121

```
caagtgcagc tggtgcagtc tggcgccgaa gtgaagaaac ccggctcctc cgtgaaagtg      60
tcctgcaagg cctccggcgg caccttctcc agctacgcca tctcctgggt ccgacaggcc     120
ccaggccagg gcctggagtg gatgggcggc atcgtgcctt ggatgggcga ggccgtgtac     180
gcccagaaat tccagggcag agtgaccatc accgccgacg agtccacctc caccgcctac     240
atggaactgt cctccctgag gagcgaggac accgccgtgt actactgcgc ccggtcctcc     300
tccacctacg gcatccacgc cttcgactac tggggccagg gcaccctggt caccgtgtcc     360
tccgcctcca ccaagggacc ctccgtgttc cctctggccc cttccagcaa gtccacctct     420
ggcggcaccg ccgctctggg ctgcctggtc aaggactact cccccgagcc cgtgaccgtg     480
tcctggaact ctggcgccct gacctccggc gtgcacacct ccctgccgt gctgcagtcc      540 tccggcctgt actccctgtc ctccgtcgtg accgtgccct ccagctctct gggcacccag     600
acctacatct gcaacgtgaa ccacaagccc tccaacacca agtggacaa gcgggtggaa      660 cccaagtcct gcggctctgg cggcggagga tctggcggag gcgtagcgg aggcggagaa      720 gtccagctgg tggaatccgg cggaggcctg gtgcagccag gcggatccct gaggctgtct     780
tgcaccgcct ccgcttctc cctgaccgac tactactaca tgacttgggt ccgccaggct      840
cccggaaaag gactggagtg ggtcggattc atcgaccccg acgacgaccc ctactacgcc     900
acctgggcca agggccggtt caccatctcc cgggacaact ccaagaacac cctgtacctg     960
cagatgaact ccctgagggc cgaagataca gctgtgtact attgcgctgg cggcgaccac    1020
aactccggct ggggcctgga tatctgggga cagggaacac tcgtgacagt gtccagcgcc    1080
agcaccaagg gcccctccgt gttccctctg gccccttcca gcaagtctac ctctggcggc    1140
accgctgctc tgggctgcct ggtgaaggac tacttccctg agcctgtgac agtgtcctgg    1200
aactctggcg ccctgacctc cggcgtgcac accttccctg ccgtgctgca gtcctccggc    1260
ctgtactccc tgtcctccgt ggtgacagtg ccttcctcca gcctgggcac ccagacctat    1320
atctgcaacg tgaaccacaa gccttccaac accaaggtgg acaagcgggt ggagcctaag    1380
tcatgc                                                               1386
```

<210> SEQ ID NO 122
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 122

```
gacatccaga tgacccagag ccccctccagc ctgtccgcct ccgtgggcga cagagtgacc     60
atcacctgtc gggcctccca gtctatctcc aacttcctga actggtatca gcagaagccc    120
ggcaaggccc ctaagctgct gatctacgcc gcctccaacc tgcagtccgg cgtgccctcc    180
agattctccg gctctggctc cggcaccgac ttcaccctga ccatctccag cctgcagccc    240
gaggacttcg ccacctacta ctgccagcag tacgacgact cccccatgac cttcggccag    300
ggcaccaaag tggaaatcaa g                                              321
```

<210> SEQ ID NO 123
<211> LENGTH: 333
<212> TYPE: DNA
<213> ORGANISM: Artificial Sequence
<220> FEATURE:
<223> OTHER INFORMATION: Synthetic polynucleotide -continued

<400> SEQUENCE: 123

```
gagatcgtga tgacccagtc ccctagcacc ctgagcgcca gcgtgggaga tcgcgtgatc        60
atcacatgcc aggcctccga gatcatccac agctggctgg cttggtatca gcagaaacct       120
ggaaaagctc ccaagctcct gatctatctg ccagcaccc tggcctctgg cgtgcccagc        180
agattcagcg gctccggcag cggcgctgag tttaccctga caatcagctc cctgcagcct       240
gacgattttg ctacctacta ttgtcagaac gtgtacctgg cctccaccaa cggcgccaac       300
tttggccagg gaacaaagct gaccgtgctg aag                                    333
```

<210> SEQ ID NO 124
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 124

```
ggctccggcg gaggcggatc tggtggcgga ggatctggcg gtggc                        45
```

<210> SEQ ID NO 125
<211> LENGTH: 447
<212> TYPE: PRT
<213> ORGANISM: Artificial Sequence
<220> FEATURE:
<223> OTHER INFORMATION: Synthetic polypeptide

<400> SEQUENCE: 125

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Phe
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Asp Phe Pro Met
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Ser Gly Gly Gly Gly Ser Gly Gly Gly
    210                 215                 220

Gly Ser Gly Gly Gly Glu Ile Val Met Thr Gln Ser Pro Ser Thr Leu
```

```
                225                 230                 235                 240
Ser Ala Ser Val Gly Asp Arg Val Ile Ile Thr Cys Gln Ala Ser Glu
                    245                 250                 255

Ile Ile His Ser Trp Leu Ala Trp Tyr Gln Gln Lys Pro Gly Lys Ala
                260                 265                 270

Pro Lys Leu Leu Ile Tyr Leu Ala Ser Thr Leu Ala Ser Gly Val Pro
            275                 280                 285

Ser Arg Phe Ser Gly Ser Gly Ser Gly Ala Glu Phe Thr Leu Thr Ile
        290                 295                 300

Ser Ser Leu Gln Pro Asp Asp Phe Ala Thr Tyr Tyr Cys Gln Asn Val
305                 310                 315                 320

Tyr Leu Ala Ser Thr Asn Gly Ala Asn Phe Gly Gln Gly Thr Lys Leu
                325                 330                 335

Thr Val Leu Lys Arg Thr Val Ala Ala Pro Ser Val Phe Ile Phe Pro
                340                 345                 350

Pro Ser Asp Glu Gln Leu Lys Ser Gly Thr Ala Ser Val Val Cys Leu
            355                 360                 365

Leu Asn Asn Phe Tyr Pro Arg Glu Ala Lys Val Gln Trp Lys Val Asp
        370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
                405                 410                 415

Ala Asp Tyr Glu Lys His Lys Val Tyr Ala Cys Glu Val Thr His Gln
                420                 425                 430

Gly Leu Ser Ser Pro Val Thr Lys Ser Phe Asn Arg Gly Glu Cys
            435                 440                 445

<210> SEQ ID NO 126
<211> LENGTH: 1341
<212> TYPE: DNA
<213> ORGANISM: Artificial Sequence
<220> FEATURE:
<223> OTHER INFORMATION: Synthetic polynucleotide

<400> SEQUENCE: 126
gacatccaga tgacccagag cccctccagc ctgtccgcct ccgtgggcga cagagtgacc      60
atcacctgtc gggcctccca gtctatctcc aacttcctga ctggtatca gcagaagccc     120 ggcaaggccc ctaagctgct gatctacgcc gcctccaacc tgcagtccgg cgtgccctcc    180
agattctccg gctctggctc cggcaccgac ttcaccctga ccatctccag cctgcagccc    240
gaggacttcg ccacctacta ctgccagcag tacgacgact cccccatgac cttcggccag    300
ggcaccaaag tggaaatcaa gcggaccgtg gccgctccct ccgtgttcat cttcccaccc    360
tccgacgagc agctgaagtc cggcaccgcc tccgtcgtgt gcctgctgaa caacttctac    420
cctcgcgagg ccaaagtgca gtggaaagtg gacaacgccc tgcagagcgg caactcccag    480
gaatccgtca ccgagcagga ctccaaggac agcacctact ccctgtcctc caccctgacc    540
ctgtccaagg ccgactacga aaagcacaaa gtgtacgcct gcgaagtgac ccaccagggc    600
ctgtccagcc ccgtgaccaa gtccttcaac cggggcgagt gtggctccgg cggaggcgga    660
tctggtggcg gaggatctgg cggtggcgag atcgtgatga cccagtcccc tagcaccctg    720
agcgccagcg tgggagatcg cgtgatcatc acatgccagg cctccgagat catccacagc    780
tggctggctt ggtatcagca gaaacctgga aaagctccca gctcctgat ctatctggcc    840
```

```
agcaccctgg cctctggcgt gcccagcaga ttcagcggct ccggcagcgg cgctgagttt    900
accctgacaa tcagctccct gcagcctgac gattttgcta cctactattg tcagaacgtg    960
tacctggcct ccaccaacgg cgccaacttt ggccagggaa caaagctgac cgtgctgaag   1020
cgtacggtgg ccgctcccag cgtgttcatc ttccccccca gcgacgagca gctgaagagc   1080
ggcaccgcca gcgtggtgtg cctgctgaac aacttctacc cccgggaggc caaggtgcag   1140
tggaaggtgg acaacgccct gcagagcggc aacagccagg agagcgtcac cgagcaggac   1200
agcaaggact ccacctacag cctgagcagc accctgaccc tgagcaaggc cgactacgag   1260
aagcataagg tgtacgcctg cgaggtgacc caccagggcc tgtccagccc cgtgaccaag   1320
agcttcaaca ggggcgagtg c                                              1341
```

```
<210> SEQ ID NO 127
<211> LENGTH: 357
<212> TYPE: DNA
<213> ORGANISM: Artificial Sequence
<220> FEATURE:
<223> OTHER INFORMATION: Synthetic polynucleotide

<400> SEQUENCE: 127
gaagtgcagc tgctggaatc tggcggcgga ctggtgcagc ctggcggctc cctgaggctg     60
tcttgtgccg cctccggctt caccttctcc agctacgcca tgtcctgggt ccgacaggcc    120
cctggcaagg gcctggagtg ggtgtccgcc atctccggct ccggcggctc tacctactac    180
gccgactccg tgaagggccg gttcaccatc tcccgggaca actccaagaa caccctgtac    240
ctgcagatga actccctgag ggccgaggac accgccgtgt actactgcgc cagacagcgg    300
tactacttcg gcgagttcga cctgtggggc cagggcaccc tggtcaccgt gtcctcc       357
```

```
<210> SEQ ID NO 128
<211> LENGTH: 360
<212> TYPE: DNA
<213> ORGANISM: Artificial Sequence
<220> FEATURE:
<223> OTHER INFORMATION: Synthetic polynucleotide

<400> SEQUENCE: 128
gaagtccagc tggtggaaag cggcggaggc ctggtccagc caggcggatc cctgaggctc     60
agctgcaccg cctctggctt ctccctgacc gactactact atatgacttg ggtccgccag    120
gctcccggaa aaggactcga atgggtcgga ttcatcgacc ccgacgacga cccttactac    180
gccacctggg ccaagggcag attcaccatc agcagagaca acagcaagaa cacactctat    240
ctccagatga actccctgag ggctgaagat accgctgtct attactgcgc tggcggcgac    300
cacaactccg gctggggcct ggatatctgg ggacagggca cactcgtgac agtgtccagc    360
```

```
<210> SEQ ID NO 129
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 129
ggctctggcg gaggcggaag tggtggcgga ggatcaggcg gcgga                     45
```

```
<210> SEQ ID NO 130
<211> LENGTH: 460
<212> TYPE: PRT
<213> ORGANISM: Artificial Sequence
```

<220> FEATURE:
<223> OTHER INFORMATION: Synthetic polypeptide

<400> SEQUENCE: 130

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Arg Tyr Tyr Phe Gly Glu Phe Asp Leu Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Gly Ser
    210                 215                 220

Gly Gly Gly Gly Ser Gly Gly Gly Ser Gly Gly Gly Gly Glu Val Gln
225                 230                 235                 240

Leu Val Glu Ser Gly Gly Gly Leu Val Gln Pro Gly Gly Ser Leu Arg
                245                 250                 255

Leu Ser Cys Thr Ala Ser Gly Phe Ser Leu Thr Asp Tyr Tyr Tyr Met
            260                 265                 270

Thr Trp Val Arg Gln Ala Pro Gly Lys Gly Leu Glu Trp Val Gly Phe
        275                 280                 285

Ile Asp Pro Asp Asp Pro Tyr Tyr Ala Thr Trp Ala Lys Gly Arg
    290                 295                 300

Phe Thr Ile Ser Arg Asp Asn Ser Lys Asn Thr Leu Tyr Leu Gln Met
305                 310                 315                 320

Asn Ser Leu Arg Ala Glu Asp Thr Ala Val Tyr Tyr Cys Ala Gly Gly
                325                 330                 335

Asp His Asn Ser Gly Trp Gly Leu Asp Ile Trp Gly Gln Gly Thr Leu
            340                 345                 350

Val Thr Val Ser Ser Ala Ser Thr Lys Gly Pro Ser Val Phe Pro Leu
        355                 360                 365

Ala Pro Ser Ser Lys Ser Thr Ser Gly Gly Thr Ala Ala Leu Gly Cys
    370                 375                 380

Leu Val Lys Asp Tyr Phe Pro Glu Pro Val Thr Val Ser Trp Asn Ser
385                 390                 395                 400
```

Gly Ala Leu Thr Ser Gly Val His Thr Phe Pro Ala Val Leu Gln Ser
              405                 410                 415

Ser Gly Leu Tyr Ser Leu Ser Ser Val Val Thr Val Pro Ser Ser Ser
              420                 425                 430

Leu Gly Thr Gln Thr Tyr Ile Cys Asn Val Asn His Lys Pro Ser Asn
              435                 440                 445

Thr Lys Val Asp Lys Arg Val Glu Pro Lys Ser Cys
              450                 455                 460

<210> SEQ ID NO 131
<211> LENGTH: 1380
<212> TYPE: DNA
<213> ORGANISM: Artificial Sequence
<220> FEATURE:
<223> OTHER INFORMATION: Synthetic polynucleotide

<400> SEQUENCE: 131
gaagtgcagc tgctggaatc tggcggcgga ctggtgcagc ctggcggctc cctgaggctg      60
tcttgtgccg cctccggctt caccttctcc agctacgcca tgtcctgggt ccgacaggcc     120
cctggcaagg gcctggagtg ggtgtccgcc atctccggct ccggcggctc tacctactac     180
gccgactccg tgaagggccg gttcaccatc tcccgggaca actccaagaa caccctgtac     240
ctgcagatga actccctgag ggccgaggac accgccgtgt actactgcgc cagacagcgg     300
tactacttcg gcgagttcga cctgtggggc cagggcaccc tggtcaccgt gtcctccgcc     360
tccaccaagg gcccctccgt gttccctctg gccccttcca gcaagtccac ctctggcggc     420
accgccgctc tgggctgcct ggtcaaggac tacttccccg agcccgtgac cgtgtcctgg     480
aactccggcg ctctgacctc cggcgtgcac accttccctg ccgtgctgca gtcctccggc     540
ctgtactccc tgtcctccgt cgtgaccgtg ccctccagct ctctgggcac ccagacctac     600
atctgcaacg tgaaccacaa gcccaacacc aaagtggaca agcgggtgga acccaag       660
tcctgcggct ctggcggagg cggaagtggt ggcggaggat caggcggcgg agaagtccag     720
ctggtggaaa gcggcggagg cctggtccag ccaggcggat ccctgaggct cagctgcacc     780
gcctctggct ctcccctgac cgactactac tatatgactt gggtccgcca ggctcccgga     840
aaaggactcg aatgggtcgg attcatcgac cccgacgacg accttacta cgccacctgg     900
gccaagggca gattcaccat cagcagagac aacagcaaga cacactcta tctccagatg     960
aactccctga ggctgaaga taccgctgtc tattactgcg ctggcggcga ccacaactcc    1020
ggctggggcc tggatatctg gggacagggc acactcgtga cagtgtccag cgccagcacc    1080
aagggcccct ccgtgttccc tctggccccct ccagcaagt ctacctctgg cggcaccgct    1140
gctctgggct gcctggtgaa ggactacttc cctgagcctg tgacagtgtc ctggaactct    1200
ggcgccctga cctccggcgt gcacaccttc cctgccgtgc tgcagtcctc cggcctgtac    1260
tccctgtcct ccgtggtgac agtgccttcc tccagcctgg caccagac ctatatctgc    1320
aacgtgaacc acaagccttc caacaccaag gtggacaagc gggtggagcc taagtcatgc    1380

<210> SEQ ID NO 132
<211> LENGTH: 324
<212> TYPE: DNA
<213> ORGANISM: Artificial Sequence
<220> FEATURE:
<223> OTHER INFORMATION: Synthetic polynucleotide

<400> SEQUENCE: 132

```
tcctacgagc tgacccagcc tccctccgtg tccgtgtctc ctggccagac cgcctccatc    60
acctgttccg gcgacaagct gggcgataag tacgcctact ggtatcagca gaagcccggc   120
cagtcccctg tgctggtcat ctaccaggac tccaagcggc cctccggcat ccctgagcgg   180
ttctccggct ccaactccgg caacaccgcc accctgacca tccccggcac ccaggccgag   240
gacgaggccg actactactg ccaggccttc gactacctgt actccctggg cgtgttcggc   300
ggaggcacca agctgaccgt gctg                                          324

<210> SEQ ID NO 133
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 133
gagatcgtga tgacccagtc cccttccacc ctgtccgcct ccgtgggcga cagagtgatc    60
atcacctgtc aggcctccga gatcatccac agctggctgg cttggtatca gcagaaacct   120
ggcaaggccc ctaagctgct gatctacctg gcctccaccc tggcctccgg cgtgccctcc   180
agattctccg gatctggctc tggcgccgag ttcaccctga caatcagctc cctgcagccc   240
gacgacttcg ccacctacta ctgtcagaac gtgtacctgg ccagcaccaa cggcgccaac   300
ttcggccagg gcacaaaact gacagtgctg aag                                333

<210> SEQ ID NO 134
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 134
ggctctggtg gcggaggatc tggcggaggc ggttctggcg gcgga                    45

<210> SEQ ID NO 135
<211> LENGTH: 447
<212> TYPE: PRT
<213> ORGANISM: Artificial Sequence
<220> FEATURE:
<223> OTHER INFORMATION: Synthetic polypeptide

<400> SEQUENCE: 135

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Tyr Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ala Phe Asp Tyr Leu Tyr Ser Leu
                85                  90                  95

Gly Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125
```

Ala Asn Lys Ala Thr Leu Val Cys Leu Ile Ser Asp Phe Tyr Pro Gly
      130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Gly Gly Gly Gly Ser Gly Gly Gly
    210                 215                 220

Gly Ser Gly Gly Gly Glu Ile Val Met Thr Gln Ser Pro Ser Thr Leu
225                 230                 235                 240

Ser Ala Ser Val Gly Asp Arg Val Ile Ile Thr Cys Gln Ala Ser Glu
                245                 250                 255

Ile Ile His Ser Trp Leu Ala Trp Tyr Gln Gln Lys Pro Gly Lys Ala
            260                 265                 270

Pro Lys Leu Leu Ile Tyr Leu Ala Ser Thr Leu Ala Ser Gly Val Pro
        275                 280                 285

Ser Arg Phe Ser Gly Ser Gly Ser Gly Ala Glu Phe Thr Leu Thr Ile
    290                 295                 300

Ser Ser Leu Gln Pro Asp Asp Phe Ala Thr Tyr Tyr Cys Gln Asn Val
305                 310                 315                 320

Tyr Leu Ala Ser Thr Asn Gly Ala Asn Phe Gly Gln Gly Thr Lys Leu
                325                 330                 335

Thr Val Leu Lys Arg Thr Val Ala Ala Pro Ser Val Phe Ile Phe Pro
            340                 345                 350

Pro Ser Asp Glu Gln Leu Lys Ser Gly Thr Ala Ser Val Val Cys Leu
        355                 360                 365

Leu Asn Asn Phe Tyr Pro Arg Glu Ala Lys Val Gln Trp Lys Val Asp
    370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
                405                 410                 415

Ala Asp Tyr Glu Lys His Lys Val Tyr Ala Cys Glu Val Thr His Gln
            420                 425                 430

Gly Leu Ser Ser Pro Val Thr Lys Ser Phe Asn Arg Gly Glu Cys
        435                 440                 445

<210> SEQ ID NO 136
<211> LENGTH: 1341
<212> TYPE: DNA
<213> ORGANISM: Artificial Sequence
<220> FEATURE:
<223> OTHER INFORMATION: Synthetic polynucleotide

<400> SEQUENCE: 136
tcctacgagc tgacccagcc tccctccgtg tccgtgtctc tggccagac cgcctccatc      60 acctgttccg gcgacaagct gggcgataag tacgcctact ggtatcagca gaagcccggc     120
cagtcccctg tgctggtcat ctaccaggac tccaagcggc cctccggcat ccctgagcgg     180
ttctccggct ccaactccgg caacaccgcc accctgacca tctccggcac ccaggccgag     240

```
gacgaggccg actactactg ccaggccttc gactacctgt actccctggg cgtgttcggc      300
ggaggcacca agctgaccgt gctgggccag cccaaggccg ctccttccgt gaccctgttc      360
cctccatcct ccgaggaact gcaggccaac aaggccaccc tcgtgtgcct gatctccgac      420
ttctaccctg gcgccgtgac cgtggcctgg aaggccgaca gctctcctgt gaaggccggc      480
gtggaaacca ccacccctc caagcagtcc aacaacaaat acgccgcctc ctcctacctg      540
tccctgaccc ctgagcagtg gaagtcccac cggtcctaca gctgccaagt cacacacgag      600
ggctccaccg tggaaaagac cgtggcccct accgagtgct ccggctctgg tggcggagga      660
tctggcggag gcggttctgg cggcggagag atcgtgatga cccagtcccc ttccaccctg      720
tccgcctccg tgggcgacag agtgatcatc acctgtcagg cctccgagat catccacagc      780
tggctggctt ggtatcagca gaaacctggc aaggccccta agctgctgat ctacctggcc      840
tccaccctgg cctccggcgt gccctccaga ttctccggat ctggctctgg cgccgagttc      900
accctgacaa tcagctccct gcagcccgac gacttcgcca cctactactg tcagaacgtg      960
tacctggcca gcaccaacgg cgccaacttc ggccagggca caaaactgac agtgctgaag     1020
cgtacggtgg ccgctcccag cgtgttcatc ttcccccca gcgacgagca gctgaagagc     1080
ggcaccgcca gcgtggtgtg cctgctgaac aacttctacc ccggaggc caaggtgcag     1140 tggaaggtgg acaacgccct gcagagcggc aacagccagg agagcgtcac cgagcaggac     1200
agcaaggact ccacctacag cctgagcagc accctgaccc tgagcaaggc cgactacgag     1260
aagcataagg tgtacgccct cgaggtgacc caccagggcc tgtccagccc cgtgaccaag     1320
agcttcaaca ggggcgagtg c                                               1341

<210> SEQ ID NO 137
<211> LENGTH: 357
<212> TYPE: DNA
<213> ORGANISM: Artificial Sequence
<220> FEATURE:
<223> OTHER INFORMATION: Synthetic polynucleotide

<400> SEQUENCE: 137
caagtgcagc tgctggaatc tggcggcgga ctggtgcagc ctggcggctc cctgaggctg       60
tcttgtgccg cctccggctt caccttctcc agctacgcca tgtcctgggt ccgacaggcc      120
cctggcaagg gcctggagtg ggtgtccggc ctgggccacg tgggctacac cacctacacc      180
gactccgtga agggccggtt caccatctcc cgggacaact ccaagaacac cctgtacctg      240
cagatgaact ccctgagggc cgaggacacc gccgtgtact actgcgccag agactacctg      300
gacttcggct actacttcga cgtgtgggc cagggcaccc tggtcaccgt gtcctcc          357

<210> SEQ ID NO 138
<211> LENGTH: 360
<212> TYPE: DNA
<213> ORGANISM: Artificial Sequence
<220> FEATURE:
<223> OTHER INFORMATION: Synthetic polynucleotide

<400> SEQUENCE: 138
gaagtgcagc tggtcgagag tggcggaggc ctcgtccagc caggcggatc cctgaggctc       60
agctgcaccg cctctggctt ctccctgacc gactactact atatgacttg ggtccgccag      120
gctcccggaa aaggactcga atgggtcgga ttcatcgacc ccgacgacga ccctactac      180 gccacctggg ccaagggcag attcaccatc agcagagaca cagcaagaa cacactctat      240 ctccagatga actccctgag ggctgaagat accgctgtct attactgcgc tggcggcgac      300
```

```
                                     -continued
cacaactccg gctggggcct ggatatctgg ggacagggca cactcgtgac agtgtccagc   360
```

<210> SEQ ID NO 139
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 139

```
ggctctggcg gaggcggaag tggtggcgga ggatcaggcg gcgga                  45
```

<210> SEQ ID NO 140
<211> LENGTH: 460
<212> TYPE: PRT
<213> ORGANISM: Artificial Sequence
<220> FEATURE:
<223> OTHER INFORMATION: Synthetic polypeptide

<400> SEQUENCE: 140

Gln Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Leu Gly His Val Gly Tyr Thr Thr Tyr Thr Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Tyr Leu Asp Phe Gly Tyr Tyr Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Gly Ser
    210                 215                 220

Gly Gly Gly Gly Ser Gly Gly Gly Ser Gly Gly Gly Gly Glu Val Gln
225                 230                 235                 240

Leu Val Glu Ser Gly Gly Gly Leu Val Gln Pro Gly Gly Ser Leu Arg
                245                 250                 255

Leu Ser Cys Thr Ala Ser Gly Phe Ser Leu Thr Asp Tyr Tyr Tyr Met
            260                 265                 270

Thr Trp Val Arg Gln Ala Pro Gly Lys Gly Leu Glu Trp Val Gly Phe
        275                 280                 285

```
Ile Asp Pro Asp Asp Pro Tyr Tyr Ala Thr Trp Ala Lys Gly Arg
    290                 295                 300

Phe Thr Ile Ser Arg Asp Asn Ser Lys Asn Thr Leu Tyr Leu Gln Met
305                 310                 315                 320

Asn Ser Leu Arg Ala Glu Asp Thr Ala Val Tyr Tyr Cys Ala Gly Gly
                325                 330                 335

Asp His Asn Ser Gly Trp Gly Leu Asp Ile Trp Gly Gln Gly Thr Leu
                340                 345                 350

Val Thr Val Ser Ser Ala Ser Thr Lys Gly Pro Ser Val Phe Pro Leu
                355                 360                 365

Ala Pro Ser Ser Lys Ser Thr Ser Gly Gly Thr Ala Ala Leu Gly Cys
370                 375                 380

Leu Val Lys Asp Tyr Phe Pro Glu Pro Val Thr Val Ser Trp Asn Ser
385                 390                 395                 400

Gly Ala Leu Thr Ser Gly Val His Thr Phe Pro Ala Val Leu Gln Ser
                405                 410                 415

Ser Gly Leu Tyr Ser Leu Ser Ser Val Val Thr Val Pro Ser Ser Ser
                420                 425                 430

Leu Gly Thr Gln Thr Tyr Ile Cys Asn Val Asn His Lys Pro Ser Asn
                435                 440                 445

Thr Lys Val Asp Lys Arg Val Glu Pro Lys Ser Cys
450                 455                 460
```

<210> SEQ ID NO 141
<211> LENGTH: 1380
<212> TYPE: DNA
<213> ORGANISM: Artificial Sequence
<220> FEATURE:
<223> OTHER INFORMATION: Synthetic polynucleotide

<400> SEQUENCE: 141

```
caagtgcagc tgctggaatc tggcggcgga ctggtgcagc ctggcggctc cctgaggctg      60
tcttgtgccg cctccggctt caccttctcc agctacgcca tgtcctgggt ccgacaggcc     120
cctggcaagg gcctggagtg ggtgtccggc ctgggccacg tgggctacac cacctacacc     180
gactccgtga agggccggtt caccatctcc cgggacaact ccaagaacac cctgtacctg     240
cagatgaact ccctgagggc cgaggacacc gccgtgtact actgcgccag agactacctg     300
gacttcggct actacttcga cgtgtggggc cagggcaccc tggtcaccgt gtcctccgcc     360
tccaccaagg gaccctccgt gttccctctg gccccttcca gcaagtccac ctctggcggc     420
accgccgctc tgggctgcct ggtcaaggac tacttccccg agcccgtgac cgtgtcctgg     480
aactctggcg ccctgacctc cggcgtgcac accttccctg ccgtgctgca gtcctccggc     540
ctgtactccc tgtcctccgt cgtgaccgtg ccctccagct ctctgggcac ccagacctac     600
atctgcaacg tgaaccacaa gccctccaac accaaagtgg acaagcgggt ggaacccaag     660
tcctgcggct ctggcggagg cggaagtggt ggcggaggat caggcggcgg agaagtgcag     720
ctggtcgaga gtgcggagg cctcgtccag ccaggcggat ccctgaggct cagctgcacc     780
gcctctggct ctcccctgac cgactactac tatatgactt gggtccgcca ggctcccgga     840
aaaggactcg aatgggtcgg attcatcgac ccgacgacg accctactac gccacctgg      900
gccaagggca gattcaccat cagcagagac aacagcaaga acacactcta tctccagatg     960
aactccctga ggctgaaga taccgctgtc tattactgcg ctggcggcga ccacaactcc    1020
ggctggggcc tggatatctg gggacagggc acactcgtga cagtgtccag cgccagcacc    1080
```

```
aagggcccct ccgtgttccc tctggcccct tccagcaagt ctacctctgg cggcaccgct    1140
gctctgggct gcctggtgaa ggactacttc cctgagcctg tgacagtgtc ctggaactct    1200
ggcgccctga cctccggcgt gcacaccttc cctgccgtgc tgcagtcctc cggcctgtac    1260
tccctgtcct ccgtggtgac agtgccttcc tccagcctgg cacccagac ctatatctgc     1320 aacgtgaacc acaagccttc caacaccaag gtggacaagc gggtggagcc taagtcatgc    1380
```

<210> SEQ ID NO 142
<211> LENGTH: 318
<212> TYPE: DNA
<213> ORGANISM: Artificial Sequence
<220> FEATURE:
<223> OTHER INFORMATION: Synthetic polynucleotide

<400> SEQUENCE: 142

```
tcctacgagc tgacccagcc cctgtccgtg tctgtggctc tgggccagac cgcccggatc     60
acctgttccg gcgacaagat cggcaagaaa tacgtgcact ggtatcagca gaagcccggc    120
caggcccctg tgctggtcat ctacgacgac tccgaccggc cctccggcat ccctgagcgg    180
ttctccggct ccaactccgg caacaccgcc accctgacca tctccagagc ccaggccggc    240
gacgaggccg actactactg ccaggcctgg gacatgcagt ccgtggtgtt cggcggaggc    300
accaagctga ccgtgctg                                                  318
```

<210> SEQ ID NO 143
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 143

```
gagatcgtga tgacccagtc cccttccacc ctgtccgcct ccgtgggcga cagagtgatc     60
atcacctgtc aggcctccga gatcatccac agctggctgg cttggtatca gcagaaacct    120
ggcaaggctc ccaagctgct gatctacctg gcctccaccc tggcctccgg cgtgccctcc    180
agattctccg gatctggctc tggcgccgag ttcaccctga caatcagctc cctgcagccc    240
gacgacttcg ccacctacta ctgtcagaac gtgtacctgg ccagcaccaa cggcgccaac    300
ttcggccagg gcacaaaact gacagtgctg aag                                 333
```

<210> SEQ ID NO 144
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 144

```
ggctctggtg gcggaggatc tggcggaggc ggttctggcg gcgga                     45
```

<210> SEQ ID NO 145
<211> LENGTH: 445
<212> TYPE: PRT
<213> ORGANISM: Artificial Sequence
<220> FEATURE:
<223> OTHER INFORMATION: Synthetic polypeptide

<400> SEQUENCE: 145

```
Ser Tyr Glu Leu Thr Gln Pro Leu Ser Val Ser Val Ala Leu Gly Gln
1               5                   10                  15
```

```
Thr Ala Arg Ile Thr Cys Ser Gly Asp Lys Ile Gly Lys Lys Tyr Val
            20                  25                  30
His Trp Tyr Gln Gln Lys Pro Gly Gln Ala Pro Val Leu Val Ile Tyr
            35                  40                  45
Asp Asp Ser Asp Arg Pro Ser Gly Ile Pro Glu Arg Phe Ser Gly Ser
 50                  55                  60
Asn Ser Gly Asn Thr Ala Thr Leu Thr Ile Ser Arg Ala Gln Ala Gly
 65                  70                  75                  80
Asp Glu Ala Asp Tyr Tyr Cys Gln Ala Trp Asp Met Gln Ser Val Val
                85                  90                  95
Phe Gly Gly Gly Thr Lys Leu Thr Val Leu Gly Gln Pro Lys Ala Ala
            100                 105                 110
Pro Ser Val Thr Leu Phe Pro Pro Ser Ser Glu Glu Leu Gln Ala Asn
            115                 120                 125
Lys Ala Thr Leu Val Cys Leu Ile Ser Asp Phe Tyr Pro Gly Ala Val
130                 135                 140
Thr Val Ala Trp Lys Ala Asp Ser Ser Pro Val Lys Ala Gly Val Glu
145                 150                 155                 160
Thr Thr Thr Pro Ser Lys Gln Ser Asn Asn Lys Tyr Ala Ala Ser Ser
            165                 170                 175
Tyr Leu Ser Leu Thr Pro Glu Gln Trp Lys Ser His Arg Ser Tyr Ser
            180                 185                 190
Cys Gln Val Thr His Glu Gly Ser Thr Val Glu Lys Thr Val Ala Pro
            195                 200                 205
Thr Glu Cys Ser Gly Ser Gly Gly Gly Ser Gly Gly Gly Ser
210                 215                 220
Gly Gly Gly Glu Ile Val Met Thr Gln Ser Pro Ser Thr Leu Ser Ala
225                 230                 235                 240
Ser Val Gly Asp Arg Val Ile Ile Thr Cys Gln Ala Ser Glu Ile Ile
            245                 250                 255
His Ser Trp Leu Ala Trp Tyr Gln Gln Lys Pro Gly Lys Ala Pro Lys
            260                 265                 270
Leu Leu Ile Tyr Leu Ala Ser Thr Leu Ala Ser Gly Val Pro Ser Arg
            275                 280                 285
Phe Ser Gly Ser Gly Ser Gly Ala Glu Phe Thr Leu Thr Ile Ser Ser
            290                 295                 300
Leu Gln Pro Asp Asp Phe Ala Thr Tyr Tyr Cys Gln Asn Val Tyr Leu
305                 310                 315                 320
Ala Ser Thr Asn Gly Ala Asn Phe Gly Gln Gly Thr Lys Leu Thr Val
            325                 330                 335
Leu Lys Arg Thr Val Ala Ala Pro Ser Val Phe Ile Phe Pro Pro Ser
            340                 345                 350
Asp Glu Gln Leu Lys Ser Gly Thr Ala Ser Val Val Cys Leu Leu Asn
            355                 360                 365
Asn Phe Tyr Pro Arg Glu Ala Lys Val Gln Trp Lys Val Asp Asn Ala
            370                 375                 380
Leu Gln Ser Gly Asn Ser Gln Glu Ser Val Thr Glu Gln Asp Ser Lys
385                 390                 395                 400
Asp Ser Thr Tyr Ser Leu Ser Ser Thr Leu Thr Leu Ser Lys Ala Asp
                405                 410                 415
Tyr Glu Lys His Lys Val Tyr Ala Cys Glu Val Thr His Gln Gly Leu
            420                 425                 430
Ser Ser Pro Val Thr Lys Ser Phe Asn Arg Gly Glu Cys
```

<210> SEQ ID NO 146
<211> LENGTH: 1335
<212> TYPE: DNA
<213> ORGANISM: Artificial Sequence
<220> FEATURE:
<223> OTHER INFORMATION: Synthetic polynucleotide

<400> SEQUENCE: 146

```
tcctacgagc tgacccagcc cctgtccgtg tctgtggctc tgggccagac cgcccggatc      60
acctgttccg gcgacaagat cggcaagaaa tacgtgcact ggtatcagca gaagcccggc     120
caggcccctg tgctggtcat ctacgacgac tccgaccggc cctccggcat ccctgagcgg     180
ttctccggct ccaactccgg caacaccgcc accctgacca tctccagagc ccaggccggc     240
gacgaggccg actactactg ccaggcctgg gacatgcagt ccgtggtgtt cggcggaggc     300
accaagctga ccgtgctggg ccagcccaag gccgctccct ctgtgaccct gttccctcca     360
tcctccgagg aactgcaggc caacaaggcc accctcgtgt gcctgatctc cgacttctac     420
cctggcgccg tgaccgtggc ctggaaggcc gacagctctc ctgtgaaggc cggcgtggaa     480
accaccaccc cttccaagca gtccaacaac aaatacgccg cctcctccta cctgtccctg     540
accccctgagc agtggaagtc ccaccggtcc tacagctgcc aagtcacaca cgagggctcc     600
accgtggaaa agaccgtggc ccctaccgag tgctccggct ctggtggcgg aggatctggc     660
ggaggcggtt ctggcggcgg agagatcgtg atgacccagt ccccttccac cctgtccgcc     720
tccgtgggcg acagagtgat catcacctgt caggcctccg agatcatcca cagctggctg     780
gcttggtatc agcagaaacc tggcaaggct cccaagctgc tgatctacct ggcctccacc     840
ctggcctccg gcgtgccctc cagattctcc ggatctggct ctggcgccga gttcaccctg     900
acaatcagct ccctgcagcc cgacgacttc gccacctact actgtcagaa cgtgtacctg     960
gccagcacca acggcgccaa cttcggccag ggcacaaaac tgacagtgct gaagcgtacg    1020
gtggccgctc ccagcgtgtt catcttcccc cccagcgacg agcagctgaa gagcggcacc    1080
gccagcgtgg tgtgcctgct gaacaacttc taccccgggg aggccaaggt gcagtggaag    1140
gtggacaacg ccctgcagag cggcaacagc caggagagcg tcaccgagca ggacagcaag    1200
gactccacct acagcctgag cagcaccctg accctgagca aggccgacta cgagaagcat    1260
aaggtgtacg cctgcgaggt gacccaccag ggcctgtcca gccccgtgac caagagcttc    1320
aacagggggcg agtgc                                                     1335
```

<210> SEQ ID NO 147
<211> LENGTH: 348
<212> TYPE: DNA
<213> ORGANISM: Artificial Sequence
<220> FEATURE:
<223> OTHER INFORMATION: Synthetic polynucleotide

<400> SEQUENCE: 147

```
caagtgcagc tgctggaatc tggcggcgga ctggtgcagc ctggcggctc cctgaggctg      60
tcttgtgccg cctccggctt caccttctcc cggtactgga tctcctgggt ccgacaggcc     120
cctggcaagg gcctggagtg ggtgtcctac atcgactcca ccggcacctt catcaactac     180
gccgactccg tgaagggccg gttcaccatc agccgggaca actccaagaa caccctgtac     240
ctgcagatga actccctgag ggccgaggac accgccgtgt actactgcgc cagaggcggc     300
agcctgttcg actactgggg ccagggcacc ctggtcaccg tgtcctcc                   348
```

<210> SEQ ID NO 148
<211> LENGTH: 360
<212> TYPE: DNA
<213> ORGANISM: Artificial Sequence
<220> FEATURE:
<223> OTHER INFORMATION: Synthetic polynucleotide

<400> SEQUENCE: 148

```
gaagtgcagc tggtcgagag tggcggaggc ctcgtccagc caggcggatc cctgaggctc      60
agctgcaccg cctctggctt ctccctgacc gactactact acatgacatg ggtccgccag     120
gctcccggaa aaggactcga atgggtcgga ttcatcgacc ccgacgacga ccctactac     180 gccacctggg ccaagggcag attcaccatc tccagagata acagcaagaa cacactctat     240
ctccagatga actccctgag ggctgaagat accgctgtct attactgcgc tggcggcgac     300
cacaactccg gctggggcct ggatatctgg ggacaggaa cactcgtgac agtgtccagc      360
```

<210> SEQ ID NO 149
<211> LENGTH: 457
<212> TYPE: PRT
<213> ORGANISM: Artificial Sequence
<220> FEATURE:
<223> OTHER INFORMATION: Synthetic polypeptide

<400> SEQUENCE: 149

```
Gln Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Trp Ile Ser Trp Val Arg Gln Ala Pro Gly Lys Gly Leu Glu Trp Val
        35                  40                  45

Ser Tyr Ile Asp Ser Thr Gly Thr Phe Ile Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Leu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Gly Ser Gly Gly Gly
    210                 215                 220

Gly Ser Gly Gly Gly Gly Ser Gly Gly Gly Glu Val Gln Leu Val Glu
225                 230                 235                 240

Ser Gly Gly Gly Leu Val Gln Pro Gly Gly Ser Leu Arg Leu Ser Cys
```

```
              245                 250                 255
Thr Ala Ser Gly Phe Ser Leu Thr Asp Tyr Tyr Met Thr Trp Val
            260                 265                 270
Arg Gln Ala Pro Gly Lys Gly Leu Glu Trp Val Gly Phe Ile Asp Pro
                275                 280                 285
Asp Asp Asp Pro Tyr Tyr Ala Thr Trp Ala Lys Gly Arg Phe Thr Ile
290                 295                 300
Ser Arg Asp Asn Ser Lys Asn Thr Leu Tyr Leu Gln Met Asn Ser Leu
305                 310                 315                 320
Arg Ala Glu Asp Thr Ala Val Tyr Tyr Cys Ala Gly Gly Asp His Asn
                325                 330                 335
Ser Gly Trp Gly Leu Asp Ile Trp Gly Gln Gly Thr Leu Val Thr Val
                340                 345                 350
Ser Ser Ala Ser Thr Lys Gly Pro Ser Val Phe Pro Leu Ala Pro Ser
                355                 360                 365
Ser Lys Ser Thr Ser Gly Gly Thr Ala Ala Leu Gly Cys Leu Val Lys
370                 375                 380
Asp Tyr Phe Pro Glu Pro Val Thr Val Ser Trp Asn Ser Gly Ala Leu
385                 390                 395                 400
Thr Ser Gly Val His Thr Phe Pro Ala Val Leu Gln Ser Ser Gly Leu
                405                 410                 415
Tyr Ser Leu Ser Ser Val Val Thr Val Pro Ser Ser Ser Leu Gly Thr
                420                 425                 430
Gln Thr Tyr Ile Cys Asn Val Asn His Lys Pro Ser Asn Thr Lys Val
                435                 440                 445
Asp Lys Arg Val Glu Pro Lys Ser Cys
450                 455

<210> SEQ ID NO 150
<211> LENGTH: 1371
<212> TYPE: DNA
<213> ORGANISM: Artificial Sequence
<220> FEATURE:
<223> OTHER INFORMATION: Synthetic polynucleotide

<400> SEQUENCE: 150
caagtgcagc tgctggaatc tggcggcgga ctggtgcagc ctggcggctc cctgaggctg      60
tcttgtgccg cctccggctt caccttctcc cggtactgga tctcctgggt ccgacaggcc     120
cctggcaagg gcctggagtg ggtgtcctac atcgactcca ccggcacctt catcaactac     180
gccgactccg tgaagggccg gttcaccatc agccgggaca ctccaagaa caccctgtac      240
ctgcagatga actccctgag ggccgaggac accgccgtgt actactgcgc cagaggcggc     300
agcctgttcg actactgggg ccagggcacc ctggtcaccg tgtcctccgc tccaccaag      360
ggaccctccg tgttccctct ggccccttcc agcaagtcca cctctggcgg caccgccgct     420
ctgggctgcc tggtcaagga ctacttcccc gagcccgtga ccgtgtcctg gaactctggc     480
gccctgacct ccggcgtgca caccttccct gccgtgctgc agtcctccgg cctgtactcc     540
ctgtcctccg tcgtgaccgt gccctccagc tctctgggca cccagaccta catctgcaac     600
gtgaaccaca gccctccaa caccaaagtg gacaagcggg tggaacccaa gtcctgcggc     660
tctggcggag gcggaagtgg tggcggagga tcaggcggcg gagaagtgca gctggtcgag     720
agtggcggag gcctcgtcca gccaggcgga tccctgaggc tcagctgcac cgcctctggc     780
ttctcccctga ccgactacta ctacatgaca tgggtccgcc aggctccgg aaaaggactc     840
```

```
gaatgggtcg gattcatcga ccccgacgac gaccccact acgccacctg ggccaagggc    900
agattcacca tctccagaga taacagcaag aacacactct atctccagat gaactccctg    960
agggctgaag ataccgctgt ctattactgc gctggcggcg accacaactc cggctggggc   1020
ctggatatct ggggacaggg aacactcgtg acagtgtcca gcgccagcac caagggcccc   1080
tccgtgttcc ctctggcccc ttccagcaag tctacctctg gcggcaccgc tgctctgggc   1140
tgcctggtga aggactactt ccctgagcct gtgacagtgt cctggaactc tggcgccctg   1200
acctccggcg tgcacacctt ccctgccgtg ctgcagtcct ccggctgta ctccctgtcc    1260 tccgtggtga cagtgccttc ctccagcctg ggcacccaga cctatatctg caacgtgaac   1320
cacaagcctt ccaacaccaa ggtggacaag cgggtggagc ctaagtcatg c             1371
```

<210> SEQ ID NO 151
<211> LENGTH: 318
<212> TYPE: DNA
<213> ORGANISM: Artificial Sequence
<220> FEATURE:
<223> OTHER INFORMATION: Synthetic polynucleotide

<400> SEQUENCE: 151

```
gacatccaga tgacccagag cccctccagc ctgtccgcct ccgtgggcga cagagtgacc     60
atcacctgtc gggcctccca gggcatcatc tcctacctgg ctggtatca gcagaagccc    120 ggcaaggccc ctaagctgct gatctacgcc gccagctccc tgcagtccgg cgtgccctcc    180
agattctccg gctctggctc cggcaccgac ttcaccctga ccatctccag cctgcagccc    240
gaggacttcg ccacctacta ctgccagcag tacgacgccc tgaacacctt cggccagggc    300
accaaagtgg aaatcaag                                                  318
```

<210> SEQ ID NO 152
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 152

```
gagatcgtga tgacccagtc ccctagcacc ctgagcgcca gcgtgggaga tcgcgtgatc     60
atcacatgcc aggcctccga gatcatccac agctggctgg cttggtatca gcagaaacct    120
ggaaaagctc ccaagctcct gatctatctg gccagcaccc tggcctctgg cgtgcccagc    180
agattcagcg gctccggcag cggcgctgag tttaccctga caatcagctc tctgcagcct    240
gacgattttg ctacctacta ttgtcagaac gtgtacctgg cctccaccaa cggcgccaac    300
tttggccagg gaacaaagct gaccgtgctg aag                                 333
```

<210> SEQ ID NO 153
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 153

```
ggctccggcg gaggcggatc tggtggcgga ggatctggcg gtggc                     45
```

<210> SEQ ID NO 154
<211> LENGTH: 446
<212> TYPE: PRT
<213> ORGANISM: Artificial Sequence

```
<220> FEATURE:
<223> OTHER INFORMATION: Synthetic polypeptide

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ile Ser Tyr
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ala Leu Asn Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Ser Gly Gly Gly Ser Gly Gly Gly Gly
210                 215                 220

Ser Gly Gly Gly Glu Ile Val Met Thr Gln Ser Pro Ser Thr Leu Ser
225                 230                 235                 240

Ala Ser Val Gly Asp Arg Val Ile Ile Thr Cys Gln Ala Ser Glu Ile
                245                 250                 255

Ile His Ser Trp Leu Ala Trp Tyr Gln Gln Lys Pro Gly Lys Ala Pro
            260                 265                 270

Lys Leu Leu Ile Tyr Leu Ala Ser Thr Leu Ala Ser Gly Val Pro Ser
        275                 280                 285

Arg Phe Ser Gly Ser Gly Ser Gly Ala Glu Phe Thr Leu Thr Ile Ser
290                 295                 300

Ser Leu Gln Pro Asp Asp Phe Ala Thr Tyr Tyr Cys Gln Asn Val Tyr
305                 310                 315                 320

Leu Ala Ser Thr Asn Gly Ala Asn Phe Gly Gln Gly Thr Lys Leu Thr
                325                 330                 335

Val Leu Lys Arg Thr Val Ala Ala Pro Ser Val Phe Ile Phe Pro Pro
            340                 345                 350

Ser Asp Glu Gln Leu Lys Ser Gly Thr Ala Ser Val Val Cys Leu Leu
        355                 360                 365

Asn Asn Phe Tyr Pro Arg Glu Ala Lys Val Gln Trp Lys Val Asp Asn
370                 375                 380

Ala Leu Gln Ser Gly Asn Ser Gln Glu Ser Val Thr Glu Gln Asp Ser
385                 390                 395                 400
```

```
Lys Asp Ser Thr Tyr Ser Leu Ser Ser Thr Leu Thr Leu Ser Lys Ala
                405                 410                 415

Asp Tyr Glu Lys His Lys Val Tyr Ala Cys Glu Val Thr His Gln Gly
            420                 425                 430

Leu Ser Ser Pro Val Thr Lys Ser Phe Asn Arg Gly Glu Cys
        435                 440                 445

<210> SEQ ID NO 155
<211> LENGTH: 1338
<212> TYPE: DNA
<213> ORGANISM: Artificial Sequence
<220> FEATURE:
<223> OTHER INFORMATION: Synthetic polynucleotide

<400> SEQUENCE: 155
gacatccaga tgacccagag cccctccagc ctgtccgcct ccgtgggcga cagagtgacc      60
atcacctgtc gggcctccca gggcatcatc tcctacctgg ctggtatca gcagaagccc     120 ggcaaggccc ctaagctgct gatctacgcc gccagctccc tgcagtccgg cgtgccctcc     180
agattctccg gctctggctc cggcaccgac ttcaccctga ccatctccag cctgcagccc     240
gaggacttcg ccacctacta ctgccagcag tacgacgccc tgaacacctt cggccagggc     300
accaaagtgg aaatcaagcg gaccgtggcc gctccctccg tgttcatctt cccaccctcc     360
gacgagcagc tgaagtccgg caccgcctcc gtcgtgtgcc tgctgaacaa cttctaccct     420
cgcgaggcca agtgcagtg aaagtggac aacgccctgc agagcggcaa ctcccaggaa     480
tccgtcaccg agcaggactc caaggacagc acctactccc tgtcctccac cctgaccctg     540
tccaaggccg actacgagaa gcacaaagtg tacgcctgcg aagtgaccca ccagggcctg     600
tccagccccg tgaccaagtc cttcaaccgg ggcgagtgtg gctccggcgg aggcggatct     660
ggtggcggag gatctggcgg tggcgagatc gtgatgaccc agtcccctag caccctgagc     720
gccagcgtgg gagatcgcgt gatcatcaca tgccaggcct ccgagatcat ccacagctgg     780
ctggcttggt atcagcagaa acctggaaaa gctcccaagc tcctgatcta tctggccagc     840 acctggcct ctggcgtgcc cagcagattc agcggctccg gcagcggcgc tgagtttacc     900
ctgacaatca gctctctgca gcctgacgat tttgctacct actattgtca gaacgtgtac     960
ctggcctcca ccaacggcgc caactttggc cagggaacaa agctgaccgt gctgaagcgt    1020
acggtggccg ctcccagcgt gttcatcttc cccccagcg acgagcagct gaagagcggc    1080
accgccagcg tggtgtgcct gctgaacaac ttctacccc gggaggccaa ggtgcagtgg    1140
aaggtggaca acgccctgca gagcggcaac agccaggaga gcgtcaccga gcaggacagc    1200
aaggactcca cctacagcct gagcagcacc ctgaccctga gcaaggccga ctacgagaag    1260
cataaggtgt acgcctgcga ggtgacccac cagggcctgt ccagccccgt gaccaagagc    1320
ttcaacaggg gcgagtgc                                                  1338

<210> SEQ ID NO 156
<211> LENGTH: 178
<212> TYPE: PRT
<213> ORGANISM: Homo sapiens

<400> SEQUENCE: 156

Met Asp Arg Ala Ala Arg Cys Ser Gly Ala Ser Ser Leu Pro Leu Leu
1               5                   10                  15

Leu Ala Leu Ala Leu Gly Leu Val Ile Leu His Cys Val Val Ala Asp
            20                  25                  30
```

```
Gly Asn Ser Thr Arg Ser Pro Glu Thr Asn Gly Leu Leu Cys Gly Asp
            35                  40                  45

Pro Glu Glu Asn Cys Ala Ala Thr Thr Thr Gln Ser Lys Arg Lys Gly
 50                  55                  60

His Phe Ser Arg Cys Pro Lys Gln Tyr Lys His Tyr Cys Ile Lys Gly
 65                  70                  75                  80

Arg Cys Arg Phe Val Val Ala Glu Gln Thr Pro Ser Cys Val Cys Asp
                 85                  90                  95

Glu Gly Tyr Ile Gly Ala Arg Cys Glu Arg Val Asp Leu Phe Tyr Leu
            100                 105                 110

Arg Gly Asp Arg Gly Gln Ile Leu Val Ile Cys Leu Ile Ala Val Met
            115                 120                 125

Val Val Phe Ile Ile Leu Val Ile Gly Val Cys Thr Cys Cys His Pro
            130                 135                 140

Leu Arg Lys Arg Arg Lys Arg Lys Lys Glu Glu Met Glu Thr
145                 150                 155                 160

Leu Gly Lys Asp Ile Thr Pro Ile Asn Glu Asp Ile Glu Glu Thr Asn
            165                 170                 175

Ile Ala

<210> SEQ ID NO 157
<211> LENGTH: 87
<212> TYPE: PRT
<213> ORGANISM: Homo sapiens

<400> SEQUENCE: 157

Met Asp Gly Asn Ser Thr Arg Ser Pro Glu Thr Asn Gly Leu Leu Cys
 1               5                  10                  15

Gly Asp Pro Glu Glu Asn Cys Ala Ala Thr Thr Thr Gln Ser Lys Arg
            20                  25                  30

Lys Gly His Phe Ser Arg Cys Pro Lys Gln Tyr Lys His Tyr Cys Ile
        35                  40                  45

Lys Gly Arg Cys Arg Phe Val Val Ala Glu Gln Thr Pro Ser Cys Val
    50                  55                  60

Cys Asp Glu Gly Tyr Ile Gly Ala Arg Cys Glu Arg Val Asp Leu Phe
65                  70                  75                  80

Tyr His His His His His His
                85

<210> SEQ ID NO 158
<211> LENGTH: 80
<212> TYPE: PRT
<213> ORGANISM: Homo sapiens

<400> SEQUENCE: 158

Asp Gly Asn Ser Thr Arg Ser Pro Glu Thr Asn Gly Leu Leu Cys Gly
 1               5                  10                  15

Asp Pro Glu Glu Asn Cys Ala Ala Thr Thr Thr Gln Ser Lys Arg Lys
            20                  25                  30

Gly His Phe Ser Arg Cys Pro Lys Gln Tyr Lys His Tyr Cys Ile Lys
        35                  40                  45

Gly Arg Cys Arg Phe Val Val Ala Glu Gln Thr Pro Ser Cys Val Cys
    50                  55                  60

Asp Glu Gly Tyr Ile Gly Ala Arg Cys Glu Arg Val Asp Leu Phe Tyr
65                  70                  75                  80
```

```
<210> SEQ ID NO 159
<211> LENGTH: 108
<212> TYPE: PRT
<213> ORGANISM: Homo sapiens

<400> SEQUENCE: 159

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 160
<211> LENGTH: 103
<212> TYPE: PRT
<213> ORGANISM: Homo sapiens

<400> SEQUENCE: 160

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys
            100

<210> SEQ ID NO 161
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 161

Gly Gly Gly Gly Ser Gly Gly Gly Ser Gly Gly Gly Ser Gly
1               5                   10                  15

Gly Gly Gly Ser
            20

<210> SEQ ID NO 162
<211> LENGTH: 15
<212> TYPE: PRT
<213> ORGANISM: Artificial Sequence
```

<220> FEATURE:
<223> OTHER INFORMATION: Synthetic polypeptide

<400> SEQUENCE: 162

Gly Gly Gly Gly Ser Gly Gly Gly Gly Ser Gly Gly Gly Gly Ser
1               5                   10                  15

<210> SEQ ID NO 163
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 163

Gly Gly Gly Ser Gly Gly Gly Gly Ser Gly Ser
1               5                   10

<210> SEQ ID NO 164
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 164

Glu Ala Ala Ala Lys
1               5

<210> SEQ ID NO 165
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 165

Gly Ser Gly Gly Gly
1               5

<210> SEQ ID NO 166
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 166

Gly Ser Gly Gly
1

<210> SEQ ID NO 167
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 167

Ser Gly Gly Gly Ser Gly Gly Gly Ser Gly Gly Gly
1               5                   10

<210> SEQ ID NO 168
<211> LENGTH: 222
<212> TYPE: PRT
<213> ORGANISM: Artificial Sequence
<220> FEATURE:

-continued

<223> OTHER INFORMATION: Synthetic polypeptide

<400> SEQUENCE: 168

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asp Tyr
            20                  25                  30

Ala Ile Ser Trp Val Arg Gln Ala Pro Gly Gly Leu Glu Trp Met Gly
        35                  40                  45

Gly Ile Ile Pro Ile Phe Gly Asn Ala Asn Tyr Ala Gln Lys Phe Gln
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ser Ser Ser Thr Tyr Gly Ile His Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser
    210                 215                 220

<210> SEQ ID NO 169
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Phe
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Asp Phe Pro Met
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 170
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 170

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Val Pro Trp Met Gly Ile Pro Val Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Ser Thr Tyr Gly Ile His Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val
    210                 215
```

<210> SEQ ID NO 171
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 171

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Phe
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Phe Pro Met
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 172
<211> LENGTH: 221
<212> TYPE: PRT
<213> ORGANISM: Artificial Sequence
<220> FEATURE:
<223> OTHER INFORMATION: Synthetic polypeptide

<400> SEQUENCE: 172

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Arg Tyr Tyr Phe Gly Glu Phe Asp Leu Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser
    210                 215                 220

<210> SEQ ID NO 173
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 173

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Tyr Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Leu Tyr Asp Tyr Leu Ser Ser Thr
                85                  90                  95

Gly Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala
    210

<210> SEQ ID NO 174
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 174
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Arg Tyr Tyr Phe Gly Glu Phe Asp Leu Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys
210                 215                 220

<210> SEQ ID NO 175
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 175

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Tyr Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Thr Phe Asp Tyr Lys Leu Ser Leu
                85                  90                  95

Gly Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
    130                 135                 140

```
Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
            210
```

<210> SEQ ID NO 176
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 176

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Arg Tyr Tyr Phe Gly Glu Phe Asp Leu Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys
    210                 215                 220
```

<210> SEQ ID NO 177
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 177

```
Ser Tyr Glu Leu Thr Gln Pro Pro Ser Val Ser Val Ser Pro Gly Gln
1               5                   10                  15
```

Thr Ala Ser Ile Thr Cys Ser Gly Asp Lys Leu Gly Asp Lys Tyr Ala
            20                  25                  30

Tyr Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ala Phe Asp Tyr Arg Ser Ser
                85                  90                  95

Gly Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 178
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 178

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Arg Tyr Tyr Phe Gly Glu Phe Asp Leu Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys
    210                 215                 220

<210> SEQ ID NO 179
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 179

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Tyr Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ala Phe Asp Tyr Lys Ser Asp Val
                85                  90                  95

Gly Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 180
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 180

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                    20                  25                  30
Ala Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Arg Tyr Tyr Phe Gly Glu Phe Asp Leu Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys
    210                 215                 220
```

<210> SEQ ID NO 181
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 181

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Tyr Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ala Phe Ser Tyr Leu Thr Ser Val
                85                  90                  95

Gly Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
```

165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 182
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 182

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Arg Tyr Tyr Phe Gly Glu Phe Asp Leu Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys
    210                 215                 220

<210> SEQ ID NO 183
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 183

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

```
Tyr Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
65                   70                  75                  80

Asp Glu Ala Asp Tyr Tyr Cys Gln Ser Phe Asp Tyr Leu Tyr Ser Ser
                85                  90                  95

Gly Val Phe Gly Gly Gly Thr Lys Leu Thr Val Leu Gly Gln Pro Lys
               100                 105                 110

Ala Ala Pro Ser Val Thr Leu Phe Pro Pro Ser Ser Glu Glu Leu Gln
               115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
                180                 185                 190

Tyr Ser Cys Gln Val Thr His Glu Gly Ser Thr Val Glu Lys Thr Val
            195                 200                 205

Ala Pro Thr Glu Cys Ser
            210

<210> SEQ ID NO 184
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 184

Glu Val Gln Leu Leu Glu Ser Gly Gly Gly Leu Val Gln Pro Gly Gly
1                5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
65                   70                  75                  80

Leu Gln Met Asn Ser Leu Arg Ala Glu Asp Thr Ala Val Tyr Tyr Cys
                85                  90                  95

Ala Arg Gln Arg Tyr Tyr Phe Gly Glu Phe Asp Leu Trp Gly Gln Gly
               100                 105                 110

Thr Leu Val Thr Val Ser Ser Ala Ser Thr Lys Gly Pro Ser Val Phe
               115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys
    210                 215                 220

<210> SEQ ID NO 185
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 185

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Tyr Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Phe Tyr Tyr Leu Ser Ser Leu
                85                  90                  95

Gly Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 186
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 186

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gln Arg Tyr Tyr Phe Gly Glu Phe Asp Leu Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys
210                 215                 220
```

<210> SEQ ID NO 187
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 187

```
Ser Tyr Glu Leu Thr Gln Pro Pro Ser Val Ser Val Ser Pro Gly Gln
 1               5                  10                  15

Thr Ala Ser Ile Thr Cys Ser Gly Asp Lys Leu Gly Asp Lys Tyr Ala
             20                  25                  30

Tyr Trp Tyr Gln Gln Lys Pro Gly Gln Ser Pro Val Leu Val Ile Tyr
         35                  40                  45

Gln Asp Ser Lys Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ala Phe Asp Tyr Leu Ala Ser Ser
                 85                  90                  95

Gly Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190
```

Tyr Ser Cys Gln Val Thr His Glu Gly Ser Thr Val Glu Lys Thr Val
        195                 200                 205

Ala Pro Thr Glu Cys Ser
    210

<210> SEQ ID NO 188
<211> LENGTH: 207
<212> TYPE: PRT
<213> ORGANISM: Artificial Sequence
<220> FEATURE:
<223> OTHER INFORMATION: Synthetic polypeptide

<400> SEQUENCE: 188

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Ala Ile Ser Gly Ser Gly Gly Ser Thr Tyr Tyr Ala Asp Ser
65                  70                  75                  80

Val Lys Gly Gln Arg Tyr Tyr Phe Gly Glu Phe Asp Leu Trp Gly Gln
                85                  90                  95

Gly Thr Leu Val Thr Val Ser Ser Ala Ser Thr Lys Gly Pro Ser Val
            100                 105                 110

Phe Pro Leu Ala Pro Ser Ser Lys Ser Thr Ser Gly Gly Thr Ala Ala
        115                 120                 125

Leu Gly Cys Leu Val Lys Asp Tyr Phe Pro Glu Pro Val Thr Val Ser
    130                 135                 140

Trp Asn Ser Gly Ala Leu Thr Ser Gly Val His Thr Phe Pro Ala Val
145                 150                 155                 160

Leu Gln Ser Ser Gly Leu Tyr Ser Leu Ser Ser Val Val Thr Val Pro
                165                 170                 175

Ser Ser Ser Leu Gly Thr Gln Thr Tyr Ile Cys Asn Val Asn His Lys
            180                 185                 190

Pro Ser Asn Thr Lys Val Asp Lys Arg Val Glu Pro Lys Ser Cys
        195                 200                 205

<210> SEQ ID NO 189
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 189

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Tyr Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu

```
              65                  70                  75                  80
        Asp Glu Ala Asp Tyr Tyr Cys Gln Ala Phe Asp Tyr Leu His Ser Ile
                            85                  90                  95

Gly Val Phe Gly Gly Gly Thr Lys Leu Thr Val Leu Gly Gln Pro Lys
                        100                 105                 110

Ala Ala Pro Ser Val Thr Leu Phe Pro Pro Ser Ser Glu Glu Leu Gln
                    115                 120                 125

Ala Asn Lys Ala Thr Leu Val Cys Leu Ile Ser Asp Phe Tyr Pro Gly
                130                 135                 140

Ala Val Thr Val Ala Trp Lys Ala Asp Ser Ser Pro Val Lys Ala Gly
        145                 150                 155                 160

Val Glu Thr Thr Thr Pro Ser Lys Gln Ser Asn Asn Lys Tyr Ala Ala
                        165                 170                 175

Ser Ser Tyr Leu Ser Leu Thr Pro Glu Gln Trp Lys Ser His Arg Ser
                    180                 185                 190

Tyr Ser Cys Gln Val Thr His Glu Gly Ser Thr Val Glu Lys Thr Val
                195                 200                 205

Ala Pro Thr Glu Cys Ser
            210

<210> SEQ ID NO 190
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 190

Glu Val Gln Leu Leu Glu Ser Gly Gly Gly Leu Val Gln Pro Gly Gly
        1               5                   10                  15

Ser Leu Arg Leu Ser Cys Ala Ala Ser Gly Phe Thr Phe Ser Asp His
                    20                  25                  30

Ala Met His Trp Val Arg Gln Ala Pro Gly Lys Gly Leu Glu Trp Val
                35                  40                  45

Ser Ser Ile Val Tyr Asp Gly Ser Asn Thr Phe Tyr Ala Asp Ser Val
        50                  55                  60

Lys Gly Arg Phe Thr Ile Ser Arg Asp Asn Ser Lys Asn Thr Leu Tyr
        65                  70                  75                  80

Leu Gln Met Asn Ser Leu Arg Ala Glu Asp Thr Ala Val Tyr Tyr Cys
                        85                  90                  95

Ala Arg Asp Tyr Leu Asp Phe Gly Tyr Tyr Phe Asp Val Trp Gly Gln
                    100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
        145                 150                 155                 160

Trp Asn Ser Gly Ala Leu Thr Ser Gly Val His Thr Phe Pro Ala Val
                        165                 170                 175

Leu Gln Ser Ser Gly Leu Tyr Ser Leu Ser Ser Val Val Thr Val Pro
                    180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser
```

<210> SEQ ID NO 191
<211> LENGTH: 211
<212> TYPE: PRT
<213> ORGANISM: Artificial Sequence
<220> FEATURE:
<223> OTHER INFORMATION: Synthetic polypeptide

<400> SEQUENCE: 191

```
Asp Ile Glu Leu Thr Gln Pro Pro Ser Val Ser Val Ser Pro Gly Gln
1               5                   10                  15

Thr Ala Ser Ile Thr Cys Ser Gly Asp Lys Ile Gly Lys Lys Tyr Val
            20                  25                  30

His Trp Tyr Gln Gln Lys Pro Gly Gln Ala Pro Val Leu Val Ile Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ala Trp Asp Met Gln Ser Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys
    210
```

<210> SEQ ID NO 192
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 192

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Leu Gly His Val Gly Tyr Thr Thr Tyr Thr Asp Ser Val Lys
    50                  55                  60

Gly Arg Phe Thr Ile Ser Arg Asp Asn Ser Lys Asn Thr Leu Tyr Leu
65                  70                  75                  80
```

Gln Met Asn Ser Leu Arg Ala Glu Asp Thr Ala Val Tyr Tyr Cys Ala
                85                  90                  95

Arg Asp Tyr Leu Asp Phe Gly Tyr Tyr Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys
    210                 215                 220

<210> SEQ ID NO 193
<211> LENGTH: 212
<212> TYPE: PRT
<213> ORGANISM: Artificial Sequence
<220> FEATURE:
<223> OTHER INFORMATION: Synthetic polypeptide

<400> SEQUENCE: 193

Asp Ile Glu Leu Thr Gln Pro Pro Ser Val Ser Val Ser Pro Gly Gln
1               5                   10                  15

Thr Ala Ser Ile Thr Cys Ser Gly Asp Lys Ile Gly Lys Lys Tyr Val
            20                  25                  30

His Trp Tyr Gln Gln Lys Pro Gly Gln Ala Pro Val Leu Val Ile Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ala Trp Asp Met Gln Ser Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 194
<211> LENGTH: 218
<212> TYPE: PRT
<213> ORGANISM: Artificial Sequence
<220> FEATURE:
<223> OTHER INFORMATION: Synthetic polypeptide

<400> SEQUENCE: 194

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Ile Ser Trp Val Arg Gln Ala Pro Gly Lys Gly Leu Glu Trp Val
        35                  40                  45

Ser Tyr Ile Asp Ser Trp Gly Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Leu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser
    210                 215

<210> SEQ ID NO 195
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 195

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ile Ser Tyr
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ala Leu Asn Thr
                85                  90                  95

```
Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
                195                 200                 205

Asn Arg Gly Glu Ala
        210

<210> SEQ ID NO 196
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 196

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Ile Ser Trp Val Arg Gln Ala Pro Gly Lys Gly Leu Glu Trp Val
        35                  40                  45

Ser Tyr Ile Asp Ser Trp Gly Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Leu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
    210                 215

<210> SEQ ID NO 197
```

<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 197

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ile Ser Tyr
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Asp Trp Asp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 198
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 198

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Ile Ser Trp Val Arg Gln Ala Pro Gly Lys Gly Leu Glu Trp Val
        35                  40                  45

Ser Tyr Ile Asp Ser Trp Gly Ser Tyr Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Leu Phe Asp Tyr Trp Gly Gln Gly Thr Leu Val
```

```
                100                 105                 110
Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
210                 215
```

<210> SEQ ID NO 199
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 199

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ile Ser Tyr
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Asp Phe Asp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 200
<211> LENGTH: 219
<212> TYPE: PRT

<213> ORGANISM: Artificial Sequence
<220> FEATURE:
<223> OTHER INFORMATION: Synthetic polypeptide

<400> SEQUENCE: 200

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Ile Ser Trp Val Arg Gln Ala Pro Gly Lys Gly Leu Glu Trp Val
        35                  40                  45

Ser Tyr Ile Asp Ser Gly Gly Thr Phe Ile Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Leu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
    210                 215

<210> SEQ ID NO 201
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 201

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ile Ser Tyr
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ala Leu Asn Thr
                85                  90                  95

Phe Gly Gln Gly Thr Lys Val Glu Ile Lys Arg Thr Val Ala Ala Pro
            100                 105                 110

```
Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 202
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 202

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Ile Ser Trp Val Arg Gln Ala Pro Gly Lys Gly Leu Glu Trp Val
        35                  40                  45

Ser Tyr Ile Asp Ser Thr Gly Thr Phe Ile His Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Gly Ser Leu Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys
    210                 215

<210> SEQ ID NO 203
<211> LENGTH: 213
<212> TYPE: PRT
<213> ORGANISM: Artificial Sequence
<220> FEATURE:
```

<223> OTHER INFORMATION: Synthetic polypeptide

<400> SEQUENCE: 203

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ile Ser Tyr
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ala Leu Asn Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 204
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 204

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Ile Ser Trp Val Arg Gln Ala Pro Gly Lys Gly Leu Glu Trp Val
        35                  40                  45

Ser His Ile Asp Ser Asn Ser Asp Trp Thr Ser Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Leu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125
```

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
    210                 215

<210> SEQ ID NO 205
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 205

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ile Ser Tyr
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ala Leu Asn Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 206
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 206

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Ile Ser Trp Val Arg Gln Ala Pro Gly Lys Gly Leu Glu Trp Val
        35                  40                  45

Ser His Ile Asn Tyr Glu Gly Thr Trp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Leu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
    210                 215
```

<210> SEQ ID NO 207
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 207

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ile Ser Tyr
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ala Leu Asn Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
```

-continued

```
                130                 135                 140
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```